US012655398B2

(12) United States Patent
Hall et al.

(10) Patent No.: US 12,655,398 B2
(45) Date of Patent: Jun. 16, 2026

(54) MULTIPARTITE LUCIFERASE

(71) Applicant: Promega Corporation, Madison, WI (US)

(72) Inventors: Mary Hall, Madison, WI (US); Lance P. Encell, Madison, WI (US); Michael Killoran, Madison, WI (US); Keith Wood, Madison, WI (US); Thomas Smith, Madison, WI (US); Virginia Kincaid, Madison, WI (US); Thomas Kirkland, Madison, WI (US); Melanie Dart, Madison, WI (US)

(73) Assignee: Promega Corporation, Madison, WI (US)

(*) Notice: Subject to any disclaimer, the term of this patent is extended or adjusted under 35 U.S.C. 154(b) by 954 days.

(21) Appl. No.: 16/439,565

(22) Filed: Jun. 12, 2019

(65) Prior Publication Data

US 2020/0270586 A1 Aug. 27, 2020

Related U.S. Application Data

(60) Provisional application No. 62/684,014, filed on Jun. 12, 2018.

(51) Int. Cl.
*C07K 14/00* (2006.01)
*C12N 9/02* (2006.01)
*G01N 21/76* (2006.01)
*G01N 33/58* (2006.01)
*G01N 33/68* (2006.01)

(52) U.S. Cl.
CPC .......... *C12N 9/0069* (2013.01); *C12Y 113/12* (2013.01); *G01N 21/763* (2013.01); *G01N 33/582* (2013.01); *G01N 33/6845* (2013.01)

(58) Field of Classification Search
CPC .. C12N 9/0069; C12Y 113/12; G01N 21/763; G01N 33/582; G01N 33/6845
See application file for complete search history.

(56) References Cited

U.S. PATENT DOCUMENTS

| | | | |
|---|---|---|---|
| 4,946,778 A | 8/1990 | Ladner et al. | |
| 5,260,203 A | 11/1993 | Ladner et al. | |
| 8,669,103 B2 | 3/2014 | Binkowski et al. | |
| 8,697,359 B1 | 4/2014 | Zhang | |
| 9,056,885 B2 | 6/2015 | Kirkland et al. | |
| 9,797,889 B2 | 10/2017 | Dixon et al. | |
| 9,797,890 B2 | 10/2017 | Dixon et al. | |
| 9,908,918 B2 | 3/2018 | Lin et al. | |
| 2006/0194256 A1* | 8/2006 | Miao | C07C 323/63 435/7.1 |
| 2010/0281552 A1 | 11/2010 | Encell et al. | |
| 2012/0056073 A1 | 3/2012 | Ahn | |
| 2012/0107849 A1 | 5/2012 | Klaubert et al. | |
| 2012/0174242 A1 | 7/2012 | Binkowski et al. | |
| 2014/0068797 A1 | 3/2014 | Doudna et al. | |
| 2014/0099654 A1 | 4/2014 | Cali et al. | |
| 2014/0348747 A1 | 11/2014 | Dixon et al. | |
| 2015/0152395 A1 | 6/2015 | Branchini | |
| 2017/0233789 A1 | 8/2017 | Shakhmin et al. | |
| 2018/0030059 A1 | 2/2018 | Hall et al. | |
| 2018/0172692 A1* | 6/2018 | Dixon | C12Q 1/66 |
| 2020/0333346 A1* | 10/2020 | Dixon | G01N 33/542 |

FOREIGN PATENT DOCUMENTS

| | | | | |
|---|---|---|---|---|
| WO | WO88/01649 | 3/1988 | | |
| WO | WO93/06868 | 4/1993 | | |
| WO | WO94/08629 | 4/1994 | | |
| WO | WO94/09056 | 4/1994 | | |
| WO | WO96/26754 | 9/1996 | | |
| WO | WO2003/040100 | 5/2003 | | |
| WO | WO-2009128056 A2 * | 10/2009 | | A61P 31/14 |
| WO | WO2012/061529 | 5/2012 | | |
| WO | WO 2014/151736 | 9/2014 | | |
| WO | WO 2017/189751 | 11/2017 | | |
| WO | WO-2017189751 A1 * | 11/2017 | | C07K 16/241 |

OTHER PUBLICATIONS

Inouye et al 2014; Biochem & Biophys Res Commun: vol. 445; pp. 157-162. (Year: 2014).*
Extended European Search Report for PCT/U.S. Pat. No. 2019036844. Mailed May 8, 2022. 10 pages.
Dec. 14, 2017. Split enzyme developing beta-barrel protein peptide beta 9, seq id:2. XP002807009, retrieved from EBI accession No. GSP:BEN35145 Data base accession No. BEN 35145. 1 page.
Dec. 14, 2017. Split enzyme developing luciferase third polypeptide, SEQ ID:3. XP002807010, retrieved from EBI accession No. GSP:BEN35146. Database accession No. BEN35146. 1 page.
Dec. 14, 2017 Target screening beta 10*-His Tag-heavy chain polypeptide, SEQ ID:22. XP002807011. Retrieved from EBI accession No. GSP:BEN35165. 1 page.
Jiang et al., Lighting up bioluminescence with coelenterazine: strategies and applications. Photochem Photobiol Sci. Apr. 2016;15(4):466-80.
Barrangou et al., CRISPR provides acquired resistance against viruses in prokaryotes. Science. Mar. 23, 2007;315(5819):1709-12.
Bhaya et al., CRISPR-Cas systems in bacteria and archaea: versatile small RNAs for adaptive defense and regulation. Annu Rev Genet. 2011;45:273-97.
Bolotin et al., Clustered regularly interspaced short palindrome repeats (CRISPRs) have spacers of extrachromosomal origin. Microbiology (Reading). Aug. 2005;151(Pt 8):2551-2561.
Boutureira et al., Advances in chemical protein modification. Chem Rev. Mar. 11, 2015;115(5):2174-95.

(Continued)

*Primary Examiner* — Catherine S Hibbert
(74) *Attorney, Agent, or Firm* — David W. Staple; Casimir Jones, S.C.

(57) ABSTRACT

Provided herein are compositions and methods for the assembly of a tripartite or multipartite bioluminescent complex. In particular, a bioluminescent complex is formed upon the interaction of two or more peptide tags (e.g., separately or fused as a dipeptide or tripeptide) and a polypeptide component.

8 Claims, 189 Drawing Sheets

Specification includes a Sequence Listing.

(56)     References Cited

OTHER PUBLICATIONS

Brouns et al., Small CRISPR RNAs guide antiviral defense in prokaryotes. Science. Aug. 15, 2008;321(5891):960-4.

Cong et al., Multiplex genome engineering using CRISPR/Cas systems. Science. Feb. 15, 2013;339(6121):819-23.

Deltcheva et al., CRISPR RNA maturation by trans-encoded small RNA and host factor RNase III. Nature. Mar. 31, 2011;471(7340):602-7.

Xiao-Jie et al., CRISPR-Cas9: a new and promising player in gene therapy. J Med Genet. May 2015;52(5):289-96.

Deveau et al., CRISPR/Cas system and its role in phage-bacteria interactions. Annu Rev Microbiol. 2010;64:475-93.

Garneau et al., The CRISPR/Cas bacterial immune system cleaves bacteriophage and plasmid DNA. Nature. Nov. 4, 2010;468(7320):67-71.

Gasiunas et al, Cas9-crRNA ribonucleoprotein complex mediates specific DNA cleavage for adaptive immunity in bacteria. Proc Natl Acad Sci U S A. Sep. 25, 2012;109(39):E2579-86.

Hale et al., RNA-guided RNA cleavage by a CRISPR RNA-Cas protein complex. Cell. Nov. 25, 2009;139(5):945-56.

Horvath et al., CRISPR/Cas, the immune system of bacteria and archaea. Science. Jan. 8, 2010;327(5962):167-70.

Huang et al., Production of Gene-Corrected Adult Beta Globin Protein in Human Erythrocytes Differentiated from Patient iPSCs After Genome Editing of the Sickle Point Mutation. Stem Cells. May 2015;33(5):1470-9.

Hudson et al., Engineered antibodies. Nat Med. Jan. 2003;9(1):129-34.

Inagaki et al., Genetically encoded bioluminescent voltage indicator for multi-purpose use in wide range of bioimaging. Sci Rep. Feb. 13, 2017;7:42398.

Isidro-Llobet et al., Amino acid-protecting groups. Chem Rev. Jun. 2009;109(6):2455-504.

Jinek et al., A programmable dual-RNA-guided DNA endonuclease in adaptive bacterial immunity. Science. Aug. 17, 2012;337(6096):816-21.

Koniev et al., Developments and recent advancements in the field of endogenous amino acid selective bond forming reactions for bioconjugation. Chem Soc Rev. Aug. 7, 2015;44(15):5495-551.

Makarova et al., A putative RNA-interference-based immune system in prokaryotes: computational analysis of the predicted enzymatic machinery, functional analogies with eukaryotic RNAi, and hypothetical mechanisms of action. Biol Direct. Mar. 16, 2006;1:7.

Makarova et al., Evolution and classification of the CRISPR-Cas systems. Nat Rev Microbiol. Jun. 2011;9(6):467-77.

Mali et al., RNA-guided human genome engineering via Cas9. Science. Feb. 15, 2013;339(6121):823-6.

Marraffini et al., CRISPR interference limits horizontal gene transfer in staphylococci by targeting DNA. Science. Dec. 19, 2008;322(5909):1843-5.

Mojica et al., Intervening sequences of regularly spaced prokaryotic repeats derive from foreign genetic elements. J Mol Evol. Feb. 2005;60(2):174-82.

Patterson et al., Finding the right (bioorthogonal) chemistry. ACS Chem Biol. Mar. 21, 2014;9(3):592-605.

Pourcel et al., CRISPR elements in Yersinia pestis acquire new repeats by preferential uptake of bacteriophage DNA, and provide additional tools for evolutionary studies. Microbiology (Reading). Mar. 2005;151(Pt 3):653-663.

Sapranauskas et al., The *Streptococcus thermophilus* CRISPR/Cas system provides immunity in *Escherichia coli*. Nucleic Acids Res. Nov. 2011;39(21):9275-82.

Schaub et al., Fluorophore-NanoLuc BRET Reporters Enable Sensitive In Vivo Optical Imaging and Flow Cytometry for Monitoring Tumorigenesis. Cancer Res. Dec. 1, 2015;75(23):5023-33.

Smith et al., Efficient and allele-specific genome editing of disease loci in human iPSCs. Mol Ther. Mar. 2015;23(3):570-7.

Suzuki et al., Five colour variants of bright luminescent protein for real-time multicolour bioimaging. Nat Commun. Dec. 14, 2016;7:13718.

Tomalia et al., Starburst Dendrimers: Molecular-level control of size, shape, surface chemistry, topology, and flexibility from atoms to macroscopic Matter. Angewandte Chemie International Edition in English, 1990, 29(2), 138-175.

Xie et al., Seamless gene correction of β-thalassemia mutations in patient-specific iPSCs using CRISPR/Cas9 and piggyBac. Genome Res. Sep. 2014;24(9):1526-33.

Office Action for Chinese Application No. 2019800531393, dated Jan. 30, 2024 (10 pages).

* cited by examiner

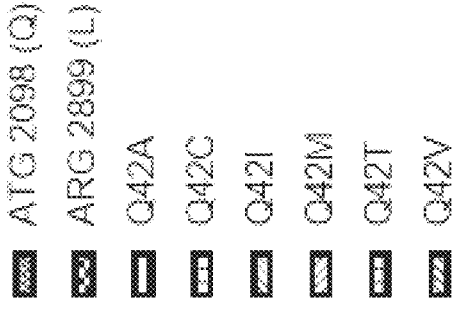
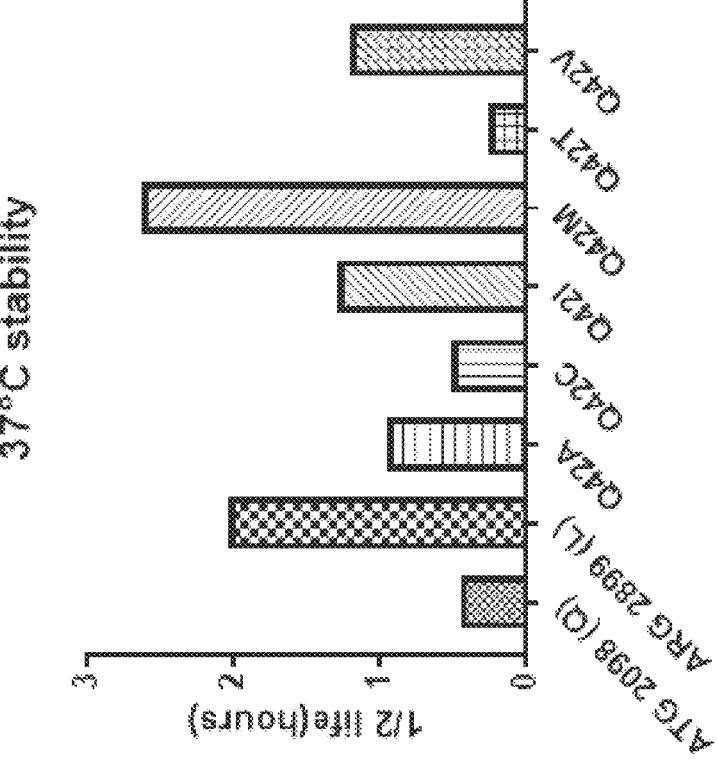
FIG. 5

ATG 3121=3092+N105S
ATG 3440=3092+V102D+E115D
ATG 3092=Q42M+E4E+M106K)
ATG 2098=W.T. LgTrip

FIG. 10A

Titrate SmTrip 9 (286)
TBS+0.01% BSA

FIG. 10B

Titrate SmTrip 10 (86)
TBS+0.01% BSA

[SmTrip10]μM

LgTrip 3092
LgTrip 3482
LgTrip 3497
LgTrip 3125
LgTrip 3118
LgTrip 3546

Calculated Kd (µM)

| | ATG 3092 | ATG 3482 | ATG 3497 | ATG 3125 | ATG 3118 | ATG 3548 |
|---|---|---|---|---|---|---|
| Half Life | 2.81 | 2.389 | 5.686 | 3.391 | 3.587 | 3.746 |

FIG. 14A
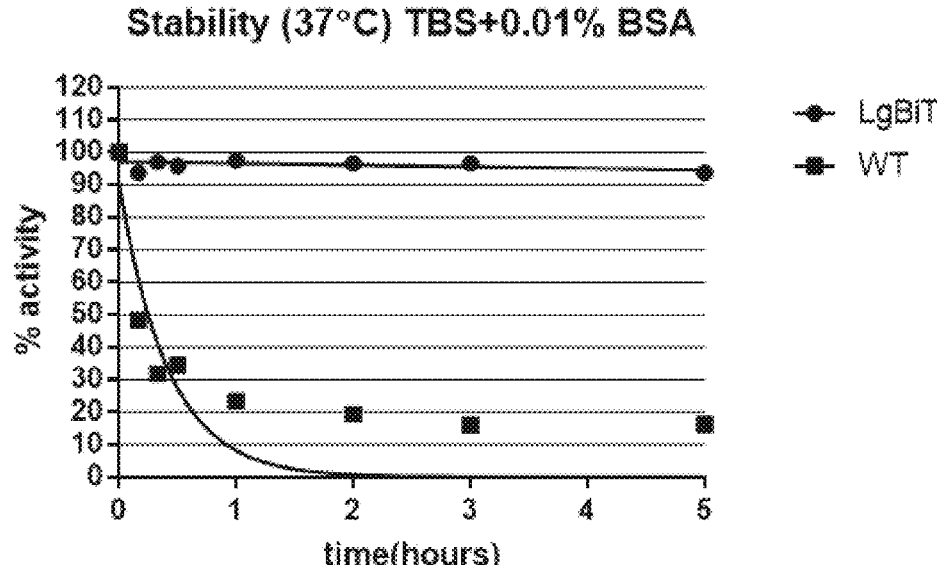
FIG. 14B
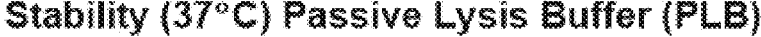
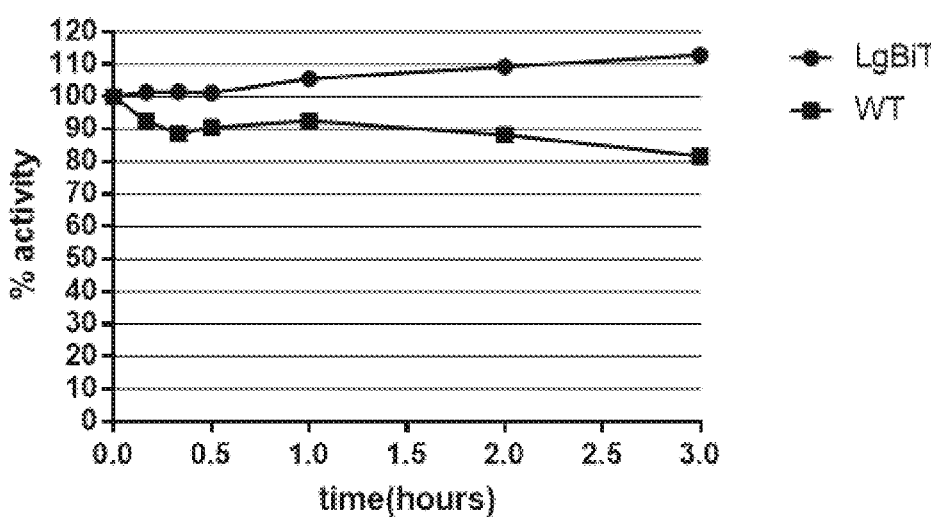

Effect of NaCl on activity
Normalized to RLU from 25mM Tris pH 7.5 (no salt)

Activity=Salt in the furimazine assay buffer 26 hour exposure to NaCl
Dilute samples 1:10,000 prior to assay

Exposure=Incubate in presence of salt titration, then dilute
and assay under standard assay conditions FIG. 18A
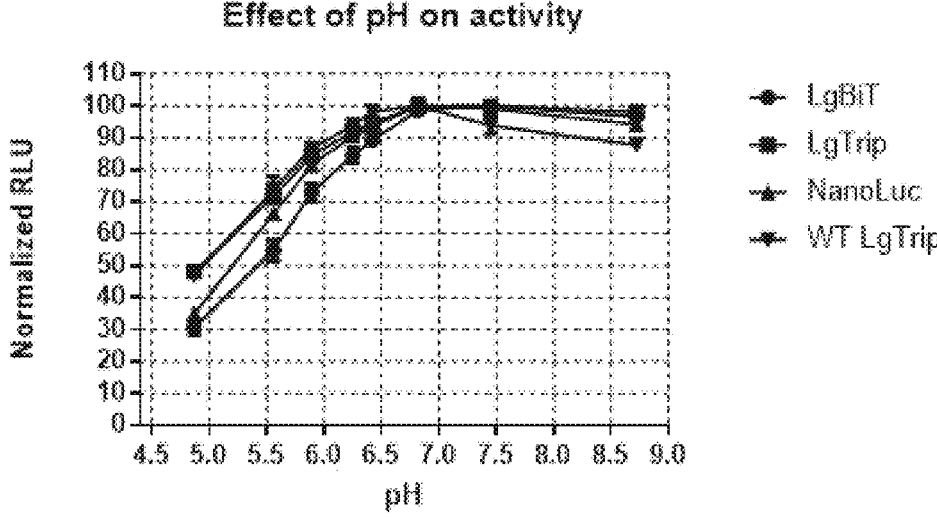
FIG. 18B
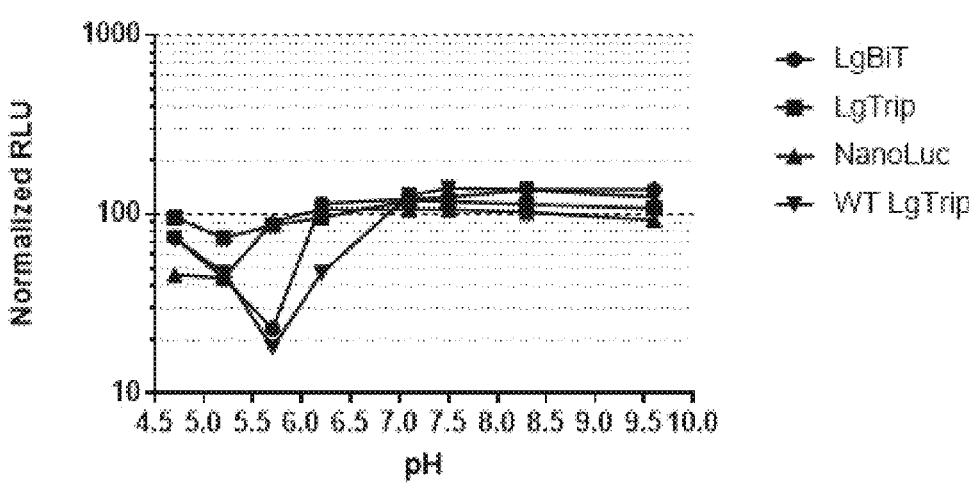

FIG. 19
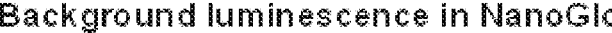
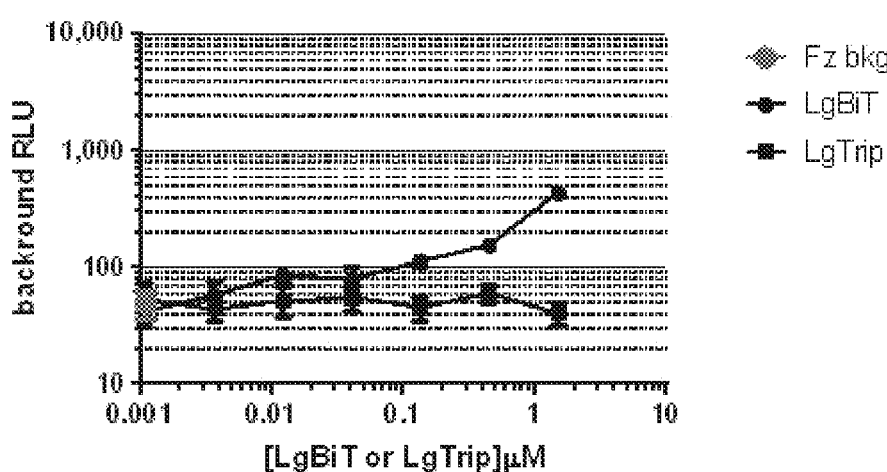
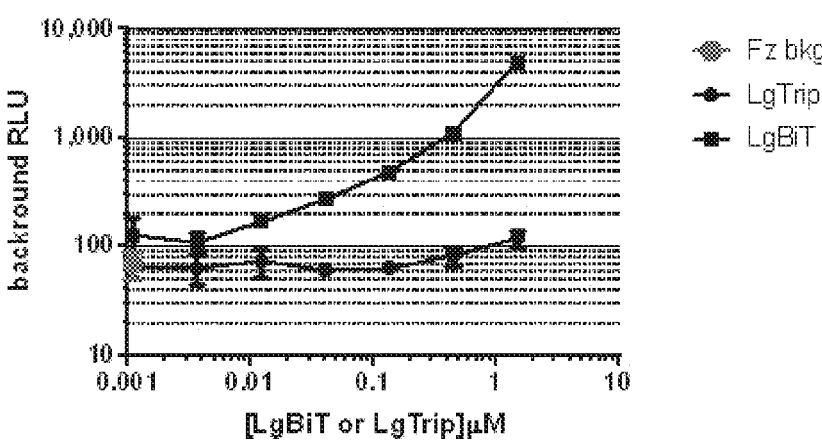

| | WT | LgTrip |
|---|---|---|
| EC50 | 3.552 | 8.131 |

| | WT | LgTrip |
|---|---|---|
| EC50 | 3.551 | 8.13 |

| | HiBiT (pep86) | pep78 | pep79 | pep80 | pep99 |
|---|---|---|---|---|---|
| Kd | 0.8432 | 1.354 | 4.226 | 0.8704 | 15.94 |

FIG. 25A
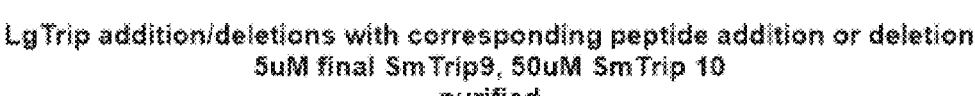
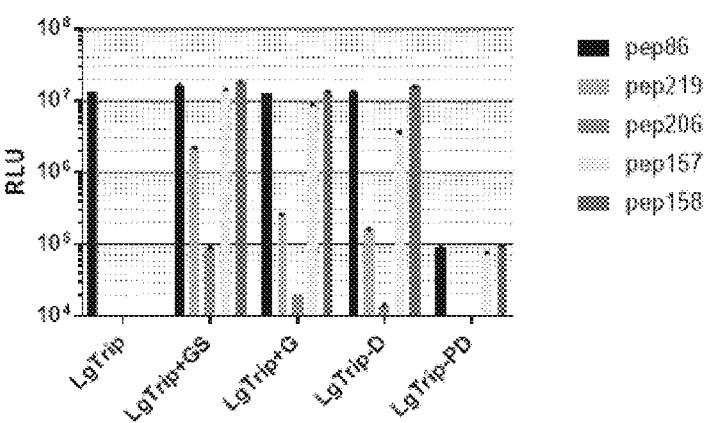
FIG. 25B
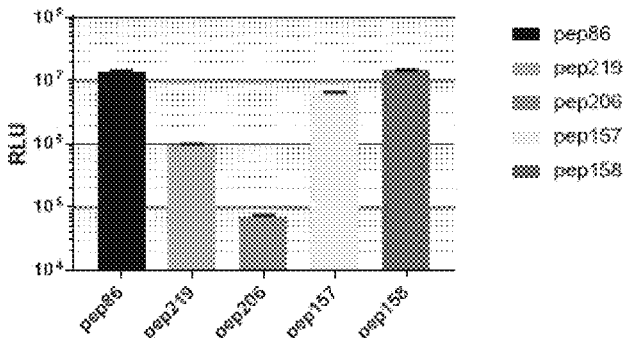

| | pep286 | pep293 | pep294 | pep298 | pep299 | pep303 |
|---|---|---|---|---|---|---|
| Kd | 0.09691 | 0.2926 | 0.4541 | 0.1292 | 0.1362 | 0.1321 |

Titration of β9 peptide in the presence of
constant β10 and polypeptide

| | pep286 (WT) | pep293 | pep294 | pep298 | pep299 | pep303 |
|---|---|---|---|---|---|---|
| Kd | 0.7467 | 2.174 | 3.511 | 45.2 | 97.08 | 42.38 |

Titration of β10 peptide in the presence
of constant β9 and polypeptide

| | Bmax | Kd |
|---|---|---|
| HiBiT(86) | 58330355 | 0.6791 |
| pep81 | 10033932 | 14.28 |
| pep82 | 1093350 | 21.84 |
| pep228 | 47056110 | 13.7 |
| pep229 | 60603642 | 1.012 |
| pep243 | 26193641 | 1.236 |
| pep219 | 10613885 | 1.105 |
| pep316 | 51521729 | 0.5413 |
| pep317 | 57096748 | 0.654 |
| pep318 | 57910752 | 0.6036 |
| pep319 | 62774228 | 0.766 |
| pep320 | 48479473 | 33.87 |

| | SmTrip 10- 86 | SmTrip 10- 206 | SmTrip 10- 219 | SmTrip 10- 228 | SmTrip 10- 229 |
|---|---|---|---|---|---|
| Kd | 0.1225 | 2.183 | 1.614 | 1.13 | 0.1409 |

| | SmTrip 10- 86 | SmTrip 10- 206 | SmTrip 10- 219 | SmTrip 10- 228 | SmTrip 10- 229 |
|---|---|---|---|---|---|
| Kd | 0.3971 | 2.54 | 1.833 | 1.556 | 0.4337 |

FIG. 33
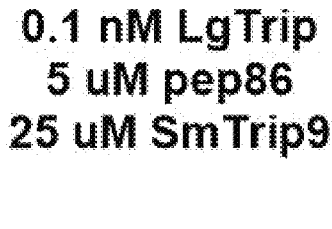
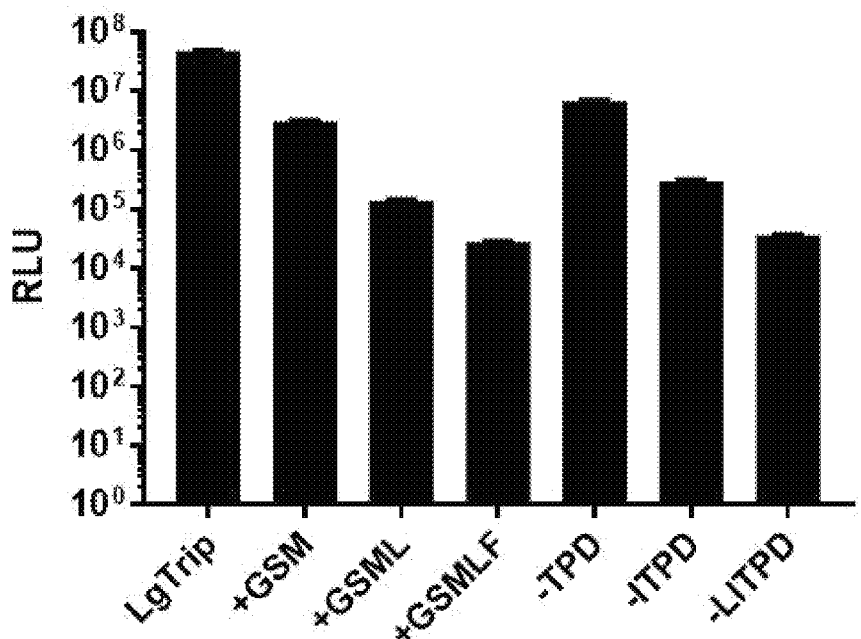
| ATG# | LgTrip | SmTrip 9 | Pep Sequence | SEQ ID NO. |
|---|---|---|---|---|
| 3546 | LgTrip | 286 | SSWKRGSMLFRVTINS | 37 |
| 3722 | LgTrip + GSM | 380 | SSWKRLFRVTINS | 180 |
| 3723 | LgTrip + GSML | 383 | SSWKRFRVTINS | 181 |
| 3724 | LgTrip + GSMLF | 386 | SSWKRRVTINS | 182 |
| 3725 | LgTrip – TPD | 389 | SSWKRTPDGSMLFRVTINS | 183 |
| 3726 | LgTrip – ITPD | 392 | SSWKRITPDGSMLFRVTINS | 184 |
| 3727 | LgTrip - LITPD | 395 | SSWKRLITPDGSMLFRVTINS | 185 |

| ATG# | LgTrip |
|------|--------|
| 3546 | LgTrip |
| 3722 | LgTrip + GSM |
| 3723 | LgTrip + GSML |
| 3724 | LgTrip + GSMLF |
| 3725 | LgTrip – TPD |
| 3726 | LgTrip – ITPD |
| 3727 | LgTrip - LITPD |

FIG. 35
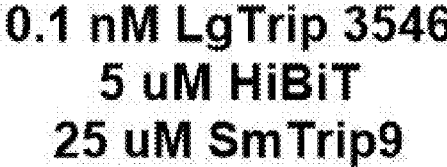
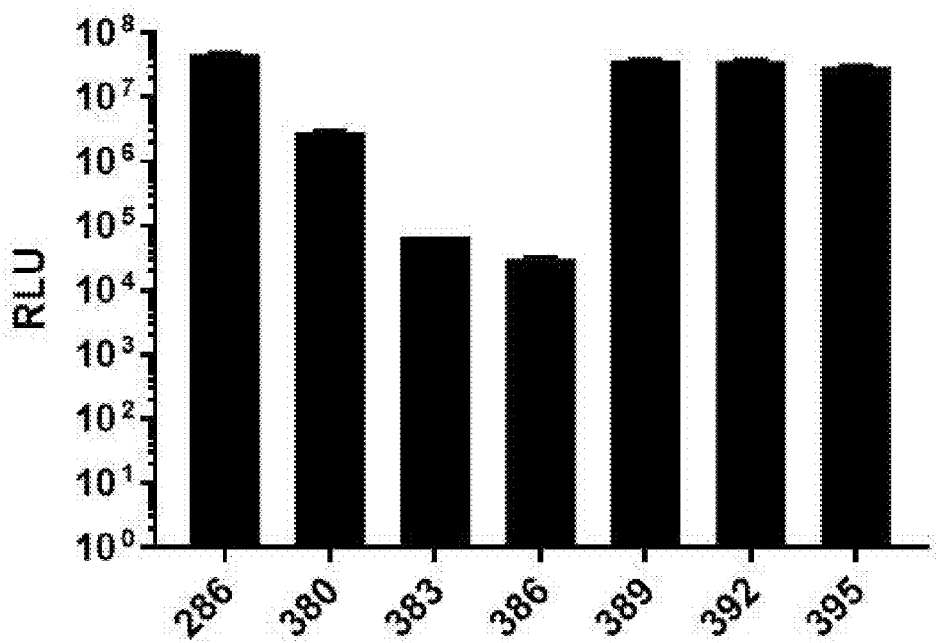
| SmTrip 9 | Pep Sequence | SEQ ID NO. |
|---|---|---|
| 286 | SSWKRGSMLFRVTINS | 37 |
| 380 | SSWKRLFRVTINS | 180 |
| 383 | SSWKRFRVTINS | 181 |
| 386 | SSWKRRVTINS | 182 |
| 389 | SSWKRTPDGSMLFRVTINS | 183 |
| 392 | SSWKRITPDGSMLFRVTINS | 184 |
| 395 | SSWKRLITPDGSMLFRVTINS | 185 |

FIG. 36

| SmTrip9 Titrations with 0.05 nM LgTrip and 25 uM HiBiT | | | | |
|---|---|---|---|---|
| Pep ID | Pep Sequence | SEQ ID NO. | SmTrip9 Kd (uM) | Bmax (RLU) |
| 286 | SSWKRGSMLFRVTINS | 37 | 0.09 | 1.65E7 |
| 292 | SSWKRMLFRVTINS | 153 | 0.10 | 1.65E7 |
| 305 | SSWKRGSMLFRVTIN | 164 | 0.60 | 1.16E7 |
| 306 | SSWKRGSMLFRVTI | 165 | 0.17 | 1.77E7 |
| 307 | SSWKRSMLFRVTIN | 166 | 0.10 | 1.47E7 |
| 308 | SSWKRMLFRVTIN | 167 | 0.11 | 1.55E7 |
| 312 | SSWKRMLFRVTI | 171 | 0.05 | 1.77E7 |

FIG. 37

| HiBiT Titrations with 0.05 nM LgTrip and 5 uM SmTrip9 pep286 | | | | |
|---|---|---|---|---|
| Pep ID | Pep Sequence | SEQ ID NO. | SmTrip9 Kd (uM) | Bmax (RLU) |
| 286 | SSWKRGSMLFRVTINS | 37 | 0.47 | 1.75E7 |
| 292 | SSWKRMLFRVTINS | 153 | 0.47 | 1.69E7 |
| 305 | SSWKRGSMLFRVTIN | 164 | 3.81 | 1.55E7 |
| 306 | SSWKRGSMLFRVTI | 165 | 0.66 | 1.86E7 |
| 307 | SSWKRSMLFRVTIN | 166 | 1.22 | 1.42E7 |
| 308 | SSWKRMLFRVTIN | 167 | 0.60 | 1.59E7 |
| 312 | SSWKRMLFRVTI | 171 | 0.25 | 1.79E7 |

FIG. 38

SmTrip9 Titrations with 0.1 nM LgTrip and 25 uM HiBiT

| SEQ ID NO: | Pep ID | Sequence | SmTrip9 Kd (uM) | Bmax (RLU) |
|---|---|---|---|---|
| 37 | 286 | SSWKRGSMLFRVTINS | 0.19 | 3.45E7 |
| 190 | 401 | SSWKRGSMLYRVTINS | 0.16 | 1.69E6 |
| 191 | 402 | SSWKRGSMLWRVTINS | 0.02 | 2.29E5 |
| 192 | 403 | SSWKRGSMLHRVTINS | 0.07 | 1.01E6 |
| 193 | 404 | SSWKRGSLLFRVTINS | 0.18 | 3.41E7 |
| 194 | 405 | SSWKRGSKLFRVTINS | 33.07 | 7.12E6 |
| 195 | 406 | SSWKRGSRLFRVTINS | 9.23 | 2.65E6 |
| 196 | 407 | SSWKRGSFLFRVTINS | 0.65 | 1.51E7 |
| 197 | 408 | SSWKRGSWLFRVTINS | 3.93 | 4.64E6 |
| 198 | 409 | SSWKRGSMLFRVSINS | 0.47 | 3.48E7 |
| 199 | 410 | SSWKRGSMLFRVQINS | 0.46 | 2.58E7 |
| 200 | 411 | SSWKRGSMLFRVNINS | 1.69 | 2.99E7 |

FIG. 39

SmTrip9 Titrations with 0.1 nM LgTrip and 25 uM HiBiT

| SEQ ID NO: | Pep ID | Sequence | SmTrip9 Kd (uM) | Bmax (RLU) |
|---|---|---|---|---|
| 37 | 286 | SSWKRGSMLFRVTINS | 0.19 | 3.45E7 |
| 153 | 292 | SSWKRMLFRVTINS | 0.21 | 2.93E7 |
| 157 | 297 | SSWKRMLFRVTINSV | 0.2 | 2.06E7 |
| 160 | 302 | SSWKRMLFRVTINSVS | 0.52 | 1.27E7 |
| 186 | 396 | SSRGSMLFRVTINSWK | 0.66 | 2.89E7 |
| 187 | 397 | SKRGSMLFRVTINSWS | 0.37 | 2.80E7 |
| 188 | 398 | SWRGSMLFRVTINS | 1.28 | 2.33E7 |
| 297 | 399 | SSKRGSMLFRVTIWS | 0.12 | 4.02E7 |
| 189 | 400 | SSRGSMLFRVTIWK | 0.07 | 4.06E7 |

FIG. 40

SmTrip9 or HiBiT Titrations with 0.1 nM LgTrip

| SEQ ID NO: | Pep ID | Sequence | SmTrip9 Kd in uM (Bmax in RLU) | HiBiT Kd in uM (Bmax in RLU) |
|---|---|---|---|---|
| 37 | 286 | SSWKRGSMLFRVTINS | 0.19 (3.45E7) | 0.73 (3.66E7) |
| 153 | 292 | SSWKRMLFRVTINS | 0.21 (2.93E7) | 1.55 (3.05E7) |
| 157 | 297 | SSWKRMLFRVTINSV | 0.2 (2.06E7) | 5.09 (1.36E7) |
| 160 | 302 | SSWKRMLFRVTINSVS | 0.52 (1.27E7) | 8.15 (1.75E7) |

| ATG# | Detail |
|------|--------|
| 1634 | FRB-15GS-AI-86 |
| 3586 | FRB-15GS-AI-289 |
| 3743 | FRB-15GS-AI-86-His6 |
| 3744 | FRB-15GS-AI-289-His6 |
| 3760 | His6-FRB-5GS-86 |
| 3761 | His6-FRB-10GS-86 |
| 3762 | His6-FRB-15GS-86 |
| 3763 | His6-FRB-5GS-289 |
| 3764 | His6-FRB-10GS-289 |
| 3765 | His6-FRB-15GS-289 |

| ATG# | Detail |
|---|---|
| 1634 | FRB-15GS-AI-86 |
| 3586 | FRB-15GS-AI-289 |
| 3743 | FRB-15GS-AI-86-His6 |
| 3744 | FRB-15GS-AI-289-His6 |
| 3760 | His6-FRB-5GS-86 |
| 3761 | His6-FRB-10GS-86 |
| 3762 | His6-FRB-15GS-86 |
| 3763 | His6-FRB-5GS-289 |
| 3764 | His6-FRB-10GS-289 |
| 3765 | His6-FRB-15GS-289 |

| Pep | Sequence |
|------|-----------|
| 245 | GSMLFRVTINS |
| 292.x | MLFRVTINS |
| 297.x | MLFRVTINSV |
| 302.x | MLFRVTINSVS |
| 305.x | GSMLFRVTIN |
| 306.x | GSMLFRVTI |
| 307.x | SMLFRVTIN |
| 308.x | MLFRVTIN |
| 312.x | MLFRVTI |

| Pep ID | SEQ ID NO. | Sequence |
|--------|-----------|----------|
| 245 | 23 | GSMLFRVTINS |
| 292.x | 289 | MLFRVTINS |
| 297.x | 290 | MLFRVTINSV |
| 302.x | 291 | MLFRVTINSVS |
| 305.x | 292 | GSMLFRVTIN |
| 306.x | 293 | GSMLFRVTI |
| 307.x | 294 | SMLFRVTIN |
| 308.x | 295 | MLFRVTIN |
| 312.x | 296 | MLFRVTI |

| Pep | Sequence |
|------|-----------|
| 245 | GSMLFRVTINS |
| 292.x | MLFRVTINS |
| 297.x | MLFRVTINSV |
| 302.x | MLFRVTINSVS |
| 305.x | GSMLFRVTIN |
| 306.x | GSMLFRVTI |
| 307.x | SMLFRVTIN |
| 308.x | MLFRVTIN |
| 312.x | MLFRVTI |

| Pep ID | SEQ ID NO. | Sequence |
|--------|-----------|-----------|
| 245 | 23 | GSMLFRVTINS |
| 292.x | 289 | MLFRVTINS |
| 297.x | 290 | MLFRVTINSV |
| 302.x | 291 | MLFRVTINSVS |
| 305.x | 292 | GSMLFRVTIN |
| 306.x | 293 | GSMLFRVTI |
| 307.x | 294 | SMLFRVTIN |
| 308.x | 295 | MLFRVTIN |
| 312.x | 296 | MLFRVTI |

| Pep ID | SEQ ID NO. | Sequence |
|--------|-----------|--------------|
| 89 | 824 | VSGWRLFKKIS |
| 289 | 826 | VSVSGWRLFKKIS |
| 245 | 23 | GSMLFRVTINS |
| 292.x | 289 | MLFRVTINS |
| 297.x | 290 | MLFRVTINSV |
| 302.x | 291 | MLFRVTINSVS |

FIG. 46
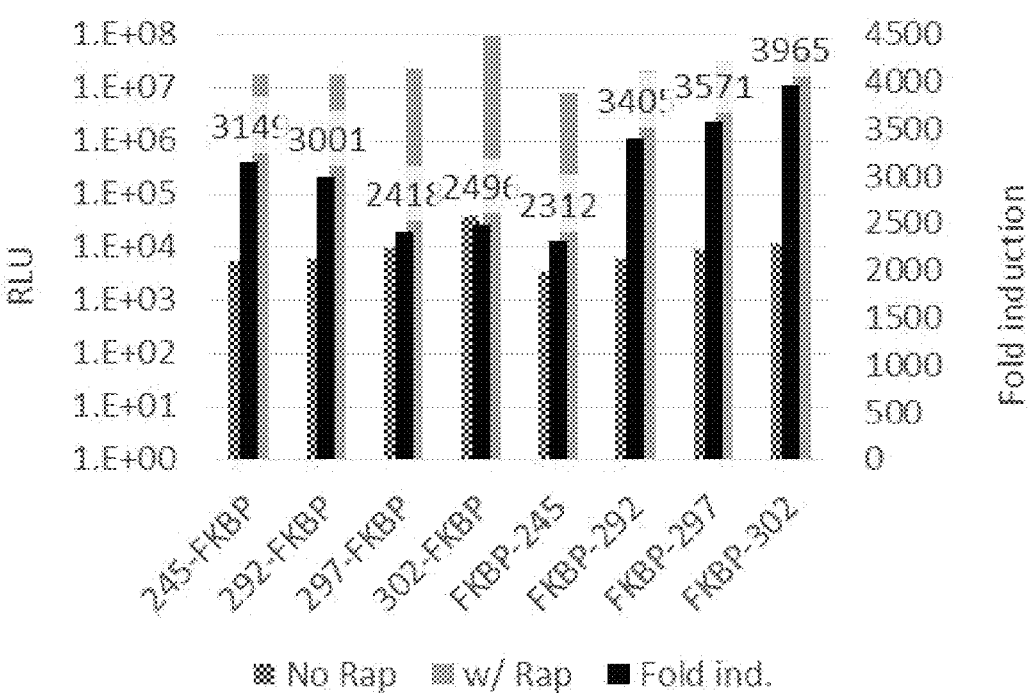
| Pep ID | SEQ ID NO. | Sequence |
|--------|-----------|----------------|
| 89 | 824 | VSGWRLFKKIS |
| 289 | 826 | VSVSGWRLFKKIS |
| 245 | 23 | GSMLFRVTINS |
| 292.x | 289 | MLFRVTINS |
| 297.x | 290 | MLFRVTINSV |
| 302.x | 291 | MLFRVTINSVS |

FRB-FKBP in E. coli lysates
Fold induction

| Pep ID | SEQ ID NO. | Sequence |
|--------|-----------|-----------|
| 89 | 824 | VSGWRLFKKIS |
| 289 | 826 | VSVSGWRLFKKIS |
| 245 | 23 | GSMLFRVTINS |
| 292.x | 289 | MLFRVTINS |
| 297.x | 290 | MLFRVTINSV |
| 302.x | 291 | MLFRVTINSVS |

| Pep ID | SEQ ID NO. | Sequence |
|--------|-----------|----------|
| 245 | 23 | GSMLFRVTINS |
| 292.x | 289 | MLFRVTINS |
| 297.x | 290 | MLFRVTINSV |
| 302.x | 291 | MLFRVTINSVS |
| 305.x | 292 | GSMLFRVTIN |
| 306.x | 293 | GSMLFRVTI |
| 307.x | 294 | SMLFRVTIN |
| 308.x | 295 | MLFRVTIN |
| 312.x | 296 | MLFRVTI |

| Pep ID | SEQ ID NO. | Sequence |
|--------|-----------|----------|
| 245 | 23 | GSMLFRVTINS |
| 292.x | 289 | MLFRVTINS |
| 297.x | 290 | MLFRVTINSV |
| 302.x | 291 | MLFRVTINSVS |
| 305.x | 292 | GSMLFRVTIN |
| 306.x | 293 | GSMLFRVTI |
| 307.x | 294 | SMLFRVTIN |
| 308.x | 295 | MLFRVTIN |
| 312.x | 296 | MLFRVTI |

| Pep ID | SEQ ID NO. | Sequence |
|--------|-----------|-------------|
| 245 | 23 | GSMLFRVTINS |
| 292.x | 289 | MLFRVTINS |
| 297.x | 290 | MLFRVTINSV |
| 302.x | 291 | MLFRVTINSVS |
| 305.x | 292 | GSMLFRVTIN |
| 306.x | 293 | GSMLFRVTI |
| 307.x | 294 | SMLFRVTIN |
| 308.x | 295 | MLFRVTIN |
| 312.x | 296 | MLFRVTI |

Panel of mAbs 1-10 all SmTrip9 fusions to identify strains 1 2 3 4 5 6 7 8 9 10 control Panel of mAbs 1- 10 all SmTrip10 fusions and recognizing different epitopes to the same targets as the antibodies in test sample window Pre-loaded with substrate and LgTrip or substrate and LgTrip are added exogenously when sample is added

FIG. 55

| Pep ID | SEQ ID NO. | Sequence |
|--------|-----------|----------|
| 245 | 23 | GSMLFRVTTINS |
| 292.x | 289 | MLFRVTINS |
| 297.x | 290 | MLFRVTINSV |
| 302.x | 291 | MLFRVTINSVS |

| Pep ID | SEQ ID NO. | Sequence |
|---|---|---|
| 245 | 23 | GSMLFRVTINS |
| 292.x | 289 | MLFRVTINS |
| 297.x | 290 | MLFRVTINSV |
| 302.x | 291 | MLFRVTINSVS |

| Pep ID | SEQ ID NO. | Sequence |
|--------|-----------|----------|
| 245 | 23 | GSMLFRVTINS |
| 295.x | 220 | GSMLFRVTINSV |
| 300.x | 221 | GSMLFRVTINSVS |
| 418.x | 226 | GSMLFRVTINSVSG |
| 419.x | 227 | GSMLFRVTINSVSGW |
| 422 | 228 | GSMLFRVTINSVSGWR |
| 423 | 229 | GSMLFRVTINSVSGWK |

| Pep ID | SEQ ID NO. | Sequence |
|--------|-----------|----------|
| 245 | 23 | GSMLFRVTINS |
| 295.x | 220 | GSMLFRVTINSV |
| 300.x | 221 | GSMLFRVTINSVS |
| 418.x | 226 | GSMLFRVTINSVSG |
| 419.x | 227 | GSMLFRVTINSVSGW |
| 422 | 228 | GSMLFRVTINSVSGWR |
| 423 | 229 | GSMLFRVTINSVSGWK |

| Pep ID | SEQ ID NO. | Sequence |
|--------|-----------|----------|
| 245 | 23 | GSMLFRVTINS |
| 295.x | 220 | GSMLFRVTINSV |
| 300.x | 221 | GSMLFRVTINSVS |
| 418.x | 226 | GSMLFRVTINSVSG |
| 419.x | 227 | GSMLFRVTINSVSGW |
| 422 | 228 | GSMLFRVTINSVSGWR |
| 423 | 229 | GSMLFRVTINSVSGWK |

| Pep ID | SEQ ID NO. | Sequence |
|--------|-----------|----------|
| 245 | 23 | GSMLFRVTINS |
| 295.x | 220 | GSMLFRVTINSV |
| 300.x | 221 | GSMLFRVTINSVS |
| 416 | 225 | MLFRVTINSVSGWR |
| 413.x | 222 | MLFRVTINSVSGW |
| 412.x | 222 | MLFRVTINSVSG |
| 415.x | 224 | MLFRVTINSVSGWK |

FIG. 63

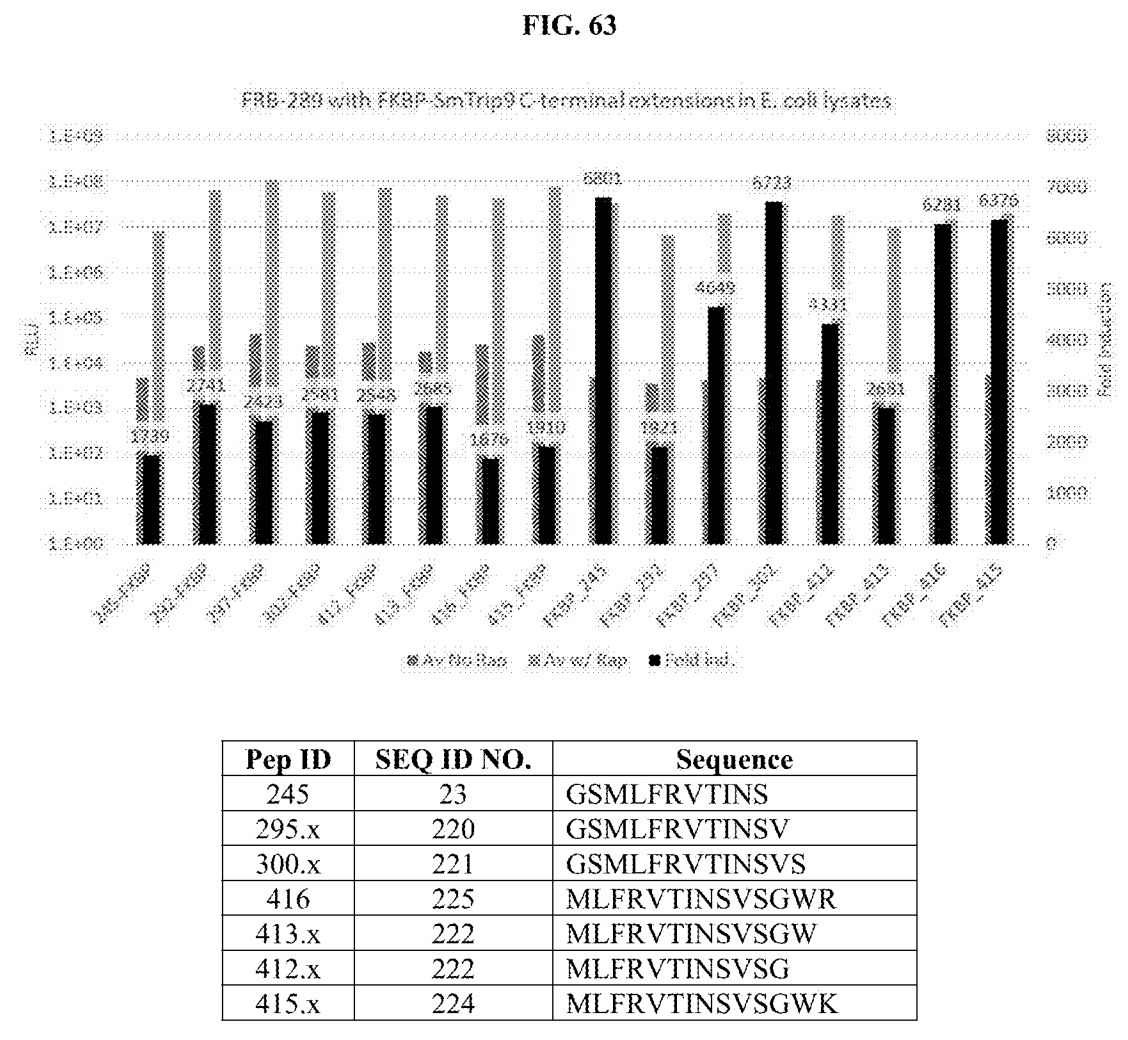

| Pep ID | SEQ ID NO. | Sequence |
|--------|-----------|----------|
| 245 | 23 | GSMLFRVTINS |
| 295.x | 220 | GSMLFRVTINSV |
| 300.x | 221 | GSMLFRVTINSVS |
| 416 | 225 | MLFRVTINSVSGWR |
| 413.x | 222 | MLFRVTINSVSGW |
| 412.x | 222 | MLFRVTINSVSG |
| 415.x | 224 | MLFRVTINSVSGWK |

FIG. 64

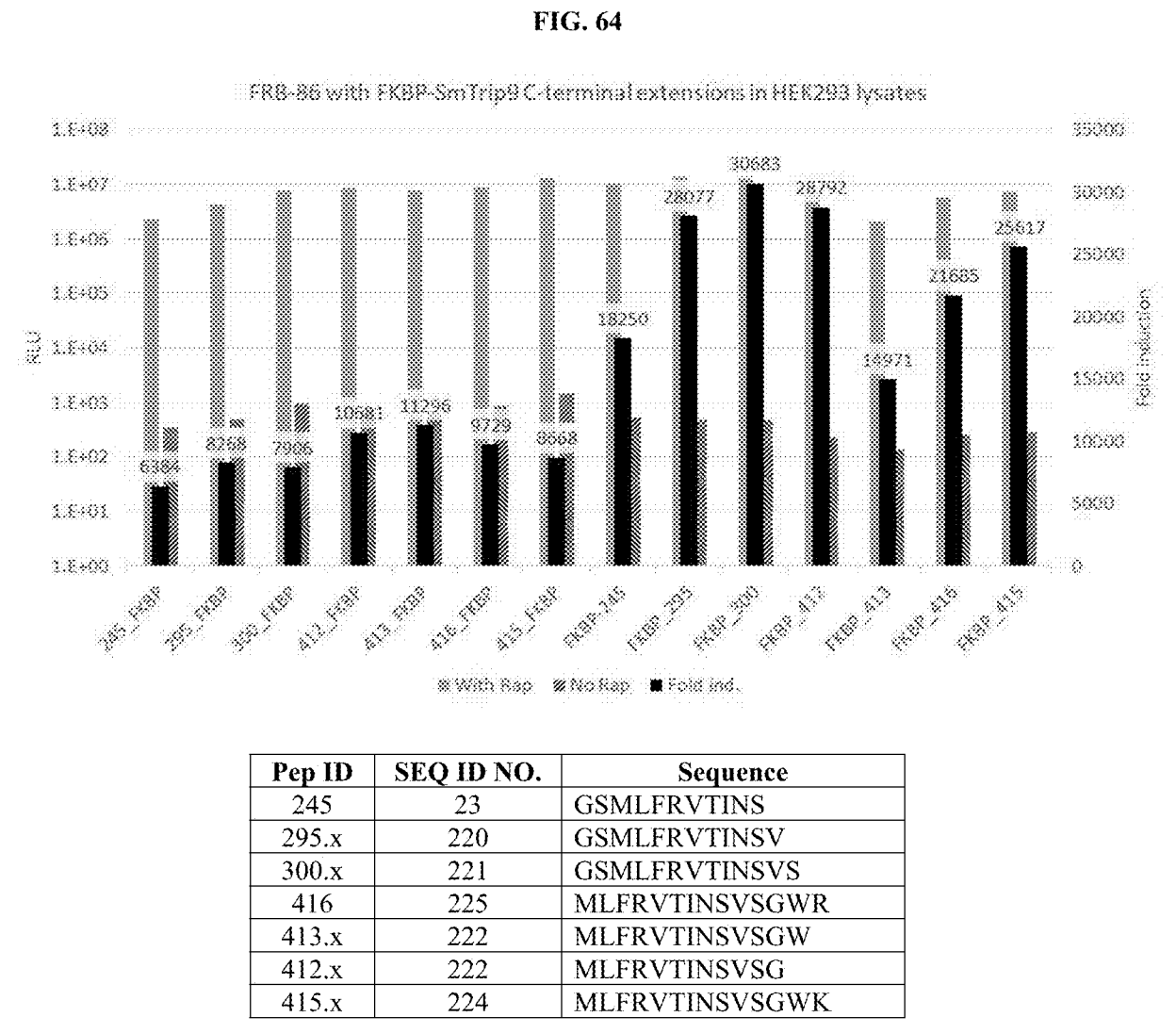

| Pep ID | SEQ ID NO. | Sequence |
|--------|-----------|----------|
| 245 | 23 | GSMLFRVTINS |
| 295.x | 220 | GSMLFRVTINSV |
| 300.x | 221 | GSMLFRVTINSVS |
| 416 | 225 | MLFRVTINSVSGWR |
| 413.x | 222 | MLFRVTINSVSGW |
| 412.x | 222 | MLFRVTINSVSG |
| 415.x | 224 | MLFRVTINSVSGWK |

| Pep ID | SEQ ID NO. | Sequence |
|---|---|---|
| 286 | 37 | SSWKRGSMLFRVTINS |
| 396 | 186 | SSRGSMLFRVTINSWK |
| 397 | 187 | SKRGSMLFRVTINSWS |
| 398 | 188 | SWRGSMLFRVTINS |
| 399 | 297 | SSKRGGSMLFRVTIWS |
| 477 | 232 | MLFRVTINSWK |
| 478 | 233 | MLFRVTINSWS |
| 479 | 234 | MLFRVTIWS |
| 480 | 235 | MLFRVTIWK |
| 481 | 236 | MLFRVKINS |
| 485 | 240 | MLFRVNINS |
| 486 | 241 | MLFRVWINS |
| 487 | 242 | LLFRVKINS |
| 488 | 243 | FLFRVTINS |

FIG. 67

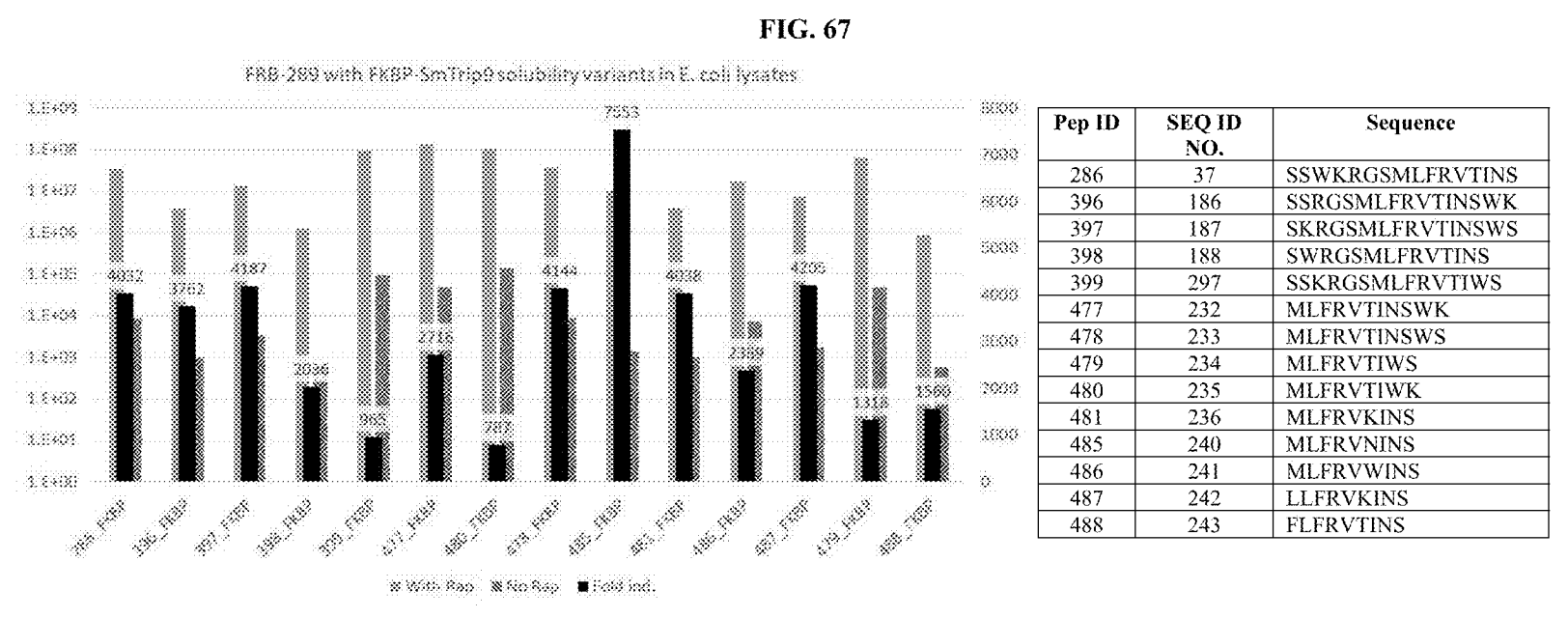

| Pep ID | SEQ ID NO. | Sequence |
|--------|-----------|----------|
| 286 | 37 | SSSWKRGSMLFRVTINS |
| 396 | 186 | SSSRGSMLFRVTINSWK |
| 397 | 187 | SKRGSMLFRVTINSWS |
| 398 | 188 | SWRGSMLFRVTINS |
| 399 | 297 | SSSKRGSMLFRVTIWS |
| 477 | 232 | MLFRVTINSWK |
| 478 | 233 | MLFRVTINSWS |
| 479 | 234 | MLFRVTIWS |
| 480 | 235 | MLFRVTIWK |
| 481 | 236 | MLFRVKINS |
| 485 | 240 | MLFRVNINS |
| 486 | 241 | MLFRVWINS |
| 487 | 242 | LLFRVKINS |
| 488 | 243 | FLFRVTINS |

FAB-2393 with FKBP Sm triple solubility variants in E. coli lysates

| Pep ID | SEQ ID NO. | Sequence |
|---|---|---|
| 286 | 37 | SSWKRGSMLFRVTINS |
| 396 | 186 | SSRGSMLFRVTINSWK |
| 397 | 187 | SKRGSMLFRVTINSWS |
| 398 | 188 | SWRGSMLFRVTINS |
| 399 | 297 | SSKRGSMLFRVTIWS |
| 477 | 232 | MLFRVTINSWK |
| 478 | 233 | MLFRVTINSWS |
| 479 | 234 | MLFRVTIWS |
| 480 | 235 | MLFRVTIWK |
| 481 | 236 | MLFRVKINS |
| 485 | 240 | MLFRVNINS |
| 486 | 241 | MLFRVWINS |
| 487 | 242 | LLFRVKINS |
| 488 | 243 | FLFRVTINS |

| Pep ID | SEQ ID NO. | Sequence |
|---|---|---|
| 286 | 37 | SSWKRGSMLFRVTINS |
| 396 | 186 | SSRGSMLFRVTINSWK |
| 397 | 187 | SKRGSMLFRVTINSWS |
| 398 | 188 | SWRGSMLFRVTINS |
| 399 | 297 | SSKRGSMLFRVTIWS |
| 477 | 232 | MLFRVTINSWK |
| 478 | 233 | MLFRVTINSWS |
| 479 | 234 | MLFRVTIWS |
| 480 | 235 | MLFRVTIWK |
| 481 | 236 | MLFRVKINS |
| 485 | 240 | MLFRVNINS |
| 486 | 241 | MLFRVWINS |
| 487 | 242 | LLFRVKINS |
| 488 | 243 | FLFRVTINS |

| Pep ID | SEQ ID NO. | Sequence |
|---|---|---|
| 245 | 23 | GSMLFRVTINS |
| 286 | 37 | SSWKRGSMLFRVTINS |
| 434 | 187 | SKRGSMLFRVTINSWS |
| 435 | 188 | SWRGSMLFRVTINS |
| 477 | 232 | MLFRVTINSWK |
| 478 | 233 | MLFRVTINSWS |
| 479 | 234 | MLFRVTIWS |
| 480 | 235 | MLFRVTIWK |
| 481 | 236 | MLFRVKINS |
| 482 | 237 | GSMLFRVTINSWS |
| 483 | 238 | GSMLFRVKINS |
| 484 | 239 | GSMLFRTIWS |

| Pep ID | SEQ ID NO. | Sequence |
|--------|------------|----------|
| 245 | 23 | GSMLFRVTINS |
| 286 | 37 | SSWKRGSMLFRVTINS |
| 434 | 187 | SKRGSMLFRVTINSWS |
| 435 | 188 | SWRGSMLFRVTINS |
| 477 | 232 | MLFRVTINSWK |
| 478 | 233 | MLFRVTINSWS |
| 479 | 234 | MLFRVTIWS |
| 480 | 235 | MLFRVTIWK |
| 481 | 236 | MLFRVKINS |
| 482 | 237 | GSMLFRVTINSWS |
| 483 | 238 | GSMLFRVKINS |
| 484 | 239 | GSMLFRTIWS |

| Pep ID | SEQ ID NO. | Sequence |
|---|---|---|
| 245 | 23 | GSMLFRVTINS |
| 286 | 37 | SSWKRGSMLFRVTINS |
| 434 | 187 | SKRGSMLFRVTINSWS |
| 435 | 188 | SWRGSMLFRVTINS |
| 477 | 232 | MLFRVTINSWK |
| 478 | 233 | MLFRVTINSWS |
| 479 | 234 | MLFRVTIWS |
| 480 | 235 | MLFRVTIWK |
| 481 | 236 | MLFRVKINS |
| 482 | 237 | GSMLFRVTINSWS |
| 483 | 238 | GSMLFRVKINS |
| 484 | 239 | GSMLFRTIWS |

| Pep ID | SEQ ID NO. | Sequence |
|---|---|---|
| 245 | 23 | GSMLFRVTINS |
| 286 | 37 | SSWKRGSMLFRVTINS |
| 434 | 187 | SKRGSMLFRVTINSWS |
| 435 | 188 | SWRGSMLFRVTINS |
| 477 | 232 | MLFRVTINSWK |
| 478 | 233 | MLFRVTINSWS |
| 479 | 234 | MLFRVTIWS |
| 480 | 235 | MLFRVTIWK |
| 481 | 236 | MLFRVKINS |
| 482 | 237 | GSMLFRVTINSWS |
| 483 | 238 | GSMLFRVKINS |
| 484 | 239 | GSMLFRTIWS |

FIG. 74

Biochemical analysis of synthetic SmTrip9 variants

| Pep ID | Sequence | SmTrip9 Kd in uM (Bmax in RLU) | HiBiT Kd in uM (Bmax in RLU) |
|---|---|---|---|
| 286 | SSWKRGSMLFRVTINS | 0.10 (2.47E7) | 4.05 (2.76E7) |
| 416 | MLFRVTINSVSGWR | 3.54 (9.38E6) | 29.88 (1.13E7) |
| 417 | MLFRVTINSVSGWK | 1.15 (1.30E7) | 19.56 (1.68E7) |
| 422 | GSMLFRVTINSVSGWR | 0.24 (2.05E7) | 4.91 (2.48E7) |
| 423 | GSMLFRVTINSVSGWK | 0.18 (2.09E7) | 3.48 (2.52E7) |
| 434 | GSMLFRVTIWK | 0.03 (2.35E7) | 0.52 (2.38E7) |
| 435 | GSMLFRVTINSWK | 0.28 (2.27E7) | 6.11 (2.34E7) |

FIG. 75

| Biochemical analysis of synthetic SmTrip9 variants | | | |
|---|---|---|---|
| Pep ID | Sequence | SmTrip9 Kd (uM) | Bmax (RLU) |
| 286 | SSWKRGSMLFRVTINS | 0.10 | 2.47E7 |
| 412 | SSWKRMLFRVTINSVSG | 0.11 | 2.24E7 |
| 413 | SSWKRMLFRVTINSVSGW | 0.15 | 2.20E7 |
| 414 | SSWKRMLFRVTINSVSGWR | 0.16 | 2.27E7 |
| 415 | SSWKRMLFRVTINSVSGWK | 0.18 | 2.34E7 |
| 418 | SSWKRGSMLFRVTINSVSG | 0.31 | 2.20E7 |
| 419 | SSWKRGSMLFRVTINSVSGW | 0.33 | 2.03E7 |
| 420 | SSWKRGSMLFRVTINSVSGWR | 0.29 | 2.27E7 |
| 421 | SSWKRGSMLFRVTINSVSGWK | 0.26 | 2.38E7 |
| 424 | SSWKRGSYLFRVTINS | 3.33 | 4.03E6 |
| 425 | SSWKRGSMLFRVKINS | 0.85 | 2.19E7 |
| 426 | SSWKRGSMLFRVRINS | 0.29 | 1.76E7 |
| 427 | SSWKRGSMLFRVWINS | 0.23 | 2.46E7 |
| 428 | SSKRGSMLFRVTIWSV | 0.04 | 2.38E7 |
| 430 | SSWRGSMLFRVTIKS | 0.28 | 2.35E7 |
| 431 | KRSSGSMLFRVTIWS | 0.03 | 2.38E7 |
| 432 | SSKRMLFRVTIWS | 0.01 | 2.39E7 |
| 433 | KRSSMLFRVTIWS | 0.02 | 2.56E7 |
| 422 | GSMLFRVTINSVSGWR | 0.24 | 2.05E7 |
| 423 | GSMLFRVTINSVSGWK | 0.18 | 2.09E7 |
| 434 | GSMLFRVTIWK | 0.03 | 2.35E7 |
| 435 | GSMLFRVTINSWK | 0.28 | 2.27E7 |
| 492 | GSMLFRVTINKWK | 0.71 | 1.89E07 |
| 493 | GSMLFRVTIKSWK | 0.47 | 2.19E07 |
| 494 | GSMLFRVTINRWK | 0.86 | 1.93E07 |
| 495 | GSMLFRVTIRSWK | 0.48 | 1.98E07 |
| 496 | GSMLFRVTINDWK | 2.17 | 9.85E06 |
| 497 | GSMLFRVTIDSWK | 5.25 | 1.76E07 |
| 498 | GSMLFRVTINEWK | 1.02 | 1.22E07 |
| 499 | GSMLFRVTIESWK | 4.25 | 1.71E07 |

FIG. 76

| Pep ID | Sequence | SmTrip9 Kd (uM) | Bmax (RU) |
|--------|----------|-----------------|-----------|
| 286 | SSWKRGSMLFRVTINS | 0.10 | 2.75E7 |
| 445 | *GSMKFRVTINSWK | 1.02 | 1.81E7 |
| 450 | *GSMLFRKTINSWK | 1.14 | 4.92E4 |
| 455 | *GSMLFRVTKNSWK | 0.55 | 3.57E4 |
| 436 | *GSMLFRVTINS | 0.24 | 2.48E7 |
| 437 | *GSMLFRVSINS | 0.33 | 2.32E7 |
| 438 | *GSMLFRVNINS | 5.67 | 2.46E7 |
| 439 | *GSRLFRVTINS | 9.86 | 3.92E5 |
| 440 | *GSRLFRVTINS | 0.01 | 1.39E4 |
| 441 | *GSMWFRVTINS | 6.15 | 9.89E6 |
| 442 | *GSMSFRVTINS | 7.03 | 1.79E7 |
| 443 | *GSMNFRVTINS | 8.97 | 5.11E6 |
| 444 | *GSMKFRVTINS | 0.73 | 1.69E7 |
| 446 | *GSMLFRWTINS | 0.31 | 7.35E4 |
| 447 | *GSMLFRSTINS | 4.34 | 6.92E5 |
| 448 | *GSMLFRNTINS | 3.98 | 1.47E5 |
| 449 | *GSMLFRKTINS | 0.12 | 2.20E4 |
| 451 | *GSMLFRVTWNS | 2.24 | 5.51E5 |
| 452 | *GSMLFRVTSNS | 9.99 | 1.32E6 |
| 453 | *GSMLFRVTNNS | 14.58 | 2.51E6 |
| 454 | *GSMLFRVTKNS | 0.21 | 2.60E4 |
| 456 | *GSMLFRVTIKS | 0.07 | 2.56E7 |
| 489 | *GSMLFRVTINSWK | 0.51 | 1.36E07 |
| 490 | GSMLFRVTINSWK* | 12.49 | 8.55E06 |
| 491 | *GSMLFRVTINSWK* | 0.28 | 1.33E07 |
| 465 | *GSMRFRVTINSWK* | 10.57 | 1.42E7 |
| 466 | *GSMDFRVTINSWK* | 0.66 | 4.43E4 |
| 467 | *GSMEFRVTINSWK* | NA | NA |
| 468 | *GSMLFRKTINSWK* | NA | 1.27E4 |
| 469 | *GSMLFRDTINSWK* | NA | 1.29E4 |
| 470 | *GSMLFRETINSWK* | NA | 1.26E4 |
| 472 | *GSMLFRVTDNSWK* | 0.09 | 2.60E4 |
| 473 | *GSMLFRVTENSWK* | 0.02 | 1.70E4 |
| 474 | *GSMKFRVTINSWK* | 0.24 | 1.35E7 |
| 475 | *GSMLFRKTINSWK* | 1.97 | 1.64E5 |
| 476 | *GSMLFRVTKNSWK* | 0.97 | 5.63E4 |

*Terminus not blocked, NA = not applicable

FIG. 77A

| Pep ID | Sequence | Solubility# |
|--------|----------|-------------|
| | Solubility of synthetic SmTrip9 peptides | |
| 296 | SSWKRGSMLFRVTINS | Y |
| 292 | SSWKRMLFRVTINS | N |
| 297 | SSWKRMLFRVTINSV | Y |
| 302 | SSWKRMLFRVTINSVS | Y |
| 305 | SSWKRGSMLFRVTIN | Y |
| 306 | SSWKRGSMLFRVTI | Y |
| 307 | SSWKRSMLFRVTIN | Y |
| 308 | SSWKRMLFRVTIN | N |
| 312 | SSWKRMLFRVTI | Y |
| 396 | SSRGSMLFRVTINSWK | Y |
| 397 | SKRGSMLFRVTINSWS | Y |
| 398 | SWRGSMLFRVTINS | Y |
| 399 | SSKRGSMLFRVTIWS | Y |
| 400 | SSRGSMLFRVTIWK | Y |
| 401 | SSWKRGSMLYRVTINS | Y |
| 402 | SSWKRGSMLWRVTINS | Y |
| 403 | SSWKRGSMLHRVTINS | Y |
| 404 | SSWKRGSLLFRVTINS | Y |
| 405 | SSWKRGSKLFRVTINS | Y |
| 406 | SSWKRGSRLFRVTINS | Y |
| 407 | SSWKRGSFLFRVTINS | Y |
| 408 | SSWKRGSWLFRVTINS | Y |
| 409 | SSWKRGSMLFRVSINS | Y |
| 410 | SSWKRGSMLFRVQINS | Y |
| 411 | SSWKRGSMLFRVNINS | Y |
| 412 | SSWKRMLFRVTINSVSG | Y |
| 413 | SSWKRMLFRVTINSVSGW | N |
| 414 | SSWKRMLFRVTINSVSGWR | Y |
| 415 | SSWKRMLFRVTINSVSGWK | Y |
| 416 | MLFRVTINSVSGWR | N |
| 417 | MLFRVTINSVSGWK | Y |
| 418 | SSWKRGSMLFRVTINSVSG | N |
| 419 | SSWKRGSMLFRVTINSVSGW | Y |
| 420 | SSWKRGSMLFRVTINSVSGWR | Y |
| 421 | SSWKRGSMLFRVTINSVSGWK | Y |
| 422 | GSMLFRVTINSVSGWR | Y |
| 423 | GSMLFRVTINSVSGWK | Y |
| 424 | SSWKRGSYLFRVTINS | Y |
| 425 | SSWKRGSMLFRVKINS | Y |
| 426 | SSWKRGSMLFRVRINS | Y |
| 427 | SSWKRGSMLFRVWINS | Y |
| 428 | SSKRGSMLFRVTIWSV | Y |
| 430 | SSWRGSMLFRVTIKS | Y |
| 431 | KRSSGSMLFRVTIWS | Y |
| 432 | SSKRMLFRVTIWS | Y |
| 433 | KRSSMLFRVTIWS | Y |
| 434 | GSMLFRVTIWK | Y |
| 435 | GSMLFRVTINSWK | N |
| 445 | GSMKFRVTINSWK* | Y |
| 450 | GSMLFRKTINSWK* | Y |
| 455 | GSMLFRVTKNSWK* | Y | in water at ~1 mM after multiple freeze/thaws
*terminus not blocked

FIG. 77B

Solubility of synthetic SmTrip9 peptides

| Pep ID | Sequence | Solubility# |
|---|---|---|
| 521 | GKMLFRVTINSxK | Y |
| 522 | GKMLFRVTIxK | Y |
| 523 | GSMxFRVTINSxK | Y |
| 524 | GSMKFRVTIxK | Y |
| 525 | GRMLFRVTINSxK | N |
| 526 | GRMLFRVTIxK | Y |
| 527 | GSMRFRVTINSxK | N |
| 528 | GSMRFRVTIxK | Y |
| 529 | GDMLFRVTINSxK | Y |
| 530 | GDMLFRVTIxK | Y |
| 531 | GSMDFRVTINSxK | Y |
| 532 | GSMDFRVTIxK | Y |
| 533 | GEMLFRVTINSxK | Y |
| 535 | GSMEFRVTINSxK | Y |
| 536 | GSMEFRVTIxK | Y |
| 538 | GSRLFRVTIxKVK | Y |
| 539 | GSRLFRVTIxSVK | Y |
| 540 | GSRLFRVTIxSK | Y |
| 541 | GSRLFRVTIxxxK | N |
| 542 | GSRLFRVTIxKK | Y |
| 436 | *GSMLFRVTINS | Y |
| 437 | *GSMLFRVSINS | Y |
| 438 | *GSMLFRVNINS | Y |
| 439 | *GSKLFRVTINS | Y |
| 440 | *GSRLFRVTINS | Y |
| 441 | *GSMWFRVTINS | N |
| 442 | *GSMSFRVTINS | Y |
| 443 | *GSMNFRVTINS | Y |
| 444 | *GSMKFRVTINS | Y |
| 446 | *GSMLFRWTINS | Y |
| 447 | *GSMLFRSTINS | Y |
| 448 | *GSMLFRNTINS | Y |
| 449 | *GSMLFRKTINS | Y |
| 451 | *GSMLFRVTWNS | Y |
| 452 | *GSMLFRVTSNS | Y |
| 453 | *GSMLFRVTNNS | Y |
| 454 | *GSMLFRVTKNS | Y |
| 456 | *GSMLFRVTKS | Y |
| 489 | *GSMLFRVTINSWK | Y |
| 490 | GSMLFRVTINSWK* | N |
| 491 | *GSMLFRVTINSWK* | Y |
| 465 | *GSMRFRVTINSWK* | Y |
| 466 | *GSMDFRVTINSWK* | Y |
| 467 | *GSMEFRVTINSWK* | Y |
| 468 | *GSMLFRRTINSWK* | Y |
| 469 | *GSMLFRDTINSWK* | N |
| 470 | *GSMLFRETINSWK* | N |
| 472 | *GSMLFRVTDNSWK* | Y |
| 473 | *GSMLFRVTENSWK* | Y |
| 474 | *GSMKFRVTINSWK* | Y |
| 475 | *GSMLFRKTINSWK* | Y |
| 476 | *GSMLFRVTKNSWK* | Y |

In water at ~1 mM after multiple freeze/thaws
*Terminus unblocked

FIG. 79
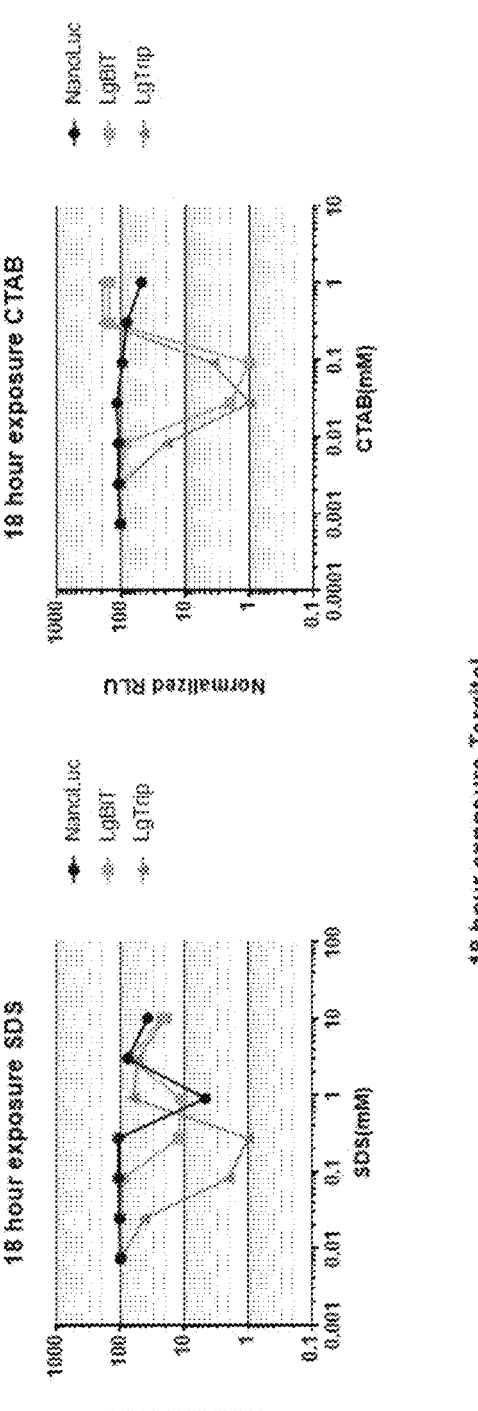
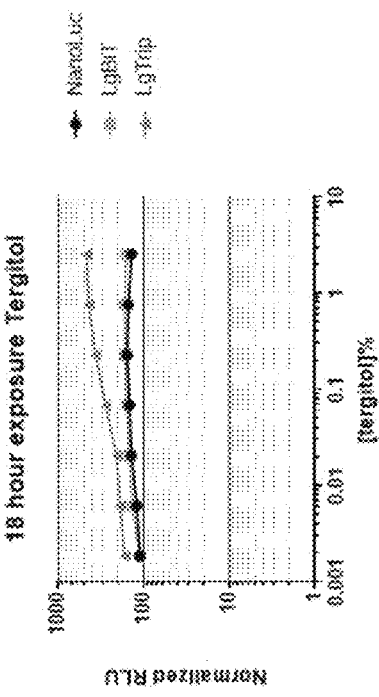

FIG. 80
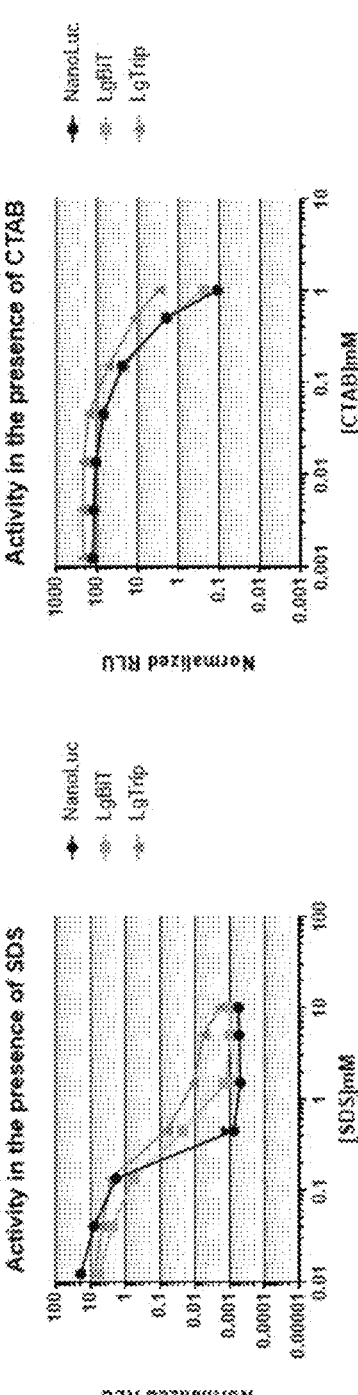
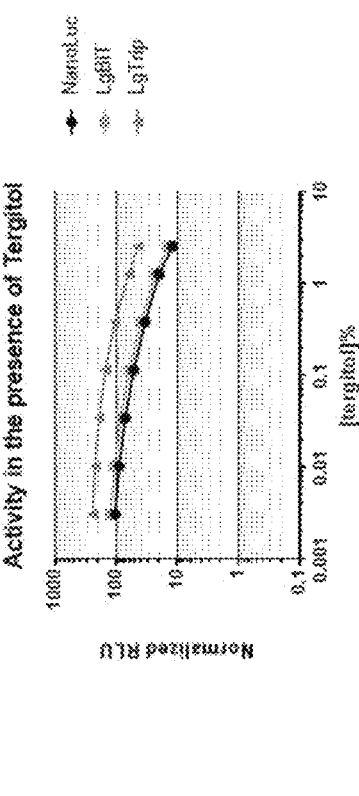

Compare NanoBIT and NanoTrip with FK506 titration

FIG. 82

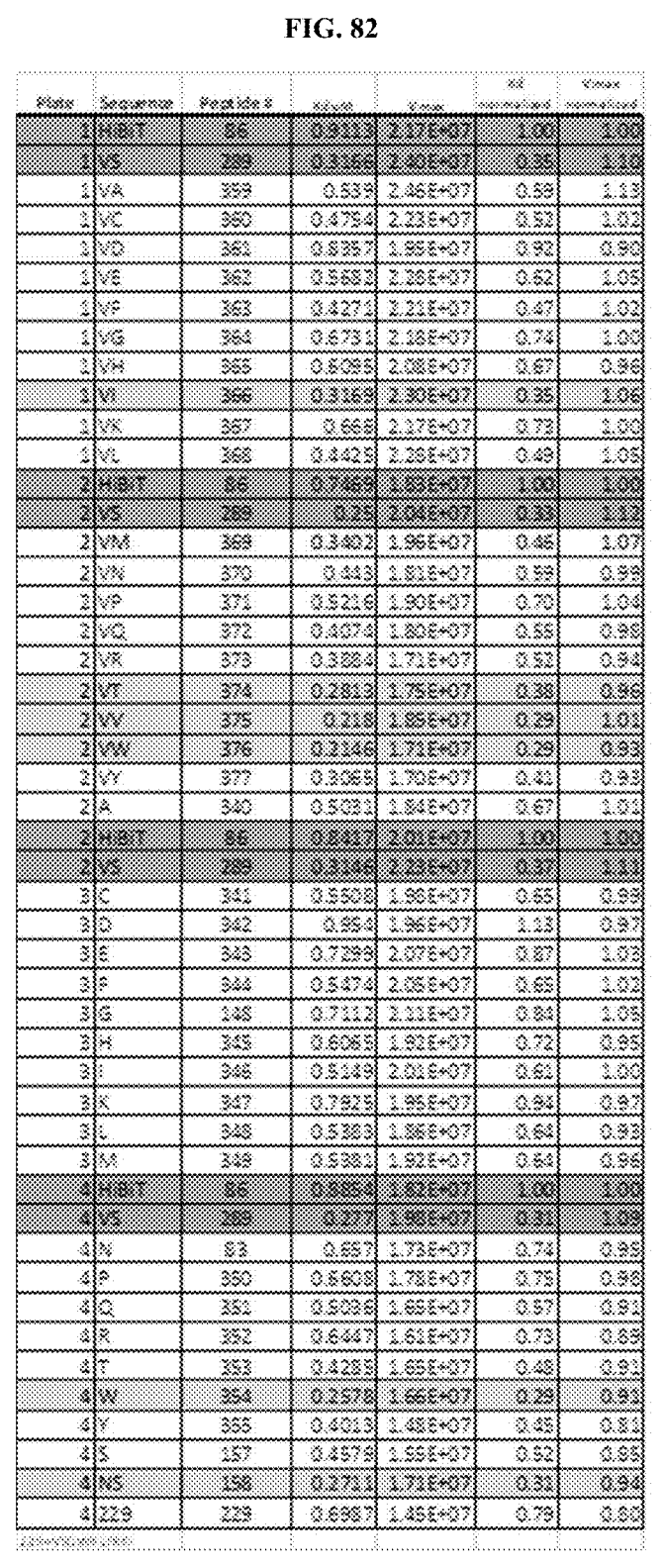

| Rate | Sequence | Peptide # | kon | kdis | kd normalized | Vmax normalized |
|---|---|---|---|---|---|---|
| 1 | HBT | 86 | 0.9313 | 2.31E+07 | 1.00 | 1.00 |
| 1 | S | 288 | 0.3369 | 2.86E+07 | 0.36 | 1.11 |
| 1 | VA | 359 | 0.539 | 2.86E+07 | 0.58 | 1.13 |
| 1 | VC | 360 | 0.4794 | 2.23E+07 | 0.51 | 1.02 |
| 1 | VD | 361 | 0.8391 | 1.99E+07 | 0.92 | 0.90 |
| 1 | VE | 362 | 0.5683 | 2.29E+07 | 0.62 | 1.05 |
| 1 | VF | 363 | 0.4271 | 2.21E+07 | 0.47 | 1.03 |
| 1 | VG | 364 | 0.6731 | 2.18E+07 | 0.74 | 1.00 |
| 1 | VH | 365 | 0.6095 | 2.08E+07 | 0.67 | 0.96 |
| 1 | VI | 366 | 0.3168 | 2.30E+07 | 0.35 | 1.06 |
| 1 | VK | 367 | 0.666 | 2.17E+07 | 0.73 | 1.00 |
| 1 | VL | 368 | 0.4423 | 2.29E+07 | 0.49 | 1.05 |
| 2 | HBT | 86 | 0.7469 | 1.85E+07 | 1.00 | 1.00 |
| 2 | S | 288 | 0.25 | 2.04E+07 | 0.33 | 1.11 |
| 2 | VM | 369 | 0.3403 | 1.96E+07 | 0.46 | 1.07 |
| 2 | VN | 370 | 0.443 | 1.81E+07 | 0.59 | 0.99 |
| 2 | VP | 371 | 0.5216 | 1.90E+07 | 0.70 | 1.04 |
| 2 | VQ | 372 | 0.4074 | 1.80E+07 | 0.55 | 0.98 |
| 2 | VR | 373 | 0.3884 | 1.71E+07 | 0.52 | 0.94 |
| 2 | VT | 374 | 0.2813 | 1.75E+07 | 0.38 | 0.96 |
| 2 | VV | 375 | 0.218 | 1.85E+07 | 0.29 | 1.01 |
| 2 | VW | 376 | 0.2146 | 1.71E+07 | 0.29 | 0.93 |
| 2 | VY | 377 | 0.3065 | 1.70E+07 | 0.41 | 0.93 |
| 2 | A | 340 | 0.503 | 1.84E+07 | 0.67 | 1.01 |
| 3 | HBT | 86 | 0.841 | 1.95E+07 | 1.00 | 1.00 |
| 3 | S | 289 | 0.3144 | 2.09E+07 | 0.37 | 1.11 |
| 3 | C | 341 | 0.5503 | 1.90E+07 | 0.65 | 0.98 |
| 3 | D | 342 | 0.954 | 1.96E+07 | 1.13 | 0.97 |
| 3 | E | 343 | 0.7299 | 2.07E+07 | 0.87 | 1.03 |
| 3 | F | 344 | 0.5474 | 2.06E+07 | 0.65 | 1.02 |
| 3 | G | 145 | 0.7113 | 2.11E+07 | 0.84 | 1.05 |
| 3 | H | 345 | 0.6065 | 1.92E+07 | 0.72 | 0.95 |
| 3 | I | 346 | 0.5149 | 2.01E+07 | 0.61 | 1.00 |
| 3 | K | 347 | 0.7925 | 1.95E+07 | 0.94 | 0.97 |
| 3 | L | 348 | 0.5383 | 1.86E+07 | 0.64 | 0.93 |
| 3 | M | 349 | 0.5381 | 1.92E+07 | 0.64 | 0.96 |
| 4 | HBT | 86 | 0.884 | 1.92E+07 | 1.00 | 1.00 |
| 4 | S | 289 | 0.27 | 1.96E+07 | 0.31 | 1.02 |
| 4 | N | 83 | 0.657 | 1.73E+07 | 0.74 | 0.98 |
| 4 | P | 350 | 0.6609 | 1.73E+07 | 0.75 | 0.98 |
| 4 | Q | 351 | 0.5036 | 1.65E+07 | 0.57 | 0.91 |
| 4 | R | 352 | 0.6447 | 1.61E+07 | 0.73 | 0.83 |
| 4 | T | 353 | 0.4285 | 1.65E+07 | 0.48 | 0.91 |
| 4 | W | 354 | 0.2578 | 1.66E+07 | 0.29 | 0.91 |
| 4 | Y | 355 | 0.4013 | 1.45E+07 | 0.45 | 0.81 |
| 4 | S | 157 | 0.4579 | 1.99E+07 | 0.52 | 0.98 |
| 4 | NS | 158 | 0.271 | 1.71E+07 | 0.31 | 0.94 |
| 4 | 229 | 229 | 0.6997 | 1.45E+07 | 0.79 | 0.85 |

FIG. 83

| Extension | peptide ID | Kd (uM) | Bmax | Kd normalized | Bmax normalized |
|---|---|---|---|---|---|
| HiBiT | 86 | 0.68 | 2.50E+07 | 1.00 | 1.00 |
| VS | 289 | 0.23 | 2.92E+07 | 0.34 | 1.17 |
| AW | 457 | 0.19 | 2.75E+07 | 0.29 | 1.10 |
| GW | 458 | 0.19 | 2.88E+07 | 0.27 | 1.15 |
| SW | 459 | 0.19 | 2.90E+07 | 0.28 | 1.16 |
| LW | 460 | 0.22 | 2.84E+07 | 0.32 | 1.14 |
| IW | 461 | 0.20 | 2.70E+07 | 0.30 | 1.08 |
| CW | 462 | 0.38 | 2.72E+07 | 0.57 | 1.09 |
| WW | 463 | 0.46 | 2.62E+07 | 0.68 | 1.05 |
| YW | 464 | 0.22 | 2.77E+07 | 0.33 | 1.11 |

NanoLuc, LgBiT, and LgBiT Antares fusions
Compare RLU at 100pM

| NanoLuc |
| Antares |
| Antares LgBiT |
| Antares LgTrip |
| LgBiT GS one fluor |
| LgBiT RH one fluor |
| LgTrip GS one fluor |
| LgTrip RH one fluor |

| 2465 | NanoLuc |
| 3802 | Antares NanoLuc |
| 3803 | Antares LgBiT |
| 3804 | Antares LgTrip |
| 3815 | LgBiT-8GS-CyOFP1 |
| 3816 | LgBiT-RH-CyOFP1 |
| 3817 | LgTrip-8GS-CyOFP1 |
| 3818 | LgTrip-RH-CyOFP1 |

FIG. 85
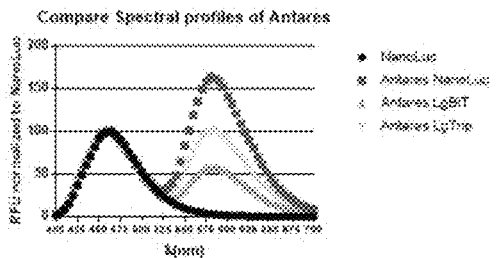
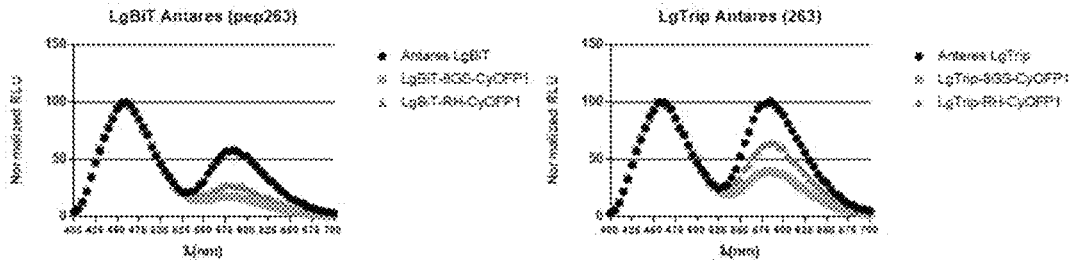
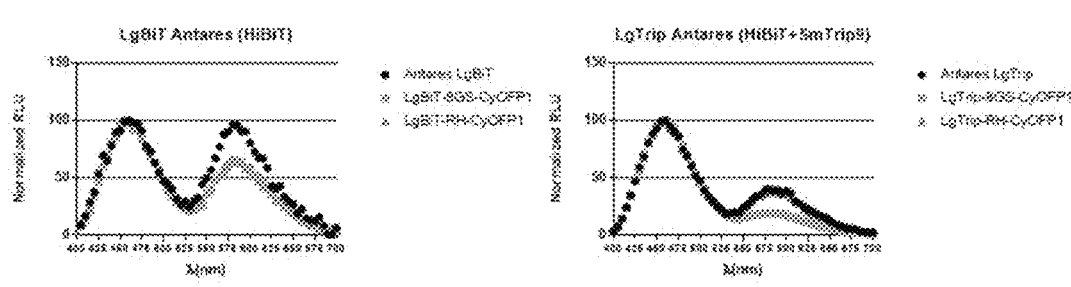

FIG. 86
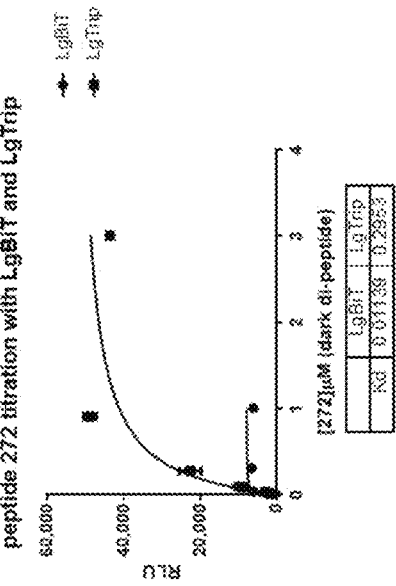
peptide 272 titration with LgBiT and LgTrip
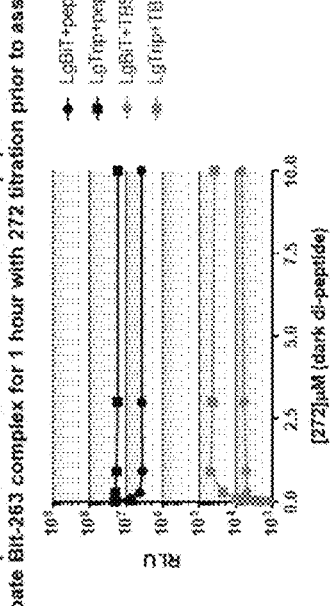
Compare inhibition and activation of dark peptide 272
Pre-incubate Bit-263 complex for 1 hour with 272 titration prior to assay
Pep 272 GSMLFRVTINSVSGWALFKKIS    SEQ ID NO: 146

Peptide 273  GSMLFRVTINSGVSGWALFKKIS   SEQ ID NO. 298
Peptide 264  GSMLFRVTINSGVSGWRLFKKIS   SEQ ID NO. 299

Compare inhibition of LgBiT or LgTrip with DarkBiT (167)

- LgBiT/0.5nM HiBiT
- LgTrip/0.25uM SmTrip9/50nM HiBiT

Peptide 167 VSGWALFKKIS    SEQ ID NO. 300

| Pep ID | Sequence | SEQ ID NO. |
|---|---|---|
| 245 | GSMLFRVTINS | 23 |
| 286 | SSWKRGSMLFRVTINS | 37 |
| 492 | GSMLFRVTINKWK | 313 |
| 493 | GSMLFRVTIKSWK | 314 |
| 521 | GKMLFRVTINSWK | 827 |
| 522 | GKMLFRVTIWK | 269 |
| 523 | GSMKFRVTINSWK | 270 |
| 524 | GSMKFRVTIWK | 271 |
| 538 | GSMLFRVTIWKVK | 283 |
| 541 | GSMLFRVTIWKWK | 286 |
| 542 | GSMLFRVTIWKK | 287 |

| Pep ID | Sequence | SEQ ID NO. |
|---|---|---|
| 245 | GSMLFRVTINS | 23 |
| 286 | SSWKRGSMLFRVTINS | 37 |
| 435 | GSMLFRVTINSWK | 310 |
| 434 | GSMLFRVTIWK | 230 |
| 492 | GSMLFRVTINKWK | 313 |
| 493 | GSMLFRVTIKSWK | 314 |
| 521 | GKMLFRVTINSWK | 827 |
| 522 | GKMLFRVTIWK | 269 |
| 523 | GSMKFRVTINSWK | 270 |
| 524 | GSMKFRVTIWK | 271 |
| 538 | GSMLFRVTIWKVK | 283 |
| 541 | GSMLFRVTIWKWK | 286 |
| 542 | GSMLFRVTIWKK | 287 |

| Pep ID | Sequence | SEQ ID NO. |
|---|---|---|
| 245 | GSMLFRVTINS | 23 |
| 286 | SSWKRGSMLFRVTINS | 37 |
| 435 | GSMLFRVTINSWK | 310 |
| 434 | GSMLFRVTIWK | 230 |
| 492 | GSMLFRVTINKWK | 313 |
| 493 | GSMLFRVTIKSWK | 314 |
| 521 | GKMLFRVTINSWK | 827 |
| 522 | GKMLFRVTIWK | 269 |
| 523 | GSMKFRVTINSWK | 270 |
| 524 | GSMKFRVTIWK | 271 |
| 538 | GSMLFRVTIWKVK | 283 |
| 541 | GSMLFRVTIWKWK | 286 |
| 542 | GSMLFRVTIWKK | 287 |

| Pep ID | Sequence | SEQ ID NO. |
|---|---|---|
| 245 | GSMLFRVTINS | 23 |
| 286 | SSWKRGSMLFRVTINS | 37 |
| 435 | GSMLFRVTINSWK | 310 |
| 434 | GSMLFRVTIWK | 230 |
| 492 | GSMLFRVTINKWK | 313 |
| 493 | GSMLFRVTIKSWK | 314 |
| 521 | GKMLFRVTINSWK | 827 |
| 522 | GKMLFRVTIWK | 269 |
| 523 | GSMKFRVTINSWK | 270 |
| 524 | GSMKFRVTIWK | 271 |
| 538 | GSMLFRVTIWKVK | 283 |
| 541 | GSMLFRVTIWKWK | 286 |
| 542 | GSMLFRVTIWKK | 287 |

FIG. 92

| FKBP construct | | | | FRB_289 + FKBP_SmTrip9 | | | FRB_86 + FKBP_SmTrip9 | | | FRB_229 + FKBP_SmTrip9 | | |
|---|---|---|---|---|---|---|---|---|---|---|---|---|
| ATG# | Pep ID | Pep Sequence | SEQ ID NO. | With Rap | No Rap | Response | With Rap | No Rap | Response | With Rap | No Rap | Response |
| 3770 | 245 | GSMLFRVTINS | 23 | 0.53 +/- 0.04 | 0.24 +/- 0.02 | 2.26 +/- 0.11 | 0.41 +/- 0.03 | 0.16 +/- 0.01 | 2.53 +/- 0.07 | 0.21 +/- 0.01 | 0.10 +/- 0.01 | 2.21 +/- 0.34 |
| 3937 | 521 | GKMLFRVTINSWK | 827 | 1.00 +/- 0.04 | 1.00 +/- 0.07 | 1.00 +/- 0.04 | 0.85 +/- 0.02 | 0.70 +/- 0.01 | 1.21 +/- 0.05 | 0.49 +/- 0.03 | 0.48 +/- 0.03 | 1.02 +/- 0.13 |
| 4543 | 759 | DKLLFTVTIEKYK | 496 | 0.35 +/- 0.01 | 0.10 +/- 0.01 | 3.70 +/- 0.58 | 0.37 +/- 0.04 | 0.09 +/- 0.02 | 4.33 +/- 1.07 | 0.27 +/- 0.01 | 0.05 +/- 0.01 | 5.02 +/- 0.71 |
| 4792 | 823 | EKLLFTVTIEKYK | 596 | 0.21 +/- 0.09 | 0.08 +/- 0.00 | 2.47 +/- 0.99 | 0.24 +/- 0.09 | 0.06 +/- 0.02 | 4.13 +/- 0.37 | 0.17 +/- 0.06 | 0.05 +/- 0.00 | 3.30 +/- 0.93 |
| 4793 | 840 | GKLLFTVTIEKYK | 597 | 0.59 +/- 0.04 | 0.26 +/- 0.03 | 2.25 +/- 0.13 | 0.68 +/- 0.04 | 0.24 +/- 0.01 | 2.82 +/- 0.09 | 0.46 +/- 0.04 | 0.15 +/- 0.01 | 3.17 +/- 0.21 |

FIG. 93

| Biochemical analysis of synthetic SmTrip9 variants | | | | |
|---|---|---|---|---|
| Pep ID | Sequence | SEQ ID NO. | SmTrip9 Kd (uM) | Bmax (RLU) |
| 286 | SSWKRGSMLFRVTINS | 37 | 0.19 | 2.57E+07 |
| 434 | GSMLFRVTIWK | 230 | 0.13 | 2.49E+07 |
| 521 | GKMLFRVTINSWK | 268 | 0.55 | 2.50E+07 |
| 522 | GKMLFRVTIWK | 269 | 0.02 | 2.47E+07 |
| 523 | GSMKFRVTINSWK | 270 | 1.34 | 1.51E+07 |
| 524 | GSMKFRVTIWK | 271 | 0.14 | 2.51E+07 |
| 525 | GRMLFRVTINSWK | 272 | 0.37 | 2.37E+07 |
| 526 | GRMLFRVTIWK | 273 | 0.01 | 2.32E+07 |
| 527 | GSMRFRVTINSWK | 274 | 0.72 | 1.06E+07 |
| 528 | GSMRFRVTIWK | 275 | 0.11 | 2.19E+07 |
| 529 | GDMLFRVTINSWK | 276 | 2.60 | 4.05E+06 |
| 530 | GDMLFRVTIWK | 277 | 0.54 | 2.23E+07 |
| 531 | GSMDFRVTINSWK | 278 | 1.74 | 1.32E+07 |
| 532 | GSMDFRVTIWK | 279 | 0.43 | 4.43E+06 |
| 533 | GEMLFRVTINSWK | 280 | 0.34 | 5.26E+06 |
| 535 | GSMEFRVTINSWK | 281 | 0.95 | 8.56E+06 |
| 536 | GSMEFRVTIWK | 282 | 0.18 | 1.63E+07 |
| 538 | GSMLFRVTIWKVK | 283 | 0.12 | 2.28E+07 |
| 539 | GSMLFRVTIWSVK | 284 | 0.03 | 1.82E+07 |
| 540 | GSMLFRVTIWSK | 285 | 0.15 | 2.11E+07 |
| 541 | GSMLFRVTIWKWK | 286 | 0.13 | 1.76E+07 |
| 542 | GSMLFRVTIWKK | 287 | 0.07 | 2.35E+07 |

FIG. 94
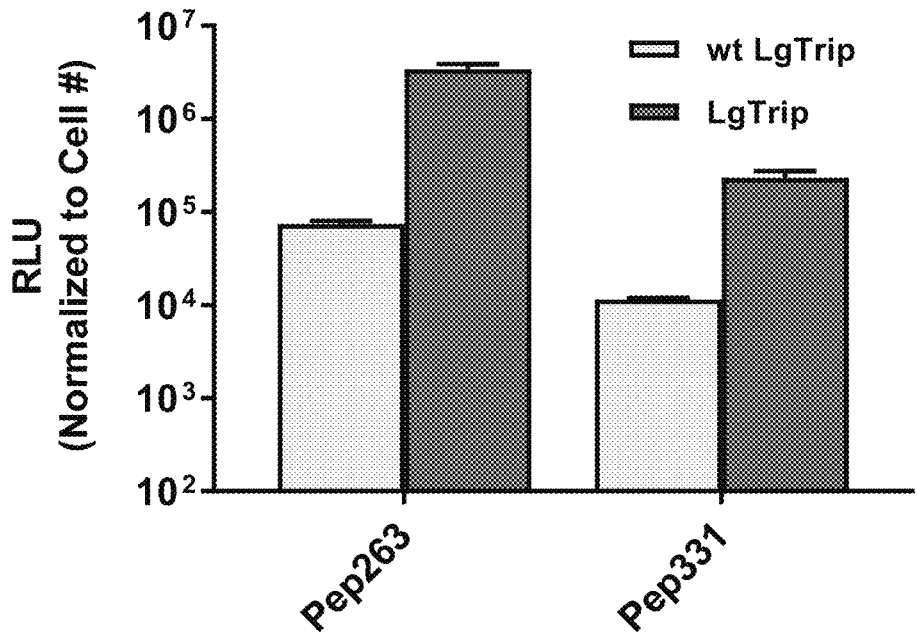
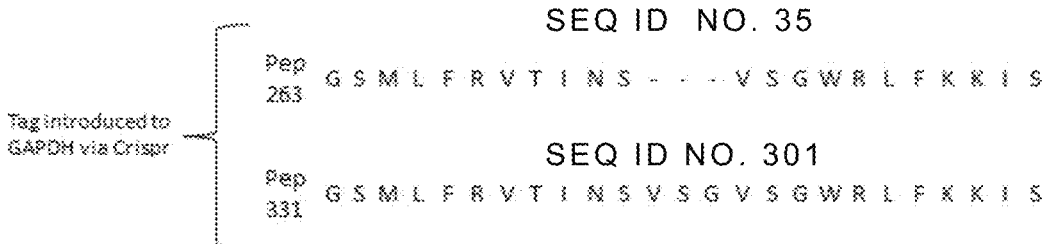

Chemical Formula: C$_{68}$H$_{112}$N$_{19}$O$_{15}$S$^{3+}$
Exact Mass: 1466.83

Chemical Formula: C$_{71}$H$_{117}$N$_{22}$O$_{15}$$^{3+}$
Exact Mass: 1517.91

Chemical Formula: C$_{75}$H$_{118}$N$_{20}$O$_{19}$S$_{2}$$^{4+}$
Exact Mass: 1666.83

Chemical Formula: $C_{70}H_{112}N_{19}O_{15}{}^{3+}$
Exact Mass: 1458.86

Chemical Formula: $C_{100}H_{139}BF_2N_{23}O_{16}{}^{3+}$
Exact Mass: 1967.08

FIG. 96A

Chemical Formula: $C_{90}H_{149}N_{30}O_{24}S^{3+}$
Exact Mass: 2066.11

FIG. 96B

Chemical Formula: $C_{89}H_{144}N_{27}O_{24}S^{3+}$
Exact Mass: 2007.06

FIG. 96C

Chemical Formula: C$_{87}$H$_{144}$N$_{27}$O$_{24}$S$_2$$^{3+}$
Exact Mass: 2015.03

FIG. 96D

Chemical Formula: C$_{117}$H$_{173}$BF$_2$N$_{31}$O$_{25}$S$_2$$^{3+}$
Exact Mass: 2525.27

FIG. 96E

Chemical Formula: C$_{94}$H$_{151}$N$_{28}$O$_{28}$S$_3^{3+}$
Exact Mass: 2216.04

FIG. 96F

Chemical Formula: C$_{88}$H$_{141}$N$_{26}$O$_{26}$S$^{3+}$
Exact Mass: 2010.02

Chemical Formula: C$_{110}$H$_{161}$BF$_{2}$N$_{29}$O$_{19}$S$^{3+}$
Exact Mass: 2273.23

Chemical Formula: $C_{81}H_{134}N_{25}O_{18}S^{3+}$
Exact Mass: 1777.00

FIG. 97C

Chemical Formula: $C_{80}H_{129}N_{22}O_{18}S^{3+}$
Exact Mass: 1717.96

Chemical Formula: $C_{78}H_{129}N_{22}O_{18}S_2^{3+}$
Exact Mass: 1725.93

FIG. 97D

Chemical Formula: $C_{85}H_{136}N_{23}O_{22}S_3^{3+}$
Exact Mass: 1926.94

FIG. 97E

Chemical Formula: $C_{79}H_{126}N_{21}O_{20}S^{3+}$
Exact Mass: 1720.92

Chemical Formula: $C_{100}H_{144}BF_2N_{26}O_{16}S^{3+}$
Exact Mass: 2046.10

FIG. 98B

Chemical Formula: $C_{71}H_{117}N_{22}O_{15}S^{3+}$
Exact Mass: 1549.88

FIG. 98C

Chemical Formula: $C_{70}H_{112}N_{19}O_{15}S^{3+}$
Exact Mass: 1490.83

FIG. 98D

Chemical Formula: $C_{68}H_{112}N_{19}O_{15}S_2^{3+}$
Exact Mass: 1498.80

Chemical Formula: $C_{75}H_{119}N_{20}O_{19}S_3{}^{3+}$
Exact Mass: 1699.81

Chemical Formula: $C_{69}H_{109}N_{18}O_{17}S_3{}^{3+}$
Exact Mass: 1493.79

FIG. 99A

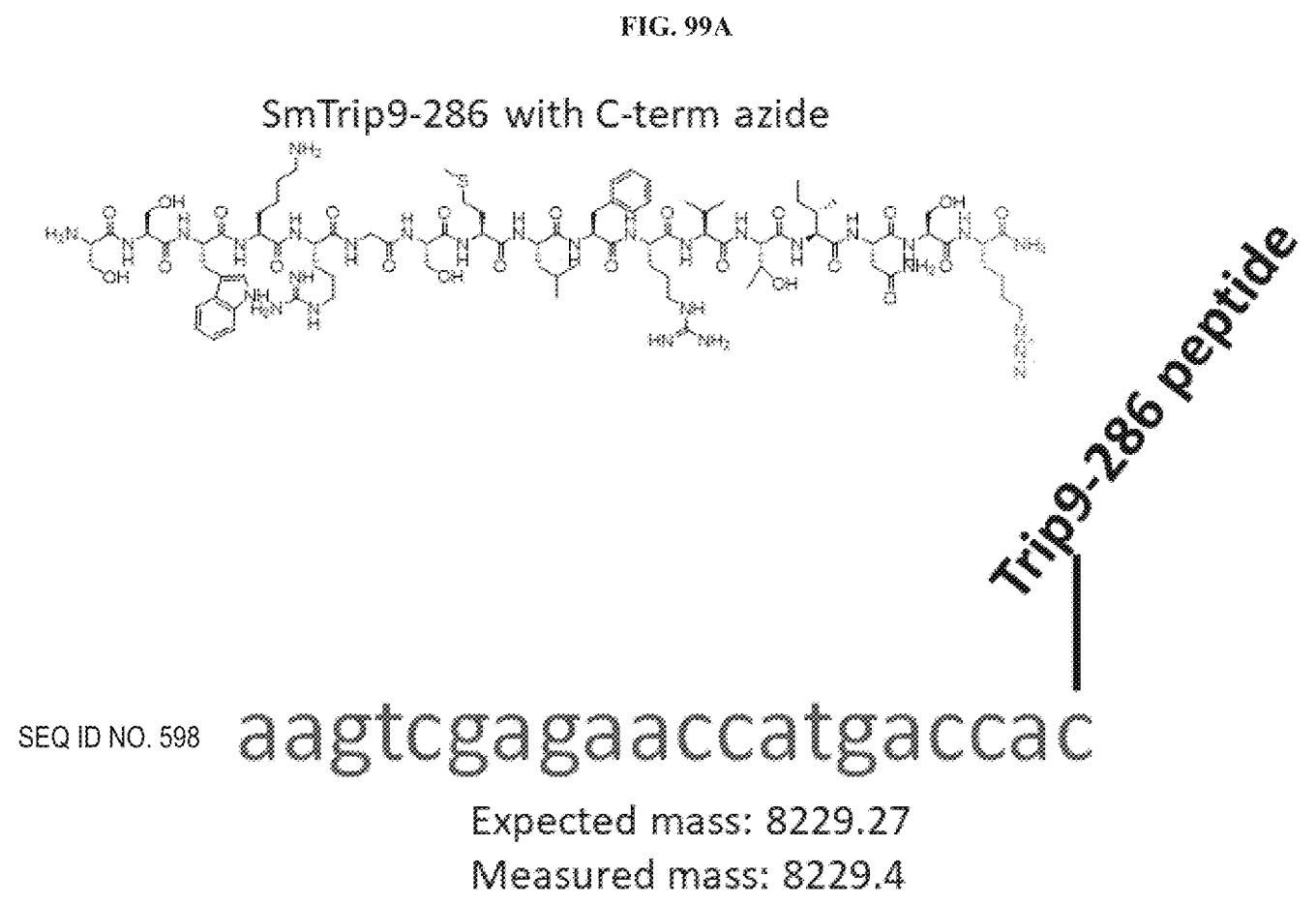

SmTrip9-286 with C-term azide

Trip9-286 peptide

SEQ ID NO. 598 aagtcgagaaccatgaccac

Expected mass: 8229.27

Measured mass: 8229.4

FIG. 99B

SmTrip10 (HiBiT) with N-term azide

HiBiT cgccgcgtccgccgaagttg   SEQ ID NO. 599

Expected mass: 7673
Measured mass: 7673.5

FIG. 113

SmTrip9 on FKBP N-term

| FKBP construct | | | FRB_289 + SmTrip9_FKBP | | | FRB_86 + SmTrip9_FKBP | | |
|---|---|---|---|---|---|---|---|---|
| ATG# | Pep ID | Pep Sequence | SEQ ID NO. | With Rap | No Rap | Response | With Rap | No Rap | Response |
| 2825 | 245 | GSMLFRVTINS | 23 | 0.05 | 0.08 | 0.63 | 0.04 | 0.06 | 0.63 |
| 3637 | 286 | SSWKRGSMLFRVTINS | 37 | 0.27 | 0.17 | 1.53 | 0.17 | 0.21 | 0.82 |
| 3823 | 435 | GSMLFRVTINSWK | 231 | 0.05 | 0.08 | 0.66 | 0.05 | 0.06 | 0.82 |
| 3826 | 434 | GSMLFRVTIWK | 230 | 0.11 | 0.25 | 0.41 | 0.12 | 0.48 | 0.25 |
| 3864 | 492 | GSMLFRVTINKWK | 313 | 0.09 | 0.09 | 1.02 | 0.10 | 0.10 | 0.95 |
| 3865 | 493 | GSMLFRVTIKSWK | 314 | 0.08 | 0.13 | 0.61 | 0.07 | 0.12 | 0.57 |
| 3866 | 521 | GKMLFRVTINSWK | 827 | 1.00 | 1.00 | 1.00 | 1.00 | 1.00 | 1.00 |
| 3867 | 522 | GKMLFRVTIWK | 269 | 1.30 | 4.79 | 0.27 | 1.68 | 10.80 | 0.16 |
| 3868 | 523 | GSMKFRVTINSWK | 265 | 0.04 | 0.05 | 0.65 | 0.01 | 0.04 | 0.26 |
| 3869 | 524 | GSMKFRVTIWK | 271 | 0.32 | 0.18 | 1.80 | 0.29 | 0.25 | 1.17 |
| 3870 | 538 | GSMLFRVTIWKVK | 283 | 0.10 | 0.35 | 0.28 | 0.10 | 0.66 | 0.15 |
| 3871 | 541 | GSMLFRVTIWKWK | 286 | 0.04 | 0.13 | 0.33 | 0.05 | 0.23 | 0.21 |
| 3872 | 542 | GSMLFRVTIWKK | 287 | 0.08 | 0.28 | 0.28 | 0.09 | 0.50 | 0.18 |

FIG. 114

SmTrip9 on FKBP C-term

Data normalized to 521

| FKBP construct | | | | FRB_289 + FKBP_SmTrip9 | | | FRB_86 + FKBP_SmTrip9 | | |
|---|---|---|---|---|---|---|---|---|---|
| ATG# | Pep ID | Pep Sequence | SEQ ID NO. | With Rap | No Rap | Response | With Rap | No Rap | Response |
| 3770 | 245 | GSMLFRVTINS | 23 | 0.38 | 0.48 | 0.81 | 0.40 | 0.53 | 0.75 |
| 3639 | 286 | SSWKRGSMLFRVTINS | 37 | 0.05 | 0.32 | 0.14 | 0.05 | 0.42 | 0.13 |
| 3828 | 434 | GSMLFRVTIWK | 230 | 1.38 | 1.55 | 0.89 | 2.47 | 2.42 | 1.02 |
| 3829 | 435 | GSMLFRVTINSWK | 231 | 0.86 | 0.72 | 1.20 | 0.86 | 0.76 | 1.13 |
| 3936 | 493 | GSMLFRVTIKSWK | 314 | 1.12 | 1.10 | 1.02 | 1.34 | 1.14 | 1.18 |
| 3937 | 521 | GKMLFRVTINSWK | 827 | 1.00 | 1.00 | 1.00 | 1.00 | 1.00 | 1.00 |
| 3938 | 522 | GKMLFRVTIWK | 269 | 1.16 | 2.30 | 0.50 | 2.09 | 3.52 | 0.59 |
| 3939 | 523 | GSMKFRVTINSWK | 265 | 0.02 | 0.33 | 0.06 | 0.01 | 0.42 | 0.03 |
| 3940 | 524 | GSMKFRVTIWK | 271 | 0.33 | 0.57 | 0.57 | 0.38 | 0.73 | 0.52 |
| 3942 | 499 | GSMLFRVTIESWK | 320 | 1.45 | 1.24 | 1.17 | 1.33 | 1.02 | 1.31 |

FIG. 115

| FKBP construct | | | SEQ ID NO. | FRB_289 + SmTrip9_FKBP | | | FRB_86 + SmTrip9_FKBP | | |
|---|---|---|---|---|---|---|---|---|---|
| ATG# | Pep ID | Pep Sequence | | With Rap | No Rap | Response | With Rap | No Rap | Response |
| 3770 | 245 | GSMLFRVTINS | 23 | 0.05 | 0.10 | 0.55 | 0.04 | 0.15 | 0.26 |
| 3639 | 286 | SSWKRGSMLFRVTINS | 37 | 0.15 | 0.16 | 0.94 | 0.10 | 0.19 | 0.51 |
| 3828 | 434 | GSMLFRVTIWK | 230 | 0.12 | 0.35 | 0.35 | 0.16 | 0.64 | 0.26 |
| 3829 | 435 | GSMLFRVTINSWK | 231 | 0.06 | 0.11 | 0.58 | 0.06 | 0.11 | 0.49 |
| 3936 | 493 | GSMLFRVTIKSWK | 314 | 0.06 | 0.13 | 0.44 | 0.06 | 0.15 | 0.36 |
| 3937 | 521 | GKMLFRVTINSWK | 827 | 1.00 | 1.00 | 1.00 | 1.00 | 1.00 | 1.00 |
| 3938 | 522 | GKMLFRVTIWK | 269 | 1.25 | 5.87 | 0.21 | 1.87 | 9.63 | 0.19 |
| 3939 | 523 | GSMKFRVTINSWK | 265 | 0.03 | 0.08 | 0.37 | 0.01 | 0.11 | 0.07 |
| 3940 | 524 | GSMKFRVTIWK | 271 | 0.24 | 0.22 | 1.06 | 0.24 | 0.29 | 0.81 |
| 3942 | 499 | GSMLFRVTIESWK | 320 | 0.14 | 0.18 | 0.76 | 0.11 | 0.16 | 0.70 |

FIG. 116A

| FKBP construct | | | | FRB_289 + FKBP_SmTrip9 | | |
|---|---|---|---|---|---|---|
| ATG# | Pep ID | Pep Sequence | SEQ ID NO. | With Rap | No Rap | Response |
| 3937 | 521 | GKMLFRVTINSWK | 827 | 1.00 | 1.00 | 1.00 |
| 4262 | 671 | GKMLFRVTIQKWK | 391 | 1.53 | 3.60 | 0.43 |
| 4259 | 668 | GKMLFRVTIGKWK | 392 | 1.32 | 2.30 | 0.57 |
| 4260 | 727 | GKMLFRVTIGRWK | 393 | 1.24 | 2.47 | 0.50 |
| 4257 | 669 | GKMLFRVTIGNWK | 394 | 1.02 | 1.35 | 0.75 |
| 4263 | 674 | GKMLFRVTIQNWK | 395 | 0.90 | 1.50 | 0.60 |
| 4339 | 702 | GKMLFRVTIDKWK | 396 | 0.58 | 0.67 | 0.87 |
| 4340 | 703 | GKMLFRVTIEKWK | 397 | 0.78 | 1.65 | 0.47 |
| 4341 | 730 | GKMLFRVTIERWK | 398 | 0.00 | 0.25 | 0.01 |
| 4342 | 731 | GKMLFRVTIDRWK | 399 | 0.67 | 0.73 | 0.92 |
| 4343 | 738 | DKMLFRVTIQKWK | 400 | 0.82 | 0.57 | 1.44 |
| 4344 | 739 | DKMLFRVTIGKWK | 401 | 0.51 | 0.45 | 1.13 |
| 4345 | 848 | DKMLFRVTIGRWK | 402 | 0.63 | 0.47 | 1.33 |
| 4346 | 740 | DKMLFRVTIGNWK | 403 | 0.55 | 0.41 | 1.35 |
| 4347 | 741 | DKMLFRVTIQNWK | 404 | 0.58 | 0.43 | 1.33 |
| 4348 | 732 | DKMLFRVTIDKWK | 405 | 0.23 | 0.33 | 0.70 |
| 4349 | 742 | DKMLFRVTIEKWK | 406 | 0.58 | 0.48 | 1.21 |
| 4350 | 735 | DKMLFRVTIERWK | 407 | 0.29 | 0.37 | 0.79 |
| 4351 | 733 | DKMLFRVTIDRWK | 408 | 0.32 | 0.34 | 0.93 |

| 4352 | 849 | EKMLFRVTIQKWK | 410 | 0.80 | 0.65 | 1.23 |
| 4353 | 708 | EKMLFRVTIGKWK | 411 | 0.78 | 0.59 | 1.33 |
| 4354 | 709 | EKMLFRVTIGRWK | 412 | 0.69 | 0.54 | 1.28 |
| 4355 | 850 | EKMLFRVTIGNWK | 439 | 0.62 | 0.47 | 1.32 |
| 4356 | 851 | EKMLFRVTIQNWK | 440 | 0.60 | 0.51 | 1.17 |
| 4357 | 706 | EKMLFRVTIDKWK | 441 | 0.32 | 0.37 | 0.87 |
| 4358 | 707 | EKMLFRVTIEKWK | 442 | 0.59 | 0.52 | 1.13 |
| 4359 | 737 | EKMLFRVTIERWK | 443 | 0.26 | 0.40 | 0.65 |
| 4360 | 736 | EKMLFRVTIDRWK | 444 | 0.32 | 0.37 | 0.86 |
| 4361 | 760 | KKMLFRVTIQKWK | 445 | 1.35 | 27.31 | 0.05 |
| 4362 | 852 | KKMLFRVTIGKWK | 446 | 1.34 | 16.45 | 0.08 |
| 4363 | 853 | KKMLFRVTIGRWK | 447 | 1.06 | 15.19 | 0.07 |
| 4364 | 854 | KKMLFRVTIGNWK | 448 | 1.48 | 12.45 | 0.12 |
| 4365 | 855 | KKMLFRVTIQNWK | 449 | 1.78 | 18.75 | 0.09 |
| 4366 | 856 | KKMLFRVTIDKWK | 450 | 1.23 | 4.82 | 0.26 |
| 4367 | 857 | KKMLFRVTIEKWK | 451 | 1.24 | 14.92 | 0.08 |
| 4368 | 858 | KKMLFRVTIERWK | 452 | 0.45 | 6.05 | 0.07 |
| 4369 | 859 | KKMLFRVTIDRWK | 453 | 0.98 | 4.05 | 0.24 |
| 4370 | 860 | RKMLFRVTIQKWK | 454 | 1.30 | 27.15 | 0.05 |
| 4371 | 861 | RKMLFRVTIGKWK | 455 | 1.50 | 20.53 | 0.07 |
| 4372 | 862 | RKMLFRVTIGRWK | 456 | 1.20 | 19.17 | 0.06 |
| 4373 | 863 | RKMLFRVTIGNWK | 457 | 1.35 | 13.87 | 0.10 |
| 4374 | 864 | RKMLFRVTIQNWK | 458 | 1.27 | 18.12 | 0.07 |
| 4375 | 865 | RKMLFRVTIDKWK | 459 | 0.85 | 4.61 | 0.18 |
| 4376 | 866 | RKMLFRVTIEKWK | 460 | 0.80 | 14.05 | 0.06 |

FIG. 116B

Figure 116C:
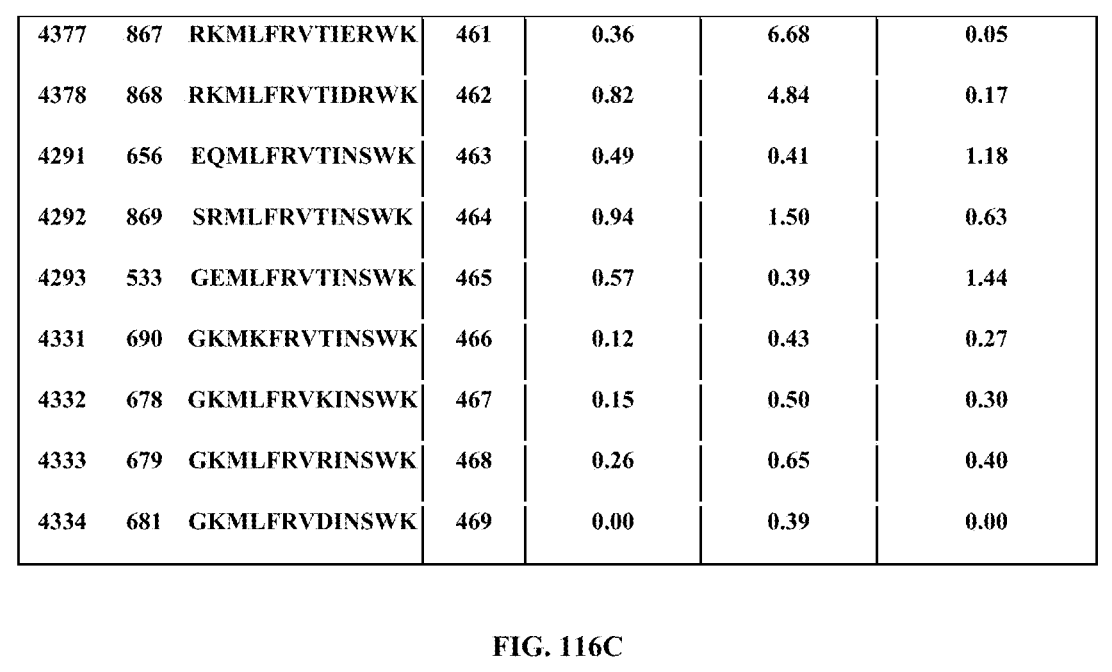

| | | | | | | |
|---|---|---|---|---|---|---|
| 4377 | 867 | RKMLFRVTIERWK | 461 | 0.36 | 6.68 | 0.05 |
| 4378 | 868 | RKMLFRVTIDRWK | 462 | 0.82 | 4.84 | 0.17 |
| 4291 | 656 | EQMLFRVTINSWK | 463 | 0.49 | 0.41 | 1.18 |
| 4292 | 869 | SRMLFRVTINSWK | 464 | 0.94 | 1.50 | 0.63 |
| 4293 | 533 | GEMLFRVTINSWK | 465 | 0.57 | 0.39 | 1.44 |
| 4331 | 690 | GKMKFRVTINSWK | 466 | 0.12 | 0.43 | 0.27 |
| 4332 | 678 | GKMLFRVKINSWK | 467 | 0.15 | 0.50 | 0.30 |
| 4333 | 679 | GKMLFRVRINSWK | 468 | 0.26 | 0.65 | 0.40 |
| 4334 | 681 | GKMLFRVDINSWK | 469 | 0.00 | 0.39 | 0.00 |

| FKBP construct | | | | FRB_289 + FKBP_SmTrip9 | | |
|---|---|---|---|---|---|---|
| ATG# | Pep ID | Pep Sequence | SEQ ID NO. | With Rap | No Rap | Response |
| 3937 | 521 | GKMLFRVTINSWK | 827 | 1.00 | 1.00 | 1.00 |
| 4339 | 702 | GKMLFRVTIDKWK | 396 | 0.90 | 0.85 | 1.05 |
| 4340 | 703 | GKMLFRVTIEKWK | 397 | 0.96 | 1.71 | 0.56 |
| 4341 | 730 | GKMLFRVTIERWK | 398 | 0.00 | 0.32 | 0.01 |
| 4342 | 731 | GKMLFRVTIDRWK | 399 | 0.74 | 0.75 | 0.99 |
| 4343 | 738 | DKMLFRVTIQKWK | 400 | 1.11 | 0.64 | 1.72 |
| 4344 | 739 | DKMLFRVTIGKWK | 401 | 1.02 | 0.54 | 1.89 |
| 4345 | 848 | DKMLFRVTIGRWK | 402 | 1.00 | 0.61 | 1.64 |
| 4346 | 740 | DKMLFRVTIGNWK | 403 | 0.75 | 0.43 | 1.74 |
| 4347 | 741 | DKMLFRVTIQNWK | 404 | 0.74 | 0.50 | 1.48 |
| 4348 | 732 | DKMLFRVTIDKWK | 405 | 0.38 | 0.37 | 1.02 |
| 4349 | 742 | DKMLFRVTIEKWK | 406 | 0.63 | 0.44 | 1.42 |
| 4350 | 735 | DKMLFRVTIERWK | 407 | 0.27 | 0.38 | 0.72 |
| 4351 | 733 | DKMLFRVTIDRWK | 408 | 0.34 | 0.35 | 0.98 |
| 4352 | 849 | EKMLFRVTIQKWK | 410 | 1.11 | 0.73 | 1.51 |
| 4353 | 708 | EKMLFRVTIGKWK | 411 | 1.07 | 0.64 | 1.67 |
| 4354 | 709 | EKMLFRVTIGRWK | 412 | 0.78 | 0.57 | 1.36 |
| 4355 | 850 | EKMLFRVTIGNWK | 439 | 0.76 | 0.47 | 1.62 |
| 4356 | 851 | EKMLFRVTIQNWK | 440 | 0.74 | 0.48 | 1.56 |
| 4357 | 706 | EKMLFRVTIDKWK | 441 | 0.41 | 0.36 | 1.14 |
| 4358 | 707 | EKMLFRVTIEKWK | 442 | 0.59 | 0.47 | 1.25 |
| 4359 | 737 | EKMLFRVTIERWK | 443 | 0.24 | 0.35 | 0.69 |
| 4360 | 736 | EKMLFRVTIDRWK | 444 | 0.41 | 0.41 | 1.02 |
| 4185 | 663 | GKMLFRVTIDSWK | 470 | 0.53 | 0.56 | 0.95 |
| 4196 | 743 | GKMLFRVTINKWK | 471 | 1.15 | 1.24 | 0.92 |

FIG. 118

| FKBP construct | | | | FRB_289 + FKBP_SmTrip9 | | |
|---|---|---|---|---|---|---|
| ATG# | Pep ID | Pep Sequence | SEQ ID NO. | With Rap | No Rap | Response |
| 3937 | 521 | GKMLFRVTINSWK | 827 | 1.00 | 1.00 | 1.00 |
| 4339 | 702 | GKMLFRVTIDKWK | 396 | 0.62 | 0.71 | 0.88 |
| 4340 | 703 | GKMLFRVTIEKWK | 397 | 0.96 | 1.47 | 0.65 |
| 4341 | 730 | GKMLFRVTIERWK | 398 | 0.00 | 0.42 | 0.00 |
| 4342 | 731 | GKMLFRVTIDRWK | 399 | 0.62 | 0.74 | 0.83 |
| 4343 | 738 | DKMLFRVTIQKWK | 400 | 0.84 | 0.63 | 1.34 |
| 4344 | 739 | DKMLFRVTIGKWK | 401 | 0.66 | 0.61 | 1.09 |
| 4345 | 848 | DKMLFRVTIGRWK | 402 | 0.71 | 0.65 | 1.09 |
| 4346 | 740 | DKMLFRVTIGNWK | 403 | 0.54 | 0.52 | 1.03 |
| 4347 | 741 | DKMLFRVTIQNWK | 404 | 0.56 | 0.52 | 1.07 |
| 4348 | 732 | DKMLFRVTIDKWK | 405 | 0.27 | 0.45 | 0.61 |
| 4349 | 742 | DKMLFRVTIEKWK | 406 | 0.57 | 0.52 | 1.10 |
| 4350 | 735 | DKMLFRVTIERWK | 407 | 0.25 | 0.45 | 0.56 |
| 4351 | 733 | DKMLFRVTIDRWK | 408 | 0.24 | 0.39 | 0.62 |
| 4352 | 849 | EKMLFRVTIQKWK | 410 | 0.81 | 0.66 | 1.24 |
| 4353 | 708 | EKMLFRVTIGKWK | 411 | 0.70 | 0.62 | 1.13 |
| 4354 | 709 | EKMLFRVTIGRWK | 412 | 0.67 | 0.59 | 1.14 |
| 4355 | 850 | EKMLFRVTIGNWK | 439 | 0.59 | 0.50 | 1.18 |
| 4356 | 851 | EKMLFRVTIQNWK | 440 | 0.62 | 0.57 | 1.08 |
| 4357 | 706 | EKMLFRVTIDKWK | 441 | 0.30 | 0.40 | 0.74 |
| 4358 | 707 | EKMLFRVTIEKWK | 442 | 0.50 | 0.55 | 0.91 |
| 4359 | 737 | EKMLFRVTIERWK | 443 | 0.23 | 0.41 | 0.56 |
| 4360 | 736 | EKMLFRVTIDRWK | 444 | 0.30 | 0.44 | 0.68 |
| 4185 | 663 | GKMLFRVTIDSWK | 470 | 0.46 | 0.58 | 0.79 |
| 4196 | 743 | GKMLFRVTINKWK | 471 | 0.92 | 1.03 | 0.89 |

FIG. 119

| FKBP construct | | | | FRB_289 + FKBP_SmTrip9 | | |
|---|---|---|---|---|---|---|
| ATG# | Pep ID | Pep Sequence | SEQ ID NO. | With Rap | No Rap | Response |
| 3937 | 521 | GKMLFRVTINSWK | 827 | 1.00 | 1.00 | 1.00 |
| 4343 | 738 | DKMLFRVTIQKWK | 400 | 0.98 | 0.56 | 1.76 |
| 4349 | 742 | DKMLFRVTIEKWK | 406 | 0.58 | 0.45 | 1.31 |
| 4196 | 743 | GKMLFRVTINKWK | 471 | 1.21 | 1.23 | 0.98 |
| 4344 | 739 | DKMLFRVTIGKWK | 401 | 0.63 | 0.38 | 1.66 |
| 4409 | 714 | EKMLFKVTIQKWK | 472 | 0.68 | 0.35 | 1.93 |
| 4410 | 870 | EKMLFTVTIQKWK | 473 | 0.42 | 0.25 | 1.69 |
| 4411 | 871 | EKMLFKVTIDKWK | 474 | 0.14 | 0.24 | 0.60 |
| 4412 | 872 | EKMLFTVTIDKWK | 475 | 0.11 | 0.20 | 0.55 |
| 4413 | 873 | EKMLFKVTIGRWK | 476 | 0.60 | 0.31 | 1.93 |
| 4415 | 744 | DKMLFKVTIQKWK | 477 | 0.57 | 0.28 | 2.03 |
| 4416 | 745 | DKMLFTVTIQKWK | 478 | 0.46 | 0.25 | 1.82 |
| 4417 | 874 | DKMLFKVTIDKWK | 479 | 0.16 | 0.17 | 0.96 |
| 4418 | 875 | DKMLFTVTIDKWK | 480 | 0.12 | 0.16 | 0.76 |
| 4419 | 876 | GKMLFKVTIEKWK | 481 | 0.72 | 0.67 | 1.07 |
| 4420 | 877 | GKMLFTVTIEKWK | 482 | 0.48 | 0.35 | 1.38 |
| 4421 | 748 | DKMLFKVTIGKWK | 483 | 0.57 | 0.26 | 2.17 |
| 4422 | 749 | DKMLFTVTIGKWK | 484 | 0.33 | 0.20 | 1.69 |
| 4423 | 878 | DKMLFKVTIGNWK | 485 | 0.39 | 0.23 | 1.70 |
| 4424 | 879 | DKMLFKVTIQNWK | 486 | 0.32 | 0.25 | 1.28 |
| 4425 | 781 | GKMLFKVTINKWK | 487 | 0.77 | 0.47 | 1.61 |
| 4426 | 782 | GKMLFTVTINKWK | 476 | 0.59 | 0.23 | 2.52 |

FIG. 120

| FKBP construct | | | | FRB_289 + FKBP_SmTrip9 | | |
|---|---|---|---|---|---|---|
| ATG# | Pep ID | Pep Sequence | SEQ ID NO. | With Rap | No Rap | Response |
| 3937 | 521 | GKMLFRVTINSWK | 827 | 1.00 | 1.00 | 1.00 |
| 3770 | 245 | GSMLFRVTINS | 23 | 0.53 | 0.32 | 1.67 |
| 4343 | 738 | DKMLFRVTIQKWK | 400 | 0.98 | 0.53 | 1.85 |
| 4349 | 742 | DKMLFRVTIEKWK | 406 | 0.77 | 0.37 | 2.08 |
| 4196 | 743 | GKMLFRVTINKWK | 471 | 1.14 | 1.37 | 0.83 |
| 4344 | 739 | DKMLFRVTIGKWK | 401 | 0.85 | 0.37 | 2.33 |
| 4409 | 714 | EKMLFKVTIQKWK | 472 | 0.69 | 0.28 | 2.49 |
| 4410 | 870 | EKMLFTVTIQKWK | 473 | 0.60 | 0.19 | 3.18 |
| 4411 | 871 | EKMLFKVTIDKWK | 474 | 0.19 | 0.13 | 1.46 |
| 4412 | 872 | EKMLFTVTIDKWK | 475 | 0.14 | 0.11 | 1.27 |
| 4413 | 873 | EKMLFKVTIGRWK | 476 | 0.64 | 0.24 | 2.72 |
| 4415 | 744 | DKMLFKVTIQKWK | 477 | 0.67 | 0.21 | 3.20 |
| 4416 | 745 | DKMLFTVTIQKWK | 478 | 0.53 | 0.13 | 4.06 |
| 4417 | 874 | DKMLFKVTIDKWK | 479 | 0.20 | 0.10 | 1.98 |
| 4418 | 875 | DKMLFTVTIDKWK | 480 | 0.14 | 0.09 | 1.53 |
| 4419 | 876 | GKMLFKVTIEKWK | 481 | 0.78 | 0.70 | 1.11 |
| 4420 | 877 | GKMLFTVTIEKWK | 482 | 0.63 | 0.27 | 2.35 |
| 4421 | 748 | DKMLFKVTIGKWK | 483 | 0.59 | 0.19 | 3.02 |
| 4422 | 749 | DKMLFTVTIGKWK | 484 | 0.41 | 0.11 | 3.77 |
| 4423 | 878 | DKMLFKVTIGNWK | 485 | 0.45 | 0.14 | 3.29 |
| 4424 | 879 | DKMLFKVTIQNWK | 486 | 0.42 | 0.17 | 2.52 |
| 4425 | 781 | GKMLFKVTINKWK | 487 | 0.67 | 0.40 | 1.69 |
| 4426 | 782 | GKMLFTVTINKWK | 488 | 0.59 | 0.17 | 3.51 |

FIG. 121

| FKBP construct | | | FRB_289 + FKBP_SmTrip9 | | | FRB_86 + FKBP_SmTrip9 | | |
| ATG# | Pep ID | Pep Sequence | SEQ ID NO. | With Rap | No Rap | Response | With Rap | No Rap | Response |
|---|---|---|---|---|---|---|---|---|---|
| 3937 | 521 | GKMLFRVTINSWK | 827 | 1.00 +/- 0.12 | 1.00 +/- 0.16 | 1.00 +/- 0.10 | 1.09 +/- 0.09 | 0.64 +/- 0.12 | 1.69 +/- 0.07 |
| 3770 | 245 | GSMLFRVTINS | 23 | 0.61 +/- 0.15 | 0.26 +/- 0.10 | 2.45 +/- 0.33 | 0.51 +/- 0.05 | 0.11 +/- 0.03 | 4.53 +/- 0.13 |
| 4416 | 745 | DKMLFTVTIQKWK | 478 | 0.56 +/- 0.10 | 0.06 +/- 0.01 | 8.72 +/- 0.65 | 0.78 +/- 0.11 | 0.08 +/- 0.02 | 9.99 +/- 0.90 |
| 4422 | 749 | DKMLFTVTIGKWK | 484 | 0.40 +/- 0.03 | 0.04 +/- 0.00 | 9.59 +/- 0.39 | 0.63 +/- 0.03 | 0.06 +/- 0.01 | 10.84 +/- 0.54 |
| 4460 | 752 | DKMLFKVTIEKWK | 489 | 0.43 +/- 0.03 | 0.08 +/- 0.01 | 5.52 +/- 0.31 | 0.51 +/- 0.01 | 0.08 +/- 0.01 | 6.72 +/- 0.37 |
| 4461 | 753 | DKMLFTVTIEKWK | 490 | 0.49 +/- 0.06 | 0.06 +/- 0.01 | 8.80 +/- 1.20 | 0.66 +/- 0.08 | 0.05 +/- 0.01 | 12.05 +/- 0.44 |
| 4466 | 750 | DKLLFKVTIGKWK | 491 | 0.47 +/- 0.01 | 0.08 +/- 0.01 | 5.71 +/- 0.54 | 0.71 +/- 0.02 | 0.09 +/- 0.01 | 7.42 +/- 0.21 |
| 4467 | 786 | DKMLFTVTINKWK | 492 | 0.26 +/- 0.02 | 0.03 +/- 0.00 | 8.97 +/- 1.17 | 0.35 +/- 0.01 | 0.03 +/- 0.00 | 10.54 +/- 0.38 |
| 4468 | 756 | DKLLFTVTIQKWK | 493 | 0.50 +/- 0.10 | 0.07 +/- 0.01 | 7.23 +/- 0.70 | 0.71 +/- 0.10 | 0.07 +/- 0.01 | 10.71 +/- 0.36 |
| 4472 | 757 | DKLLFTVTIQKYK | 494 | 0.43 +/- 0.04 | 0.05 +/- 0.01 | 8.28 +/- 0.66 | 0.60 +/- 0.06 | 0.05 +/- 0.01 | 11.68 +/- 0.77 |
| 4542 | 758 | DKLLFTVTIEKWK | 495 | 0.37 +/- 0.03 | 0.05 +/- 0.01 | 6.99 +/- 1.24 | 0.50 +/- 0.02 | 0.05 +/- 0.01 | 10.21 +/- 0.56 |
| 4543 | 759 | DKLLFTVTIEKYK | 496 | 0.38 +/- 0.04 | 0.04 +/- 0.00 | 9.36 +/- 0.47 | 0.48 +/- 0.04 | 0.05 +/- 0.00 | 9.63 +/- 0.24 |
| 4544 | 793 | DKLLFTVTIGKWK | 497 | 0.50 +/- 0.09 | 0.05 +/- 0.01 | 9.63 +/- 0.94 | 0.78 +/- 0.10 | 0.06 +/- 0.01 | 12.93 +/- 0.53 |
| 4545 | 794 | DKLLFTVTIGKYK | 498 | 0.26 +/- 0.03 | 0.02 +/- 0.00 | 11.19 +/- 1.09 | 0.38 +/- 0.04 | 0.03 +/- 0.01 | 12.97 +/- 0.40 |
| 4546 | 799 | DKLLFTVTINKWK | 499 | 0.28 +/- 0.05 | 0.03 +/- 0.00 | 9.95 +/- 2.42 | 0.36 +/- 0.04 | 0.03 +/- 0.00 | 11.60 +/- 1.03 |
| 4547 | 800 | DKLLFTVTINKYK | 500 | 0.17 +/- 0.01 | 0.02 +/- 0.01 | 7.95 +/- 2.83 | 0.23 +/- 0.01 | 0.02 +/- 0.00 | 10.95 +/- 0.86 |

FIG. 122A

| FKBP construct | | | FRB_289 + FKBP_SmTrip9 | | | |
|---|---|---|---|---|---|---|
| ATG# | Pep ID | Pep Sequence | SEQ ID NO. | With Rap | No Rap | Response |
| 3770 | 245 | GSMLFRVTINS | 23 | 0.52 +/- 0.06 | 0.23 +/- 0.07 | 2.30 +/- 0.47 |
| 3937 | 521 | GKMLFRVTINSWK | 827 | 1.00 +/- 0.00 | 1.00 +/- 0.00 | 1.00 +/- 0.00 |
| 4455 | 780 | GKMLFRVTINS | 501 | 0.58 +/- 0.04 | 0.37 +/- 0.10 | 1.65 +/- 0.52 |
| 4416 | 745 | DKMLFFTVTIQKWK | 478 | 0.63 +/- 0.19 | 0.28 +/- 0.32 | 6.34 +/- 6.31 |
| 4456 | 765 | DKMLFTVTIQK | 502 | 0.30 +/- 0.06 | 0.04 +/- 0.00 | 7.33 +/- 1.56 |
| 4415 | 744 | DKMLFKVTIQKWK | 477 | 0.60 +/- 0.05 | 0.16 +/- 0.03 | 3.93 +/- 1.03 |
| 4436 | 779 | DKMLFKVTIQK | 503 | 0.40 +/- 0.06 | 0.11 +/- 0.07 | 5.19 +/- 3.57 |
| 4544 | 793 | DKLLFTVTIGKWK | 497 | 0.42 +/- 0.00 | 0.18 +/- 0.20 | 6.36 +/- 6.96 |
| 4618 | 820 | DKLLFTVTIGK | 504 | 0.19 +/- 0.03 | 0.03 +/- 0.00 | 7.44 +/- 0.03 |
| 4422 | 749 | DKMLFTVTIGKWK | 484 | 0.49 +/- 0.04 | 0.07 +/- 0.01 | 7.21 +/- 1.89 |
| 4619 | 819 | DKMLFTVTIGK | 505 | 0.22 +/- 0.02 | 0.05 +/- 0.04 | 7.15 +/- 4.92 |
| 4461 | 753 | DKMLFTVTIEKWK | 490 | 0.52 +/- 0.02 | 0.20 +/- 0.22 | 7.29 +/- 7.94 |
| 4620 | 822 | DKMLFTVTIEK | 506 | 0.21 +/- 0.03 | 0.03 +/- 0.00 | 7.54 +/- 0.96 |
| 4542 | 758 | DKLLFTVTIEKWK | 495 | 0.39 +/- 0.03 | 0.07 +/- 0.00 | 5.34 +/- 0.80 |
| 4543 | 759 | DKLLFTVTIEKYK | 496 | 0.45 +/- 0.04 | 0.09 +/- 0.06 | 7.01 +/- 4.69 |
| 4621 | 821 | DKLLFTVTIEK | 507 | 0.21 +/- 0.00 | 0.10 +/- 0.11 | 5.94 +/- 6.30 |

FIG. 122B

| FKBP construct | | | | FRB_86 + FKBP_SmTrip9 | | | FRB_229 + FKBP_SmTrip9 | | |
| --- | --- | --- | --- | --- | --- | --- | --- | --- | --- |
| ATG# | Pep ID | Pep Sequence | SEQ ID NO. | With Rap | No Rap | Response | With Rap | No Rap | Response |
| 3770 | 245 | GSMLFRVTINS | 23 | 0.37 +/- 0.01 | 0.09 +/- 0.01 | 3.90 +/- 0.45 | 0.22 +/- 0.01 | 0.04 +/- 0.01 | 5.39 +/- 0.64 |
| 3937 | 521 | GKMLFRVTINSWK | 827 | 0.77 +/- 0.02 | 0.52 +/- 0.08 | 1.49 +/- 0.19 | 0.64 +/- 0.06 | 0.29 +/- 0.02 | 2.22 +/- 0.08 |
| 4455 | 780 | GKMLFRVTINS | 501 | 0.45 +/- 0.02 | 0.20 +/- 0.02 | 2.27 +/- 0.16 | 0.31 +/- 0.01 | 0.08 +/- 0.00 | 3.75 +/- 0.02 |
| 4416 | 745 | DKMLFTVTIQKWK | 478 | 0.56 +/- 0.01 | 0.09 +/- 0.04 | 6.94 +/- 3.13 | 0.53 +/- 0.11 | 0.06 +/- 0.04 | 10.92 +/- 4.89 |
| 4456 | 765 | DKMLFTVTIQK | 502 | 0.36 +/- 0.06 | 0.03 +/- 0.00 | 12.46 +/- 3.06 | 0.25 +/- 0.05 | 0.02 +/- 0.00 | 15.12 +/- 0.57 |
| 4415 | 744 | DKMLFKVTIQKWK | 477 | 0.56 +/- 0.03 | 0.12 +/- 0.05 | 5.19 +/- 2.29 | 0.41 +/- 0.02 | 0.06 +/- 0.01 | 6.88 +/- 0.65 |
| 4436 | 779 | DKMLFKVTIQK | 503 | 0.43 +/- 0.01 | 0.06 +/- 0.01 | 6.95 +/- 0.73 | 0.24 +/- 0.00 | 0.03 +/- 0.00 | 7.49 +/- 0.81 |
| 4544 | 793 | DKLLFTVTIGKWK | 497 | 0.48 +/- 0.01 | 0.07 +/- 0.03 | 7.10 +/- 3.14 | 0.42 +/- 0.03 | 0.04 +/- 0.02 | 12.75 +/- 6.40 |
| 4618 | 820 | DKLLFTVTIGK | 504 | 0.22 +/- 0.01 | 0.02 +/- 0.00 | 11.31 +/- 1.60 | 0.17 +/- 0.04 | 0.01 +/- 0.00 | 14.91 +/- 1.83 |
| 4422 | 749 | DKMLFTVTIGKWK | 484 | 0.58 +/- 0.01 | 0.07 +/- 0.04 | 9.94 +/- 4.88 | 0.47 +/- 0.01 | 0.03 +/- 0.00 | 16.98 +/- 0.78 |
| 4619 | 819 | DKMLFTVTIGK | 505 | 0.27 +/- 0.03 | 0.03 +/- 0.00 | 8.91 +/- 0.28 | 0.18 +/- 0.01 | 0.02 +/- 0.00 | 12.57 +/- 2.66 |
| 4461 | 753 | DKMLFTVTIEKWK | 490 | 0.43 +/- 0.03 | 0.07 +/- 0.03 | 6.47 +/- 1.99 | 0.43 +/- 0.01 | 0.05 +/- 0.03 | 11.88 +/- 6.85 |
| 4620 | 822 | DKMLFTVTIEK | 506 | 0.18 +/- 0.02 | 0.02 +/- 0.01 | 10.41 +/- 1.84 | 0.14 +/- 0.01 | 0.01 +/- 0.00 | 14.54 +/- 0.17 |
| 4542 | 758 | DKLLFTVTIEKWK | 495 | 0.39 +/- 0.09 | 0.06 +/- 0.02 | 7.91 +/- 4.43 | 0.36 +/- 0.03 | 0.03 +/- 0.00 | 13.82 +/- 0.02 |
| 4543 | 759 | DKLLFTVTIEKYK | 496 | 0.44 +/- 0.00 | 0.06 +/- 0.02 | 7.60 +/- 2.22 | 0.35 +/- 0.03 | 0.03 +/- 0.00 | 13.69 +/- 0.63 |
| 4621 | 821 | DKLLFTVTIEK | 507 | 0.19 +/- 0.00 | 0.03 +/- 0.01 | 7.30 +/- 2.11 | 0.17 +/- 0.01 | 0.02 +/- 0.01 | 11.52 +/- 5.27 |

FIG. 123

| Biochemical analysis of synthetic SmTrip9 variants | | | | | |
|---|---|---|---|---|---|
| Pep ID | Sequence | SEQ ID NO. | SmTrip9 Kd (uM) | VS-HiBiT Kd (uM) | Bmax (RLU) |
| 521 | *GKMLFRVTINSWK | 827 | 0.06 | 1.21 | 3.25E+07 |
| 627 | *DKMLFRVTINSWK | 508 | 0.29 | 11.76 | 1.29E+07 |
| 628 | *EKMLFRVTINSWK | 509 | 0.10 | 0.76 | 2.80E+07 |
| 629 | *RKMLFRVTINSWK | 510 | 0.02 | 1.23 | 2.99E+07 |
| 630 | *KKMLFRVTINSWK | 511 | 0.02 | 1.64 | 2.98E+07 |
| 631 | *HKMLFRVTINSWK | 512 | 0.03 | ND | 2.65E+07 |
| 632 | *GLMLFRVTINSWK | 513 | 0.08 | ND | 1.20E+07 |
| 633 | *GQMLFRVTINSWK | 514 | 0.09 | ND | 1.88E+07 |
| 634 | *GTMLFRVTINSWK | 515 | 0.08 | ND | 1.27E+07 |
| 635 | *GKLLFRVTINSWK | 516 | 0.06 | 1.54 | 2.81E+07 |
| 636 | *GKMLFKVTINSWK | 517 | 0.17 | 2.10 | 3.10E+07 |
| 637 | *GKMLFRVTIQSWK | 518 | 0.02 | 1.78 | 3.13E+07 |
| 638 | *GKMLFRVTIDSWK | 519 | 0.26 | 0.96 | 2.95E+07 |
| 639 | *GKMLFRVTIGSWK | 520 | 0.07 | 1.71 | 2.88E+07 |
| 640 | *GKMLFRVTINTWK | 521 | 0.13 | ND | 2.91E+07 |
| 641 | *GKMLFRVTINNWK | 522 | 0.24 | ND | 2.87E+07 |
| 642 | *GKMLFRVTINQWK | 523 | 0.14 | ND | 2.62E+07 |
| 643 | *GKMLFRVTINPWK | 524 | 0.08 | ND | 3.00E+07 |
| 644 | *GKMLFRVTINKWK | 525 | 0.09 | ND | 3.05E+07 |
| 645 | *GKMLFRVTINSWQ | 526 | 0.26 | ND | 4.96E+06 |
| 646 | *GKMLFRVTINSWN | 527 | 1.46 | ND | 8.61E+06 |
| 647 | *GKMLFRVTINSWT | 528 | 0.18 | ND | 2.47E+07 |
| 648 | *GKMLFRVTINSWH | 529 | 0.19 | ND | 2.64E+07 |
| 649 | *GKMLFRVTINSWP | 530 | 0.08 | ND | 2.97E+07 |
| 650 | *GKMLFRVTINSWR | 531 | 0.09 | ND | 2.53E+07 |
| *Terminus unblocked ND = Not Determined | | | | | |

FIG. 124

Biochemical analysis of synthetic SmTrip9 variants

| Pep ID | Sequence | SEQ ID NO. | SmTrip9 Kd (uM) | VS-HiBiT Kd (uM) | Bmax (RLU) |
|---|---|---|---|---|---|
| 521 | GKMLFRVTINSWK | 827 | 0.18 | 2.11 | 2.25E+07 |
| 677 | GKMKFRVTIDSWK | 532 | 1.47 | 1.41 | 3.16E+07 |
| 678 | GKMLFRVKINSWK | 467 | 0.74 | 1.14 | 3.01E+07 |
| 679 | GKMLFRVRINSWK | 468 | 0.36 | 1.13 | 2.86E+07 |
| 680 | GKMLFRVEINSWK | 533 | 30.23 | ND | 3.72E+07 |
| 681 | GKMLFRVDINSWK | 469 | 3.21 | ND | 4.74E+06 |
| 682 | GKMLFRVQINSWK | 534 | 0.64 | ND | 1.91E+07 |
| 683 | GKMKFRVKINSWK | 535 | 6.72 | ND | 2.38E+07 |
| 684 | GKMKFRVRINSWK | 536 | 2.23 | ND | 2.09E+07 |
| 685 | GKMKFRVEINSWK | 537 | 8.63 | ND | 3.62E+07 |
| 686 | GKMKFRVDINSWK | 541 | 26.76 | ND | 2.62E+07 |
| 687 | GKMKFRVQINSWK | 539 | 2.52 | ND | 2.81E+07 |
| 688 | GKMKFRVNINSWK | 540 | 9.04 | ND | 2.65E+07 |
| 689 | GKMKFRVSINSWK | 541 | 2.97 | ND | 3.11E+07 |
| 690 | GKMKFRVTINSWK | 466 | 0.68 | 1.59 | 3.21E+07 |

ND = Not Determined

FIG. 125

Biochemical analysis of synthetic SmTrip9 variants

| Pep ID | Sequence | SEQ ID NO. | SmTrip9 Kd (uM) | VS-HiBiT Kd (uM) | Bmax (RLU) |
|--------|----------|-----------|-----------------|------------------|------------|
| 521 | GKMLFRVTINSWK | 827 | 0.51 | ND | 2.58E+07 |
| 613 | GKMLFRVNINSWK | 535 | 5.25 | ND | 3.23E+07 |
| 614 | GKMLFRVSINSWK | 543 | 2.58 | ND | 3.66E+07 |
| 615 | GKMLFRVWINSWK | 544 | 0.35 | ND | 1.75E+07 |
| 616 | GKMSFRVTINSWK | 545 | 1.23 | ND | 2.31E+07 |
| 617 | GKMWFRVTINSWK | 546 | 0.32 | ND | 1.20E+07 |
| 618 | GKMNFRVTINSWK | 547 | 2.69 | ND | 1.10E+07 |
| 619 | GSMLFRVTINSYK | 548 | 1.51 | ND | 2.57E+07 |
| 620 | GKMLFRVTINSYK | 549 | 0.19 | ND | 2.66E+07 |
| 621 | GKMLFRVTIKSWK | 550 | 0.04 | 1.12 | 3.11E+07 |
| 622 | GKMLFRVTIESWK | 551 | 7.24 | 33.48 | 3.41E+07 |
| 716 | GKMKFRVTIQSWK | 552 | 0.29 | ND | 3.36E+07 |
| 717 | GKMKFRVTIESWK | 553 | 1.14 | ND | 3.26E+07 |
| 718 | GKMKFRVTIKSWK | 554 | 0.38 | ND | 3.36E+07 |
| 719 | GKMKFRVTIRSWK | 555 | 0.37 | ND | 3.27E+07 |

ND = Not Determined

FIG. 126

| Biochemical analysis of synthetic SmTrip9 variants | | | | | |
|---|---|---|---|---|---|
| Pep ID | Sequence | SEQ ID NO. | SmTrip9 Kd (uM) | VS-HiBiT Kd (uM) | Bmax (RLU) |
| 521 | GKMLFRVTINSWK | 827 | 0.17 | 4.20 | 2.51E+07 |
| 651 | RLMLFRVTINSWK | 556 | 0.04 | ND | 2.27E+07 |
| 652 | RQMLFRVTINSWK | 557 | 0.03 | ND | 2.86E+07 |
| 653 | KLMLFRVTINSWK | 558 | 0.16 | ND | 2.78E+07 |
| 654 | KQMLFRVTINSWK | 559 | 0.06 | ND | 2.86E+07 |
| 655 | ELMLFRVTINSWK | 560 | 15.86 | ND | 7.15E+06 |
| 656 | EQMLFRVTINSWK | 463 | 6.26 | ND | 1.52E+07 |
| 657 | DLMLFRVTINSWK | 561 | 0.07 | ND | 6.26E+05 |
| 658 | DQMLFRVTINSWK | 562 | 4.38 | ND | 2.38E+06 |
| 659 | DKMLFRVTINSWK | 563 | 0.58 | 31.91 | 3.65E+06 |
| 660 | EKMLFRVTINSWK | 564 | 0.19 | 9.75 | 1.83E+07 |
| 661 | RKMLFRVTINSWK | 565 | 0.01 | 4.34 | 3.19E+07 |
| 662 | KKMLFRVTINSWK | 566 | 0.02 | 2.72 | 3.09E+07 |
| 663 | GKMLFRVTIDSWK | 470 | 0.25 | 2.40 | 3.21E+07 |
| 665 | GKMLFRVTIGSWK | 567 | 0.14 | 6.16 | 2.81E+07 |
| 667 | GKMLFRVTINKWK | 471 | 0.07 | 2.98 | 3.63E+07 |
| 668 | GKMLFRVTIGKWK | 392 | 0.06 | 2.78 | 3.06E+07 |
| 669 | GKMLFRVTIGNWK | 394 | 0.38 | 3.06 | 2.82E+07 |
| 670 | GKMLFRVTISKWK | 569 | 0.03 | 3.96 | 3.11E+07 |
| 671 | GKMLFRVTIQKWK | 570 | 0.02 | 3.15 | 3.67E+07 |
| 672 | GKMLFRVTITKWK | 571 | 0.01 | 3.19 | 3.18E+07 |
| 673 | GKMLFRVTIKKWK | 572 | 0.04 | 2.85 | 3.53E+07 |
| 675 | GKMLFKVTINSWK | 573 | 0.17 | 8.06 | 2.61E+07 |
| 676 | RLMLFRVTIGKWK | 574 | 0.02 | 4.09 | 2.92E+07 |
| ND = Not Determined | | | | | |

FIG. 127

| Pep ID | Sequence | SEQ ID NO. | SmTrip9 Kd (uM) | VS-HiBiT Kd (uM) | Bmax (RLU) |
|---|---|---|---|---|---|
| \multicolumn{6}{c}{Biochemical analysis of synthetic SmTrip9 variants} | | | | | |
| 521 | GKMLFRVTINSWK | 827 | 0.21 | 2.18 | 2.82E+07 |
| 659 | DKMLFRVTINSWK | 563 | 0.76 | 24.39 | 5.24E+06 |
| 660 | EKMLFRVTINSWK | 564 | 0.30 | 4.38 | 2.35E+07 |
| 667 | GKMLFRVTINKWK | 471 | 0.16 | 0.79 | 4.07E+07 |
| 668 | GKMLFRVTIGKWK | 392 | 0.13 | 0.75 | 3.55E+07 |
| 671 | GKMLFRVTIQKWK | 570 | 0.06 | 0.65 | 4.21E+07 |
| 675 | GKMLFKVTINSWK | 573 | 0.47 | 9.71 | 1.65E+07 |
| 620 | GKMLFRVTINSYK | 549 | 0.12 | 2.27 | 2.82E+07 |
| 622 | GKMLFRVTIESWK | 551 | 2.88 | 1.73 | 3.16E+07 |
| 701 | GKMLFRVTINRWK | 575 | 0.12 | 1.01 | 3.69E+07 |
| 703 | GKMLFRVTIEKWK | 397 | 0.11 | 1.18 | 3.61E+07 |
| 707 | EKMLFRVTIEKWK | 442 | 1.12 | 0.90 | 3.23E+07 |
| 708 | EKMLFRVTIGKWK | 411 | 0.28 | 1.18 | 3.27E+07 |
| 709 | EKMLFRVTIGRWK | 412 | 0.18 | 1.61 | 2.99E+07 |
| 710 | EKMLFTVTIGKWK | 576 | 1.29 | 5.24 | 1.94E+07 |
| 711 | EKLLFTVTIGKWK | 577 | 0.50 | 5.52 | 1.40E+07 |
| 712 | EKMLFTVTIGRWK | 578 | 0.37 | 6.09 | 1.66E+07 |
| 714 | EKMLFKVTIQKWK | 472 | 0.22 | 1.18 | 3.34E+07 |
| 720 | EKMLFTVTIEKWK | 579 | 0.36 | 4.29 | 2.19E+07 |
| 722 | DKMLFRVTIESWK | 580 | 17.79 | 10.61 | 2.23E+07 |
| 726 | EKLLFRVTIGKYK | 581 | 0.64 | 1.49 | 2.63E+07 |
| \multicolumn{6}{c}{ND = Not Determined} | | | | | |

FIG. 128

| Biochemical analysis of synthetic SmTrip9 variants | | | | | |
|---|---|---|---|---|---|
| Pep ID | Sequence | SEQ ID NO. | SmTrip9 Kd (uM) | VS-HiBiT Kd (uM) | Bmax (RLU) |
| 521 | GKMLFRVTINSWK | 827 | 0.20 | 3.56 | 3.03E+07 |
| 738 | DKMLFRVTIQKWK | 400 | 0.23 | 3.06 | 3.64E+07 |
| 739 | DKMLFRVTIGKWK | 401 | 0.20 | 2.28 | 3.41E+07 |
| 740 | DKMLFRVTIGNWK | 403 | 3.65 | 59.23 | 1.93E+07 |
| 741 | DKMLFRVTIQNWK | 404 | 12.58 | 33.67 | 1.01E+07 |
| 742 | DKMLFRVTIEKWK | 406 | 0.75 | 1.44 | 3.55E+07 |
| 743 | GKMLFRVTINKWK | 471 | 0.10 | 1.33 | 3.98E+07 |
| 744 | DKMLFKVTIQKWK | 477 | 1.13 | 4.65 | 2.74E+07 |
| 745 | DKMLFTVTIQKWK | 478 | 0.16 | 7.52 | 2.30E+07 |
| 746 | DKLLFKVTIQKWK | 582 | 1.10 | 6.23 | 1.53E+07 |
| 747 | DKLLFKVTIQKYK | 583 | 0.10 | 4.25 | 2.76E+07 |
| 748 | DKMLFKVTIGKWK | 483 | 0.44 | 2.24 | 3.43E+07 |
| 749 | DKMLFTVTIGKWK | 484 | 1.70 | 8.26 | 1.92E+07 |
| 750 | DKLLFKVTIGKWK | 491 | 0.35 | 3.34 | 2.32E+07 |
| 751 | DKLLFKVTIGKYK | 584 | 0.61 | 3.28 | 2.55E+07 |
| 752 | DKMLFKVTIEKWK | 489 | 0.32 | 1.58 | 3.26E+07 |
| 753 | DKMLFTVTIEKWK | 490 | 0.12 | 7.59 | 2.01E+07 |
| 754 | DKLLFKVTIEKWK | 585 | 0.75 | 1.52 | 2.35E+07 |
| 755 | DKLLFKVTIEKYK | 586 | 1.45 | 1.20 | 2.70E+07 |
| ND = Not Determined | | | | | |

FIG. 129

| Biochemical analysis of synthetic SmTrip9 variants | | | | | |
|---|---|---|---|---|---|
| Pep ID | Sequence | SEQ ID NO. | SmTrip9 Kd (uM) | VS-HiBiT Kd (uM) | Bmax (RLU) |
| 521 | GKMLFRVTINSWK | 827 | 0.32 | 2.34 | 2.74E+07 |
| 756 | DKLLFTVTIQKWK | 493 | 0.48 | 4.26 | 1.73E+07 |
| 757 | DKLLFTVTIQKYK | 494 | 0.36 | 3.67 | 1.91E+07 |
| 758 | DKLLFTVTIEKWK | 495 | 0.19 | 6.34 | 1.84E+07 |
| 759 | DKLLFTVTIEKYK | 496 | 0.33 | 4.93 | 2.25E+07 |
| 760 | KKMLFRVTIQKWK | 445 | 0.00 | 1.61 | 4.48E+07 |
| 761 | KKLLFRVTIQKWK | 587 | 0.02 | 1.49 | 4.00E+07 |
| 762 | DRMLFRVTIQRWR | 588 | 0.12 | 2.83 | 3.45E+07 |
| 766 | ERMLFRVTIGRWR | 589 | 0.07 | 6.49 | 2.86E+07 |
| 768 | GRMLFRVTINRWR | 590 | 0.10 | 1.96 | 3.97E+07 |
| 770 | DRMLFRVTIERWR | 591 | 0.35 | 3.74 | 2.53E+07 |
| 738 | DKMLFRVTIQKWK | 400 | 0.11 | 2.37 | 3.97E+07 |
| 742 | DKMLFRVTIEKWK | 406 | 1.00 | 0.68 | 3.89E+07 |
| 743 | GKMLFRVTINKWK | 471 | 0.10 | 1.36 | 4.36E+07 |
| 745 | DKMLFTVTIQKWK | 478 | 0.20 | 5.84 | 2.46E+07 |
| 753 | DKMLFTVTIEKWK | 490 | 0.15 | 4.73 | 2.16E+07 |
| ND = Not Determined | | | | | |

FIG. 130

| Biochemical analysis of synthetic SmTrip9 variants | | | | | |
|---|---|---|---|---|---|
| Pep ID | Sequence | SEQ ID NO. | SmTrip9 Kd (uM) | VS-HiBiT Kd (uM) | Bmax (RLU) |
| 521 | GKMLFRVTINSWK | 827 | 0.48 | 3.95 | 2.43E+07 |
| 756 | DKLLFTVTIQKWK | 493 | 0.95 | 5.52 | 1.43E+07 |
| 757 | DKLLFTVTIQKYK | 494 | 0.19 | 7.02 | 1.87E+07 |
| 758 | DKLLFTVTIEKWK | 495 | 0.52 | 6.82 | 1.45E+07 |
| 759 | DKLLFTVTIEKYK | 496 | 0.56 | 4.94 | 1.87E+07 |
| 760 | KKMLFRVTIQKWK | 445 | 0.02 | 2.45 | 4.25E+07 |
| 781 | GKMLFKVTINKWK | 487 | 0.38 | 1.20 | 4.22E+07 |
| 782 | GKMLFTVTINKWK | 488 | 0.36 | 2.78 | 3.18E+07 |
| 783 | DKMLFKVTIQKYK | 592 | 0.24 | 2.20 | 3.24E+07 |
| 784 | DKMLFRVTINKWK | 593 | 0.41 | 11.60 | 1.67E+07 |
| 785 | DKMLFKVTIEKYK | 594 | 0.38 | 1.28 | 3.64E+07 |
| 786 | DKMLFTVTINKWK | 492 | 0.50 | 35.65 | 2.54E+06 |
| 787 | DKMLFKVTINKWK | 595 | 0.73 | 24.17 | 1.23E+07 |
| 793 | DKLLFTVTIGKWK | 497 | 0.54 | 5.65 | 1.27E+07 |
| 794 | DKLLFTVTIGKYK | 498 | 0.23 | 5.96 | 1.01E+07 |
| 799 | DKLLFTVTINKWK | 499 | 0.21 | 42.69 | 1.51E+06 |
| 800 | DKLLFTVTINKYK | 500 | 9.75 | 88.68 | 6.49E+05 |
| 743 | GKMLFRVTINKWK | 471 | 0.11 | 1.19 | 4.05E+07 |
| 745 | DKMLFTVTIQKWK | 478 | 0.30 | 25.63 | 2.66E+06 |
| 749 | DKMLFTVTIGKWK | 484 | 1.06 | 6.57 | 1.34E+07 |
| ND = Not Determined | | | | | |

FIG. 131A

| Solubility of synthetic SmTrip9 peptides | | | |
|---|---|---|---|
| Pep ID | Sequence | SEQ ID NO. | Solubility# |
| 521 | *GKMLFRVTINSWK | 827 | Y |
| 627 | *DKMLFRVTINSWK | 508 | N |
| 628 | *EKMLFRVTINSWK | 509 | Y |
| 629 | *RKMLFRVTINSWK | 510 | Y |
| 630 | *KKMLFRVTINSWK | 511 | Y |
| 631 | *HKMLFRVTINSWK | 512 | N |
| 632 | *GLMLFRVTINSWK | 513 | N |
| 633 | *GQMLFRVTINSWK | 514 | N |
| 634 | *GTMLFRVTINSWK | 515 | N |
| 635 | *GKLLFRVTINSWK | 516 | Y |
| 636 | *GKMLFKVTINSWK | 517 | Y |
| 637 | *GKMLFRVTIQSWK | 518 | Y |
| 638 | *GKMLFRVTIDSWK | 519 | Y |
| 639 | *GKMLFRVTIGSWK | 520 | Y |
| 640 | *GKMLFRVTINTWK | 521 | Y |
| 641 | *GKMLFRVTINNWK | 522 | Y |
| 642 | *GKMLFRVTINQWK | 523 | Y |
| 643 | *GKMLFRVTINPWK | 524 | Y |
| 644 | *GKMLFRVTINKWK | 525 | Y |
| 645 | *GKMLFRVTINSWQ | 526 | Y |
| 646 | *GKMLFRVTINSWN | 527 | Y |
| 647 | *GKMLFRVTINSWT | 528 | Y |
| 648 | *GKMLFRVTINSWH | 529 | Y |
| 649 | *GKMLFRVTINSWP | 530 | Y |
| 650 | *GKMLFRVTINSWR | 531 | N |
| 677 | GKMKFRVTIDSWK | 532 | Y |
| 678 | GKMLFRVKINSWK | 467 | Y |
| 679 | GKMLFRVRINSWK | 468 | Y |
| 680 | GKMLFRVEINSWK | 533 | Y |
| 681 | GKMLFRVDINSWK | 469 | N |
| 682 | GKMLFRVQINSWK | 534 | Y |
| 683 | GKMKFRVKINSWK | 535 | Y |
| 684 | GKMKFRVRINSWK | 536 | Y |
| 685 | GKMKFRVEINSWK | 537 | Y |
| 686 | GKMKFRVDINSWK | 541 | Y |
| 687 | GKMKFRVQINSWK | 539 | Y |
| 688 | GKMKFRVNINSWK | 540 | Y |
| 689 | GKMKFRVSINSWK | 541 | Y |
| 690 | GKMKFRVTINSWK | 466 | Y |
| #in water at ~1 mM after multiple freeze/thaws | | | |
| *Terminus unblocked | | | |

FIG. 131B

| Solubility of synthetic SmTrip9 peptides | | | |
|---|---|---|---|
| Pep ID | Sequence | SEQ ID NO. | Solubility# |
| 521 | GKMLFRVTINSWK | 827 | Y |
| 613 | GKMLFRVNINSWK | 535 | Y |
| 614 | GKMLFRVSINSWK | 543 | Y |
| 615 | GKMLFRVWINSWK | 544 | Y |
| 616 | GKMSFRVTINSWK | 545 | Y |
| 617 | GKMWFRVTINSWK | 546 | Y |
| 618 | GKMNFRVTINSWK | 547 | Y |
| 619 | GSMLFRVTINSYK | 548 | Y |
| 620 | GKMLFRVTINSYK | 549 | Y |
| 621 | GKMLFRVTIKSWK | 550 | Y |
| 622 | GKMLFRVTIESWK | 551 | Y |
| 716 | GKMKFRVTIQSWK | 552 | Y |
| 717 | GKMKFRVTIESWK | 553 | Y |
| 718 | GKMKFRVTIKSWK | 554 | Y |
| 719 | GKMKFRVTIRSWK | 555 | Y |
| 651 | RLMLFRVTINSWK | 556 | N |
| 652 | RQMLFRVTINSWK | 557 | N |
| 653 | KLMLFRVTINSWK | 558 | N |
| 654 | KQMLFRVTINSWK | 559 | N |
| 655 | ELMLFRVTINSWK | 560 | N |
| 656 | EQMLFRVTINSWK | 463 | N |
| 657 | DLMLFRVTINSWK | 561 | N |
| 658 | DQMLFRVTINSWK | 562 | N |
| 659 | DKMLFRVTINSWK | 563 | N |
| 660 | EKMLFRVTINSWK | 564 | Y |
| 661 | RKMLFRVTINSWK | 565 | Y |
| 662 | KKMLFRVTINSWK | 566 | Y |
| 663 | GKMLFRVTIDSWK | 470 | Y |
| 665 | GKMLFRVTIGSWK | 567 | Y |
| 667 | GKMLFRVTINKWK | 471 | Y |
| 668 | GKMLFRVTIGKWK | 392 | Y |
| 669 | GKMLFRVTIGNWK | 394 | Y |
| 670 | GKMLFRVTISKWK | 569 | Y |
| 671 | GKMLFRVTIQKWK | 391 | Y |
| 672 | GKMLFRVTITKWK | 570 | Y |
| 673 | GKMLFRVTIKKWK | 571 | Y |
| 675 | GKMLFKVTINSWK | 572 | Y |
| 676 | RLMLFRVTIGKWK | 395 | Y |
| 701 | GKMLFRVTINRWK | 575 | Y |
| 703 | GKMLFRVTIEKWK | 397 | Y |
| 707 | EKMLFRVTIEKWK | 442 | Y |
| 708 | EKMLFRVTIGKWK | 411 | Y |
| 709 | EKMLFRVTIGRWK | 412 | Y |
| 710 | EKMLFTVTIGKWK | 576 | Y |
| 711 | EKLLFTVTIGKWK | 577 | Y |
| 712 | EKMLFTVTIGRWK | 578 | Y |
| 714 | EKMLFKVTIQKWK | 472 | Y |
| 720 | EKMLFTVTIEKWK | 579 | Y |
| 722 | DKMLFRVTIESWK | 580 | Y |
| 726 | EKLLFRVTIGKYK | 581 | Y |
| #in water at ~1 mM after multiple freeze/thaws *Terminus unblocked | | | |

FIG. 131C

| | Solubility of synthetic SmTrip9 peptides |
|---|---|---|---|
| Pep ID | Sequence | SEQ ID NO. | Solubility# |
| 521 | GKMLFRVTINSWK | 827 | Y |
| 613 | GKMLFRVNINSWK | 535 | Y |
| 614 | GKMLFRVSINSWK | 543 | Y |
| 615 | GKMLFRVWINSWK | 544 | Y |
| 616 | GKMSFRVTINSWK | 545 | Y |
| 617 | GKMWFRVTINSWK | 546 | Y |
| 618 | GKMNFRVTINSWK | 547 | Y |
| 619 | GSMLFRVTINSYK | 548 | Y |
| 620 | GKMLFRVTINSYK | 549 | Y |
| 621 | GKMLFRVTIKSWK | 550 | Y |
| 622 | GKMLFRVTIESWK | 551 | Y |
| 716 | GKMKFRVTIQSWK | 552 | Y |
| 717 | GKMKFRVTIESWK | 553 | Y |
| 718 | GKMKFRVTIKSWK | 554 | Y |
| 719 | GKMKFRVTIRSWK | 555 | Y |
| 651 | RLMLFRVTINSWK | 556 | N |
| 652 | RQMLFRVTINSWK | 557 | N |
| 653 | KLMLFRVTINSWK | 558 | N |
| 654 | KQMLFRVTINSWK | 559 | N |
| 655 | ELMLFRVTINSWK | 560 | N |
| 656 | EQMLFRVTINSWK | 463 | N |
| 657 | DLMLFRVTINSWK | 561 | N |
| 658 | DQMLFRVTINSWK | 562 | N |
| 659 | DKMLFRVTINSWK | 563 | N |
| 660 | EKMLFRVTINSWK | 564 | Y |
| 661 | RKMLFRVTINSWK | 565 | Y |
| 662 | KKMLFRVTINSWK | 566 | Y |
| 663 | GKMLFRVTIDSWK | 470 | Y |
| 665 | GKMLFRVTIGSWK | 567 | Y |
| 667 | GKMLFRVTINKWK | 471 | Y |
| 668 | GKMLFRVTIGKWK | 392 | Y |
| 669 | GKMLFRVTIGNWK | 394 | Y |
| 670 | GKMLFRVTISKWK | 569 | Y |
| 671 | GKMLFRVTIQKWK | 391 | Y |
| 672 | GKMLFRVTITKWK | 570 | Y |
| 673 | GKMLFRVTIKKWK | 571 | Y |
| 675 | GKMLFKVTINSWK | 572 | Y |
| 676 | RLMLFRVTIGKWK | 395 | Y |
| 701 | GKMLFRVTINRWK | 575 | Y |
| 703 | GKMLFRVTIEKWK | 397 | Y |
| 707 | EKMLFRVTIEKWK | 442 | Y |
| 708 | EKMLFRVTIGKWK | 411 | Y |
| 709 | EKMLFRVTIGRWK | 412 | Y |
| 710 | EKMLFTVTIGKWK | 576 | Y |
| 711 | EKLLFTVTIGKWK | 577 | Y |
| 712 | EKMLFTVTIGRWK | 578 | Y |
| 714 | EKMLFKVTIQKWK | 472 | Y |
| 720 | EKMLFTVTIEKWK | 579 | Y |
| 722 | DKMLFRVTIESWK | 580 | Y |
| 726 | EKLLFRVTIGKYK | 581 | Y |
| | #in water at ~1 mM after multiple freeze/thaws<br>*Terminus unblocked |

FIG. 135

Biochemical peptide co-titration
100 nM LgTrip in PLB + NanoGlo

ATG-3930 (Strand 7,8,9,10 removed)
2nM protein, 10uM peptides

ATG-3931 (Strand 8,9,10 removed)
2nM protein, 10uM peptides

LgTrip (Strand 9+10 removed)
0.2nM protein, 10μM each peptide

Compare activity of various peptide com

FIG. 139B

| peptide ID | Bmax | Kd |
| --- | --- | --- |
| 263 | 1.00 | 1.0 |
| 592 | 1.00 | 10.3 |
| 595 | 0.68 | 4.8 |
| 603 | 0.06 | 2.7 |
| 604 | 0.93 | 0.9 |
| 605 | 0.92 | 1.7 |
| 606 | 0.94 | 4.0 |
| 607 | 1.14 | 1.7 |
| 593 | 0.78 | 8.2 |
| 594 | 0.40 | 9.9 |
| 598 | 1.08 | 15.4 |
| 599 | 0.68 | 10.5 |
| 600 | 0.52 | 7.2 |
| 602 | 0.89 | 8.9 |
| 591 | 0.11 | 3.8 |
| 596 | 0.29 | 55.9 |
| 597 | 0.05 | 7.5 |
| 601 | 0.10 | 4.1 |
| 609 | 0.42 | 371.7 |
| 610 | 0.12 | 46.2 |

| peptide ID | Bmax | Kd |
| --- | --- | --- |
| 263 | 3.01E+07 | 11.59 |
| 592 | 3.00E+07 | 119.1 |
| 595 | 2.06E+07 | 56.02 |
| 603 | 1.76E+06 | 31.17 |
| 604 | 2.78E+07 | 10.05 |
| 605 | 2.76E+07 | 19.61 |
| 606 | 2.83E+07 | 46.39 |
| 607 | 3.42E+07 | 20.18 |
| 593 | 2.34E+07 | 95.48 |
| 594 | 1.19E+07 | 115 |
| 598 | 3.24E+07 | 178.1 |
| 599 | 2.05E+07 | 122.1 |
| 600 | 1.56E+07 | 83.39 |
| 602 | 2.67E+07 | 103.2 |
| 591 | 3.44E+06 | 44.5 |
| 596 | 8.79E+06 | 648.3 |
| 597 | 1.59E+06 | 86.75 |
| 601 | 3.12E+06 | 47.6 |
| 609 | 1.26E+07 | 4308 |
| 610 | 3.60E+06 | 535.8 |

FIG. 139C

Biochemical analysis
synthetic peptides 263
598
596
609

$LOD = mean_{blank} + 2*SD_{blank}$ $LOQ = mean_{blank} + 10*SD_{blank}$ $ULOQ = mean_{[high\ in\ linear\ dynamic\ range]} + 10*SD_{[high\ in\ linear\ dynamic\ range]}$ These RLU values are then interpolated from the dose response curve to obtain concentration values

FIG. 144
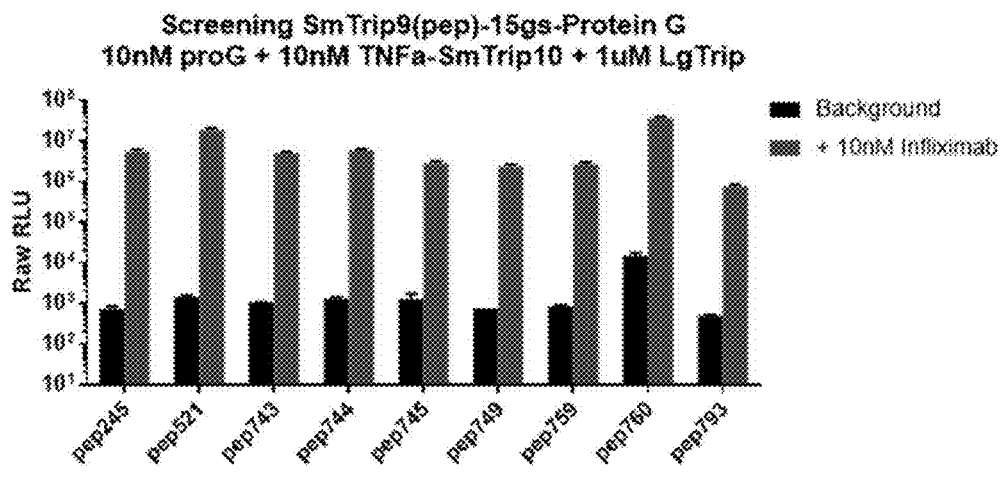
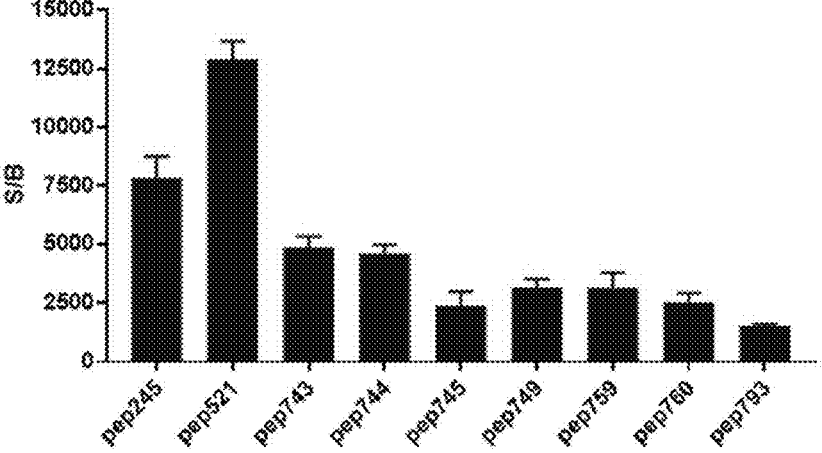

FIG. 146

FIG. 148
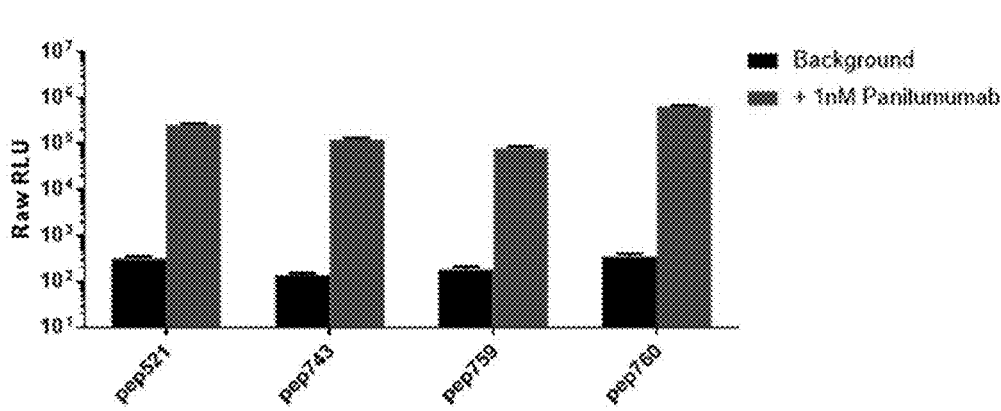
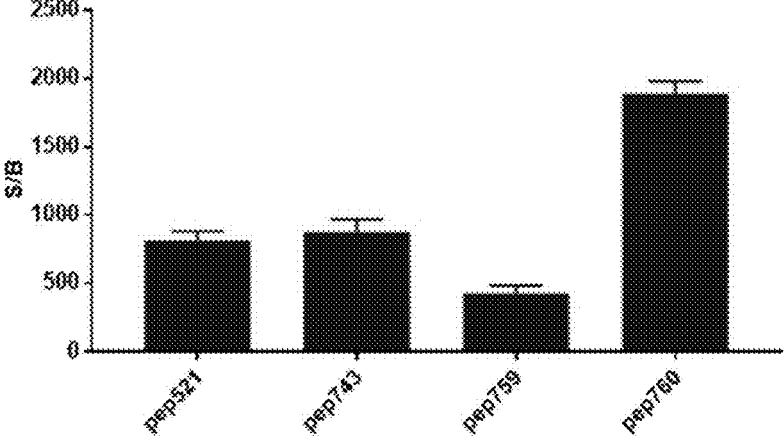

FIG. 149
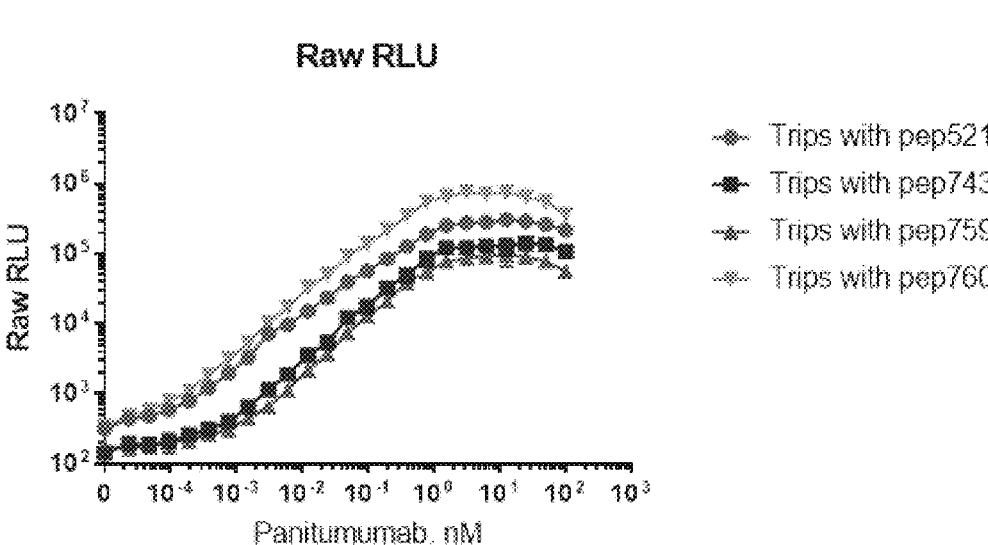
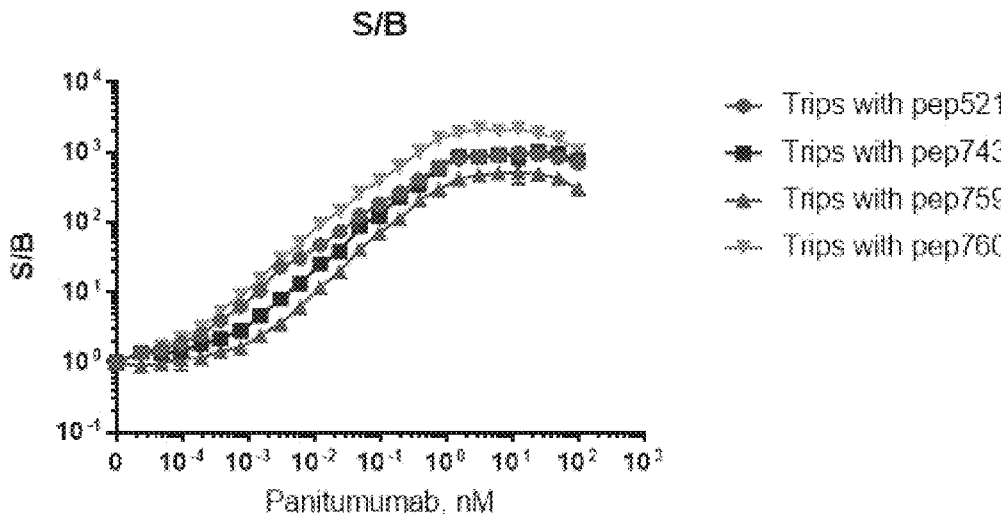

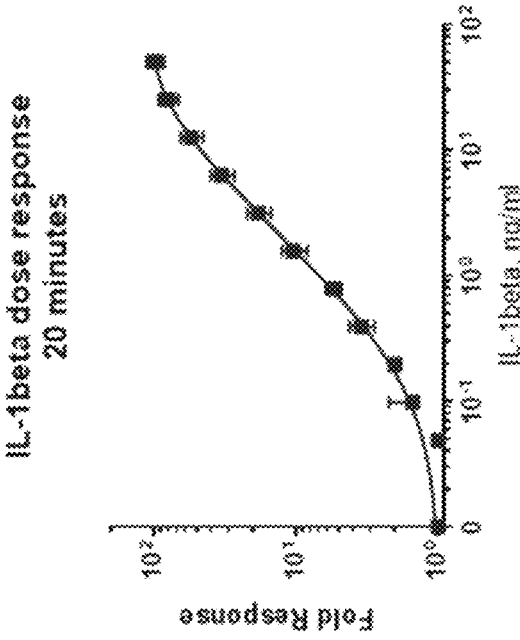
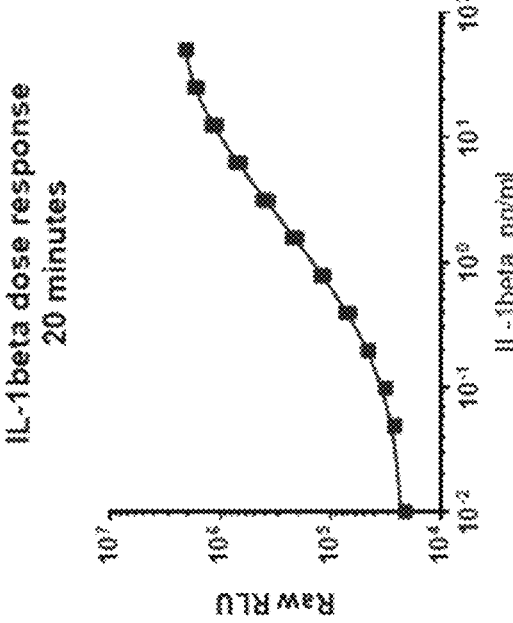
FIG. 150

FIG. 157B

| Clone | Mutations | Kd (normalized) | Bmax (normalized) |
|---|---|---|---|
| LgBiT | | 1 | 1 |
| ATG-2724 | I44M | 3 | 0.57 |
| ATG-3901 | I44M+E11K | 16 | 0.53 |
| ATG-3945 | I44M+E11K+G134D+N135V | 44 | 0.23 |
| ATG-3984 | I44M+E11K+G134D+N135V+L150S | 1958 | 0.12 |
| ATG-4147 | I44M+E11K+L150S | 613 | 0.26 |
| ATG-4166 | I44M+E11K+N135V+L150S | 1296 | 0.12 |

FIG. 158

Calculated Kd and Vmax of LgBiT mutants

|  | LgBiT | G134E | N135V | I44M |
|---|---|---|---|---|
| Bmax | 1.0 | 0.3 | 0.5 | 0.2 |
| Kd | 1.0 | 2.9 | 1.4 | 12.6 |

LgBiT
G134E——ATG-2757
N135V——ATG-2760
I44M——ATG-3882

MULTIPARTITE LUCIFERASE

CROSS REFERENCE TO RELATED APPLICATIONS

The present invention claims the priority benefit of U.S. Provisional Patent Application No. 62/684,014, filed Jun. 12, 2018, which is incorporated by reference in its entirety.

SEQUENCE LISTING

The text of the computer readable sequence listing filed herewith, titled "35432-202_SEQUENCE_LISTING_ST25", created Apr. 21, 2020, having a file size of 38,200 bytes, is hereby incorporated by reference in its entirety.

FIELD

Provided herein are compositions and methods for the assembly of a tripartite or multipartite bioluminescent complex. In particular, a bioluminescent complex is formed upon the interaction of two or more peptide tags (e.g., separately or fused as a dipeptide or tripeptide) and a polypeptide component.

BACKGROUND

Biological processes and analyte detection rely on the co-localization and interactions between molecules, macromolecules, and molecular complexes. In order to understand such processes, and to develop techniques and compounds to manipulate them for research, clinical, and other practical applications, it is necessary to have tools available to detect and monitor these co-localizations/interactions. The study of these interactions, particularly under physiological conditions (e.g., at normal expression levels for monitoring protein interactions) or in complex sample matrices (e.g. blood samples, environmental samples), requires high sensitivity.

SUMMARY

Provided herein are compositions and methods for the assembly of a tripartite or multipartite bioluminescent complex. In particular, a bioluminescent complex is formed upon the interaction of two or more peptide tags (e.g., separately or fused as a dipeptide or tripeptide) and a polypeptide component.

Experiments conducted during development of embodiments herein demonstrate the assembly of a bioluminescent complex, capable of generating luminescence in the presence of an appropriate substrate (e.g., a coelenterazine or a coelenterazine analog substrate), from complementary polypeptide(s) and peptide(s) that collectively span the length (or >75% of the length, >80% of the length, >85% of the length, >90% of the length, >95% of the length, or more) of a luciferase base sequence (or collectively comprise at least 40% sequence identity to a luciferase base sequence (e.g., >40%, >45%, >50%, >55%, >60%, >65%, >70%, >75%>80%, >85%, >90%, >95%, or more). In some embodiments, "complementary" polypeptide(s) and peptide(s) are separate molecules that each correspond to a portion of a luciferase base sequence. Through structural complementarity, they assemble to form a bioluminescent complex.

In some embodiments, the complementary polypeptide(s) and peptide(s) are fragments of a luciferase base sequence that assemble to form a bioluminescent complex. In some embodiments, the fragments collectively comprise the full length of the luciferase base sequence. In some embodiments, the fragments collectively comprise at least 75% of the full length of the luciferase base sequence (e.g., >75% of the length, >80% of the length, >85% of the length, >90% of the length, >95% of the length, or more).

In some embodiments, the complementary polypeptide(s) and peptide(s) are variants of portions of a luciferase base sequence, individually comprising at least 40% sequence identity to the corresponding portion of the luciferase base sequence (e.g., >40%, >45%, >50%, >55%, >60%, >65%, >70%, >75%>80%, >85%, >90%, >95%, or more) that assemble to form a bioluminescent complex. In some embodiments, the complementary polypeptide(s) and peptide(s) are variants of portions of a luciferase base sequence, collectively comprising at least 40% sequence identity to the entire luciferase base sequence (e.g., >40%, >45%, >50%, >55%, >60%, >65%, >70%, >75%>80%, >85%, >90%, >95%, or more) that assemble to form a bioluminescent complex. In some embodiments, the fragments collectively comprise the full length of the luciferase base sequence. In some embodiments, the complementary polypeptide(s) and peptide(s) collectively comprise at least 75% of the full length of the luciferase base sequence (e.g., >75% of the length, >80% of the length, >85% of the length, >90% of the length, >95% of the length, or more).

Examples of luciferase base sequences include SEQ ID NO: 1, SEQ ID NO: 3, SEQ ID NO: 788, and SEQ ID NO: 789. Some embodiments herein provide a polypeptide component that is a fragment of the luciferase base sequence (e.g., SEQ ID NO: 1, SEQ ID NO: 3, SEQ ID NO: 788, and SEQ ID NO: 789) or a variant thereof (e.g., >40%, >45%, >50%, >55%, >60%, >65%, >70%, >75%>80%, >85%, >90%, >95% sequence identity), and one or more complementary peptide(s) and/or polypeptide(s) that collectively span the remainder of the luciferase base sequence. For example, if a luciferase base sequence is 170 amino acid residues in length, an exemplary polypeptide component may be, for example 102, 124, 133, or 148 amino acids in length, and complementary 1, 2, 3, 4, 5, or more complementary peptides correspond to the remaining 68, 46, 37, or 22 amino acids. In some embodiments, each polypeptide component individually comprises at least 40% sequence identity (e.g., >40%, >45%, >50%, >55%, >60%, >65%, >70%, >75%>80%, >85%, >90%, >95%, or more) to the corresponding portion of the luciferase base sequence.

In some embodiments, provided herein are systems or kits comprising: (a) a polypeptide component comprising 40% or greater (e.g., 40%, 45%, 50%, 55%, 60%, 65%, 70%, 75%, 80%, 85%, 90%, 95%, or more) sequence identity to a polypeptide fragment of SEQ ID NO: 788 or SEQ ID NO: 789; and (b) one or more complementary peptides, dipeptides, tripeptide, and/or polypeptides collectively comprising 40% or greater (e.g., 40%, 45%, 50%, 55%, 60%, 65%, 70%, 75%, 80%, 85%, 90%, 95%, or more) sequence identity to the complementary portion of SEQ ID NO: 788 or SEQ ID NO: 789; wherein a bioluminescent signal produced by a bioluminescent complex assembled from the polypeptide component and one or more complementary peptides, dipeptides, tripeptide, and/or polypeptides in the presence of a coelenterazine or a coelenterazine analog substrate is substantially increased when compared to a bioluminescent signal produced by the polypeptide component or one or more complementary peptides, dipeptides, tripeptide, and/or polypeptides and the coelenterazine substrate alone. In some embodiments, the polypeptide component comprises 40% or greater (e.g., 40%, 45%, 50%, 55%, 60%, 65%, 70%, 75%, 80%, 85%, 90%, 95%, or more) sequence identity to SEQ ID NO: 790 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID NO: 794. In some embodiments, the polypeptide component comprises 40% or greater (e.g., 40%, 45%, 50%, 55%, 60%, 65%, 70%, 75%, 80%, 85%, 90%, 95%, or more) sequence identity to SEQ ID NO: 791 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID NO: 795. In some embodiments, the polypeptide component comprises 40% or greater (e.g., 40%, 45%, 50%, 55%, 60%, 65%, 70%, 75%, 80%, 85%, 90%, 95%, or more) sequence identity to SEQ ID NO: 792 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID NO: 796. In some embodiments, the polypeptide component comprises 40% or greater (e.g., 40%, 45%, 50%, 55%, 60%, 65%, 70%, 75%, 80%, 85%, 90%, 95%, or more) sequence identity to SEQ ID NO: 793 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID NO: 797. In some embodiments, the polypeptide component comprises 40% or greater (e.g., 40%, 45%, 50%, 55%, 60%, 65%, 70%, 75%, 80%, 85%, 90%, 95%, or more) sequence identity to SEQ ID NO: 790 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID NO: 798. In some embodiments, the polypeptide component comprises 40% or greater (e.g., 40%, 45%, 50%, 55%, 60%, 65%, 70%, 75%, 80%, 85%, 90%, 95%, or more) sequence identity to SEQ ID NO: 791 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID NO: 799. In some embodiments, the polypeptide component comprises 40% or greater (e.g., 40%, 45%, 50%, 55%, 60%, 65%, 70%, 75%, 80%, 85%, 90%, 95%, or more) sequence identity to SEQ ID NO: 792 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID NO: 800. In some embodiments, the polypeptide component comprises 40% or greater (e.g., 40%, 45%, 50%, 55%, 60%, 65%, 70%, 75%, 80%, 85%, 90%, 95%, or more) sequence identity to SEQ ID NO: 793 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID 801. In some embodiments, the bioluminescent signal is substantially increased when the polypeptide component associates with the one or more complementary peptides, dipeptides, tripeptide, and/or polypeptides. In some embodiments, polypeptide component and/or one or more complementary peptides, dipeptides, tripeptide, and/or polypeptides comprise amino acid sequences that are not a naturally occurring sequences or fragments thereof. In some embodiments, polypeptide component and/or one or more complementary peptides, dipeptides, tripeptide, and/or polypeptides comprise a non-natural amino acid, an amino acid analog, and/or peptoid amino acids. In some embodiments, the polypeptide component and/or one or more complementary peptides, dipeptides, tripeptide, and/or polypeptides are present as fusions with one or more additional amino acid sequences. In some embodiments, the additional amino acid sequence is selected from the group consisting of a protein of interest, an interaction element, a co-localization element, and a binding moiety. In some embodiments, the additional amino acid sequence is a binding moiety selected from the group consisting of antibody (polyclonal, monoclonal, and/or recombinant), antibody fragment, protein A, an Ig binding domain of protein A, protein G, an Ig binding domain of protein G, protein A/G, an Ig binding domain of protein A/G, protein L, an Ig binding domain of protein L, protein M, an Ig binding domain of protein M, oligonucleotide probe, peptide nucleic acid, DARPin, aptamer, affimer, a purified protein (either the analyte itself or a protein that binds to the analyte), and analyte binding domain(s) of proteins. In some embodiments, the additional amino acid sequence is a first interaction polypeptide that is configured to form a complex with a second interaction polypeptide upon contact of the first interaction polypeptide and the second interaction polypeptide. In some embodiments, the additional amino acid sequence is a first co-localization polypeptide that is configured to co-localize within a cellular compartment, a cell, a tissue, or an organism within a with a second co-localization polypeptide. In some embodiments, the additional amino acid sequence is a protein of interest and is a candidate drug target. In some embodiments, provided herein are bioluminescent complexes comprising the polypeptide component and one or more complementary peptides, dipeptides, tripeptide, and/or polypeptides of the systems or kits described herein.

In some embodiments, provided herein are systems or kits comprising two or more peptide, dipeptide, tripeptide and/or polypeptide components collectively comprising 40% or greater (e.g., 40%, 45%, 50%, 55%, 60%, 65%, 70%, 75%, 80%, 85%, 90%, 95%, or more) sequence identity to SEQ ID NO: 788 or SEQ ID NO: 789; wherein a bioluminescent signal produced by the bioluminescent complex in the presence of a coelenterazine or a coelenterazine analog substrate is substantially increased when compared to a bioluminescent signal produced by the polypeptide or one or more complementary peptides and the coelenterazine substrate alone. In some embodiments, a system of kit comprises a polypeptide component having 40% or greater (e.g., 40%, 45%, 50%, 55%, 60%, 65%, 70%, 75%, 80%, 85%, 90%, 95%, or more) sequence identity to SEQ ID NO: 790 and one or more complementary peptides, dipeptides, and or tripeptides collectively having 40% or greater (e.g., 40%, 45%, 50%, 55%, 60%, 65%, 70%, 75%, 80%, 85%, 90%, 95%, or more) sequence identity to SEQ ID NO: 794. In some embodiments, the polypeptide comprises 40% or greater (e.g., 40%, 45%, 50%, 55%, 60%, 65%, 70%, 75%, 80%, 85%, 90%, 95%, or more) sequence identity to SEQ ID NO: 791 and the one or more complementary peptides collectively comprise 40% or greater (e.g., 40%, 45%, 50%, 55%, 60%, 65%, 70%, 75%, 80%, 85%, 90%, 95%, or more) sequence identity to SEQ ID NO: 795. In some embodiments, the polypeptide comprises 40% or greater (e.g., 40%, 45%, 50%, 55%, 60%, 65%, 70%, 75%, 80%, 85%, 90%, 95%, or more) sequence identity to SEQ ID NO: 792 and the one or more complementary peptides collectively comprise 40% or greater (e.g., 40%, 45%, 50%, 55%, 60%, 65%, 70%, 75%, 80%, 85%, 90%, 95%, or more) sequence identity to SEQ ID NO: 796. In some embodiments, the polypeptide comprises 40% or greater (e.g., 40%, 45%, 50%, 55%, 60%, 65%, 70%, 75%, 80%, 85%, 90%, 95%, or more) sequence identity to SEQ ID NO: 793 and the one or more complementary peptides collectively comprise 40% or greater (e.g., 40%, 45%, 50%, 55%, 60%, 65%, 70%, 75%, 80%, 85%, 90%, 95%, or more) sequence identity to SEQ ID NO: 797. In some embodiments, the polypeptide comprises 40% or greater (e.g., 40%, 45%, 50%, 55%, 60%, 65%, 70%, 75%, 80%, 85%, 90%, 95%, or more) sequence identity to SEQ ID NO: 790 and the one or more complementary peptides collectively comprise 40% or greater (e.g., 40%, 45%, 50%, 55%, 60%, 65%, 70%, 75%, 80%, 85%, 90%, 95%, or more) sequence identity to SEQ ID NO: 798. In some embodiments, the polypeptide comprises 40% or greater (e.g., 40%, 45%, 50%, 55%, 60%, 65%, 70%, 75%, 80%, 85%, 90%, 95%, or more) sequence identity to SEQ ID NO: 791 and the one or more complementary peptides collectively comprise 40% or greater (e.g., 40%, 45%, 50%, 55%, 60%, 65%, 70%, 75%, 80%, 85%, 90%, 95%, or more) sequence identity to SEQ ID NO: 799. In some embodiments, the polypeptide comprises 40% or greater (e.g., 40%, 45%, 50%, 55%, 60%, 65%, 70%, 75%, 80%, 85%, 90%, 95%, or more) sequence identity to SEQ ID NO: 792 and the one or more complementary peptides collectively comprise 40% or greater (e.g., 40%, 45%, 50%, 55%, 60%, 65%, 70%, 75%, 80%, 85%, 90%, 95%, or more) sequence identity to SEQ ID NO: 800. In some embodiments, the polypeptide comprises 40% or greater (e.g., 40%, 45%, 50%, 55%, 60%, 65%, 70%, 75%, 80%, 85%, 90%, 95%, or more) sequence identity to SEQ ID NO: 793 and the one or more complementary peptides collectively comprise 40% or greater (e.g., 40%, 45%, 50%, 55%, 60%, 65%, 70%, 75%, 80%, 85%, 90%, 95%, or more) sequence identity to SEQ ID NO: 801. In some embodiments, the bioluminescent signal is substantially increased when the polypeptide associates with the one or more complementary peptides. In some embodiments, the polypeptide and/or one or more complementary peptides comprise amino acid sequences that are not a naturally occurring sequences or fragments thereof. In some embodiments, polypeptide and/or one or more complementary peptides comprise a non-natural amino acid, an amino acid analog, and/or peptoid amino acids. In some embodiments, the polypeptide and/or one or more complementary peptides are present as fusions with one or more additional amino acid sequences. In some embodiments, the additional amino acid sequence is selected from the group consisting of a protein of interest, an interaction element, a co-localization element, and a binding moiety. In some embodiments, the additional amino acid sequence is a binding moiety selected from the group consisting of antibody (polyclonal, monoclonal, and/or recombinant), antibody fragment, protein A, an Ig binding domain of protein A, protein G, an Ig binding domain of protein G, protein A/G, an Ig binding domain of protein A/G, protein L, an Ig binding domain of protein L, protein M, an Ig binding domain of protein M, oligonucleotide probe, peptide nucleic acid, DARPin, aptamer, affimer, a purified protein (either the analyte itself or a protein that binds to the analyte), and analyte binding domain(s) of proteins. In some embodiments, the additional amino acid sequence is a first interaction polypeptide that is configured to form a complex with a second interaction polypeptide upon contact of the first interaction polypeptide and the second interaction polypeptide. In some embodiments, the additional amino acid sequence is a first co-localization polypeptide that is configured to co-localize within a cellular compartment, a cell, a tissue, or an organism within a with a second co-localization polypeptide. In some embodiments, the additional amino acid sequence is a protein of interest and is a candidate drug target. In some embodiments, provided herein are bioluminescent complexes comprising the two or more peptide, dipeptide, tripeptide and/or polypeptide components of the systems or kits described herein.

In some embodiments, provided herein are methods comprising: (a) combining: (i) a polypeptide component comprising 40% or greater (e.g., 40%, 45%, 50%, 55%, 60%, 65%, 70%, 75%, 80%, 85%, 90%, 95%, or more) sequence identity to a polypeptide fragment of SEQ ID NO: 788 or SEQ ID NO: 789; (ii) one or more complementary peptides, dipeptide, tripeptides, and/or polypeptides collectively comprising 40% or greater (e.g., 40%, 45%, 50%, 55%, 60%, 65%, 70%, 75%, 80%, 85%, 90%, 95%, or more) sequence identity to the complementary portion of SEQ ID NO: 788 or SEQ ID NO: 789; and (iii) a coelenterazine or a coelenterazine analog substrate; and (b) detecting luminescence, wherein a greater level of luminescence compared to a level of luminescence produced by the polypeptide component and a coelenterazine or a coelenterazine analog alone indicates formation of a bioluminescent complex of the polypeptide component and the one or more complementary peptides. In some embodiments, one or more of the polypeptide component and the first and second peptides are expressed in a cell, added to a cell exogenously, and/or added to a sample. In some embodiments, (i) the polypeptide component comprises 40% or greater (e.g., 40%, 45%, 50%, 55%, 60%, 65%, 70%, 75%, 80%, 85%, 90%, 95%, or more) sequence identity to SEQ ID NO: 790 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID NO: 794; (ii) the polypeptide component comprises 40% or greater (e.g., 40%, 45%, 50%, 55%, 60%, 65%, 70%, 75%, 80%, 85%, 90%, 95%, or more) sequence identity to SEQ ID NO: 791 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID NO: 795; (iii) the polypeptide component comprises 40% or greater (e.g., 40%, 45%, 50%, 55%, 60%, 65%, 70%, 75%, 80%, 85%, 90%, 95%, or more) sequence identity to SEQ ID NO: 792 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID NO: 796; (iv) the polypeptide component comprises 40% or greater (e.g., 40%, 45%, 50%, 55%, 60%, 65%, 70%, 75%, 80%, 85%, 90%, 95%, or more) sequence identity to SEQ ID NO: 793 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID NO: 797; (v) the polypeptide component comprises 40% or greater (e.g., 40%, 45%, 50%, 55%, 60%, 65%, 70%, 75%, 80%, 85%, 90%, 95%, or more) sequence identity to SEQ ID NO: 790 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID NO: 798; (vi) the polypeptide component comprises 40% or greater (e.g., 40%, 45%, 50%, 55%, 60%, 65%, 70%, 75%, 80%, 85%, 90%, 95%, or more) sequence identity to SEQ ID NO: 791 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID NO: 799; (vii) the polypeptide component comprises 40% or greater (e.g., 40%, 45%, 50%, 55%, 60%, 65%, 70%, 75%, 80%, 85%, 90%, 95%, or more) sequence identity to SEQ ID NO: 792 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID NO: 800; or (viii) the polypeptide component comprises 40% or greater (e.g., 40%, 45%, 50%, 55%, 60%, 65%, 70%, 75%, 80%, 85%, 90%, 95%, or more) sequence identity to SEQ ID NO: 793 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID 801.

In some embodiments, provided herein are methods comprising: (a) combining: (i) two or more peptide, dipeptide, tripeptide, and/or polypeptide components collectively comprising 40% or greater (e.g., 40%, 45%, 50%, 55%, 60%, 65%, 70%, 75%, 80%, 85%, 90%, 95%, or more) sequence identity to the full length of SEQ ID NO: 788 or SEQ ID NO: 789; and (ii) a coelenterazine or a coelenterazine analog substrate; and (b) detecting luminescence, wherein a greater level of luminescence compared to a level of luminescence produced by the peptide, dipeptide, tripeptide, and/or polypeptide components and a coelenterazine or a coelenterazine analog indicates formation of a bioluminescent complex of the peptide and polypeptide components. In some embodiments, one or more of the polypeptide component and the first and second peptides are expressed in a cell, added to a cell exogenously, and/or added to a sample. In some embodiments, (i) the polypeptide component comprises 40% or greater (e.g., 40%, 45%, 50%, 55%, 60%, 65%, 70%, 75%, 80%, 85%, 90%, 95%, or more) sequence identity to SEQ ID NO: 790 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID NO: 794; (ii) the polypeptide component comprises 40% or greater (e.g., 40%, 45%, 50%, 55%, 60%, 65%, 70%, 75%, 80%, 85%, 90%, 95%, or more) sequence identity to SEQ ID NO: 791 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID NO: 795; (iii) the polypeptide component comprises 40% or greater (e.g., 40%, 45%, 50%, 55%, 60%, 65%, 70%, 75%, 80%, 85%, 90%, 95%, or more) sequence identity to SEQ ID NO: 792 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID NO: 796; (iv) the polypeptide component comprises 40% or greater (e.g., 40%, 45%, 50%, 55%, 60%, 65%, 70%, 75%, 80%, 85%, 90%, 95%, or more) sequence identity to SEQ ID NO: 793 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID NO: 797; (v) the polypeptide component comprises 40% or greater (e.g., 40%, 45%, 50%, 55%, 60%, 65%, 70%, 75%, 80%, 85%, 90%, 95%, or more) sequence identity to SEQ ID NO: 790 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID NO: 798; (vi) the polypeptide component comprises 40% or greater (e.g., 40%, 45%, 50%, 55%, 60%, 65%, 70%, 75%, 80%, 85%, 90%, 95%, or more) sequence identity to SEQ ID NO: 791 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID NO: 799; (vii) the polypeptide component comprises 40% or greater (e.g., 40%, 45%, 50%, 55%, 60%, 65%, 70%, 75%, 80%, 85%, 90%, 95%, or more) sequence identity to SEQ ID NO: 792 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID NO: 800; or (viii) the polypeptide component comprises 40% or greater (e.g., 40%, 45%, 50%, 55%, 60%, 65%, 70%, 75%, 80%, 85%, 90%, 95%, or more) sequence identity to SEQ ID NO: 793 and the one or more complementary peptides, dipeptides, tripeptide, and/or polypeptides collectively comprise 40% or greater (e.g., 40%, 45%, 50%, 55%, 60%, 65%, 70%, 75%, 80%, 85%, 90%, 95%, or more) sequence identity to SEQ ID 801.

In some embodiments, provided herein are methods of detecting an interaction between a first molecular entity and a second molecular entity, the method comprising: (a) tagging the first molecular entity with a first peptide, dipeptide, or tripeptide tag; (b) tagging the second molecular entity with a second peptide, dipeptide, or tripeptide tag; (c) combining the tagged first molecular entity and the tagged second molecular entity and/or allowing the tagged first molecular entity and the tagged second molecular entity to come into contact with one another; (d) adding peptide, dipeptide, tripeptide, and/or polypeptide components, wherein the first peptide, dipeptide, or tripeptide tag, the second peptide, dipeptide, or tripeptide tag, and the peptide, dipeptide, tripeptide, and/or polypeptide components collectively comprise an amino acid sequence having 40% or greater (e.g., 40%, 45%, 50%, 55%, 60%, 65%, 70%, 75%, 80%, 85%, 90%, 95%, or more) sequence identity with the entirety of SEQ ID NO: 788 or 789, and capable for assembling to form a bioluminescent complex; (e) adding a coelenterazine or a coelenterazine analog substrate; and (f) detecting a luminescent signal produced by the bioluminescent complex, wherein the magnitude of the luminescent signal correlates to the strength of the interaction between the first molecular entity and the second molecular entity. In some embodiments, the first molecular entity and/or the second molecular entity is a protein of interest or a peptide of interest, and tagging comprises generating a fusion of the first molecular entity and/or the second molecular entity with the first tag and/or second tag. In some embodiments, the first molecular entity and/or the second molecular entity is a small molecule and tagging comprises directly or indirectly linking the first molecular entity and/or the second molecular entity with the first tag and/or second tag. In some embodiments, one of the first molecular entity and the second molecular entity is a drug or drug candidate and the other is a drug target or candidate drug target, and the bioluminescent signal indicates binding of the drug or drug candidate to the other is a drug target or candidate drug target. In some embodiments, combining the tagged first molecular entity and the tagged second molecular entity comprises expressing one or both within a cell and/or adding one or both to a cell.

In some embodiments, provided herein are methods of detecting an interaction between a first protein or peptide entity and a second protein or peptide entity with a cell comprising, the method comprising: (a) expressing within the cell a fusion comprising the first protein or peptide entity and a first peptide, dipeptide, or tripeptide tag comprising an amino acid sequence having 40% or greater (e.g., 40%, 45%, 50%, 55%, 60%, 65%, 70%, 75%, 80%, 85%, 90%, 95%, or more) sequence identity with a first portion of SEQ ID NO: 788 or 789; (b) expressing within the cell a fusion comprising the second protein or peptide entity and a second peptide, dipeptide, or tripeptide tag comprising an amino acid sequence having 40% or greater (e.g., 40%, 45%, 50%, 55%, 60%, 65%, 70%, 75%, 80%, 85%, 90%, 95%, or more) sequence identity with a second portion of SEQ ID NO: 788 or 789; (c) expressing with the cell peptide, dipeptide, tripeptide, and/or polypeptide components comprising an amino acid sequence having 40% or greater (e.g., 40%, 45%, 50%, 55%, 60%, 65%, 70%, 75%, 80%, 85%, 90%, 95%, or more) sequence identity with a third portion of SEQ ID NO: 788 or 789, wherein the first tag, the second tag, and the components collectively comprise 40% or greater (e.g., 40%, 45%, 50%, 55%, 60%, 65%, 70%, 75%, 80%, 85%, 90%, 95%, or more) sequence identity with the entirety of SEQ ID NO: 788 or 789, and are configured to produce a bioluminescent complex upon interaction of the first protein or peptide entity and the second protein or peptide entity; (d) adding a coelenterazine or a coelenterazine analog substrate to the cell; and (e) detecting a luminescent signal produced by the bioluminescent complex, wherein the magnitude of the luminescent signal correlates to the strength of the interaction between the first protein or peptide entity and the second protein or peptide entity.

In some embodiments, provided herein are methods of detecting co-localization of a first molecular entity and a second molecular entity, the method comprising: (a) tagging the first molecular entity with a first peptide, dipeptide, or tripeptide tag comprising an amino acid sequence having 40% or greater (e.g., 40%, 45%, 50%, 55%, 60%, 65%, 70%, 75%, 80%, 85%, 90%, 95%, or more) sequence identity with a first portion of SEQ ID NO: 788 or 789; (b) tagging the second molecular entity with a second peptide, dipeptide, or tripeptide tag comprising an amino acid sequence having 40% or greater (e.g., 40%, 45%, 50%, 55%, 60%, 65%, 70%, 75%, 80%, 85%, 90%, 95%, or more) sequence identity with a second portion of SEQ ID NO: 788 or 789; (c) combining the tagged first molecular entity and the tagged second molecular entity in the same system; (d) adding peptide, dipeptide, tripeptide, and/or polypeptide components to the system, the components having 40% or greater (e.g., 40%, 45%, 50%, 55%, 60%, 65%, 70%, 75%, 80%, 85%, 90%, 95%, or more) sequence identity with a third portion of SEQ ID NO: 788 or 789, wherein the first tag, the second tag, and the components collectively comprise 40% or greater (e.g., 40%, 45%, 50%, 55%, 60%, 65%, 70%, 75%, 80%, 85%, 90%, 95%, or more) sequence identity with the entirety of SEQ ID NO: 788 or 789, wherein the first peptide tag, the second peptide tag, and components are configured to produce a bioluminescent complex upon co-localization of the first molecular entity and the second molecular entity; (e) adding a coelenterazine or a coelenterazine analog substrate to the system; and (f) detecting a luminescent signal produced by the bioluminescent complex, wherein the presence of luminescent signal above background indicates co-localization of the first molecular entity and the second molecular entity within the system, and/or wherein the magnitude of the luminescent signal correlates to the amount of co-localization within the system of the first molecular entity and the second molecular entity. In some embodiments, the system comprises a cell, tissue, organ, whole organism, a biochemical, non-cellular sample. In some embodiments, the first molecular entity and/or the second molecular entity is a protein of interest or a peptide of interest, and tagging comprises generating a fusion of the first molecular entity and/or the second molecular entity with the first tag and/or peptide tag. In some embodiments, the first molecular entity and/or the second molecular entity is a small molecule and tagging comprises directly or indirectly linking the first molecular entity and/or the second molecular entity with the first tag and/or second tag. In some embodiments, combining the tagged first molecular entity and the tagged second molecular entity comprises expressing one or both within the system and/or adding one or both to the system.

In some embodiments, provided herein are methods of detecting co-localization of a first protein or peptide entity and a second protein or peptide entity with a cell comprising, the method comprising: (a) expressing within the cell a fusion comprising the first protein or peptide entity and a first peptide, dipeptide, or tripeptide tag comprising an amino acid sequence having 40% or greater (e.g., 40%, 45%, 50%, 55%, 60%, 65%, 70%, 75%, 80%, 85%, 90%, 95%, or more) sequence identity with a first portion of SEQ ID NO: 788 or 789; (b) expressing within the cell a fusion comprising the second protein or peptide entity and a second peptide, dipeptide, or tripeptide tag comprising an amino acid sequence having 40% or greater (e.g., 40%, 45%, 50%, 55%, 60%, 65%, 70%, 75%, 80%, 85%, 90%, 95%, or more) sequence identity with a second portion of SEQ ID NO: 788 or 789; (c) expressing with the cell one or more peptide, dipeptide, tripeptide, or polypeptide components having 40% or greater (e.g., 40%, 45%, 50%, 55%, 60%, 65%, 70%, 75%, 80%, 85%, 90%, 95%, or more) sequence identity with a third portion of SEQ ID NO: 788 or 789, wherein the first tag, the second tag, and the components collectively comprise 40% or greater (e.g., 40%, 45%, 50%, 55%, 60%, 65%, 70%, 75%, 80%, 85%, 90%, 95%, or more) sequence identity with the entirety of SEQ ID NO: 788 or 789, wherein the first tag, the second tag, and the components are configured to produce a bioluminescent complex upon co-localization of the first protein or peptide entity and the second protein or peptide entity; (d) adding a coelenterazine or a coelenterazine analog substrate to the cell; and (e) detecting a luminescent signal produced by the bioluminescent complex, wherein the presence of luminescent signal above background indicates co-localization of the first protein or peptide entity and the second protein or peptide entity within the cell, and/or wherein the magnitude of the luminescent signal correlates to the amount of co-localization within the system of the first protein or peptide entity and the second protein or peptide entity.

In some embodiments, provided herein are methods of detecting a target molecule, wherein the target molecule displays a first antigen, epitope, or sequence and a distinct second antigen, epitope, or sequence, the method comprising: (a) contacting a sample containing the target molecule with (i) a first primary binding moiety that recognizes the first antigen, epitope, or sequence and (ii) a second primary binding moiety that recognizes the second antigen, epitope, or sequence, and allowing the first and second primary binding moieties to bind to the first and second antigens, epitopes, or sequences; (b) contacting the sample with (i) a first secondary binding moiety conjugated to a first tag and (ii) a second secondary binding moiety conjugated to a second tag, wherein the first secondary binding moiety recognizes the first primary binding moiety and the second secondary binding moiety recognizes the second primary binding moiety, wherein the first or second tags comprises amino acid sequences having 40% or greater (e.g., 40%, 45%, 50%, 55%, 60%, 65%, 70%, 75%, 80%, 85%, 90%, 95%, or more) sequence identity with first and second portions of SEQ ID NO: 788 or 789; (c) allowing the first and second secondary binding moieties to bind to the first and second primary binding moieties; (d) contacting the sample with comprising one or more peptide, dipeptide, tripeptide, and/or polypeptide components having 40% or greater (e.g., 40%, 45%, 50%, 55%, 60%, 65%, 70%, 75%, 80%, 85%, 90%, 95%, or more) sequence identity with a third portion of SEQ ID NO: 788 or 789; wherein the first tag, the second tag, and the components collectively comprise 40% or greater (e.g., 40%, 45%, 50%, 55%, 60%, 65%, 70%, 75%, 80%, 85%, 90%, 95%, or more) sequence identity with the entirety of SEQ ID NO: 788 or 789, wherein the first tag, the second tag, and the components are configured to produce a bioluminescent complex upon interaction; (d) contacting the sample with a coelenterazine or a coelenterazine analog substrate; and (e) detecting a luminescent signal produced by the bioluminescent complex, wherein the presence of luminescent signal above background indicates the presence of the target molecule, and/or wherein the magnitude of the luminescent signal correlates to the amount of target molecule within the sample. In some embodiments, the binding moieties are independently selected from the group consisting of an antibody (polyclonal, monoclonal, and/or recombinant), antibody fragment, protein A, an Ig binding domain of protein A, protein G, an Ig binding domain of protein G, protein A/G, an Ig binding domain of protein A/G, protein L, an Ig binding domain of protein L, protein M, an Ig binding domain of protein M, oligonucleotide probe, peptide nucleic acid, DARPin, aptamer, affimer, a purified protein (either the analyte itself or a protein that binds to the analyte), and analyte binding domain(s) of proteins. In some embodiments, the target molecule is a protein, nucleic acid, or small molecule. In some embodiments, the sample is in vitro or in vivo.

In some embodiments, provided herein are methods of detecting a target molecule, wherein the target molecule displays a first antigen, epitope, or sequence and a distinct second antigen, epitope, or sequence, the method comprising: (a) contacting the sample with (i) a first binding moiety conjugated to a first tag and (ii) a second binding moiety conjugated to second tag, wherein the first secondary binding moiety recognizes the first antigen, epitope, or sequence and the second binding moiety recognizes the second antigen, epitope, or sequence, wherein the first tag comprises an amino acid sequence having 40% or greater (e.g., 40%, 45%, 50%, 55%, 60%, 65%, 70%, 75%, 80%, 85%, 90%, 95%, or more) sequence identity with a first portion of SEQ ID NO: 788 or 789, and wherein the second tag comprises an amino acid sequence with a first portion of SEQ ID NO: 788 or 789; (b) allowing the first and second binding moieties to bind to the first and second antigens, epitope, or sequences; (c) contacting the sample with a peptide, dipeptide, tripeptide, or polypeptide component having 40% or greater (e.g., 40%, 45%, 50%, 55%, 60%, 65%, 70%, 75%, 80%, 85%, 90%, 95%, or more) sequence identity with a third portion of SEQ ID NO: 788 or 789, wherein the first tag, the second tag, and the components collectively comprise 40% or greater (e.g., 40%, 45%, 50%, 55%, 60%, 65%, 70%, 75%, 80%, 85%, 90%, 95%, or more) sequence identity with the entirety of SEQ ID NO: 788 or 789, wherein the first tag, the second tag, and the components are configured to produce a bioluminescent complex upon interaction; (d) contacting the sample with a coelenterazine or a coelenterazine analog substrate; and (e) detecting a luminescent signal produced by the bioluminescent complex, wherein the presence of luminescent signal above background indicates the presence of the target molecule, and/or wherein the magnitude of the luminescent signal correlates to the amount of target molecule within the sample. In some embodiments, the binding moieties are independently selected from the group consisting of an antibody (polyclonal, monoclonal, and/or recombinant), antibody fragment, protein A, an Ig binding domain of protein A, protein G, an Ig binding domain of protein G, protein A/G, an Ig binding domain of protein A/G, protein L, an Ig binding domain of protein L, protein M, an Ig binding domain of protein M, oligonucleotide probe, peptide nucleic acid, DARPin, aptamer, affimer, a purified protein (either the analyte itself or a protein that binds to the analyte), and analyte binding domain(s) of proteins. In some embodiments, the target molecule is a protein, nucleic acid, or small molecule. In some embodiments, the sample is in vitro, in vivo, or a biochemical sample.

In some embodiments, provided herein are peptides, dipeptides, tripeptides, and/or polypeptides listed in Table 1, Table 9, or Table 10. In some embodiments, a single peptide, dipeptide, tripeptide, or polypeptide listed in Table 1, Table 9, or Table 10 is provided (e.g., as a reagent, as a tag, etc.). In some embodiments, a pair (2) or set (e.g., 2, 3, 4, 5, or more) of peptides, dipeptides, tripeptides, and/or polypeptides listed in Table 1, Table 9, or Table 10 are provided. In particular, pairs or sets of the peptides, dipeptides, tripeptides, and/or polypeptides are provided that are complementary and are capable of forming a bioluminescent complex upon interaction (e.g., facilitated, unfacilitated) with one another.

In some embodiments, provided herein are peptides, dipeptides, tripeptides, and/or polypeptides having at least 40% (e.g., 40%, 45%, 50%, 55%, 60%, 65%, 70%, 75%, 80%, 85%, 90%, 95%, or more) sequence identity with one or more of the peptides, dipeptides, tripeptides, and/or polypeptides listed in Table 1, Table 9, or Table 10. In some embodiments, a single peptide, dipeptide, tripeptide, or polypeptide having at least 40% (e.g., 40%, 45%, 50%, 55%, 60%, 65%, 70%, 75%, 80%, 85%, 90%, 95%, or more) sequence identity with one or more of the peptides, dipeptides, tripeptides, and/or polypeptides listed in Table 1, Table 9, or Table 10 is provided (e.g., as a reagent, as a tag, etc.). In some embodiments, a pair (2) or set (e.g., 2, 3, 4, 5, or more) of peptides, dipeptides, tripeptides, and/or polypeptides having at least 40% (e.g., 40%, 45%, 50%, 55%, 60%, 65%, 70%, 75%, 80%, 85%, 90%, 95%, or more) sequence identity with one or more of the peptides, dipeptides, tripeptides, and/or polypeptides listed in Table 1, Table 9, or Table 10 is provided are provided. In particular, pairs or sets of the peptides, dipeptides, tripeptides, and/or polypeptides are provided that are complementary and are capable of forming a bioluminescent complex upon interaction (e.g., facilitated, unfacilitated) with one another.

In some embodiments, provided herein are polypeptides comprising 40% or greater (e.g., 40%, 45%, 50%, 55%, 60%, 65%, 70%, 75%, 80%, 85%, 90%, 95%, or more) sequence identity with one of SEQ ID NO: 790, 791, 792, or 793. In some embodiments, the polypeptide is provided alone or as a pair/set with complementary peptide(s), dipeptide(s), and/or tripeptide for the formation of a bioluminescent complex. In some embodiments, fusions of polypeptides herein with proteins of interest, interaction elements, colocalization elements, etc. are provided. In some embodiments, nucleic acids and vectors encoding the polypeptides and fusions thereof or provided.

In some embodiments, provided herein are peptides comprising SEQ ID NO: 817, 818, 819, 13, 15, 23, or 25. In some embodiments, provided herein are peptides comprising 40% or greater (e.g., 40%, 45%, 50%, 55%, 60%, 65%, 70%, 75%, 80%, 85%, 90%, 95%, or more) sequence identity with one of SEQ ID NO: 817, 818, 819, 13, 15, 23, or 25. In some embodiments, the peptide is provided alone or as a pair/set with complementary polypeptide and/or other peptide(s), dipeptide(s), and/or tripeptide for the formation of a bioluminescent complex. In some embodiments, fusions of peptides herein with proteins of interest, interaction elements, colocalization elements, etc. are provided. In some embodiments, nucleic acids and vectors encoding the peptides and fusions thereof or provided. In some embodiments, molecules of interest and/or proteins of interest are tagged with a peptide herein.

In some embodiments, provided herein is a β6-7-like dipeptide comprising SEQ ID NOS: 817 and 818. In some embodiments, provided herein is a β6-7-like dipeptide having 40% or greater (e.g., 40%, 45%, 50%, 55%, 60%, 65%, 70%, 75%, 80%, 85%, 90%, 95%, or more) sequence identity with SEQ ID NOS: 817 and 818. In some embodiments, the dipeptide is provided alone or as a pair/set with complementary polypeptide and/or other peptide(s), dipeptide(s), and/or tripeptide for the formation of a bioluminescent complex. In some embodiments, nucleic acids and vectors encoding the dipeptides and fusions thereof or provided. In some embodiments, molecules of interest and/or proteins of interest are tagged with a dipeptide herein.

In some embodiments, provided herein is a β7-8-like dipeptide comprising SEQ ID NOS: 818 and 819. In some embodiments, provided herein is a β7-8-like dipeptide having 40% or greater (e.g., 40%, 45%, 50%, 55%, 60%, 65%, 70%, 75%, 80%, 85%, 90%, 95%, or more) sequence identity with SEQ ID NOS: 818 and 819. In some embodiments, the dipeptide is provided alone or as a pair/set with complementary polypeptide and/or other peptide(s), dipeptide(s), and/or tripeptide for the formation of a bioluminescent complex. In some embodiments, the dipeptide is provided alone or as a pair/set with complementary polypeptide and/or other peptide(s), dipeptide(s), and/or tripeptide for the formation of a bioluminescent complex. In some embodiments, nucleic acids and vectors encoding the dipeptides and fusions thereof or provided. In some embodiments, molecules of interest and/or proteins of interest are tagged with a dipeptide herein.

In some embodiments, provided herein is a β8-9-like dipeptide comprising SEQ ID NOS: 819/23 or 819/25. In some embodiments, provided herein is a β8-9-like dipeptide having 40% or greater (e.g., 40%, 45%, 50%, 55%, 60%, 65%, 70%, 75%, 80%, 85%, 90%, 95%, or more) sequence identity with NOS: 819/23 or 819/25. In some embodiments, the dipeptide is provided alone or as a pair/set with complementary polypeptide and/or other peptide(s), dipeptide(s), and/or tripeptide for the formation of a bioluminescent complex. In some embodiments, the dipeptide is provided alone or as a pair/set with complementary polypeptide and/or other peptide(s), dipeptide(s), and/or tripeptide for the formation of a bioluminescent complex. In some embodiments, nucleic acids and vectors encoding the dipeptides and fusions thereof or provided. In some embodiments, molecules of interest and/or proteins of interest are tagged with a dipeptide herein.

In some embodiments, provided herein is a β9-10-like dipeptide comprising SEQ ID NOS: 23/13, 23/15, 25/13 or 25/15. In some embodiments, provided herein is a β8-9-like dipeptide having 40% or greater (e.g., 40%, 45%, 50%, 55%, 60%, 65%, 70%, 75%, 80%, 85%, 90%, 95%, or more) sequence identity with NOS: SEQ ID NOS: 23/13, 23/15, 25/13 or 25/15. In some embodiments, the dipeptide is provided alone or as a pair/set with complementary polypeptide and/or other peptide(s), dipeptide(s), and/or tripeptide for the formation of a bioluminescent complex. In some embodiments, the dipeptide is provided alone or as a pair/set with complementary polypeptide and/or other peptide(s), dipeptide(s), and/or tripeptide for the formation of a bioluminescent complex. In some embodiments, nucleic acids and vectors encoding the dipeptides and fusions thereof or provided. In some embodiments, molecules of interest and/or proteins of interest are tagged with a dipeptide herein.

In some embodiments, provided herein is a β6-8-like tripeptide comprising SEQ ID NOS: 817-819. In some embodiments, provided herein is a β6-8-like tripeptide having 40% or greater (e.g., 40%, 45%, 50%, 55%, 60%, 65%, 70%, 75%, 80%, 85%, 90%, 95%, or more) sequence identity with NOS: SEQ ID NOS: 817-819. In some embodiments, the tripeptide is provided alone or as a pair/set with complementary polypeptide and/or other peptide(s), dipeptide(s), and/or tripeptide for the formation of a bioluminescent complex. In some embodiments, the tripeptide is provided alone or as a pair/set with complementary polypeptide and/or other peptide(s), dipeptide(s), and/or tripeptide for the formation of a bioluminescent complex. In some embodiments, nucleic acids and vectors encoding the tripeptides and fusions thereof or provided. In some embodiments, molecules of interest and/or proteins of interest are tagged with a tripeptide herein.

In some embodiments, provided herein is a β7-9-like tripeptide comprising SEQ ID NOS: 818/819/23 or 818/819/25. In some embodiments, provided herein is a β7-9-like tripeptide having 40% or greater (e.g., 40%, 45%, 50%, 55%, 60%, 65%, 70%, 75%, 80%, 85%, 90%, 95%, or more) sequence identity with NOS: SEQ ID NOS: 818/819/23 or 818/819/25. In some embodiments, the tripeptide is provided alone or as a pair/set with complementary polypeptide and/or other peptide(s), dipeptide(s), and/or tripeptide for the formation of a bioluminescent complex. In some embodiments, the tripeptide is provided alone or as a pair/set with complementary polypeptide and/or other peptide(s), dipeptide(s), and/or tripeptide for the formation of a bioluminescent complex. In some embodiments, nucleic acids and vectors encoding the tripeptides and fusions thereof or provided. In some embodiments, molecules of interest and/or proteins of interest are tagged with a tripeptide herein.

In some embodiments, provided herein is a β8-10-like tripeptide comprising SEQ ID NOS: 819/23/13, 819/23/15, 819/25/13, or 819/25/15. In some embodiments, provided herein is a β7-9-like tripeptide having 40% or greater (e.g., 40%, 45%, 50%, 55%, 60%, 65%, 70%, 75%, 80%, 85%, 90%, 95%, or more) sequence identity with NOS: SEQ ID NOS: 819/23/13, 819/23/15, 819/25/13, or 819/25/15. In some embodiments, the tripeptide is provided alone or as a pair/set with complementary polypeptide and/or other peptide(s), dipeptide(s), and/or tripeptide for the formation of a bioluminescent complex. In some embodiments, the tripeptide is provided alone or as a pair/set with complementary polypeptide and/or other peptide(s), dipeptide(s), and/or tripeptide for the formation of a bioluminescent complex. In some embodiments, the tripeptide is provided alone or as a pair/set with complementary polypeptide and/or other peptide(s), dipeptide(s), and/or tripeptide for the formation of a bioluminescent complex. In some embodiments, nucleic acids and vectors encoding the tripeptides and fusions thereof or provided. In some embodiments, molecules of interest and/or proteins of interest are tagged with a tripeptide herein.

In some embodiments, provided herein are peptides comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 23 and less than 100% sequence identity with SEQ ID NO: 6 and SEQ ID NO: 9, wherein a bioluminescent signal produced in the presence of a coelenterazine or a coelenterazine analog substrate is substantially increased when the peptide contacts a second peptide consisting of SEQ ID NO: 25 and a polypeptide complement consisting of SEQ ID NO: 17, SEQ ID NO: 21, or SEQ ID NO: 302 when compared to a bioluminescent signal produced by the peptide and the coelenterazine or a coelenterazine analog substrate alone. In some embodiments, the bioluminescent signal is substantially increased when the peptide associates with the second peptide and the polypeptide complement. In some embodiments, the peptide exhibits enhancement of one or more traits compared to a peptide of SEQ ID NO: 6 and/or SEQ ID NO: 9, wherein the traits are selected from: affinity for the second peptide and the polypeptide complement, expression, solubility, stability, and/or bioluminescent activity when combined with the second peptide and the polypeptide complement. In some embodiments, the amino acid sequence is not a naturally occurring protein (e.g., not SEQ ID NO: 1), not a mutant version thereof (e.g., not SEQ ID NO: 3), not a fragment of a naturally occurring protein (e.g., not SEQ ID NOS: 5-7), and not a fragment of a mutant version thereof (e.g., not one of SEQ ID NOS: 8-10). In some embodiments, the amino acid sequence contains a non-natural amino acid, an amino acid analog, and/or peptoid amino acids. In some embodiments, a peptide is chemically conjugated to a linker, reactive moiety, detection element (e.g., fluorophore), interaction/binding element, etc.

In some embodiments, provided herein are fusion polypeptides (e.g., genetic fusions (or alternatively, chemical conjugations or synthetically produced)) comprising a peptide described in the preceding paragraph and an additional amino acid sequence or compound (e.g. small molecule drug). In some embodiments, the additional amino acid sequence is selected from the group consisting of a protein of interest, an interaction element, a co-localization element, and/or a binding moiety. In some embodiments, the additional amino acid sequence is a binding moiety selected from the group consisting of an antibody (e.g., polyclonal, monoclonal, and/or recombinant), antibody fragment, protein A, an Ig binding domain of protein A, protein G, an Ig binding domain of protein G, protein A/G, an Ig binding domain of protein A/G, protein L, a Ig binding domain of protein L, protein M, an Ig binding domain of protein M, peptide nucleic acid, DARPin, affimer, a purified protein (e.g., an analyte or a protein that binds to an analyte), and analyte binding domain(s) of proteins. In some embodiments, the additional amino acid sequence is a first interaction polypeptide that is configured to form a complex with a second interaction polypeptide upon contact of the first interaction polypeptide and the second interaction polypeptide. In some embodiments, the additional amino acid sequence is a first co-localization polypeptide that is configured to co-localize within a cellular compartment, a cell, a tissue, or an organism with a second co-localization polypeptide. In some embodiments, the additional amino acid sequence is a protein of interest and is a candidate drug target.

In some embodiments, provided herein are peptides comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 25 and less than 100% sequence identity with SEQ ID NO: 7 and SEQ ID NO: 10, wherein a bioluminescent signal produced in the presence of a coelenterazine or a coelenterazine analog substrate is substantially increased when the peptide contacts a second peptide consisting of SEQ ID NO: 23 and a polypeptide complement consisting of SEQ ID NO: 17, SEQ ID NO: 21, or SEQ ID NO: 302 when compared to a bioluminescent signal produced by the peptide and the coelenterazine or a coelenterazine analog substrate alone. In some embodiments, the bioluminescent signal is substantially increased when the peptide associates with the second peptide and the polypeptide complement. In some embodiments, the peptide exhibits enhancement of one or more traits compared to a peptide of SEQ ID NO: 7 and/or SEQ ID NO: 10, wherein the traits are selected from: affinity for the second peptide and the polypeptide complement, expression, solubility, stability, and bioluminescent activity when combined with the second peptide and the polypeptide complement. In some embodiments, the amino acid sequence is not a naturally occurring protein (e.g., not SEQ ID NO: 1), not a mutant version thereof (e.g., not SEQ ID NO: 3), not a fragment of a naturally occurring protein (e.g., not SEQ ID NOS: 5-7), and not a fragment of a mutant version thereof (e.g., not one of SEQ ID NOS: 8-10). In some embodiments, the amino acid sequence contains a non-natural amino acid, an amino acid analog, and/or peptoid amino acids. In some embodiments, a peptide is chemically conjugated to a linker, reactive moiety, detection element (e.g., fluorophore), interaction/binding element, etc.

In some embodiments, provided herein are fusion polypeptides (e.g., genetic fusions, synthetically-produced fusions, chemical conjugates, enzymatic conjugates, etc.) comprising a peptide described in the preceding paragraph and an additional amino acid sequence. In some embodiments, the additional amino acid sequence is selected from the group consisting of a protein of interest, an interaction element, a co-localization element, and a binding moiety. In some embodiments, the additional amino acid sequence is a binding moiety selected from the group consisting of an antibody (polyclonal, monoclonal, and/or recombinant), antibody fragment, protein A, an Ig binding domain of protein A, protein G, an Ig binding domain of protein G, protein A/G, an Ig binding domain of protein A/G, protein L, a Ig binding domain of protein L, protein M, an Ig binding domain of protein M, peptide nucleic acid, DARPin, affimer, a purified protein (either the analyte itself or a protein that binds to the analyte), and analyte binding domain(s) of proteins. In some embodiments, the additional amino acid sequence is a first interaction polypeptide that is configured to form a complex with a second interaction polypeptide upon contact of the first interaction polypeptide and the second interaction polypeptide. In some embodiments, the additional amino acid sequence is a first co-localization polypeptide that is configured to co-localize within a cellular compartment, a cell, a tissue, or an organism within a with a second co-localization polypeptide. In some embodiments, the additional amino acid sequence is a protein of interest and is a candidate drug target.

In some embodiments, provided herein are compositions comprising: (a) a first peptide comprising an amino acid sequence having greater than 40% (e.g., 40%, 45%, 50%, 55%, 60%, 65%, 70%, 75%, 80%, 85%, 90%, 95%, or more) but less than 100% sequence identity with SEQ ID NO: 25 and less than 100% sequence identity with SEQ ID NO: 7 and SEQ ID NO: 10; and (b) a second peptide comprising an amino acid sequence having greater than 40% (e.g., 40%, 45%, 50%, 55%, 60%, 65%, 70%, 75%, 80%, 85%, 90%, 95%, or more) but less than 100% sequence identity with SEQ ID NO: 23 and less than 100% sequence identity with SEQ ID NO: 6, SEQ ID NO: 9, and SEQ ID NO: 29; wherein a bioluminescent signal produced in the presence of a coelenterazine or a coelenterazine analog substrate is substantially increased when the first peptide contacts the second peptide and a polypeptide complement consisting of SEQ ID NO: 17, SEQ ID NO: 21, or SEQ ID NO: 302 when compared to a bioluminescent signal produced by the first peptide and/or the second peptide and the coelenterazine substrate alone. In some embodiments, the bioluminescent signal is substantially increased when the first peptide associates with the second peptide and the polypeptide complement. In some embodiments, the first peptide exhibits enhancement of one or more traits compared to a peptide of SEQ ID NO: 7 and/or SEQ ID NO: 10 and the second peptide exhibits enhancement of one or more traits compared to a peptide of SEQ ID NO: 6, SEQ ID NO: 9, and SEQ ID NO: 29, wherein the traits are selected from: affinity for the second peptide and the polypeptide complement, expression, solubility, stability, and bioluminescent activity when combined with the second peptide and the polypeptide complement. In some embodiments, the amino acid sequence of the first and/or second peptide is not a naturally occurring protein or a fragment thereof. In some embodiments, the amino acid sequence of the first and/or second peptide contains a non-natural amino acid, an amino acid analog, and/or peptoid amino acids.

In some embodiments, provided herein are compositions comprising fusion polypeptides comprising the first and second peptides of described in the preceding paragraph and an additional amino acid sequence. In some embodiments, the additional amino acid sequence is selected from the group consisting of a protein of interest, an interaction element, a co-localization element, and a binding moiety. In some embodiments, the additional amino acid sequence is a binding moiety selected from the group consisting of an antibody (polyclonal, monoclonal, and/or recombinant), antibody fragment, protein A, an Ig binding domain of protein A, protein G, an Ig binding domain of protein G, protein A/G, an Ig binding domain of protein A/G, protein L, a Ig binding domain of protein L, protein M, an Ig binding domain of protein M, peptide nucleic acid, DARPin, affimer, a purified protein (either the analyte itself or a protein that binds to the analyte), and analyte binding domain(s) of proteins. In some embodiments, the additional amino acid sequence is a first interaction polypeptide that is configured to form a complex with a second interaction polypeptide upon contact of the first interaction polypeptide and the second interaction polypeptide. In some embodiments, the additional amino acid sequence is a first co-localization polypeptide that is configured to co-localize within a cellular compartment, a cell, a tissue, or an organism within a with a second co-localization polypeptide. In some embodiments, the additional amino acid sequence is a protein of interest and is a candidate drug target.

In some embodiments, provided herein are polypeptides comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 17, SEQ ID NO: 21, or SEQ ID NO: 302 and less than 100% sequence identity with SEQ ID NO: 5 and SEQ ID NO: 8, wherein a bioluminescent signal produced in the presence of a coelenterazine or a coelenterazine analog substrate is substantially increased when the polypeptide contacts a first peptide consisting of SEQ ID NO: 23 and a second peptide consisting of SEQ ID NO: 25 when compared to a bioluminescent signal produced by the peptide and the coelenterazine or a coelenterazine analog substrate alone. In some embodiments, the bioluminescent signal is substantially increased when the polypeptide associates with the first and second peptides. In some embodiments, the polypeptide exhibits enhancement of one or more traits compared to a polypeptide of SEQ ID NO: 5 and/or SEQ ID NO: 8, wherein the traits are selected from: affinity for the first and/or second peptides, expression, solubility, stability, and bioluminescent activity when combined with the first and second peptides. In some embodiments, the amino acid sequence is not a naturally occurring protein (e.g., not SEQ ID NO: 1), not a mutant version thereof (e.g., not SEQ ID NO: 3), not a fragment of a naturally occurring protein (e.g., not SEQ ID NOS: 5-7), and not a fragment of a mutant version thereof (e.g., not one of SEQ ID NOS: 8-10). In some embodiments, the amino acid sequence contains a non-natural amino acid, an amino acid analog, and/or peptoid amino acids.

In some embodiments, provided herein are fusion polypeptides (e.g., genetic fusions, synthetically-produced fusions, chemical conjugates, enzymatic conjugates, etc.) comprising a polypeptide described in the preceding paragraph and an additional amino acid sequence, nucleic acid sequence, or other fused or appended molecule. In some embodiments, the additional sequence or other molecule is selected from the group consisting of a protein of interest, an interaction element, a co-localization element, and a binding moiety. In some embodiments, the additional sequence or other molecule is a binding moiety selected from the group consisting of an antibody (polyclonal, monoclonal, and/or recombinant), antibody fragment, protein A, an Ig binding domain of protein A, protein G, an Ig binding domain of protein G, protein A/G, an Ig binding domain of protein A/G, protein L, a Ig binding domain of protein L, protein M, an Ig binding domain of protein M, peptide nucleic acid, DARPin, affimer, a purified protein (either the analyte itself or a protein that binds to the analyte), and analyte binding domain(s) of proteins. In some embodiments, the additional sequence or other fused or appended molecule is a first interaction polypeptide that is configured to form a complex with a second interaction polypeptide upon contact of the first interaction polypeptide and the second interaction polypeptide. In some embodiments, the additional sequence or other fused or appended molecule is a first co-localization polypeptide that is configured to co-localize within a cellular compartment, a cell, a tissue, or an organism within a with a second co-localization polypeptide. In some embodiments, the additional sequence or other fused or appended molecule is a protein of interest and is a candidate drug target.

In some embodiments, provided herein are polypeptides comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 17, SEQ ID NO: 21, and/or SEQ ID NO: 302 and less than 100% sequence identity with SEQ ID NO: 5 and SEQ ID NO: 8, wherein a bioluminescent signal produced in the presence of a coelenterazine or a coelenterazine analog substrate is substantially increased when the polypeptide contacts a first peptide consisting of SEQ ID NO: 23 and a second peptide consisting of SEQ ID NO: 25 when compared to a bioluminescent signal produced by the peptide and the coelenterazine or a coelenterazine analog substrate alone. In some embodiments, the bioluminescent signal is substantially increased when the polypeptide associates with the first and second peptides. In some embodiments, the polypeptide exhibits enhancement of one or more traits compared to a polypeptide of SEQ ID NO: 5 and/or SEQ ID NO: 8, wherein the traits are selected from: affinity for the first and/or second peptides, expression, solubility, stability, and bioluminescent activity when combined with the first and second peptides. In some embodiments, the amino acid sequence is not a naturally occurring protein (e.g., not SEQ ID NO: 1), not a mutant version thereof (e.g., not SEQ ID NO: 3), not a fragment of a naturally occurring protein (e.g., not SEQ ID NOS: 5-7), and not a fragment of a mutant version thereof (e.g., not one of SEQ ID NOS: 8-10). In some embodiments, the amino acid sequence contains a non-natural amino acid, an amino acid analog, and/or peptoid amino acids.

In some embodiments, provided herein are fusion polypeptides (e.g., genetic fusions, synthetically-produced fusions, chemical conjugates, enzymatic conjugates, etc.) comprising a peptide described in the preceding paragraph and an additional amino acid sequence. In some embodiments, the additional amino acid sequence is selected from the group consisting of a protein of interest, an interaction element, a co-localization element, and a binding moiety. In some embodiments, the additional amino acid sequence is a binding moiety selected from the group consisting of an antibody (polyclonal, monoclonal, and/or recombinant), antibody fragment, protein A, an Ig binding domain of protein A, protein G, an Ig binding domain of protein G, protein A/G, an Ig binding domain of protein A/G, protein L, a Ig binding domain of protein L, protein M, an Ig binding domain of protein M, peptide nucleic acid, DARPin, affimer, a purified protein (either the analyte itself or a protein that binds to the analyte), and analyte binding domain(s) of proteins. In some embodiments, the additional amino acid sequence is a first interaction polypeptide that is configured to form a complex with a second interaction polypeptide upon contact of the first interaction polypeptide and the second interaction polypeptide. In some embodiments, the additional amino acid sequence is a first co-localization polypeptide that is configured to co-localize within a cellular compartment, a cell, a tissue, or an organism within a with a second co-localization polypeptide. In some embodiments, the additional amino acid sequence is a protein of interest and is a candidate drug target.

In some embodiments, provided herein are $\beta9/\beta10$-like dipeptides comprising an amino acid sequence having greater than 40% (e.g., 40%, 45%, 50%, 55%, 60%, 65%, 70%, 75%, 80%, 85%, 90%, 95%, or more) but less than 100% sequence identity with SEQ ID NO: 35 and less than 100% sequence identity with SEQ ID NO: 205 and SEQ ID NO: 206, wherein a bioluminescent signal produced in the presence of a coelenterazine or a coelenterazine analog substrate is substantially increased when the peptide contacts a polypeptide complement consisting of SEQ ID NO: 17, SEQ ID NO: 21, or SEQ ID NO: 302 when compared to a bioluminescent signal produced by the peptide and the coelenterazine or a coelenterazine analog substrate alone. In some embodiments, a dipeptide (e.g., $\beta_9/\beta_{10}$-like dipeptide) associates (e.g., forms a bioluminescent complex) with a polypeptide component described herein (e.g., $\beta_{1-8}$-like polypeptide) without facilitation (e.g., from interaction elements). In other embodiments, a dipeptide (e.g., $\beta_9/\beta_{10}$-like dipeptide) and polypeptide component described herein (e.g., $\beta_{1-8}$-like polypeptide) will not form a bioluminescent complex without facilitation (e.g., from interaction elements), but will associate (e.g., form a bioluminescent complex) with facilitation from appropriate interaction elements. In some embodiments, the bioluminescent signal is substantially increased when the peptide associates with the polypeptide complement. In some embodiments, the peptide exhibits enhancement of one or more traits compared to a peptide of SEQ ID NO: 205 and/or SEQ ID NO: 206, wherein the traits are selected from: affinity for the polypeptide complement, expression, solubility, stability, and bioluminescent activity when combined with the polypeptide complement. In some embodiments, the amino acid sequence is not a naturally occurring protein or a fragment thereof. In some embodiments, the amino acid sequence contains a non-natural amino acid, an amino acid analog, and/or peptoid amino acids.

In some embodiments, provided herein are fusion polypeptides (e.g., genetic fusions, synthetically-produced fusions, chemical conjugates, enzymatic conjugates, etc.) comprising the $\beta9/\beta10$-like dipeptides described herein and an additional amino acid sequence. In some embodiments, the additional amino acid sequence is selected from the group consisting of a protein of interest, an interaction element, a co-localization element, and a binding moiety. In some embodiments, the additional amino acid sequence or other fused or appended molecule is a binding moiety selected from the group consisting of antibody (polyclonal, monoclonal, and/or recombinant), antibody fragment, protein A, an Ig binding domain of protein A, protein G, an Ig binding domain of protein G, protein A/G, an Ig binding domain of protein A/G, protein L, a Ig binding domain of protein L, protein M, an Ig binding domain of protein M, peptide nucleic acid, DARPin, affimer, a purified protein (either the analyte itself or a protein that binds to the analyte), and analyte binding domain(s) of proteins. In some embodiments, the additional amino acid sequence or other fused or appended molecule is a first interaction polypeptide that is configured to form a complex with a second interaction polypeptide upon contact of the first interaction polypeptide and the second interaction polypeptide. In some embodiments, the additional amino acid sequence or other fused or appended molecule is a first co-localization polypeptide that is configured to co-localize within a cellular compartment, a cell, a tissue, or an organism within a with a second co-localization polypeptide. In some embodiments, the additional amino acid sequence or other fused or appended molecule is a protein of interest and is a candidate drug target.

In some embodiments, provided herein are nucleic acids and/or vectors coding for the peptides, polypeptides, and/or fusion polypeptides described herein. In some embodiments, provided herein are cells expressing nucleic acids and/or vectors coding for the peptides, polypeptides, and/or fusion polypeptides described herein. In some embodiments, synthetic production of the peptides, polypeptides, and/or fusion polypeptides described herein is provided. In some embodiments, the peptides, polypeptides, and/or fusion polypeptides described herein are chemically conjugated to additional moieties (e.g., interaction elements, co-localization elements, proteins of interest, molecules of interest, etc.).

In some embodiments, provided herein are bioluminescent complexes comprising: (a) a polypeptide comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 17, SEQ ID NO: 21, or SEQ ID NO: 302 and less than 100% sequence identity with SEQ ID NO: 5 and SEQ ID NO: 8; (b) a first peptide comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 23 and less than 100% sequence identity with SEQ ID NO: 6 and SEQ ID NO: 9; and (c) a second peptide comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 25 and less than 100% sequence identity with SEQ ID NO: 7 and SEQ ID NO: 10; wherein the bioluminescent complex produces substantially increased bioluminescence in the presence of a coelenterazine or a coelenterazine analog substrate when compared to a coelenterazine or a coelenterazine analog substrate in the presence of: the polypeptide alone, the first peptide alone, the second peptide alone, and any two of the polypeptide, the first peptide, and the second peptide. In some embodiments, the first peptide is a first peptide tag, wherein the second peptide is a second peptide tag, and wherein the first and second peptide tags are each linked to moieties that are independently selected from the group consisting of a molecule of interest, a peptide of interest, a protein of interest, an interaction element, a co-localization element, or a binding moiety. In some embodiments, the first peptide tag or the second peptide tag is linked to a drug or drug candidate, and the other peptide tag is linked to a drug target or candidate drug target, and wherein the intensity of the bioluminescence from the bioluminescent complex correlates to the affinity of the drug or drug candidate for the drug target or candidate drug target. In some embodiments, the first peptide tag is linked to a first interaction element, and the second peptide tag is linked to a second interaction element, and wherein the intensity of the bioluminescence from the bioluminescent complex correlates to the affinity of the first interaction element for the second interaction element under the conditions assayed (e.g., in some embodiments, the combination of the first peptide, second peptide, polypeptide component, and substrate do not form the bioluminescent complex (and produce significant light output (e.g., above background)) in the absence of an interaction between interaction elements). In some embodiments, the first peptide tag is linked to a first co-localization element, and the second peptide tag is linked to a second co-localization element, and wherein substantially increased bioluminescence indicates co-localization, but not necessarily interaction, of the first co-localization element and the second co-localization element, under the conditions assayed.

In some embodiments, the peptides and polypeptide provided herein are not fragments of larger (e.g., pre-existing) proteins. In other embodiments, one or more peptides and/or polypeptides provided herein are fragments of larger (e.g., pre-existing) proteins.

In some embodiments, provided herein are methods comprising: (a) combining: (i) a first peptide comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 23 and less than 100% sequence identity with SEQ ID NO: 6 and SEQ ID NO: 9, (ii) a second peptide comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 25 and less than 100% sequence identity with SEQ ID NO: 7 and SEQ ID NO: 10, (iii) a polypeptide component comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 17, SEQ ID NO: 21, or SEQ ID NO: 302 and less than 100% sequence identity with SEQ ID NO: 5 and SEQ ID NO: 8, wherein the first peptide tag, the second peptide tag, and the polypeptide component are configured to produce a bioluminescent complex upon interaction of the first molecular entity and the second molecular entity, an (iv) a coelenterazine or a coelenterazine analog substrate; and (b) detecting luminescence, wherein a greater level of luminescence compared to a level of luminescence produced by the polypeptide component and a coelenterazine or a coelenterazine analog alone indicates formation of a bioluminescent complex of the polypeptide component and the first and second peptides. In some embodiments, one or more of the polypeptide component and the first and second peptides are expressed in a cell, added to a cell exogenously, and/or added to a sample.

In some embodiments, provided herein are methods of detecting an interaction between a first molecular entity and a second molecular entity, the method comprising: (a) tagging the first molecular entity with a first peptide tag comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 23 and less than 100% sequence identity with SEQ ID NO: 6 and SEQ ID NO: 9; (b) tagging the second molecular entity with a second peptide tag comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 25 and less than 100% sequence identity with SEQ ID NO: 7 and SEQ ID NO: 10; (c) combining the tagged first molecular entity and the tagged second molecular entity; (d) adding a polypeptide component comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 17, SEQ ID NO: 21, or SEQ ID NO: 302 and less than 100% sequence identity with SEQ ID NO: 5 and SEQ ID NO: 8, wherein the first peptide tag, the second peptide tag, and the polypeptide component are configured to produce a bioluminescent complex upon interaction of the first molecular entity and the second molecular entity; (e) adding a coelenterazine or a coelenterazine analog substrate; and (f) detecting a luminescent signal produced by the bioluminescent complex, wherein the magnitude of the luminescent signal correlates with (e.g., is proportional to, is directly proportional to, etc.) the number of, strength of, favorability of, and/or stability of the interaction(s)) between the first molecular entity and the second molecular entity. In some embodiments, catalytic efficiency, substrate turnover, and/or specific activity of the resulting bioluminescent complex correlates with (e.g., is proportional to, is directly proportional to, etc.) the number of, strength of, favorability of, and/or stability of the interaction(s)) between the first molecular entity and the second molecular entity. In some embodiments, the first molecular entity and/or the second molecular entity is a protein of interest or a peptide of interest, and tagging comprises generating a fusion (or synthetic conjugation) of the first molecular entity and/or the second molecular entity with the first peptide tag and/or second peptide tag. In some embodiments, the first molecular entity and/or the second molecular entity is a small molecule, and tagging comprises directly or indirectly linking the first molecular entity and/or the second molecular entity with the first peptide tag and/or second peptide tag. In some embodiments, one of the first molecular entity and the second molecular entity is a drug or drug candidate, and the other is a drug target or candidate drug target, and the bioluminescent signal indicates binding of the drug or drug candidate to the other is a drug target or candidate drug target. In some embodiments, combining the tagged first molecular entity and the tagged second molecular entity comprises expressing one or both within a cell and/or adding one or both to a cell. In some embodiments, combining the tagged first molecular entity and the tagged second molecular entity is performed in vitro, in a non-cellular sample, etc. In some embodiments, the affinity of a drug or candidate drug for a drug target or candidate drug target is determined using the systems and methods herein by titrating unlabeled drug target or candidate drug target into the system. In some embodiments, two or more of steps (a)-(f) are performed concurrently. In some embodiments, two or more of steps (a)-(f) are performed separately.

In some embodiments, provided herein are method of performing a competition assay to detect an interaction between a first molecular entity and a second molecular entity, the method comprising: (a) combining: (i) a tracer comprising the first molecular entity tagged with a first peptide tag comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 23 and less than 100% sequence identity with SEQ ID NO: 6 and SEQ ID NO: 9, (ii) the second molecular entity tagged with a second peptide tag comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 25 and less than 100% sequence identity with SEQ ID NO: 7 and SEQ ID NO: 10, (iii) a coelenterazine or a coelenterazine analog substrate, (iv) a polypeptide component comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 17, SEQ ID NO: 21, or SEQ ID NO: 302 and less than 100% sequence identity with SEQ ID NO: 5 and SEQ ID NO: 8, and (v) a sample suspected of containing untagged first molecular entity; wherein the first peptide tag, the second peptide tag, and the polypeptide component are configured to produce a bioluminescent complex and produce a bioluminescent signal in the presence of the coelenterazine or a coelenterazine analog substrate; (b) detecting the bioluminescent signal produced by the bioluminescent complex; and (c) comparing the bioluminescent signal produced in the presence of the sample with a control bioluminescent signal produced in the absence of the sample, wherein a decrease in the bioluminescent signal indicates the presence or amount of untagged first molecular entity int the sample. In some embodiments, the first molecular entity is a small molecule or peptide (e.g., drug or candidate drug). In some embodiments, the second molecular entity is a drug target or candidate drug target (e.g., a protein).

In some embodiments, provided herein are methods of detecting an interaction between a first protein, peptide, or molecular entity and a second protein, peptide, or molecular entity within a cell comprising, the method comprising: (a) expressing within the cell (or adding to a cell or other system (e.g., non-cellular sample)), a fusion (e.g., genetic fusion, synthetic fusion, chemical conjugation, etc.) comprising the first protein, peptide, or molecular entity and a first peptide tag comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 23 and less than 100% sequence identity with SEQ ID NO: 6 and SEQ ID NO: 9; (b) expressing within the cell (or adding to a cell or other system (e.g., non-cellular sample)), a fusion (e.g., genetic fusion, synthetic fusion, chemical conjugation, etc.) comprising the second protein, peptide, or molecular entity and a second peptide tag comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 25 and less than 100% sequence identity with SEQ ID NO: 7 and SEQ ID NO: 10; (c) expressing with the cell (or adding to a cell or other system (e.g., non-cellular sample)), a polypeptide component comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 17, SEQ ID NO: 21, or SEQ ID NO: 302 and less than 100% sequence identity with SEQ ID NO: 5 and SEQ ID NO: 8, wherein the first peptide tag, the second peptide tag, and the polypeptide component are configured to produce a bioluminescent complex upon interaction of the first protein, peptide, or molecular entity and the second protein, peptide, or molecular entity; (d) adding a coelenterazine or a coelenterazine analog substrate to the cell; and (e) detecting a luminescent signal produced by the bioluminescent complex, wherein the magnitude of the luminescent signal correlates to the strength of the interaction between the first protein, peptide, or molecular entity and the second protein, peptide, or molecular entity. In some embodiments, two or more of steps (a)-(e) are performed concurrently. In some embodiments, two or more of steps (a)-(e) are performed separately.

In some embodiments, provided herein are methods of detecting co-localization of a first molecular entity and a second molecular entity, the method comprising: (a) tagging the first molecular entity with a first peptide tag comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 23 and less than 100% sequence identity with SEQ ID NO: 6 and SEQ ID NO: 9; (b) tagging the second molecular entity with a second peptide tag comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 25 and less than 100% sequence identity with SEQ ID NO: 7 and SEQ ID NO: 10; (c) combining the tagged first molecular entity and the tagged second molecular entity in the same system; (d) adding a polypeptide component to the system, the polypeptide components comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 17, SEQ ID NO: 21, or SEQ ID NO: 302 and less than 100% sequence identity with SEQ ID NO: 5 and SEQ ID NO: 8, wherein the first peptide tag, the second peptide tag, and the polypeptide component are configured to produce a bioluminescent complex upon co-localization of the first molecular entity and the second molecular entity; (e) adding a coelenterazine or a coelenterazine analog substrate to the system; and (f) detecting a luminescent signal produced by the bioluminescent complex, wherein the presence of luminescent signal above background indicates co-localization of the first molecular entity and the second molecular entity within the system, and/or wherein the magnitude of the luminescent signal correlates to the amount of co-localization within the system of the first molecular entity and the second molecular entity. In some embodiments, the system comprises a cell, tissue, organ, or whole organism. In some embodiments, the first molecular entity and/or the second molecular entity is a protein of interest or a peptide of interest, and tagging comprises generating a fusion (e.g., genetic fusion, synthetic fusion, chemical conjugation, enzymatic conjugation, etc.) of the first molecular entity and/or the second molecular entity with the first peptide tag and/or second peptide tag. In some embodiments, the first molecular entity and/or the second molecular entity is a small molecule and tagging comprises directly or indirectly linking the first molecular entity and/or the second molecular entity with the first peptide tag and/or second peptide tag. In some embodiments, combining the tagged first molecular entity and the tagged second molecular entity is performed in vitro, in a non-cellular sample, etc. In some embodiments, combining the tagged first molecular entity and the tagged second molecular entity comprises expressing one or both within the system and/or adding one or both to the system. In some embodiments, two or more of steps (a)-(f) are performed concurrently. In some embodiments, two or more of steps (a)-(f) are performed separately.

In some embodiments, provided herein are methods of detecting co-localization of a first protein, peptide, or molecular entity and a second protein, peptide, or molecular entity within a cell the method comprising: (a) expressing within the cell a fusion comprising the first protein or peptide entity and a first peptide tag comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 23 and less than 100% sequence identity with SEQ ID NO: 6 and SEQ ID NO: 9; (b) expressing within the cell a fusion comprising the second protein or peptide entity and a second peptide tag comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 25 and less than 100% sequence identity with SEQ ID NO: 7 and SEQ ID NO: 10; (c) expressing with the cell a polypeptide component comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 17, SEQ ID NO: 21, and/or SEQ ID NO: 302 and less than 100% sequence identity with SEQ ID NO: 5 and SEQ ID NO: 8, wherein the first peptide tag, the second peptide tag, and the polypeptide component are configured to produce a bioluminescent complex upon co-localization of the first protein or peptide entity and the second protein or peptide entity; (d) adding a coelenterazine or a coelenterazine analog substrate to the cell; and (e) detecting a luminescent signal produced by the bioluminescent complex, wherein the presence of luminescent signal above background indicates co-localization of the first protein or peptide entity and the second protein or peptide entity within the cell, and/or wherein the magnitude of the luminescent signal correlates to the amount of co-localization within the system of the first protein or peptide entity and the second protein or peptide entity. In some embodiments, two or more of steps (a)-(e) are performed concurrently. In some embodiments, two or more of steps (a)-(e) are performed separately.

In some embodiments, provided herein are kits comprising: (a) a first binding moiety conjugated to a first peptide tag comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 23 and less than 100% sequence identity with SEQ ID NO: 6 and SEQ ID NO: 9; and (b) a second binding moiety conjugated to second peptide tag comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 25 and less than 100% sequence identity with SEQ ID NO: 7 and SEQ ID NO: 10. In some embodiments, the first and second binding moieties are independently selected from the group consisting of an antibody (e.g., polyclonal, monoclonal, and/or recombinant), antibody fragment, protein A, an Ig binding domain of protein A, protein G, an Ig binding domain of protein G, protein A/G, an Ig binding domain of protein A/G, protein L, an Ig binding domain of protein L, protein M, an Ig binding domain of protein M, oligonucleotide probe, peptide nucleic acid, DARPin, aptamer, affimer, a purified protein (either the analyte itself or a protein that binds to the analyte), and analyte binding domain(s) of proteins. In some embodiments, the first and second binding moieties are primary binding moieties configured to bind to antigens, epitopes, or sequences on the same target entity. In some embodiments, the first and second binding moieties are secondary binding moieties configured to bind to antigens, epitopes, or sequences on primary binding moieties. In some embodiments, kits further comprise a polypeptide reagent comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 17, SEQ ID NO: 21, and/or SEQ ID NO: 302 and less than 100% sequence identity with SEQ ID NO: 5 and SEQ ID NO: 8. In some embodiments, kits further comprise a coelenterazine or a coelenterazine analog.

In some embodiments, provided herein are methods of detecting a target molecule, wherein the target molecule displays a first antigen, epitope, or sequence and a distinct second antigen, epitope, or sequence the method comprising: (a) contacting a sample containing the target molecule with (i) a first primary binding moiety that recognizes the first antigen, epitope, or sequence and (ii) a second primary binding moiety that recognizes the second antigen, epitope, or sequence and allowing the first and second primary binding moieties to bind to the first and second antigens, epitopes, or sequences; (b) contacting the sample with (i) a first secondary binding moiety conjugated or fused to a first peptide tag and (ii) a second secondary binding moiety conjugated or fused to second peptide tag, wherein the first secondary binding moiety recognizes the first primary binding moiety and the second secondary binding moiety recognizes the second primary binding moiety, wherein the first or second peptide tag comprises an amino acid sequence having 40% or greater (e.g., 40%, 45%, 50%, 55%, 60%, 65%, 70%, 75%, 80%, 85%, 90%, 95%, or more) sequence identity with SEQ ID NO: 23 (and less than 100% sequence identity with SEQ ID NO: 6 and SEQ ID NO: 9), and wherein the other of the first or second peptide tag comprises an amino acid sequence having 40% or greater (e.g., 40%, 45%, 50%, 55%, 60%, 65%, 70%, 75%, 80%, 85%, 90%, 95%, or more) sequence identity with SEQ ID NO: 25 (and less than 100% sequence identity with SEQ ID NO: 7 and SEQ ID NO: 10), and allowing the first and second secondary binding moieties to bind to the first and second primary binding moieties; (c) contacting the sample with comprising an polypeptide component having 40% or greater (e.g., 40%, 45%, 50%, 55%, 60%, 65%, 70%, 75%, 80%, 90%, 95%, or more) sequence identity with SEQ ID NO: 17, SEQ ID NO: 21, and/or SEQ ID NO: 302 (and less than 100% sequence identity with SEQ ID NO: 5 and SEQ ID NO: 8), wherein the first peptide tag, the second peptide tag, and the polypeptide component are configured to produce a bioluminescent complex upon interaction; (d) contacting the sample with a coelenterazine or a coelenterazine analog substrate; and (e) detecting a luminescent signal produced by the bioluminescent complex, wherein the presence of luminescent signal above background indicates the presence of the target molecule, and/or wherein the magnitude of the luminescent signal correlates to the amount of target molecule within the sample. In some embodiments, the binding moieties are independently selected from the group consisting of an antibody (polyclonal, monoclonal, and/or recombinant), antibody fragment, protein A, an Ig binding domain of protein A, protein G, an Ig binding domain of protein G, protein A/G, an Ig binding domain of protein A/G, protein L, an Ig binding domain of protein L, protein M, an Ig binding domain of protein M, oligonucleotide probe, peptide nucleic acid, DARPin, aptamer, affimer, a purified protein (either the analyte itself or a protein that binds to the analyte), and analyte binding domain(s) of proteins. In some embodiments, the target molecule is a protein, peptide, nucleic acid, chemical, or drug. In some embodiments, the sample is in vitro or in vivo.

In some embodiments, provided herein are methods of detecting a target molecule, wherein the target molecule displays a first antigen, epitope, or sequence and a distinct second antigen, epitope, or sequence, the method comprising: (a) contacting the sample with (i) a first binding moiety conjugated or fused to a first peptide tag and (ii) a second binding moiety conjugated or fused to second peptide tag, wherein the first binding moiety recognizes the first antigen, epitope, or sequence and the second binding moiety recognizes the second antigen, epitope, or sequence, wherein the first or second peptide tag comprises an amino acid sequence having 40% or greater (e.g., 40%, 45%, 50%, 55%, 60%, 65%, 70%, 75%, 80%, 85%, 90%, 95%, or more) sequence identity with SEQ ID NO: 23 (and less than 100% sequence identity with SEQ ID NO: 6 and SEQ ID NO: 9), and wherein the other of the first or second peptide tag comprises an amino acid sequence having 40% or greater (e.g., 40%, 45%, 50%, 55%, 60%, 65%, 70%, 75%, 80%, 85%, 90%, 95%, or more) sequence identity with SEQ ID NO: 25 (and less than 100% sequence identity with SEQ ID NO: 7 and SEQ ID NO: 10), and allowing the first and second binding moieties to bind to the first and second antigens, epitopes, or sequences; (c) contacting the sample with a polypeptide component having 40% or greater (e.g., 40%, 45%, 50%, 55%, 60%, 65%, 70%, 75%, 80%, 85%, 90%, 95%, or more) sequence identity with SEQ ID NO: 17, SEQ ID NO: 21, and/or SEQ ID NO: 302 (and less than 100% sequence identity with SEQ ID NO: 5 and SEQ ID NO: 8), wherein the first peptide tag, the second peptide tag, and the polypeptide component are configured to produce a bioluminescent complex upon interaction; (d) contacting the sample with a coelenterazine or a coelenterazine analog substrate; and (e) detecting a luminescent signal produced by the bioluminescent complex, wherein the presence of luminescent signal above background indicates the presence of the target molecule, and/or wherein the magnitude of the luminescent signal correlates to the amount of target molecule within the sample. In some embodiments, the binding moieties are independently selected from the group consisting of an antibody (polyclonal, monoclonal, and/or recombinant), antibody fragment, protein A, an Ig binding domain of protein A, protein G, an Ig binding domain of protein G, protein A/G, an Ig binding domain of protein A/G, protein L, an Ig binding domain of protein L, protein M, an Ig binding domain of protein M, oligonucleotide probe, peptide nucleic acid, DARPin, aptamer, affimer, a purified protein (either the analyte itself or a protein that binds to the analyte), and analyte binding domain(s) of proteins. In some embodiments, the target molecule is a protein, peptide, nucleic acid, chemical, or drug. In some embodiments, the sample is in vitro or in vivo.

In some embodiments, provided herein are methods comprising: (a) combining: (i) a peptide component comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 35 and less than 100% sequence identity with SEQ ID NO: 205 and SEQ ID NO: 206, (ii) a polypeptide component comprising an amino acid sequence having 40% or greater (e.g., 40%, 45%, 50%, 55%, 60%, 65%, 70%, 75%, 80%, 85%, 90%, 95%, or more) sequence identity with SEQ ID NO: 17, SEQ ID NO: 21, and/or SEQ ID NO: 302 and less than 100% sequence identity with SEQ ID NO: 5 and SEQ ID NO: 8, and (iii) a coelenterazine or a coelenterazine analog substrate, wherein the peptide component and the polypeptide component are configured to produce a bioluminescent complex upon interaction; and (b) detecting luminescence, wherein a greater level of luminescence compared to a level of luminescence produced by the polypeptide component and a coelenterazine or a coelenterazine analog alone indicates formation of a bioluminescent complex of the polypeptide component with the peptide. In some embodiments, the peptide is a fusion (e.g., genetic, synthetic, chemical conjugate, enzymatic conjugate, etc.) with a first interaction element, and the polypeptide component is a fusion (e.g., genetic, synthetic, chemical conjugate, enzymatic conjugate, etc.) with a second interaction element, wherein the peptide and the polypeptide component form a bioluminescent complex upon interaction of the interaction elements, but do not form a bioluminescent complex in the absence of an interaction between the interaction elements. In some embodiments, the peptide and the polypeptide component form a bioluminescent complex in the absence of facilitation (e.g., by interaction elements). In some embodiments, the peptide is a fusion or conjugate (e.g., genetic, synthetic, chemical conjugate, enzymatic conjugate, etc.) with a protein, peptide, or molecule of interest (e.g., not an interaction element) and/or the polypeptide component is a fusion or conjugate (e.g., genetic, synthetic, chemical conjugate, enzymatic conjugate, etc.) with a protein, peptide, or molecule of interest (e.g., not an interaction element). In some embodiments, the peptide component and the polypeptide component form a bioluminescent complex upon co-localization (e.g., in a sample, in a cell, in a tissue, in a subject, etc.) without facilitation by interaction elements. In some embodiments, the peptide component and the polypeptide component form a bioluminescent complex upon facilitation by interaction elements but not without facilitation.

BRIEF DESCRIPTION OF THE DRAWINGS

FIG. 5. Graph depicting the relative stability of amino acid changes at position 42 of LgTrip 2098 mutants.

FIG. 10A-C. Graphs depicting (A) titration of various LgTrip variants with SmTrip9 pep286 (SEQ ID NO: 37), (B) titration of various LgTrip variants with SmTrip10 pep86 (SEQ ID NO: 25), and (C) the affinity of various LgTrip variants for SmTrip9 pep286 and SmTrip10 pep86.

FIG. 14A-B. Graphs comparing the stability at 37° C. of LgBIT (SEQ ID NO: 11) and LgTrip 2098 (WT) (SEQ ID NO: 31 in (A) TBS+0.01% BSA and (B) Passive Lysis Buffer (PLB).

FIG. 18A-B. Graphs comparing LgBIT (SEQ ID NO: 11), NanoLuc (SEQ ID NO: 3), and LgTrip 3546 (SEQ ID NO: 51) and LgTrip 2098 (WT) (SEQ ID NO: 31) variants (A) at varying pH and (B) after 26 hour exposure to varying pH.

FIG. 19. Graph comparing the autoluminescence of LgBIT (SEQ ID NO: 11) and LgTrip 3546 (SEQ ID NO: 51).

FIG. 25A-B. (A) Graph depicting luminescence resulting from complementation of various combinations of polypeptide components (with additions or deletions relative to LgTrip 3546) with SmTrip9 pep286 (SEQ ID NO: 37) and various β10-like peptides (SmTrip10 peptides); (B) Graph depicting luminescence resulting from complementation of LgTrip 3546 (SEQ ID NO: 51) and SmTrip9 pep286 (SEQ ID NO: 37) with various β10-like peptides (SmTrip10 peptides).

FIG. 33. Graph and table depicting luminescence from combinations of components having varied split sites between the polypeptide component LgTrip 3546 (SEQ ID NO: 51) and the β9-like peptide.

FIG. 35. Graph depicting luminescence from NanoTrip component combinations with gaps and/or overlaps in sequence between the β9-like peptides (SmTrip9 peptides) and polypeptide component LgTrip 3546 (SEQ ID NO: 51) in the presence of SmTrip10 pep86 (HiBiT; SEQ ID NO: 25).

FIG. 36. Table depicting a biochemical analysis of β9-like peptide (SmTrip9 peptides) length influence on β9-like peptide affinity and maximum light output with LgTrip 3546 (SEQ ID NO: 51) and SmTrip10 pep86.

FIG. 37. Table depicting a biochemical analysis of β9-like peptide (SmTrip9 peptides) length influence on HiBiT affinity and maximum light output with LgTrip 3546 (SEQ ID NO: 51) and SmTrip10 pep86 (SEQ ID NO: 25).

FIG. 38. Table depicting Kd and Bmax of β9-like SmTrip9 pep286 (SEQ ID NO: 37) point mutants with LgTrip 3546 (SEQ ID NO: 51) and SmTrip10 pep86 (SEQ ID NO: 25).

FIG. 39. Table depicting the effect of various solubility tags on β9-like peptide affinity with LgTrip 3546 (SEQ ID NO: 51) and SmTrip9 pep86 (SEQ ID NO: 25).

FIG. 40. Table depicting the effect of various C-terminal extension sequences on β9-like or β10-like peptide affinity and maximum light output. β9-like peptide titrations (pep286 (SEQ ID NO: 37), pep292 (SEQ ID NO: 153), pep297 (SEQ ID NO: 157), pep302 (SEQ ID NO: 161)) and β10-like peptide SmTrip10 pep86 (HiBIT; SEQ ID NO: 25) are depicted.

FIG. 46. Graph depicting the effect of β9 sequence truncations, extensions, and construct orientation (β9-FKBP or FKBP-β9) on facilitated complementation with FRB-SmTrip10 pep289 (β10) (SEQ ID NO 150) in *E. coli* lysates with LgTrip 3546 (SEQ ID NO: 51).

Figure 45:
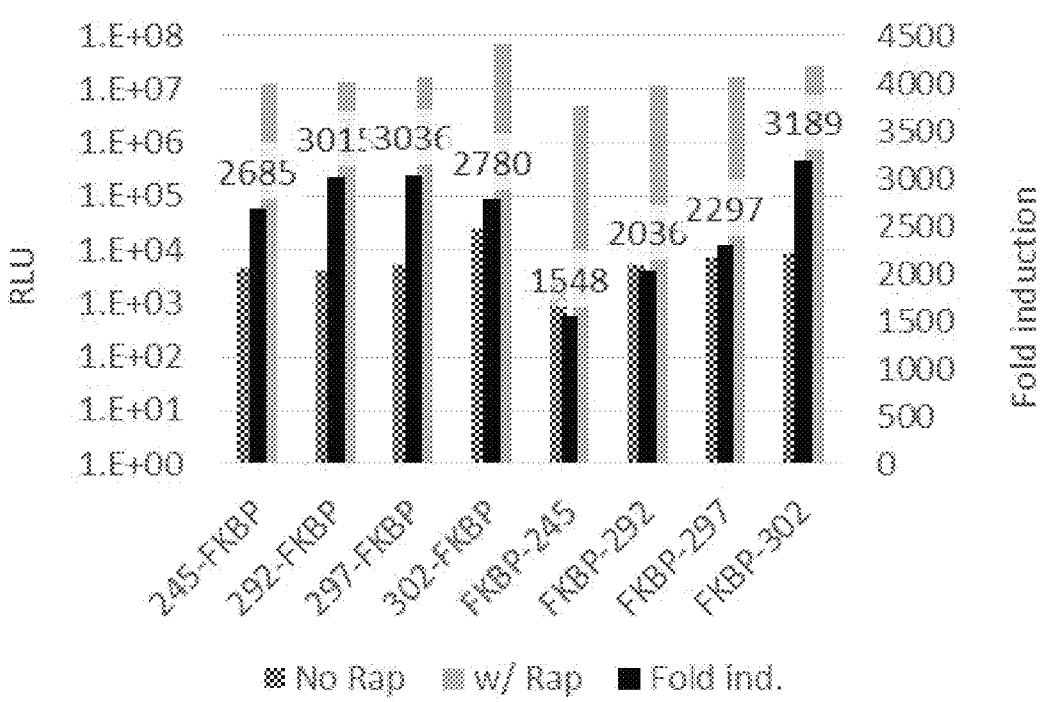
FIG. 45. Graph depicting the effect of β9 sequence truncations, extensions, and construct orientation (β9-FKBP or FKBP-β9) on facilitated complementation with FRB-SmTrip10 pep86 (β10) (SEQ ID NO: 25) in *E. coli* lysates with LgTrip 3546 (SEQ ID NO: 51).
Figure 47:
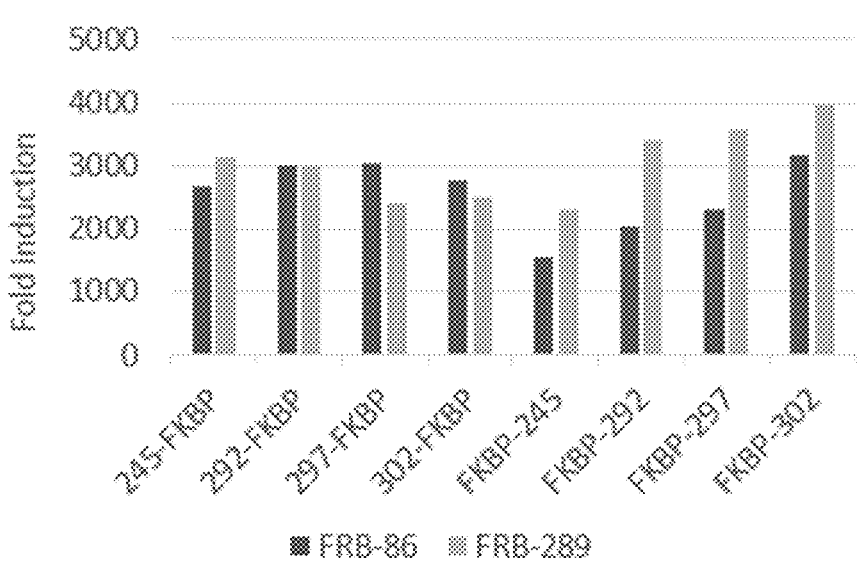
FIG. 47. Graph depicting the effect of β9 sequence truncations, extensions, and construct orientation (β9-FKBP or FKBP-β9) on fold induction (facilitated complementation/spontaneous complementation) with FRB-β10 (SmTrip10 pep86 (SEQ ID NO: 25) or SmTrip10 pep289

(SEQ ID NO: 150)) in *E. coli* lysates (Summary of FIGS. 45 and 46) with LgTrip 3546 (SEQ ID NO: 51).

Figure 48:
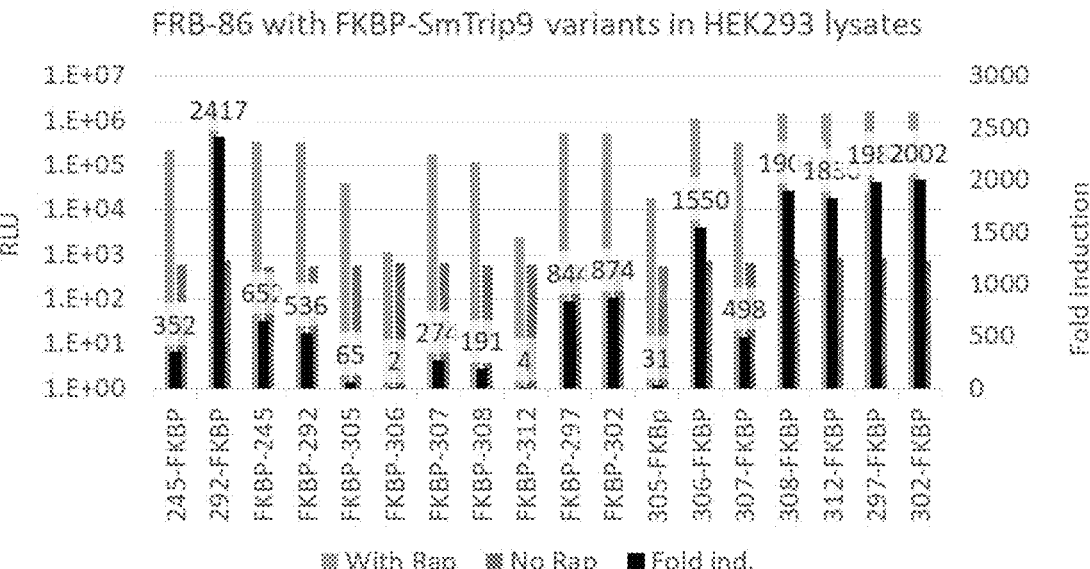

FIG. 48. Graph depicting the effect of β9 sequence truncations and extensions and construct orientation (β9-FKBP or FKBP-β9) on facilitated complementation with FRB-SmTrip10 pep86 (SEQ ID NO: 25) in HEK293 lysates with LgTrip 3546 (SEQ ID NO: 51).

Figure 49:
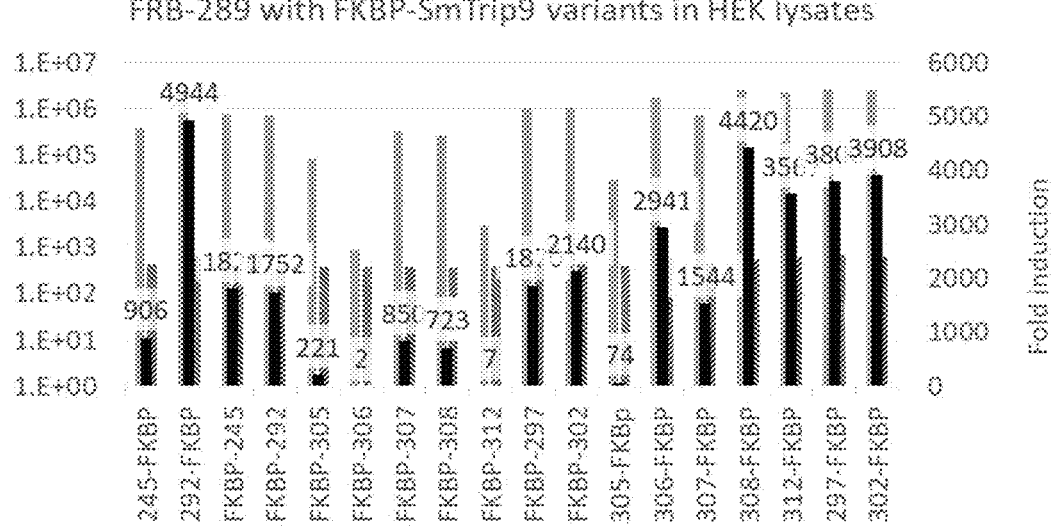

FIG. 49. Graph depicting the effect of β9 sequence truncations and extensions and construct orientation (β9-FKBP or FKBP-β9) on facilitated complementation with FRB-SmTrip10 pep289 (SEQ ID NO: 150) in HEK293 lysates. (LgTrip 3546 (SEQ ID NO: 51).

Figure 50:
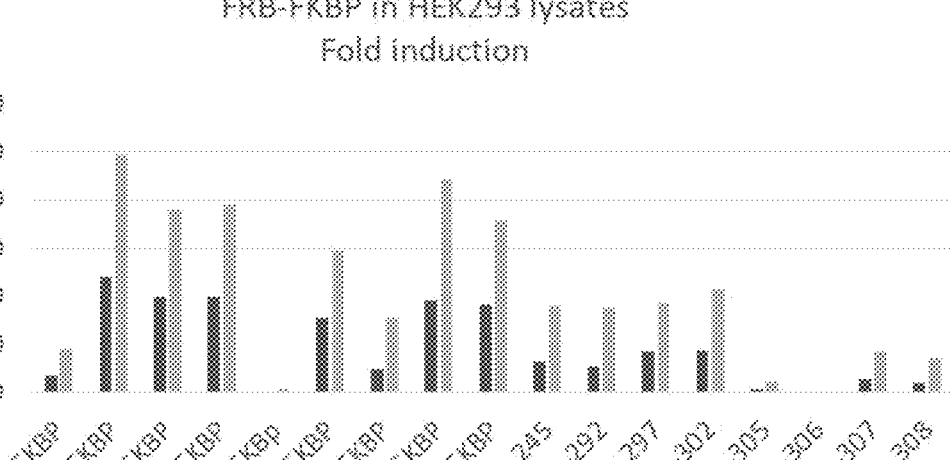
Figures 51E, 51F:
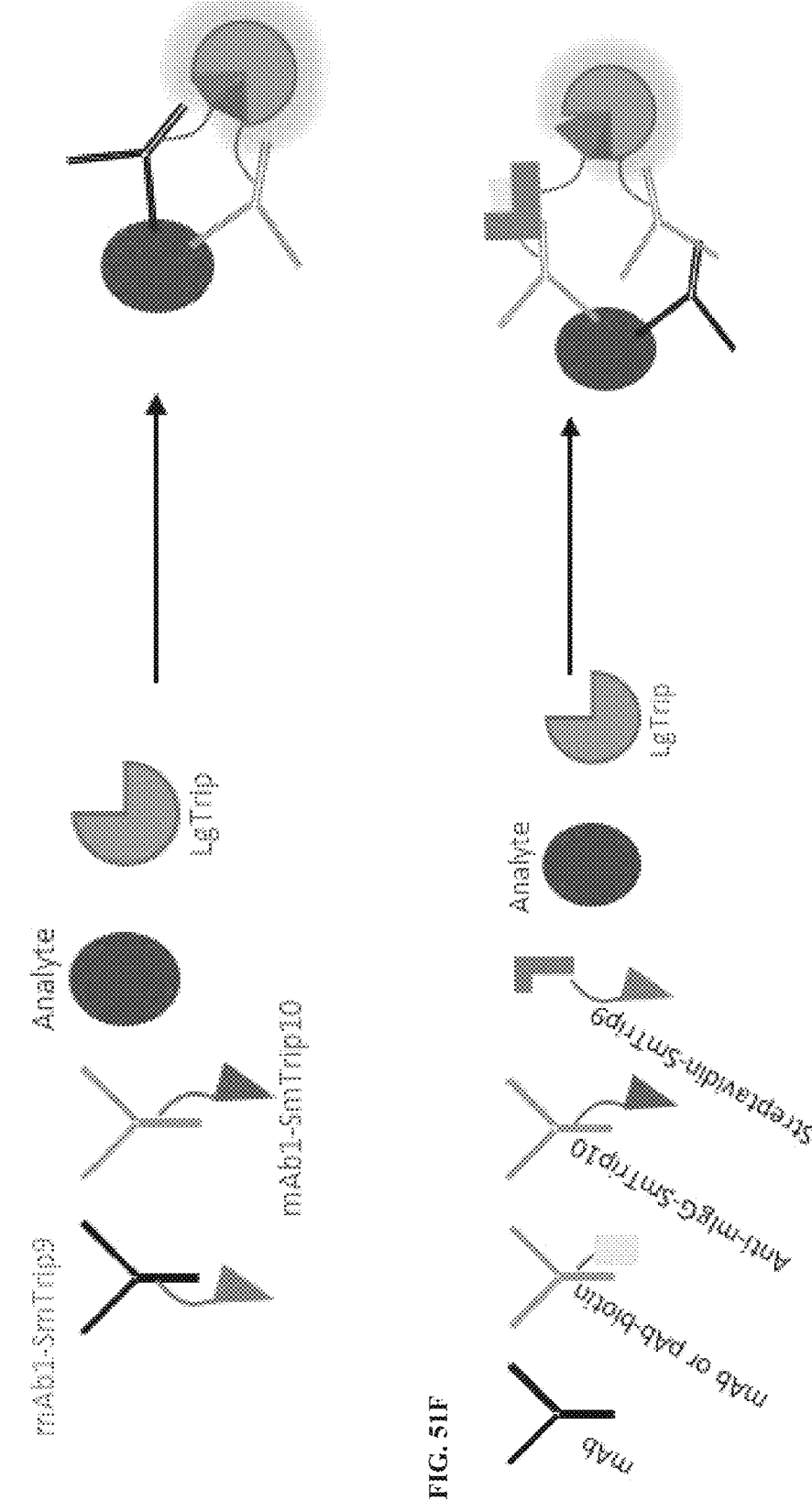
Figures 51G, 51H:
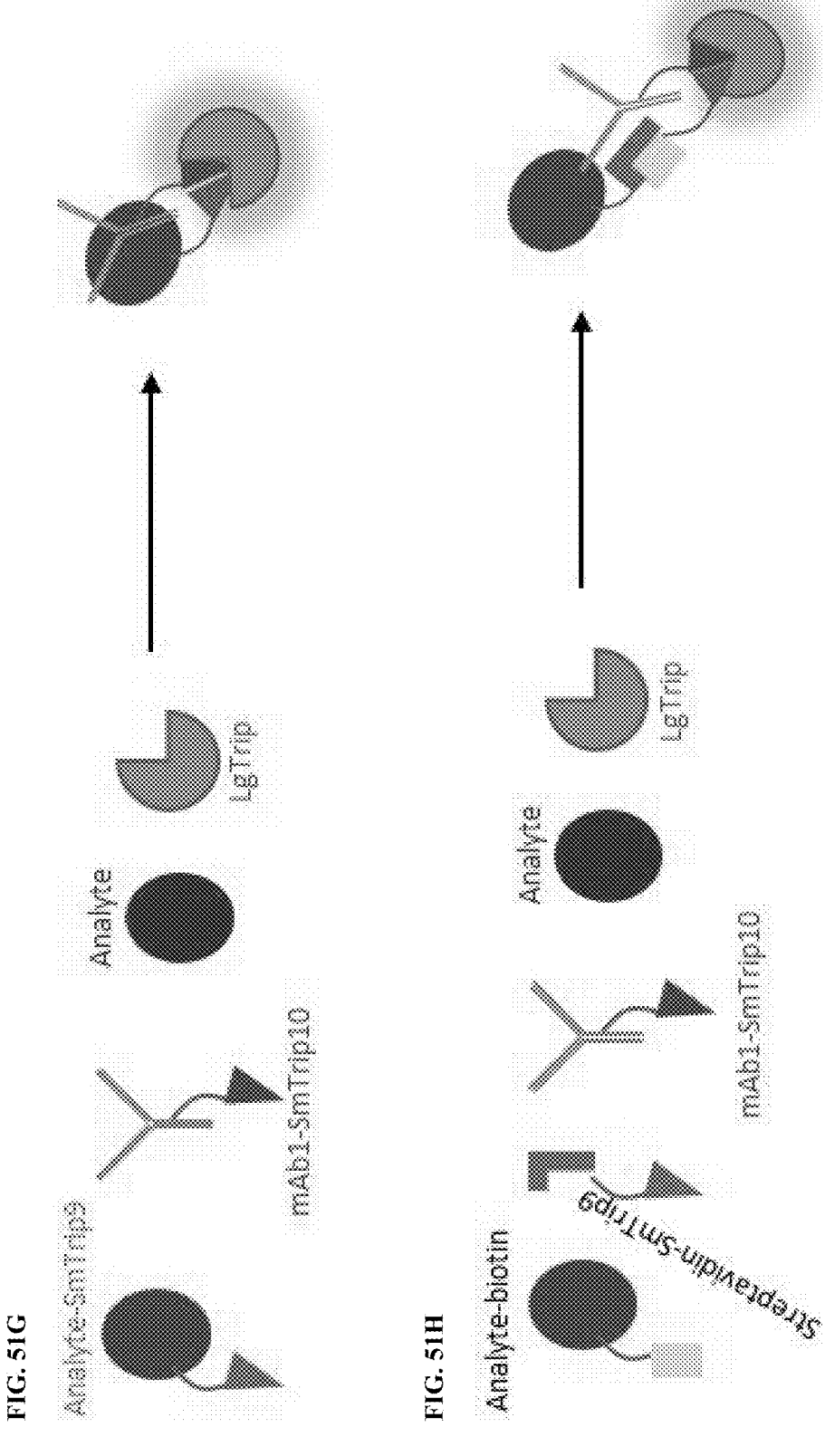

FIG. 50. Graph depicting the effect of β9 sequence truncations, extensions, and construct orientation (β9-FKBP or FKBP-β9) on fold induction (facilitated complementation/spontaneous complementation) with FRB-β10 (SmTrip10 pep86 (SEQ ID NO: 25) or SmTrip10pep289 (SEQ ID NO: 150)) in HEK293 lysates (Summary of FIGS. 48 and 49). (LgTrip 3546 (SEQ ID NO: 51)).

Figures 51A, 51B:
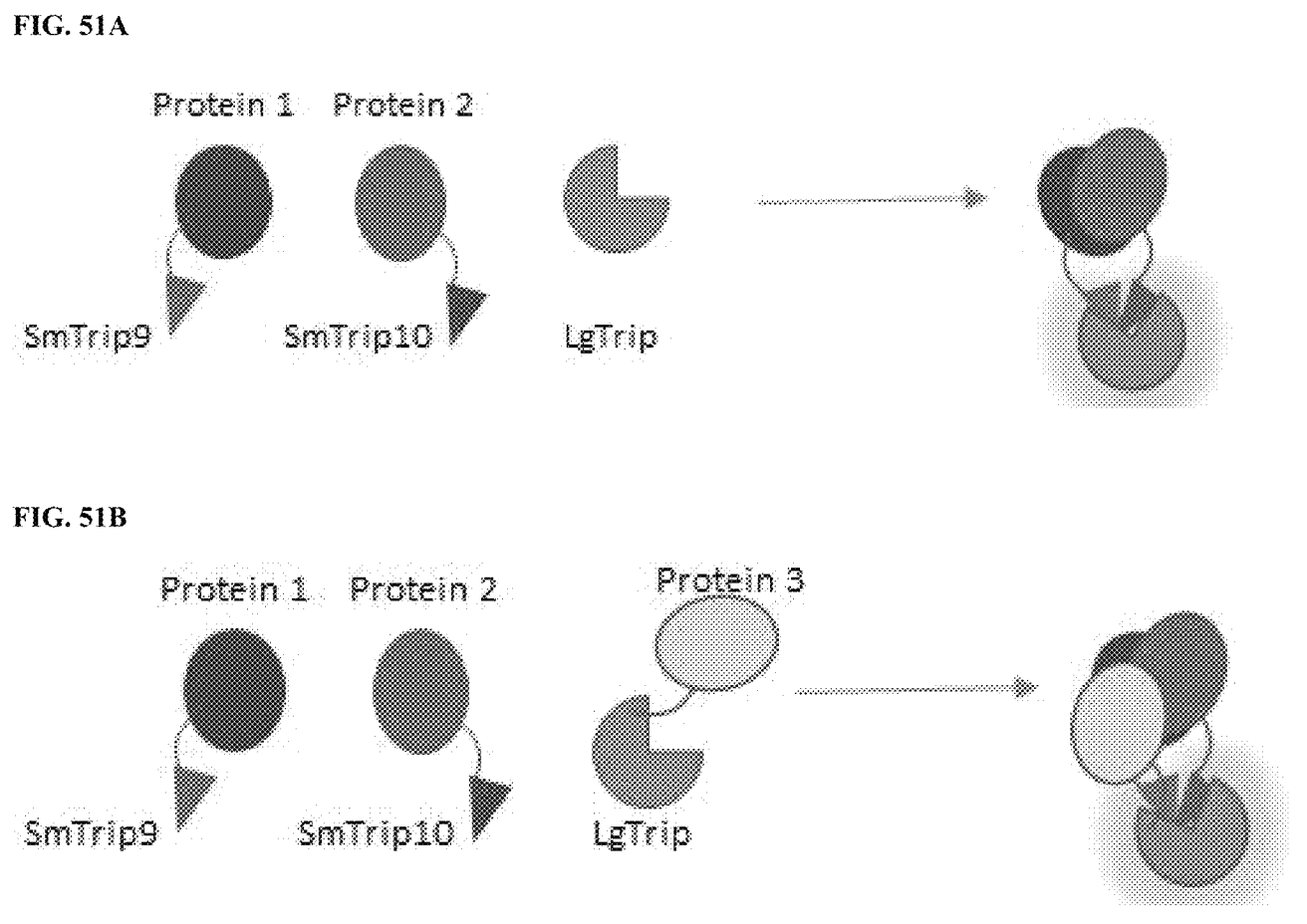
Figures 51C, 51D:
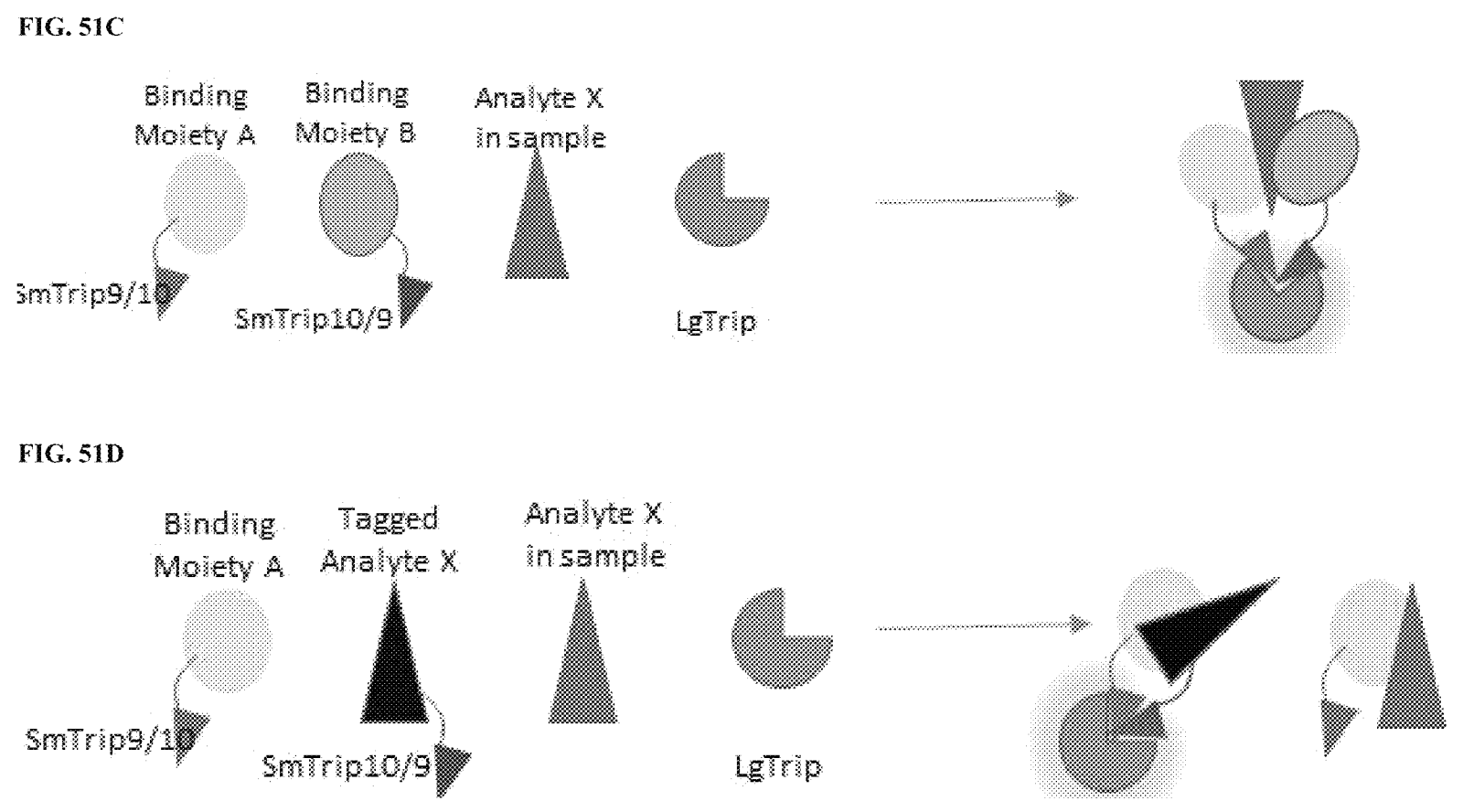

FIG. 51A-D. Schematic illustrations depicting exemplary protein-protein interaction assays or analyte detection assays using binding moieties tagged with peptides.

FIG. 51E-H. Schematic illustrations depicting exemplary immunoassays using components and reagents described herein: (A) direct immunoassay, (B) indirect immunoassay, (C) competition direct immunoassay, and (D) competition indirect immunoassay.

Figure 52:
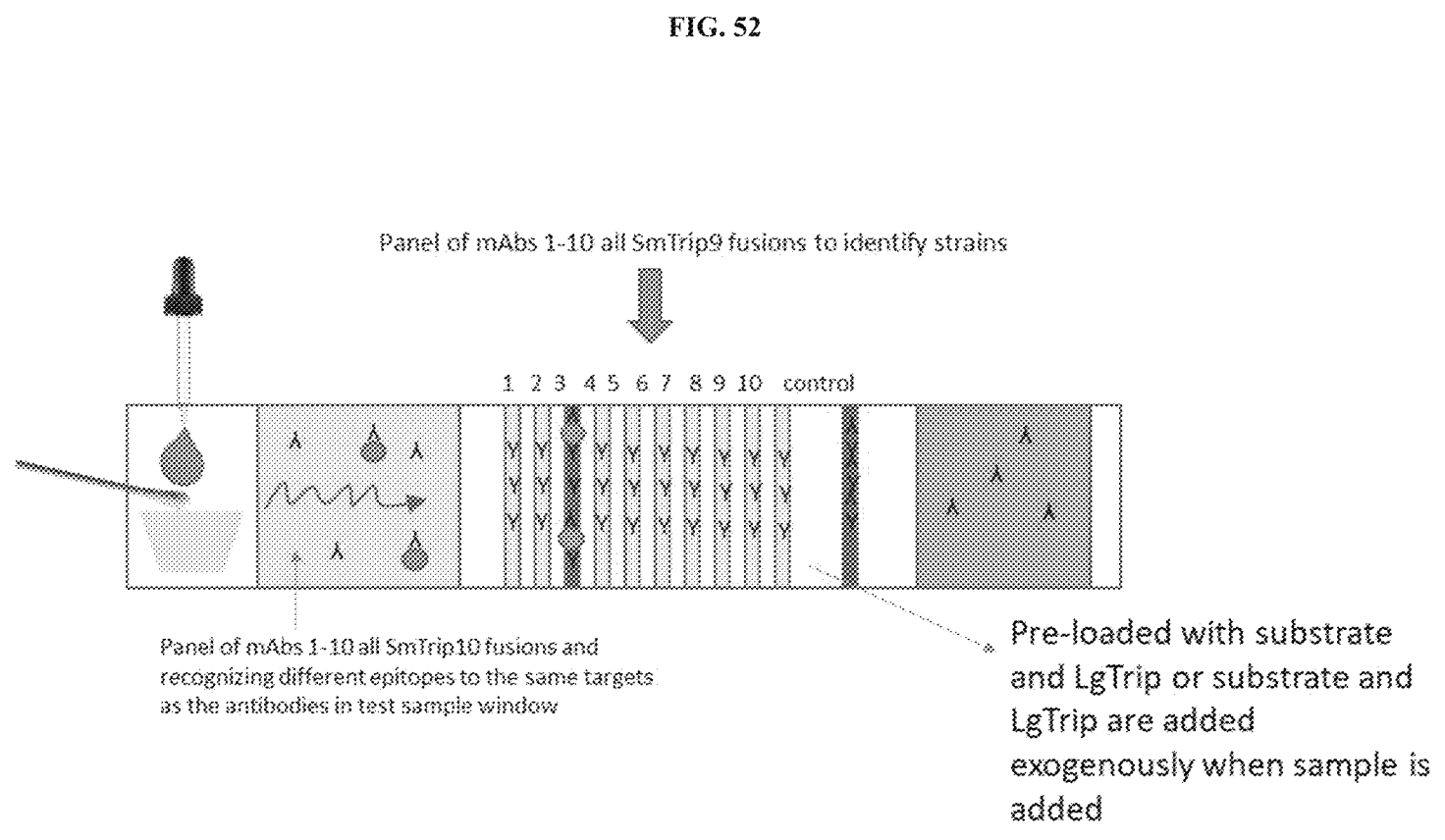

FIG. 52. Schematic illustration of an exemplary multiplexed tripartite lateral flow assay. Such an assay finds use, for example, in the detection of pathogens.

Figure 53:
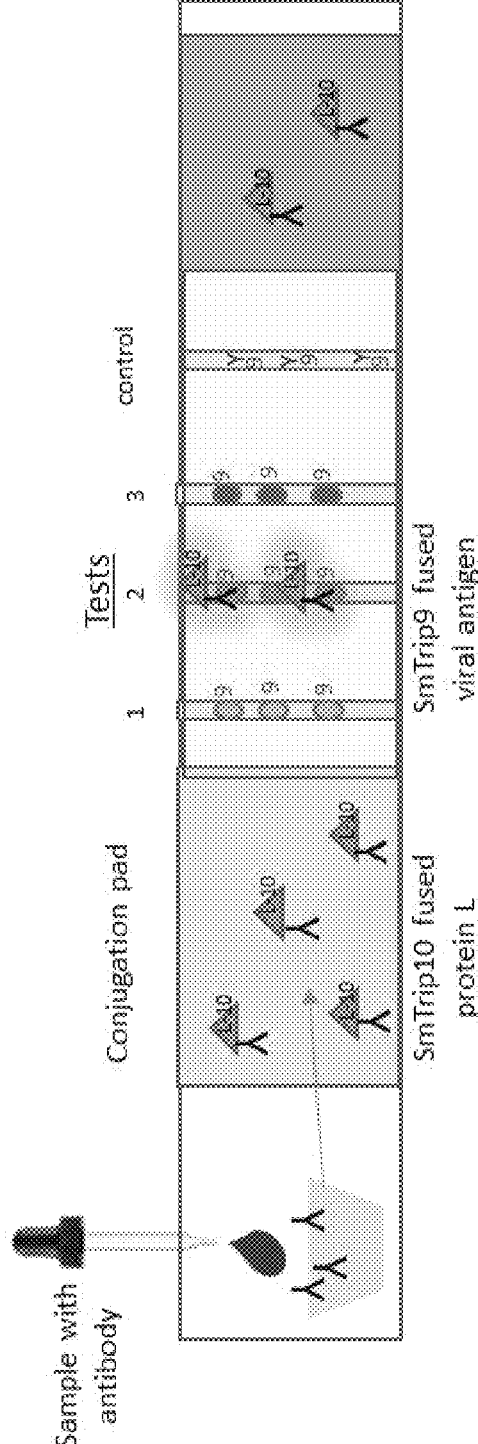

FIG. 53. Schematic illustration of an exemplary multiplexed tripartite lateral flow assay. Such an assay finds use, for example, in the detection of antiviral antibodies.

Figure 54:
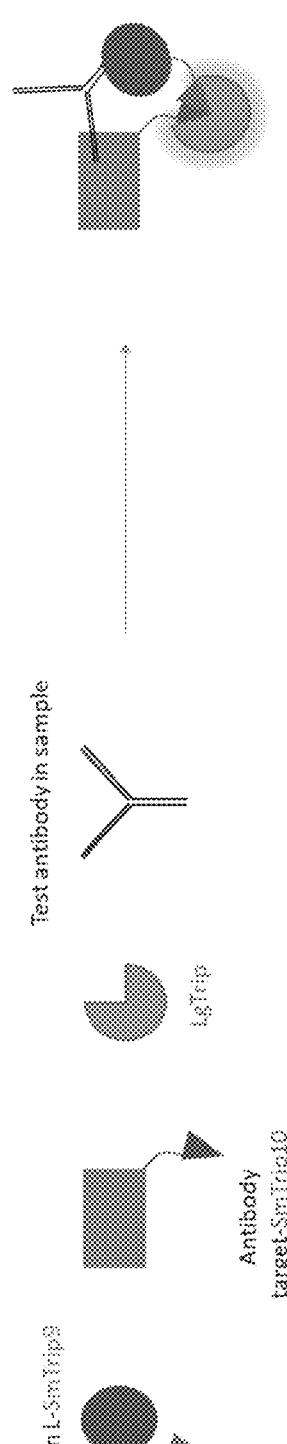

FIG. 54. Schematic illustration of an exemplary antibody detection assay.

Figure 55:
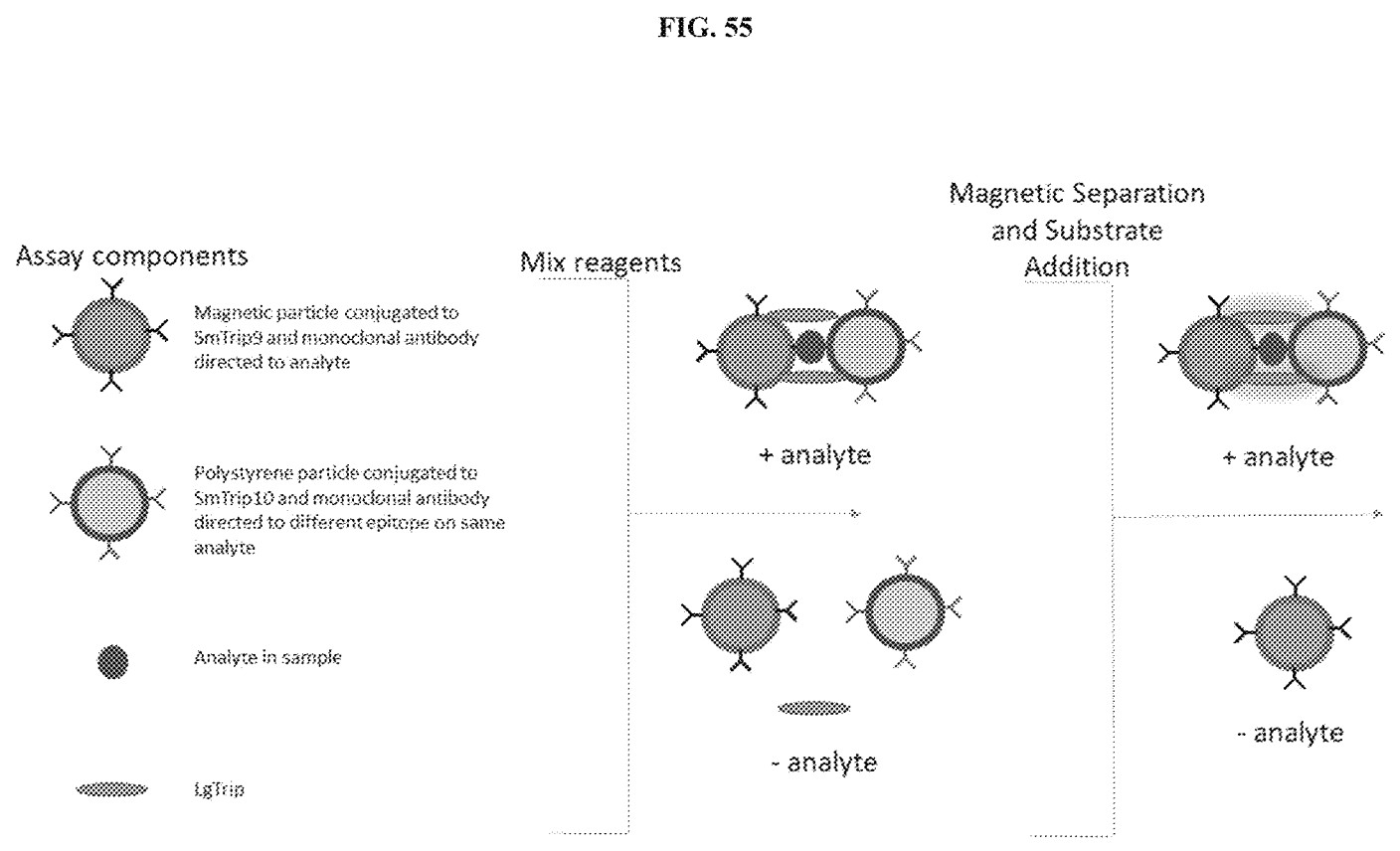

FIG. 55. Schematic illustration of an exemplary bead-based assay.

Figure 56:
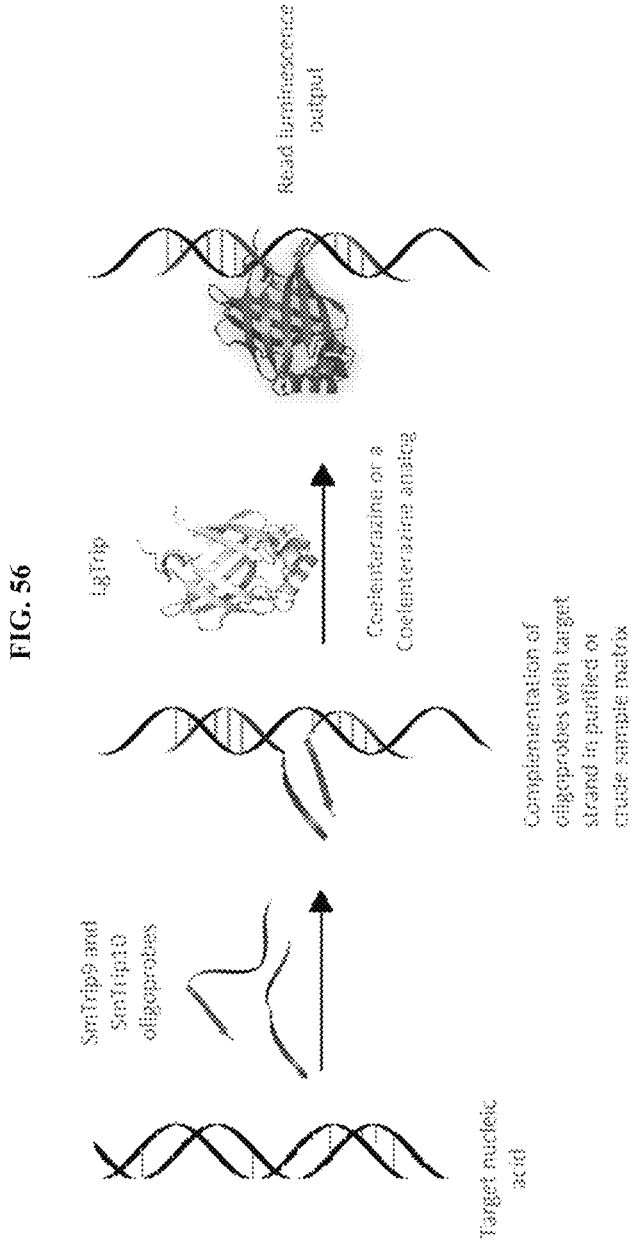

FIG. 56. Schematic illustration of an exemplary nucleic acid detection assay.

Figure 57:
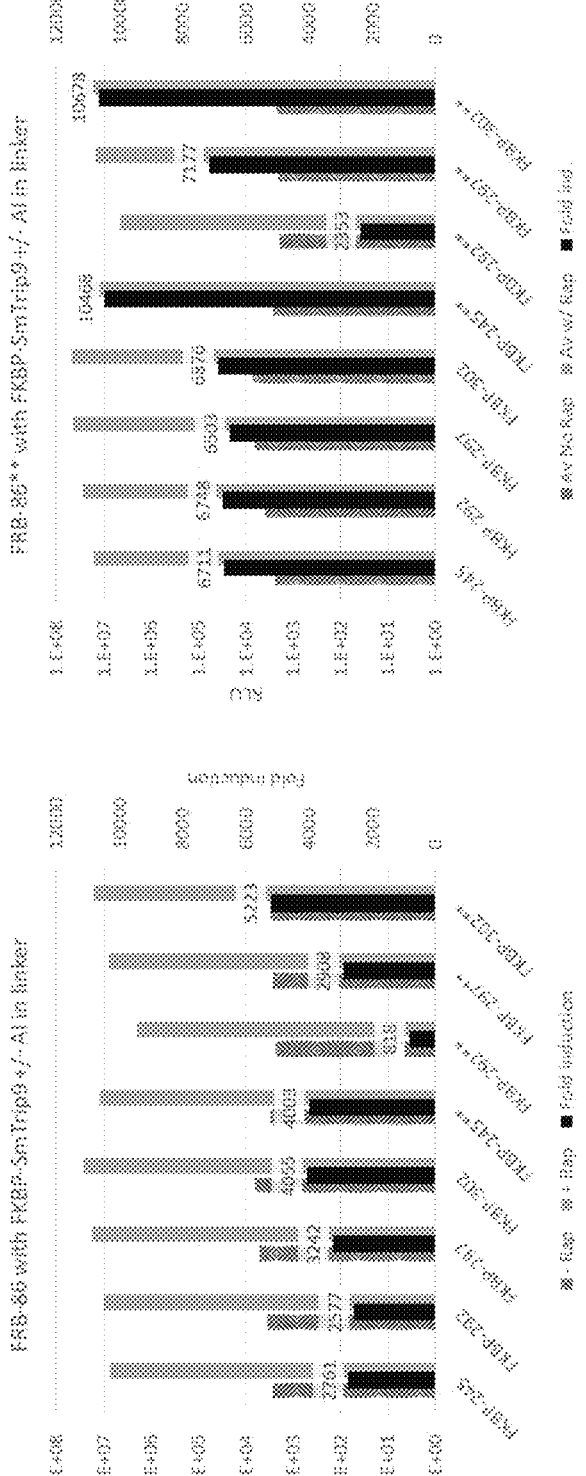

FIG. 57. Graph depicting FRB-FKBP facilitated complementation in *E. coli* lysates with AI (Ala-Ile) dipeptide absent from linker in constructs denoted by **. (LgTrip 3546 (SEQ ID NO: 51)).

Figure 58:
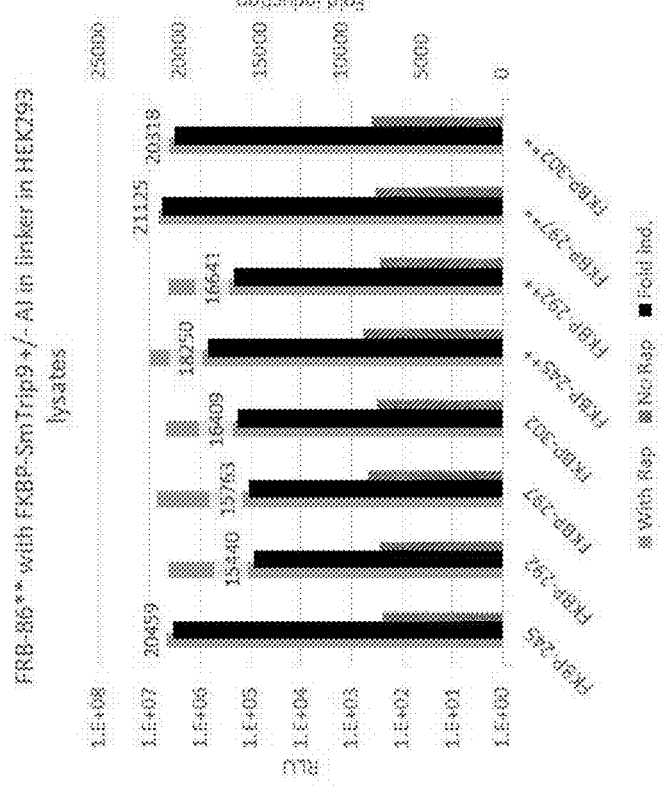

FIG. 58. Graph depicting FRB-FKBP facilitated complementation in HEK293 lysates with AI sequence dipeptide absent from linker in constructs denoted by **. (LgTrip 3546 (SEQ ID NO: 51)).

Figure 59:
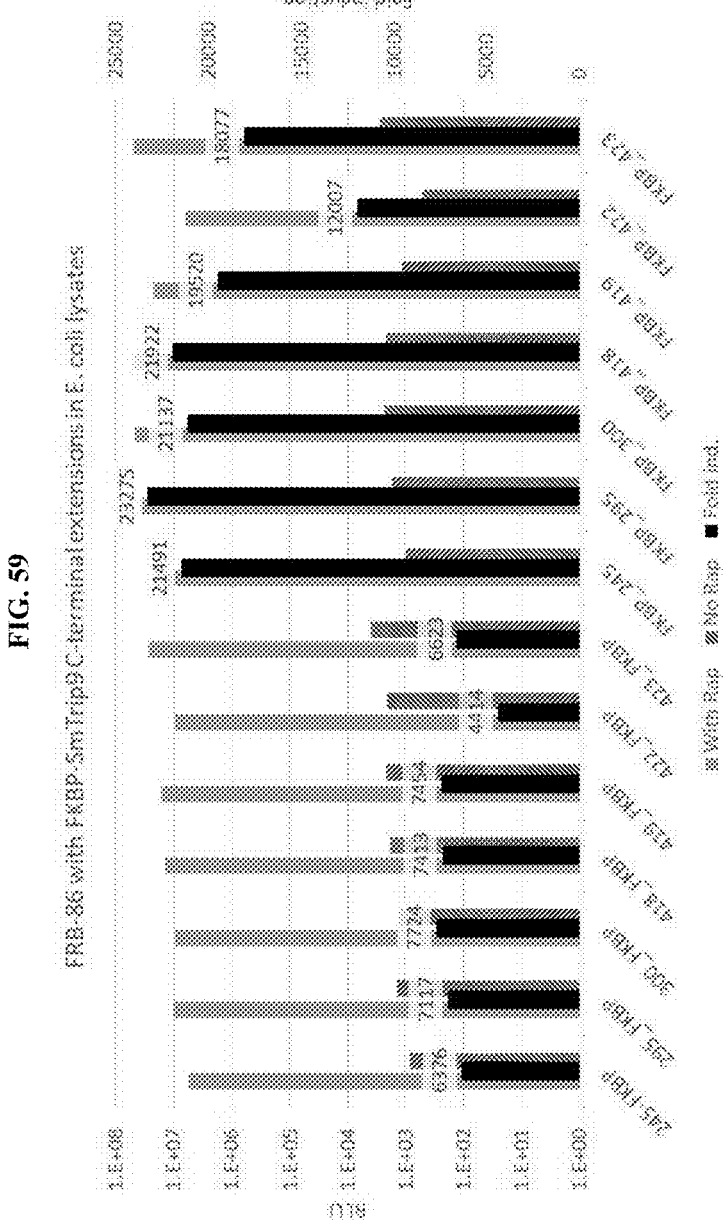

FIG. 59. Graph depicting FRB-FKBP facilitation of luminescent complex formation with FRB-SmTrip10 pep86 and C-terminally extended FKBP-SmTrip9 peptides in *E. coli* lysate. (LgTrip 3546 (SEQ ID NO: 51)).

Figure 60:
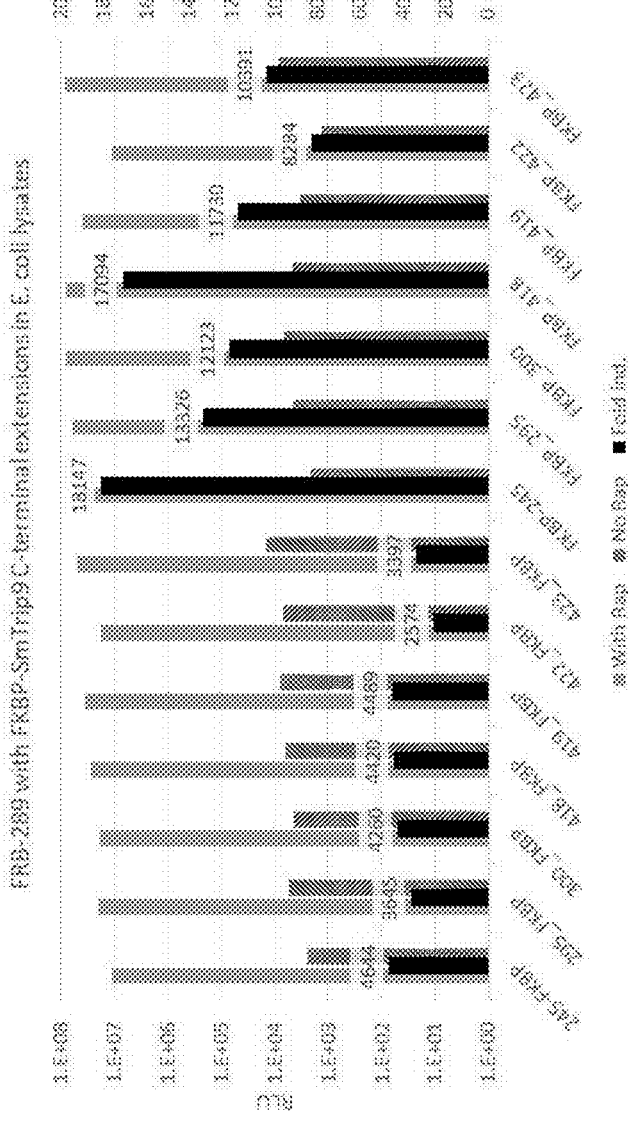

FIG. 60. Graph depicting FRB-FKBP facilitation of luminescent complex formation with FRB-SmTrip10 pep289 and C-terminally extended FKBP-SmTrip9 peptides in *E. coli* lysate. (LgTrip 3546 (SEQ ID NO: 51)).

Figure 61:
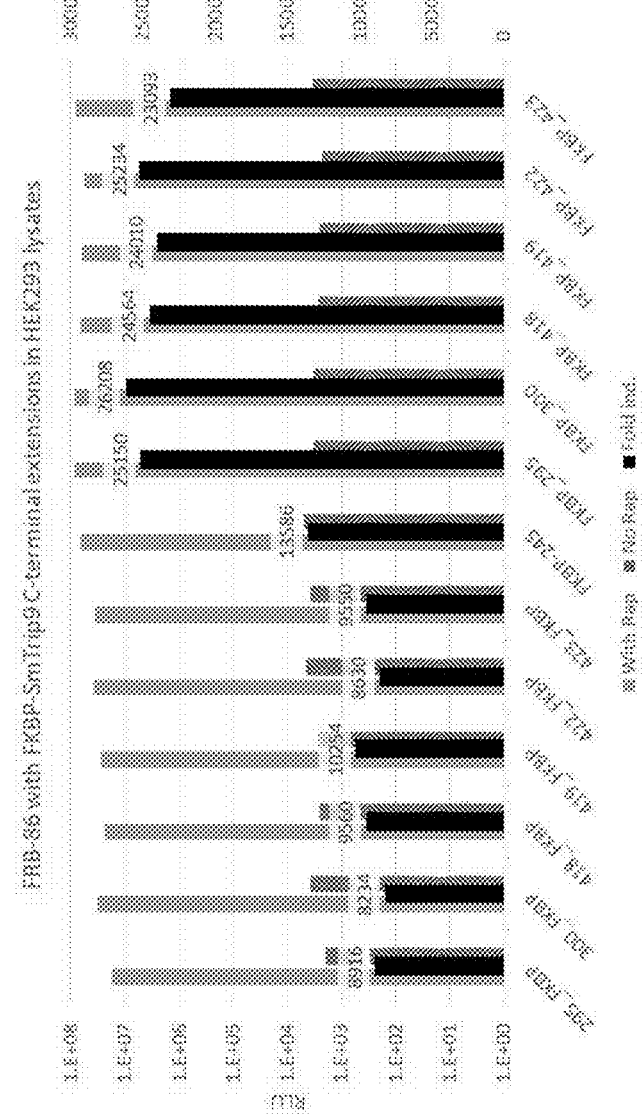

FIG. 61. Graph depicting FRB-FKBP facilitation of luminescent complex formation with FRB-SmTrip10 pep86 and C-terminally extended FKBP-SmTrip9 peptides in HEK293 lysate. (LgTrip 3546 (SEQ ID NO: 51)).

Figure 62:
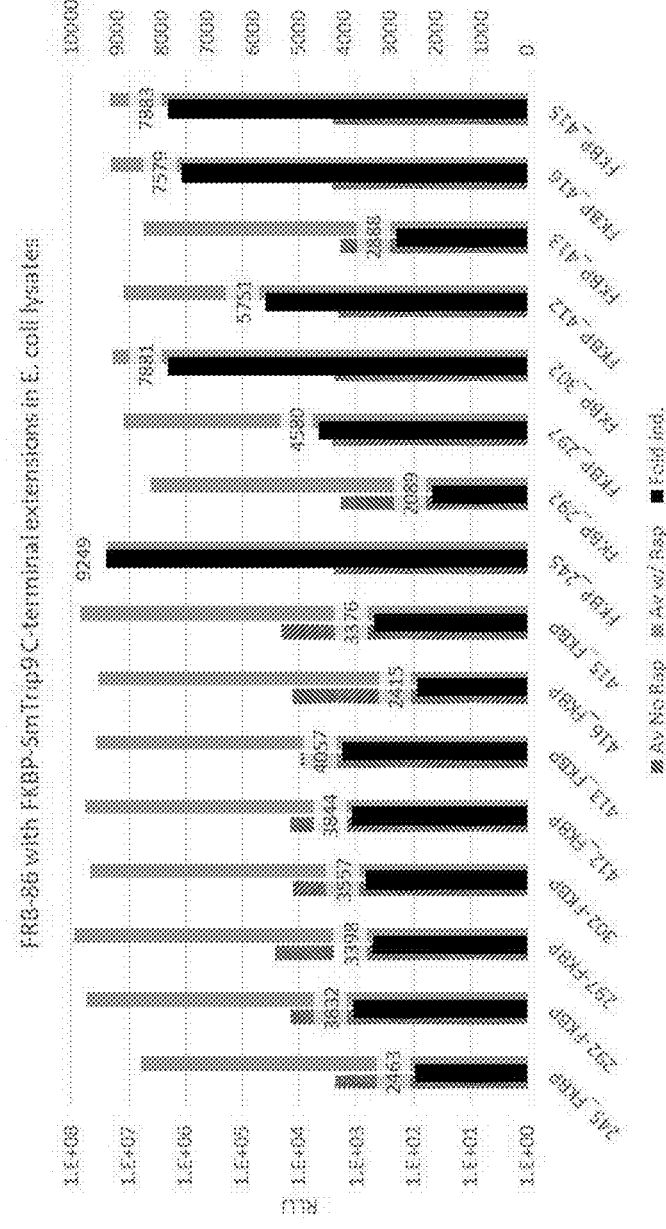

FIG. 62. Graph depicting FRB-FKBP facilitation of luminescent complex formation with FRB-SmTrip10 pep86 and SmTrip9 peptide sequence trunctions and extensions in FKBP fusions in *E. coli* lysate. (LgTrip 3546 (SEQ ID NO: 51)).

FIG. 63. Graph depicting FRB-FKBP facilitation of luminescent complex formation with FRB-SmTrip10 pep289 and SmTrip9 peptide sequence trunctions and extensions in FKBP fusions in *E. coli* lysate. (LgTrip 3546 (SEQ ID NO: 51)).

FIG. 64. Graph depicting FRB-FKBP facilitation of luminescent complex formation with FRB-SmTrip10 pep86 and SmTrip9 peptide sequence trunctions and extensions in FKBP fusions in HEK293 lysate. (LgTrip 3546 (SEQ ID NO: 51)).

Figure 65:
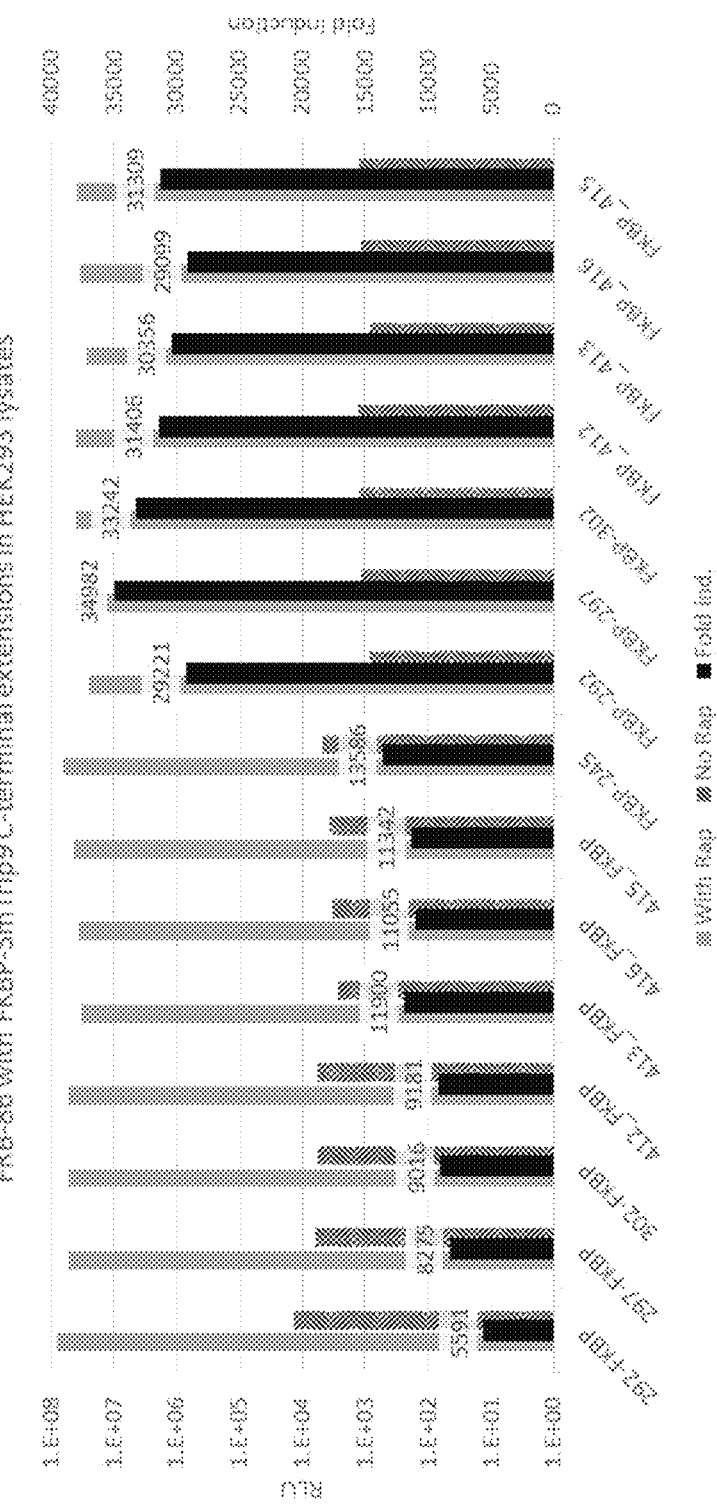

FIG. 65. Graph depicting FRB-FKBP facilitation of luminescent complex formation with FRB-SmTrip10 pep86 and SmTrip9 peptide sequence trunctions and extensions in FKBP fusions in HEK293 lysate. (LgTrip 3546 (SEQ ID NO: 51)).

Figure 66:
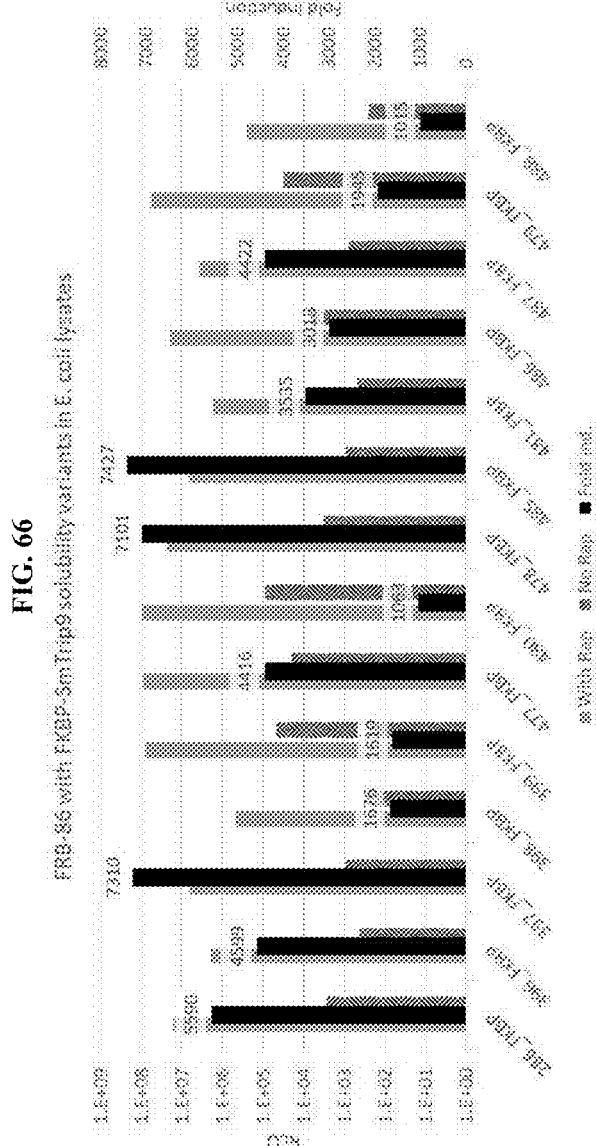

FIG. 66. Graph depicting FRB-FKBP facilitation of luminescent complex formation with FKBP-SmTrip9 solubility variants and FRB-SmTrip10 pep86 in *E. coli* lysate. (LgTrip 3546 (SEQ ID NO: 51)).

FIG. 67. Graph depicting FRB-FKBP facilitation of luminescent complex formation with FKBP-SmTrip9 solubility variants and FRB-SmTrip10 pep289 in *E. coli* lysate. (LgTrip 3546 (SEQ ID NO: 51)).

Figure 68:
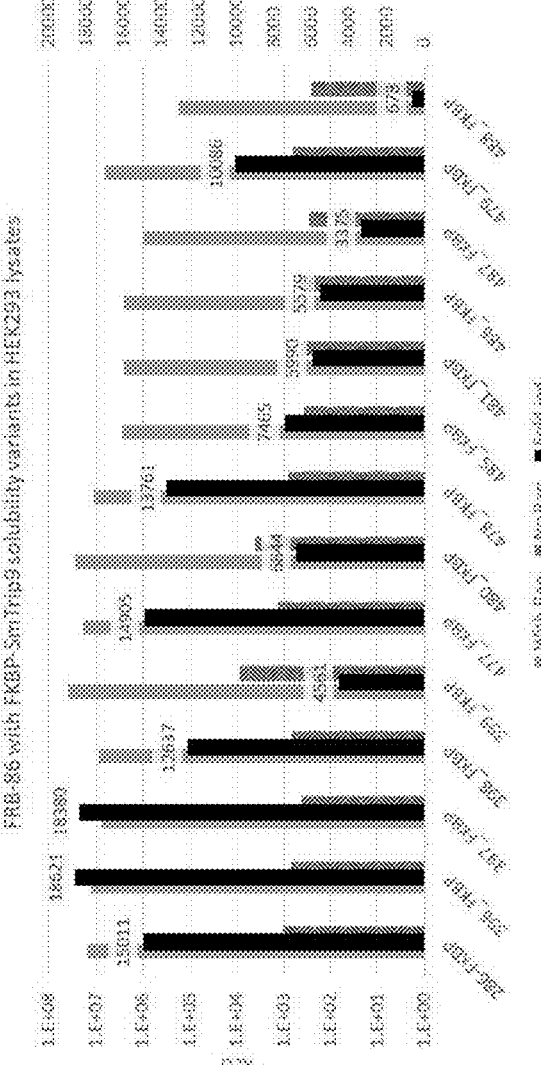

FIG. 68. Graph depicting FRB-FKBP facilitation of luminescent complex formation with FKBP-SmTrip9 solubility variants and FRB-SmTrip10 pep86 in HEK293 lysate. (LgTrip 3546 (SEQ ID NO: 51)).

Figure 69:
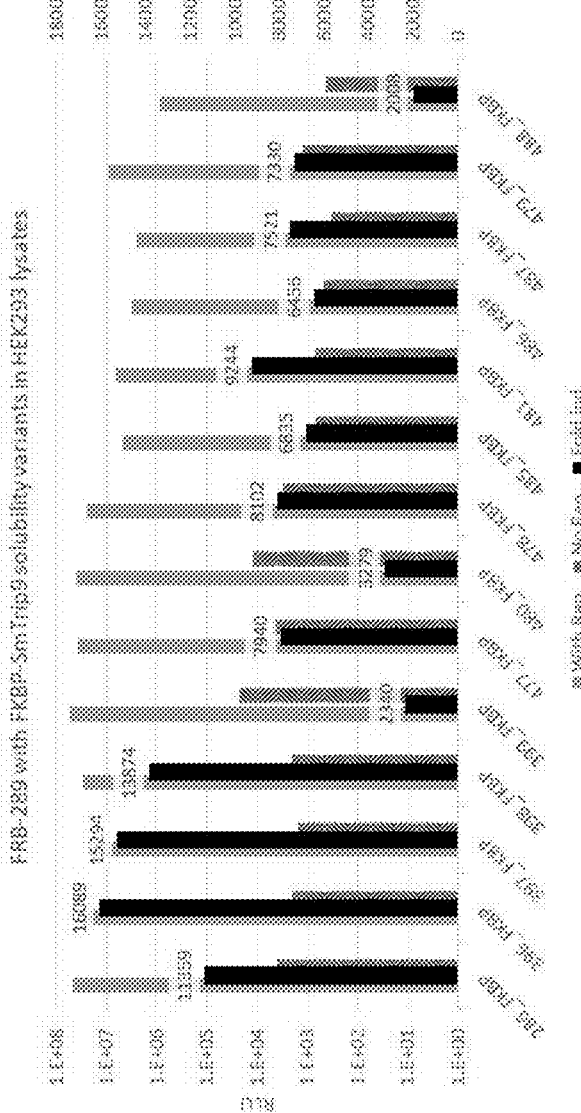

FIG. 69. Graph depicting FRB-FKBP facilitation of luminescent complex formation with FKBP-SmTrip9 solubility variants and FRB-SmTrip10 pep289 in HEK293 lysate. (LgTrip 3546 (SEQ ID NO: 51)).

Figure 70:
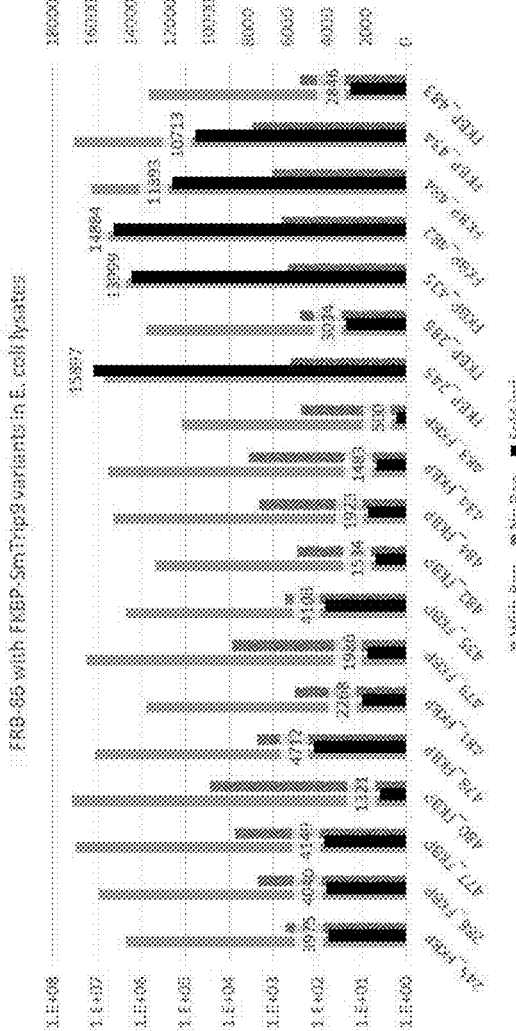

FIG. 70. Graph depicting FRB-FKBP facilitation of luminescent complex formation with FKBP-SmTrip9 solubility variants and FRB-SmTrip pep86 in *E. coli* lysate. (LgTrip 3546 (SEQ ID NO: 51)).

Figure 71:
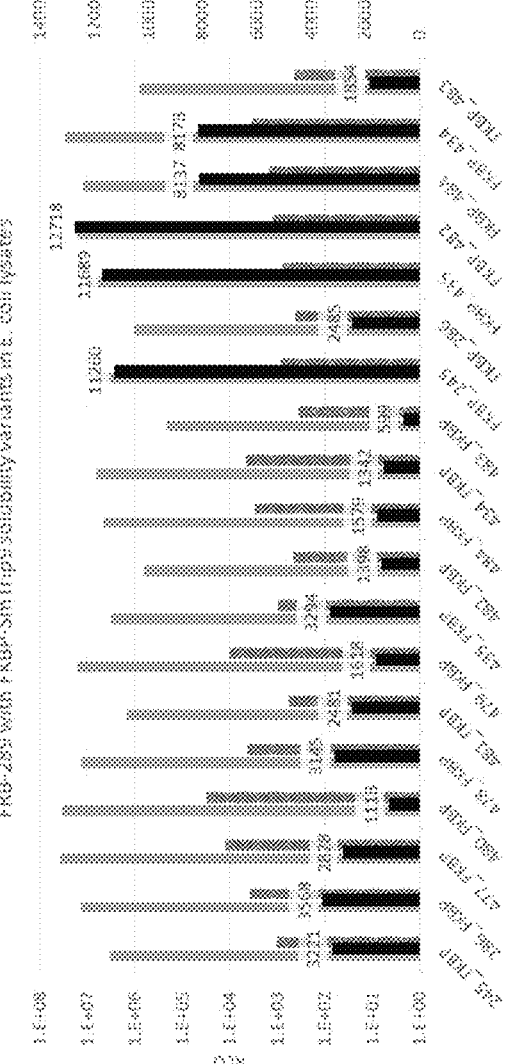

FIG. 71. Graph depicting FRB-FKBP facilitation of luminescent complex formation with FKBP-SmTrip9 solubility variants and FRB-SmTrip pep289 in *E. coli* lysate. (LgTrip 3546 (SEQ ID NO: 51)).

Figure 72:
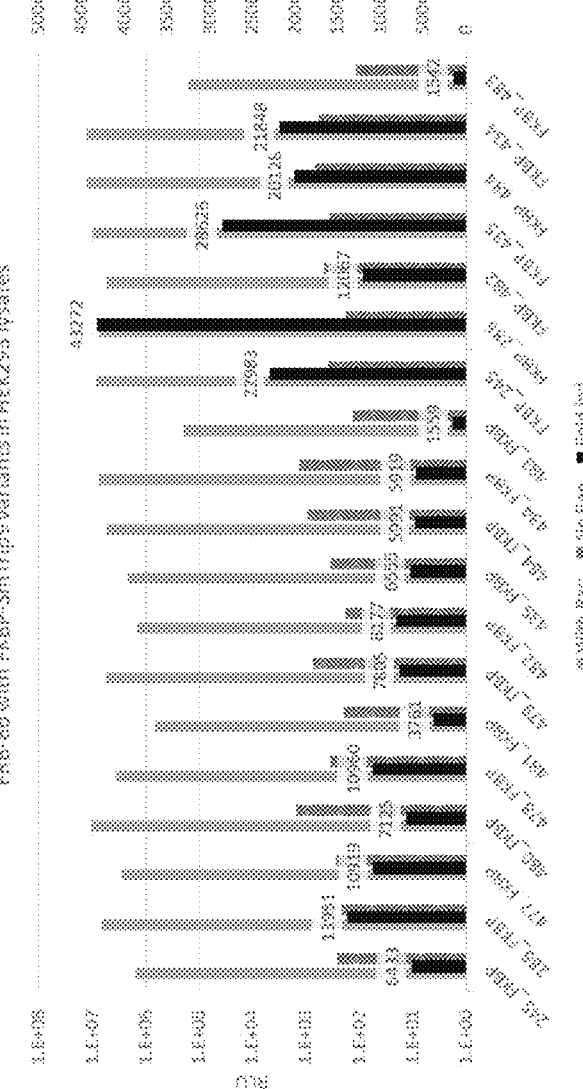

FIG. 72. Graph depicting FRB-FKBP facilitation of luminescent complex formation with FKBP-SmTrip9 solubility variants and FRB-SmTrip pep86 in HEK293 lysate. (LgTrip 3546 (SEQ ID NO: 51)).

Figure 73:
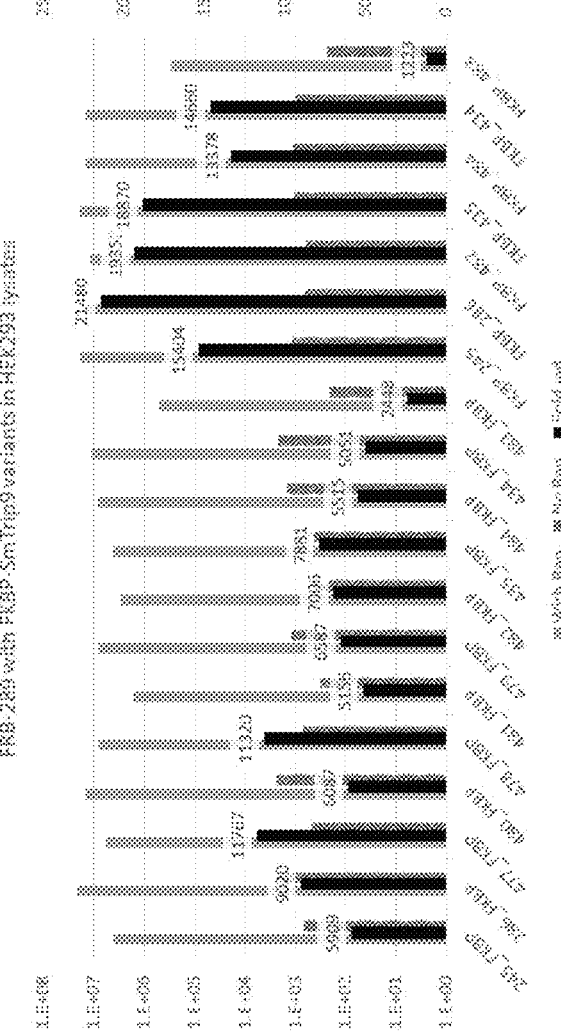

FIG. 73. Graph depicting FRB-FKBP facilitation of luminescent complex formation with FKBP-SmTrip9 solubility variants and FRB-SmTrip pep289 in HEK293 lysate. (LgTrip 3546 (SEQ ID NO: 51)).

FIG. 74. Table listing affinity and Bmax of synthetic SmTrip9 solubility variants with C-terminal extensions (SEQ ID NOS: 37, 225, 224, and 228-231). (LgTrip 3546 (SEQ ID NO: 51)).

FIG. 75. Table listing affinity and Bmax of synthetic SmTrip9 solubility variants with C-terminal extensions (SEQ ID NOS: 37, 246-249, 251-259, 261, 263-264, 228-231, and 313-320). (LgTrip 3546 (SEQ ID NO: 51)).

FIG. 76. Table listing Kd and Bmax of synthetic SmTrip9 variants with differentially blocked termini. (SEQ ID NOS: 37, 329-349, 231, 274, 278, 281, 324, 325-328, and 265-267). (LgTrip 3546 (SEQ ID NO: 51)).

FIG. 77A. Table listing the solubility of synthetic SmTrip9 peptides (SEQ ID NOS: 37, 153, 157, 161, 164, 165, 166, 167, 171, 186, 187, 188, 297, 189, 190, 191, 192, 193, 194, 195, 196, 197, 198, 199, 200, 246, 247, 248, 249, 250, 225, 224, 251, 252, 253, 254, 228, 229, 255, 256, 257, 258, 259, 261, 262, 263, 264, 230, 231, 266, and 267).

FIG. 77B. Table listing the solubility of synthetic SmTrip9 peptides (SEQ ID NOS: 268, 269, 270, 271, 272, 273, 274, 275, 276, 277, 278, 279, 280, 281, 282, 283, 284, 285, 286, 287, 288, 333, 334, 335, 336, 337, 338, 339, 340, 341, 342, 343, 344, 345, 346, 347, 348, 349, 231, 274, 278, 281, 324, 325, 326, 327, 328, 329, 330, 331).

Figure 78A:
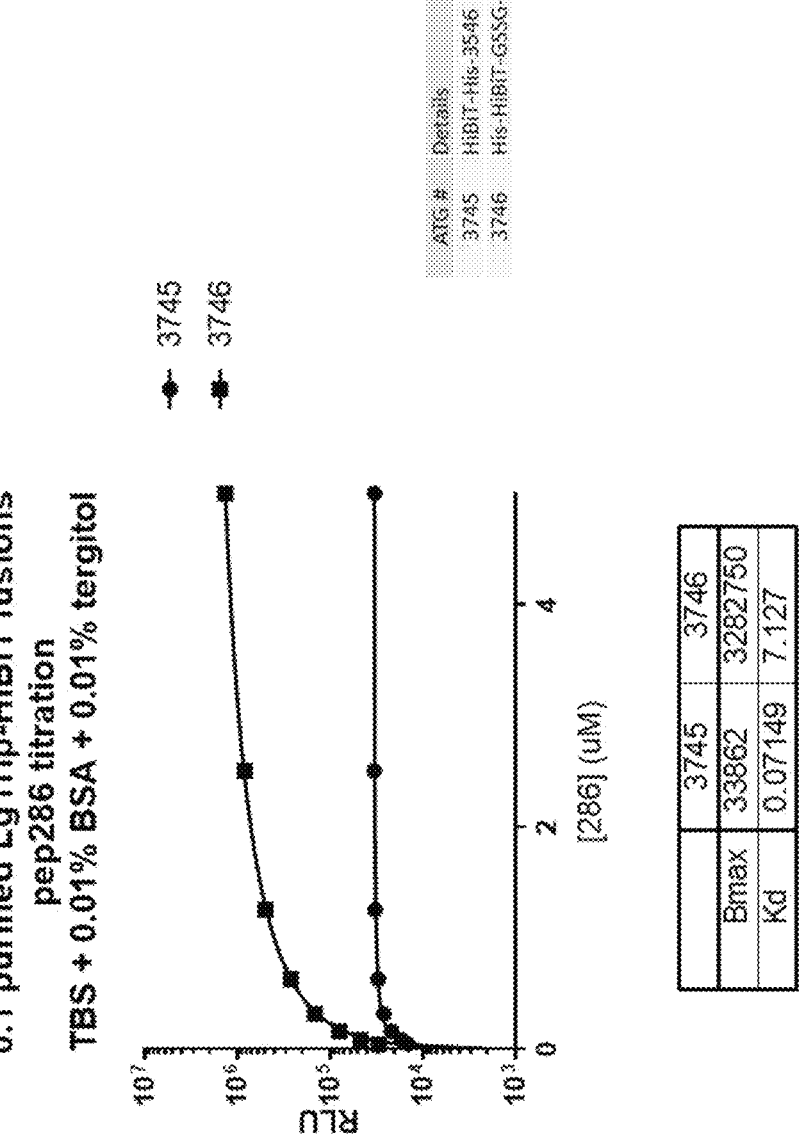
Figure 78B:
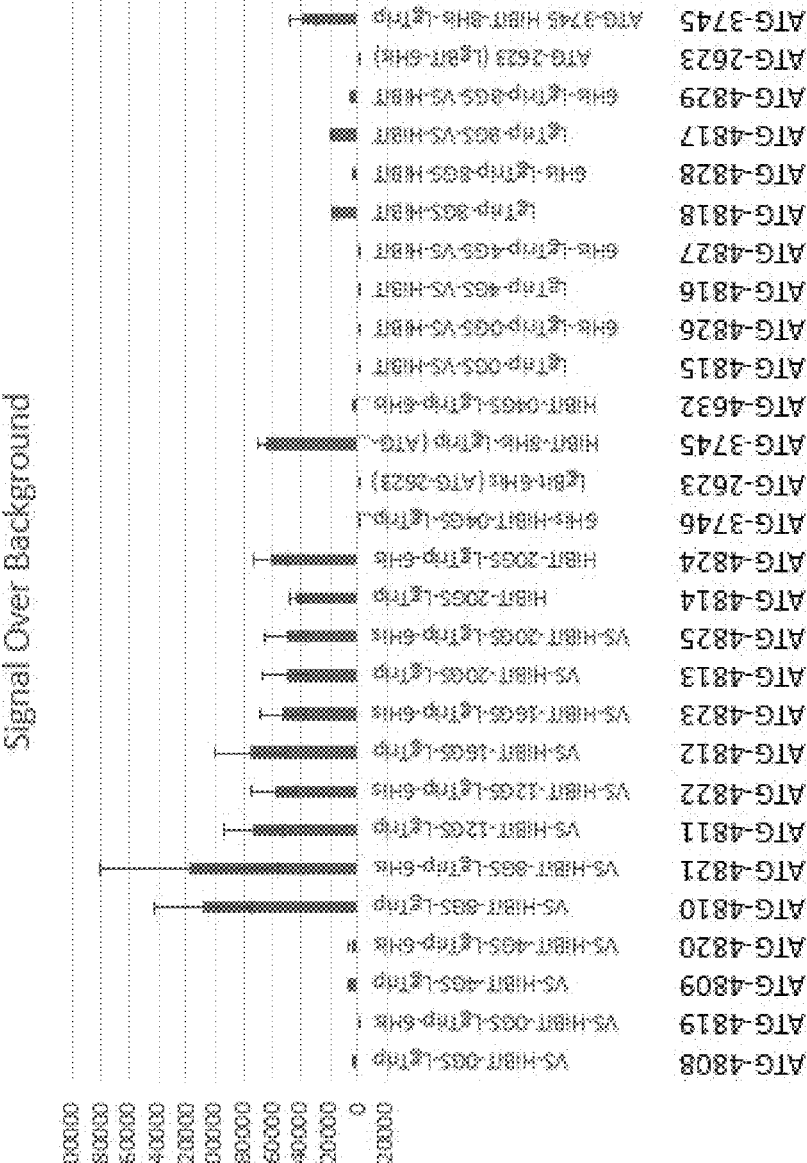

FIG. 78A-B. (A) Graph depicting the affinity of SmTrip9 pep286 (SEQ ID NO: 37) for SmTrip10 pep86 (HiBiT)/LgTrip fusions (SEQ ID NO: 210 and 212). (B) Graph depicting the affinity of SmTrip9 pep759 (SEQ ID NO: 496) for various SmTrip10 pep86 (HiBiT)/LgTrip fusions.

FIG. 79. Graphs depicting bioluminescence following an 18 hour exposure to increasing detergent concentrations. NanoLuc (SEQ ID NO: 3), LgBIT (SEQ ID NO: 11), (LgTrip 3546 (SEQ ID NO: 51)).

FIG. 80. Graphs depicting enzyme activity in the presence of increasing detergent concentrations. NanoLuc (SEQ ID NO: 3), LgBIT (SEQ ID NO: 11), LgTrip 3546 (SEQ ID NO: 51).

Figure 81:
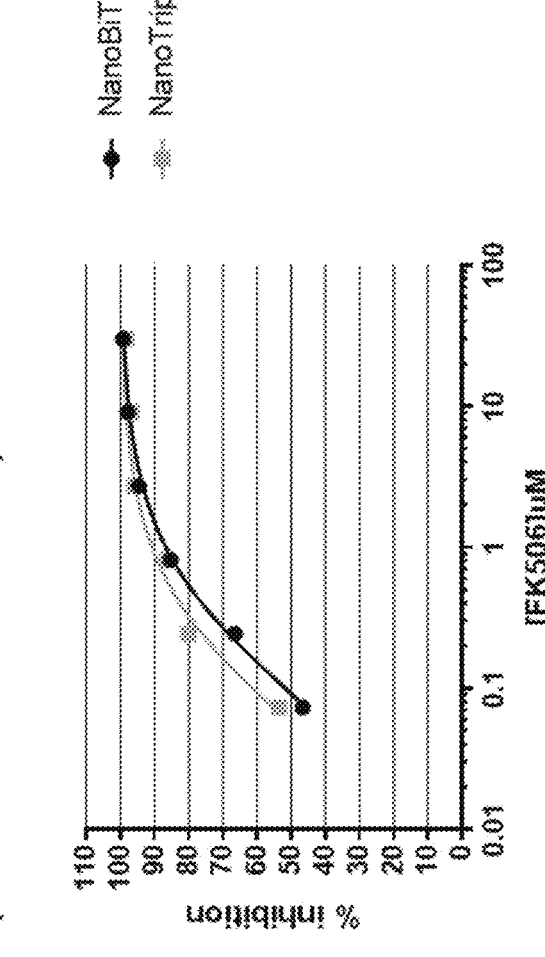

FIG. 81. Graph demonstrating the reversibility of FRB-FKBP facilitated bioluminescent complex formation with LgBIT (SEQ ID NO: 11) and LgTrip 3546 (SEQ ID NO: 51).

FIG. 82. Table listing results of titration of various SmTrip10 peptides in the presence of constant SmTrip9 pep286 (SEQ ID NO: 37) and LgTrip 3546 (SEQ ID NO: 51).

Figure 84:
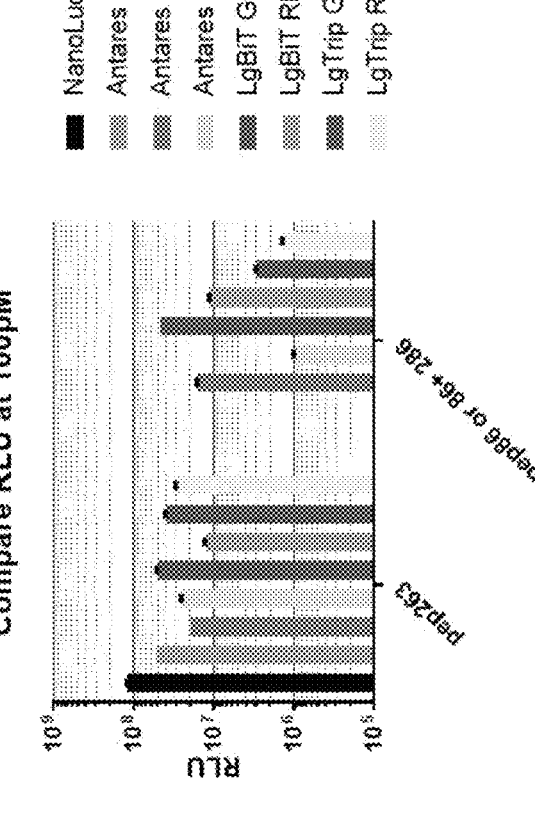

FIG. 83. Table listing results of titration of various SmTrip10 peptides in the presence of constant SmTrip9 pep286 (SEQ ID NO: 37) and LgTrip 3546 (SEQ ID NO: 51) titration FIG. 84. Graph depicting bioluminescence from Antares-type fusions (LgTrip 3546) with SmTrip9 pep263 (SEQ ID NO: 35) and SmTrip10 pep86 (SEQ ID NO: 25) or SmTrip10 pep86+SmTrip9 pep286 (SEQ ID NO: 37).

FIG. 85. Graphs depicting emission spectra from Antares-type fusions (LgTrip 3546) (SEQ ID NO: 51) with SmTrip9 pep263 (SEQ ID NO: 35) and SmTrip pep86 (HiBIT; SEQ ID NO: 25) or SmTrip10 pep86 (HiBIT; SEQ ID NO: 25)+SmTrip9 pep286 (SEQ ID NO: 37).

FIG. 86. Graphs depicting titration of LgBIT (SEQ ID NO: 11) and LgTrip 3546 (SEQ ID NO: 51) with "dark" dipeptide 272 (SEQ ID NO: 146) in the presence of dipeptide pep263 (SEQ ID NO: 35).

Figure 87:
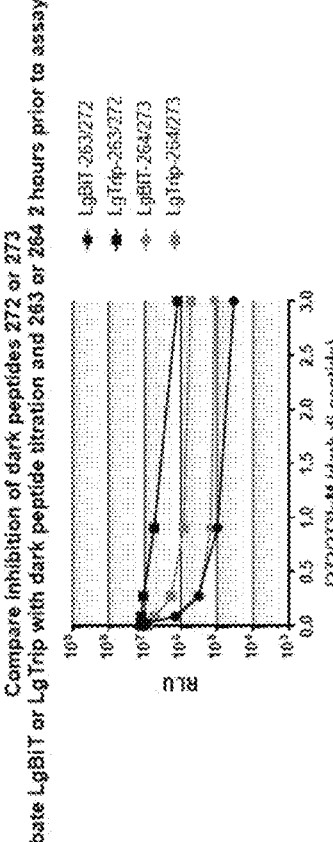

FIG. 87. Graphs comparing the inhibition of dark dipeptides 272 (SEQ ID NO: 146) and 273 (SEQ ID NO: 298) with LgTrip 3546 (SEQ ID NO: 51) and LgBiT (SEQ ID NO: 11).

Figure 88:
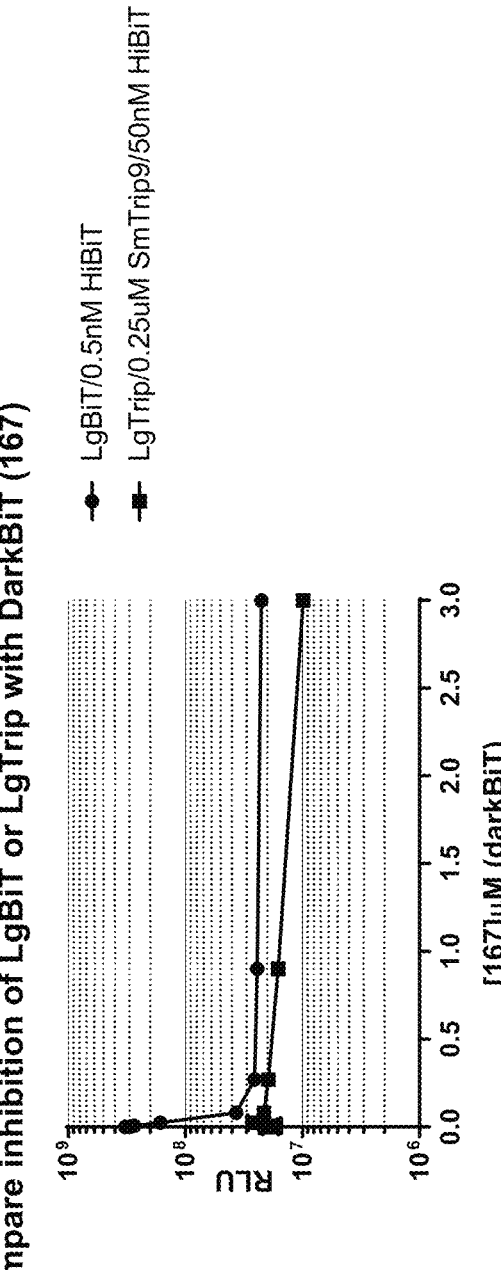

FIG. 88. Graph depicting inhibition of LgBIT (SEQ ID NO: 11) and LgTrip 3546 (SEQ ID NO: 51) with dark BiT167 (SEQ ID NO: 300).

Figure 89:
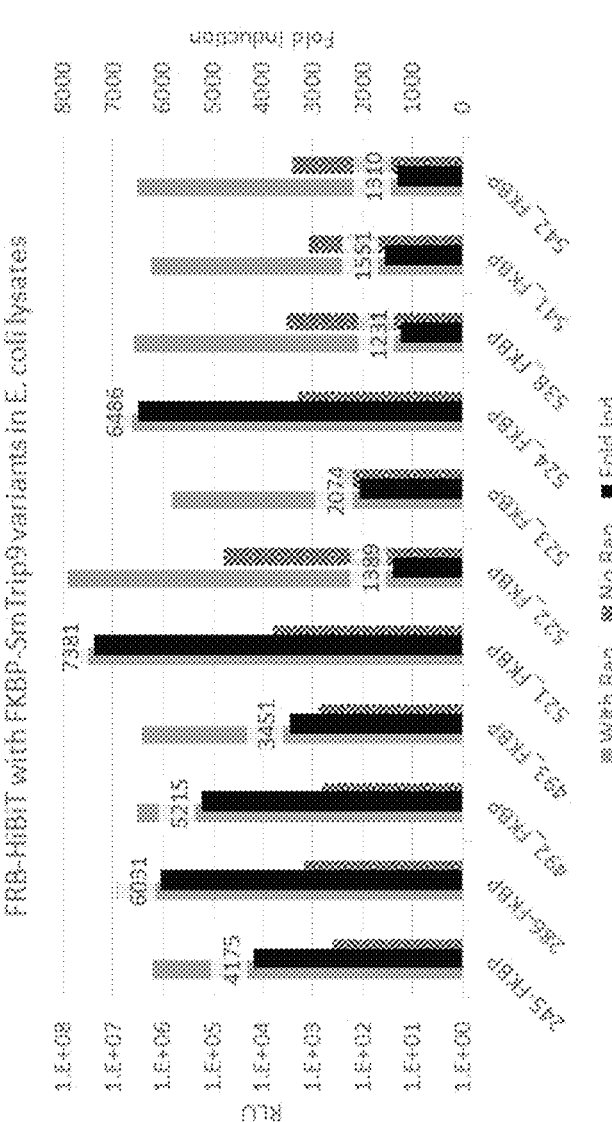

FIG. 89. Graph depicting FRB-FKBP facilitation of luminescent complex formation in *E. coli* lysate with FKBP-SmTrip9 pep434 (SEQ ID NO: 230) variants' complementation with LgTrip 3546 (SEQ ID NO: 51) and FRB-HiBIT (SEQ ID NO: 25).

Figure 90:
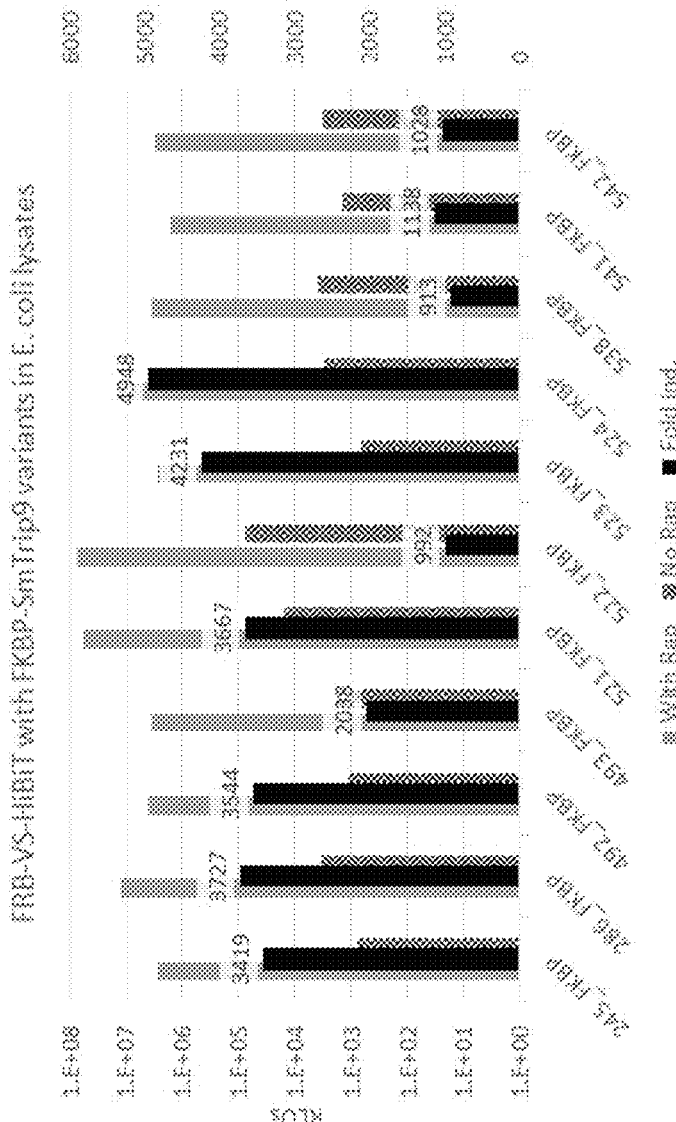

FIG. 90. Graph depicting FRB-FKBP facilitation of luminescent complex formation in *E. coli* lysate with SmTrip9 pep434 (SEQ ID NO: 230) variants' complementation with LgTrip 3546 (SEQ ID NO: 51) and FRB-SmTrip10 pep289 (VS-HiBIT; SEQ ID NO: 150).

Figure 91A:
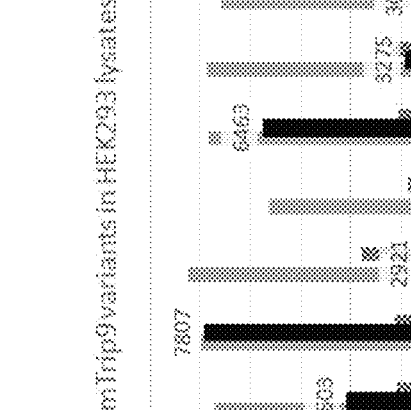
Figure 91B:
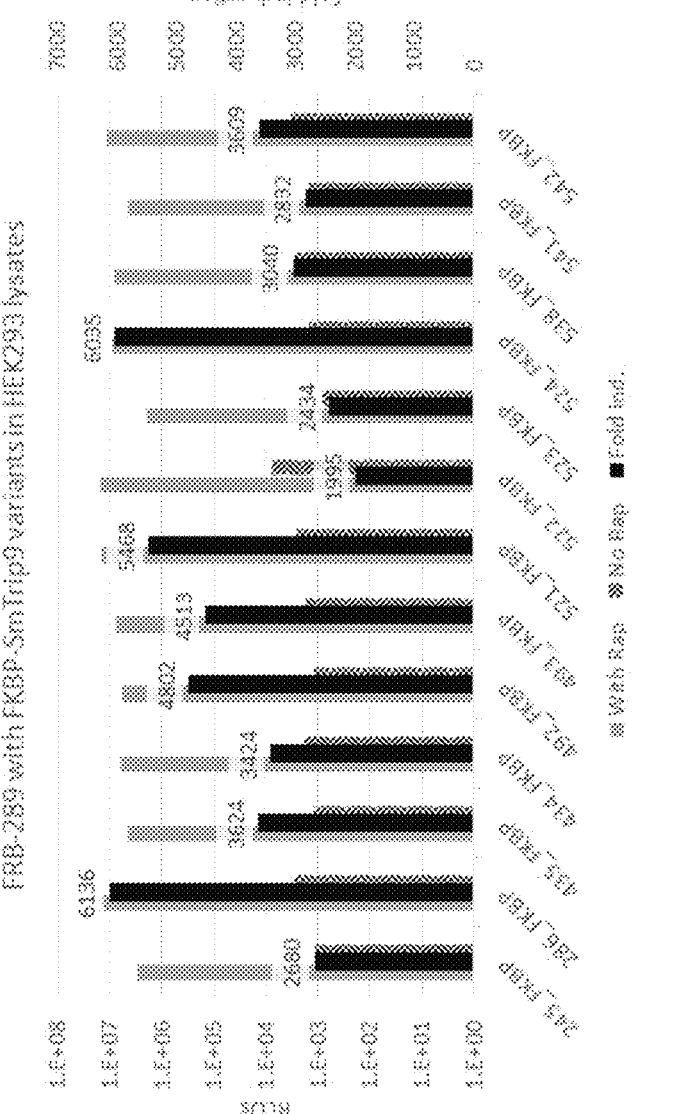
Figures 95A, 95B, 95C:
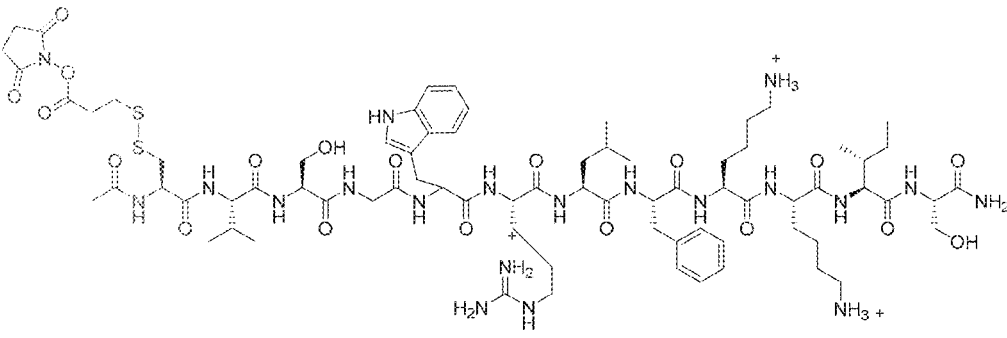
Figures 95D, 95E:
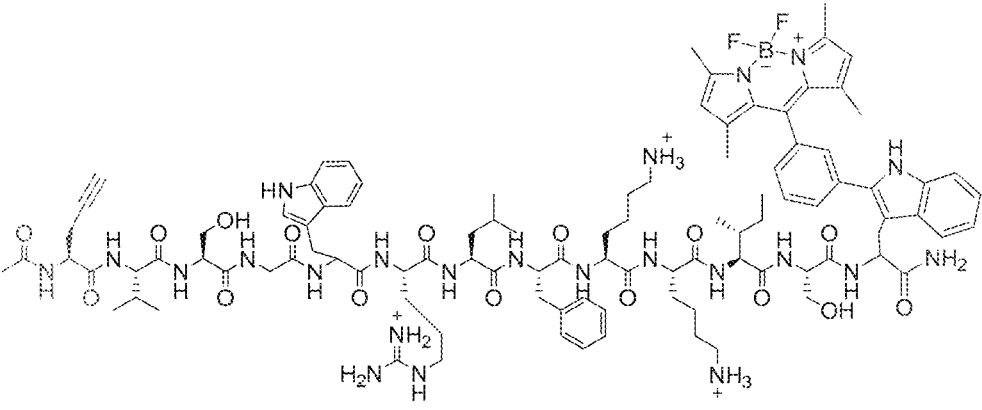
Figures 98E, 98F:
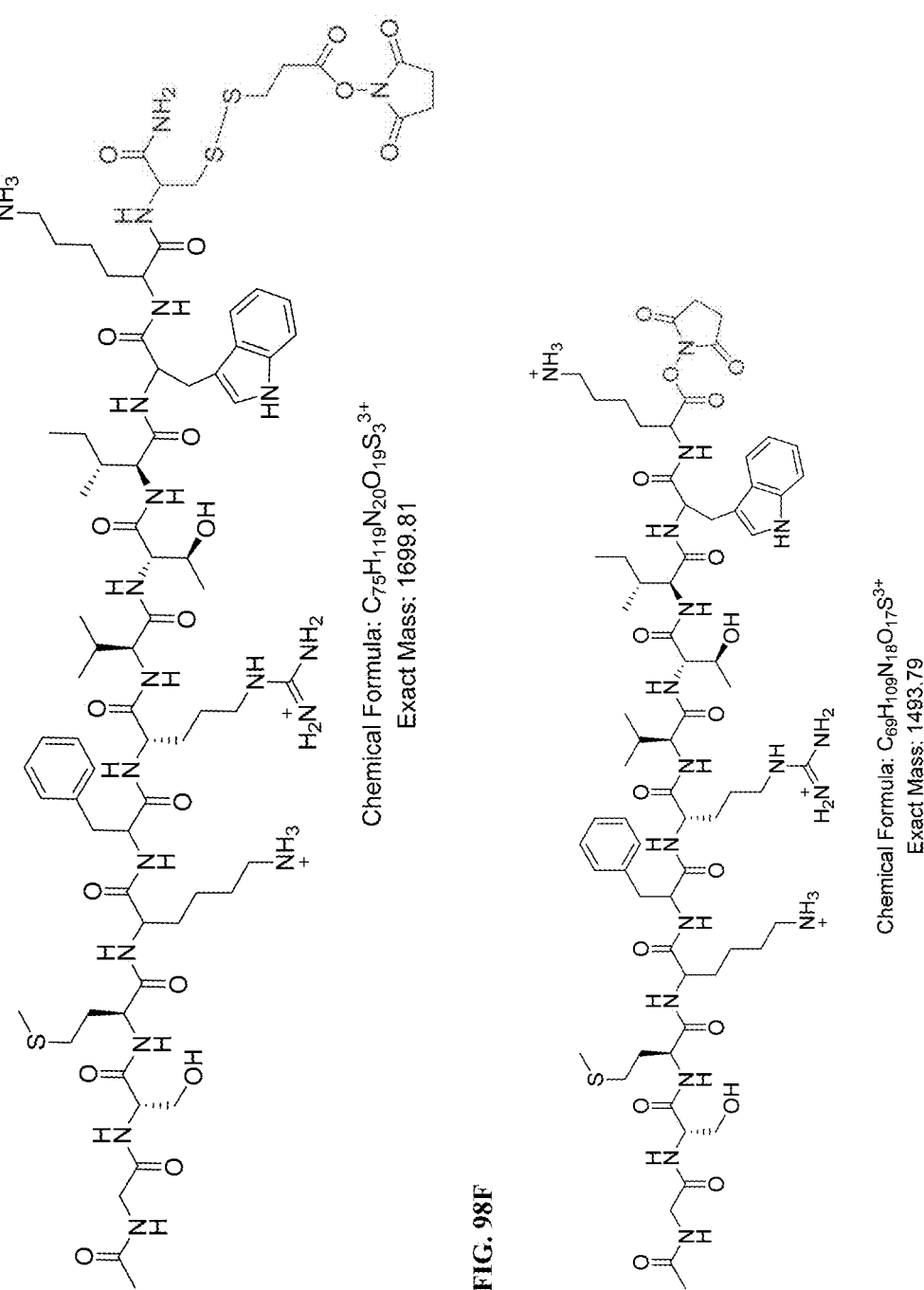

FIG. 91A-B. (A) Graph depicting FRB-FKBP facilitation of luminescent complex formation in HEK293 lysate with SmTrip9 pep435 (SEQ ID NO: 231) and SmTrip9 pep434 (SEQ ID NO: 230) variants' complementation with LgTrip 3546 (SEQ ID NO: 51) and FRB-SmTrip10 pep86 (HiBIT; SEQ ID NO: 25). (B) Graph depicting FRB-FKBP facilitation of luminescent complex formation in HEK293 lysate with SmTrip9 pep435 (SEQ ID NO: 231) and SmTrip9 pep434 (SEQ ID NO: 230) variants' complementation with LgTrip 3546 (SEQ ID NO: 51) and FRB-SmTrip10 pep289 (SEQ ID NO: 150).

FIG. 92. Table depicting the results of a FRB-FKBP assay screen with SmTrip9s 823 and 840

FIG. 93. Table listing Kd and Bmax of synthetic SmTrip9 pep435 (SEQ ID NO: 231) and SmTrip9 pep434 (SEQ ID NO: 230) variants with LgTrip 3546 (SEQ ID NO: 51).

FIG. 94. Graph demonstration of wt LgTrip 2098 (SEQ ID NO: 31) and LgTrip 3546 (SEQ ID NO: 51) with pep263 (SEQ ID NO: 35) or pep331 (SEQ ID NO: 301) as bioluminescence reagents for detecting endogenously tagged (e.g., by CRISPR/Cas9) GAPDH.

FIG. 95A-E. Exemplary SmTrip10 chemical conjugates. (A) Example of SmTrip10 with N-terminal cysteine modification for disulfide bond formation on solvent exposed or protected cysteine targets on proteins/peptides/DNA and RNA oligonucleotides/small molecules or proteins/peptides/DNA and RNA oligonucleotides/small molecules that have been prepared with maleimide for reaction with a thiol such as cysteine or N-hydroxysuccinimide esters (NHS-ester) for reaction with an amine such as lysine. (B) Exemplary SmTrip10 with N-terminal azido-lysine modification for copper catalyzed or copper free 1,3-dipolar cycloaddition reactions ("Click") with unstrained or strained alkyne targets separately installed on proteins/peptides/DNA and RNA oligonucleotides/small molecules. (C) Exemplary SmTrip10 with N-terminal N-hydroxylsuccinimide ester (NHS-ester) for general conjugation to nucleophiles (e.g., lysines, other primary amines) on proteins/peptides/DNA and RNA oligonucleotides/small molecules. Nucleophiles can be present on unmodified proteins/oligos/small molecules or may be chemically added for the purposes of this conjugation. (D) Exemplary SmTrip10 with an N-terminal propargyl glycine modification for copper catalyzed or copper free 1,3-dipolar cycloaddition reactions ("Click") with azide, diazo, or tetrazine targets separately introduced chemically or biologically on proteins/peptides/DNA and RNA oligonucleotides/small molecules. (E) Exemplary SmTrip10 with a N-terminal propargyl glycine modification for copper catalyzed or copper free 1,3-dipolar cycloaddition reactions ("Click") and a C-terminal fluorophore (e.g., BODIPY dye).

Figures 96A, 96B:
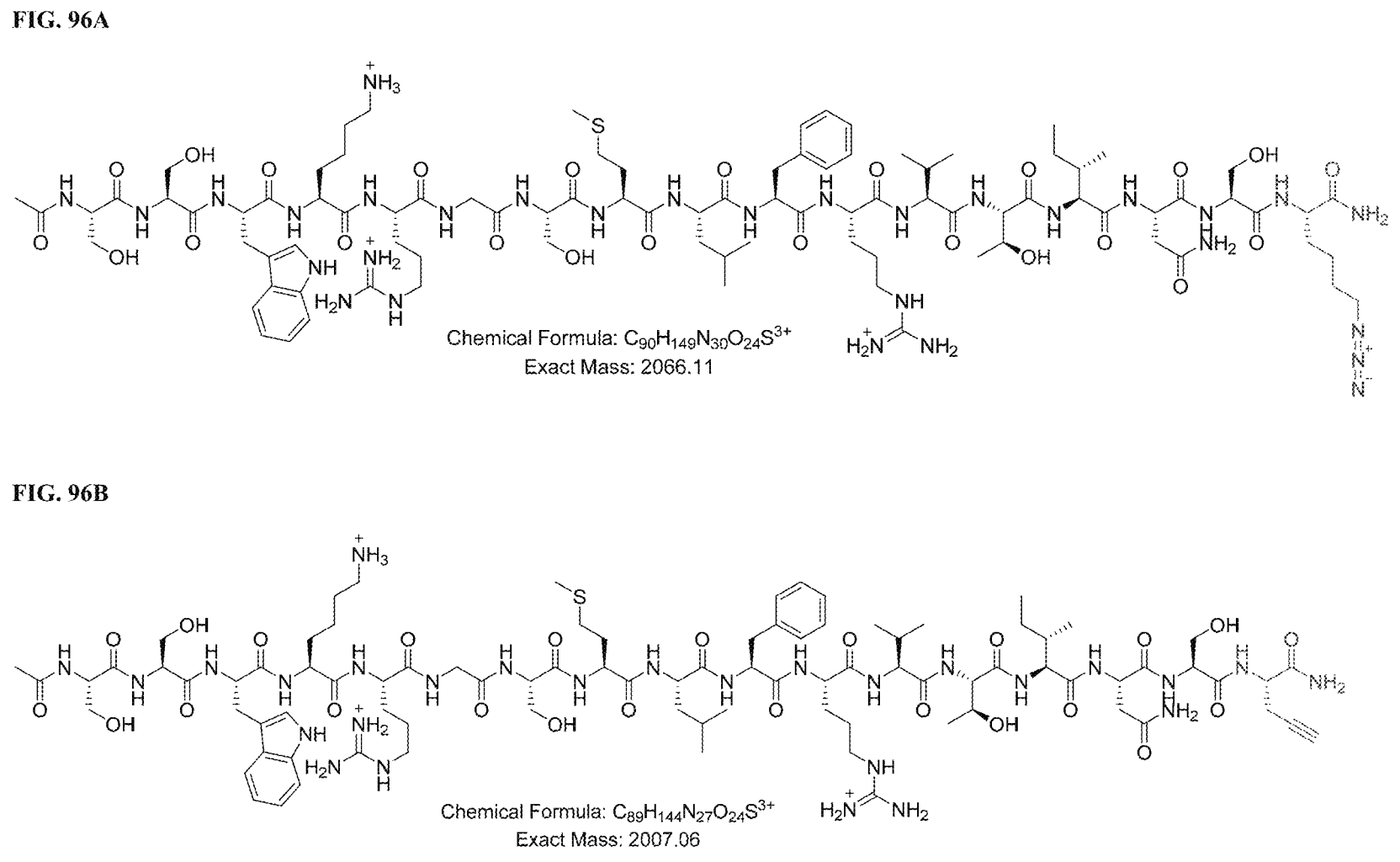
Figures 96C, 96D:
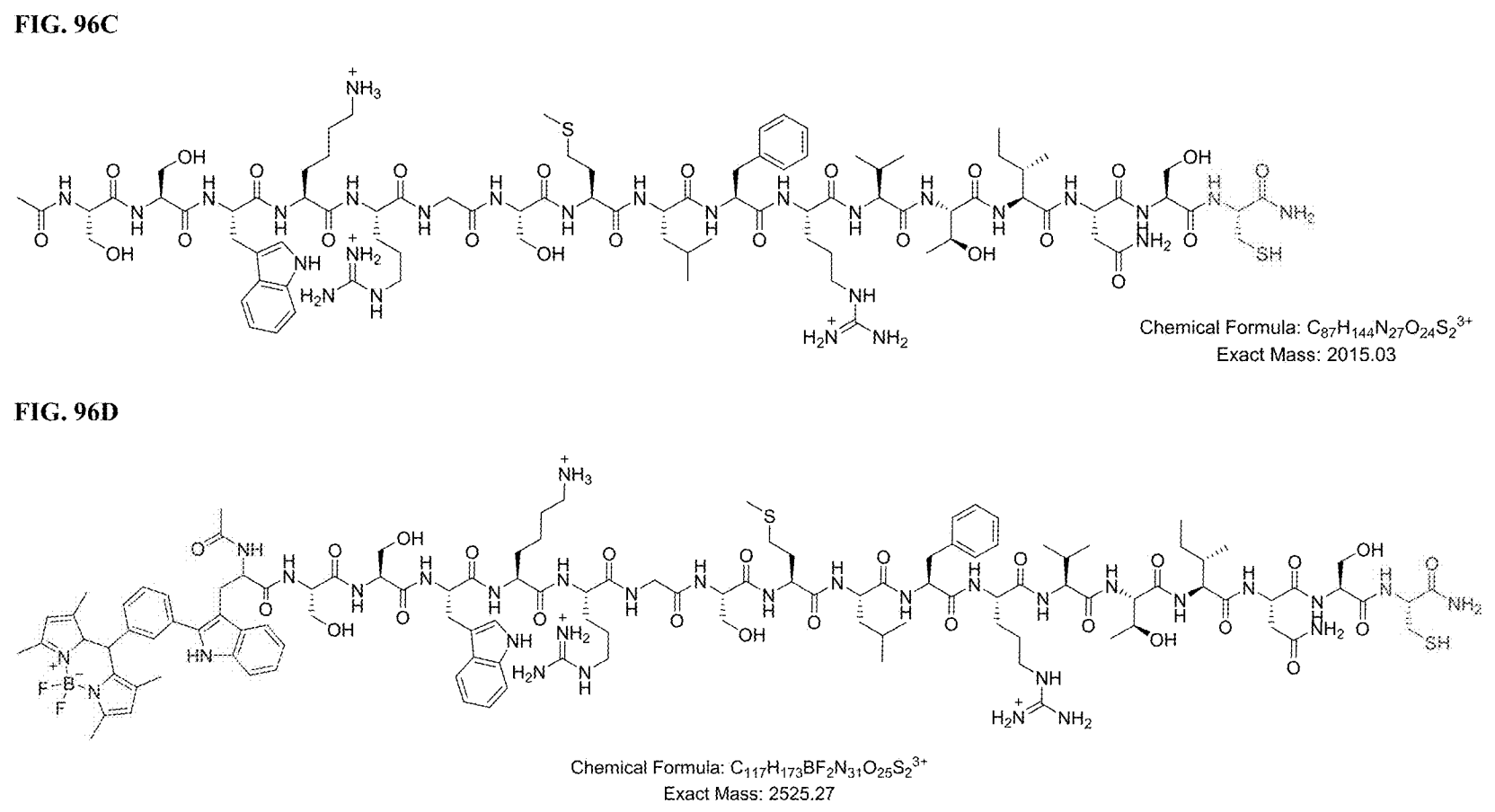
Figures 96E, 96F:
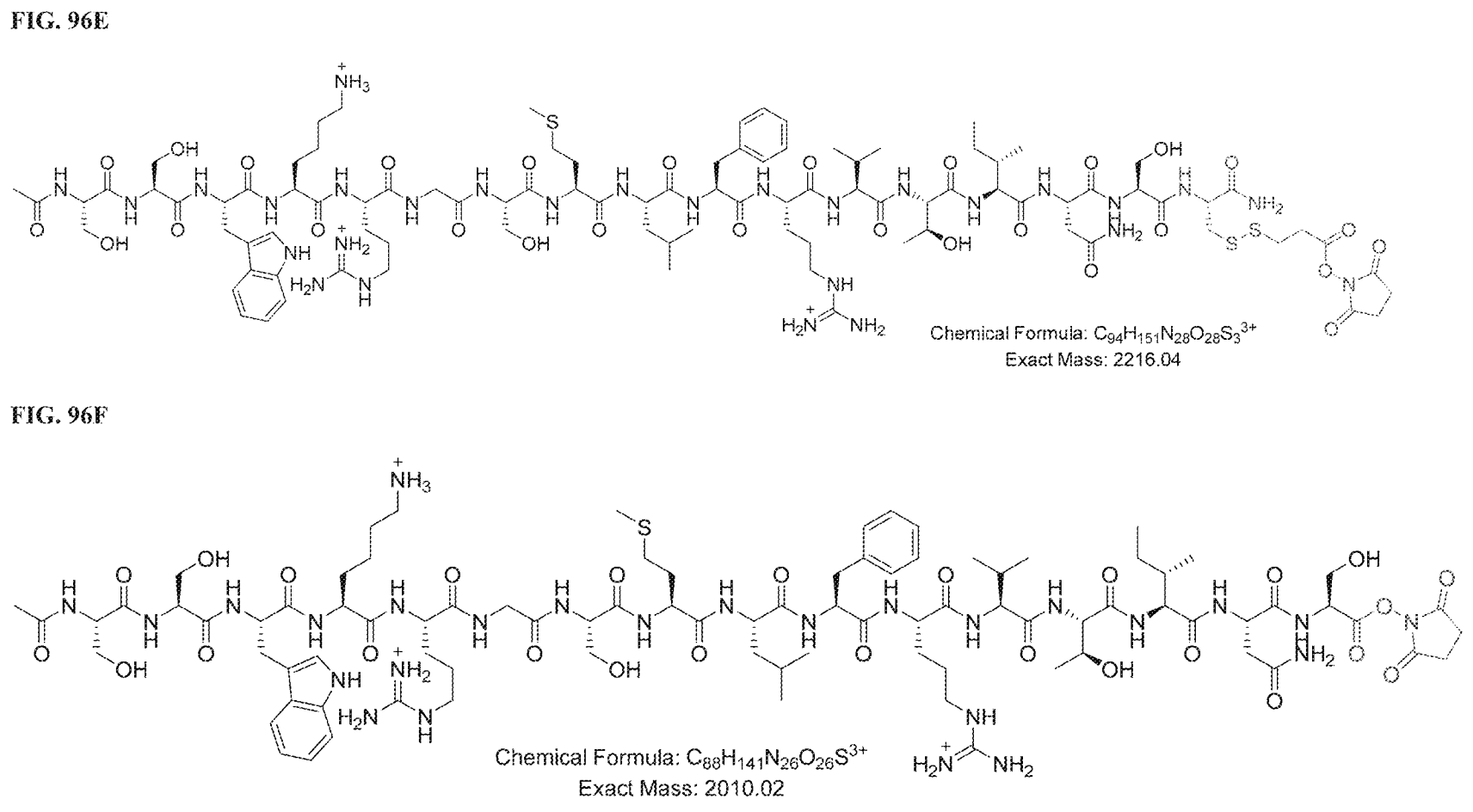

FIG. 96A-F. Exemplary SmTrip9 pep286 chemical conjugates. (A) Example of SmTrip9-286 with C-terminal azido-lysine modification for copper catalyzed or copper free 1,3-dipolar cycloaddition reactions ("Click") with unstrained or strained alkyne targets separately introduced chemically or biologically on proteins/peptides/DNA and RNA oligonucleotides/small molecules. (B) Example of SmTrip9 pep286 with C-terminal propargyl glycine modification for copper catalyzed or copper free 1,3-dipolar cycloaddition reactions ("Click") with azide, diazo, tetrazine targets separately introduced chemically or biologically on proteins/peptides/DNA and RNA oligonucleotides/small molecules. (C) Example of SmTrip9 pep286 with C-terminal cysteine modification for disulfide bond formation on solvent exposed or protected cysteine targets on proteins/peptides/DNA and RNA oligonucleotides/small molecules or proteins/peptides/DNA and RNA oligonucleotides/small molecules that have been prepared with maleimide handles or N-hydroxysuccinimide esters. (D) Example of SmTrip9 pep286 with C-terminal cysteine modification and a N-terminal BODIPY dye. The dye is not limited to BODIPY and could be any fluorophore, BRET partner, or FRET dye/quencher partner. Dyes can be incorporated with any other combination of conjugation handles prepared on the C-terminus. (E) Example of SmTrip9 pep286 with C-terminal N-hydroxysuccinimide esters (NHS-ester) for general conjugation to nucleophilic targets (e.g., lysines) on proteins/peptides/DNA and RNA oligonucleotides/small molecules or proteins/peptides/DNA and RNA oligonucleotides/small molecules. (F) Example of SmTrip9 pep286 with C-terminal N-hydroxysuccinimide ester (NHS-ester) for general conjugation to nucleophilic targets (i.e. lysines) on proteins/peptides/DNA and RNA oligonucleotides/small molecules or proteins/peptides/DNA and RNA oligonucleotides/small molecules.

Figure 97A:
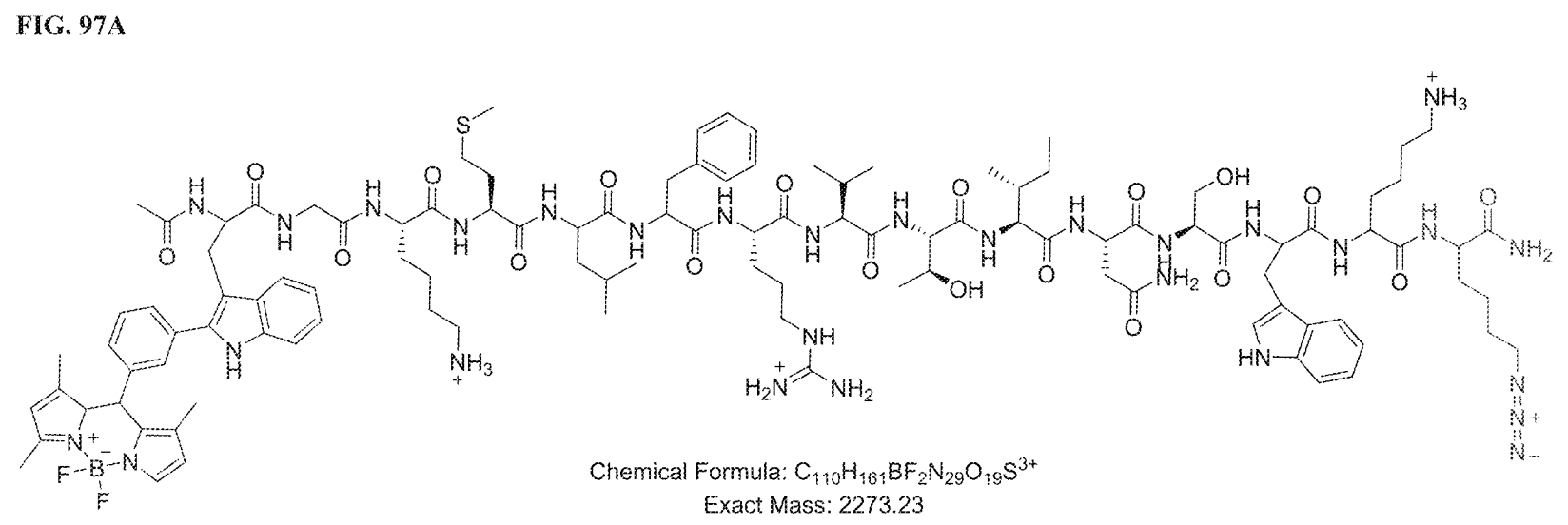
Figures 97B, 97C:
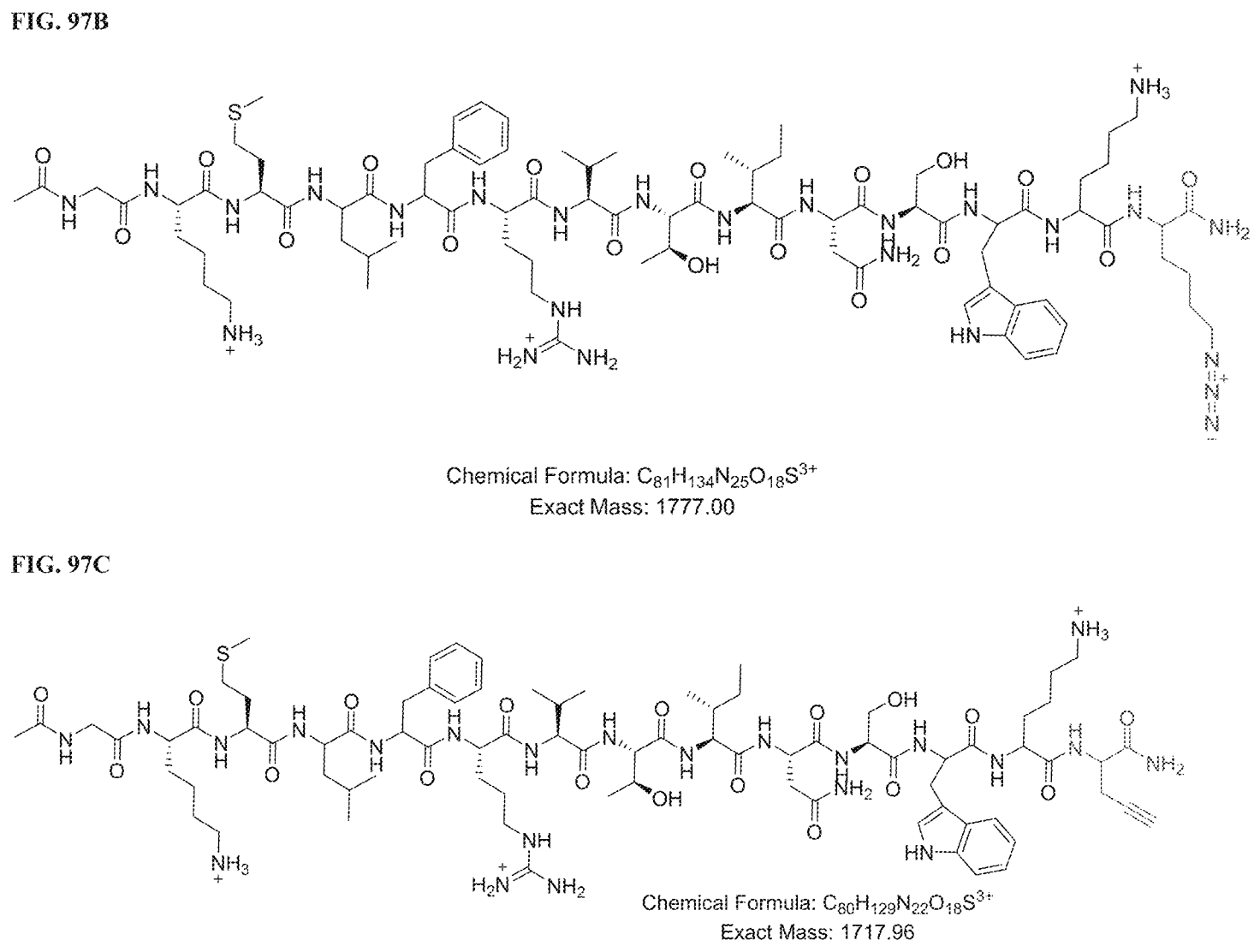
Figure 97D:
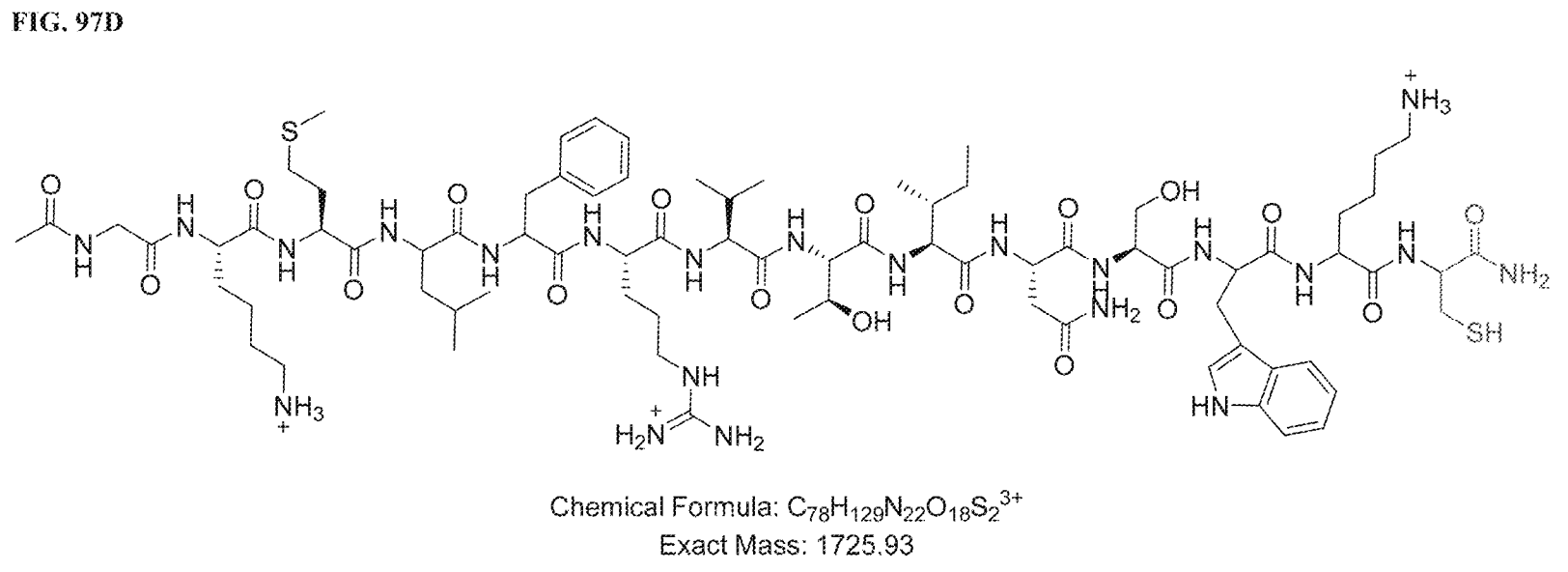
Figures 97E, 97F:
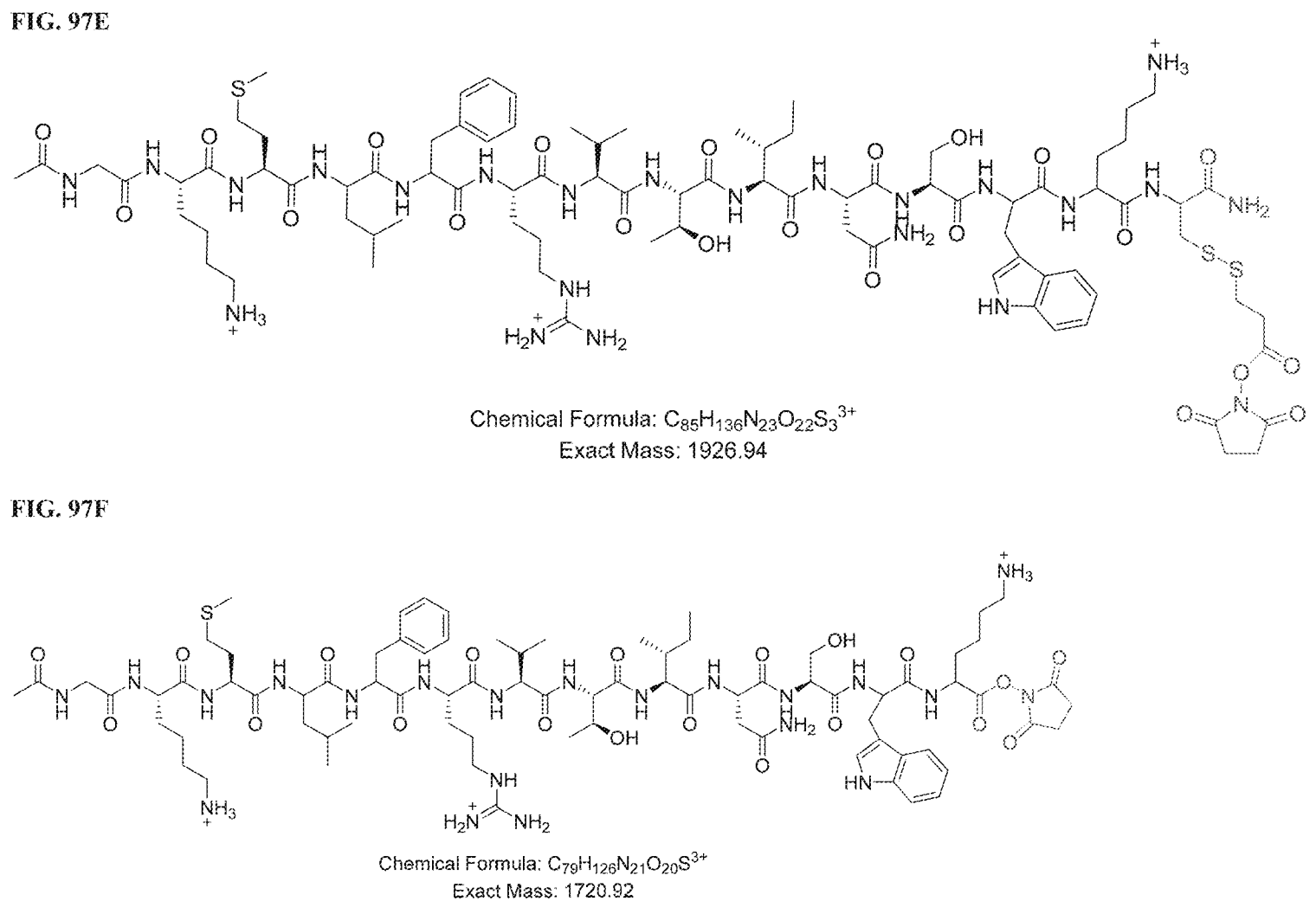

FIG. 97A-F. Exemplary SmTrip9 pep521 chemical conjugates. (A) Example of SmTrip9 pep521 with C-terminal azido-lysine modification and a N-terminal BODIPY dye. The dye is not limited to BODIPY and could be any fluorophore, BRET partner, or FRET dye/quencher partner. Dyes can be incorporated with any other combination of conjugation handles prepared on the C-terminus. (B) Example of SmTrip9 pep521 with C-terminal azido-lysine modification for copper catalyzed or copper free 1,3-dipolar cycloaddition reactions ("Click") with unstrained or strained alkyne targets separately introduced chemically or biologically on proteins/peptides/DNA and RNA oligonucleotides/small molecules. (C) Example of SmTrip9 pep521 with C-terminal propargyl glycine modification for copper catalyzed or copper free 1,3-dipolar cycloaddition reactions ("Click") with azide, diazo, tetrazine targets separately introduced chemically or biologically on proteins/peptides/DNA and RNA oligonucleotides/small molecules. (D) Example of SmTrip9 pep521 with C-terminal cysteine modification for disulfide bond formation on solvent exposed or protected cysteine targets on proteins/peptides/DNA and RNA oligonucleotides/small molecules or proteins/peptides/DNA and RNA oligonucleotides/small molecules that have been prepared with maleimide handles or an NHS-ester. (E) Example of SmTrip9 pep521 with C-terminal N-hydroxysuccinimide ester (NHS-ester) for general conjugation to nucleophilic targets (i.e. lysines) on proteins/peptides/DNA and RNA oligonucleotides/small molecules. (F) Example of SmTrip9 pep521 with C-terminal N-hydroxysuccinimide ester (NHS-ester) for general conjugation to nucleophilic targets (i.e. lysines) on proteins/peptides/DNA and RNA oligonucleotides/small molecules.

Figures 98A, 98B:
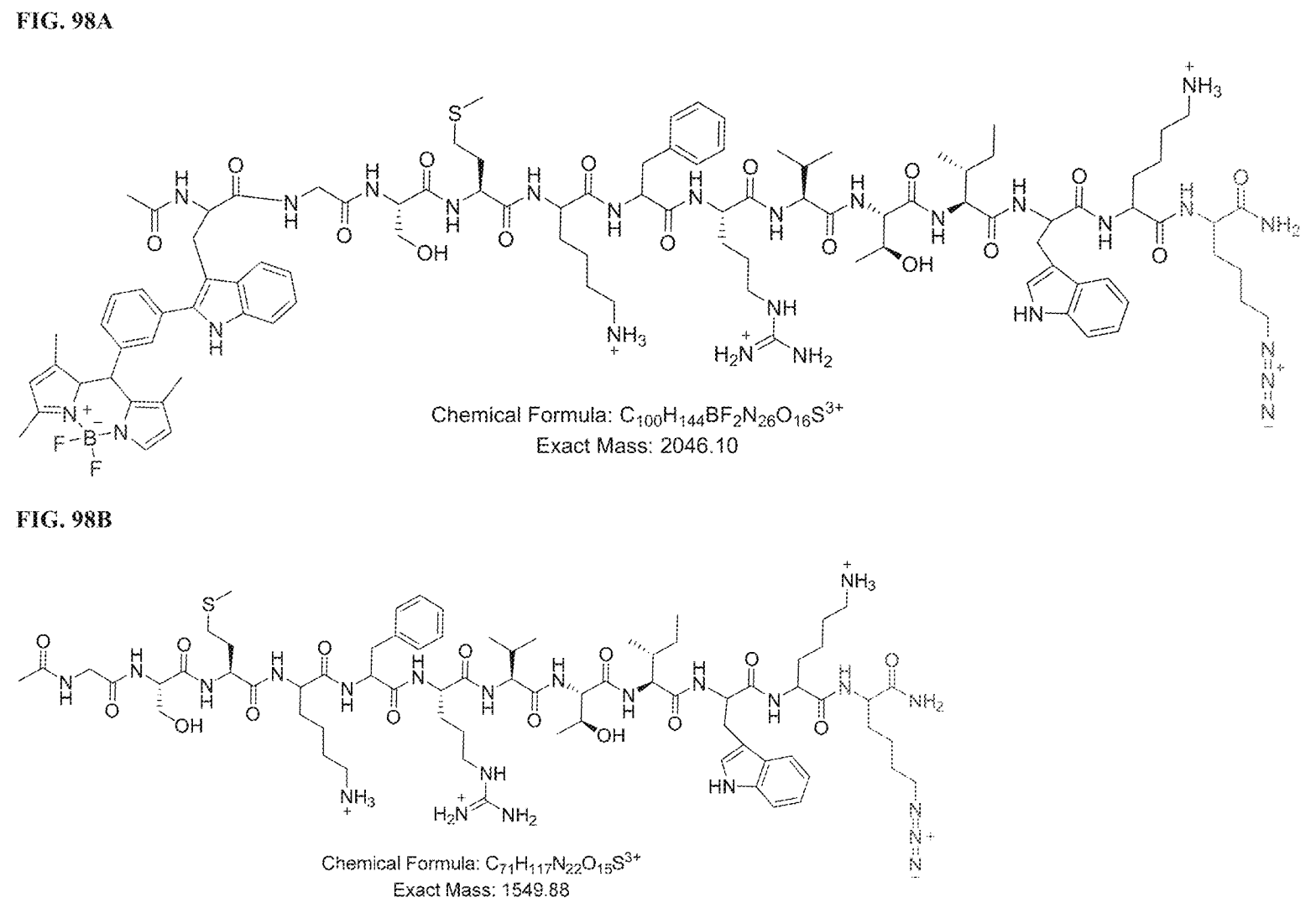
Figures 98C, 98D:
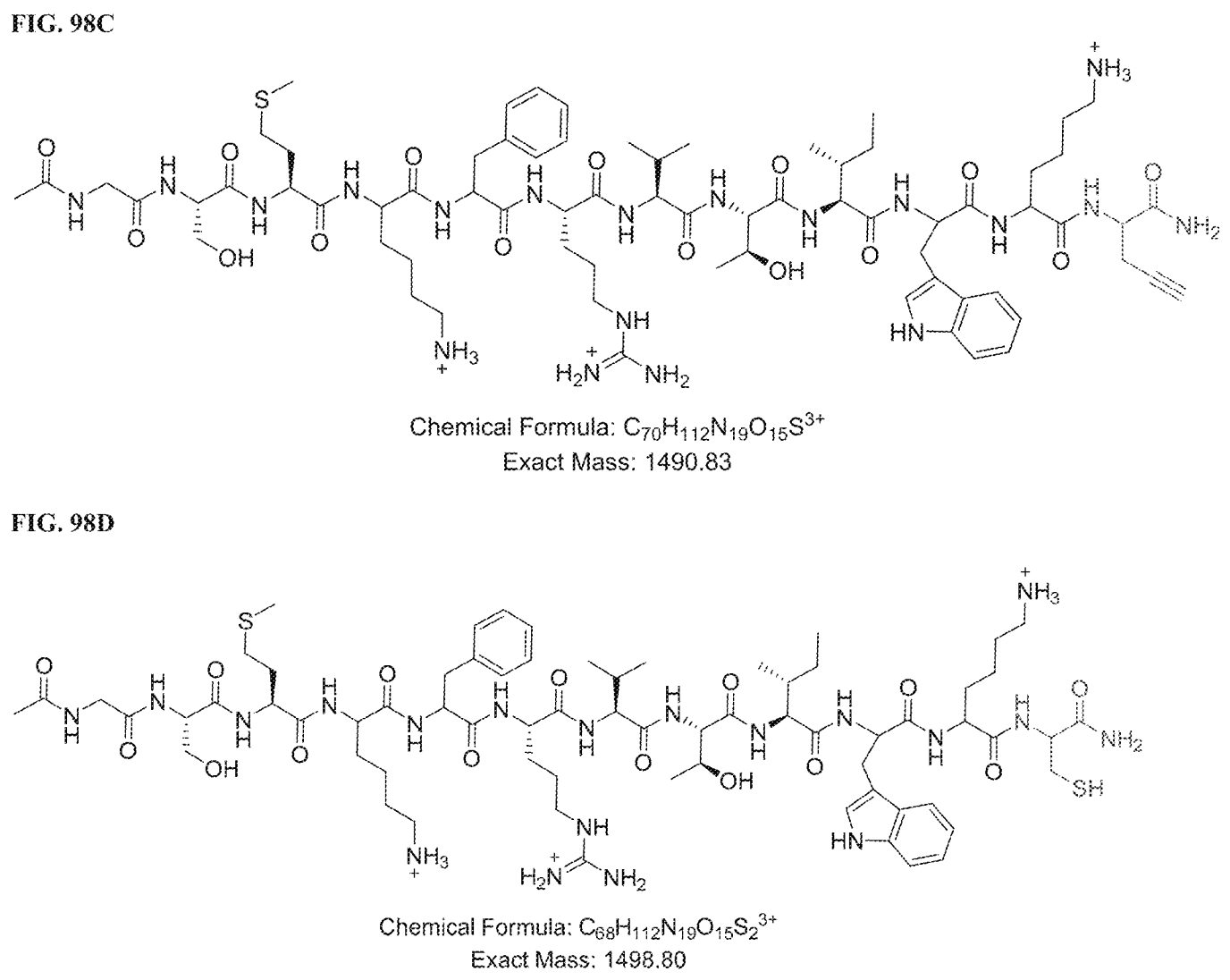

FIG. 98A-F. Exemplary SmTrip9 pep524 chemical conjugates. (A) Example of SmTrip9 pep524 with C-terminal azido-lysine modification and a N-terminal BODIPY dye. The dye is not limited to BODIPY and could be any fluorophore, BRET partner, or FRET dye/quencher partner. Dyes can be incorporated with any other combination of conjugation handles on the C-terminus. (B) Example of SmTrip9 pep524 with C-terminal azido-lysine modification for copper catalyzed or copper free 1,3-dipolar cycloaddition reactions ("Click") with unstrained or strained alkyne targets separately introduced chemically or biologically on proteins/peptides/DNA and RNA oligonucleotides/small molecules. (C) Example of SmTrip9 pep524 with C-terminal propargyl glycine modification for copper catalyzed or copper free 1,3-dipolar cycloaddition reactions ("Click") with azide, diazo, tetrazine targets separately introduced chemically or biologically on proteins/peptides/DNA and RNA oligonucleotides/small molecules. (D) Example of SmTrip9 pep524 with C-terminal cysteine modification for disulfide bond formation on solvent exposed or protected cysteine targets on proteins/peptides/DNA and RNA oligonucleotides/small molecules or proteins/peptides/DNA and RNA oligonucleotides/small molecules that have been prepared with maleimide handles or an NHS-ester. (E) Example of SmTrip9 pep524 with C-terminal N-hydroxysuccinimide ester (NHS-ester) for general conjugation to nucleophilic targets (i.e. lysines) on proteins/peptides/DNA and RNA oligonucleotides/small molecules. (F) Example of SmTrip9 pep524 with C-terminal N-hydroxysuccinimide ester (NHS-ester) for general conjugation to nucleophilic targets (i.e. lysines) on proteins/peptides/DNA and RNA oligonucleotides/small molecules.

Figure 99B:
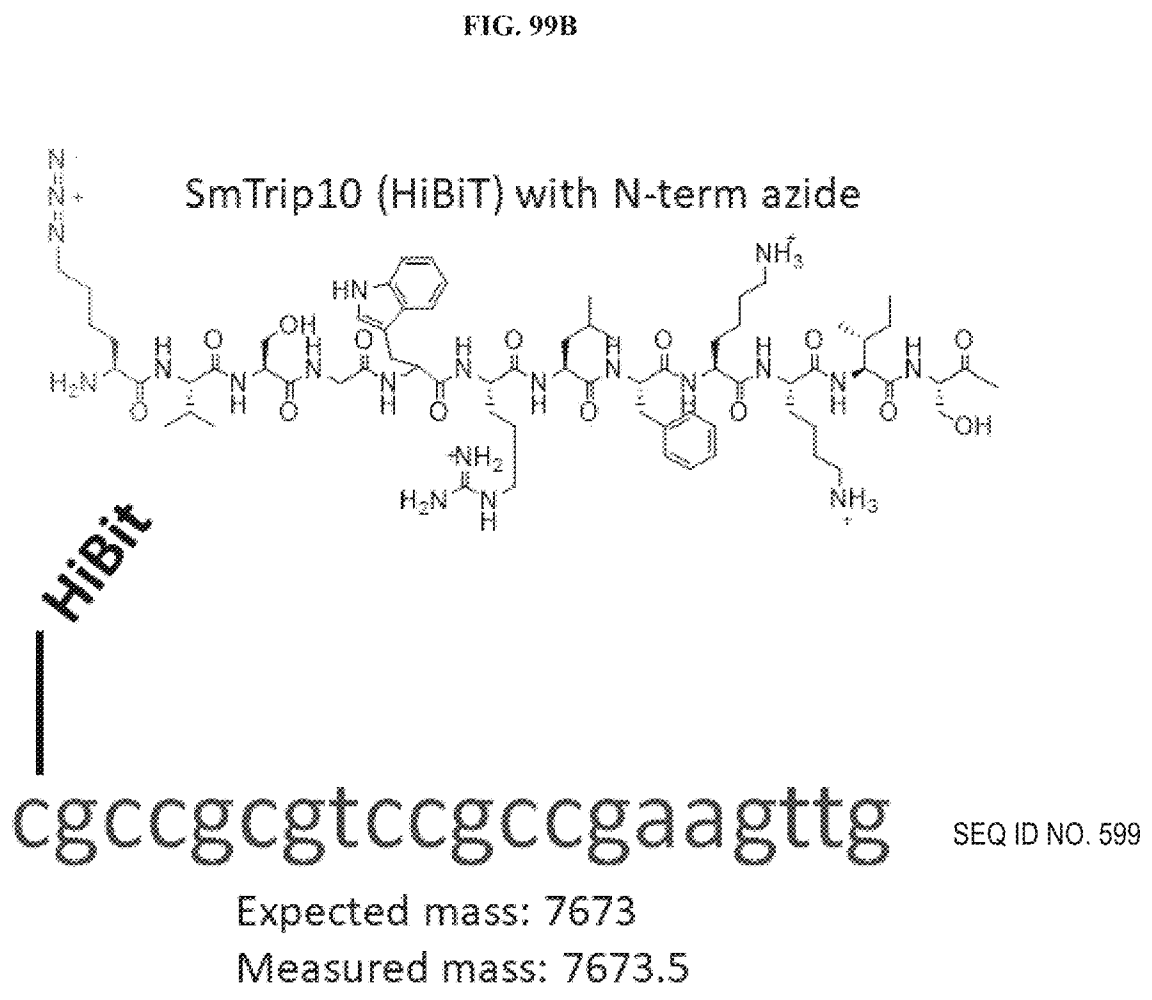

FIG. 99A-B. Exemplary peptide-oligomer probes. Peptides displaying reactive azido groups are conjugated to oligonucleotides displaying reactive alkyne groups to form exemplary peptide-oligomer probes. (A) Peptide oligomer conjugate of SmTrip9 pep286 (w/azido group) conjugated to a DNA oligomer containing 5'-terminal alkyne functionality via a copper "click" 1,3-cycloaddition. (B) Peptide oligomer conjugate of SmTrip10 pep86 (HiBiT) (w/azido group) conjugated to a DNA oligomer containing 3'-terminal alkyne functionality via a copper "click" 1,3-cycloaddition.

Figure 100:
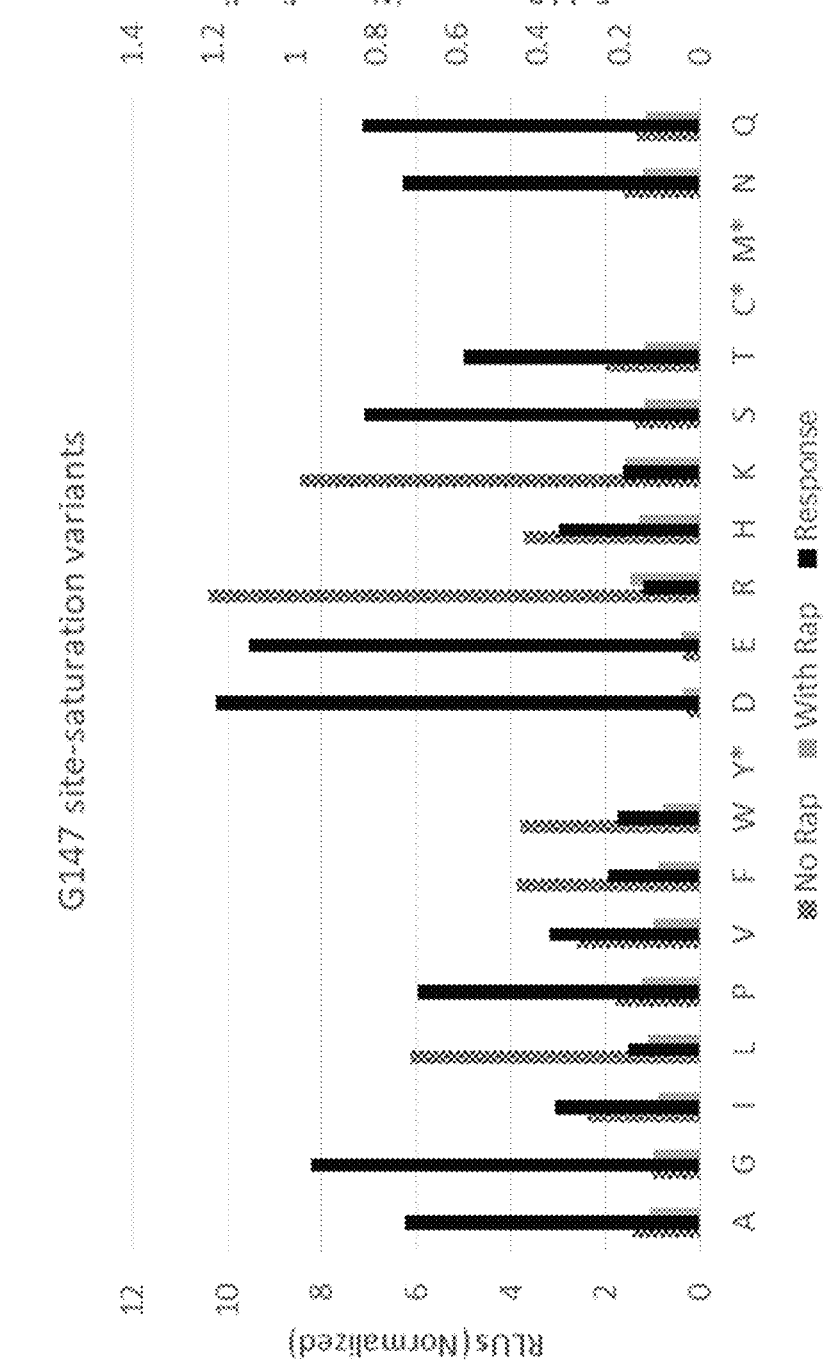

FIG. 100. Graph depicting a screen of SmTrip9 G147 site-saturation variants.

Figure 101:
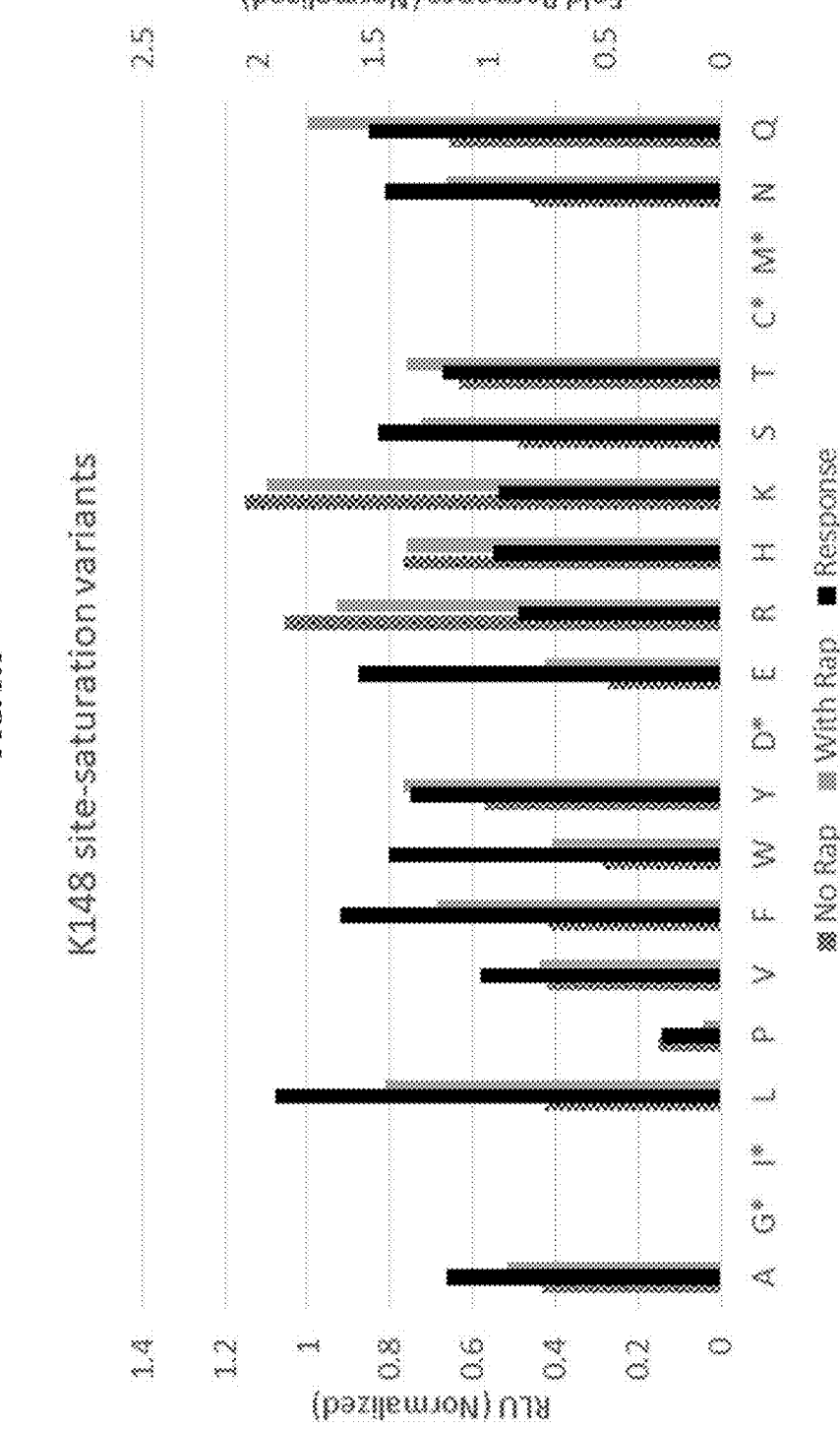

FIG. 101. Graph depicting a screen of SmTrip9 K148 site-saturation variants.

Figure 102:
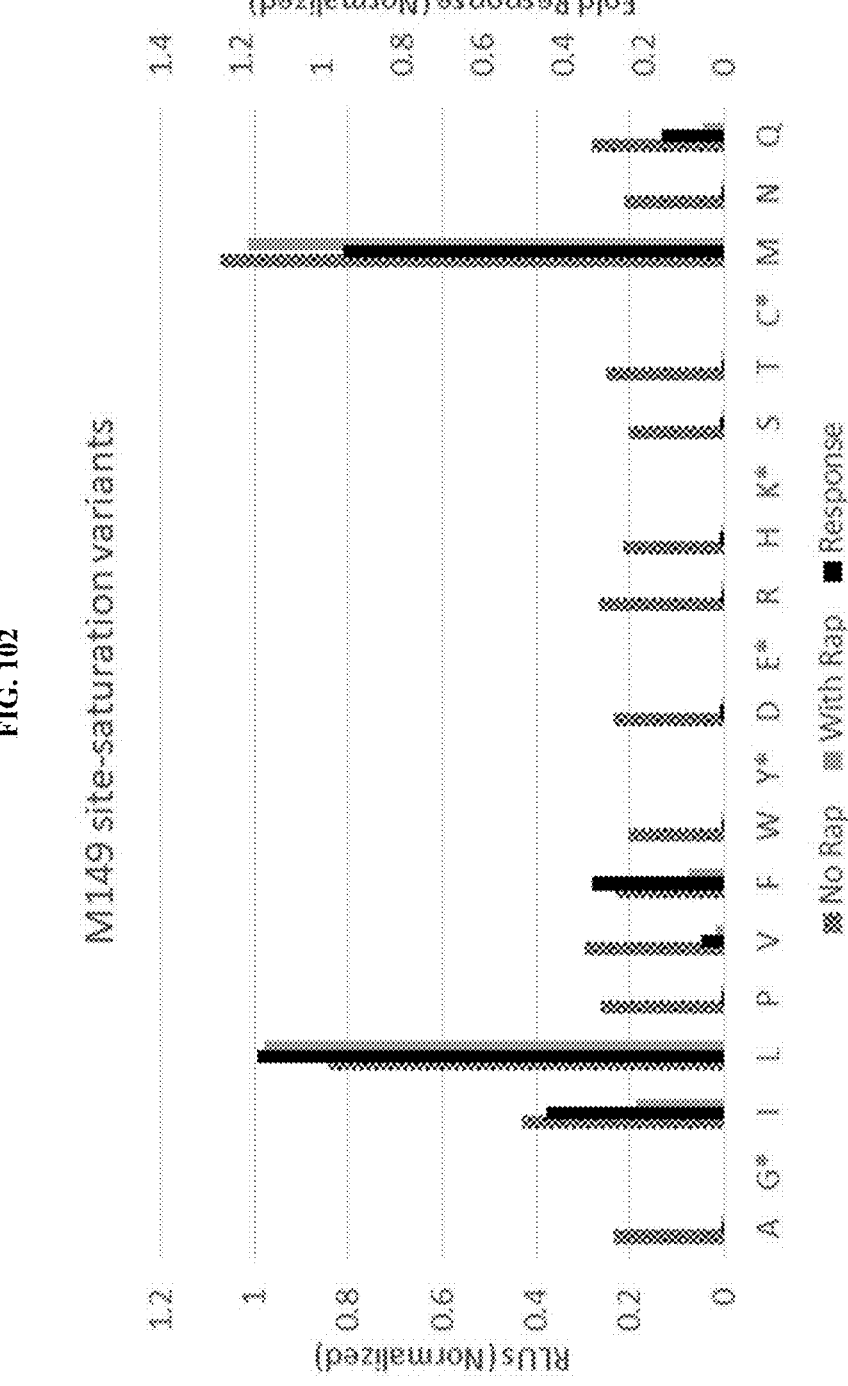

FIG. 102. Graph depicting a screen of SmTrip9 M149 site-saturation variants.

Figure 103:
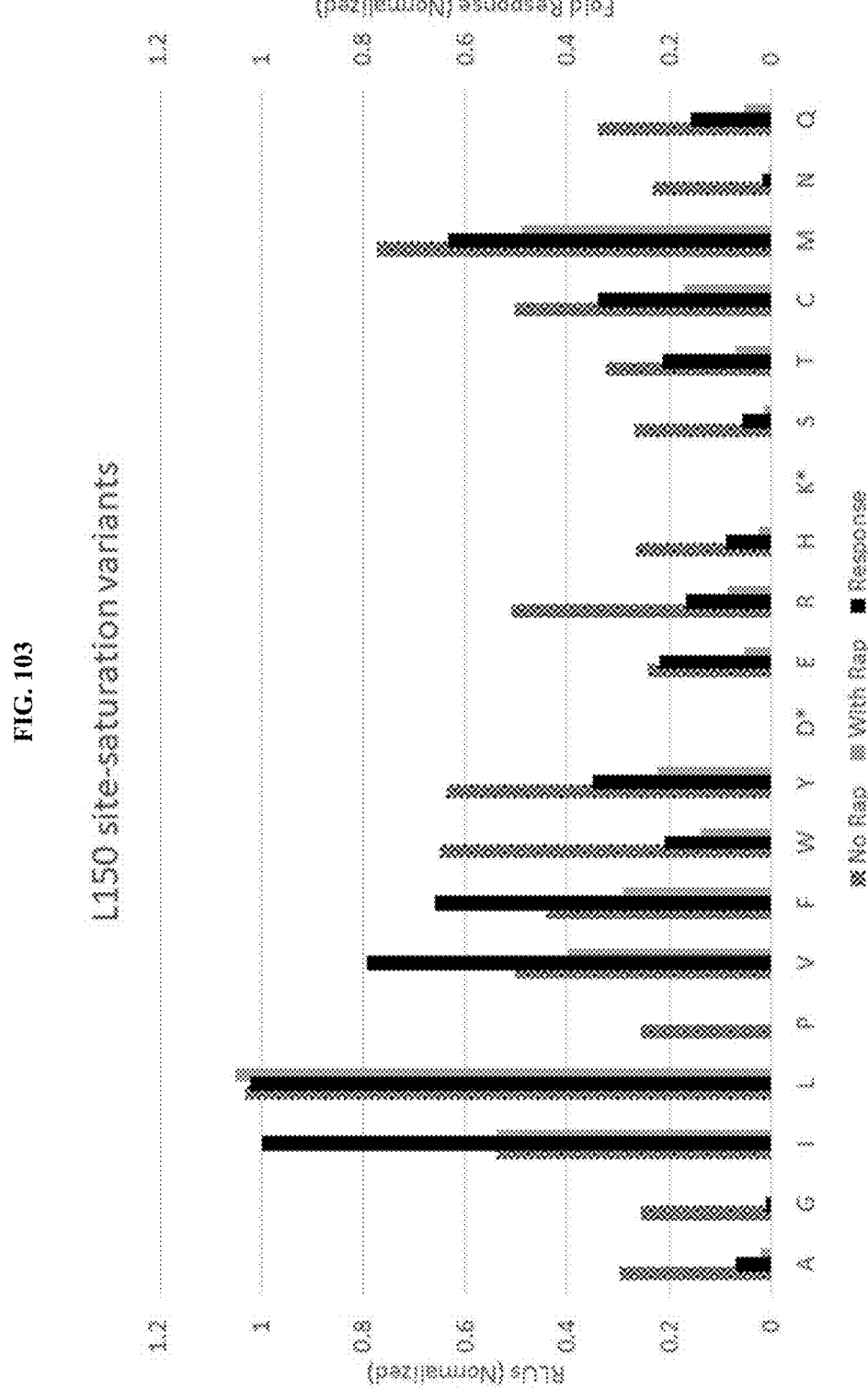

FIG. 103. Graph depicting a screen of SmTrip9 L150 site-saturation variants.

Figure 104:
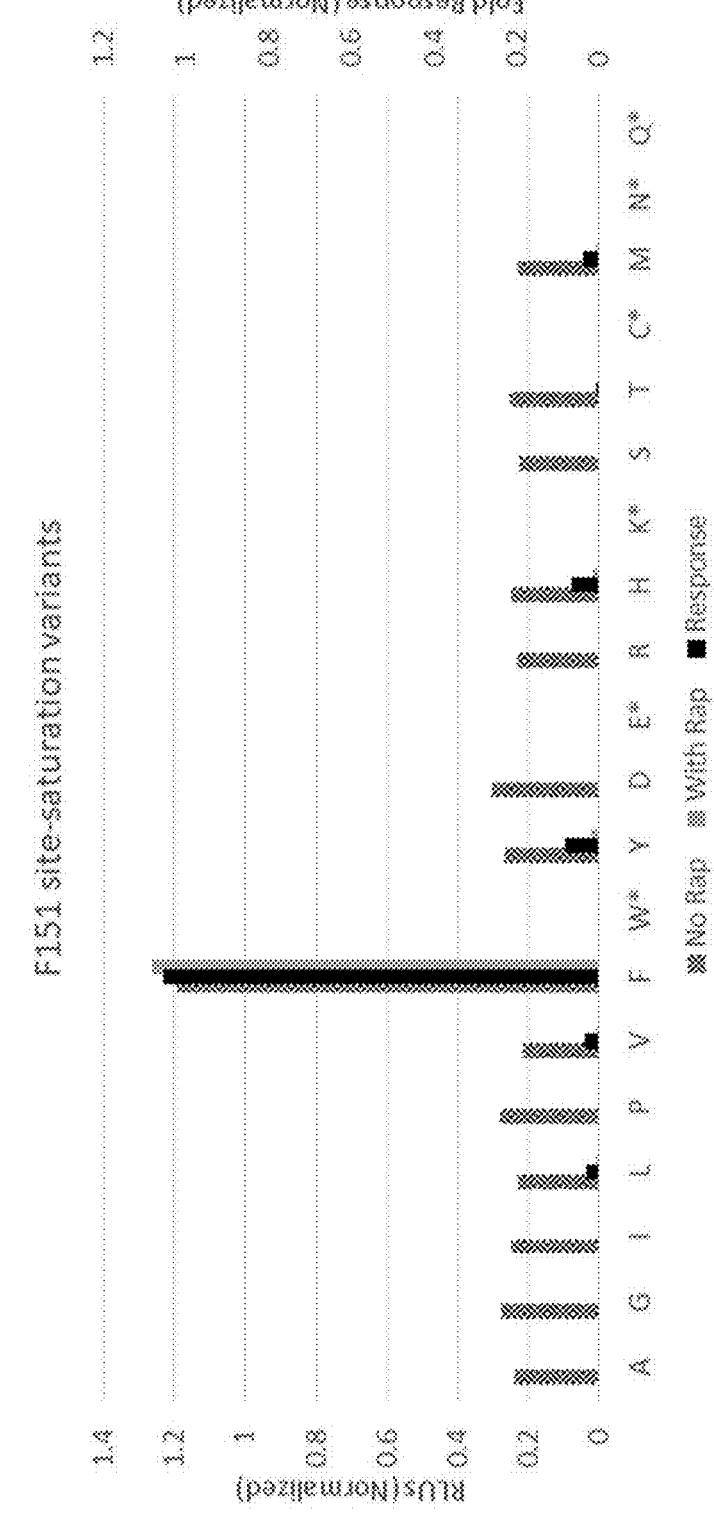

FIG. 104. Graph depicting a screen of SmTrip9 F151 site-saturation variants.

Figure 105:
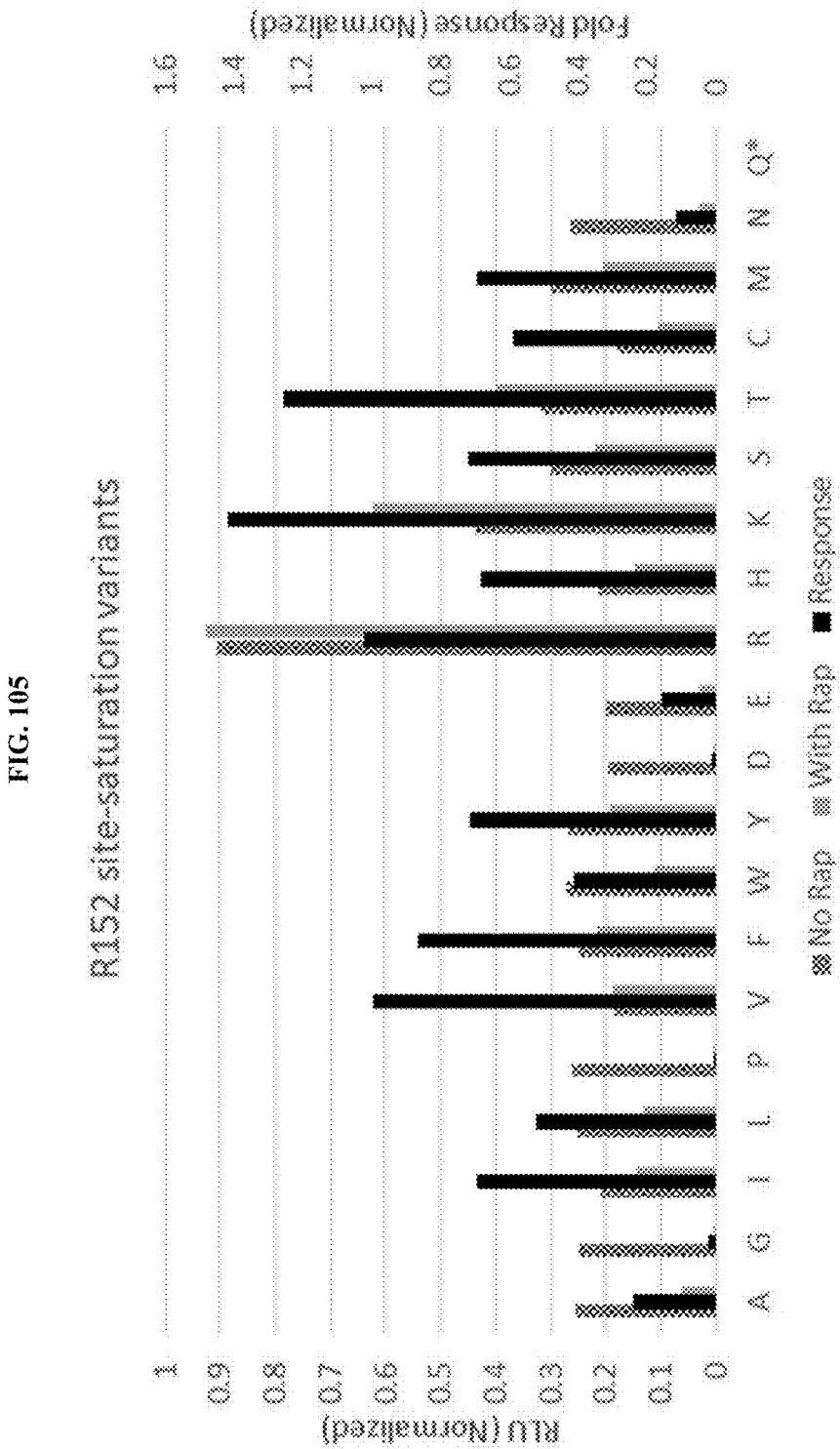

FIG. 105. Graph depicting a screen of SmTrip9 R152 site-saturation variants.

Figure 106:
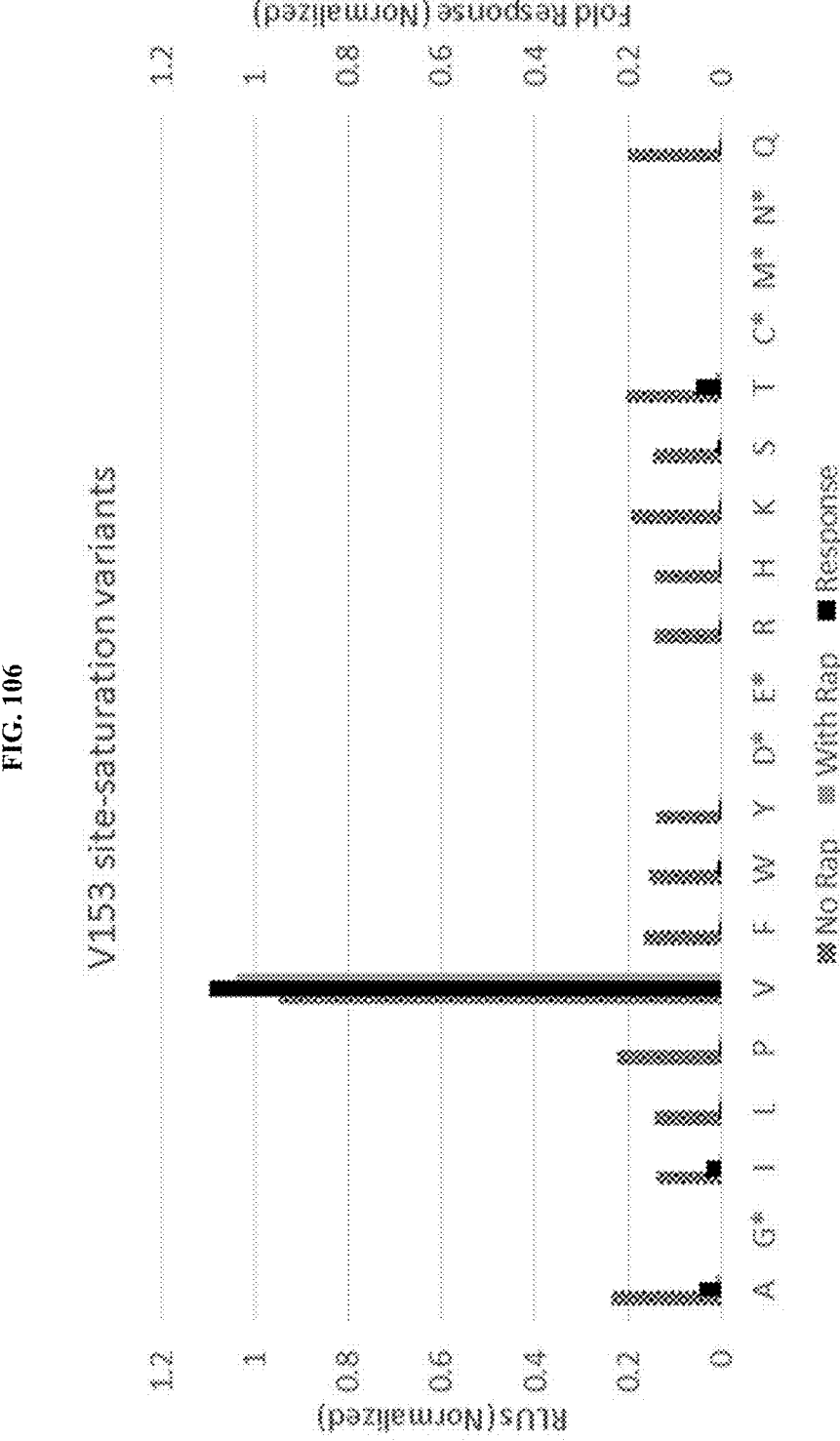

FIG. 106. Graph depicting a screen of SmTrip9 V153 site-saturation variants.

Figure 107:
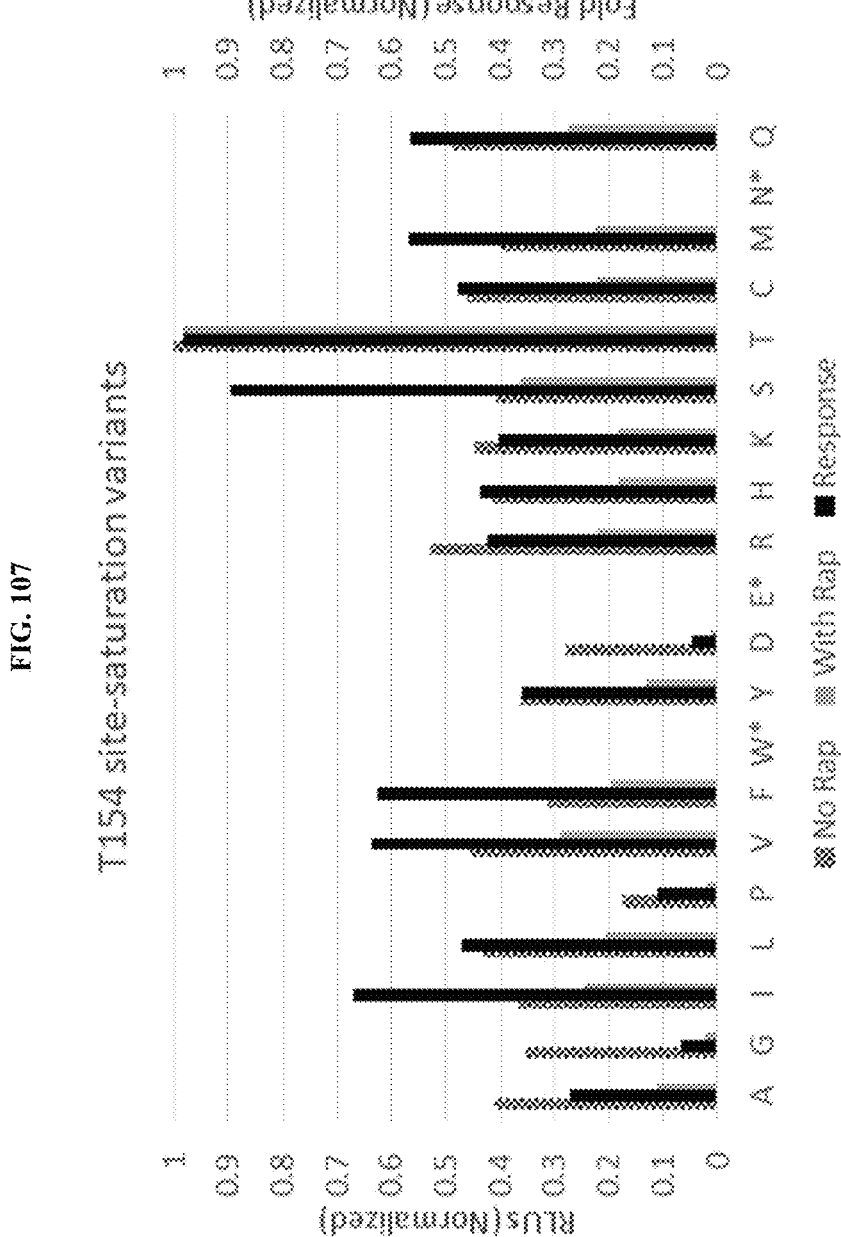

FIG. 107. Graph depicting a screen of SmTrip9 T154 site-saturation variants.

Figure 108:
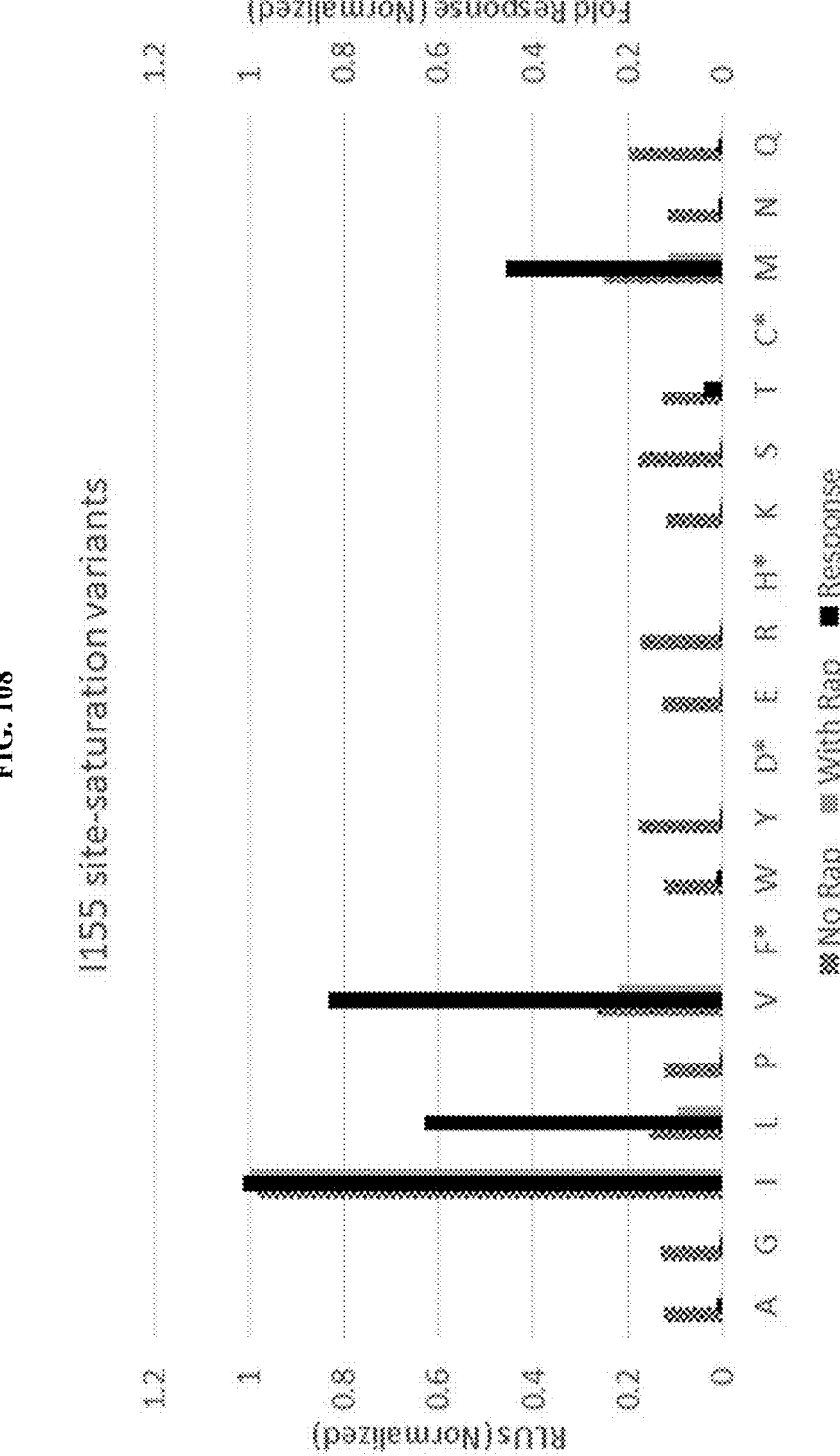

FIG. 108. Graph depicting a screen of SmTrip9 I155 site-saturation variants.

Figure 109:
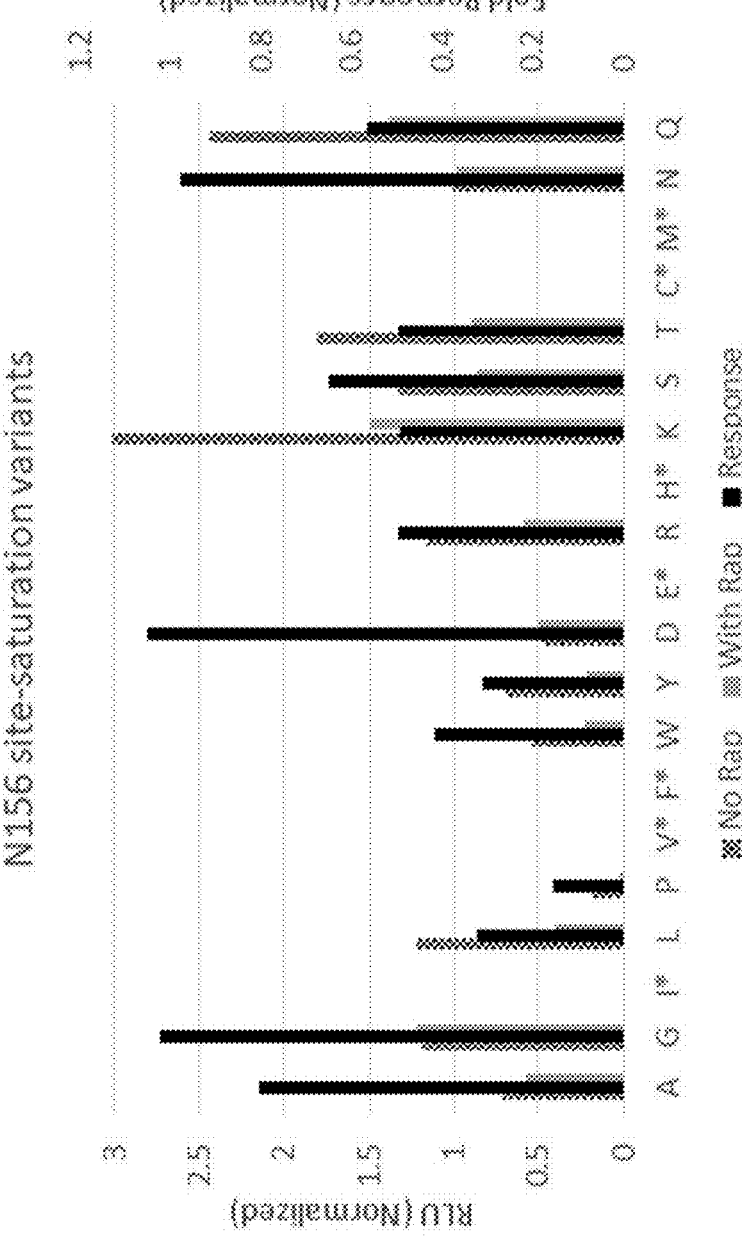

FIG. 109. Graph depicting a screen of SmTrip9 N156 site-saturation variants.

Figure 110:
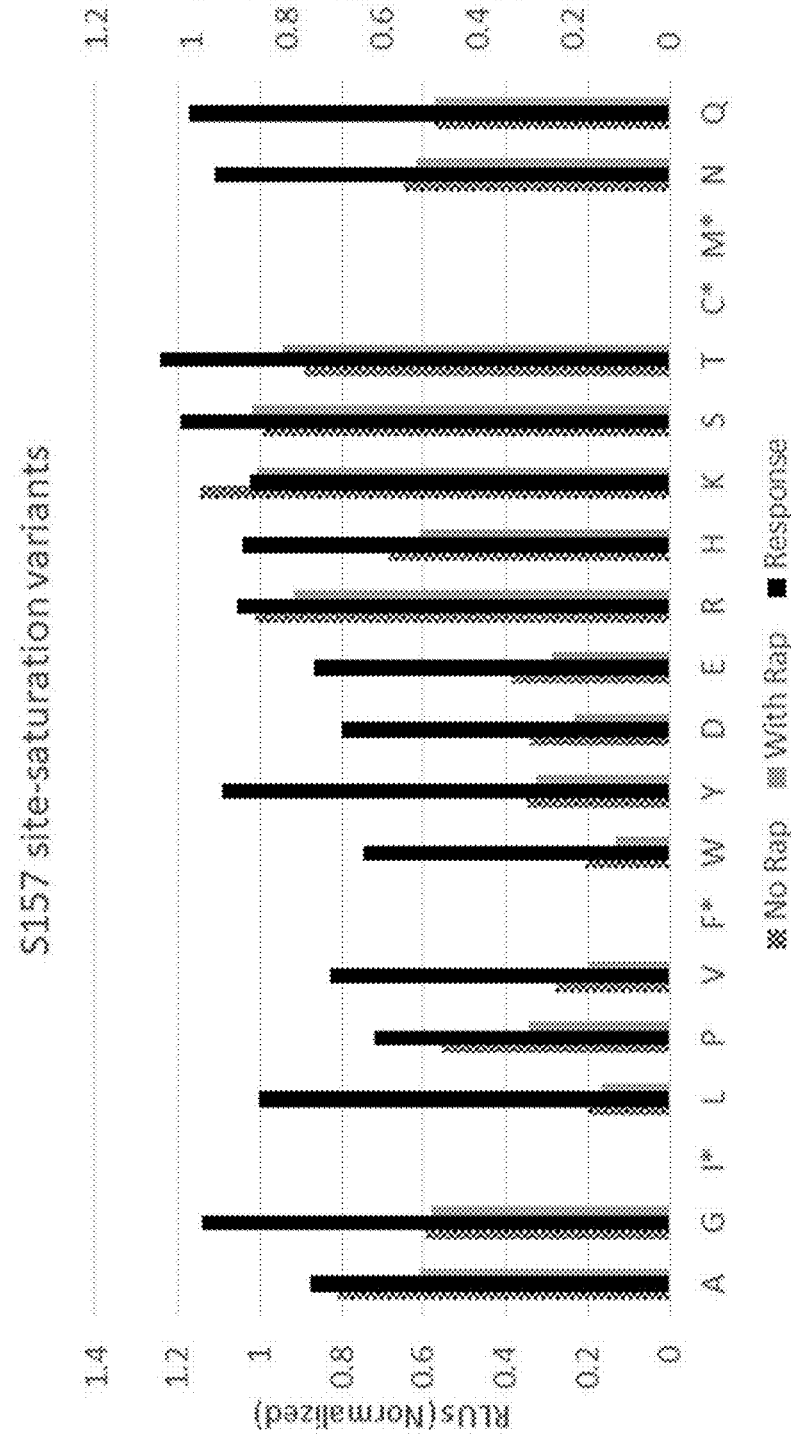

FIG. 110. Graph depicting a screen of SmTrip9 S157 site-saturation variants.

Figure 111:
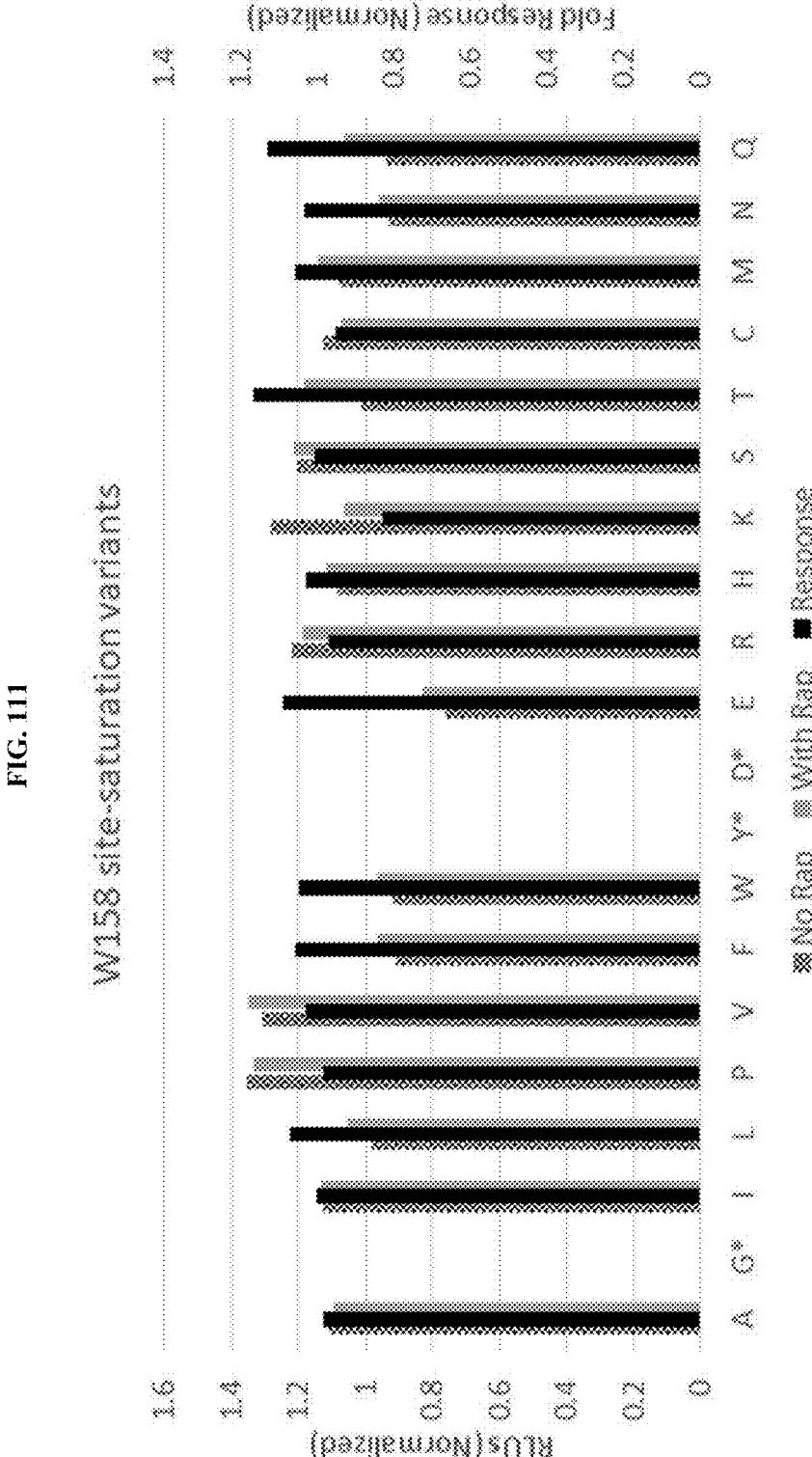

FIG. 111. Graph depicting a screen of SmTrip9 W158 site-saturation variants.

Figure 112:
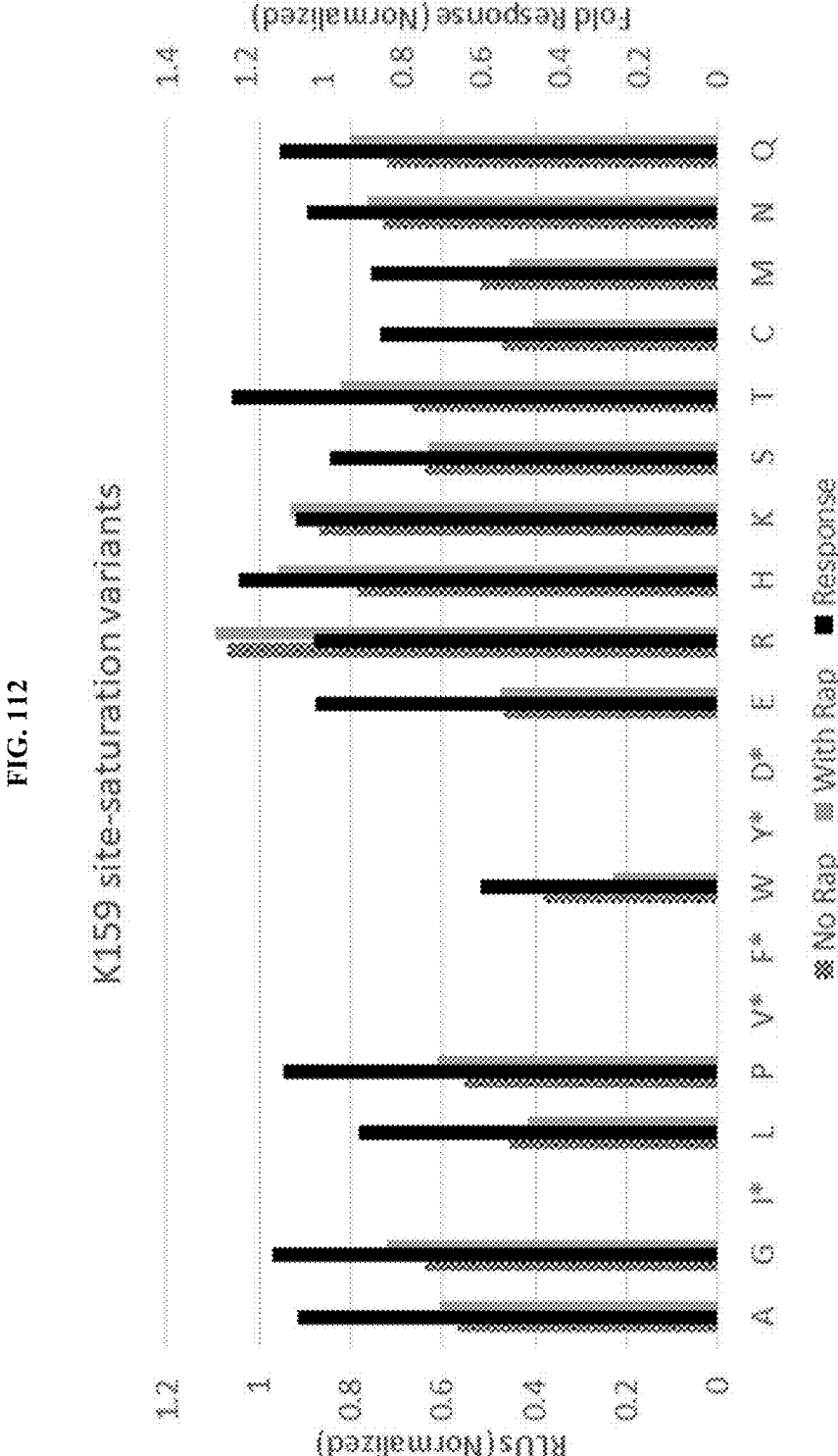

FIG. 112. Graph depicting a screen of SmTrip9 K149 site-saturation variants.

FIG. 113. Table of the results of FRB-FKBP facilitated complementation in E. coli lysates with SmTrip9 pep435/434.

FIG. 114. Table of the results of FRB-FKBP facilitated complementation in E. coli lysates with SmTrip9 pep435/434.

FIG. 115. Table of the results of FRB-FKBP facilitated complementation in E. coli lysates with SmTrip9 pep435/434.

FIG. 116A-C. Table of the results FRB-FKBP facilitated complementation assay screen with combinational SmTrip9 variants.

FIG. 117. Table of the results FRB-FKBP facilitated complementation assay screen with combinational SmTrip9 variants.

FIG. 118. Table of the results FRB-FKBP facilitated complementation assay screen with combinational SmTrip9 variants.

FIG. 119. Table of the results FRB-FKBP facilitated complementation assay screen with combinational SmTrip9 variants.

FIG. 120. Table of the results FRB-FKBP facilitated complementation assay screen with combinational SmTrip9 variants.

FIG. 121. Table of the results FRB-FKBP facilitated complementation assay screen with combinational SmTrip9 variants.

FIG. 122A-B. Table of the results FRB-FKBP facilitated complementation assay screen with combinational SmTrip9 variants.

FIG. 123. Table of Kd and Bmax of SmTrip9 synthetic peptides.

FIG. 124. Table of Kd and Bmax of SmTrip9 synthetic peptides.

FIG. 125. Table of Kd and Bmax of SmTrip9 synthetic peptides.

FIG. 126. Table of Kd and Bmax of SmTrip9 synthetic peptides.

FIG. 127. Table of Kd and Bmax of SmTrip9 synthetic peptides.

FIG. 128. Table of Kd and Bmax of SmTrip9 synthetic peptides.

FIG. 129. Table of Kd and Bmax of SmTrip9 synthetic peptides.

FIG. 130. Table of Kd and Bmax of SmTrip9 synthetic peptides.

FIG. 131A-C. Table of Solubility of synthetic SmTrip9 peptides.

Figure 132:
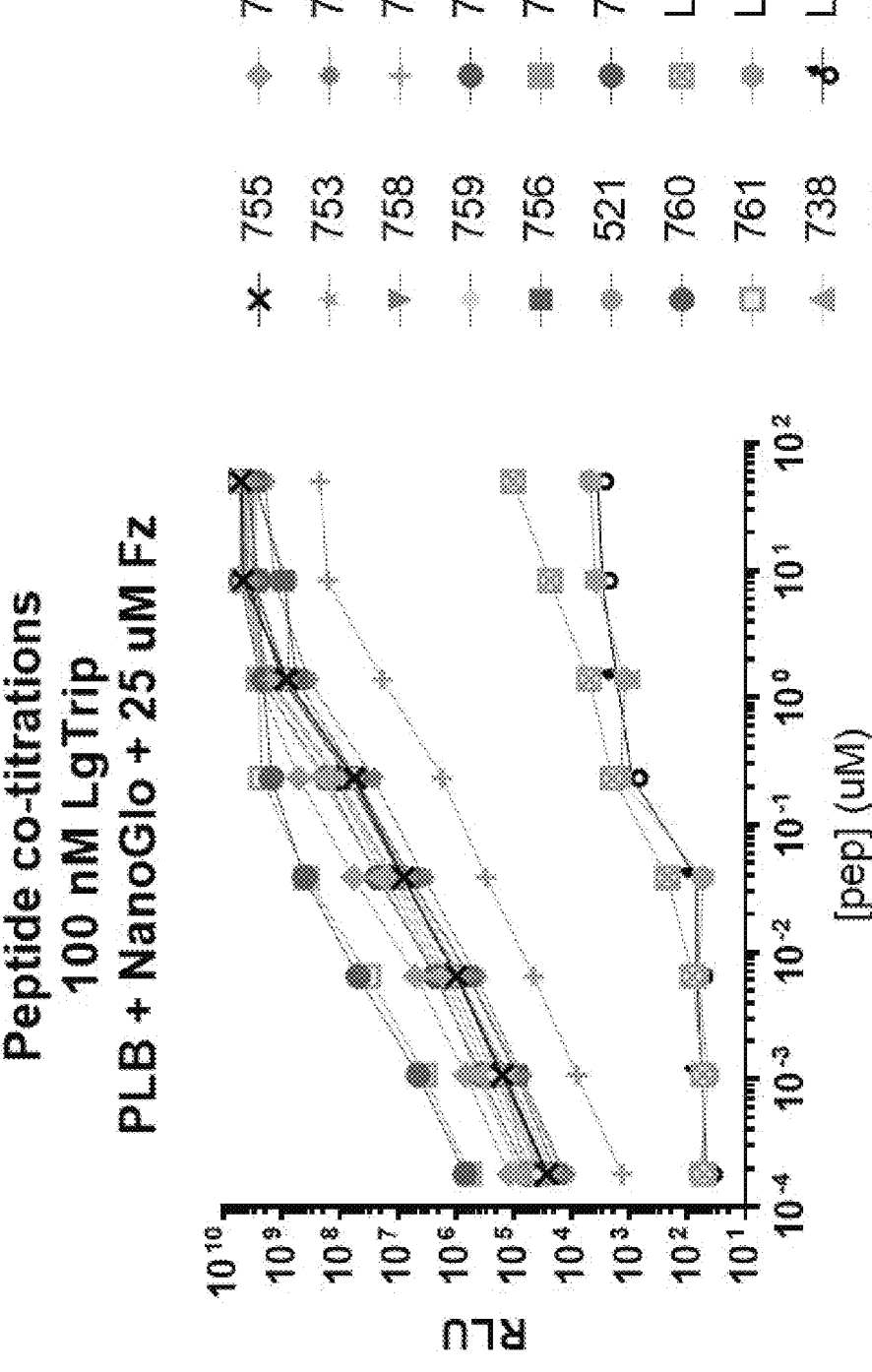

FIG. 132. Graph of biochemical co-titration of SmTrip9 synthetic peptides and pep289.

Figure 133:
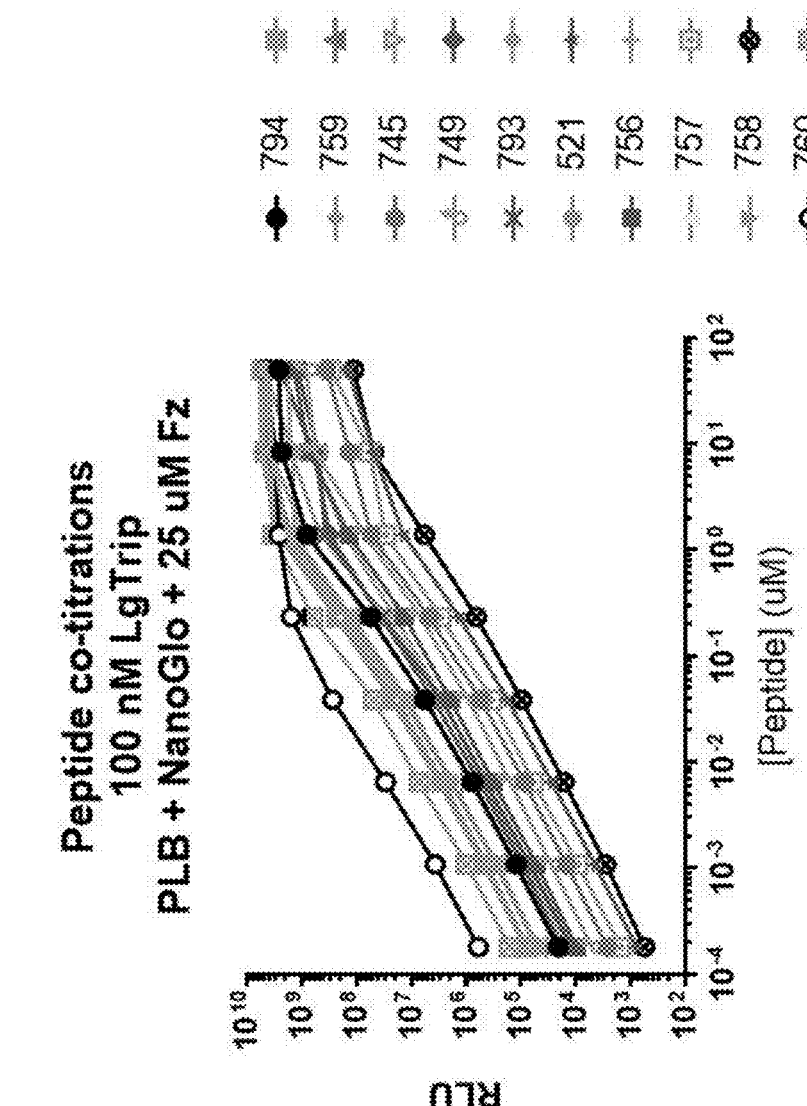

FIG. 133. Graph of biochemical co-titration of SmTrip9 synthetic peptides and pep289.

Figure 134:
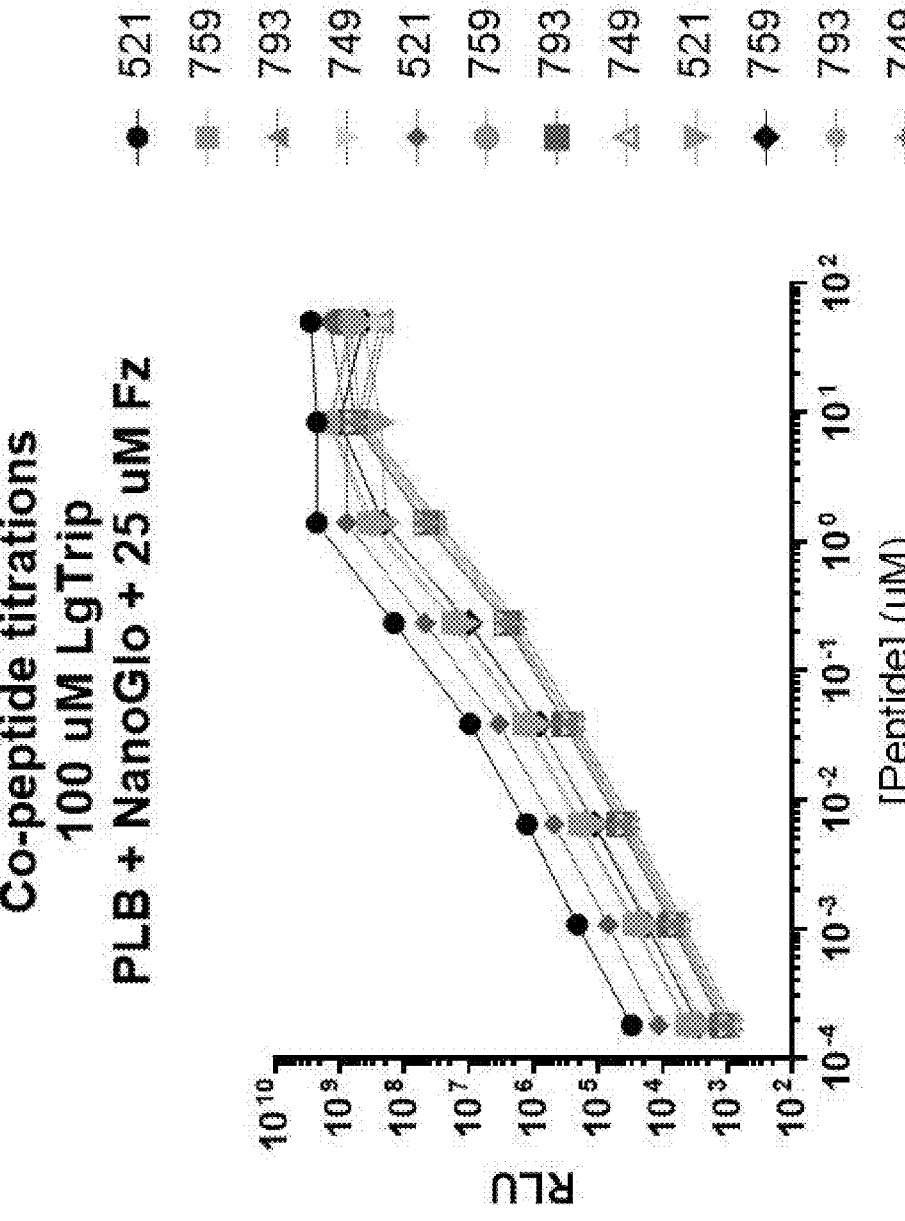

FIG. 134. Graph of biochemical co-titration of SmTrip9 and SmTrip 10 synthetic peptides.

Figure 135:
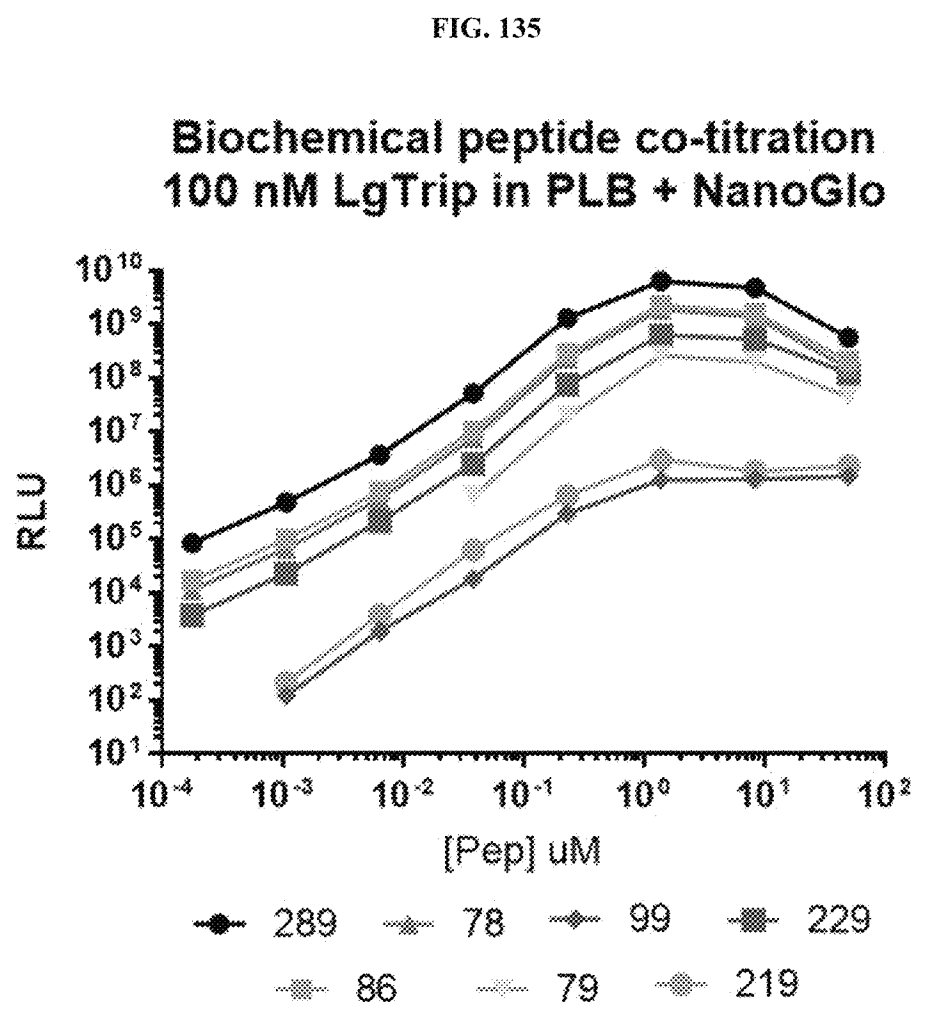

FIG. 135. Graph of biochemical co-titration of pep521 and alternative SmTrip 10 synthetic peptides.

Figure 136:
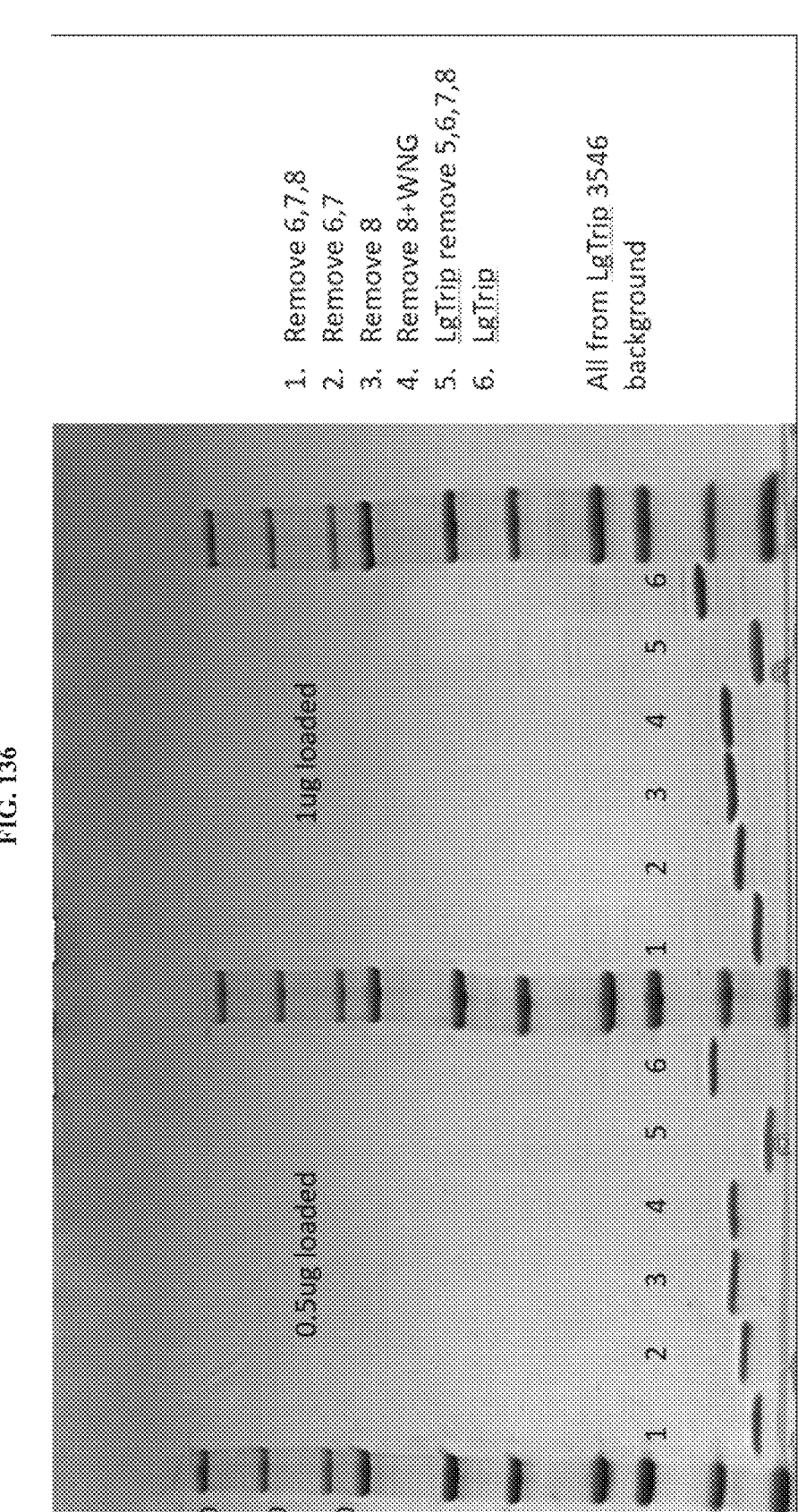
Figure 137A:
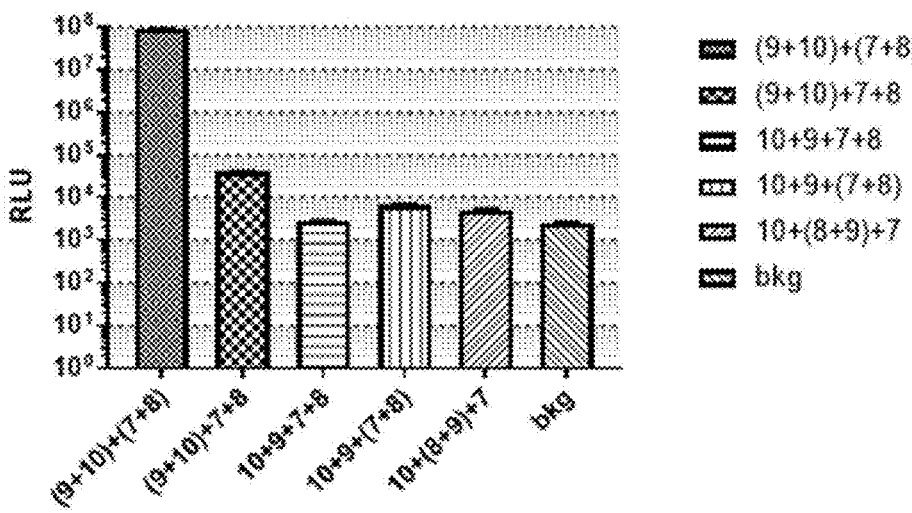
Figure 137B:
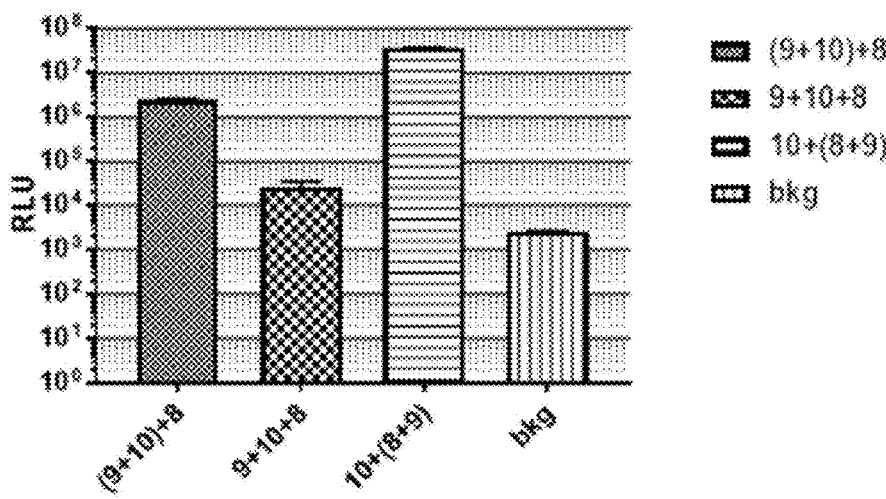
Figure 137C:
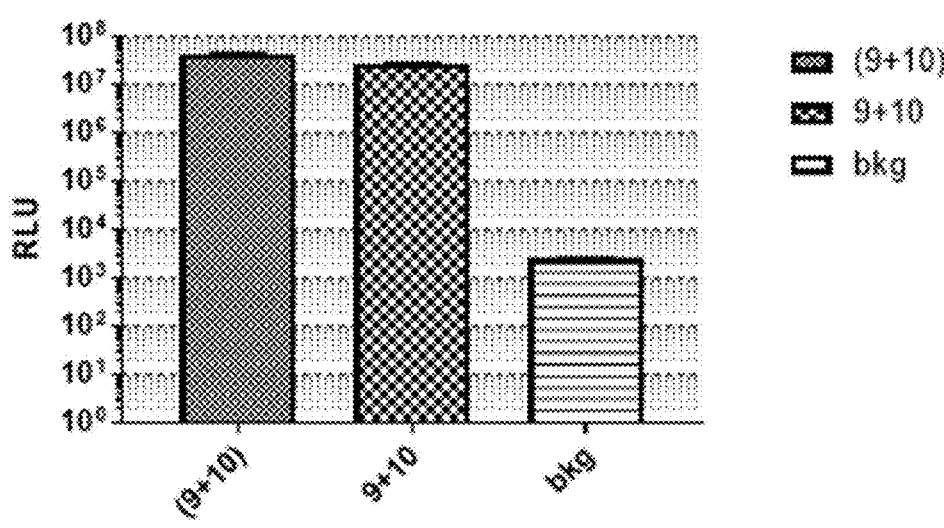
Figure 137D:
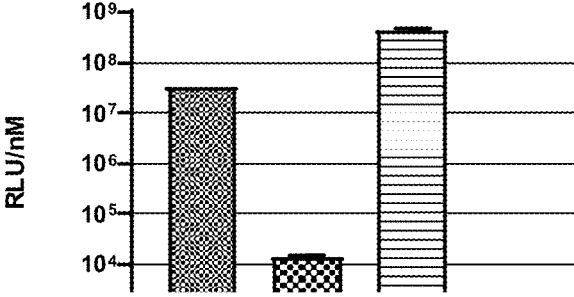

FIG. 136. SDS PAGE gel of strand removal (purification) from LgTrip 3546 template.

FIG. 137A-D. Graphs of strand removal proteins with various combinations of peptides.

Figure 138A:
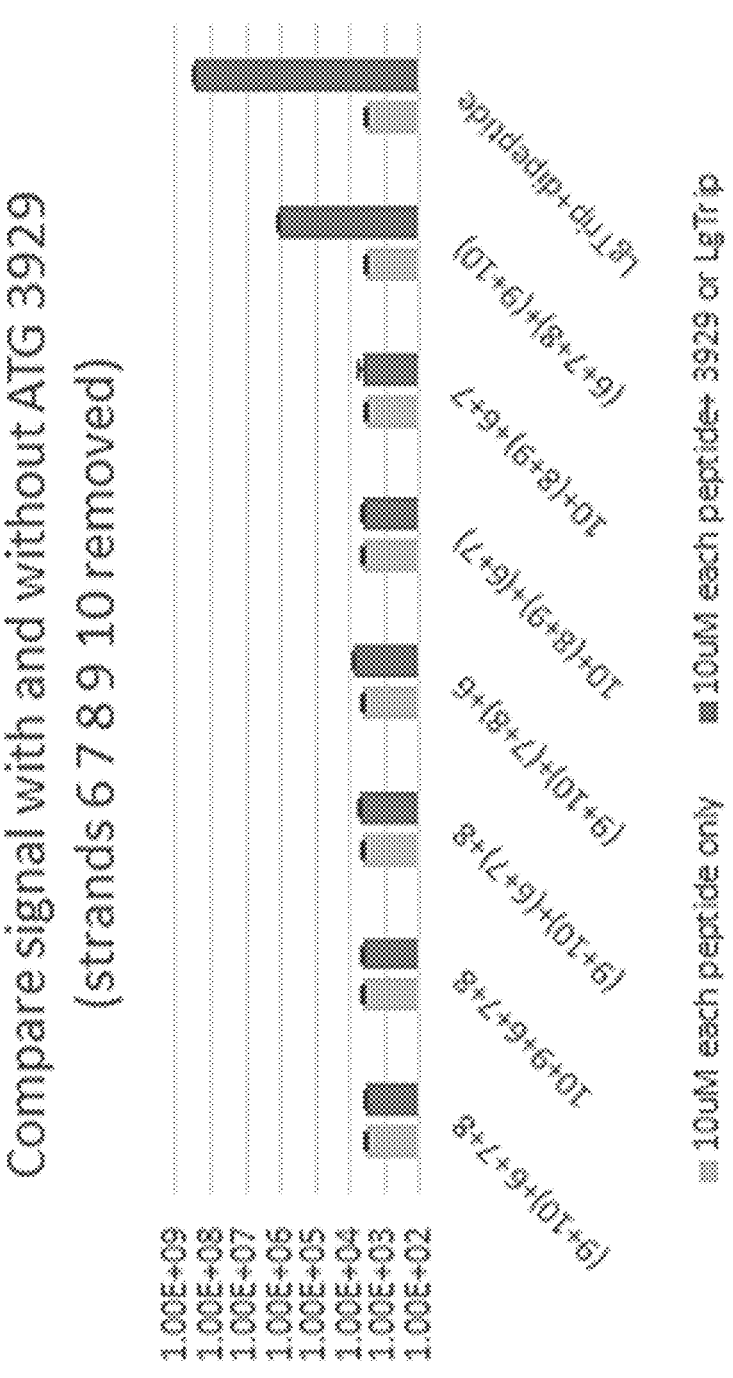
Figure 138B:
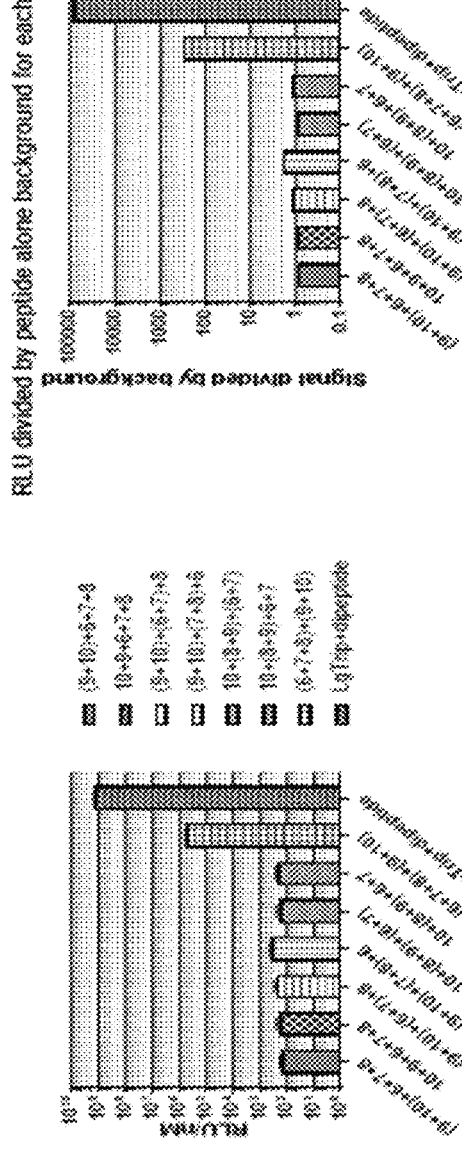

FIG. 138A-B. graphs of strands 6, 7, 8, 9, or 10 removal (purification) from LgTrip 3546 template.

FIG. 139A-E. Graphs of Kd and Bmax values of the dipeptide titrations.

Figure 140:
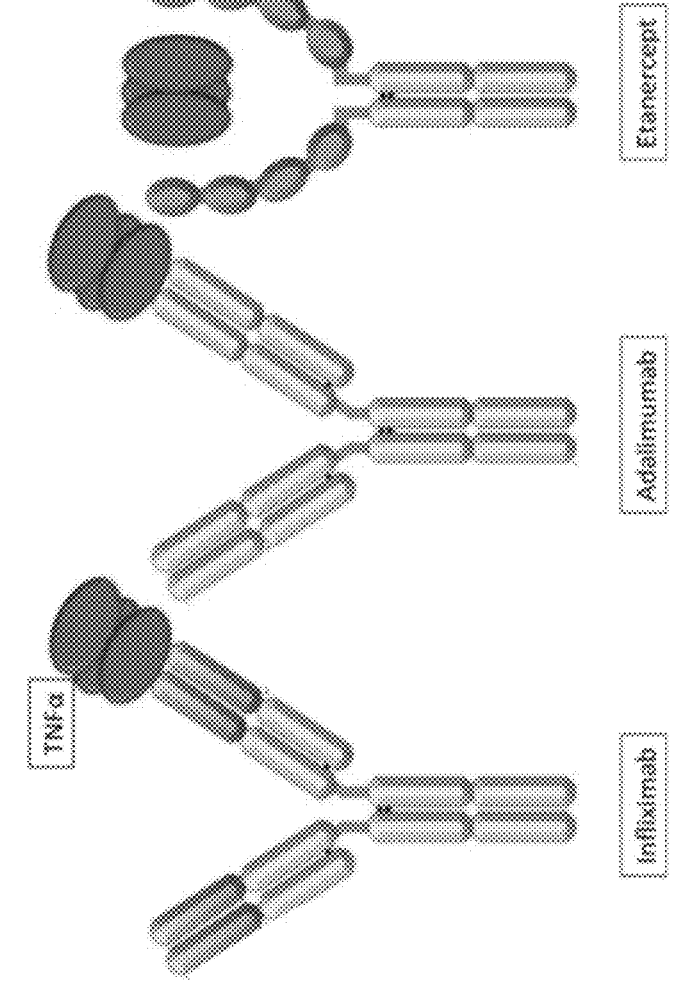

FIG. 140. Schematic depicting the approach taken to develop a solution-based homogeneous, quantitative assay for anti-TNFa biologic agents Remicade, Humira, and Enbrel using tripartite protein G and TNFa fusion proteins.

Figure 141:
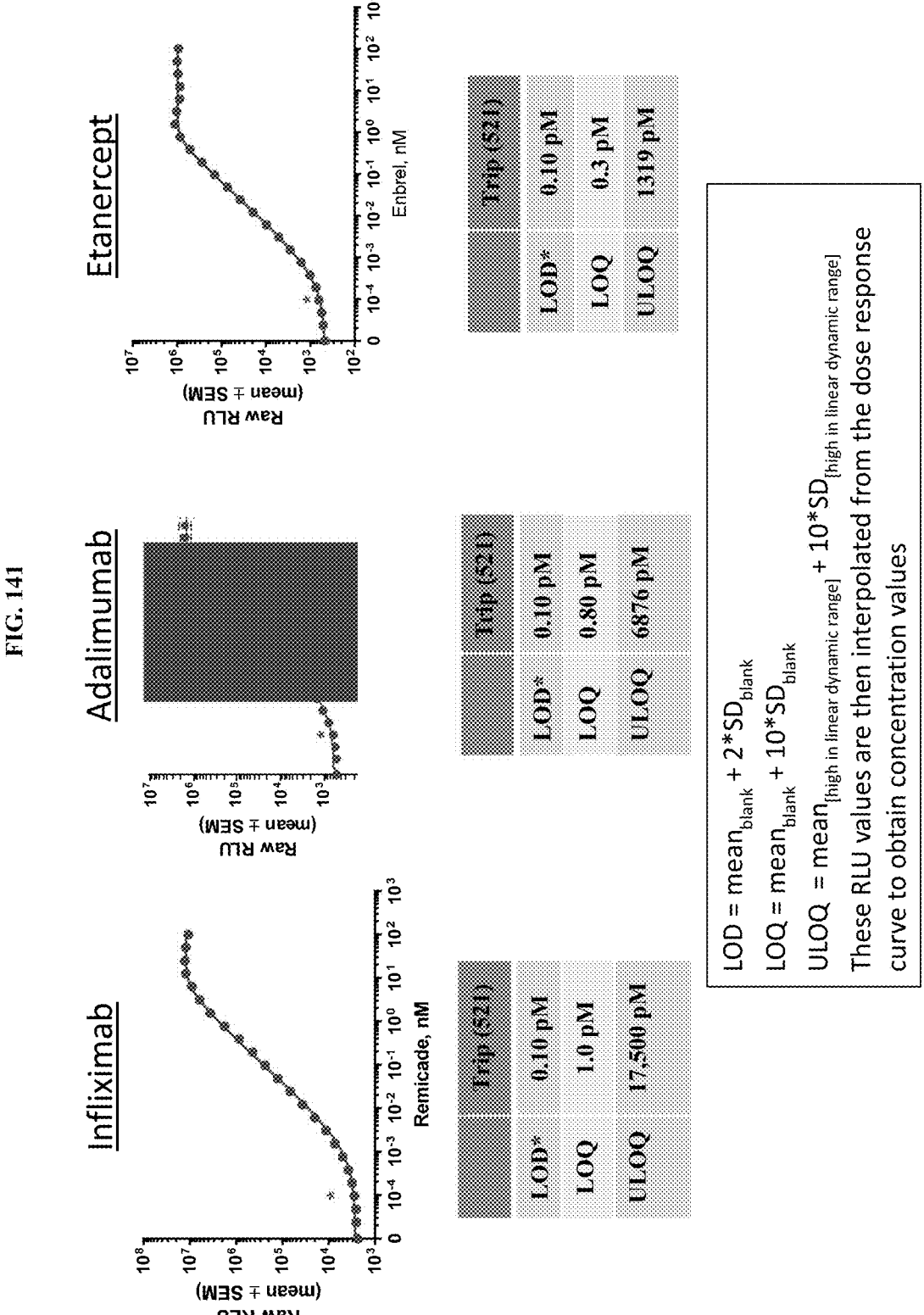

FIG. 141. Graphs depicting quantitative analysis of TNFa inhibitor dose responses via facilitated complementation with SmTrip9 pep521-protein G (SEQ ID NO: 268) and TNFa-SmTrip10 pep289 (VS-HiBIT; SEQ ID NO:150) fusion proteins with purified LgTrip 3546 (SEQ ID NO: 51) in a solution-based homogeneous assay.

Figure 142:
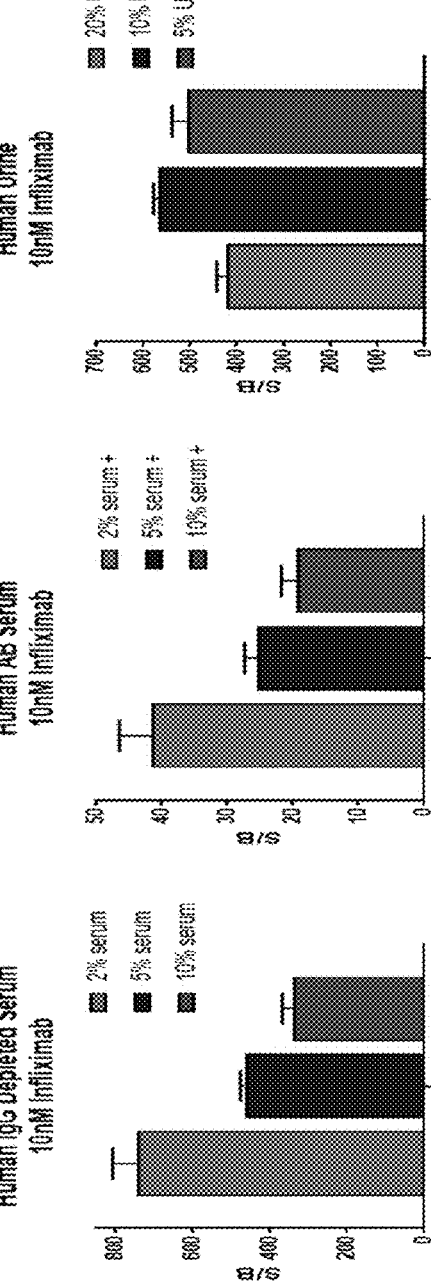

FIG. 142. Graphs depicting quantitative analysis of 10 nM infliximab via facilitated complementation with SmTrip9 pep521-protein G (SEQ ID NO: 268) and TNFa-SmTrip10 pep289 (VS-HiBiT; SEQ ID NO:150) fusion proteins with purified LgTrip 3546 (SEQ ID NO: 51) in the presence of complex sample matrices including human serum and urine using a solution-based homogenous assay.

Figure 143:
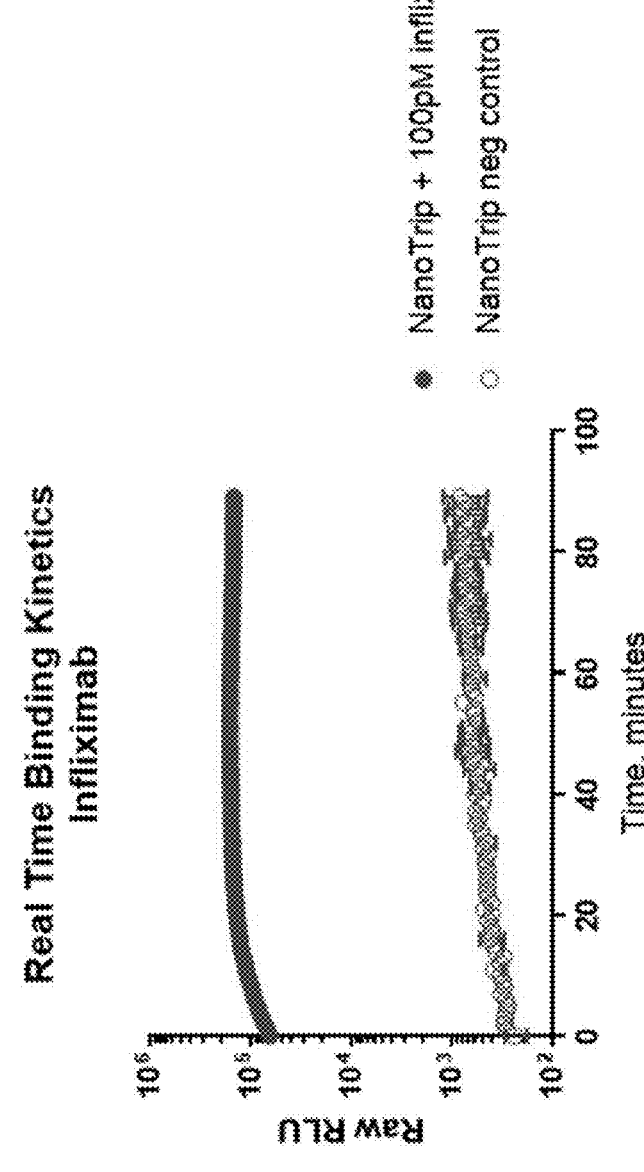

FIG. 143. Graph depicting the binding kinetics of signal generation measuring 100 pM of infliximab via facilitated complementation with SmTrip9 pep521-protein G (SEQ ID NO: 268) and TNFa-SmTrip10 pep289 (VS-HiBIT; SEQ ID NO:150) fusion proteins with purified LgTrip 3546 (SEQ ID NO: 51) in a solution-based homogenous assay.

FIG. 144. Graph depicting signal generation measuring 10 nM of infliximab via facilitated complementation of different SmTrip9 pep(X)-protein G variants and TNFa-SmTrip10 pep289 (VS-HiBIT; SEQ ID NO:150) fusion proteins with purified LgTrip 3546 (SEQ ID NO: 51) in a solution-based homogenous assay.

Figure 145:
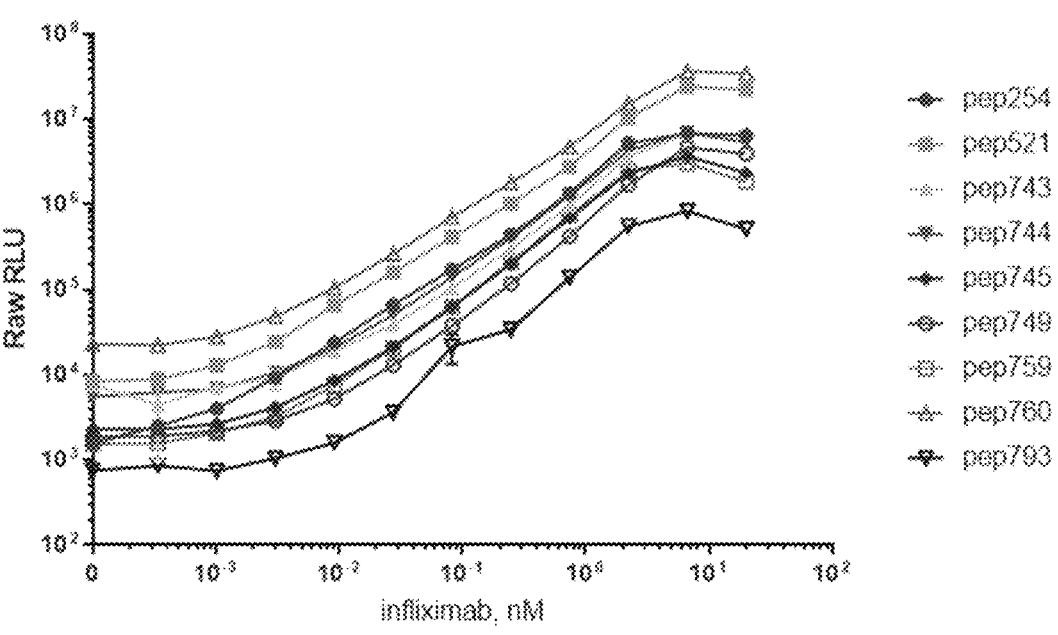

FIG. 145. Schematic depicting the approach taken to develop a homogenous cell-based, quantitative assay for anti-EGFR biologic agents panitumumab and cetuximab using SmTrip9-protein G fusion proteins and HEK293 cells expressing SmTrip10 pep289-EGFR (SEQ ID NO: 150).

Figure 146:
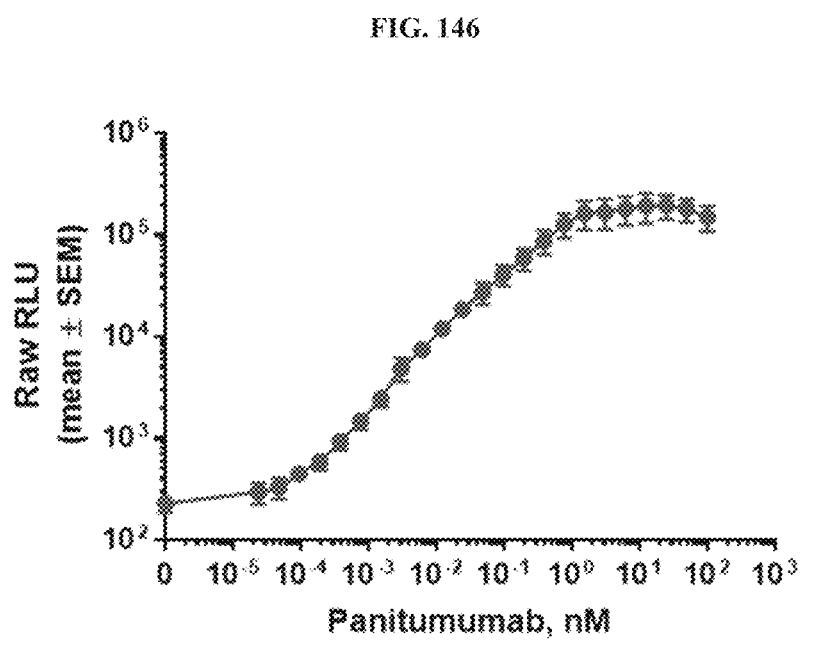

FIG. 146. Graph depicting quantitation of Panitumumab via facilitated complementation with SmTrip9 pep521-protein G (SEQ ID NO: 268) fusion protein and SmTrip10 pep289-EGFR (VS-HiBIT; SEQ ID NO:150) expressing cells with purified LgTrip 3546 (SEQ ID NO: 51) in a cell-based homogeneous assay.

Figure 147:
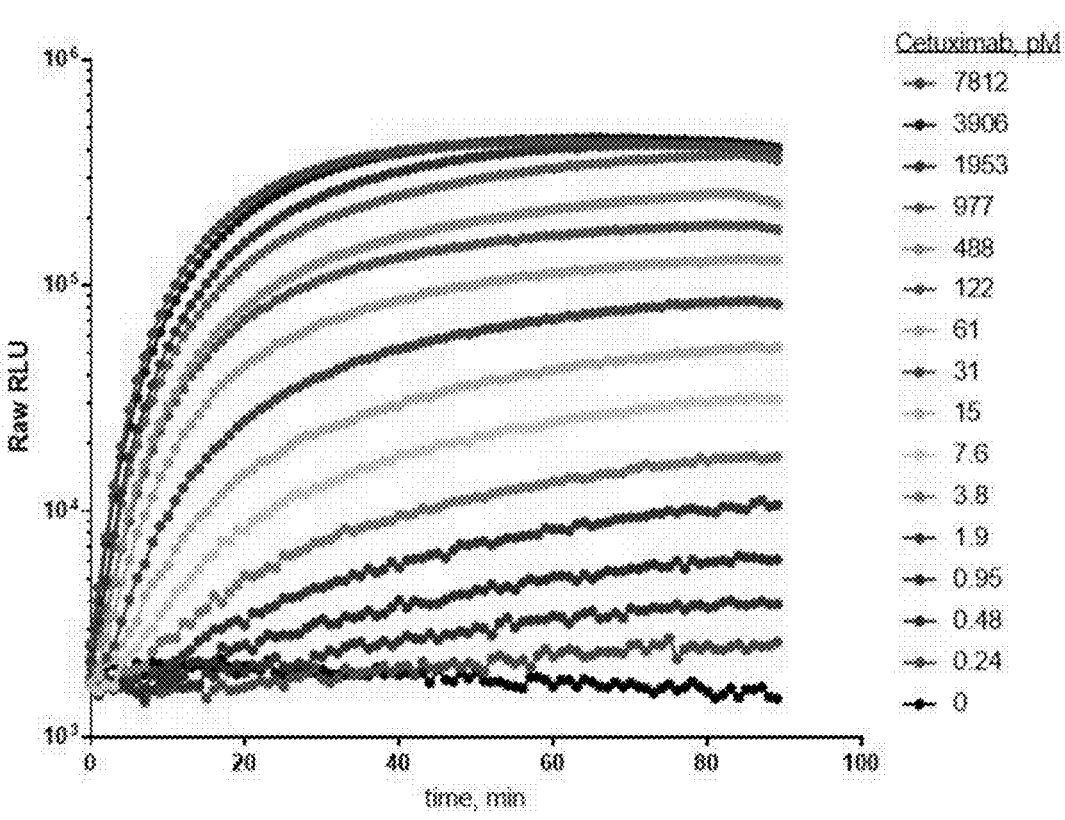

FIG. 147. Graph depicting the real time binding kinetics of signal generation measuring Cetuximab via facilitated complementation with SmTrip9 pep521-protein G (SEQ ID NO: 268) fusion protein and SmTrip10 pep289-EGFR (VS-HiBIT; SEQ ID NO:150) expressing cells with purified LgTrip 3546 (SEQ ID NO: 51) in a cell-based homogeneous assay.

FIG. 148. Graph depicting signal generation measuring 1 nM of panitumumab via facilitated complementation of different SmTrip9 pep(X)-protein G variants and SmTrip10 pep289-EGFR (VS-HiBIT; SEQ ID NO:150) expressing cells paired with purified LgTrip 3546 (SEQ ID NO: 51) in a cell-based homogenous assay.

FIG. 149. Graph depicting quantitation of panitumumab dose response via facilitated complementation of different SmTrip9 pep(X)-protein G variants and SmTrip10 pep289-EGFR (VS-HiBIT; SEQ ID NO: 150) expressing cells paired with purified LgTrip 3546 (SEQ ID NO: 51) in a cell-based homogenous assay.

FIG. 150. Graphs depicting quantitation of human IL-1beta using Halotag-SmTrip9 pep521 (SEQ ID NO: 268) and HaloTag-SmTrip10 pep289 (SEQ ID NO: 150) chemically labeled paired antibodies in a solution-based homogeneous assay. Real time binding kinetics for human Troponin using NanoTrip chemically labeled paired antibodies.

Figure 151:
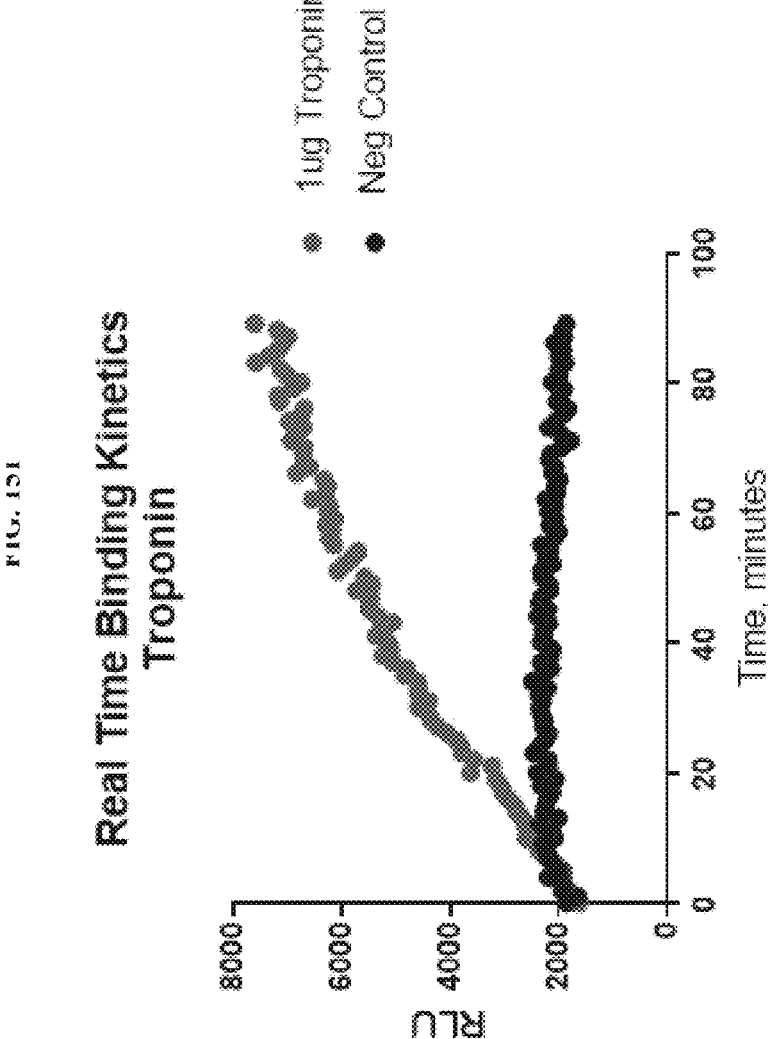

FIG. 151. Graphs depicting real time binding kinetics for quantitation of human Troponin using Halotag-SmTrip9 pep521 (SEQ ID NO: 268) and HaloTag-SmTrip10 pep289 (SEQ ID NO: 150) chemically labeled paired antibodies in a solution-based homogeneous assay.

Figure 152:
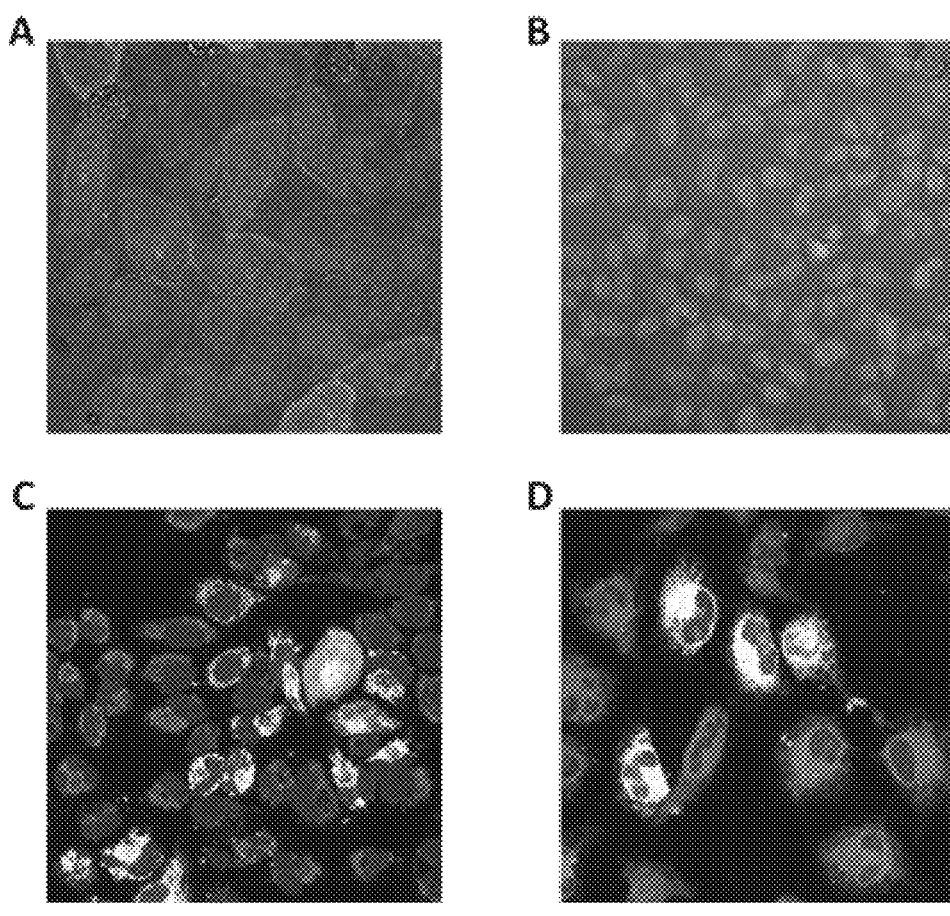

FIG. 152, Panels A-D. Specialized peptides responsible to direct proteins to specific cellular compartments were fused to LgBiT-HaloTag. (A) LgBiT-membrane sensor: LgBiT is in green and nucleus is in blue. (B) LgBiT-nuclear sensor: LgBiT is in green and nucleus is in blue. (C) LgBiT-mitochondria sensor: LgBiT is in green, MitoTracker is in red, and nucleus is in blue. (D) LgBiT-ER sensor: LgBiT is in green, ER marker is in red, and nucleus is in blue.

Figure 153:
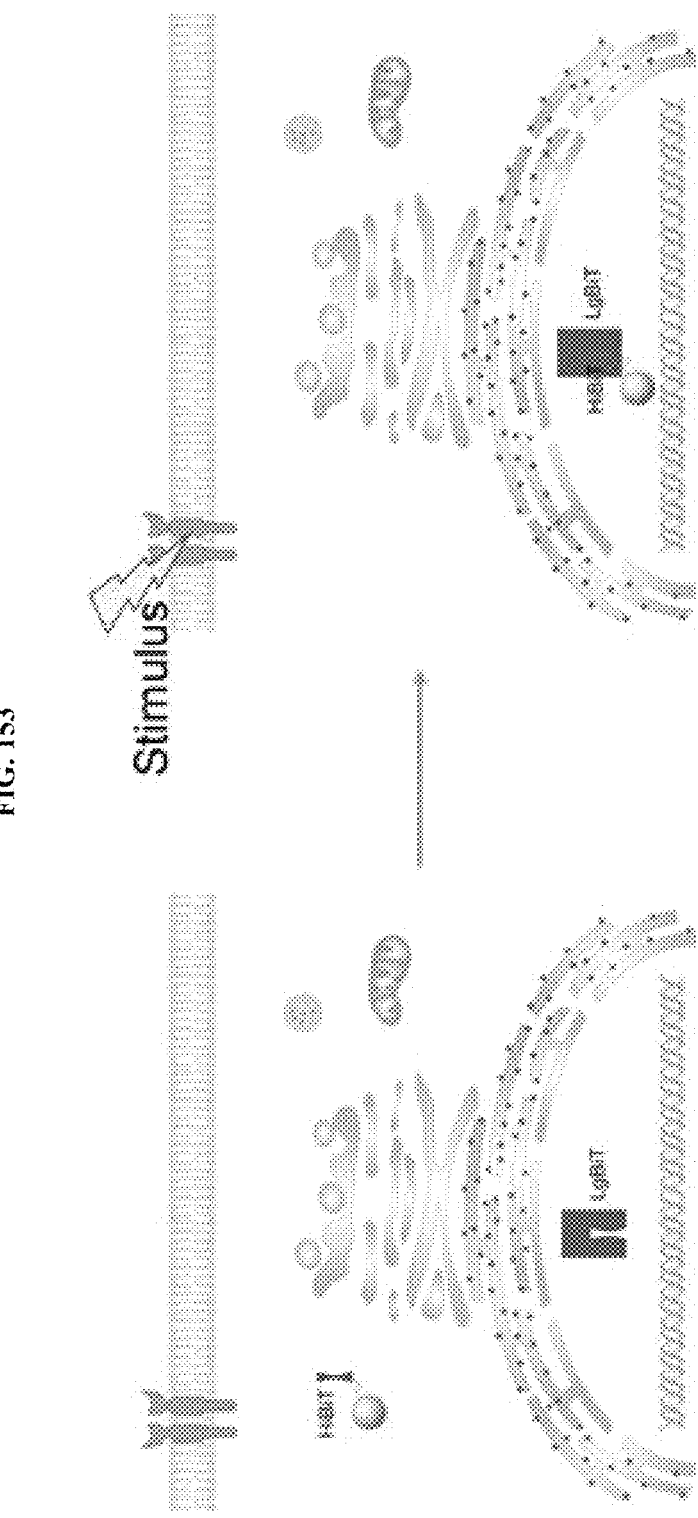

FIG. 153. Translocation assay. POI is endogenously tagged with HiBiT. Upon stimulation, the POI translocates to a different cellular compartment, for example the nucleus. A LgBiT-nuclear sensor could be used to detect this translocation event as the HiBiT meets LgBiT resulting in luminescence signal.

Figure 154:
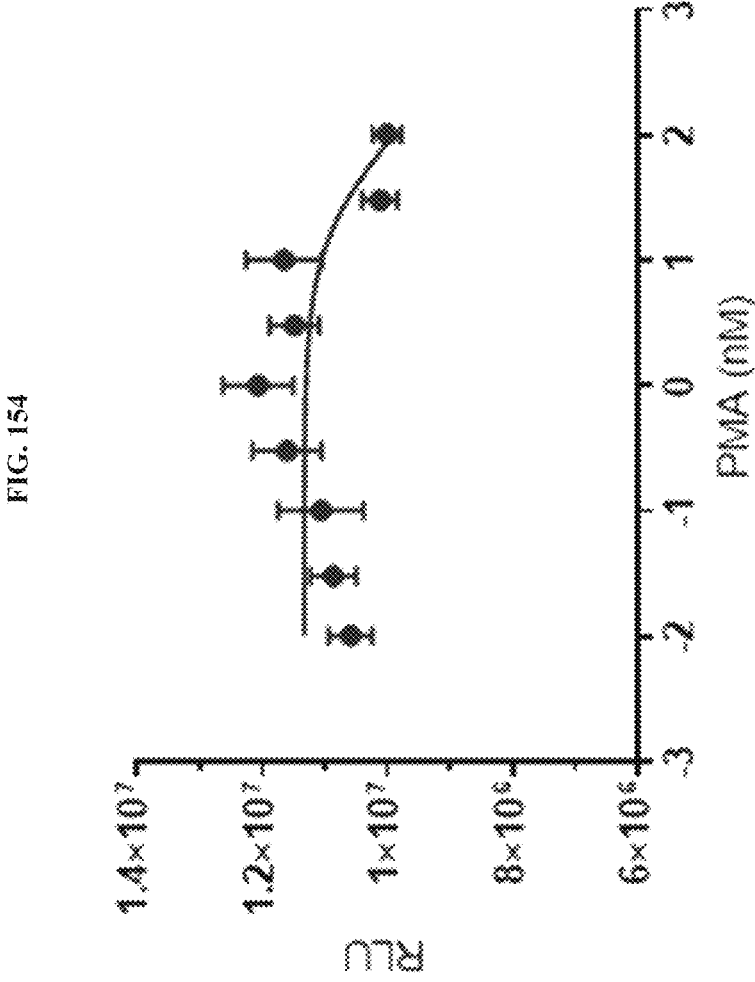

FIG. 154. Membrane translocation assay with wild-type LgBiT sensor. PKCα-HiBiT cell line was transfected with wild-type LgBiT-membrane sensor. Due to the strong interaction between LgBiT and HiBiT, the spontaneous complementation occurs, leading to no response to PMA stimuli.

Figure 155:
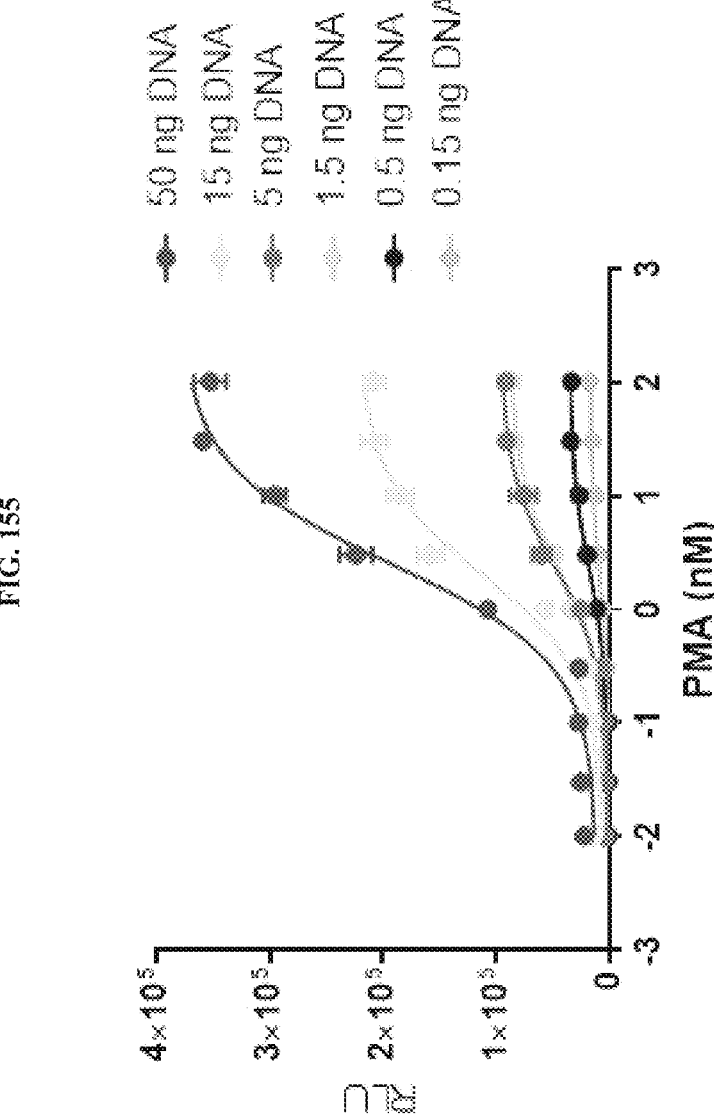

FIG. 155. Membrane translocation assay with LgBiT* sensor. PKCα-HiBiT cell line was transfected with different amount of DNA encoding LgBiT*-membrane sensor. Upon PMA treatment, PKCα-HiBiT migrates to the plasma membrane, where the LgBiT*-membrane sensor anchors. The assembly between HiBiT and LgBiT* produces luminescence signal, and the signal is proportional to the amount of PKCα-HiBiT on the membrane. The assay is sensitive and robust. Titration of PMA yielded similar $EC_{50}$ ($EC_{50}$=2.0 nM) regardless of the amount of sensor input. Fold response is varied between 12- to 19-fold depending on the amount of sensor input.

Figure 156:
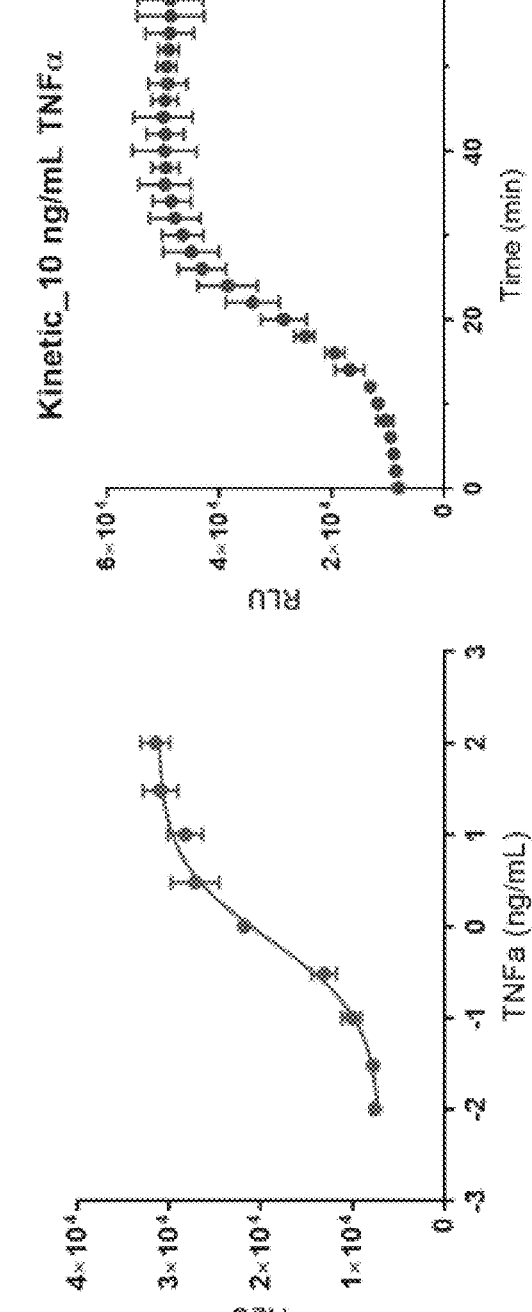

FIG. 156. Nuclear translocation assay with LgBiT* sensor. p65-HiBiT cell line was transfected with DNA encoding LgBiT*-nuclear sensor. Addition of TNFα recruits p65 to the nucleus where LgBiT*-nuclear sensor localizes. Complementation occurs between HiBiT and LgBiT* to produce light. The signal intensity reflects the concentration of p65 in the nucleus. Titration of TNFα yielded $EC_{50}$ of 0.7 ng/ml with fold-response of 4. Real time measurement showed that it requires 30 min to reach the maximum accumulation of p65 in the nucleus upon stimulation.

Figure 157A:
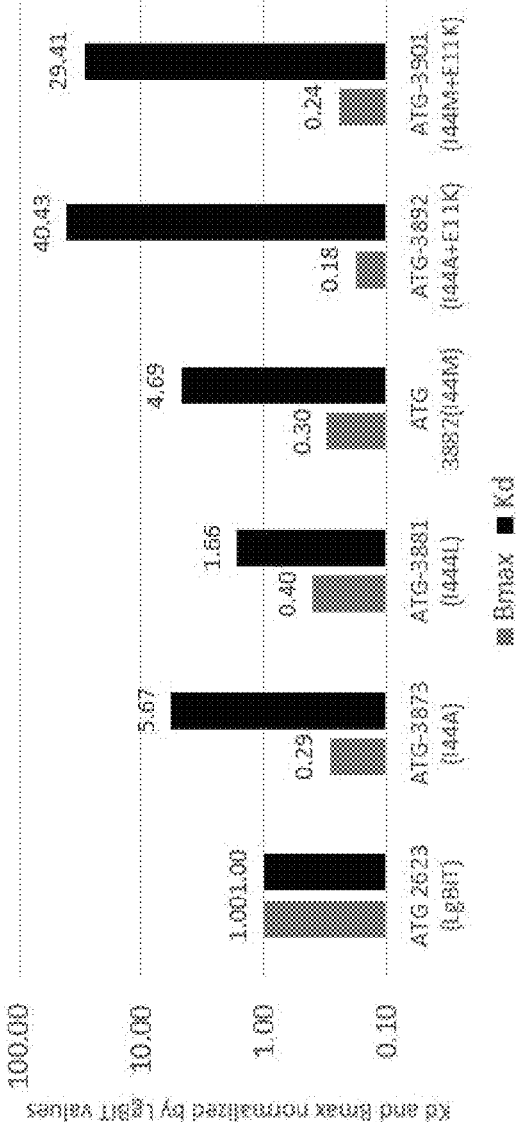

FIG. 157A-B. (A) Graph and (B) table depicting affinity and Bmax of LgBiT mutants with HiBiT.

FIG. 158. Graph depicting affinity of LgBiT mutant lysates for HiBiT.

DEFINITIONS

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide" is a reference to one or more peptides and equivalents thereof known to those skilled in the art, and so forth.

As used herein, the term "and/or" includes any and all combinations of listed items, including any of the listed items individually. For example, "A, B, and/or C" encompasses A, B, C, AB, AC, BC, and ABC, each of which is to be considered separately described by the statement "A, B, and/or C."

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "substantially" means that the recited characteristic, parameter, and/or value need not be achieved exactly, but that deviations or variations, including for example, tolerances, measurement error, measurement accuracy limitations and other factors known to skill in the art, may occur in amounts that do not preclude the effect the characteristic was intended to provide. A characteristic or feature that is substantially absent (e.g., substantially non-luminescent) may be one that is within the noise, beneath background, below the detection capabilities of the assay being used, or a small fraction (e.g., <1%, <0.1%, <0.01%, <0.001%, <0.00001%, <0.000001%, <0.0000001%) of the significant characteristic (e.g., luminescent intensity of a bioluminescent protein or bioluminescent complex).

As used herein, the term "bioluminescence" refers to production and emission of light by a chemical reaction catalyzed by, or enabled by, an enzyme, protein, protein complex, or other biomolecule (e.g., bioluminescent complex). In typical embodiments, a substrate for a bioluminescent entity (e.g., bioluminescent protein or bioluminescent complex) is converted into an unstable form by the bioluminescent entity; the substrate subsequently emits light.

As used herein the term "complementary" refers to the characteristic of two or more structural elements (e.g., peptide, polypeptide, nucleic acid, small molecule, etc.) of being able to hybridize, dimerize, or otherwise form a complex with each other. For example, a "complementary peptide and polypeptide" are capable of coming together to form a complex. Complementary elements may require assistance (facilitation) to form a complex (e.g., from interaction elements), for example, to place the elements in the proper conformation for complementarity, to place the elements in the proper proximity for complementarity, to co-localize complementary elements, to lower interaction energy for complementary, to overcome insufficient affinity for one another, etc.

As used herein, the term "complex" refers to an assemblage or aggregate of molecules (e.g., peptides, polypeptides, etc.) in direct and/or indirect contact with one another. In one aspect, "contact," or more particularly, "direct contact" means two or more molecules are close enough so that attractive noncovalent interactions, such as Van der Waal forces, hydrogen bonding, ionic and hydrophobic interactions, and the like, dominate the interaction of the molecules. In such an aspect, a complex of molecules (e.g., peptides and polypeptide) is formed under assay conditions such that the complex is thermodynamically favored (e.g., compared to a non-aggregated, or non-complexed, state of its component molecules). As used herein the term "complex," unless described as otherwise, refers to the assemblage of two or more molecules (e.g., peptides, polypeptides or a combination thereof).

As used herein, the term "non-luminescent" refers to an entity (e.g., peptide, polypeptide, complex, protein, etc.) that exhibits the characteristic of not emitting a detectable amount of light in the visible spectrum (e.g., in the presence of a substrate). For example, an entity may be referred to as non-luminescent if it does not exhibit detectable luminescence in a given assay. As used herein, the term "non-luminescent" is synonymous with the term "substantially non-luminescent. In some embodiments, an entity is considered "non-luminescent" if any light emission is sufficiently minimal so as not to create interfering background for a particular assay.

As used herein, the terms "non-luminescent peptide" and "non-luminescent polypeptide" refer to peptides and polypeptides that exhibit substantially no luminescence (e.g., in the presence of a substrate), or an amount that is beneath the noise (e.g., 100-fold, 200-fold, 500-fold, $1\times10^3$-fold, $1\times10^4$-fold, $1\times10^5$-fold, $1\times10^6$-fold, $1\times10^7$-fold, etc.) when compared to a significant signal (e.g., a bioluminescent complex) under standard conditions (e.g., physiological conditions, assay conditions, etc.) and with typical instrumentation (e.g., luminometer, etc.). In some embodiments, such non-luminescent peptides and polypeptides assemble, according to the criteria described herein, to form a bioluminescent complex.

As used herein, the term "interaction element" refers to a moiety that assists or facilitates the bringing together of non-luminescent elements to form a bioluminescent complex. In some embodiments, a pair of interaction elements (a.k.a. "interaction pair") is attached to a pair of non-luminescent elements (e.g., non-luminescent peptides), and the attractive interaction between the two interaction elements facilitates formation of the bioluminescent complex; although the present invention is not limited to such a mechanism, and an understanding of the mechanism is not required to practice the invention. Interaction elements may facilitate formation of the bioluminescent complex by any suitable mechanism (e.g., bringing non-luminescent elements into close proximity, placing a non-luminescent element in proper conformation for stable interaction, reducing activation energy for complex formation, combinations thereof, etc.). An interaction element may be a protein, polypeptide, peptide, small molecule, cofactor, nucleic acid, lipid, carbohydrate, antibody, etc. An interaction pair may be made of two of the same interaction elements (i.e., homopair) or two different interaction elements (i.e., heteropair). In the case of a heteropair, the interaction elements may be the same type of moiety (e.g., polypeptides) or may be two different types of moieties (e.g., polypeptide and small molecule). In some embodiments, in which complex formation by the interaction pair is studied, an interaction pair may be referred to as a "target pair" or a "pair of interest," and the individual interaction elements are referred to as "target elements" (e.g., "target peptide," "target polypeptide," etc.) or "elements of interest" (e.g., "peptide of interest," "polypeptide or interest," etc.).

As used herein, the term "low affinity" describes an intermolecular interaction between two or more (e.g., three) entities that is too weak to result in significant complex formation between the entities, except at concentrations substantially higher (e.g., 2-fold, 5-fold, 10-fold, 100-fold, 1000-fold, or more) than physiologic or assay conditions, or with facilitation from the formation of a second complex of attached elements (e.g., interaction elements).

As used herein, the term "high affinity" describes an intermolecular interaction between two or more (e.g., three) entities that is of sufficient strength to produce detectable complex formation under physiologic or assay conditions, without facilitation from the formation of a second complex of attached elements (e.g., interaction elements).

As used herein, the term "co-localization element" refers to a moiety that facilitates co-localization of non-luminescent elements. In some embodiments, a set of non-luminescent elements has sufficient affinity to form a complex when the non-luminescent elements are co-localized at sufficient concentration. In such embodiments, a set (e.g., pair) of co-localization elements (a.k.a. "co-localization pair") is attached to a pair of non-luminescent elements (e.g., non-luminescent peptides), and the co-localization (e.g., within a cellular compartment, within a tissue, within a solution, on a solid matrix support, etc.) of the two co-localization elements facilitates co-localization of the non-luminescent elements, thereby facilitating formation of the biolumines-cent complex; although the present invention is not limited to such a mechanism, and an understanding of the mecha-nism is not required to practice the invention. In some embodiments, due to the capacity of the non-luminescent elements to self-assemble into a luminescent complex, the co-localization elements need not directly interact to facili-tate complex formation. A co-localization element may be a protein, polypeptide, peptide, small molecule, cofactor, nucleic acid, lipid, carbohydrate, antibody, etc. A co-local-ization pair may be made of two of the same co-localization elements (i.e., homopair) or two different co-localization elements (i.e., heteropair). In the case of a heteropair, the co-localization elements may be the same type of moiety (e.g., polypeptides) or may be two different types of moieties (e.g., polypeptide and small molecule). In some embodi-ments, in which the localization of the co-localization pair is studied, a co-localization pair may be referred to as a "target pair" or a "pair of interest," and the individual co-localiza-tion elements are referred to as "target elements" (e.g., "target peptide," "target polypeptide," etc.) or "elements of interest" (e.g., "peptide of interest," "polypeptide or inter-est," etc.).

As used herein, the term "coelenterazine" refers to natu-rally-occurring ("native") coelenterazine. As used herein, the term "coelenterazine analog" or "coelenterazine deriva-tive" refers to synthetic (e.g., derivative or variant) and natural analogs thereof, including furimazine, coelentera-zine-n, coelenterazine-f, coelenterazine-h, coelenterazine-hcp, coelenterazine-cp, coelenterazine-c, coelenterazine-e, coelenterazine-fcp, bis-deoxycoelenterazine ("coelentera-zine-hh"), coelenterazine-i, coelenterazine-icp, coelentera-zine-v, and 2-methyl coelenterazine, in addition to those disclosed in WO 2003/040100; U.S. application Ser. No. 12/056,073 (paragraph [0086]); U.S. Pat. No. 8,669,103; WO 2012/061529, U.S. Pat. Pub. 2017/0233789 and U.S. Pat. Pub. 2018/0030059; the disclosures of which are incor-porated by reference herein in their entireties. In some embodiments, coelenterazine analogs include pro-substrates such as, for example, those described in U.S. application Ser. No. 12/056,073; U.S. Pub. No. 2012/0707849; U.S. Pub. No. 2014/0099654; herein incorporated by reference in their entireties.

As used herein, the term "preexisting protein" refers to an amino acid sequence that was in physical existence prior to a certain event or date. A "peptide that is not a fragment of a preexisting protein" is a short amino acid chain that is not a fragment or sub-sequence of a protein (e.g., synthetic or naturally-occurring) that was in physical existence prior to the design and/or synthesis of the peptide.

As used herein, the term "fragment" refers to a peptide or polypeptide that results from dissection or "fragmentation" of a larger whole entity (e.g., protein, polypeptide, enzyme, etc.), or a peptide or polypeptide prepared to have the same sequence as such. Therefore, a fragment is a subsequence of the whole entity (e.g., protein, polypeptide, enzyme, etc.) from which it is made and/or designed. A peptide or poly-peptide that is not a subsequence of a preexisting whole protein is not a fragment (e.g., not a fragment of a preexisting protein). A peptide or polypeptide that is "not a fragment of a preexisting bioluminescent protein" is an amino acid chain that is not a subsequence of a protein (e.g., natural or synthetic) that: (1) was in physical existence prior to design and/or synthesis of the peptide or polypeptide, and (2) exhibits substantial bioluminescent activity.

As used herein, the term "subsequence" refers to peptide or polypeptide that has 100% sequence identify with a portion of another, larger peptide or polypeptide. The sub-sequence is a perfect sequence match for a portion of the larger amino acid chain.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, pentafluorophenylalanine ("Z"), azetidinecarboxylic acid, 2-aminoadipic acid, 3-aminoadipic acid, beta-alanine, naph-thylalanine ("naph"), aminopropionic acid, 2-aminobutyric acid, 4-aminobutyric acid, 6-aminocaproic acid, 2-amino-heptanoic acid, 2-aminoisobutyric acid, 3-aminoisobutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethyl-asparagine, homoproline ("hPro" or "homoP"), hydroxyly-sine, allo-hydroxylysine, 3-hydroxyproline ("3Hyp"), 4-hy-droxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpen-tylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg"). Unnatural reactive amino acids are described in, for example, Boutureira, O. and G. J. Bernardes (2015) "Advances in chemical protein modification." Chem Rev 115(5): 2174-2195; herein incor-porated by reference in its entirety.

The term "amino acid analog" refers to a natural or unnatural amino acid where one or more of the C-terminal carboxy group, the N-terminal amino group and side-chain bioactive group has been chemically blocked, reversibly or irreversibly, or otherwise modified to another bioactive group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(car-boxymethyl)-cysteine, S-(carboxymethyl)-cysteine sulfox-ide and S-(carboxymethyl)-cysteine sulfone. Amino acid analogs may comprise amino acids with various protecting groups (Isidro-Llobet, A., et al. (2009). "Amino Acid-Pro-tecting Groups." Chemical Reviews 109(6): 2455-2504; herein incorporated by reference in its entirety).

As used herein, unless otherwise specified, the terms "peptide" and "polypeptide" refer to polymer compounds of two or more amino acids joined through the main chain by peptide amide bonds (—C(O)NH—). The term "peptide"

typically refers to short amino acid polymers (e.g., chains having fewer than 30 amino acids), whereas the term "polypeptide" typically refers to longer amino acid polymers (e.g., chains having more than 30 amino acids).

As used herein, unless otherwise specified, the term "dipeptide" refers to a peptide or small polypeptide (e.g., <70 amino acids, <60 amino acids, <50 amino acids, etc.) comprising two peptide segments (e.g., corresponding to two beta strands of a luciferase (e.g., a "β9/β10 dipeptide," corresponding to the β9 and β10 strands of an OgLuc luciferase polypeptide), fused/attached directly or indirectly (e.g., via a linker (e.g., peptide linker (e.g., 1-10 amino acids (e.g., a single glycine)))).

As used herein, unless otherwise specified, the term "tripeptide" refers to a peptide or small polypeptide (e.g., <100 amino acids, <90 amino acids, <80 amino acids, etc.) comprising three peptide segments (e.g., corresponding to three beta strands of a luciferase (e.g., a "β8-10 tripeptide," corresponding to the β8-10 strands of an OgLuc luciferase polypeptide), fused/attached directly or indirectly (e.g., via a linker (e.g., peptide linker (e.g., 1-10 amino acids (e.g., a single glycine)))).

As used herein, terms "peptidomimetic" and "peptide mimetic" refer to peptide-like or polypeptide-like molecules that emulate a sequence derived from a protein or peptide. A peptidomimetic may contain amino acids analogs, peptoid amino acids, and/or non-amino acid components either exclusively or in combination with amino acids (e.g., natural or non-natural amino acids). Examples of peptidomimetics include chemically modified peptides/polypeptides, peptoids (side chains are appended to the nitrogen atom of the peptide backbone rather than to the α-carbons), β-peptides (amino group bonded to the β carbon rather than the a carbon), etc.

As used herein, the term "peptoid" refers to a class of peptidomimetics where the side chains are functionalized on the nitrogen atom of the peptide backbone rather than to the α-carbon.

As used herein, the term "artificial" refers to compositions and systems that are designed or prepared by man and are not naturally occurring. For example, an artificial peptide, peptoid, or nucleic acid is one comprising a non-natural sequence (e.g., a peptide without 100% identity with a naturally-occurring protein or a fragment thereof).

As used herein, a "conservative" amino acid substitution refers to the substitution of an amino acid in a peptide or polypeptide with another amino acid having similar chemical properties such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine(S) and Threonine (T); and
8) Cysteine (C) and Methionine (M).

Naturally occurring residues may be divided into classes based on common side chain properties, for example: polar positive (or basic) (histidine (H), lysine (K), and arginine (R)); polar negative (or acidic) (aspartic acid (D), glutamic acid (E)); polar neutral (serine(S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families, e.g., acidic (e.g., aspartate, glutamate), basic (e.g., lysine, arginine, histidine), non-polar (e.g., alanine, valine, leucine, isoleucine, proline, phenylalanine, methionine, tryptophan) and uncharged polar (e.g., glycine, asparagine, glutamine, cysteine, serine, threonine, tyrosine). The "percent sequence identity" (or "percent sequence similarity") is calculated by: (1) comparing two optimally aligned sequences over a window of comparison (e.g., the length of the longer sequence, the length of the shorter sequence, a specified window), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any peptide/polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence having at least Y % sequence identity (e.g., 90%) with SEQ ID NO:Z (e.g., 100 amino acids) may have up to X substitutions (e.g., 10) relative to SEQ ID NO:Z, and may therefore also be expressed as "having X (e.g., 10) or fewer substitutions relative to SEQ ID NO:Z."

As used herein, the term "wild-type," refers to a gene or gene product (e.g., protein, polypeptide, peptide, etc.) that has the characteristics (e.g., sequence) of that gene or gene product isolated from a naturally occurring source, and is most frequently observed in a population. In contrast, the term "mutant" or "variant" refers to a gene or gene product that displays modifications in sequence when compared to the wild-type gene or gene product. It is noted that "naturally-occurring variants" are genes or gene products that occur in nature, but have altered sequences when compared to the wild-type gene or gene product; they are not the most commonly occurring sequence. "Artificial variants" are genes or gene products that have altered sequences when compared to the wild-type gene or gene product and do not occur in nature. Variant genes or gene products may be naturally occurring sequences that are present in nature, but not the most common variant of the gene or gene product, or "synthetic," produced by human or experimental intervention.

As used herein, the term "physiological conditions" encompasses any conditions compatible with living cells, e.g., predominantly aqueous conditions of a temperature, pH, salinity, chemical makeup, etc. that are compatible with living cells.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum, and the like. Sample may also refer to cell lysates or purified forms of the enzymes, peptides, and/or polypeptides described herein. Cell lysates may include cells that have been lysed with a lysing agent or lysates such as rabbit reticulocyte or wheat germ lysates. Sample may also include cell-free expression systems. Environmental samples include environmental material such as surface matter, soil, water, crystals, and industrial samples. Such examples are not however to be construed as limiting the sample types applicable to the present invention.

As used herein, the terms "fusion," "fusion polypeptide," and "fusion protein" refer to a chimeric protein containing a first protein or polypeptide of interest (e.g., substantially non-luminescent peptide) joined to a second different peptide, polypeptide, or protein (e.g., interaction element).

As used herein, the terms "conjugated" and "conjugation" refer to the covalent attachment of two molecular entities (e.g., post-synthesis and/or during synthetic production). The attachment of a peptide or small molecule tag to a protein or small molecule, chemically (e.g., "chemically" conjugated) or enzymatically, is an example of conjugation.

The term "binding moiety" refers to a domain that specifically binds an antigen or epitope independently of a different epitope or antigen binding domain. A binding moiety may be an antibody, antibody fragment, a receptor domain that binds a target ligand, proteins that bind to immunoglobulins (e.g., protein A, protein G, protein A/G, protein L, protein M), a binding domain of a proteins that bind to immunoglobulins (e.g., protein A, protein G, protein A/G, protein L, protein M), oligonucleotide probe, peptide nucleic acid, DARPin, aptamer, affimer, a purified protein (either the analyte itself or a protein that binds to the analyte), and analyte binding domain(s) of proteins etc. Table A provides a lists of exemplary binding moieties that could be used singly or in various combinations in methods, systems, and assays (e.g., immunoassays) herein.

TABLE A

| Exemplary binding moieties | |
|---|---|
| Binding Moiety A | Binding Moiety B |
| Protein A | Protein A |
| Ig Binding domain of protein A | Ig binding domain of protein A |
| Protein G | Protein G |
| Ig Binding domain of protein G | Ig binding domain of protein G |
| Protein L | Protein L |
| Ig Binding domain of protein L | Ig binding domain of protein L |
| Protein M | Protein M |
| Ig Binding domain of protein M | Ig binding domain of protein M |
| polyclonal antibody against analyte X | polyclonal antibody: same antibody or second polyclonal antibody recognizing same target analyte X |
| monoclonal antibody | monoclonal antibody recognizing different epitope on same target analyte X |
| recombinant antibody | recombinant antibody recognizing different epitope on same target analyte X |
| scFv | scFv recognizing different epitope on same target analyte X |
| variable light chain ($V_L$) of antibody (monoclonal, recombinant, polyclonal) recognizing target analyte X | variable heavy chain ($V_H$) of same antibody (monoclonal, recombinant, polyclonal) recognizing target analyte X |
| protein (e.g. receptor) binding domain 1 that binds to analyte X | protein (e.g. receptor) binding domain 2 that binds to analyte X |
| (Fab) fragment | (Fab) fragment from different antibody recognizing different epitope to same target analyte X |
| Fab' fragment | Fab' from different antibody recognizing different epitope to same target analyte X |
| Fv fragment | Fv from different antibody recognizing different epitope to same target analyte X |
| F(ab')2 fragment | F(ab')2 from different antibody recognizing different epitope to same target analyte X |
| oligonucleotide probe | oligonucleotide probe to same DNA or RNA target but recognizing non-overlapping sequence |

TABLE A-continued

Exemplary binding moieties

| Binding Moiety A | Binding Moiety B |
| --- | --- |
| DARPin | DARPin recognizing non-overlapping domain of same target |
| peptide nucleic acid | peptide nucleic acid recognizing same DNA or RNA target but non-overlapping sequence |
| aptamer | aptamer binding to same target analyte X but recognizing non-overlapping sequence or epitope |
| affimer | aptamer binding to same target analyte X but recognizing different epitope |

As used herein, the term "antibody" refers to a whole antibody molecule or a fragment thereof (e.g., fragments such as Fab, Fab', and F(ab')$_2$, variable light chain, variable heavy chain, Fv, it may be a polyclonal or monoclonal or recombinant antibody, a chimeric antibody, a humanized antibody, a human antibody, etc. As used herein, when an antibody or other entity "specifically recognizes" or "specifically binds" an antigen or epitope, it preferentially recognizes the antigen in a complex mixture of proteins and/or macromolecules, and binds the antigen or epitope with affinity which is substantially higher than to other entities not displaying the antigen or epitope. In this regard, "affinity which is substantially higher" means affinity that is high enough to enable detection of an antigen or epitope which is distinguished from entities using a desired assay or measurement apparatus. Typically, it means binding affinity having a binding constant ($K_a$) of at least $10^7$ M$^{-1}$ (e.g., $>10^7$ M$^{-1}$, $>10^8$ M$^{-1}$, $>10^9$ M$^{-1}$, $>10^{10}$ M$^{-1}$, $>10^{11}$ M$^{-1}$, $>10^{12}$ M$^{-1}$, $>10^{13}$ M$^{-1}$, etc.). In certain such embodiments, an antibody is capable of binding different antigens so long as the different antigens comprise that particular epitope. In certain instances, for example, homologous proteins from different species may comprise the same epitope.

As used herein, the term "antibody fragment" refers to a portion of a full-length antibody, including at least a portion of the antigen binding region or a variable region. Antibody fragments include, but are not limited to, Fab, Fab', F(ab')$_2$, Fv, scFv, Fd, variable light chain, variable heavy chain, diabodies, and other antibody fragments that retain at least a portion of the variable region of an intact antibody. See, e.g., Hudson et al. (2003) Nat. Med. 9:129-134; herein incorporated by reference in its entirety. In certain embodiments, antibody fragments are produced by enzymatic or chemical cleavage of intact antibodies (e.g., papain digestion and pepsin digestion of antibody) produced by recombinant DNA techniques, or chemical polypeptide synthesis. For example, a "Fab" fragment comprises one light chain and the CH1 and variable region of one heavy chain. The heavy chain of a Fab molecule cannot form a disulfide bond with another heavy chain molecule. A "Fab" fragment comprises one light chain and one heavy chain that comprises additional constant region, extending between the C$_{H1}$ and C$_{H2}$ domains. An interchain disulfide bond can be formed between two heavy chains of a Fab' fragment to form a "F(ab') 2" molecule. An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946,778 and 5,260,203; herein incorporated by reference in their entireties. In certain instances, a single variable region (e.g., a heavy chain variable region or a light chain variable region) may have the ability to recognize and bind antigen. Other antibody fragments will be understood by skilled artisans.

As used herein, the term "peptide tag" refers to a peptide that may be attached (e.g., post-synthesis or during synthetic production) or fused to another entity (e.g., protein of interest, molecule of interest, interaction element, co-localization element, etc.). The peptide tag may or may not be attached to another entity. Typically, as used herein, a peptide tag is capable of forming a bioluminescent complex with another peptide tag and a polypeptide under appropriate conditions. In embodiments in which a peptide tag is attached to another entity, a peptide tag is chemically conjugated to another molecule (e.g., peptide, polypeptide, nucleic acid, other small molecules or macromolecules), chemically synthesized to be a part of another molecule, or genetically fused to another peptide or polypeptide molecule, etc.

As used herein, the term "polypeptide component" is used synonymously with the term "polypeptide component of a bioluminescent complex." Typically, as used herein, a polypeptide component is capable of forming a bioluminescent complex with a pair of peptide tags, under appropriate conditions.

As used herein, the term "an Oplophorus luciferase" ("an OgLuc") refers to a luminescent polypeptide having significant sequence identity, structural conservation, and/or the functional activity of the luciferase produce by and derived from the deep-sea shrimp Oplophorus gracilirostris. In particular, an OgLuc polypeptide refers to a luminescent polypeptide having significant sequence identity, structural conservation, and/or the functional activity of the mature 19 kDa subunit of the Oplophorus luciferase protein complex (e.g., without a signal sequence) such as SEQ ID NOs: 1 (WT OgLuc) and 3 (NanoLuc), which comprises 10 β strands (β1, β2, β3, β4, β5, β6, β7, β8, β9, β10) and utilize substrates such as coelenterazine or coelenterazine derivatives to produce luminescence.

As used herein, the term "β9-like peptide" refers to a peptide (or peptide tag) comprising significant sequence identity, structural conservation, and/or the functional activity of the β(beta) 9 strand of an OgLuc polypeptide. In particular, a β9-like peptide is a peptide capable of structurally complementing an OgLuc polypeptide lacking a β9 strand resulting in enhanced luminescence of the complex compared to the OgLuc polypeptide in the absence of the β9-like peptide. Other "βX-like peptides" may be similarly named (e.g., β1-like, β2-like, β3-like, β4-like, β5-like, β6-like, β7-like, β8-like, β9-like).

As used herein, the term "β10-like peptide" refers to a peptide (or peptide tag) comprising significant sequence identity, structural conservation, and/or the functional activity of the β (beta) 10 strand of an OgLuc polypeptide. In particular, a β10-like peptide is a peptide capable of structurally complementing an OgLuc polypeptide lacking a β10 strand resulting in enhanced luminescence of the complex compared to the OgLuc polypeptide in the absence of the β10-like peptide. Other "βX-like peptides" may be similarly named (e.g., β1-like, β2-like, β3-like, β4-like, β5-like, β6-like, β7-like, β8-like, β9-like).

As used herein, the term "β$_{1-8}$-like polypeptide" refers to a polypeptide bearing sequence and structural similarity to β (beta) strands 1-8 of an OgLuc polypeptide, but lacking β (beta) strands 9 and 10. Other "β$_{Y-Z}$-like polypeptides" may be similarly named (e.g., β$_{1-4}$-like polypeptide, β$_{2-8}$-like polypeptide, β$_{5-10}$-like polypeptide, etc.).

As used herein, the term "NANOLUC" refers to an artificial luciferase or bioluminescent polypeptide produced commercially by the Promega Corporation and corresponding to SEQ ID NO: 3.

As used herein, the term "LgBiT" refers to a polypeptide corresponding to β$_{1-9}$-like polypeptide that finds use in, for example, binary complementation to form a bioluminescent complex and corresponds to SEQ ID NO: 11.

As used herein, the term "SmBiT" refers to a peptide corresponding to β$_{10}$-like peptide that finds use in, for example, binary complementation to form a bioluminescent complex, but has low affinity for LgBiT (e.g., requires facilitation for complex formation) and corresponds to SEQ ID NO: 13.

As used herein, the term "HiBiT" refers to a peptide corresponding to β$_{10}$-like peptide that finds use in, for example, binary complementation to form a bioluminescent complex, but has low affinity for LgBiT (e.g., requires facilitation for complex formation) and corresponds to SEQ ID NO: 15. HiBiT is has the same sequence as "SmHiTrip10" (SEQ ID NO: 25) and "pep86," terms which may be used interchangeably (also SmTrip10 pep86, etc.).

As used herein, the term "LgTrip" refers to a polypeptide corresponding to β$_{1-8}$-like polypeptide that corresponds to SEQ ID NO: 17 and finds use in, for example, tripartite complementation with β$_9$-like and β$_{10}$-like peptides to form a bioluminescent complex, or binary complementation, with a β$_{9-10}$-like dipeptide to form a bioluminescent complex. LgTrip variants include: LgTrip 2098 (w/His tag: SEQ ID NO: 31; w/o His tag: SEQ ID NO: 304) and LgTrip 3546 (w/His tag: SEQ ID NO: 51; w/o His tag: SEQ ID NO: 302).

As used herein, the term "SmTrip10" refers to a peptide corresponding to β$_{10}$-like peptide that finds use in, for example, tripartite complementation to form a bioluminescent complex.

As used herein, the term "SmTrip9" refers to a peptide corresponding to β9-like peptide that finds use in, for example, tripartite complementation to form a bioluminescent complex.

DETAILED DESCRIPTION

Provided herein are compositions and methods for the assembly of a tripartite or multipartite bioluminescent complex. In particular, a bioluminescent complex is formed upon the interaction of two or more peptide tags (e.g., separately or fused as a dipeptide or tripeptide) and a polypeptide component.

Experiments conducted during development of embodiments herein demonstrate that a tripartite luciferase comprising two small peptide elements (e.g., a β10-like peptide and β9-like peptide) and one polypeptide element (e.g., β1-8-like polypeptide) assemble to form a luminescent complex. Experiments conducted during development of embodiments herein further demonstrate the formation of a bioluminescent complex from up to five fragments of a luciferase (or variants of such fragments), such as a polypeptide fragment (or variant thereof) and one or more peptide, dipeptide, or tripeptide fragments (or variants of such fragments).

The commercially-available NANOLUC luciferase (Promega Corporation) comprises 10 β (beta) strands (β1, β2, β3, β4, β5, β6, β7, β8, β9, β10). U.S. Pat. No. 9,797,889 (herein incorporated by reference in its entirety) describes development and use of a complementation system comprising a β$_{1-9}$-like polypeptide and a β$_{10}$-like peptide (the actual polypeptide and peptide sequences in U.S. Pat. No. 9,797,889 differ from the corresponding sequences in NANOLUC and wild-type native OgLuc).

In experiments conducted during development of embodiments herein, a β$_{1-9}$-like polypeptide was further split by removal of the β9 strand. The remaining portion (a β$_{1-8}$-like polypeptide) is referred to herein as LgTrip 2098 (SEQ ID NO: 17; or SEQ ID NO: 31 (with His tag)). Experiments attempted to reconstitute a luminescent complex from LgTrip and two peptides corresponding to the β9 (SmTrip9 pep245; SEQ ID NO: 23) and β10 (SmTrip10 pep86; HiBit, a β10 sequence optimized for use in a high affinity bipartite system; SEQ ID NO: 15) strands. Experiments demonstrated that LgTrip 2098 (SEQ ID NO: 17; or SEQ ID NO: 31 (with His tag)) expressed poorly in E. coli, was unstable, and was susceptible to surface inactivation. Experiments were conducted during development of embodiments herein to develop artificial variants that exhibit one or more (e.g., all) of enhanced stability, enhanced expression, enhanced activity, enhanced molecular interactions, etc., and is capable of being used in a system to reconstitute a bioluminescent complex with peptides corresponding to the β9 (e.g., β9-like peptides (e.g., SmTrip9 pep245; SEQ ID NO: 23)) and β10 (e.g., β10-like peptides (e.g., SmTrip10 pep86; HiBiT; SEQ ID NO: 25)) strands. Experiments conducted during development of embodiments herein demonstrate, for example, that LgTrip 3092 (SEQ ID NO: 19) or LgTrip 3546 (SEQ ID NO: 51) are capable of forming a luminescent complex with suitable β9-like (e.g., SmTrip9 pep245; SEQ ID NO: 23) and β10-like (e.g., SmTrip10 pep86; HiBiT; SEQ ID NO: 25) peptides. Experiments were conducted during development of embodiments herein to develop artificial polypeptide components (e.g., SEQ ID NOs: 19, 21, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, and additional variants thereof) and peptide tags (e.g., the peptides listed in Table 1 and additional variants thereof) with enhanced characteristics for luminescent complex reconstitution.

Further experiments conducted during development of embodiments herein demonstrate that NANOLUC-based bioluminescent complexes can be formed using constructs comprising other polypeptide components (e.g., β$_{1-5}$-like, β$_{1-6}$-like, β$_{1-7}$-like, etc.) and corresponding combinations of complimentary peptides (e.g., β$_6$-like, β$_7$-like, β$_8$-like, β$_9$-like, β$_{10}$-like), dipeptides (e.g., β$_{6-7}$-like, β$_{7-8}$-like, β$_{8-9}$-like, β$_{9-10}$-like), tripeptides (e.g., β$_{6-8}$-like, β$_{7-9}$-like, β$_{8-10}$-like), polypeptides (e.g., β$_{6-10}$-like, β$_{6-9}$-like, β$_{7-10}$-like, etc.) derived from the NANOLUC-based, NanoBiT-based, and NanoTrip-based systems, polypeptides, and peptide described herein. The experiments conducted during development of embodiments herein demonstrate the formation of a bioluminescent complex from two or more (e.g., 2, 3, 4, 5, etc.) peptide and polypeptide components that collectively comprise the full length of a luciferase construct (e.g., a full length luciferase polypeptide comprising 40% or greater (e.g., 40%, 45%, 50%, 55%, 60%, 65%, 70%, 75%, 80%, 85%, 90%, 95%, 100%, or rages therebetween) sequence identity with SEQ ID NO: 788 or 789).

In some embodiments, provided herein are compositions and methods for the assembly of a bioluminescent complex from two peptide tags (e.g., β9-like (e.g., SmTrip9) and β10-like (e.g., SmTrip10) peptides) and a polypeptide component (e.g., $\beta_{1-8}$-like (e.g., LgTrip) polypeptide).

In some embodiments, provided herein are compositions and methods for the assembly of a bioluminescent complex from a polypeptide component (e.g., a $\beta_{1-5}$-like, $\beta_{1-6}$-like, $\beta_{1-7}$-like, or $\beta_{1-8}$-like polypeptide), and complementary peptide(s) (e.g., $\beta_6$-like, $\beta_7$-like, Ba-like, $\beta_9$-like, $\beta_{10}$-like), dipeptide(s) (e.g., $\beta_{6-7}$-like, $\beta_{7-8}$-like, $\beta_{8-9}$-like, $\beta_{9-10}$-like), tripeptide (e.g., $\beta_{6-8}$-like, $\beta_{7-9}$-like, $\beta_{8-10}$-like), and/or polypeptides (e.g., $\beta_{6-10}$-like, $\beta_{6-9}$-like, $\beta_{7-10}$-like, etc.).

In some embodiments, one or more (e.g., two, three, four, five, etc.) of the peptide tags and the polypeptide component are not fragments of a preexisting protein (e.g., are not structurally-complementary subsequences of a known polypeptide sequence). However, in other embodiments, one or more of the peptide tags and the polypeptide component may be fragments of a known or existing protein, polypeptide, or peptide. In certain embodiments, the bioluminescent activity of the polypeptide component (of the bioluminescent complex) is enhanced (e.g., 2-fold, 3-fold, 4-fold, 5-fold, 10-fold, $10^2$-fold, $10^3$-fold, $10^4$-fold, $10^5$-fold, $10^6$-fold, or more) via structural complementation with the two peptide tags. In some embodiments, provided herein are peptide (peptide tags)/polypeptide elements that are capable of assembling into a bioluminescent complex for the purpose of, for example, detecting and monitoring molecular interactions (e.g., protein-protein, protein-DNA, protein-RNA interactions, RNA-DNA, protein-small molecule, RNA-small-molecule, DNA-DNA, RNA-RNA, PNA-DNA, PNA-RNA, etc.). In some embodiments, the peptide/dipeptide/tripeptide tags (e.g., β6-like, β7-like, β8-like, β9-like (e.g., SmTrip9), and/or β10-like (e.g., SmTrip10) peptides, and/or dipeptides and tripeptide thereof) are fused, or otherwise linked to interaction elements. In particular embodiments, the peptide/dipeptide/tripeptide tags and polypeptide components, when for the purpose of detecting/monitoring molecular interactions, do not form a complete bioluminescent complex without facilitation by the interaction between interaction elements. However, upon interaction (e.g., binding) of the interaction elements to each other (or to a target molecule or complex), formation of the bioluminescent complex is facilitated. In some embodiments, the bioluminescent signal from the bioluminescent complex (or the capacity to produce such a signal in the presence of substrate) serves as a reporter for the formation of a complex by the interaction elements. If an interaction complex is formed, then a bioluminescent complex is formed, and a bioluminescent signal is detected/measured/monitored (e.g., in the presence of substrate). If an interaction complex fails to form (e.g., due to unfavorable conditions, due to unstable interaction between the interaction elements, due to incompatible interaction elements), then a bioluminescent complex does not form, and a bioluminescent signal is not produced (e.g., in the presence of substrate). In some embodiments, the bioluminescent signal from the bioluminescent complex (or the capacity to produce such a signal in the presence of substrate) serves as a reporter for the binding of the interaction elements to a target. If target-binding occurs, then a bioluminescent complex is formed and a bioluminescent signal is detected/measured/monitored (e.g., in the presence of substrate). If target-binding fails to occur (e.g., due to unfavorable conditions, due to unstable interaction between an interaction element and target, due to the absence of target, etc.), then a bioluminescent complex does not form and a bioluminescent signal is not produced.

In certain embodiments, interaction elements are two molecules of interest (e.g., protein(s) of interest, small molecule(s) of interest, etc.). For example, assays can be performed to detect the interaction of two molecules of interest by tethering each one to separate peptide/dipeptide/tripeptide tag (e.g., β6-like, β7-like, β8-like, β9-like (e.g., SmTrip9), and/or β10-like (e.g., SmTrip10) peptides, and/or dipeptides and tripeptide thereof) . If the molecules of interest interact (e.g., transiently interact, stably interact, etc.), the peptide/dipeptide/tripeptide tags are brought into close proximity in a suitable conformation, and a bioluminescent complex is formed between the peptide/dipeptide/tripeptide tags and the polypeptide component of the bioluminescent complex (and bioluminescent signal is produced/detected (e.g., in the presence of substrate)). In the absence of an interaction between the molecules of interest, the peptide/dipeptide/tripeptide tags are not brought into close proximity and/or arranged in an orientation to facilitate complex formation with the polypeptide component of the bioluminescent complex, the bioluminescent complex is not formed, and a bioluminescent signal is not produced (in the presence of substrate). Such embodiments can be used to study the effect of inhibitors on complex formation, the effect of mutations on complex formation, the effect of conditions (e.g., temperature, pH, etc.) on complex formation, the interaction of a small molecule (e.g., potential therapeutic) with a target molecule, etc.

In some embodiments, peptide/dipeptide/tripeptide tags (e.g., β6-like, β7-like, β8-like, β9-like (e.g., SmTrip9), and/or β10-like (e.g., SmTrip10) peptides, and/or dipeptides and tripeptide thereof) and a polypeptide component (e.g., β1-5-like, β1-6-like, β1-7-like, β1-8-like (e.g., LgTrip) polypeptide) are provided that are capable of assembling into a bioluminescent complex without facilitation by interaction elements. In such embodiments, a bioluminescent complex will form when the peptide/dipeptide/tripeptide tags and polypeptide component are together within the same sample, subcellular compartment, cell, tissue, etc. (e.g., co-localized). In some embodiments, provided herein peptide/dipeptide/tripeptide (tags)/polypeptide elements that are capable of assembling into a bioluminescent complex for use in detecting and monitoring co-localization (e.g., without molecular interaction) of molecular elements (e.g., protein(s), nucleic acid(s), small molecule(s), lipid, carbohydrate, cellular structure, etc.). In some embodiments, a bioluminescent complex is formed from peptide/dipeptide/tripeptide tags and a polypeptide component that collectively span a full β1-like to β10-like sequence. In some embodiments, the peptide/dipeptide/tripeptide tags are fused or otherwise linked to co-localization elements. In particular embodiments, particularly for the purpose of detecting/monitoring co-localization (e.g., without molecular interaction), the peptide/dipeptide/tripeptide tags and polypeptide components are capable of forming a bioluminescent complex without facilitation (e.g., without interaction elements). Upon co-localization (e.g., within the same cell, on the same surface, with the same cellular compartment, within the same tissue, etc.) of the co-localization elements (e.g., fused to the peptide/dipeptide/tripeptide tags), formation of the bioluminescent complex (from the peptide/dipeptide/tripeptide tags and the polypeptide component), with or without interaction of the co-localization elements, is facilitated. In some embodiments, the bioluminescent signal from the bioluminescent complex (or the capacity to produce such a signal in the presence of substrate) serves as a reporter for co-localization of the co-localization elements. If the co-localization elements co-localize, then a bioluminescent complex of the polypeptide component and the peptide/dipeptide/tripeptide tags fused to the co-localization elements is formed, and a bioluminescent signal is detected/measured/monitored (e.g., in the presence of substrate). If the co-localization elements do not co-localize, then a bioluminescent complex does not form, and a bioluminescent signal is not produced (e.g., in the presence of substrate).

In certain embodiments, the co-localization pair comprises two molecules of interest (e.g., protein(s) of interest, small molecule(s) of interest, etc.). For example, assays can be performed to detect the co-localization (e.g., within a cell, within a cellular compartment, within a tissue, etc.) of two molecules of interest by tethering each one to a separate dipeptide/tripeptide tags (e.g., $\beta$6-like, $\beta$7-like, $\beta$8-like, $\beta$9-like (e.g., SmTrip9), and/or $\beta$10-like (e.g., SmTrip10) peptides, and/or dipeptides and tripeptides thereof). If the molecules of interest co-localize, the peptide tags are brought into close proximity in a suitable conformation, and a bioluminescent complex is formed with the polypeptide component polypeptide component (e.g., $\beta$1-5-like, $\beta$1-6-like, $\beta$1-7-like, $\beta$1-8-like (e.g., LgTrip) polypeptide), and bioluminescent signal is produced/detected (e.g., in the presence of substrate). In the absence of co-localization of the molecules of interest, the polypeptide components and peptide/dipeptide/tripeptide tags tags do not interact to form a complex, and a bioluminescent signal is not produced (e.g., in the presence of substrate). Such embodiments can be used to study co-localization of molecules of interest under various conditions.

In some embodiments, systems, assays, and devices comprising dipeptide/tripeptide tags tags e.g., $\beta$6-like, $\beta$7-like, $\beta$8-like, $\beta$9-like (e.g., SmTrip9), and/or $\beta$10-like (e.g., SmTrip10) peptides, and/or dipeptides and tripeptides thereof) and a polypeptide component (e.g., $\beta$1-5-like, $\beta$1-6-like, $\beta$1-7-like, $\beta$1-8-like (e.g., LgTrip) polypeptide) are provided for the detection of an analyte (e.g., small molecule, peptide, protein, antibody, nucleic acid, etc.) in a sample. In some embodiments, peptide/dipeptide/tripeptide tags are tethered or fused with detection/binding agents (e.g., binding moiety, binding sequence, etc.) that recognize the target analyte, target analytes, secondary analytes that are bound by the target analyte, secondary binding agents that bind to primary binding agents, etc. In some embodiments, various combinations of peptide/dipeptide/tripeptide tags tethered/fused to the aforementioned detection/binding agents are used in assays and devices for the detection/quantification/identification of analytes in a sample. Exemplary systems that find use in assays and devices are depicted in, for example, FIGS. 51-56 and described herein.

In some embodiments, provided herein are compositions and methods for the assembly of a bioluminescent complex from a dipeptide (e.g., a $\beta$9/$\beta$10-like dipeptide) and a polypeptide component (e.g., $\beta_{1-8}$-like (e.g., LgTrip) polypeptide). In some embodiments, the dipeptide and the polypeptide component are not fragments of a preexisting protein (e.g., are not structurally-complementary subsequences of a known polypeptide sequence). However, in other embodiments, the dipeptide and/or the polypeptide component may be fragments of a known or existing protein, polypeptide, or peptide. In certain embodiments, the bioluminescent activity of the polypeptide component (of the bioluminescent complex) is enhanced (e.g., 2-fold, 3-fold, 4-fold, 5-fold, 10-fold, $10^2$-fold, $10^3$-fold, $10^4$-fold, $10^5$-fold, 106-fold, or more) via structural complementation with the dipeptide. In some embodiments, a $\beta_{1-8}$-like polypeptide exhibits lower background luminescence than a $\beta_{1-9}$-like polypeptide. In some embodiments, a $\beta_{1-8}$-like polypeptide exhibits increased thermal and chemical stability compared to a $\beta_{1-9}$-like polypeptide.

In some embodiments, provided herein are bioluminescent complexes, including but not limited to those comprising any of the following combinations of peptide, dipeptide, tripeptide, and polypeptide components:

$\beta$1-5-like polypeptide+$\beta$6-like peptide+$\beta$7-like peptide+$\beta$8-like peptide+$\beta$9-like peptide+$\beta$10-like peptide;

$\beta$1-5-like polypeptide+$\beta$6-like peptide+$\beta$7-like peptide+$\beta$8-like peptide+$\beta$9/10-like dipeptide;

$\beta$1-5-like polypeptide+$\beta$6-like peptide+$\beta$7/8-like dipeptide+$\beta$9/10-like dipeptide;

$\beta$1-5-like polypeptide+$\beta$6/7/8-like tripeptide+$\beta$9/10-like dipeptide;

$\beta$1-5-like polypeptide+$\beta$6-like peptide+$\beta$7/8/9-like tripeptide+$\beta$10-like peptide;

$\beta$1-6-like polypeptide+$\beta$7-like peptide+$\beta$8-like peptide+$\beta$9-like peptide+$\beta$10-like peptide;

$\beta$1-6-like polypeptide+$\beta$7-like peptide+$\beta$8-like peptide+39/10-like dipeptide;

$\beta$1-6-like polypeptide+$\beta$7/8-like dipeptide+$\beta$9/10-like dipeptide;

$\beta$1-6-like polypeptide+$\beta$6/7/8-like dipeptide+$\beta$9-like peptide+$\beta$10-like peptide;

$\beta$1-6-like polypeptide+$\beta$7/8/9-like tripeptide+$\beta$10-like peptide;

$\beta$1-7-like polypeptide+$\beta$8-like peptide+$\beta$9-like peptide+$\beta$10-like peptide;

$\beta$1-7-like polypeptide+$\beta$8-like peptide+$\beta$9/10-like dipeptide;

$\beta$1-7-like polypeptide+8/9-like dipeptide+$\beta$10-like peptide;

$\beta$1-7-like polypeptide+$\beta$8/9/10-like tripeptide;

$\beta$1-8-like polypeptide+$\beta$9-like peptide+$\beta$10-like peptide;

$\beta$1-8-like polypeptide+$\beta$9/10-like dipeptide;

$\beta$1-5-like polypeptide+$\beta$6-10-like polypeptide;

$\beta$1-5-like polypeptide+$\beta$6-9-like polypeptide+$\beta$10-like peptide; and $\beta$1-5-like polypeptide+$\beta$7-10-like polypeptide+$\beta$6-like peptide.

The above combinations are not limiting and other combinations of peptide, dipeptide, tripeptide, and polypeptide components are within the scope herein.

In some embodiments, a $\beta$1-5-like polypeptide comprises positions 1-102 of SEQ ID NO: 788. In some embodiments, a $\beta$1-6-like polypeptide comprises positions 1-124 of SEQ ID NO: 788. In some embodiments, a $\beta$1-7-like polypeptide comprises positions 1-133 of SEQ ID NO: 788. In some embodiments, a $\beta$1-8-like polypeptide comprises positions 1-148 of SEQ ID NO: 788.

In some embodiments, a set of $\beta$5-10-like peptides/dipeptide/tripeptides/polypeptide collectively comprise positions 103-170 of SEQ ID NO: 788 or 789. In some embodiments, a set of $\beta$6-10-like peptides/dipeptide/tripeptides/polypeptide collectively comprise positions 125-170 of SEQ ID NO: 788 or 789. In some embodiments, a set of $\beta$7-10-like peptides/dipeptide/tripeptides/polypeptide collectively comprise positions 134-170 of SEQ ID NO: 788 or 789. In some embodiments, a set of $\beta$8-10-like peptides/dipeptide/tripeptides/polypeptide collectively comprise positions 149-170 of SEQ ID NO: 788 or 789.

In some embodiments, one or more components of a bioluminescent complex span partial beta strands of the base luciferases (e.g., OgLuc, NANOLUC, SEQ ID NO: 788, SEQ ID NO: 789, etc.) described herein. The separations between peptide, dipeptide, tripeptide, and polypeptide components may reside at the split points between the beta strands or may appear at a position −1, −2, −3, −4, −5, +1, +2, +3, +4, +5, or more from the split points identified by the sequences herein. In some embodiments, peptide, dipeptide, tripeptide, and polypeptide components that span the full sequence of a base luciferases (e.g., OgLuc, NANOLUC, SEQ ID NO: 788, SEQ ID NO: 789, etc.) described herein are capable of forming a bioluminescent complex, even if the split points for the components are not between the beta strands.

For example, a split site between β5 and β6 may occur between positions 102 and 103 of SEQ ID NO: 788, or in some embodiments such a split site may occur at a position up to 5 residues before or after that position (e.g., after position 96, 97, 98, 99, 100, 101, 103, 104, 105, 106, 107). In some embodiments, a split site between β6 and β7 may occur between positions 124 and 125 of SEQ ID NO: 788, or in some embodiments such a split site may occur at a position up to 5 residues before or after that position (e.g., after position 118, 119, 120, 121, 122, 123, 125, 126, 127, 128, 129). In some embodiments, a split site between β7 and β8 may occur between positions 133 and 134 of SEQ ID NO: 788, or in some embodiments such a split site may occur at a position up to 5 residues before or after that position (e.g., after position 127, 128, 129, 130, 131, 132, 134, 135, 136, 137, 138). In some embodiments, a split site between β8 and β9 may occur between positions 148 and 149 of SEQ ID NO: 788, or in some embodiments such a split site may occur at a position up to 5 residues before or after that position (e.g., after position 142, 143, 144, 145, 146, 147, 149, 150, 151, 152, 153).

In some embodiments, two peptide, dipeptide, tripeptide, and polypeptide components that are sequentially adjuvant within the base luciferase (e.g., OgLuc, NANOLUC, SEQ ID NO: 788, SEQ ID NO: 789, etc.) sequence comprise all of the amino acids of that corresponding portion of the base sequence. In some embodiments, one or more (e.g., 1, 2, 3, 4, 5, or more) amino acids adjacent to the split point in the base sequence are absent from the corresponding peptide, dipeptide, tripeptide, and/or polypeptide components.

In some embodiments, provided herein are peptides comprising 40% or greater (e.g., 40%, 45%, 50%, 55%, 60%, 65%, 70%, 75%, 80%, 85%, 90%, 95%, or 100%) sequence identity with one of the following:

```
                                    (SEQ ID NO: 802)
β6-like - GVTPNKLNYFGRPYEGIAVFDG;

(SEQ ID NO: 803
β7-like - KKITTTGTL (SEQ ID NO: 804
β8-like - WNGNKIIDERLITPD (SEQ ID NO: 805
β9-like - GSMLFRVTINS (SEQ ID NO: 806
β10-like (Hi affinity) - VSGWRLFKKIS
and (SEQ ID NO: 807
β10-like (Lo affinity) - VTGYRLFEEIL
```

In some embodiments, provided herein are dipeptides comprising 40% or greater (e.g., 40%, 45%, 50%, 55%, 60%, 65%, 70%, 75%, 80%, 85%, 90%, 95%, or 100%) sequence identity with one of the following:

```
                                    (SEQ ID NO: 808
β6/7-like - GVTPNKLNYFGRPYEGIAVFDGKKITTTGTL (SEQ ID NO: 809)
β7/8-like - KKITTTGTLWNGNKIIDERLITPD;

(SEQ ID NO: 810)
β8/9-like - WNGNKIIDERLITPDGSMLFRVTINS;

(SEQ ID NO: 811)
β9/10-like (Hi affinity) - GSMLFRVTINSVSGWRLFKKIS;
and (SEQ ID NO: 812)
β9/10-like (Lo affinity) - GSMLFRVTINSVTGYRLFEEIL.
```

In some embodiments, provided herein are tridipeptides comprising 40% or greater (e.g., 40%, 45%, 50%, 55%, 60%, 65%, 70%, 75%, 80%, 85%, 90%, 95%, or 100%) sequence identity with one of the following:

```
                                    (SEQ ID NO: 813)
β6/7/8-like - GVTPNKLNYFGRPYEGIAVFDGKKITTTGTLWNGNK

IIDERLITPD;

(SEQ ID NO: 814)
β7/8/9-like - KKITTTGTLWNGNKIIDERLITPDGSMLFRVTINS;

(SEQ ID NO: 815
β8/9/10-like (Hi affinity) - WNGNKIIDERLITPDGSMLFR

VTINSVSGWRLFKKIS);
and (SEQ ID NO: 816)
β8/9/10-like (Lo affinity) - WNGNKIIDERLITPDGSMLFR

VTINSVTGYRLFEEIL.
```

In some embodiments, provided herein are polypeptide comprising 40% or greater (e.g., 40%, 45%, 50%, 55%, 60%, 65%, 70%, 75%, 80%, 85%, 90%, 95%, or 100%) sequence identity with one of the following:

```
β1-5-like -
                                    (SEQ ID NO: 790)
MVFTLDDFVGDWEQTAAYNLDQVLEQGGVSSLLQNLAVSVTPIMRIVRSG

ENALKIDIHVIIPYEGLSADQMAQIEEVFKVVYPVDDHHFKVILPYGTLV

ID;

(SEQ ID NO: 794)
β6-10-like (Hi affinity) -
GVTPNKLNYFGRPYEGIAVFDGKKITTTGTLWNGNKIIDERLITPDGSML

FRVTINSVSGWRLFKKIS;

β6-10-like (Lo affinity) -
                                    (SEQ ID NO: 798)
GVTPNKLNYFGRPYEGIAVFDGKKITTTGTLWNGNKIIDERLITPDGSML

FRVTINSVTGYRLFEEIL;

β6-9-like -
                                    (SEQ ID NO: 829)
GVTPNKLNYFGRPYEGIAVFDGKKITTTGTLWNGNKIIDERLITPDGSML

FRVTINS;
```

-continued

```
β7-10-like (Hi affinity) -
                                    (SEQ ID NO: 795)
KKITTTGTLWNGNKIIDERLITPDGSMLFRVTINSVSGWRLFKKIS;
and β7-10-like (Lo affinity) -
                                    (SEQ ID NO: 799)
KKITTTTGTLWNGNKIIDERLITPDGSMLFRVTINSVTGYRLFEEIL.
```

In some embodiments, a polypeptide component (e.g., of a set of peptides/polypeptides, or a bioluminescent complex, etc.) comprises 40% or greater (e.g., 40%, 45%, 50%, 55%, 60%, 65%, 70%, 75%, 80%, 85%, 90%, 95%, or 100%) sequence identity with one of SEQ ID NOS: 788, 789, 790, 791, 792, and 793.

In some embodiments, peptide/dipeptide/tripeptide components (e.g., tags) (e.g., of a set of peptides/polypeptides, or a bioluminescent complex, etc.) collectively comprise 40% or greater (e.g., 40%, 45%, 50%, 55%, 60%, 65%, 70%, 75%, 80%, 85%, 90%, 95%, or 100%) sequence identity with one of SEQ ID NOS: 794, 795, 796, 797, 798, 799, 800, and 801.

In some embodiments, provided herein are sets of components and complexes of the peptides, dipeptides, tripeptide, and polypeptides listed above. In particular embodiments, sets of components are selected that span all ten of the beta strands of a base luciferase sequence.

In some embodiments, the interaction, co-localization, detection, and other methods, assays, and technologies described for use with the two-peptide tag systems herein (e.g., β9-like (e.g., SmTrip9) peptide, β10-like (e.g., SmTrip10) peptides and polypeptide component ((e.g., β1-8-like (e.g., LgTrip) polypeptide)), also find use with the dipeptide systems described herein (e.g., β9/10-like dipeptide and polypeptide component). In some embodiments, a dipeptide has high affinity for a polypeptide component; in such embodiments, a bioluminescent complex forms when the dipeptide and polypeptide component are brought into contact (e.g., co-localize, are added to the sample, etc.) without facilitation. In some embodiments, a dipeptide has low affinity for a polypeptide component; in such embodiments, a bioluminescent complex will not form when the dipeptide and polypeptide component are brought into contact (e.g., co-localize, are added to the sample, etc.) without facilitation. Like the two-peptide tag systems herein (e.g., β9-like (e.g., SmTrip9) peptide, β10-like (e.g., SmTrip10) peptides and polypeptide component (e.g., β1-8-like (e.g., LgTrip) polypeptide)), dipeptide/polypeptide pairs of varying affinities may be selected for different applications. In some embodiments, systems, methods, and assays for two-component complementation systems are described in U.S. Pat. No. 9,797,890 (herein incorporated by reference in its entirety), and all such systems, methods, and assays find use with the dipeptide/polypeptide systems described herein.

In some embodiments, the interaction, co-localization, detection, and other methods, assays, and technologies described for use with the two-peptide tag systems herein (e.g., β9-like (e.g., SmTrip9) peptide, β10-like (e.g., SmTrip10) peptides and polypeptide component ((e.g., β1-8-like (e.g., LgTrip) polypeptide)), also find use with systems comprising any suitable combination of peptides, dipeptide, tripeptide, and polypeptides, as described herein. In some embodiments, the components have high affinity for one another; in such embodiments, a bioluminescent complex forms when the components are brought into contact (e.g., co-localize, are added to the sample, etc.) without facilitation. In some embodiments, one or more of the components have low affinity for one or more of the other components; in such embodiments, a bioluminescent complex will not form when the components are brought into contact (e.g., co-localize, are added to the sample, etc.) without facilitation. Like the two-peptide tag systems herein (e.g., β9-like (e.g., SmTrip9) peptide, β10-like (e.g., SmTrip10) peptides and polypeptide component (e.g., β1-8-like (e.g., LgTrip) polypeptide)), the other systems described herein may be provided with varying affinities for different applications. In some embodiments, systems, methods, and assays for two-component complementation systems are described in U.S. Pat. No. 9,797,890 (herein incorporated by reference in its entirety), and all such systems, methods, and assays find use with the various peptide, dipeptide, tripeptide, and polypeptide systems described herein.

In some embodiments, provided herein are complementary panels of interchangeable peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and polypeptide components (e.g., β1-5-like, β1-6-like, β1-7-like, β1-8-like (e.g., LgTrip) polypeptide) that have variable affinities and luminescence upon formation of bioluminescent complexes therefrom (e.g., a high-affinity/high-luminescence, a moderate-affinity/high-luminescence, a low-affinity/moderate-luminescence, etc.). Utilizing different combinations of peptide/dipeptide/tripeptide tags and polypeptide components provides an adaptable system comprising various sets ranging from lower to higher affinities, luminescence, expression level, stability, solubility, and other variable characteristics. This adaptability allows the detection/monitoring/identification/quantification of analytes, molecular interactions, co-localization, and/or other characteristics to be fine-tuned to the specific molecule(s) of interest and/or conditions to be studied and expands the range of molecular interactions and/or co-localizations that can be detected/monitored/identified/quantified to include interactions with very high or low affinities. Further provided herein are methods by which non-luminescent elements and panels of non-luminescent elements are developed and tested.

In some embodiments, due to the small size of the tags (e.g., peptide tags) herein (e.g., compared to larger polypeptides and proteins), they are resistant to denaturation (they have no tertiary structure required for function).

In some embodiments, peptide/dipeptide/tripeptide tags and a polypeptide components may be selected based on the molecules or proteins of interest to be studied. In some embodiments, different peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and polypeptide components (e.g., β1-5-like, β1-6-like, β1-7-like, β1-8-like (e.g., LgTrip) polypeptide) may require different strength, duration, and/or stability of an interaction complex (e.g., complex of interaction elements) to result in bioluminescent complex formation. In some embodiments, a highly stable interaction complex is required to produce a detectable bioluminescent signal (e.g., in the presence of a substrate). In other embodiments, even a weak or transient interaction complex results in bioluminescent complex formation. In still other embodiments, a bioluminescent complex will form in the absence of an interaction complex as long as the peptide/dipeptide/tripeptide tags and polypeptide component are co-localized. In some embodiments, the strength or extent of an interaction complex is directly proportional to the strength of the resulting bioluminescent signal. Some peptide/dipeptide/tripeptide tags/polypeptide component sets produce a detectable signal when combined with an interaction complex with a high millimolar dissociation constant (e.g., $K_d > 100$ mM). Other peptide/dipeptide/tripeptide tags/polypeptide component sets require an interaction pair with a low millimolar (e.g., $K_d < 100$ mM), micromolar (e.g., $K_d < 1$ mM), nanomolar (e.g., $K_d < 1$ μM), or even picomolar (e.g., $K_d < 1$ nM) dissociation constant in order to produce a bioluminescent complex with a detectable signal.

In some embodiments, the peptide/dipeptide/tripeptide tags and/or polypeptide components herein are not fragments of a pre-existing protein (e.g., a pre-existing bioluminescent protein). In some embodiments, none of the peptide/dipeptide/tripeptide tags and polypeptide component used to form a complex are fragments of a pre-existing protein (e.g., the same pre-existing protein, a pre-existing bioluminescent protein, etc.). In some embodiments, neither the peptide tags (e.g., β9-like (e.g., SmTrip9) and β10-like (e.g., SmTrip10) peptides; β9/β10-like dipeptides; etc.) nor polypeptide component (e.g., $β_{1-8}$-like (e.g., LgTrip) polypeptide)) that assemble together to form a bioluminescent complex are fragments of a pre-existing protein (e.g., the same pre-existing protein, a pre-existing bioluminescent protein, etc.). In some embodiments, the peptide/dipeptide/tripeptide tags or polypeptide component of a bioluminescent complex for use in embodiments of the present invention is not a subsequence of a preexisting protein. In some embodiments, non-luminescent elements for use in embodiments described herein do not comprise structurally-complementary subsequences of a preexisting protein.

In some embodiments, the peptide/dipeptide/tripeptide tags (e.g., 6-like, β7-like, β8-like, β9-like (e.g., SmTrip9), and/or β10-like (e.g., SmTrip10) peptides, and/or dipeptides and tripeptides thereof) herein are non-luminescent or substantially non-luminescent in isolation (e.g., in the presence or absence of substrate). In some embodiments, the peptide/dipeptide/tripeptide tags herein are non-luminescent or substantially non-luminescent when associated together, in the absence of the polypeptide component (e.g., β1-5-like, β1-6-like, β1-7-like, β1-8-like (e.g., LgTrip) polypeptide) (e.g., in the presence or absence of substrate). In some embodiments, a polypeptide component is non-luminescent or substantially non-luminescent in isolation (e.g., in the presence or absence of substrate). In some embodiments, a single peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and the polypeptide component are non-luminescent or substantially non-luminescent in the absence of the second or third or fourth peptide/dipeptide/tripeptide tag (e.g., in the presence or absence of substrate). In certain embodiments, when placed in suitable conditions (e.g., physiological conditions), multiple peptide/dipeptide/tripeptide tags and a polypeptide component interact to form a bioluminescent complex and produce a bioluminescent signal in the presence of substrate.

In certain embodiments, an interaction element and/or co-localization element and a peptide/dipeptide/tripeptide tag are attached, fused, linked, connected, etc. In typical embodiments, a first peptide/dipeptide/tripeptide tag and a first interaction element (or first co-localization element) are attached to each other, and a second peptide/dipeptide/tripeptide tag and a second interaction element (or second co-localization element) are attached to each other. Attachment of peptide/dipeptide/tripeptide tags to interaction elements (or co-localization elements) may be achieved by any suitable mechanism, chemistry, linker, etc. The interaction elements (or co-localization elements) and peptide/dipeptide/tripeptide tags are typically attached through covalent connection, but non-covalent linking of the two elements is also provided. In some embodiments, the peptide/dipeptide/tripeptide tags and interaction elements (or co-localization elements) are directly connected and, in other embodiments, they are connected by a linker. In some embodiments, the peptide/dipeptide/tripeptide tags and interaction elements (or co-localization elements) are provided as genetic/recombinant fusions. In some embodiments, endogenous tagging with the peptide/dipeptide/tripeptide tags herein (e.g., under endogenous regulatory control), allows for monitoring of normal cellular functions with the tools described herein. For example, a protein of interest may be endogenously tagged (e.g., using CRISPR/Cas9) with a high affinity β9/β10-like dipeptide, and then spontaneous complementation with LgTrip (or a variant thereof) is monitored in a cell, animal, lysate, etc. In other embodiments, the peptide tags and interaction elements (or co-localization elements) are connected by chemical modification/conjugation, such as by Native chemical ligation, Staudinger ligation, "traceless" Staudinger ligation, amide coupling, methods that employ activated esters, methods to target lysine, tyrosine and cysteine residues, imine bond formation (with and without ortho-boronic acid), boronic acid/diol interactions, disulfide bond formation, copper/copper free azide, diazo, and tetrazine "click" chemistry, UV promoted thiolene conjugation, diazirine photolabeling, Diels-Alder cycloaddition, metathesis reaction, Suzuki cross-coupling, thiazolidine (Step-4) coupling, streptavidin/biotin complementation, HaloTag/chloroalkane substrate complementation, etc. In some embodiments, peptide/dipeptide/tripeptide tags and interaction elements (or co-localization elements) are produced synthetically (e.g., solid-state synthesis, solution-phase synthesis, etc.). In some embodiments, interaction elements (or co-localization elements) are produced (e.g., synthetically or recombinantly) or obtained (e.g., from crude lysate, extracted proteins, purified proteins, etc.) by any suitable means.

In some embodiments, in which the interaction element (or co-localization element) is a peptide or polypeptide, a peptide/dipeptide/tripeptide tag (e.g., β6-like, β7-like, β8-like, β9-like (e.g., SmTrip9), and/or β10-like (e.g., SmTrip10) peptides, and/or dipeptides and tripeptides thereof) and an interaction element (or co-localization element) are contained within a single amino acid chain. In some embodiments, a single amino acid chain comprises, consists of, or consists essentially of a peptide/dipeptide/tripeptide tag and an interaction element (or co-localization element). In some embodiments, a single amino acid chain comprises, consists of, or consists essentially of a peptide/dipeptide/tripeptide tag, an interaction element (or co-localization element), optionally one or more an N-terminal sequence, a C-terminal sequence, regulatory elements (e.g., promoter, translational start site, etc.), and a linker sequence. In some embodiments, the peptide/dipeptide/tripeptide tag and interaction element (or co-localization element) are contained within a fusion polypeptide. In some embodiments, the first fusion of peptide/dipeptide/tripeptide tag and interaction element (or co-localization element) and the second fusion of peptide/dipeptide/tripeptide tag and interaction element (or co-localization element) are expressed separately; however, in other embodiments, a fusion protein is expressed that comprises or consist of both of the interaction (or co-localization) and peptide/dipeptide/tripeptide tags.

In some embodiments, a first fusion protein comprising a first peptide/dipeptide/tripeptide tag (e.g., β6-like, β7-like, β8-like, β9-like (e.g., SmTrip9), and/or β10-like (e.g., SmTrip10) peptides, and/or dipeptides and tripeptides thereof) and first interaction element as well as a second fusion protein comprising a second peptide/dipeptide/tripeptide tag (e.g., β6-like, β7-like, β8-like, β9-like (e.g., SmTrip9), and/or β10-like (e.g., SmTrip10) peptides, and/or dipeptides and tripeptides thereof) and second interaction element are expressed within the same cells. In some embodiments, a first fusion protein comprising a first peptide/dipeptide/tripeptide tag and first co-localization element as well as a second fusion protein comprising a second peptide/dipeptide/tripeptide tag and second co-localization element are expressed within the same cells. In some embodiments, the first and second fusion proteins are purified and/or isolated from the cells. In some embodiments, the interaction and/or co-localization of the fusion proteins is assayed within the cells. In some embodiments, the interaction and/or co-localization of the fusion proteins is assayed within a lysate of the cells. In other embodiments, first and second fusion proteins are expressed in separate cells and combined (e.g., following purification and/or isolation, following fusion of the cells or portions of the cells, by transfer of a fusion protein from one cell to another, or by secretion of one or more fusion proteins into the extracellular medium) for signal detection. In some embodiments, one or more fusion proteins are expressed in cell lysate (e.g., rabbit reticulocyte lysate) or in a cell-free system. In some embodiments, one or more fusion proteins are expressed from the genome of a virus or other cellular pathogen. In some embodiments, the polypeptide component (e.g., β1-5-like, β1-6-like, β1-7-like, β1-8-like (e.g., LgTrip) polypeptide) and any other peptide/dipeptide/tripeptide components (e.g., β6-like, β7-like, β8-like, β9-like (e.g., SmTrip9), and/or β10-like (e.g., SmTrip10) peptides, and/or dipeptides and tripeptides thereof) for complex formation (with the first and second fusion proteins) is expressed in the same cell or cell lysate as one or both of the tag-containing fusion proteins. In some embodiments, the peptide/dipeptide/tripeptide/polypeptide components for complex formation with the peptide/dipeptide/tripeptide tags (within the first and second fusion proteins) are expressed in a different cell or cell lysate as one or both of the peptide-tag-containing fusion proteins. In some embodiments, the peptide/dipeptide/tripeptide/polypeptide components for complex formation with the peptide/dipeptide/tripeptide tags (within the first and second fusion proteins) is added to a cell, cell lysate, or other sample comprising the peptide-tag-containing fusion proteins.

In some embodiments, the systems (e.g., peptide/dipeptide/tripeptide tags, peptide/dipeptide/tripeptide/polypeptide components, substrates, vectors, etc.) and methods herein find use in the analysis of a sample (e.g., detection/quantification/identification/monitoring of co-localization, a molecular interaction, a target, etc.). In some embodiments, one or more of the components of a system herein are added to and/or provided or expressed within a sample. Suitable samples that may find use in embodiments herein include, but are not limited to: blood, plasma, sera, urine, saliva, cells, cell lysates, tissues, tissue homogenates, purified nucleic acids, stool, vaginal secretions, cerebrospinal fluid, allantoic fluid, water, biofilm, soil, dust, food, beverage, agriculture products, plants, etc.

In certain embodiments, nucleic acids, DNA, RNA, vectors, etc. are provided that encode the peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and a polypeptide components (e.g., β1-5-like, β1-6-like, β1-7-like, β1-8-like (e.g., LgTrip) polypeptide), fusion polypeptides, fusion proteins, etc. described herein. Such nucleic acids and vectors may be used for expression, transformation, transfection, injection, etc.

In some embodiments, a peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and interaction, co-localization element, or binding agent are connected by a linker. In some embodiments, a linker connects the signal and interaction or co-localization elements while providing a desired amount of space/distance between the elements. In some embodiments, a linker allows both the signal and interaction elements to form their respective complexes (e.g., luminescent complex and interaction complex) simultaneously. In some embodiments, a linker assists the interaction element in facilitating the formation of a luminescent complex. In some embodiments, when an interaction complex is formed, the linkers that connect each peptide/dipeptide/tripeptide tag to their respective interaction elements position the peptide tags at the proper distance and conformation to form a bioluminescent complex. In some embodiments, an interaction or co-localization element and peptide/dipeptide/tripeptide tag are held in close proximity (e.g., <4 monomer units) by a linker. In some embodiments, a linker provides a desired amount of distance (e.g., 1, 2, 3, 4, 5, 6 . . . 10 . . . 20, or more monomer units) between peptide tags and interaction elements (e.g., to prevent undesirable interactions between peptide/dipeptide/tripeptide tags and interaction or co-localization elements, for steric considerations, to allow proper orientation of non-luminescent element upon formation of interaction complex, to allow propagation of a complex-formation from interaction complex to luminescent complex, etc.). In certain embodiments, a linker provides appropriate attachment chemistry between the peptide/dipeptide/tripeptide tags and interaction elements. A linker may also improve the synthetic process of making the peptide/dipeptide/tripeptide tag and interaction or co-localization element (e.g., allowing them to be synthesized as a single unit, allowing post synthesis connection of the two elements, etc.).

In some embodiments, a linker is any suitable chemical moiety capable of linking, connecting, or tethering a peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) or polypeptide component (e.g., β1-5-like, β1-6-like, β1-7-like, β1-8-like (e.g., LgTrip) polypeptide) to an interaction element or co-localization element. In some embodiments, a linker is a polymer of one or more repeating or non-repeating monomer units (e.g., nucleic acid, amino acid, carbon-containing polymer, carbon chain, etc.). When a peptide/dipeptide/tripeptide tag and an interaction, co-localization element, or binding agent are part of a fusion protein, a linker (when present) is typically an amino acid chain. When a peptide/dipeptide/tripeptide tag and interaction element, co-localization element, or binding agent are tethered together after the expression of the individual elements, a linker may comprise any chemical moiety with functional (or reactive) groups at either end that are reactive with functional groups on the peptide tag and interaction or co-localization elements, respectively. Any suitable moiety capable of tethering the signal and interaction elements, co-localization element, and/or binding agent may find use as a linker.

A wide variety of linkers may be used. In some embodiments, the linker is a single covalent bond. In some embodiments, the linker comprises a linear or branched, cyclic or heterocyclic, saturated or unsaturated, structure having 1-20 nonhydrogen atoms (e.g., C, N, P, O and S) and is composed of any combination of alkyl, ether, thioether, imine, carboxylic, amine, ester, carboxamide, sulfonamide, hydrazide bonds and aromatic or heteroaromatic bonds. In some embodiments, linkers are longer than 20 nonhydrogen atoms (e.g. 21 non-hydrogen atoms, 25 non-hydrogen atoms, 30 non-hydrogen atoms, 40 non-hydrogen atoms, 50 non-hydrogen atoms, 100 non-hydrogen atoms, etc.) In some embodiments, the linker comprises 1-50 non-hydrogen atoms (in addition to hydrogen atoms) selected from the group of C, N, P, O and S (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 non-hydrogen atoms).

The scope of embodiments herein is not limited by the types of linkers available. The peptide/dipeptide/tripeptide tags, polypeptide components, and interaction elements, co-localization elements, or binding agents are linked either directly (e.g. linker consists of a single covalent bond) or linked via a suitable linker. Embodiments are not limited to any particular linker group. A variety of linker groups are contemplated, and suitable linkers could comprise, but are not limited to, alkyl groups, methylene carbon chains, ether, polyether, alkyl amide linker, a peptide linker, a modified peptide linker, a Poly(ethylene glycol) (PEG) linker, a streptavidin-biotin or avidin-biotin linker, polyaminoacids (e.g. polylysine), functionalized PEG, polysaccharides, glycosaminoglycans, dendritic polymers (WO93/06868 and by Tomalia et al. in Angew. Chem. Int. Ed. Engl. 29:138-175 (1990), herein incorporated by reference in their entireties), PEG-chelant polymers (W94/08629, WO94/09056 and WO96/26754, herein incorporated by reference in their entireties), oligonucleotide linker, phospholipid derivatives, alkenyl chains, alkynyl chains, disulfide, or a combination thereof. In some embodiments, the linker is cleavable (e.g., enzymatically (e.g., TEV protease site), chemically, photoinduced, etc. In some embodiments, a peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and a polypeptide component (e.g., β1-5-like, β1-6-like, β1-7-like, β1-8-like (e.g., LgTrip) polypeptide), recognition element, interaction element, co-localization element, binding agent, analyte, substrate, etc. is attached (e.g., via any suitable chemistry) to, or contained within, a solid surface or matrix. In some embodiments, one or more system components are attached (e.g., via any suitable chemistry) to, or contained within, a solid surface or matrix and other components are added (e.g., in solution (e.g., in a sample)) to the solid surface or matrix. Suitable solid surfaces include, but are not limited to: beads (e.g., magnetic beads), chips, tubes, plates, particles, membranes, paper, etc. In some embodiments, solid surfaces/matrix is made of any suitable materials, such as: Ahlstrom CytoSep, Cellulose nitrate, Cellulose acetate, Cellulose (e.g., Whatman FTA-DMPK-A, B, and C cards; Whatman ET 3/Chr; Whatman protein saver 903 cards; Whatman Grade 1 filter paper; Whatman FTA Elute; Ahlstrom 226 specimen collection paper; etc.), Noviplex Plasma Prep Cards, Polypropylene membrane, PVDF, Nitrocellulose membrane (Millipore Nitrocellular Hi Flow Plus) Polytetrafluoroethylene film, Mixed cellulose esters, Glass fiber media (e.g., Whatman unifilter plates glass fiber filter membrane, Agilent dried matrix spotting cards, Ahlstrom grade 8950, etc.), Plastic (e.g., Polyester, Polypropylene, Polythersulfene, poly (methacrylate), Acrylic polymers, polytetrafluoroten, etc.), natural and synthetic polymers (e.g., mixture of polymers, co-block polymers, etc.), sugars (e.g., pullulan, trehalose, maltose, sucrose, cellulose, etc.), polyamides (e.g., natural (e.g., wool, silk, etc.), synthetic (e.g., aramids, nylon, etc.), etc.), metals (e.g., aluminum, cadmium, chromium, cobalt, copper, iron, manganese, nickel, platinum, palladium, rhodium, silver, gold, tin, titanium, tungsten, vanadium, zinc, etc.), alloys (e.g., alloys of aluminium (e.g., Al—Li, alumel, duralumin, magnox, zamak, etc.), alloys of iron (e.g., steel, stainless steel, surgical stainless steel, silicon steel, tool steel, cast iron, Spiegeleisen, etc.), alloys of cobalt (e.g., stellite, talonite, etc.), alloys of nickel (e.g., German silver, chromel, mumetal, monel metal, nichrome, nicrosil, nisil, nitinol, etc.), alloys of copper (e.g., beryllium copper, billon, brass, bronze, phosphor bronze, constantan, cupronickel, bell metal, Devarda's alloy, gilding metal, nickel silver, nordic gold, prince's metal, tumbaga, etc.), alloys of silver (e.g., sterling silver, etc.), alloys of tin (e.g., Britannium, pewter, solder, etc.), alloys of gold (electrum, white gold, etc.), amalgam, etc.), ELISPot plates, Immunoassay plates, Tissue culture plates, etc.

In some embodiments, peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and a polypeptide component (e.g., β1-5-like, β1-6-like, β1-7-like, β1-8-like (e.g., LgTrip) polypeptide) of a luminescent complex are provided with less than 100% sequence identity and/or similarity to any portion of an existing luciferase (e.g., a firefly luciferase, a Renilla luciferase, an Oplophorus luciferase, enhanced Oplophorus luciferases as described in U.S. Pat. App. 2010/0281552 and U.S. Pat. App. 2012/0174242, herein incorporated by reference in their entireties). Certain embodiments involve the formation of bioluminescent complexes of peptide/dipeptide/tripeptide tags and a polypeptide component with less than 100% sequence identity with all or a portion (e.g., 8 or more amino acids, less than about 25 amino acids for peptides) of SEQ ID NO: 1 (e.g., complete wild type Oplophorus luciferase sequence) and/or SEQ ID NO: 3 (e.g., complete NANOLUC sequence). Certain embodiments involve the formation of bioluminescent complexes from peptide/dipeptide/tripeptide tags and a polypeptide component with less than 100%, but more than 40% (e.g., >40%, >45%, >50%, >55%, >60%, >65%, >70%, >75%, >80%, >85%, >90%, >95%, >98%, >99%) sequence identity with all or a portion (e.g., 8 or more amino acids, less than about 25 amino acids for peptides) of SEQ ID NO: 1 (e.g., complete wild type Oplophorus luciferase sequence) and/or SEQ ID NO: 3 (e.g., complete NANOLUC sequence). In some embodiments, peptide/dipeptide/tripeptide tags and a polypeptide component are provided with less than 100% sequence similarity with a portion (e.g., 8 or more amino acids, less than about 25 amino acids for peptides) of SEQ ID NO: 1 (e.g., complete wild type Oplophorus luciferase sequence) and/or SEQ ID NO: 3 (e.g., complete NANOLUC sequence). In some embodiments, peptide/dipeptide/tripeptide tags and a polypeptide component are provided with less than 100%, but more than 40% (e.g., >40%, >45%, >50%, >55%, >60%, >65%, >70%, >75%, >80%, >85%, >90%, >95%, >98%, >99%) sequence similarity with a portion (e.g., 8 or more amino acids, less than about 25 amino acids for peptides) of SEQ ID NO: 1 (e.g., complete wild type Oplophorus luciferase sequence) and/or SEQ ID NO: 3 (e.g., complete NANOLUC sequence). In some embodiments, peptide/dipeptide/tripeptide tags are provided that have less than 100% sequence identity and/or similarity with about a 25 amino acid or less portion of SEQ ID NO: 1 (e.g., complete wild type *Oplophorus* luciferase sequence) and/or SEQ ID NO: 3 (e.g., complete NANOLUC sequence), wherein two of such peptides form a bioluminescent complex when combined under appropriate conditions (e.g., stabilized by an interaction pair, brought into proximity by co-localization elements, etc.) with a polypeptide component having less than 100%, but more than 40% (e.g., >40%, >45%, >50%, >55%, >60%, >65%, >70%, >75%, >80%, >85%, >90%, >95%, >98%, >99%) sequence identity and/or similarity with another portion SEQ ID NO: 1 (e.g., complete wild type *Oplophorus* luciferase sequence) and/or SEQ ID NO: 3 (e.g., complete NANOLUC sequence). In some embodiments, peptide/dipeptide/tripeptide tags are provided that have less than 100% sequence identity and/or similarity with about a 25 amino acid or less portion of SEQ ID NO: 1 (e.g., complete wild type *Oplophorus* luciferase sequence) and/or SEQ ID NO: 3 (e.g., complete NANOLUC sequence), wherein a pair of such peptide tags form a bioluminescent complex when combined under appropriate conditions (e.g., stabilized by an interaction pair, brought into proximity by co-localization elements, etc.) with a polypeptide component having less than 100%, but more than 40% (e.g., >40%, >45%, >50%, >55%, >60%, >65%, >70%, >75%, >80%, >85%, >90%, >95%, >98%, >99%) sequence identity and/or similarity with another portion SEQ ID NO: 1 (e.g., complete wild type *Oplophorus* luciferase sequence) and/or SEQ ID NO: 3 (e.g., complete NANOLUC sequence). In some embodiments, peptide/dipeptide/tripeptide tags are provided that have less than 100%, but more than 40% (e.g., >40%, >45%, >50%, >55%, >60%, >65%, >70%, >75%, >80%, >85%, >90%, >95%, >98%, >99%) sequence identity and/or similarity with about a 25 amino acid or less portion of SEQ ID NO: 1 (e.g., complete wild type *Oplophorus* luciferase sequence) and/or SEQ ID NO: 3 (e.g., complete NANOLUC sequence), wherein a pair of such peptides form a bioluminescent complex when combined under appropriate conditions (e.g., stabilized by an interaction pair, brought into proximity by co-localization elements, etc.) with a polypeptide having less than 100%, but more than 40% (e.g., >40%, >45%, >50%, >55%, >60%, >65%, >70%, >75%, >80%, >85%, >90%, >95%, >98%, >99%) sequence identity and/or similarity with another portion of SEQ ID NO: 1 (e.g., complete wild type *Oplophorus* luciferase sequence) and/or SEQ ID NO: 3 (e.g., complete NANOLUC sequence). Similarly, polypeptide components are provided that have less than 100%, but more than 40% (e.g., >40%, >45%, >50%, >55%, >60%, >65%, >70%, >75%, >80%, >85%, >90%, >95%, >98%, >99%) sequence identity or similarity with a portion of SEQ ID NO: 1 (e.g., complete wild type *Oplophorus* luciferase sequence) and/or SEQ ID NO: 3 (e.g., complete NANOLUC sequence), wherein such polypeptide components form a bioluminescent complex when combined under appropriate conditions with a pair of peptide tags having less than 100%, but optionally more than 40% (e.g., >40%, >45%, >50%, >55%, >60%, >65%, >70%, >75%, >80%, >85%, >90%, >95%, >98%, >99%) sequence identity and/or similarity with another portion SEQ ID NO: 1 (e.g., complete wild type *Oplophorus* luciferase sequence) and/or SEQ ID NO: 3 (e.g., complete NANOLUC sequence). In some embodiments, peptide tags with less than 100% sequence identity or similarity with SEQ ID NO: 6, SEQ ID NO: 7, SEQ ID NO: 9, and/or SEQ ID NO: 10 are provided. In some embodiments, peptide tags with less than 100%, but more than 40% (e.g., >40%, >45%, >50%, >55%, >60%, >65%, >70%, >75%, >80%, >85%, >90%, >95%, >98%, >99%) sequence identity or similarity with SEQ ID NO: 6, SEQ ID NO: 7, SEQ ID NO:9, and/or SEQ ID NO: 10 are provided. In some embodiments, peptide tags with less than 100% sequence identity or similarity with SEQ ID NO: 23, SEQ ID NO: 25, and/or SEQ ID NO: 29 are provided. In some embodiments, peptide tags with less than 100%, but more than 40% (e.g., >40%, >45%, >50%, >55%, >60%, >65%, >70%, >75%, >80%, >85%, >90%, >95%, >98%, >99%) sequence identity or similarity with SEQ ID NO: 23, SEQ ID NO: 25, and/or SEQ ID NO: 29 are provided. In some embodiments, polypeptide components with less than 100% sequence identity or similarity with SEQ ID NO: 5 and/or SEQ ID NO: 8 are provided. In some embodiments, polypeptide components with less than 100% sequence identity or similarity with SEQ ID NO: 17 and/or SEQ ID NO: 27 are provided. In some embodiments, polypeptide components with less than 100%, but more than 40% (e.g., >40%, >45%, >50%, >55%, >60%, >65%, >70%, >75%, >80%, >85%, >90%, >95%, >98%, >99%) sequence identity or similarity with SEQ ID NO: 5, SEQ ID NO: 8, and/or SEQ ID NO: 27 are provided. In some embodiments, polypeptide components with less than 100%, but more than 40% (e.g., >40%, >45%, >50%, >55%, >60%, >65%, >70%, >75%, >80%, >85%, >90%, >95%, >98%, >99%) sequence identity or similarity with SEQ ID NO: 17 are provided.

In some embodiments, one or more (e.g., all) peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and a polypeptide components (e.g., β1-5-like, β1-6-like, β1-7-like, β1-8-like (e.g., LgTrip) polypeptide) in a set, kit, or system herein comprise 100% sequence identity with a portion of a luciferase (e.g., SEQ ID NO: 1, SEQ ID NO: 3, etc.).

In some embodiments, peptide tags (e.g., β9-like (e.g., SmTrip9) and β10-like (e.g., SmTrip10) peptides; β9/β10-like dipeptides; etc.) that find use in embodiments of the present invention include peptides with one or more amino acid substitutions, deletions, or additions from SEQ ID NO: 6, SEQ ID NO: 7, SEQ ID NO:9, SEQ ID NO: 10, SEQ ID NO: 23, SEQ ID NO: 25, SEQ ID NO: 29. In some embodiments, a peptide tag comprises at least 40% (e.g., >40%, >45%, >50%, >55%, >60%, >65%, >70%, >75%, >80%, >85%, >90%, >95%, >98%, >99%) sequence identity or similarity with SEQ ID NO: 13. In some embodiments, a peptide tag comprises 6 or fewer (e.g., 6, 5, 4, 3, 2, 1, or ranges there between) substitutions (e.g., conservative substitutions, semi-conservative substitutions, non-conservative substations, etc.) relative to SEQ ID NO: 13. In some embodiments, a peptide tag comprises at least 40% (e.g., >40%, >45%, >50%, >55%, >60%, >65%, >70%, >75%, >80%, >85%, >90%, >95%, >98%, >99%) sequence identity or similarity with SEQ ID NO: 25. In some embodiments, a peptide tag comprises 6 or fewer (e.g., 6, 5, 4, 3, 2, 1, or ranges there between) substitutions (e.g., conservative substitutions, semi-conservative substitutions, non-conservative substations, etc.) relative to SEQ ID NO: 25. In some embodiments, a peptide tag comprises at least 40% (e.g., >40%, >45%, >50%, >55%, >60%, >65%, >70%, >75%, >80%, >85%, >90%, >95%, >98%, >99%) sequence identity or similarity with SEQ ID NO: 23. In some embodiments, a peptide tag comprises 6 or fewer (e.g., 6, 5, 4, 3, 2, 1, or ranges there between) substitutions (e.g., conservative substitutions, semi-conservative substitutions, non-conservative substations, etc.) relative to SEQ ID NO: 23. In some embodiments, a peptide tag comprises at least 40% (e.g., >40%, >45%, >50%, >55%, >60%, >65%, >70%, >75%, >80%, >85%, >90%, >95%, >98%, >99%) sequence identity or similarity with SEQ ID NO: 25. In some embodiments, a peptide tag comprises 6 or fewer (e.g., 6, 5, 4, 3, 2, 1, or ranges there between) substitutions (e.g., conservative substitutions, semi-conservative substitutions, non-conservative substations, etc.) relative to SEQ ID NO: 25.

In some embodiments, peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and a polypeptide component (e.g., β1-5-like, β1-6-like, β1-7-like, β1-8-like (e.g., LgTrip) polypeptide) that find use in embodiments of the present invention include the peptides, dipeptides, tripeptides, and polypeptides disclosed herein and in the tables provided herein. In some embodiments, peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and a polypeptide component (e.g., β1-5-like, β1-6-like, β1-7-like, β1-8-like (e.g., LgTrip) polypeptide) that find use in embodiments of the present invention comprise one or more amino acid substitutions, deletions, or additions relative to the peptides, dipeptides, tripeptides, and polypeptides disclosed herein and in the tables provided herein. In some embodiments, a peptide/ dipeptide/tripeptide tags (e.g., 36-like, β7-like, β8-like, β9-like (e.g., SmTrip9), and/or β10-like (e.g., SmTrip10) peptides, and/or dipeptides and tripeptides thereof) and a polypeptide component (e.g., β1-5-like, β1-6-like, β1-7-like, β1-8-like (e.g., LgTrip) polypeptide) that find use in embodiments of the present invention comprise at least 40% (e.g., >40%, >45%, >50%, >55%, >60%, >65%, >70%, >75%, >80%, >85%, >90%, >95%, >98%, >99%) sequence identity or similarity with the peptides, dipeptides, tripeptides, and polypeptides disclosed herein and in the tables provided herein.

In some embodiments, dipeptides and tripeptides that find use in embodiments herein comprise any suitable combinations of the peptides described herein and/or listed in the tables herein.

In some embodiments, a peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) or a polypeptide component (e.g., β1-5-like, β1-6-like, β1-7-like, β1-8-like (e.g., LgTrip) polypeptide) is linked (e.g., chemically) or fused to one or more additional elements (e.g., recognition element, interaction element, co-localization element, detectable element (e.g., a fluorophore (e.g., to facilitate BRET)), protein of interest, HALOTAG, etc.). In some embodiments, a peptide/ dipeptide/tripeptide tag or polypeptide component is linked or fused to a cyOFP (e.g., in an Antares construct such as those described in U.S. Pat. No. 9,908,918; herein incorporated by reference in its entirety) or other fluorescent protein (e.g., to facilitate BRET). In some embodiments, a peptide/ dipeptide/tripeptide tag or polypeptide component comprises one or more chemical modifications and/or unnatural amino acids or amino acid analogs to facilitate chemical conjugation of the polypeptide component with additional elements. In some embodiments, provided herein is a single peptide/dipeptide/tripeptide tag or polypeptide component fused to an acceptor fluorescent protein. In some embodiments, two or more peptide/dipeptide/tripeptide and/or polypeptide components are fused to an acceptor fluorescent protein (e.g., sandwich fusion). In some embodiments, a peptide/dipeptide/tripeptide tag or polypeptide component is fused to two or more acceptor fluorescent protein (e.g., sandwich fusion). In some embodiments, a LgTrip polypeptide (e.g., a β1-8-like polypeptide described herein) is fused to a single fluorescent protein (e.g., cyOFP) or placed between two fluorescent proteins (e.g., two copies of a cyOFP) in a sandwich fusion.

In some embodiments, peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) that find use in the present invention incorporate reactive groups suitable for chemical conjugation to an additional element (e.g., recognition element, interaction element, etc.). These reactive groups may be present on the N-terminus, C-terminus, or within the sequence. These reactive groups may optionally be attached to the peptide with a linker. In some cases, these peptide/ dipeptide/tripeptide bearing reactive groups may be synthesized using standard synthesis and incorporated on an unnatural amino acid bearing the desired group. In some cases, the reactive group may be present on a natural amino acid (e.g. the sulfhydryl of cysteine). The additional element intended to react with a peptide tag bearing a reactive group may be a protein, an antibody, a nucleic acid, a small molecule such as a drug or a fluorophore or a surface. The peptide/dipeptide/tripeptide tag may incorporate a reactive group that is designed to react specifically with a reactive partner that has been chemically or biologically introduced on the additional element using bioorthogonal, or click, chemistry. An exemplary click reaction is copper catalyzed click where the peptide tag bears an alkyne or an azide, and the additional element bears the complementary group. Mixing these two species together in the presence of an appropriate copper catalyst causes the peptide to be covalently conjugated to the additional element through a triazole. Many other bioorthogonal reactions have been reported (for example Patterson, D. M., et al. (2014). "Finding the Right (Bioorthogonal) Chemistry." ACS Chemical Biology 9(3): 592-605.), and peptide tags and additional elements incorporating complementary reactive species are embodiments of the present invention.

Another embodiment of the present invention are peptide/ dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and/or a polypeptide components (e.g., β1-5-like, β1-6-like, β1-7-like, β1-8-like (e.g., LgTrip) polypeptide) bearing reactive groups that react with naturally occurring amino acids. Exemplary reactive groups include maleimides for reaction with cysteine and succinimidyl esters for reaction with lysine. A more comprehensive list of reactive groups can be found in Koniev, O. and A. Wagner (2015). "Developments and recent advancements in the field of endogenous amino acid selective bond forming reactions for bioconjugation." Chem Soc Rev 44: 5495-5551. These reactive groups may be chemically or biologically introduced on a peptide/ dipeptide/tripeptide/polypeptide through peptide synthesis or through other chemical modification of a peptide tag. In some embodiments, the peptide tag exists in a protected form (Isidro-Llobet, A., et al. (2009). "Amino Acid-Protecting Groups." Chemical Reviews 109(6): 2455-2504; herein incorporated by reference in its entirety), preventing the peptide/dipeptide/tripeptide/polypeptide itself from reacting with the reactive group. These reactive groups may react with a protein in a selective fashion or in a random fashion, yielding either one conjugate or a mixture of conjugates. In some embodiments, either a defined single conjugate or a mixture can be used successfully in this invention.

Examples of peptides (e.g., β9-like (e.g., SmTrip9) and β10-like (e.g., SmTrip10) peptides; β9/β10-like dipeptides; etc.) described herein bearing reactive groups suitable for chemical conjugation to an additional element (e.g., recognition element, interaction element, etc.) are displayed in FIGS. 95-98. Other combinations of reactive groups and peptides/dipeptides/tripeptides/polypeptides are within the scope herein.

In some embodiments, peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and a polypeptide component (e.g., β1-5-like, β1-6-like, β1-7-like, β1-8-like (e.g., LgTrip) polypeptide) described herein is fused or conjugated to a detectable element such as a fluorophore or fluorescent protein. In such embodiments, complementation to form the bioluminescent complex, and the resultant bioluminescence, results in BRET and excitement of/emission from the attached detectable element (e.g., fluorophore or fluorescent protein). In such embodiments, the bioluminescent complex is a BRET energy donor, and the detectable element (e.g., fluorophore or fluorescent protein) attached to a component of the complex (e.g., peptide tag or polypeptide component) is the BRET energy acceptor.

Suitable fluorophores for use in a BRET system with the tripartite/multipartite complementation systems described herein include, but are not limited to: xanthene derivatives (e.g., fluorescein, rhodamine, Oregon green, eosin, Texas red, etc.), cyanine derivatives (e.g., cyanine, indocarbocyanine, oxacarbocyanine, thiacarbocyanine, merocyanine, etc.), naphthalene derivatives (e.g., dansyl and prodan derivatives), oxadiazole derivatives (e.g., pyridyloxazole, nitrobenzoxadiazole, benzoxadiazole, etc.), pyrene derivatives (e.g., cascade blue), oxazine derivatives (e.g., Nile red, Nile blue, cresyl violet, oxazine 170, etc.), acridine derivatives (e.g., proflavin, acridine orange, acridine yellow, etc.), arylmethine derivatives (e.g., auramine, crystal violet, malachite green, etc.), tetrapyrrole derivatives (e.g., porphin, phtalocyanine, bilirubin, etc.), CF dye (Biotium), BODIPY (Invitrogen), ALEXA FLOUR (Invitrogen), DYLIGHT FLUOR (Thermo Scientific, Pierce), ATTO and TRACY (Sigma Aldrich), FluoProbes (Interchim), DY and MEGA-STOKES (Dyomics), SULFO CY dyes (CYANDYE, LLC), SETAU AND SQUARE DYES (SETA BioMedicals), QUA-SAR and CAL FLUOR dyes (Biosearch Technologies), SURELIGHT DYES (APC, RPE, PerCP, Phycobilisomes) (Columbia Biosciences), APC, APCXL, RPE, BPE (Phyco-Biotech), autofluorescent proteins (e.g., YFP, RFP, mCherry, mKate), quantum dot nanocrystals, etc. In some embodiments, a fluorophore is a rhodamine analog (e.g., carboxy rhodamine analog), such as those described in U.S. patent application Ser. No. 13/682,589, herein incorporated by reference in its entirety.

In other embodiments, peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and a polypeptide component (e.g., β1-5-like, β1-6-like, β1-7-like, β1-8-like (e.g., LgTrip) polypeptide) described herein is fused or conjugated to a detectable element such as a fluorophore or fluorescent protein (e.g., green fluorescent protein (GFP), enhanced GFP (EGFP), cyan fluorescent protein (CFP), yellow fluorescent protein (YFP), and variants thereof. In other embodiments, a peptide tag or polypeptide component described herein is fused or conjugated to a cyan-excitable orange-red fluorescent protein (CyOFP), such as those described in U.S. Pat. No. 9,908,918; herein incorporated by reference in its entirety. In some embodiments, the CyOFP and BRET systems described in U.S. Pat. No. 9,908,918 find use with the peptide tags and/or polypeptide components described herein (e.g., CyOFP-($\beta_9$-like peptide), CyOFP-($\beta_{10}$-like peptide), CyOFP-($\beta_{1-8}$-like polypeptide), CyOFP-($\beta_{9-10}$-like peptide), CyOFP-($\beta_9$-like peptide)-CyOFP, CyOFP-($\beta_{10}$-like peptide)-CyOFP, CyOFP-($\beta_{1-8}$-like polypeptide)-Cy-OFP, CyOFP-($\beta_{9-10}$-like peptide)-CyOFP, etc.). In some embodiments, such systems comprising CyOFP linked to peptide/dipeptide/tripeptide tags and/or polypeptide components herein may be referred to herein as "Antares constructs" or "Antares systems." Such BRET systems are particularly useful in certain imaging applications (Schaub, F. X., et al. (2015) "Fluorophore-NanoLuc BRET Reporters Enable Sensitive In Vivo Optical Imaging and Flow Cytometry for Monitoring Tumorigenesis." Cancer Research 75(23): 5023-5033; herein incorporated by reference in its entirety).

In other embodiments, peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and a polypeptide component (e.g., β1-5-like, β1-6-like, β1-7-like, β1-8-like (e.g., LgTrip) polypeptide) described herein are linked to fluorophores (e.g., directly or via a linker) for use in a constitutive BRET system (e.g., an Antares-like system). In constitutive BRET systems, the emission spectrum is shifted from the bioluminescence spectrum toward that of the fluorophore (e.g., for better sensitivity, lower scattering, desired emission wavelength, etc.). In other embodiments, peptide/dipeptide/tripeptide tags and/or polypeptide components described herein find use as functional sensors (e.g., for monitoring cellular/intracellular/intercellular processes (e.g., for detecting calcium flux or voltage (Suzuki, K., et al. (2016). "Five colour variants of bright luminescent protein for real-time multicolour bioimaging." Nature Communications 7: 13718.; Inagaki, S., et al. (2017). "Genetically encoded bioluminescent voltage indicator for multi-purpose use in wide range of bioimaging." Sci Rep 7:42398; herein incorporated by reference in their entireties)), for imaging, for optogenetics, etc.).

In some embodiments, two or more of the peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and a polypeptide component (e.g., β1-5-like, β1-6-like, β1-7-like, β1-8-like (e.g., LgTrip) polypeptide) are attached to a single interaction element that can access multiple conformations. In one conformation, the peptide/dipeptide/tripeptide tags and the polypeptide are unable to form a luminescent complex. Upon changing conformation, i.e., in response to a stimulus, the peptide/dipeptide/tripeptide tags are brought into a conformation where they can form a bioluminescent complex. As an example, a SmTrip9 peptide and a SmTrip10 peptide can be conjugated to calmodulin such that they do not form a luminescent complex even in the presence of LgTrip and furimazine. Upon exposure to calcium, the conformational change of calmodulin bring the SmTrip9 peptide and SmTrip10 peptide into a position whereupon addition of LgTrip makes a complex that is bioluminescent in the presence of furimazine. Many other biosensors for calcium and other stimuli (pH, voltage, etc.) are known in the literature.

In some embodiments, systems herein find use in multiplexable analyte detection. In some embodiments, peptide/dipeptide/tripeptide tags (e.g., β6-like, β7-like, β8-like, β9-like (e.g., SmTrip9), and/or β10-like (e.g., SmTrip10)

peptides, and/or dipeptides and tripeptides thereof) that find use in the present invention are conjugated to both an interaction element and a reporter element. In some embodiments, the interaction element is an antibody or the like, and the reporter element is a small molecule fluorophore. In some embodiments, antibodies to different pathogens (e.g. Zika virus, Dengue virus, etc.) are conjugated to a peptide/dipeptide/tripeptide tag (e.g., a SmTrip9 peptide) and a fluorophore with a different and distinguishable wavelength. In this embodiment, the luminescent complex that is formed upon the antibody binding to its antigen emits light at the emission wavelength of the bound fluorophore due to bioluminescence resonance energy transfer. This allows the antibodies to all be present in the same well, device, etc., and the identity of the antigen detected to be determined by the color of the light emitted by the luminescent complex formed.

In some embodiments, polypeptide components (e.g., β1-8-like (e.g., LgTrip) polypeptide) that find use in embodiments of the present invention include polypeptides with one or more amino acid substitutions, deletions, or additions from SEQ ID NO: 5 and/or SEQ ID NO: 8. In some embodiments, a polypeptide component comprises at least 40% (e.g., >40%, >45%, >50%, >55%, >60%, >65%, >70%, >75%, >80%, >85%, >90%, >95%, >98%, >99%) sequence identity or similarity with SEQ ID NO: 11. In some embodiments, polypeptide component comprises 100 or fewer (e.g., 100, 90, 80, 70, 60, 50, 40, 30, 25, 20, 15, 10, 9, 8, 7, 6, 5, 4, 3, 2, 1, or ranges there between) substitutions (e.g., conservative substitutions, semi-conservative substitutions, non-conservative substations, etc.) relative to SEQ ID NO: 11. In some embodiments, a polypeptide component comprises at least 40% (e.g., >40%, >45%, >50%, >55%, >60%, >65%, >70%, >75%, >80%, >85%, >90%, >95%, >98%, >99%) sequence identity or similarity with SEQ ID NO: 17. In some embodiments, a polypeptide component comprises 100 or fewer (e.g., 100, 90, 80, 70, 60, 50, 40, 30, 25, 20, 15, 10, 9, 8, 7, 6, 5, 4, 3, 2, 1, or ranges there between) substitutions (e.g., conservative substitutions, semi-conservative substitutions, non-conservative substations, etc.) relative to SEQ ID NO: 17. In some embodiments, a polypeptide component comprises at least 40% (e.g., >40%, >45%, >50%, >55%, >60%, >65%, >70%, >75%, >80%, >85%, >90%, >95%, >98%, >99%) sequence identity or similarity with SEQ ID NO: 17, SEQ ID NO: 21, and/or SEQ ID NO: 302. In some embodiments, a polypeptide component comprises 100 or fewer (e.g., 100, 90, 80, 70, 60, 50, 40, 30, 25, 20, 15, 10, 9, 8, 7, 6, 5, 4, 3, 2, 1, or ranges there between) substitutions (e.g., conservative substitutions, semi-conservative substitutions, non-conservative substations, etc.) relative to SEQ ID NO: 17, SEQ ID NO: 21, and/or SEQ ID NO: 302. In some embodiments, a polypeptide component comprises at least 40% (e.g., >40%, >45%, >50%, >55%, >60%, >65%, >70%, >75%, >80%, >85%, >90%, >95%, >98%, >99%) sequence identity or similarity with SEQ ID NO: 788. In some embodiments, polypeptide component comprises 100 or fewer (e.g., 100, 90, 80, 70, 60, 50, 40, 30, 25, 20, 15, 10, 9, 8, 7, 6, 5, 4, 3, 2, 1, or ranges there between) substitutions (e.g., conservative substitutions, semi-conservative substitutions, non-conservative substations, etc.) relative to SEQ ID NO: 788. In some embodiments, a polypeptide component comprises at least 40% (e.g., >40%, >45%, >50%, >55%, >60%, >65%, >70%, >75%, >80%, >85%, >90%, >95%, >98%, >99%) sequence identity or similarity with SEQ ID NO: 789. In some embodiments, polypeptide component comprises 100 or fewer (e.g., 100, 90, 80, 70, 60, 50, 40, 30, 25, 20, 15, 10, 9, 8, 7, 6, 5, 4, 3, 2, 1, or ranges there between) substitutions (e.g., conservative substitutions, semi-conservative substitutions, non-conservative substations, etc.) relative to SEQ ID NO: 789.

In some embodiments, a polypeptide component (e.g., β1-5-like, β1-6-like, β1-7-like, β1-8-like (e.g., LgTrip) polypeptide) is linked (e.g., chemically) or fused to one or more additional elements (e.g., recognition element, interaction element, co-localization element, detectable element (e.g., a fluorophore (e.g., to facilitate BRET)), protein of interest, HALOTAG, etc.). In some embodiments, a polypeptide component is linked or fused to a cyOFP (e.g., in an Antares construct such as those described in U.S. Pat. No. 9,908,918; herein incorporated by reference in its entirety) or other fluorescent protein (e.g., to facilitate BRET). In some embodiments, a polypeptide component comprises one or more chemical modifications and/or unnatural amino acids or amino acid analogs to facilitate chemical conjugation of the polypeptide component with additional elements.

In some embodiments, a peptide tag (e.g., β9-like (e.g., SmTrip9) and β10-like (e.g., SmTrip10) peptides; β9/β10-like dipeptides; etc.) and/or peptide component is not identical to and/or is not exact subsequences of one or more (e.g., all) of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 17, SEQ ID NO: 21, SEQ ID NO: 23, SEQ ID NO: 25, SEQ ID NO: 27, SEQ ID NO: 29, SEQ ID NO: 51, SEQ ID NO: 302 (or any combinations thereof). In other embodiments, a peptide tag and/or peptide component is identical to and/or is an exact subsequences one or more (e.g., all) of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 17, SEQ ID NO: 21, SEQ ID NO: 23, SEQ ID NO: 25, SEQ ID NO: 27, and/or SEQ ID NO: 29, SEQ ID NO: 51, SEQ ID NO: 302 (or any combinations thereof).

In some embodiments, a polypeptide component (e.g., β1-8-like (e.g., LgTrip) polypeptide) corresponds to and comprises substantial sequence identity (e.g., >40%, >45%, >50%, >55%, >60%, >65%, >70%, >75%, >80%, >85%, >90%, >95%, >99%, 100%) with a portion of SEQ ID NO: 3. For example, in some embodiments, a polypeptide component corresponds to, and comprises substantial sequence identity (e.g., >40%, >45%, >50%, >55%, >60%, >65%, >70%, >75%, >80%, >85%, >90%, >95%, >99%, 100%) with positions 1, 2, 3, 4, 5, 6, 7, 8, 9, 10, 11, or 12 through 142, 143, 144, 145, 146, 147, 148, 149, 150, 152, 153 of SEQ ID NO: 3 (e.g., positions 1-148).

In some embodiments, a peptide tag (β10-like (e.g, SmTrip10) peptide) corresponds to and comprises substantial sequence identity (e.g., >40%, >50%, >60%, >70%, >80%, >90%, 100%) with a portion of SEQ ID NO: 3. For example, in some embodiments, a peptide tag corresponds to, and comprises substantial sequence identity (e.g., >40%, >45%, >50%, >55%, >60%, >65%, >70%, >75%, >80%, >85%, >90%, >95%, >99%, 100%) with positions 154, 155, 156, 157, 158, 159, 160, 161, 162, 163, or 164 through 166, 167, 168, 169, 170, or 171 of SEQ ID NO: 3 (e.g., positions 160-171).

In some embodiments, a peptide tag (β9-like (e.g., SmTrip9) peptide) corresponds to and comprises substantial sequence identity (e.g., >40%, >50%, >60%, >70%, >80%, >90%, 100%) with a portion of SEQ ID NO: 3. For example, in some embodiments, a peptide tag corresponds to, and comprises substantial sequence identity (e.g., >40%, >45%, >50%, >55%, >60%, >65%, >70%, >75%, >80%, >85%, >90%, >95%, >99%, 100%) with positions 142, 143, 144, 145, 146, 147, 148, 149, 150, 152, 153 through 154, 155, 156, 157, 158, 159, 160, 161, 162, 163, 163, or 164 of SEQ ID NO: 3.

In some embodiments, a polypeptide component e.g., β1-8-like (e.g., LgTrip) polypeptide), a first peptide tag (β9-like (e.g., SmTrip9) peptide) and a second peptide tag (β10-like (e.g., SmTrip10) peptide) together correspond to and comprise substantial sequence identity (e.g., >40%, >50%, >60%, >70%, >80%, >90%, 100%) with at least 90% of the length of SEQ ID NO: 3.

In some embodiments, peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and a polypeptide component (e.g., β1-5-like, β1-6-like, β1-7-like, β1-8-like (e.g., LgTrip) polypeptide) comprise one or more substitutions relative to SEQ ID NO: 1 and/or SEQ ID NO: 3. For example, in some embodiments, a polypeptide component comprises 40% or greater (e.g., 40%, 45%, 50%, 55%, 60%, 65%, 70%, 75%, 80%, 85%, 90%, 95%, 99%) sequence identity with SEQ ID NO: 3 or a portion thereof (e.g., SEQ ID NO: 11, SEQ ID NO: 17, etc.), but comprise a substitution at one or more of positions 4, 30, 42, and/or 106 relative to SEQ ID NO: 17. In some embodiments, a polypeptide component comprises an E4D substitution relative to SEQ ID NO: 17. In some embodiments, a polypeptide component comprises an A, D, E, G, K, L, M, N, Q, S, T, V, or Y at position 30 relative to SEQ ID NO: 17. In some embodiments, a polypeptide component comprises an A, C, F, G, I, L, M, S, T, or V at position 42 relative to SEQ ID NO: 17. In some embodiments, a polypeptide component comprises a D, K, or Q at position 106 relative to SEQ ID NO: 17.

In some embodiments, a polypeptide component (e.g., β1-5-like, β1-6-like, β1-7-like, β1-8-like (e.g., LgTrip) polypeptide) is an artificial sequence that comprises 70% or greater (e.g., 75%, 80%, 85%, 90%, 95%, 100%, or ranges there between) sequence identity and/or sequence similarity with one or more of SEQ ID NOS: 19, 21, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, and 131 (or the r $1-5-like, β1-6-like, or β1-7-like portion thereof). In some embodiments, a polypeptide component is an artificial sequence that comprises all or a portion (e.g., 50 amino acids, 60 amino acids, 70 amino acids, 80 amino acids, 90 amino acids, 100 amino acids, 110 amino acids, 120 amino acids, 130 amino acids, 140, or more, or ranges there between) of one of SEQ ID NOs: 19, 21, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, and 131 (or the r β1-5-like, β1-6-like, or β1-7-like portion thereof). In some embodiments, a polypeptide component is a sequence consisting of one of SEQ ID NOs: 19, 21, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, and 131 (or the r β1-5-like, β1-6-like, or β1-7-like portion thereof).

In some embodiments, a peptide/dipeptide/tripeptide tag ((e.g., β6-like, β7-like, β8-like, β9-like (e.g., SmTrip9), and/or β10-like (e.g., SmTrip10) peptides, and/or dipeptides and tripeptides thereof) is an artificial sequence that comprises 70% or greater (e.g., 75%, 80%, 85%, 90%, 95%, 100%, or ranges there between) sequence identity and/or sequence similarity with one or more of the peptide sequences listed in Table 1, Table 9, Table 10, or dipeptide/ tripeptide combinations thereof. In some embodiments, a peptide/dipeptide/tripeptide tag component is an artificial sequence that comprises all or a portion (e.g., 5 amino acids, 6 amino acids, 7 amino acids, 8 amino acids, 9 amino acids, 10 amino acids, 11 amino acids, 12 amino acids, 13 amino acids, 14, or more, or ranges there between) of one of the peptide sequences listed in Table 1, Table 9, Table 10, or dipeptide/tripeptide combinations thereof. In some embodiments, a peptide/dipeptide/tripeptide tag component is a sequence consisting of one of the peptide sequences listed in Table 1, Table 9, Table 10, or dipeptide/tripeptide combinations thereof.

Although referred to herein as peptide/dipeptide/tripeptide e.g., β6-like, β7-like, β8-like, β9-like (e.g., SmTrip9), and/or β10-like (e.g., SmTrip10) peptides, and/or dipeptides and tripeptides thereof), in some embodiments, one or more of the peptide/dipeptide/tripeptide components of a bioluminescent complex within the scope herein are not attached to an interaction element, co-localization element, binding agent, protein of interest, molecule of interest, or any other moiety. In some embodiments, one or both of the peptide/dipeptide/tripeptide components interact with the polypeptide and other peptide/dipeptide/tripeptide components to form a luminescent complex without being fused or otherwise tethered to another element.

In some embodiments, a peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and a polypeptide component (e.g., β1-5-like, β1-6-like, β1-7-like, β1-8-like (e.g., LgTrip) polypeptide) of a luminescent complex, a co-localization element, and/or an interaction element comprises a synthetic peptide/polypeptide, a peptide/polypeptide containing one or more non-natural amino acids, a peptide/polypeptide containing one or more amino acid analogs, a peptide/polypeptide mimetic, a conjugated synthetic peptide (e.g., conjugated to a functional group (e.g., fluorophore, luminescent substrate, etc.)), etc.

Provided herein are compositions and methods that are useful in a variety of fields including basic research, medical research, molecular diagnostics, etc. Although the reagents and assays described herein are not limited to any particular applications, and any useful application should be viewed as being within the scope of the present invention, the following are exemplary assays, kits, fields, experimental set-ups, etc. that make use of the presently claimed invention.

Typical applications that make use of embodiments herein involve the monitoring/detection of protein dimerization (e.g., heterodimers, homodimers), protein-protein interactions, protein-RNA interactions, protein-DNA interactions, antibody (or other recognition element) binding to a target, nucleic acid hybridization, protein-small molecule interactions, analyte quantitation or detection, or any other combinations of molecular entities. In an exemplary embodiment, a first entity of interest is attached to a first peptide/dipeptide/tripeptide tags (e.g., β6-like, β7-like, β8-like, 9-like (e.g., SmTrip9), and/or β10-like (e.g., SmTrip10) peptides, and/or dipeptides and tripeptides thereof) and a second entity of interest is attached to the second peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof). If a detectable signal is produced under the particular assay conditions (e.g., in the presence of a polypeptide component of the luminescent complex (e.g., β1-5-like, β1-6-like, β1-7-like, β1-8-like (e.g., LgTrip) polypeptide) and a coelenterazine or a coelenterazine analog substrate), then interaction and/or co-localization of the first and second entities is inferred. Such assays are useful for monitoring molecular interactions and/or localization under any suitable conditions (e.g., in vitro, in vivo, in situ, whole animal, etc.), and find use in, for example, drug discovery, elucidating molecular pathways, studying equilibrium or kinetic aspects of complex assembly, high throughput screening, proximity sensor, etc.

In some embodiments, the systems and methods provided herein are useful for the detection, quantification, analysis, characterization, etc. of: an analyte, analytes, co-localization of analytes, and/or molecular interaction of analytes. In some embodiments, a peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) is tethered/fused to an analyte. In some embodiments, a peptide/dipeptide/tripeptide tag is tethered/fused to a recognition element agent that binds to a target analyte.

Suitable analytes that find use (e.g., are analyzed) in embodiments herein include, but are not limited to: nucleic acids (e.g., DNA, RNA, miRNA, etc.), proteins (ex: bacterial antigens, viral antigens, biomarkers, antibodies, etc.), small molecules, toxins, biomarkers, environmental or food contaminants, surfactants, pathogens (e.g., viral antigens and proteins, bacterial antigens and proteins, etc.), drugs (e.g., therapeutic drugs, drugs of abuse, etc.), vitamins, cytokines, antibodies (e.g., autoantibodies, infectious disease exposure, therapeutic drug monitoring, anti-HLA transplantation rejection, etc.), cells, cell receptor proteins, biomarker based diagnostics, cell free nucleic acids and non-cell free nucleic acids (e.g., DNA, RNA, mRNA, miRNA, etc.), nucleic acid SNPs, extracted nucleic acids, non-amplified nucleic acid samples, genomic DNA, ssDNA, bacterial resistance genes, immunocomplexes (e.g., antigen: antibody complex; antigen: complement complex, etc.), blood sugars, hormones, metabolites, microbes, parasites, enzymes, transcription factors, metal ions/heavy metals, etc.

Suitable recognition elements or binding moieties that find use (e.g., fused/tethered to a peptide tag, binding to an analyte, etc.) in embodiments herein, include, but are not limited to: antibodies (e.g., monoclonal, polyclonal, recombinant, animal derived, autoantibody, biotherapeutic, etc.), antibody variable heavy chain, antibody variable light chain, antibody binding fragment (Fab) [F(ab)'2], camelid, single chain variable fragment (scFv), monomeric proteins, receptor domains, affibodies, monobodies, natural and derivatized nucleic acid aptamers (e.g., RNA aptamer, DNA aptamer, chemical modified aptamer, etc.), peptide nucleic acids (PNA), locked nucleic acids (LNA), hexitol nucleic acids (HNA), protein A, G, L, M and/or domains thereof, sequence specific oligonucleotide probes (e.g., DNA probe, RNA probe, etc.), small molecule drug, antibody-oligonucleotide conjugates, darpins, nanobodies, affimers, adhirons, anticalins, phage, magnetic particles (e.g., labeled directly or labeled with a tagged recognition element), nanoparticles (e.g., polystyrene nanospheres, etc.) labeled directed or labeled with a tagged recognition element, streptavidin, antigens, etc.

In some embodiments, a peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and a polypeptide component (e.g., β1-5-like, β1-6-like, β1-7-like, β1-8-like (e.g., LgTrip) polypeptide) is linked to an oligonucleotide recognition element or binding moiety. Such constructs may find use in nucleic acid (e.g., DNA, RNA, etc.) complementation and/or detection. Exemplary peptide/oligomer probes are depicted in FIG. 99. In such exemplary constructs, a peptide/dipeptide/tripeptide comprising a reactive group (e.g., azido group (e.g., N-terminal, C-terminal, internal, etc.) or other reactive group herein) is conjugated to an oligonucleotide comprising a complementary reactive group (e.g., alkyne group (e.g., 5'-terminal, 3'-terminal, internal, etc.) or other reactive group herein). In an exemplary embodiment, peptide oligonucleotide probes are prepared by combing components and reagents (e.g., oligonucleotide (1 mg, 161 nmol, in water); triethylammonium acetate buffer (40 uL, 1M in water); aminoguanidine hydrochloride (8 uL, 50 mM in water); peptide (2.8 mg, 1.93 umol, in DMSO); copper (II) TBTA solution (10 mM in 1:1 water/DMSO); ascorbic acid solution (50 mM in water); final volume is 300 μL, 1:1 Water: DMSO); vortexing and heat for 30 min at 60° C.; filtering using Illustra NAP-5 column; exchanging buffer into TE buffer that is RNase and DNase free; and storing at −20° C.

In embodiments, in which a molecular interaction is being monitored/detected, peptide/dipeptide/tripeptide tags and a polypeptide component are selected that have affinities for each other such that a significant increase in signal is detectable/measurable upon interaction (e.g., binding) of the associated first and second entities. In some embodiments, one or both (or more) peptide/dipeptide/tripeptide tags have sufficiently low affinity for the other peptide tag and/or the polypeptide component that only background luminescence is detected in the absence of the interaction (e.g., binding) between the associated first and second entities. In other embodiments, the peptide/dipeptide/tripeptide tags and polypeptide component will form a complex and produce a signal in the absence of interaction between the associated first and second entities, but the signal is increased (e.g., 2-fold, 3-fold, 4-fold, 5-fold, 6-fold, 7-fold, 8-fold, 9-fold, 10-fold, $10^2$-fold, $10^3$-fold, $10^4$-fold, $10^5$-fold, $10^6$-fold, or more or ranges there between) upon interaction (e.g., binding) of the associated first and second entities.

In embodiments in which a co-localization is being monitored/detected, peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and a polypeptide component (e.g., β1-5-like, β1-6-like, β1-7-like, β1-8-like (e.g., LgTrip) polypeptide) are selected that have affinities for each other, such that a signal from the luminescent complex is detectable/measurable even in the absence of an interaction (e.g., binding) of the associated first and second entities. In such embodiments, if the associated first and second entities co-localize (e.g., in the same tissue, in the same cell, in the same subcellular compartment, etc.), the peptide/dipeptide/tripeptide tags and polypeptide component will form a complex and emit a signal (in the presence of coelenterazine or a coelenterazine analog), whether or not the first and second entities interact with each other. In some embodiments, two or more (e.g., both, all) of the peptide/dipeptide/tripeptide tags have sufficiently high affinity for the other components that luminescence is detected in the absence of the interaction (e.g., binding) between the associated first and second entities. In some embodiments, no significant increase in signal is detected upon interaction of the first and second entities. In other embodiments, the peptide/dipeptide/tripeptide tags and polypeptide component will form a complex and produce a signal in the absence of interaction between the associated first and second entities, but the signal is increased (e.g., 2-fold, 3-fold, 4-fold, 5-fold, 6-fold, 7-fold, 8-fold, 9-fold, 10-fold, $10^2$-fold, $10^3$-fold, $10^4$-fold, $10^5$-fold, $10^6$-fold, or more or ranges there between) upon interaction (e.g., binding) of the associated first and second entities.

In some embodiments, peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and a polypeptide component (e.g., β1-5-like, β1-6-like, β1-7-like, β1-8-like (e.g., LgTrip) polypeptide) having known characteristics (e.g., spectral characteristics, mutual affinity, etc.) are used to elucidate the affinity of, or understand the interaction of, an interaction pair of interest. In other embodiments, a well-characterized interaction pair is used to determine the characteristics (e.g., spectral characteristics, mutual affinity, etc.) of one or more elements of a set of peptide/dipeptide/tripeptide tags and a polypeptide component. In some embodiments, peptide/dipeptide/tripeptide tags and a polypeptide component having known characteristics (e.g., spectral characteristics, mutual affinity, etc.) are used to characterize/monitor the co-localization of a co-localization par of interest (e.g., under desired conditions).

Embodiments described herein may find use in drug screening and/or drug development. For example, the interaction of a small molecule drug or an entire library of small molecules with a target protein of interest (e.g., therapeutic target) is monitored under one or more relevant conditions (e.g., physiological conditions, disease conditions, etc.). Such an assay may comprise a first peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) attached to a drug candidate (or a library of candidates) and a second peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) attached to a therapeutic target; luminescence in the present of the polypeptide component (e.g., β1-5-like, β1-6-like, β1-7-like, β1-8-like (e.g., LgTrip) polypeptide) and substrate indicates interaction and/or co-localization of the candidate and target.

Some embodiments herein find use in the diagnostic or criminal setting for monitoring for drugs (e.g., drugs of abuse in human) as well as for therapeutic drug monitoring of patients in biological samples. For example, two peptide/dipeptide/tripeptide tagged binding moieties (e.g., binding moieties separately tagged with peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) that recognize a drug analyte facilitate such embodiments. In some embodiments, a competitive displacement assay utilizing a peptide/dipeptide/tripeptide-tagged target in a system described herein to identify untagged target in a sample finds use in embodiments herein. Some embodiments find use in detecting environmental contamination, for example, soil samples, water supply, etc. being contaminated by a specific drug or other specific contaminant (e.g., small molecule contaminant).

In other embodiments, the ability of a drug (e.g., small molecule drug) or an entire library of drugs (e.g., small molecules) to enhance or inhibit the interactions between two entities (e.g., receptor and ligand, protein-protein, etc.) is assayed (e.g., by gain or loss of the bioluminescent signal). In some embodiments, drug screening applications are carried out in a high through-put format to allow for the detection of the binding of thousands, or tens of thousands, of different molecules to a target, or to test the effect of those molecules on the binding of other entities.

In some embodiments, provided herein is the detection of molecular interactions in living organisms (e.g., bacteria, yeast, eukaryotes, mammals, primates, human, etc.) and/or cells. In some embodiments, pep peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) fused to interaction (target) polypeptides are co-expressed in a cell or whole organism, and a signal is detected in the presence of a polypeptide component (e.g., β1-5-like, β1-6-like, β1-7-like, β1-8-like (e.g., LgTrip) polypeptide) and substrate (e.g., coelenterazine or coelenterazine analog), wherein the signal is correlated to the formation of the interaction complex. In some embodiments, cells are transiently and/or stably transformed or transfected with vector(s) coding for fusions comprising peptide tags and interaction elements. In some embodiments, CRISPR is utilized to generate cells that express fusions comprising peptide/dipeptide/tripeptide tags and interaction elements. In some embodiments, fusions (e.g., of a cellular target and a peptide/dipeptide/tripeptide or polypeptide described herein) generated by CRISPR replace endogenous protein (e.g., non-fused cellular target) and are regulated in a similar manner to endogenous protein. In some embodiments, such endogenous tagging is used to monitor the level of the endogenously tagged protein, especially in complex systems such as live cells, whole organisms, etc. In some embodiments, transgenic organisms are generated that code for the necessary fusions (e.g., fusions comprising peptide tags and interaction elements) for carrying out the assays described herein. In other embodiments, vectors are injected into whole organisms.

In some embodiments, provided herein is the detection of molecular co-localization in living organisms (e.g., bacteria, yeast, eukaryotes, mammals, primates, human, etc.) and/or cells. In some embodiments, peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) fused to co-localization (target) polypeptides are co-expressed in a cell or whole organism, and a signal is detected in the presence of a polypeptide component (e.g., β1-5-like, β1-6-like, β1-7-like, β1-8-like (e.g., LgTrip) polypeptide) and substrate (e.g., coelenterazine or coelenterazine analog), wherein the signal is correlated to the co-localization of the co-localization elements. In some embodiments, cells are transiently and/or stably transformed or transfected with vector(s) coding for fusions comprising peptide tags and co-localization elements. In some embodiments, CRISPR is utilized to generate cells that express fusions comprising peptide tags and co-localization elements. In some embodiments, transgenic organisms are generated that code for the necessary fusions (e.g., fusions comprising peptide tags and co-localization elements) for carrying out the assays described herein. In other embodiments, vectors are injected into whole organisms.

In certain embodiments, cells are engineered to express one or more peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof), polypeptide component (e.g., β1-5-like, β1-6-like, β1-7-like, β1-8-like (e.g., LgTrip) polypeptide), or fusions thereof (e.g., with cellular targets) using gene transfer technology or other engineering techniques. For example, the cells may be genetically engineered to express one or more peptide/dipeptide/tripeptide tags, polypeptide components, or fusions thereof (e.g., with cellular targets) using gene editing methodologies such as CRISPR (clustered regularly interspaced short palindromic repeat). The terms "CRISPR"

or "CRISPR-Cas9," as used herein, refer to the various CRISPR-Cas9 and -CPF1 (and other) systems that can be programmed to target specific stretches of a genome and to edit DNA at precise locations. CRISPR-Cas9 gene editing systems are based on the RNA-guided Cas9 nuclease from the type II prokaryotic clustered regularly interspaced short palindromic repeats (CRISPR) adaptive immune system (see, e.g., Jinek et al., Science, 337:816 (2012); Gasiunas et al, Proc. Natl. Acad. Set U.S.A., 109, E2579 (2012); Garneau et al., Nature, 468: 67 (2010); Deveau et al., Annu. Rev. Microbiol, 64: 475 (2010); Horvath and Barrangou, Science, 327: 167 (2010); Makarova et al., Nat. Rev. Microbiol., 9, 467 (2011); Bhaya et al., Annu. Rev. Genet., 45, 273 (2011); and Cong et al., Science, 339: 819-823 (2013); herein incorporated by reference in their entireties). CRISPR gene editing systems have been developed to enable targeted modifications to a specific gene of interest in eukaryotic cells (see, e.g., Cong et al., supra; Xiao-Jie et al., J. Med. Genet., 52(5): 289-96 (2015); U.S. Pat. No. 8,697,359; Xie et al., Genome Res., 24(9): 1526-1533 (2014); Huang et al., Stem Cells, 33(5): 1470-1479 (2015); Smith et al., Molecular Therapy, 23(3): 570-577 (2015); and U.S. Patent Application Publication 2014/0068797; herein incorporated by reference in their entireties). Methods for utilizing CRISPR technology for gene editing are described in, for example, Barrangou et al., Science 315, 1709-1712 (2007); Bolotin et al., Microbiology, 151, 2551-2561 (2005); Brouns et al., Science 321, 960-964 (2008); Cong et al., supra; Deltcheva et al., Nature 471, 602-607 (2011); Gasiunas et al., supra; Hale et al., Cell 139, 945-956 (2009); Jinek et al., Science 337, 816-821 (2012); Makarova et al., Biology Direct 2006, 1:7 (2006); Mali et al., Science 339, 823-826 (2013); Marraffini et al., Science 322, 1843-1845 (2008); Mojica et al., J Mol Evol 60, 174-182 (2005); Pourcel et al., Microbiology 151, 653-663 (2005); and Sapranauskas et al., Nucl. Acids Res. 39, gkr606-gkr9282 (2011); herein incorporated by reference in their entireties.

In some embodiments, one or more peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) are employed as a protein tag (e.g., within cells, within a whole animal). In such embodiments, the complement components to the peptide/dipeptide/tripeptide tag(s) (e.g., polypeptide components, the other peptide/dipeptide/tripeptide tag, substrate) are applied to the system (e.g., cells, animal, etc.) (e.g., as part of a reagent) to detect/quantify the presence of tagged proteins.

In some embodiments, the small size of the peptide tags herein (e.g., β9-like (e.g., SmTrip9) and β10-like (e.g., SmTrip10) peptides) is useful for protein tagging.

In some embodiments, the components of the bioluminescent complexes herein (e.g., peptide/dipeptide/tripeptide tags herein (e.g., β6-like, β7-like, β8-like, β9-like (e.g., SmTrip9), and/or β10-like (e.g., SmTrip10) peptides, and/or dipeptides and tripeptides thereof), polypeptide components (e.g., β1-5-like, β1-6-like, β1-7-like, β1-8-like (e.g., LgTrip) polypeptide) are stable enough to exist in a suitable buffer for extended periods of time (e.g., in the presence of coelenterazine or a coelenterazine analog (e.g., furimazine) substrate). In certain embodiments, components of the bioluminescent complexes herein (e.g., peptide/dipeptide/tripeptide tags, polypeptide components, etc.) exhibit minimal detectable luminescence in the absence of the complementing components (e.g., even in the presence of coelenterazine or coelenterazine analog (e.g., furimazine) substrate). In some embodiments, optimized buffer conditions are utilized to meet criteria necessary for protein tagging.

The compositions and methods provided herein, as well as any techniques or technologies based thereon find use in a variety of applications and fields.

Provided herein are methods for the design and/or optimization of peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and a polypeptide components (e.g., β1-5-like, β1-6-like, β1-7-like, β1-8-like (e.g., LgTrip) polypeptide), and the bioluminescent complexes that form therefrom. Any suitable method for the design of non-luminescent pairs/groups that are consistent with embodiments described herein, and/or panels thereof, is within the scope herein. In some embodiments, characteristics of peptide/dipeptide/tripeptide tags and polypeptide components, and combinations thereof are optimized by substitutions (e.g., substitution of natural amino acids, non-natural amino acids, amino acid analogs, etc.); such characteristics include, but are not limited to structural stability (e.g., of the peptide/dipeptide/tripeptide tag or polypeptide component, of a complex, etc.), expression, stickiness (e.g., to tubes, wells, etc.), brightness (or complexes formed therefrom), affinity for other components of the bioluminescent complex, solubility, thermal and chemical stability, low autoluminescence, etc.

In certain embodiments, peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and a polypeptide components (e.g., β1-5-like, β1-6-like, β1-7-like, β1-8-like (e.g., LgTrip) polypeptide) are designed de novo to lack luminescence individually and exhibit luminescence upon association. In such embodiments, the strength of the interaction between the non-luminescent elements is insufficient to produce a bioluminescent signal in the absence of interaction elements to facilitate formation of the bioluminescent complex. In other embodiments, peptide/dipeptide/tripeptide tags and polypeptide components and/or bioluminescent complexes thereof are rationally designed, for example, using a bioluminescent protein as a starting point. For example, such methods may comprise: (a) aligning the sequences of three or more related proteins; (b) determining a consensus sequence for the related proteins; (c) providing fragments (e.g., one or more peptides/dipeptides/tripeptides and a polypeptide) of a bioluminescent protein that is related to the ones from which the consensus sequence was determined, wherein the fragments are individually substantially non-luminescent but exhibit luminescence upon interaction of the fragments; and (d) testing the fragments for the absence of luminescence when unassociated and luminescence upon association of the non-luminescent pair. In some embodiments, the fragments are mutated at one or more positions (e.g., in vitro, in silico, etc.), wherein said mutations alter the sequences of the fragments and result in optimization of characteristics.

In some embodiments, a peptide/dipeptide/tripeptide tag is a 'dark peptide,' or one that forms a complex with the other peptide tag and polypeptide components (e.g., with low or high affinity), but produces minimal or no luminescence. In some embodiments, a high affinity dark peptide/dipeptide/tripeptide finds use in inverse complementation or gain of signal assays for biosensors or for measuring inhibitors. In some embodiments, a low affinity dark peptide/dipeptide/tripeptide is used to bring down background luminescence of a complex for the detection of binding of a high affinity bright peptide/dipeptide/tripeptide tag to the complex.

In some embodiments, a peptide/dipeptide/tripeptide tag is a 'quencher peptide,' or one that contains a quencher moiety (e.g., DAB), and the quencher absorbs the light/energy produced by either or both of a polypeptide component (e.g., the signal produced independent of a complementing peptide/dipeptide/tripeptide tags) and/or bioluminescent complex.

In some embodiments, the luminescent complexes herein find use in systems, methods, assays, devices, etc. that utilize BRET between the complex and a fluorophore (e.g., small molecule fluorophore, fluorescent protein (e.g., cyOFP)). In some embodiments, a fluorophore (e.g., small molecule fluorophore, fluorescent protein (e.g., cyOFP)) is linked or fused to an analyte, cellular target, etc. In some embodiments, a fluorophore (e.g., small molecule fluorophore, fluorescent protein (e.g., cyOFP)) is linked or fused to a peptide/dipeptide/tripeptide tag and/or polypeptide component. In some embodiments, energy is transferred from a bioluminescent complex to an energy acceptor. In certain embodiments, an energy acceptor is a fluorophore or other detectable chromophore. Suitable fluorophores include, but are not limited to: xanthene derivatives (e.g., fluorescein, rhodamine, Oregon green, eosin, Texas red, etc.), cyanine derivatives (e.g., cyanine, indocarbocyanine, oxacarbocyanine, thiacarbocyanine, merocyanine, etc.), naphthalene derivatives (e.g., dansyl and prodan derivatives), oxadiazole derivatives (e.g., pyridyloxazole, nitrobenzoxadiazole, benzoxadiazole, etc.), pyrene derivatives (e.g., cascade blue), oxazine derivatives (e.g., Nile red, Nile blue, cresyl violet, oxazine 170, etc.), acridine derivatives (e.g., proflavin, acridine orange, acridine yellow, etc.), arylmethine derivatives (e.g., auramine, crystal violet, malachite green, etc.), tetrapyrrole derivatives (e.g., porphin, phtalocyanine, bilirubin, etc.), CF dye (Biotium), BODIPY (Invitrogen), ALEXA FLOUR (Invitrogen), DYLIGHT FLUOR (Thermo Scientific, Pierce), ATTO and TRACY (Sigma Aldrich), Fluo-Probes (Interchim), DY and MEGASTOKES (Dyomics), SULFO CY dyes (CYANDYE, LLC), SETAU AND SQUARE DYES (SETA BioMedicals), QUASAR and CAL FLUOR dyes (Biosearch Technologies), SURELIGHT DYES (APC, RPE, PerCP, Phycobilisomes) (Columbia Biosciences), APC, APCXL, RPE, BPE (Phyco-Biotech), autofluorescent proteins (e.g., YFP, RFP, mCherry, mKate), quantum dot nanocrystals, etc. In some embodiments, a fluorophore is a rhodamine analog (e.g., carboxy rhodamine analog), such as those described in U.S. patent application Ser. No. 13/682,589, herein incorporated by reference in its entirety. In some embodiments, a fluorophore is a small molecule fluorophore; embodiments herein reciting a fluorophore may be read as or limited to a small molecule fluorophore. In some embodiments, a fluorophore is a fluorescent protein (e.g., cyOFP, GFP, CFP, etc.; embodiments herein reciting a fluorophore may be read as or limited to a fluorescent protein (e.g., cyOFP, GFP, CFP, etc.).

In various embodiments, the bioluminescent complexes described herein, and components thereof, find use in a variety of different immunoassay concepts. For example, in some embodiments, a peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) is tethered/fused to a primary or secondary antibody to provide a method of detection for a particular analyte. As another example, a peptide tag is tethered/fused to an antibody-binding protein (e.g., protein A or protein G)

and used to detect a specific antibody bound to a particular analyte (e.g., wherein the analyte is bound to the complementary peptide tag). As another example, a peptide/dipeptide/tripeptide tag is tethered/fused to streptavidin and used to detect a specific biotinylated antibody bound to a particular analyte (e.g., wherein the analyte is bound to the complementary peptide tag). As yet another example, peptide/dipeptide/tripeptide tags are tethered/fused to primary and secondary antibodies, where the primary antibody recognizes a particular analyte, and the secondary antibody recognizes the primary antibody. As still another example, a peptide/dipeptide/tripeptide tag is tethered/fused to an analyte and used in a competitive sandwich ELISA format. A peptide/dipeptide/tripeptide tag is tethered/fused conjugated to an analyte may also be used to detect antibodies capable of binding the analyte.

Various embodiments herein find use in small molecule detection via immunoassay. Exemplary embodiments comprise the use of a small molecule directly (e.g., identical or similar to the target small molecule) labeled with a first peptide/dipeptide/tripeptide described herein and a binding moiety for the target small molecule fused or linked to a peptide/dipeptide/tripeptide described herein. In the presence of polypeptide component and substrate (e.g., coelenterazine or coelenterazine analog), a bioluminescent signal is produced by the system. When the system is exposed to a sample (e.g., biological sample, environmental sample, etc.), the bioluminescent signal will be reduced if the small molecule target is present in the sample (the labeled small molecule will be competed out of the complex allowing, in some cases, quantitation of the small molecule target). Alternative configurations for such assays are also within the scope herein. In some embodiments, the target small molecule is a toxin (e.g., mycotoxin, etc.), metabolite (e.g., amino acid, glucose molecule, fatty acid, nucleotide, cholesterol, steroid, etc.), vitamin (e.g., vitamin A, vitamin B1, vitamin B2, Vitamin B3, vitamin B5, vitamin B7, vitamin B9, vitamin B12, vitamin C, vitamin D, vitamin E, vitamin H or vitamin K, etc.), coenzyme or cofactor (e.g., coenzyme A, coenzyme B, coenzyme M, coenzyme Q, cytidine triphosphate, acetyl coenzyme A, reduced nicotinamide adenine dinucleodtide (NADH), nicotinamide adenine (NAD+), nucleotide adenosine monophosphoate, nucleotide adenosine triphosphate, glutathione, heme, lipoamide, molybdopterin, 3'-phosphoadenosine-5'-phsphosulfate, pyrroloquinoline quinone, tetrahydrobiopterin, etc.), biomarker or antigen (e.g., erythropoietin (EPO), ferritin, folic acid, hemoglobin, alkaline phosphatase, transferrin, apolipoprotein E, CK, CKMB, parathyroid hormone, insulin, cholesteryl ester transfer protein (CETP), cytokines, cytochrome c, apolipoprotein AI, apolipoprotein AII, apolipoprotein BI, apolipoprotein B-100, apolipoprotein B48, apolipoprotein CII, apolipoprotein CIII, apolipoprotein E, triglycerides, HD cholesterol, LDL cholesterol, lecithin cholesterol acyltransferase, paraxonase, alanine aminotransferase (ALT), asparate transferase (AST), CEA, HER-2, bladder tumor antigen, thyroglobulin, alpha-fetoprotein, PSA, CA 125, CA 19.9, CA 15.3, leptin, prolactin, osteoponitin, CD 98, fascin, troponin I, CD20, HER2, CD33, EGFR, VEGFA, etc.), drug (cannabinoid (e.g., tetrahydrocannabinol (THC), cannabidiol (CBD) and cannabinol (CBN), etc.), opioid (e.g., heroin, opium, fentanyl, etc.), stimulant (e.g., cocaine, amphetamine, methamphetamine, etc.), club drug (e.g., MDMA, flunitrazepam, gama-hydroxybutyrate, etc.), dissociative drug (e.g., ketamine, phencyclidine, salvia, dextromethorphan, etc.), hallucinogens (e.g., LSD, mescaline, psilocybin, etc.), etc.), explosive (e.g., 2,4,6-trinitrotoluene (TNT) and hexahydro-1,3,5-trinitro-1,3,5-triazine (RDX), pentaerythritol tetranitrate (PETN), etc.), toxic chemical (e.g., tabun (GA), sarin (GB), soman (GD), cyclosarin (GF), 2-(dimethylamino) ethyl N, N-dimethylphosphoramido-fluoridate (GV), VE, VG, VM, VP, VR, VS, or VX nerve agent), etc.

The systems and methods described herein find use in a wide variety of applications and formats. The following are non-exhaustive exemplary examples of methods and formats utilizing the systems described herein.

In some embodiments, provided herein are intracellular two protein systems for dynamic protein-protein interaction analysis with SmTrip peptide-labeled proteins expressed as fusions via traditional transfection or endogenously tagged proteins via CRISPR; LgTrip can be used as a detection reagent either by co-transfection, of LgTrip, providing a stable cell line expressing LgTrip, or providing LgTrip in the detection reagent and adding it to lysed cells expressing SmTrip-labeled proteins. (FIG. 51A).

In some embodiments, provided herein are intracellular three protein systems for dynamic protein-protein interaction analysis with SmTrip- and LgTrip-labeled proteins expressed as fusions via traditional transfection or as endogenously-tagged proteins generated via CRISPR (FIG. 51B).

In some embodiments, provided herein are target specific assays to measure analyte X with binding moiety A and binding moiety B (See Table A; purified genetic fusions or chemically conjugated SmTrip9 or SmTrip 10 peptide) for a gain of signal assay (e.g. diagnostic test, non-cellular, etc.) (FIG. 51C).

In some embodiments, provided herein are target specific competition assays for analyte measurement through loss of signal (e.g. diagnostic test, noncellular, etc.) (FIG. 51D). Such a system use a purified binding moiety A (e.g., purified genetic fusion or chemically conjugated comprising synthetic SmTrip9 or SmTrip 10 peptide) that binds the tagged target analyte to generate light in the presence of LgTrip and a coelenterazine substrate or coelenterazine analog, which may be provided as part of a detection reagent. In the presence of sample analyte X, SmTrip9 or SmTrip 10 peptide will compete with the sample analyte X to cause a loss of signal specific to the presence of the sample analyte in the sample and proportional to the concentration of the analyte.

In some embodiments, two or three of the peptide tags peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and polypeptide components (e.g., β1-5-like, β1-6-like, β1-7-like, β1-8-like (e.g., LgTrip) polypeptide) are linked (or fused) to recognition elements for proximal, but non-overlapping (mutually exclusive or distinct), epitopes on the same target analyte. A signal generated from the luminescent complex (e.g., in the presence of a substrate) indicates the presence of the target analyte.

In some embodiments, the peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and polypeptide components (e.g., β1-5-like, β1-6-like, β1-7-like, β1-8-like (e.g., LgTrip) polypeptide) herein find use in immunoassays or various formats. Immunoassays employing the peptide/dipeptide/tripeptide tags and polypeptide components herein are not limited to full length antibodies and may also employ antibody fragments or non-antibody binding moieties (e.g., DARPins, aptamers, affimers, etc.). In an exemplary direct immunoassay (See, e.g., FIG. 51E), two monoclonal or recombinant antibodies (mAbs or rAbs) against an analyte are labeled with β9-like (e.g., SmTrip9) and β10-like (e.g., SmTrip10) peptide tags; a polypeptide component (e.g., β1-8-like (e.g., LgTrip) polypeptide) of the luminescent complex is included as part of detection reagent (e.g., with substrate). For an exemplary indirect immunoassay (See, e.g., FIG. 51F), generic reagents labeled with β9-like (e.g., SmTrip9) and β10-like (SmTrip10) peptide tags are used in combination with any paired antibody system specific to an analyte (e.g., mAb or rAb+Biotin-pAb, Biotin-mAb, or Biotin-rAb etc.); a polypeptide component of the luminescent complex is included as part of detection reagent (e.g., with substrate). An exemplary competition direct immunoassay (See, e.g., FIG. 51G) is provided by labeling one antibody with a first peptide tag (β9—(e.g, SmTrip9) or β10-like (e.g., SmTrip10) peptide) and labeling a analyte with a second peptide tag (β10- (e.g., SmTrip10) or β9-like (e.g., SmTrip9) peptide); a polypeptide component (e.g., β1-8-like (e.g., LgTrip) polypeptide) of the luminescent complex is included as part of detection reagent (e.g., with substrate); loss of signal indicates the presence of unlabeled target analyte. To provide a competition indirect immunoassay (See, e.g., FIG. 51H), one antibody is labeled with a first peptide tag (β9- (e.g., SmTrip9) or β10-like (e.g., SmTrip10) peptide), a generic binding reagent (e.g., streptavidin) is labeled with a second peptide tag (β10- (e.g., SmTrip10) or β9-like (e.g., SmTrip9) peptide), and analyte is labeled with a binding moiety for the generic binding reagent (e.g., biotin); a polypeptide component of the luminescent complex is included as part of detection reagent (e.g., with substrate); loss of signal indicates the presence of unlabeled test analyte. Alternative immunoassays utilizing other peptide/dipeptide/tripeptide/polypeptide combinations described herein are within the scope of the present invention.

In some embodiments, provided herein are homogeneous assays using peptide/dipeptide/tripeptide tag-labelled (e.g., β6-like, β7-like, β8-like, β9-like (e.g., SmTrip9), and/or β10-like (e.g., SmTrip10) peptides, and/or dipeptides and tripeptides thereof) recognition elements with the polypeptide component (e.g., β1-5-like, β1-6-like, β1-7-like, β1-8-like (e.g., LgTrip) polypeptide) as component of a detection reagent (e.g., along with a substrate for the luminescent complex).

In some embodiments, provided herein are homogeneous assays utilizing peptide/dipeptide/tripeptide-tag-labelled (e.g., SmTrip9, SmTrip10, etc.) and/or polypeptide-component-labelled (e.g., LgTrip variants) recognition elements. In some embodiments, homogeneous assays are provided for detection/quantification of a single analyte or multiple analytes.

In some embodiments, the peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and polypeptide components (e.g., β1-5-like, β1-6-like, β1-7-like, β1-8-like (e.g., LgTrip) polypeptide) herein find use in sandwich hybridization assays (e.g. non-target amplified, amplified, etc.).

In some embodiments, the peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and polypeptide components (e.g., β1-5-like, β1-6-like, β1-7-like, β1-8-like (e.g., LgTrip) polypeptide) herein find use in the detection of analyte(s) in liquid/solution phase or solid phase.

In some embodiments, the peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and polypeptide components (e.g., β1-5-like, β1-6-like, β1-7-like, β1-8-like (e.g., LgTrip) polypeptide) herein find use in surface-based assays (e.g., plate-based (e.g., microtiter plate), paper-based (e.g., Whatman protein saver 903 cards), plastic-based, swab-based, cuvette-based, membrane-based (e.g., PVDF, nitrocellulose, etc.), etc.

In some embodiments, the peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and polypeptide components (e.g., β1-5-like, β1-6-like, β1-7-like, β1-8-like (e.g., LgTrip) polypeptide) herein find use in lateral flow and other capillary driven based methods. In some embodiments, such lateral flow assays allow multiplexed detection/identification/characterization of analytes (e.g., pathogens). In some embodiments, lateral flow assays find use in performing immunoassays described herein.

An exemplary multiplexed tripartite lateral flow assay for the detection and identification of pathogens using tripartite antibody fusions in a direct immunoassay is depicted in FIG. 52. In this example, a set of monoclonal or recombinant antibodies (mAbs or rAbs), each fused to a peptide tag (e.g., β10-like (e.g., SmTrip10) peptides) are added to a liquid sample, the sample is passed over a detection window comprising a second set of mAbs or rAbs, each fused to a peptide tag (e.g., β9-like (e.g., SmTrip9) peptides), immobilized in lanes within the detection window, and each recognizing a distinct epitope on the same target as one of the mAbs or rAbs in the liquid sample. When the liquid sample is passed through the detection window in the presence of a polypeptide component and substrate (e.g., preloaded in the detection window, added with the sample, added separately to the device, etc.), luminescence in a particular lane indicates the binding of mAbs or rAbs to separate epitopes on a target, and thereby provide for detection and identification of the target. The above described assay, and alternatives thereof utilizing the systems and methods herein, may find use in providing various detection panels (e.g., Respiratory Panel: *Streptococcus, Pseudomonas, Mycobacterium, Staphylococcus*; Urinary Tract Panel: *E. Coli, Klebsiella, Enterobacter, Streptococcus*; Food Borne Panel: *Shigella, Campylobacter, Salmonella, E. Coli, Listeria*; Waste Water Management: Coliform panel; Panel for strain identification within one type of bacteria; etc.), as well as for other applications (e.g., toxin detection).

An exemplary multiplexed tripartite lateral flow assay for the detection and identification of anti-viral antibodies, e.g., for disease diagnosis, using tripartite antibody fusions in a direct immunoassay is depicted in FIG. 53. In this example, a sample is added to the lateral flow device and allowed to flow into a conjugation zone (e.g., pad). The conjugation zone comprises a generic antibody-binding agent (e.g., Protein L), tethered or fused to a first peptide tag (e.g., β10-like (e.g., SmTrip10) peptide). If antibodies are present in the sample, they will be bound by the labeled antibody-binding agent. A detection window of the device comprises separate lanes, each comprising distinct immobilized viral antigens tethered or fused to a second peptide tag (e.g., β9-like (e.g., SmTrip9) peptide). As the labeled antibody flows from the conjugation zone into the detection window, the antibodies will bind to appropriate antigens, binging the peptide tags into proximity and producing a luminescent signal in the presence of the polypeptide component and substrate (e.g., preloaded in the detection window, added with the sample, added separately to the device, etc.). Such a device and assay would allow detection and discrimination of multiple viruses and viral infections using a single device/assay. For example, Zika, Dengue, and Chicungkunga could all be independently detected using a single test.

In some embodiments, the details of the above lateral flow assays are carried out in a plate-based format for solution phase assay (e.g., with the binding moiety combinations in wells provided with a map). In some embodiments, such an assay is performed in a multiplexed dot blot/spot array assay format. In some embodiments, any multiplexed assays described herein in a particular format (e.g., lateral flow) may also be performed in alternative formats described herein or understood in the field (e.g., dot blot, spot array, etc.).

In some embodiments, the peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and polypeptide components (e.g., β1-5-like, β1-6-like, β1-7-like, β1-8-like (e.g., LgTrip) polypeptide) herein find use in aerosol-based detection (e.g., (1) protease to lyse cells, (2) spray detection reagents, (3) visualize to detect/quantify).

In some embodiments, the peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and polypeptide components (e.g., β1-5-like, β1-6-like, β1-7-like, β1-8-like (e.g., LgTrip) polypeptide) herein find use with isothermal amplification of nucleic acids.

In some embodiments, the peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and polypeptide components (e.g., β1-5-like, β1-6-like, β1-7-like, β1-8-like (e.g., LgTrip) polypeptide) herein find use with rapid cycling PCR detection of nucleic acids.

In some embodiments, the peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and polypeptide components (e.g., β1-5-like, β1-6-like, β1-7-like, β1-8-like (e.g., LgTrip) polypeptide) herein find use in the detection of protein-protein interaction (e.g., between 2 proteins, between 3 proteins, etc.).

In some embodiments, analysis of the assays and methods described herein is performed using stationary or portable devices and readers, a luminometer plate reader or handheld reader, smart phone camera or CCD camera, etc.

In some embodiments, analyte is detected/quantified via gain of signal through recognition elements via luminometer or imaging based techniques.

In some embodiments, analyte is detected/quantified measured via loss of signal through competitive displacement via luminometer or imaging based techniques.

In some embodiments, systems and methods herein allow for multiple tags on each recognition element, either genetically or through chemical conjugation, thereby providing signal amplification by adding increasing stoichiometry of peptide tags per recognition element.

In some embodiments, systems and methods herein find use in detection of native proteins in heterogeneous solutions.

In some embodiments, the peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and polypeptide components (e.g., β1-5-like, β1-6-like, β1-7-like, β1-8-like (e.g., LgTrip) polypeptide) herein find use in nucleic acid detection, for example, peptide-tagged complimentary recognition elements hybridize to a nucleic acid target sequence in tandem.

In some embodiments, assays are provided herein for the detection of an antibody (e.g., antibody as analyte). One such assay is depicted in FIG. 54. A first peptide tag (e.g., β9-like (e.g., SmTrip9) peptide) is fused or tethered to an antibody-binding protein (e.g., Protein L) and a second peptide tag (e.g., β10-like (e.g., SmTrip10) peptide) is fused or tethered to the analyte that the antibody is specific to; a polypeptide component (e.g., β1-8-like (e.g., LgTrip) polypeptide) of the luminescent complex is included as part of detection reagent (e.g., with substrate); presence of the analyte specific antibody in a sample results in complex formation and luminescence.

In some embodiments, the peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and polypeptide components (e.g., β1-5-like, β1-6-like, β1-7-like, β1-8-like (e.g., LgTrip) polypeptide) herein find use in FISH-like applications utilizing bioluminescence or BRET for detection/quantification.

In some embodiments, the peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and polypeptide components (e.g., β1-5-like, β1-6-like, β1-7-like, β1-8-like (e.g., LgTrip) polypeptide) herein find use in detection of nucleic acids (e.g., single stranded and/or double stranded DNA and/or RNA) via, for example amplification-free detection of nucleic acids. For example, as depicted in FIG. 56, a pair of peptide tag-labelled nucleic acid probes, when hybridized to nearby locations on a nucleic acid target, will allow formation of a luminescent complex, facilitated by complementation with the nucleic acid target. Such and assay could be performed on a solid surface, in solution, for a single nucleic acid target, or multiplexed (e.g., using an array).

In some embodiments, peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and polypeptide components (e.g., β1-5-like, β1-6-like, β1-7-like, β1-8-like (e.g., LgTrip) polypeptide) herein find use in lab-on-chip and/or microfluidics applications.

In some embodiments, systems and methods herein find use in heterogeneous assays, such as, immunoassays (e.g., PCR amplification combined with homogeneous immunoassay analysis).

In some embodiments, a peptide/dipeptide/tripeptide-based sensor is provided is which a chemical (e.g., removal of a blocking moiety) or enzymatic (e.g., proteolytic cleavage) event is required to render a peptide tag capable of bioluminescent complex formation. For example, a protease is required to cleave a blocked dipeptide (e.g., incapable of bioluminescent complex formation) into two non-blocked peptides capable of complementation.

In some embodiments, the peptide/dipeptide/tripeptide tags (e.g., β6-like, β7-like, β8-like, β9-like (e.g., SmTrip9), and/or β10-like (e.g., SmTrip10) peptides, and/or dipeptides and tripeptides thereof) and polypeptide components (e.g., β1-5-like, β1-6-like, β1-7-like, β1-8-like (e.g., LgTrip) polypeptide) herein find use with bead-based assays, utilizing magnetic enrichment for increased assay sensitivity. One such assay is depicted in FIG. 55. In such an assay, a magnetic particle is conjugated to a first peptide tag (e.g., β9-like (e.g., SmTrip9) peptide) and to a first binding agent directed to a first epitope on an analyte; a non-magnetic particle (e.g., polystyrene particle) is conjugated to a second peptide tag (e.g., β10-like (e.g., SmTrip10) peptide) and to a second binding agent directed to the first epitope or a second epitope on an analyte. The beads are combined with a sample, along with a polypeptide component (e.g., β1-8-like (e.g., LgTrip) polypeptide) of the luminescent complex. Magnetic separation is used to capture the magnetic beads and any components of the sample or other reagents bound thereto. Luminescence of the magnetically-captured elements is then detected in the presence of substrate for the luminescent complex. If the analyte is present in the sample, both the magnetic and non-magnetic beads will be captured, resulting in the capture of the luminescent complex. In the absence of analyte, the non-magnetic beads will not be captured, and the luminescent complex will not be formed. The above applications and formats are exemplary and non-limiting. Other embodiments consistent with the description herein are within the scope of the present invention. Systems comprising and method utilizing peptides, dipeptides, and polypeptides bearing structural (although not necessarily sequence identity) and functional correlation to portions of NanoLuc® commercial luciferase and/or natural luciferase from *Oplophorus gracilirostris*, and bioluminescent complexes formed by complementation thereof, are described herein. In particular, detailed description is provided of complementation between β1-8-like (e.g., LgTrip) polypeptides and either β9-like (e.g., SmTrip9) and β10-like (e.g., SmTrip10) peptides or β9/10-like dipeptides. However, embodiments herein are not limited to complementation between β1-8-like polypeptides (e.g., LgTrip) and β9-like (e.g., SmTrip9) and β10-like (e.g., SmTrip10) peptides or β9/10-like dipeptides. In some embodiments, peptides, dipeptides, and polypeptides bearing structural (although not necessarily sequence identity) and functional correlation to portions of NanoLuc® commercial luciferase and/or natural luciferase from *Oplophorus gracilirostris* are provided. For example, also provided herein are systems and methods for complementation between a β1-5-like polypeptide and β6-10-like polypeptide; between a β1-2-like dipeptide and β3-10-like polypeptide; between a β1-like peptide, β2-like peptide and $\beta_{3-10}$-like polypeptide; between a $\beta_{7-8}$-like dipeptide and $\beta_{9-10/1-6}$-like polypeptide fusion; between a $\beta_{1-7}$-like polypeptide and $\beta_8$-like, $\beta_9$-like, and $\beta_{10}$-like peptides; and/or between a $\beta_{1-6}$-like polypeptide and $\beta_7$-like, $\beta_8$-like, $\beta_9$-like, and $\beta_{10}$-like peptides.

In some embodiments, the peptides, dipeptides, tripeptides, and/or polypeptides herein find use in translocation assays. In some embodiments, a translocation assay is composed of two components: a complementary polypeptide sensor (e.g., LgBiT-based, LgTrip-based, etc.) and a peptide/dipeptide/tripeptide-tagged protein of interest (POI). A variety of LgBiT sensors were generated that localize at specific cellular compartments such as plasma membrane, nucleus, mitochondria and endoplasmic reticulum (ER) (FIG. 152). These LgBiT sensors can be introduced to cells via transfection or establishment of stable cell lines. The POI is endogenously tagged with peptide/dipeptide/tripeptide complementary to the polypeptide (e.g., LgBiT). Under stimuli, the POI translocates to a different cellular compartment where the polypeptide (e.g., LgBiT) sensor resides, complementation occurs leading to the assembly of peptide/polypeptide complex (e.g., HiBiT·LgBiT) to yield luminescence signal (FIG. 153). Thus, the translocation activity of POI is quantitatively measured via luminescence output. Experiments conducted during development of embodiments of the translocation assay are described in Example 89.

EXPERIMENTAL

Example 1

Further Truncated Version of (LgBiT) is Activated by Peptide

Figure 1:
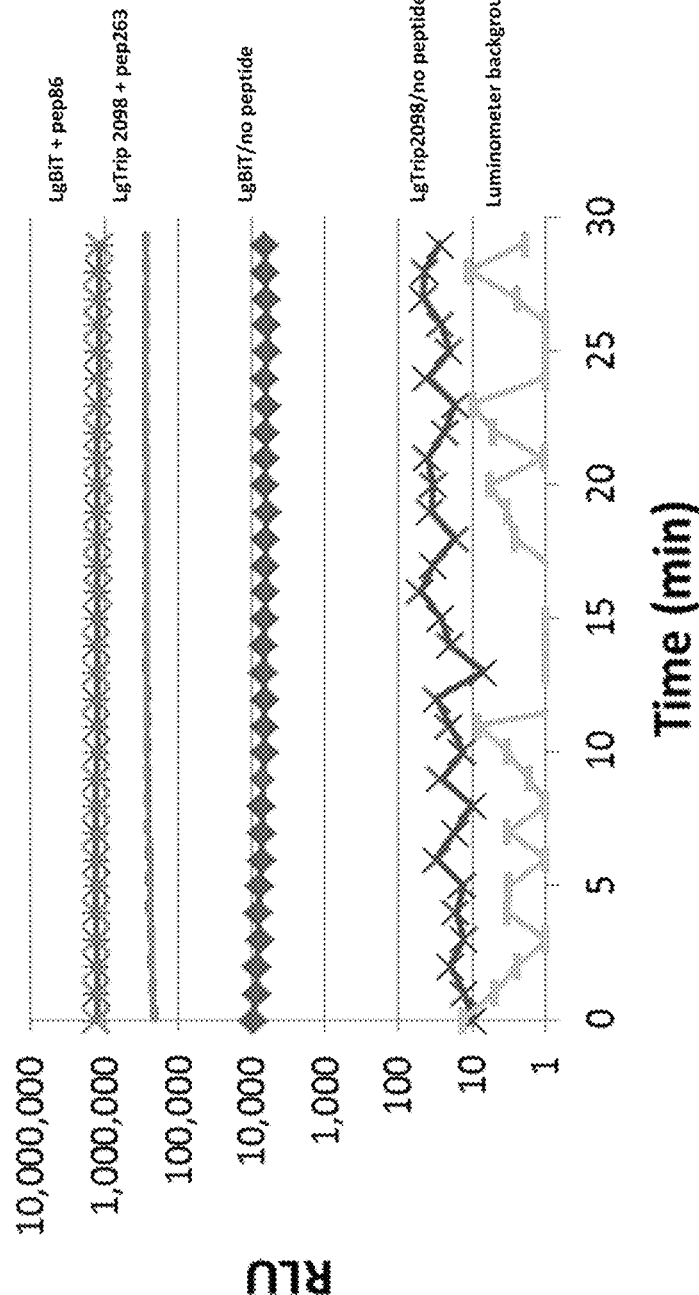
FIG. 1. Graph demonstrating that a polypeptide lacking β9 and β10 portions (LgTrip 2098; SEQ ID NO: 17) exhibits reduced background luminescence compared to LgBIT (SEQ ID NO: 11) and is activated by complementation with a peptide corresponding to β9 and β10.

The luminescence of LgBiT (background and in the presence of complementary SmTrip10 pep86) (SEQ ID NO: 15, 25) was compared with a further truncated polypeptide (LgTrip 2098, SEQ ID NO: 17) lacking both the $\beta10$ and $\beta9$ strands of the full-length luciferase (background and in the presence of complementary pep263 (SEQ. ID 35)) (FIG. 1).

*E. coli* KRX harboring LgBIT (SEQ ID NO: 11) or LgTrip 2098 (SEQ ID NO: 17) were grown for 20 h from a single colony in LB+amp (50 ug/mL) at 30° C. (275 rpm) in a volume of 50 mL. From these cultures, 100× dilutions were made into the same media and the cultures grown at 37 C (275 rpm) for 3 h and then cooled to 25° C. before adding rhamnose (inducing agent for protein overexpression) to a final concentration of 0.2%. Cultures were then grown (induced) for 22 h at 25° C. (275 rpm) at which time cultures were harvested, and the resulting pellets stored at −20° C. until processing. To lyse cells, pellets were removed from −20° C., resuspended in 50 mL of PBS pH 7.2, and taken through 3 sequential freeze thaw cycles (−70° C. to 22° C.), centrifuged to produce soluble fractions, and then kept cold (on ice) until assaying. Lysates and peptide(s) (25 nm final concentration) were incubated together for 10 minutes at 25° C. prior to the addition of NanoGlo® reagent. After addition of reagent, plates were incubated for another 5 min at 35° C. and read over time to measure luminescence (RLU) using a Tecan Infinite F500 plate reader.

Experiments conducted during development of embodiments herein demonstrate that both LgBIT (SEQ ID NO: 11) and LgTrip 2098 (SEQ ID NO: 17) produce some background luminescence, but the level is much higher for LgBiT. Data shows that both LgBiT and LgTrip 2098 produce more luminescence in the presence of their respective complementary peptide. The magnitude of the gain in signal in the presence of peptide is greater for LgTrip 2098. These data demonstrate that the further truncated LgBiT (and with the A51G substitution) is activated by a single complementary peptide corresponding to the $\beta10$ and $\beta9$ beta strands that are absent from LgTrip 2098.

Example 2

Figure 2:
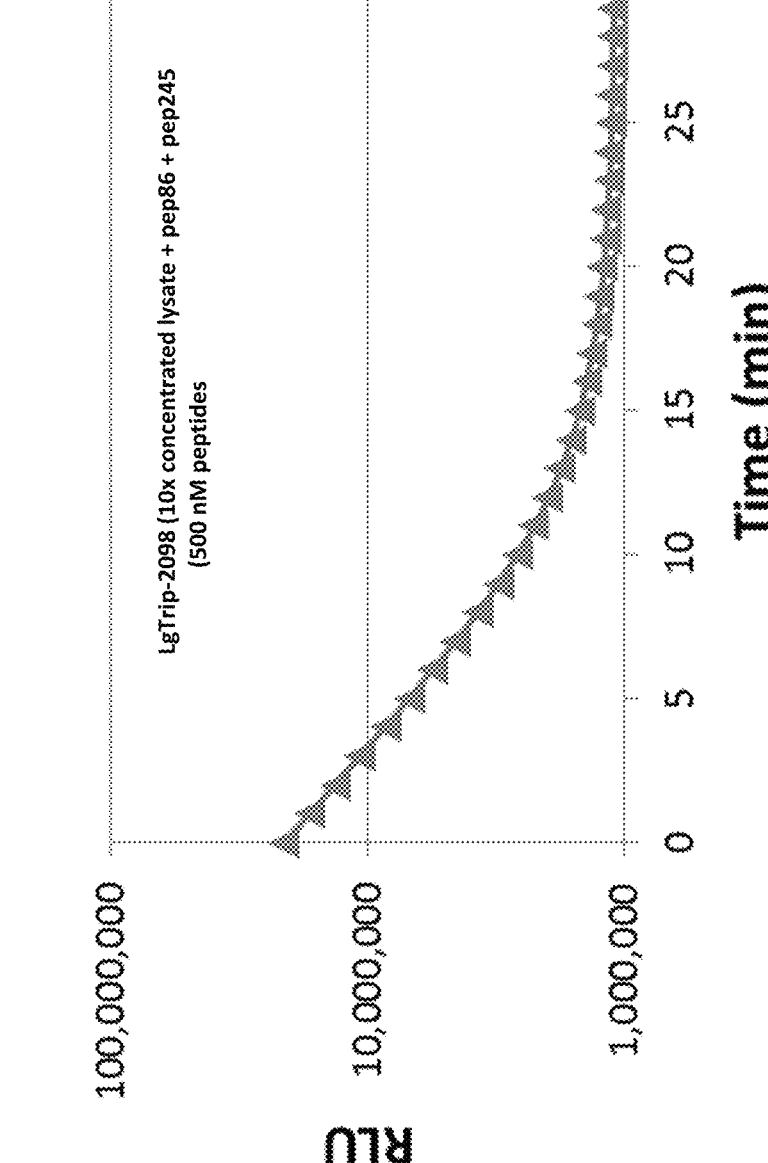
FIG. 2. Graph demonstrating activation of LgTrip 2098 (SEQ ID NO: 17) by separate peptide corresponding to β9 and 10, respectively.

LgTrip 2098 is Activated by Pair of Separate $\beta9$ and $\beta10$-Like Peptides The luminescence of LgTrip 2098 (SEQ ID NO: 31) was monitored over time in the presence of separate peptides corresponding to the $\beta10$ and $\beta9$ portions of the full-length luciferase (SmTrip10 pep86 (SEQ ID NO: 25) and SmTrip9 pep245) (SEQ ID NO: 23) (FIG. 2). Similar experimental protocols were used as in Example 1; however, a 10× concentrated lysate was used, Peptides SmTrip10 pep86 and SmTrip9 pep245 were used at 500 nM, and 0.001% Prionex added to reactions. Experiments conducted during development of embodiments herein demonstrate that LgTrip 2098 (SEQ ID NO: 31) is activated by the addition of SmTrip10 pep86 and SmTrip9 pep245. Controls with no peptides added or only one of the peptides added produced near the background of the plate reader.

Example 3

LgTrip Mutagenesis—Round 1 (Luminescence)

Overnight cultures used for sequencing were used to inoculate cultures (30 ul of cells in 3 ml of media+0.1% Rhamnose+0.15% glucose). Cells were grown overnight at 25° C. for 20 hours. Cells were diluted 10 ul into 250 ul of Passive Lysis Buffer (PLB) and allowed to lyse for 5 minutes. The lysate was mixed and then diluted 1:100 into PLB lysis buffer (0.3×PLB, 25 mM HEPES pH 7.5, 0.001 U/ml RQ DNase 1 (10 ul in 990 ul). 50 µl of the diluted lysate was combined with 50 ul of NanoGlo® buffer+2 uM pep263 (SmTrip9-10 dipeptide) (SEQ ID NO: 35) at a 1 uM final concentration (saturating dipeptide concentration). Samples were incubated for 5 minutes, read on GloMax® Multi+ (GMM+) luminometer, and normalized to LgTrip 2098 (SEQ ID NO: 31) (Table 2).

TABLE 2

| | | Relative luminescence of LgTrip variants compared to LgTrip 2098. | |
|---|---|---|---|
| Clone # | Cell plate | Sequence | Secondary screen (normalize to 2098) |
| #7 | | F1L | 1.1 |
| #10 | | Q42L | 1.8 |
| #14 | | I44V, E63D, L142Q | 2.5 |
| #15 | | L30S | 8.3 |
| #19 | | N17D | 3.0 |
| #22 | | Y16C, I56T | 2.6 |
| | | L142Q | 1.8 |
| #38 | | T2S, M106K | 1.8 |
| #39 | | E4D, V27A | 3.7 |
| #42 | | E4D | 2.5 |

Example 4

LgTrip Mutagenesis—Round 1 (Stability)

Figure 3:
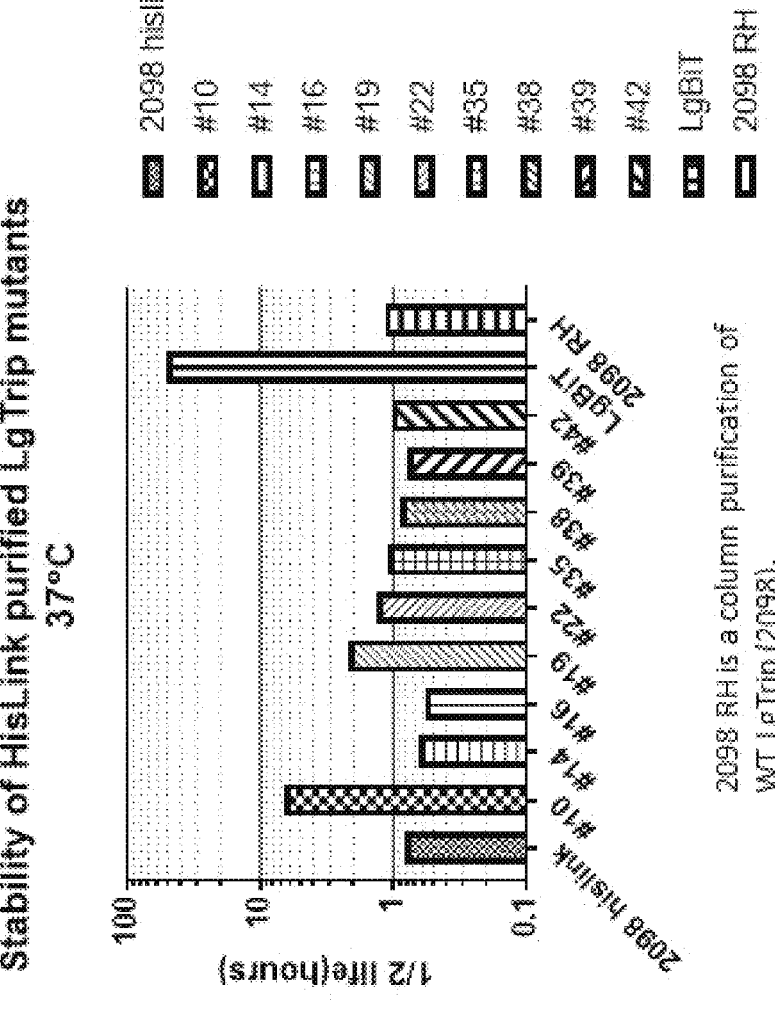
FIG. 3. Graph depicting the relative stability of exemplary LgTrip 2098 mutants.

Experiments were conducted during development of embodiments herein to determine the stability of HisLink purified LgTrip mutants. LgTrip 2098 (SEQ ID NO: 31), LgTrip 2098 (RH) (SEQ ID NO: 31) (column purified LgTrip 2098), #10, #14, #16, #19, #22, #35, #38, #39, and #42 polypeptides (Table 3) were diluted 1:1000 into PLB lysis buffer (2 ul into 2 ml). 100 ul of each sample was transferred into one column of wells in a 96-well PCR tray. Samples were incubated at 37° C., and aliquots were remove at various time-points. Samples were placed on ice when thermal treatment was complete. When all samples were processed, the PCR tray was equilibrated to room temperature. Samples were mixed and then diluted 1:100 in PLB lysis buffer (5 ul into 495 ul buffer). 50 ul of each sample was combined with 50 ul of NanoGlo® buffer reagent+2 uM pep263. The plate was incubated for 5 minutes and then read on GMM+. Results are depicted in FIG. 3. Stability studies identified position 42 of LgTrip 2098 (SEQ ID NO: 31) as a position of interest for further analysis.

TABLE 3

Experimental nomenclature for LgTrip mutants
(mutations relative to LgTrip 2098).

| Clone # | Sequence |
| --- | --- |
| #10 | Q42L |
| #14 | I44V, E63D, L142Q |
| #16 | L30S |
| #19 | N17D |
| #22 | Y16C, I56T |
| #35 | L142Q |
| #38 | T2S, M106K |
| #39 | E4D, V27A |
| #42 | E4D |

Example 5

Position 42 Site Saturation (Luminescence)

Figure 4:
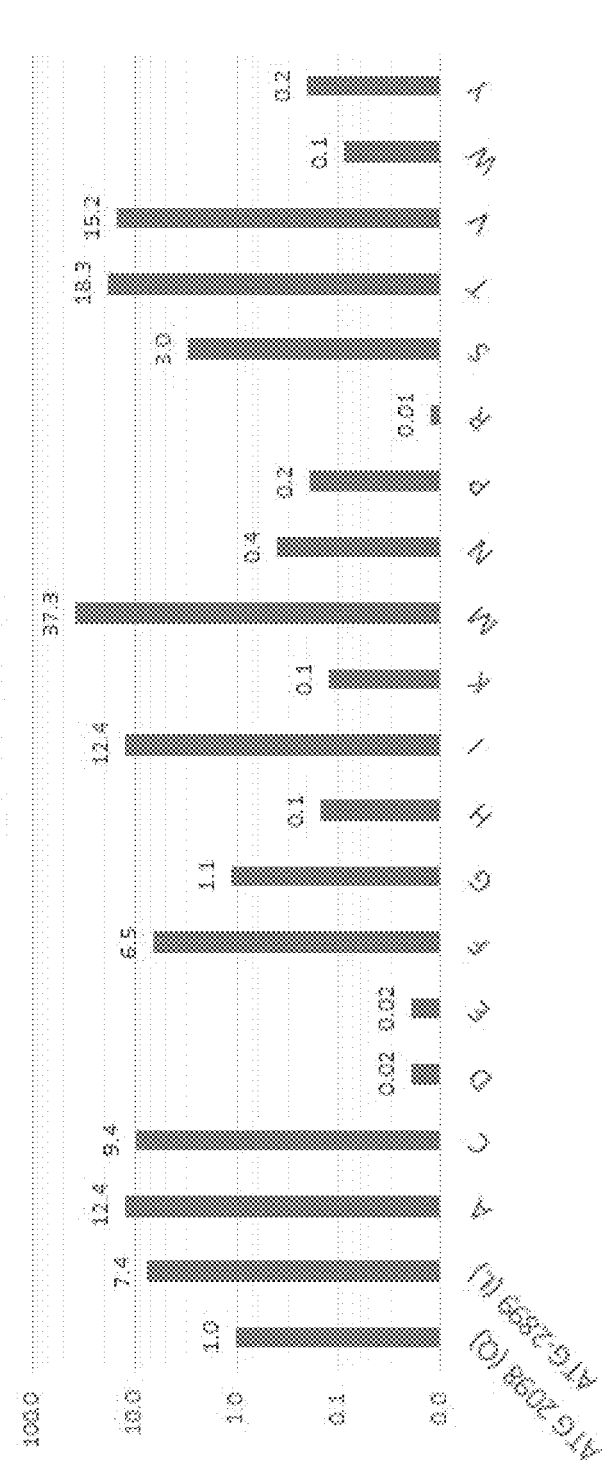
FIG. 4. Graph depicting the relative luminescent activity of amino acid site saturation at position 42 of LgTrip 2098 mutants.

Experiments were conducted during development of embodiments herein to optimize the identity of the amino acid at position 42 of LgTrip 2098 (SEQ ID NO: 31) (FIG. 4). E. coli cultures (3 ml) were prepared for each sample and grown overnight at 37° C. in LB media+100 ug/ml ampicillin. Cultures were then diluted in quadruplicate at a 20× concentration (10 μl in 200 μl) into induction media (LB+ampicllin+0.1% Rhamnose). Samples were grown at 37° C. for 6 hours. Samples were then lysed with 0.3×PLB, 25 mM HEPES pH 7.5, and 0.001 U/ml RQ1 DNase (10 μl of cells to 250 μl of Lysis buffer). 50 μl of the lysate was then combined with 50 μl of NanoGlo® buffer+50 μM furimazine+20 nM of dipeptide 263 (SEQ ID NO: 35). Samples were measured on a BMG Clariostar luminometer. RLU values were normalized to LgTrip 2098 (SEQ ID NO: 31).) (FIG. 4)

Example 6

37° C. Stability of Purified LgTrip Position 42 Mutants

Experiments were conducted during development of embodiments herein to determine the stability of position 42 in LgTrip 2098 mutants (FIG. 5). Polypeptides were diluted to 20 nM in TBS+0.01% BSA. In triplicate, 100 μl aliquots of each sample were loaded into 200 μl thin walled PCR tubes. Samples were incubated at 37° C. in thermal cycler. Samples were removed at various time-points, placed on ice, and then allowed to equilibrate to room temperature. Samples were diluted to 0.2 nM (5 in 495 μl) in PLB lysis buffer (0.3×PLB+25 mM HEPES pH 7.5). 50 μl of each diluted sample was combined with 50 μl of 50 μM Furimazine+6 μM pep263 (SEQ ID NO: 35) in NanoGlo® buffer. Samples were incubated for 10 minutes and then read on GMM+. Half-life was calculated by non-linear regression (FIG. 5).

Example 7

Site Saturation of LgTrip

Figure 6A:
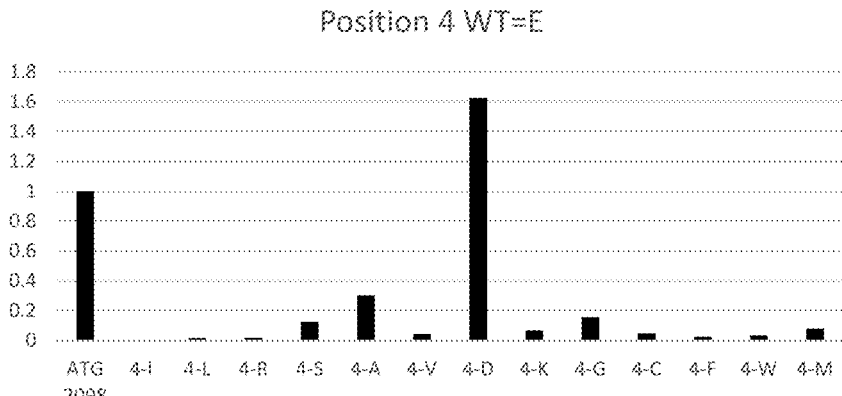
FIG. 6A-C. Graph depicting the relative luminescent activity of amino acid changes at (A) position 4, (B) position 30, and (C) position 106 of LgTrip 2098 mutants.
Figure 6B:
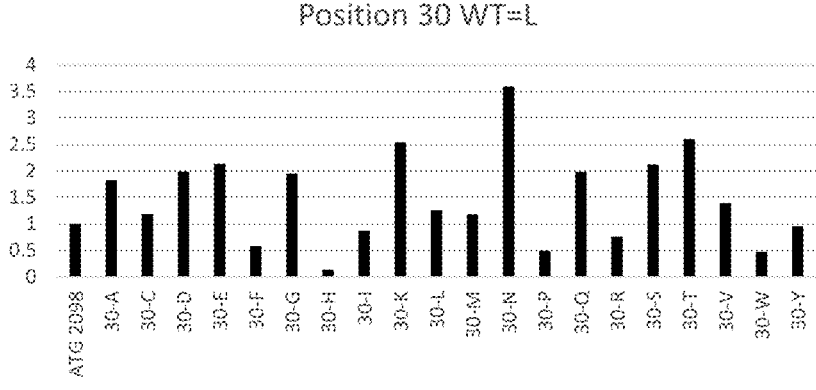
Figure 6C:
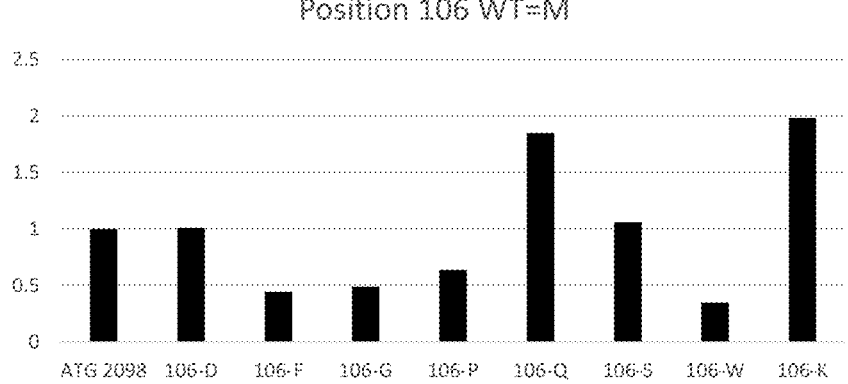
Figure 7A:
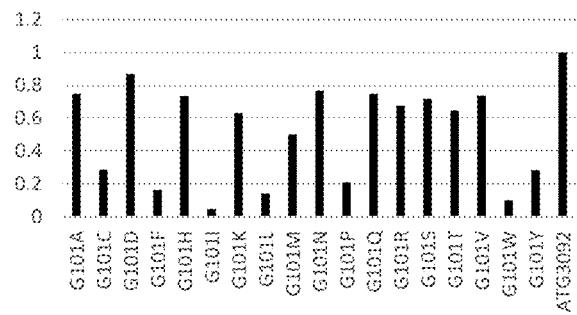
FIG. 7A-E. Graph depicting the relative luminescent activity of amino acid changes at (A) position 101, (B) position 117, (C) position 127, (D) position 120, and (E) position 126 of LgTrip 3092 mutants.
Figure 7B:
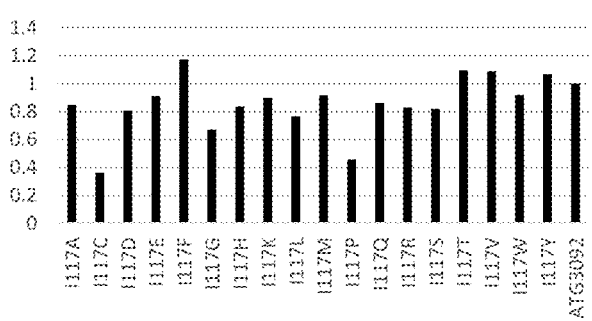
Figure 7C:
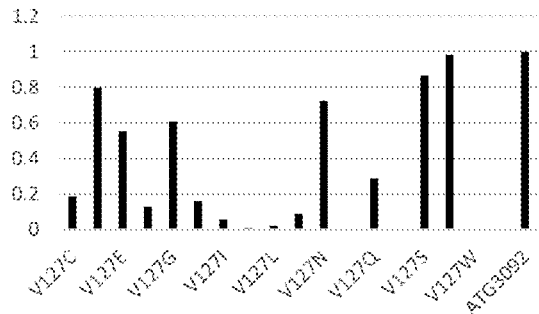
Figure 7D:
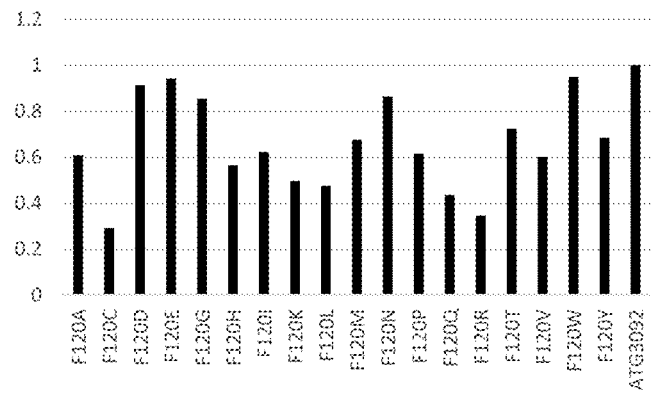
Figure 7E:
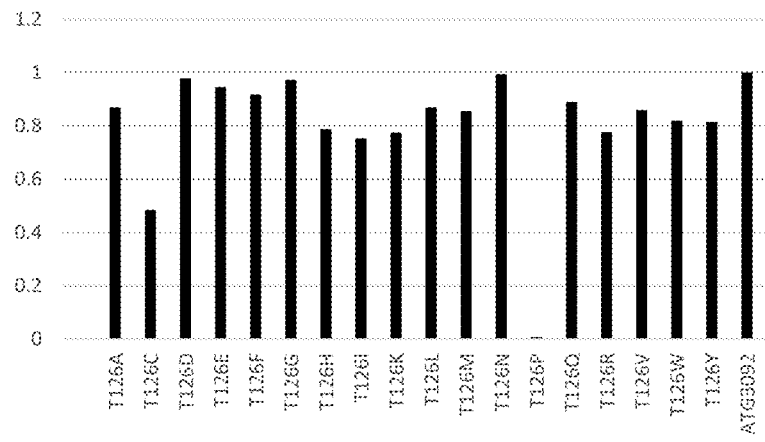

Experiments were conducted during development of embodiments herein to optimize the identity of the amino acid at various positions of LgTrip 2098 (SEQ ID NO: 31) (FIG. 6). E. coli cultures (3 ml) were prepared for each sample and grown overnight at 37° C. in LB media+100 μg/ml ampicillin. Cultures were then diluted in quadruplicate to a 20× concentration (10 μl in 200 μl) into induction media (LB+ampicilin+0.1% Rhamnose). Samples were grown at 37° C. for 6 hours. Samples were then lysed with 0.3×PLB+25 mM HEPES pH 7.5+0.001 U/ml DNase (10 μl of cells to 250 μl of Lysis buffer). 50 μl of the lysate was then combined with 50 μl of NanoGlo® buffer+50 μM furimazine+20 nM of dipeptide 263 (SEQ ID NO: 35). Samples were measured on a BMG Clariostar luminometer. RLU values were normalized to LgTrip 2098 (SEQ ID NO: 31) (FIG. 6).

Example 8

Mutations on LgTrip 3092 Template

Experiments were conducted during development of embodiments herein to determine the effect of various amino acid substitutions relative to the LgTrip 3092 (SEQ ID NO: 19) variant (Table 4). E. coli cultures (3 ml) were prepared for each sample and grown overnight at 37° C. in LB media+100 ug/ml ampicillin. Cultures were then diluted in quadruplicate to a 20× concentration (10 μl in 200 μl) into induction media (LB+ampicllin+0.1% Rhamnose). Samples were grown at 37° C. for 6 hours. Samples were then lysed with 0.3×PLB+25 mM HEPES pH 7.5+0.001 U/ml DNase. (10 μl of cells to 250 μl of Lysis buffer). 50 μl of the lysate was then combined with 50 μl of NanoGlo® buffer+50 μM furimazine+2 nM of dipeptide 263 (SEQ ID NO: 35). The mutant lysates were further diluted 1:100 in PLB (5 μl in 495 μl). 50 μl of the diluted lysate was added to 50 μl of NanoGlo® buffer+50 μM furimazine+6 μM pep263 or 50 μl of TBS+20 μM LCS (furimazine)+6 μM pep263 (SEQ ID NO: 35). Samples were measured on a GMM+ after a 10 minute incubation. RLU values were normalized to LgTrip 3092 (SEQ ID NO: 19)

TABLE 4

Relative luminescence of LgTrip
variants compared to LgTrip 3092.

| Sample | LCS 6 uM 263 | Nglo 6 uM 263 | NGLo 2 nM 263 |
| --- | --- | --- | --- |
| ATG 3092 | 1.0 | 1.0 | 1.0 |
| V127A | 4.2 | 3.5 | 3.7 |

TABLE 4-continued

Relative luminescence of LgTrip
variants compared to LgTrip 3092.

| Sample | LCS 6 uM 263 | Nglo 6 uM 263 | NGLo 2 nM 263 |
|---|---|---|---|
| Y16S | 1.3 | 1.3 | 3.1 |
| V119A | 1.4 | 1.2 | 2.0 |
| V127A + T128A | 4.9 | 3.7 | 3.7 |
| I117N | 2.9 | 2.1 | 2.5 |
| F120S | 2.0 | 1.6 | 2.1 |
| G122D | 1.2 | 1.3 | 2.3 |
| N105S | 1.2 | 1.4 | 1.6 |
| T126S | 2.3 | 1.4 | 2.1 |
| G101E | 2.3 | 1.4 | 3.9 |
| V36E + V102D + E115D | 2.4 | 1.4 | 1.7 |

Example 9

Site Saturation of LgTrip 3092 Template

Experiments were conducted during development of embodiments herein to optimize the identity of the amino acid at various positions of LgTrip 3092 (SEQ ID NO: 19). *E. coli* cultures (3 ml) were prepared for each sample and grown overnight at 37° C. in LB media+100 ug/ml ampicillin. Cultures were then diluted in quadruplicate to a 20× concentration (10 μl in 200 μl) into induction media (LB+ampicilin+0.1% Rhamnose). Samples were grown at 37° C. for 6 hours. Samples were then lysed with 0.3×PLB+25 mM HEPES pH 7.5+0.001 U/ml DNase (10 μl of cells to 250 μl of Lysis buffer). 50 μl of the lysate was then combined with 50 μl of NanoGlo® buffer+50 μM furimazine+2 nM of dipeptide 263 (1 nM final). Samples were measured on a BMG Clariostar luminometer. RLU values were normalized to LgTrip 3092 (FIG. 7).

Example 10

Stability of LgTrip 2098 and LgTrip 3092 Compared to LgBiT

Figure 8:
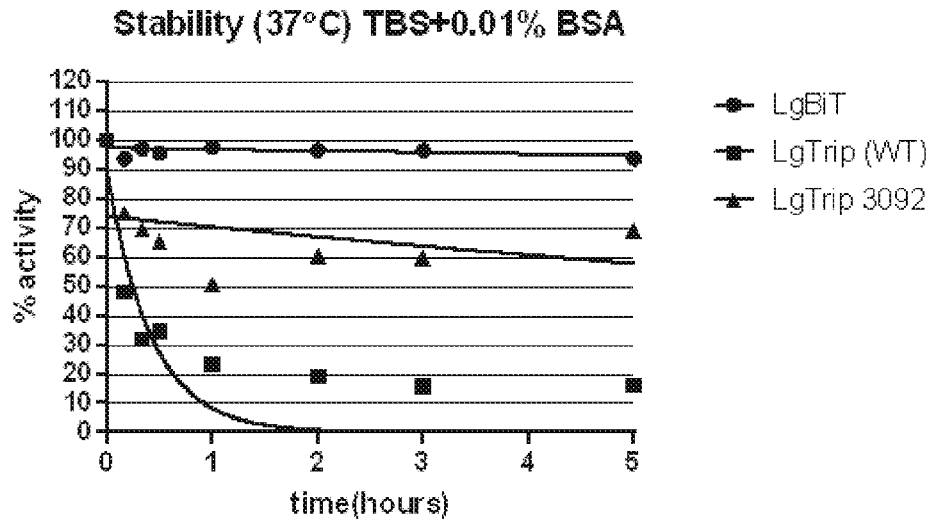
FIG. 8. Graph depicting the relative stability of LgTrip 2098 (WT) (SEQ ID NO: 31), LgTrip 3092 (SEQ ID NO: 19), and LgBIT (SEQ ID NO: 11) at 37° C.

Experiments were conducted during development of embodiments herein to compare the stability of positions in LgTrip 2098 (SEQ ID NO: 31) and LgTrip 3092 (SEQ ID NO: 33) to LgBiT (SEQ ID NO: 11) (FIG. 8). Purified LgTrip 2098, LgTrip 3092, and LgBiT samples were diluted to 20 nM in TBS+0.01% BSA. 100 μl of each sample was aliquoted into 200 μl thin walled PCR tubes. Samples were incubated at 37° C. in thermal cycler. Samples were removed at various time-points and placed on ice. Samples were equilibrated to RT and then diluted to 0.2 nM (5 μl in 495 μl) in PLB lysis buffer (0.3×PLB+25 mM HEPES pH 7.5). 50 μl of each sample was diluted with 50 μl of 50 μM Furimazine+6 μM pep263 (SEQ ID NO: 35) in NanoGlo® buffer. Samples were incubated for 10 minutes and then read on GMM+ (FIG. 8).

Example 11

Stability of LgTrip Variants at 42° C. And 60° C.

Figure 9A:
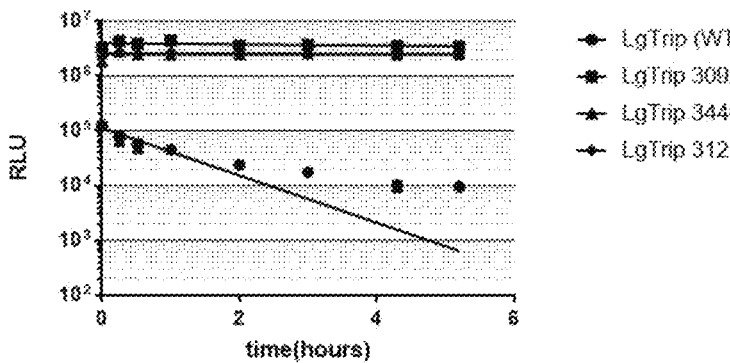
FIG. 9A-B. Graph depicting the relative stability of LgTrip variants at (A) 42° C. and (B) 60° C.
Figure 9B:
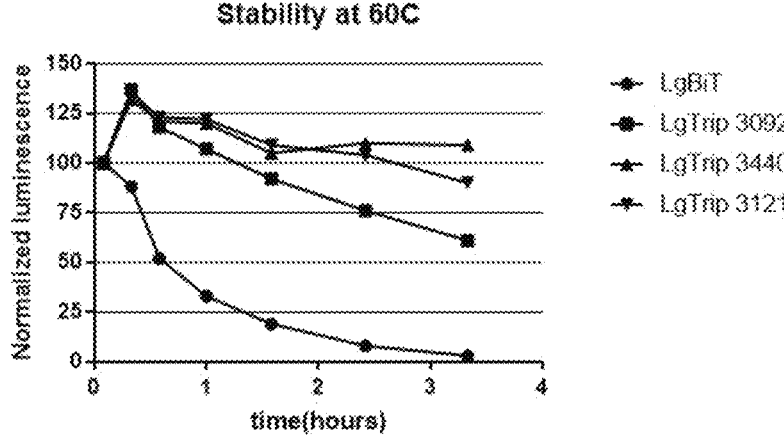

Experiments were conducted during development of embodiments herein to compare the stability of LgTrip variants at 42° C. and 60° C. (FIG. 9). The LgTrip variant samples were diluted to 20 nM in TBS+0.01% BSA. 100 μl aliquots were added into 200 μl thin walled PCR tubes.

Samples were incubated at 42° C. or 60° C. in thermal cycler. Samples were removed at various time-points and placed on ice. Samples were equilibrated to RT and then each diluted to 0.2 nM (5 μl in 495 μl) in PLB lysis buffer (0.3×PLB+25 mM HEPES pH 7.5). 50 μl of each diluted sample was combined with 50 μl of 50 μM Furimazine+6 μM pep263 (SEQ ID NO: 35) in NanoGlo® buffer. Samples were incubated for 10 minutes and then read on GMM+ (FIG. 9).

Example 12

Affinity of LgTrip Variants with SmTrip9 and SmTrip10

Figure 10A:
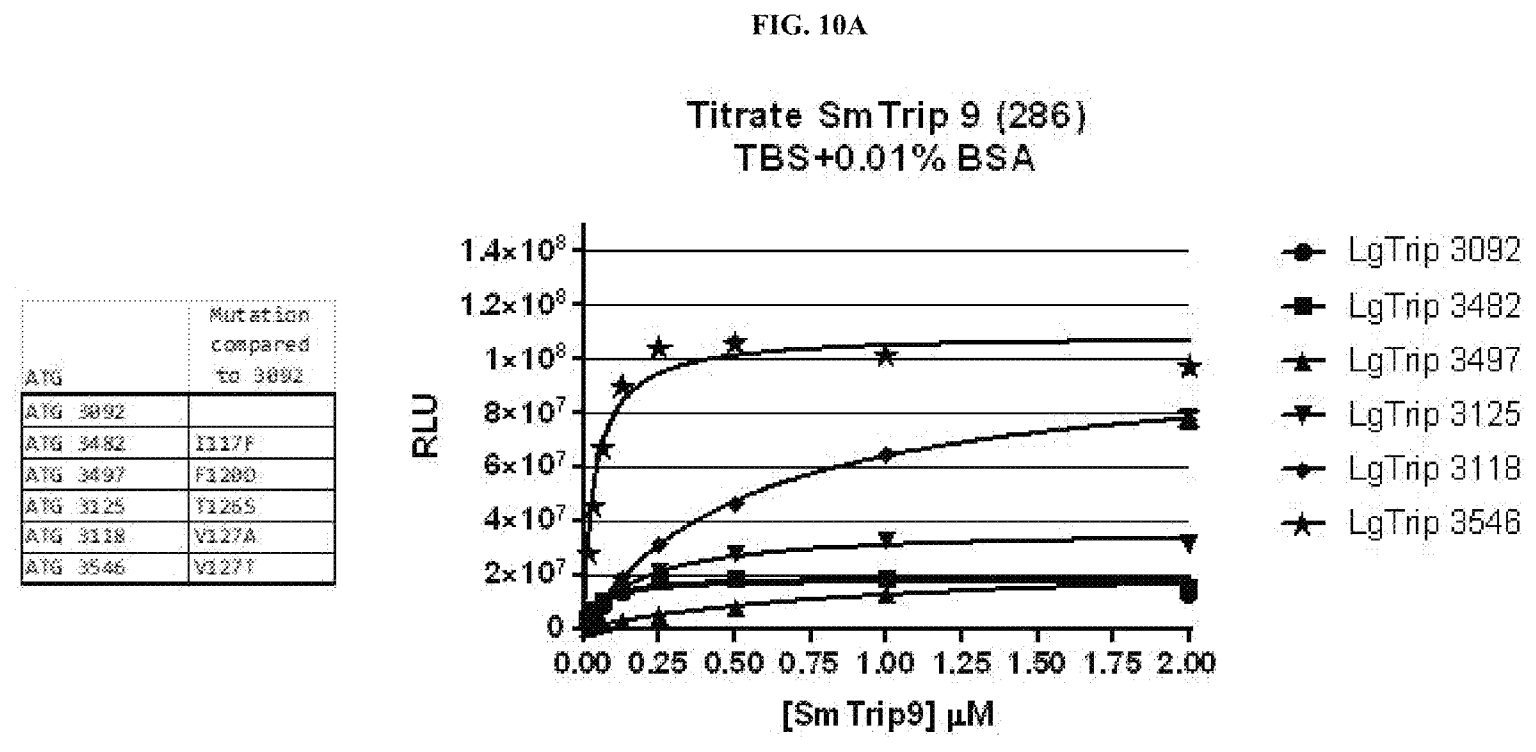
Figure 10B:
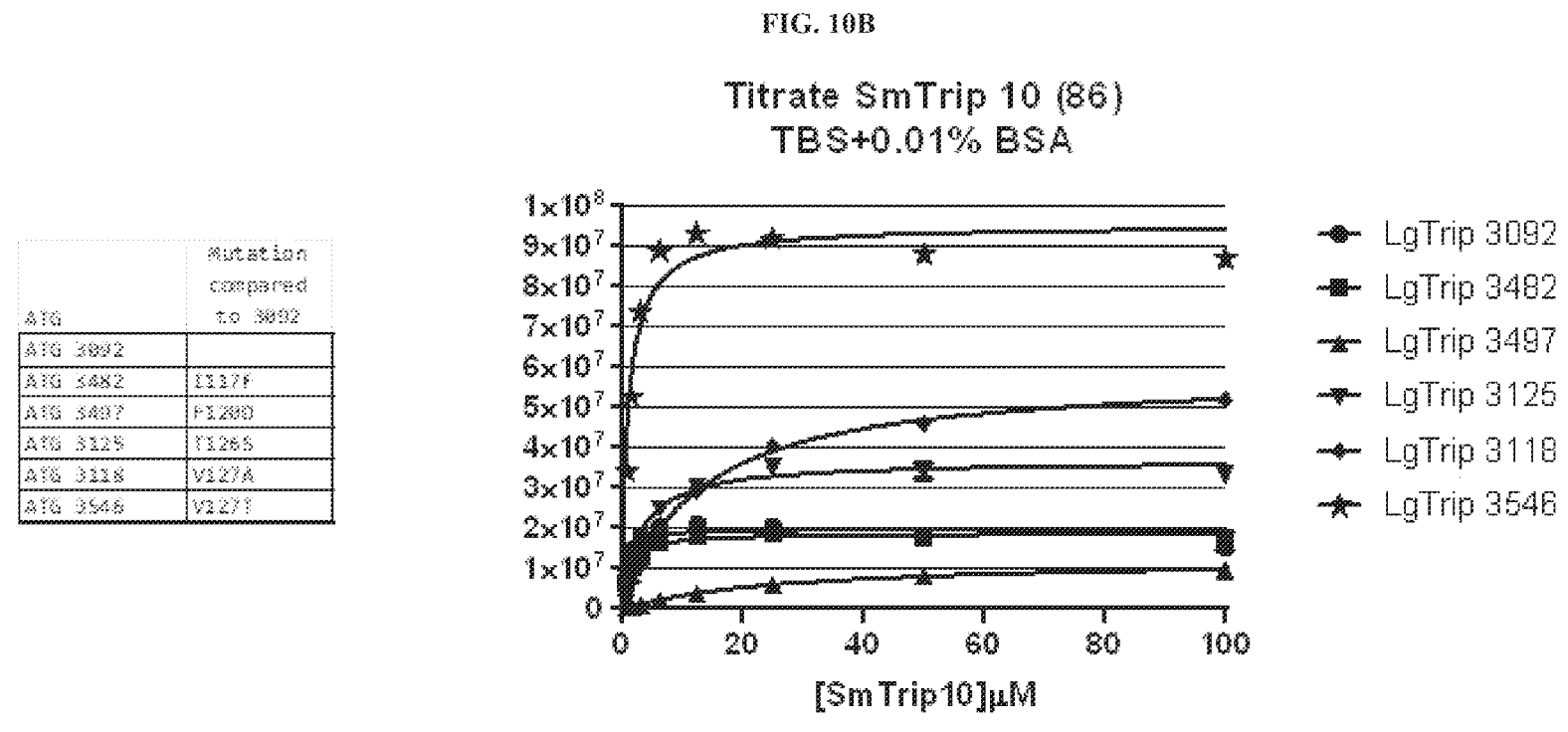
Figure 10C:
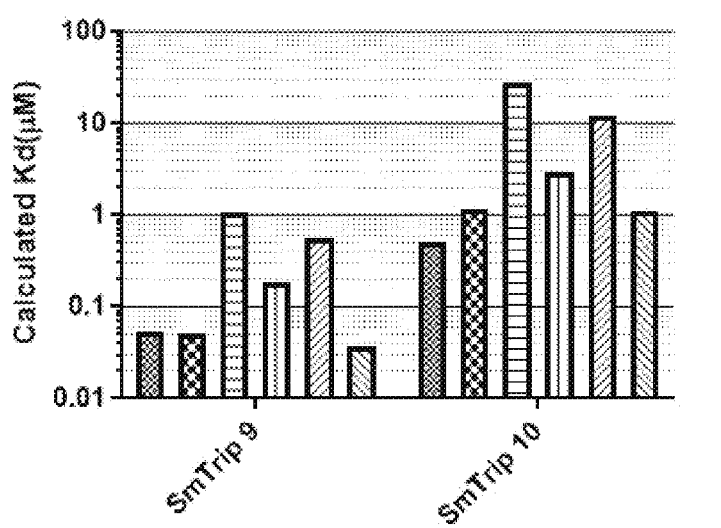

Experiments were conducted during development of embodiments herein to determine the affinity of various LgTrip variants for the SmTrip9- and SmTrip10-like peptides (FIG. 10).

For the SmTrip9 pep286 (SEQ ID NO: 37) titration, purified LgTrip samples were diluted to 2 nM in TBS+0.01% BSA+0.005% IGEPAL. Assay reagent containing TBS+0.01% BSA+0.005% IGEPAL+20 μM furimazine+200 μM SmTrip10 pep86 (SmHiTrip; SEQ ID NO: 25) was prepared. 4 uM of SmTrip9 pep286 (SEQ ID NO: 37) was added to the assay reagent and then serially diluted 500 μl to 500 μl in assay reagent containing Furimazine+200 μM SmTrip10 pep86 (HiBIT; SEQ ID NO: 15). 25 ul of each peptide titration was added to 25 ul of diluted LgTrip solution. Luminescence was read on a plate reader at 10 and 15 minutes.

For the SmTrip10 pep86 (SmHiTrip; SEQ ID NO: 25) titration, purified LgTrip samples were diluted to 2 nM in TBS+0.01% BSA+0.005% IGEPAL. Assay reagent containing TBS+0.01% BSA+0.005% IGEPAL+20 μM furimazine+4 μM SmTrip9 pep286 (SEQ ID NO: 37) was prepared. 200 uM of SmTrip10 pep86 (SmHiTrip; SEQ ID NO:25) was added to then assay reagent and then serially diluted 500 μl to 500 μl in assay reagent containing Furimazine+4 μM SmTrip9 pep286 (SEQ ID NO: 37). 25 ul of each peptide titration was added to 25 ul of diluted LgTrip solutions. Luminescence was read on plate reader at 10 and 15 minutes.

Example 13

Stability of LgTrip Variants (60° C.)

Figure 11A:
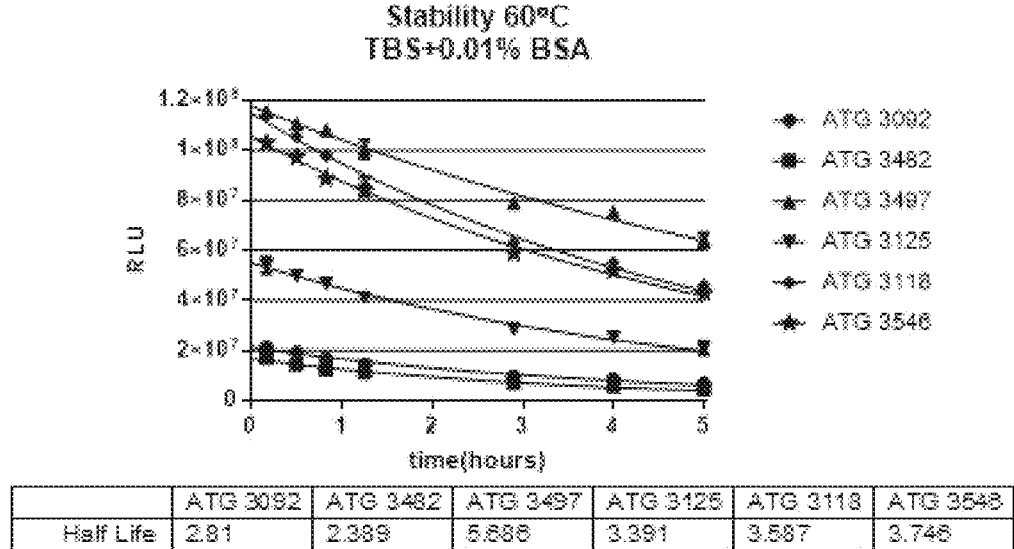
FIG. 11A-B. Graphs depicting the (A) stability (half-life) and (B) relative stability of various LgTrip variants at 60° C.
Figure 11B:
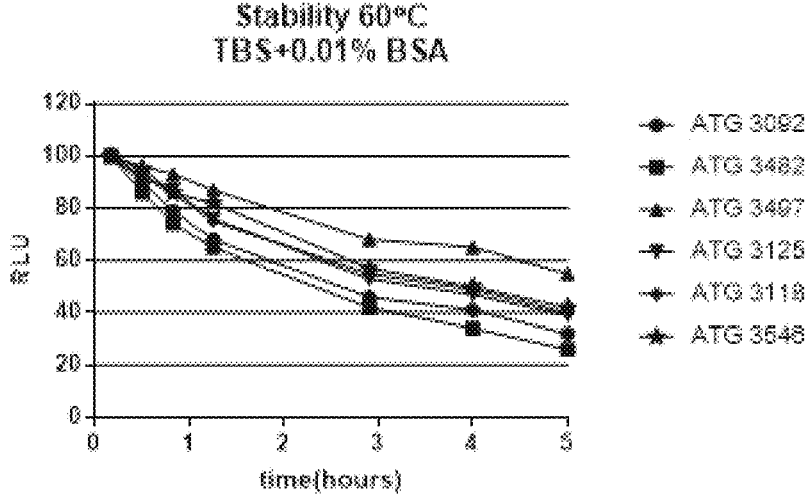

Experiments were conducted during development of embodiments herein to compare the stability of LgTrip variants at 60° C. (FIG. 11). Purified LgTrip mutants were diluted to 20 nM in TBS+0.01% BSA. 100 μl of each sample was aliquoted into 200 μl thin walled PCR tubes. Samples were incubated at 60° C. in thermal cycler and then were removed at various time-points, placed on ice, equilibrated to room temperature, and then diluted to 0.2 nM (5 μl in 495 μl) in PLB lysis buffer (0.3×PLB+25 mM HEPES pH 7.5). 50 μl of each diluted sample was combined with 50 μl of 50 μM Furimazine+6 μM pep263 (SEQ ID NO: 35) in NanoGlo® buffer. Samples were incubated for 10 minutes and then read on GMM+. Half-life was calculated using GraphPad Prism non-linear regression (One-Phase Decay plateau set to zero).

Example 14

Comparison of Kinetic Profiles of LgBiT and LgTrip Variants

Figure 12A:
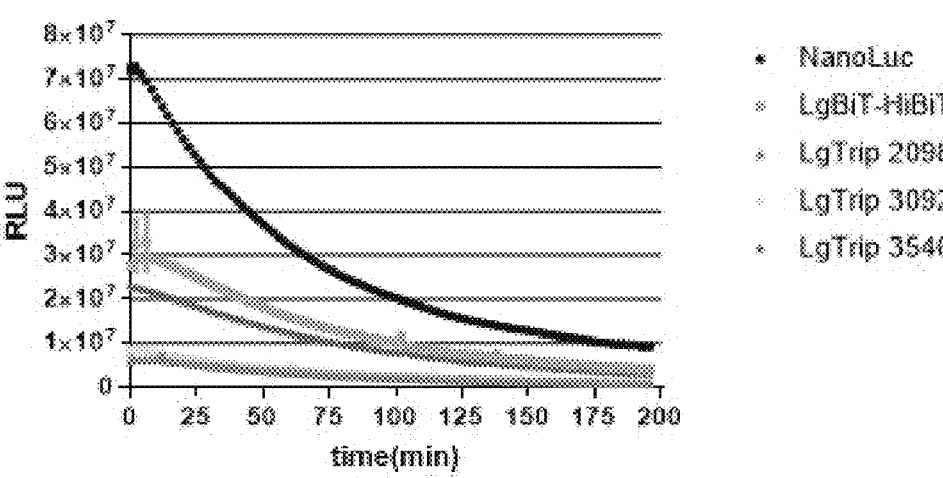
FIG. 12A-B. Graphs depicting the kinetic profiles of LgTrip variants in the presence of SmTrip9 pep286 (SEQ ID NO: 37) and SmTrip10 pep86 (HiBIT; SEQ ID NO: 25) compared to NanoLuc (SEQ ID NO: 3) and LgBIT (SEQ ID NO: 11) and SmTrip10 pep86 (HiBIT; SEQ ID NO: 25) (A) assayed in TBS+0.01% BSA and (B) assayed with Nano-Glo® assay buffer.
Figure 12B:
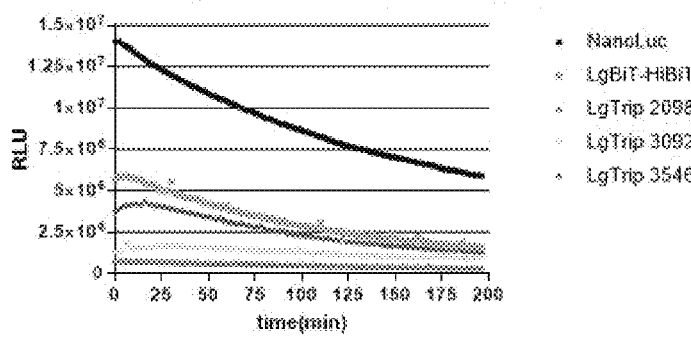

Experiments were conducted during development of embodiments herein to compare the kinetic profiles of various LgTrip variants with NanoLuc® luciferase (SEQ ID NO: 3) and a LgBIT (SEQ ID NO: 11)/HiBIT (SmTrip10 pep86) (SEQ ID NO: 25) two component system (FIG. 12). NanoLuc, LgBiT, LgTrip 2098 (SEQ ID NO: 31), LgTrip 3092 (SEQ ID NO: 33), and LgTrip 3546 (SEQ ID NO: 51) were diluted to 20 µM in TBS+0.01% BSA+0.005% IGEPAL. Samples were diluted 1:100 (2 µl in 198 µl) and then 1:1000 (10 µl in 10 ml) or 10E$^{-5}$ dilution total to a 0.2 nM final concentration. To the LgBiT polypeptide, 200 nM of SmTrip10 pep86 (SmHiTrip; SEQ ID NO: 25) was added. To the LgTrip variants, 200 µM SmTrip10 pep86 (SmHiTrip; SEQ ID NO: 25) and 20 µM SmTrip9 pep286 (SEQ ID NO: 37) were added. Samples were incubated for 15 minutes, 50 ul of each enzyme/peptide dilution combined with either TBS+0.01% BSA+20 µM Live Cell Substrate (LCS; Promega Cat. No. N205) or NanoGlo® buffer+50 µM Furimazine, and immediately read on a GMM+ luminometer.

Example 15

Detecting Protein-Protein Interactions with a Tripartite System

Figure 13A:
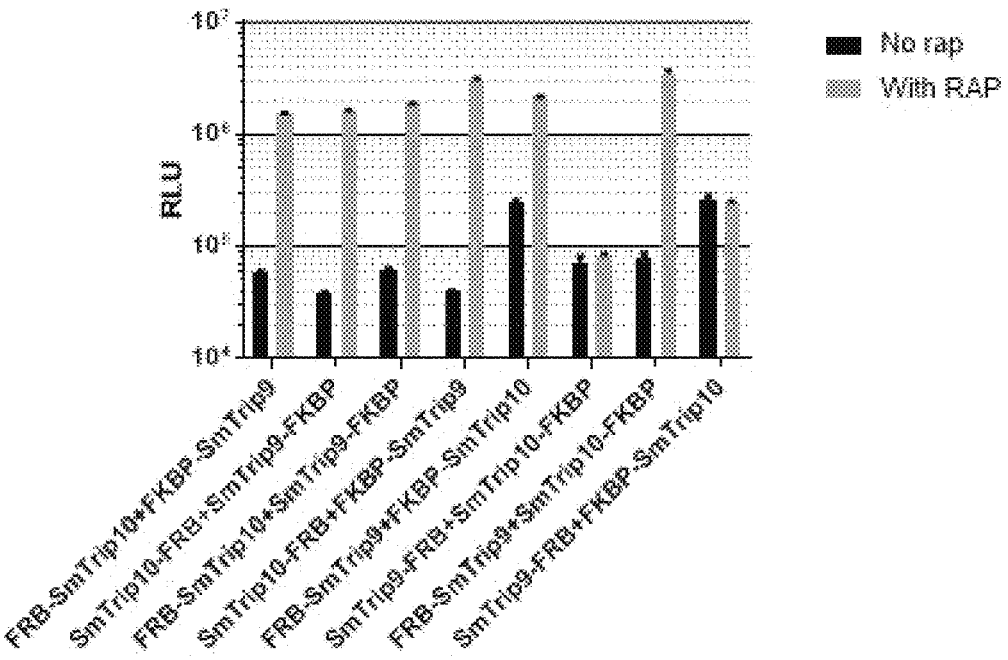
FIG. 13A-B. Graphs depicting facilitated complementation of various tripartite systems via rapamycin-induced formation of a FRB/FKBP complex: (A) SmTrip10 pep86 (SEQ ID NO: 25), SmTrip9 pep245 (SEQ ID NO: 23), and LgTrip 2098 (SEQ ID NO: 31); and (B) SmBIT (SEQ ID NO: 13), SmTrip9 pep245 (SEQ ID NO: 23), and LgTrip 2098 (SEQ ID NO: 31).
Figure 13B:
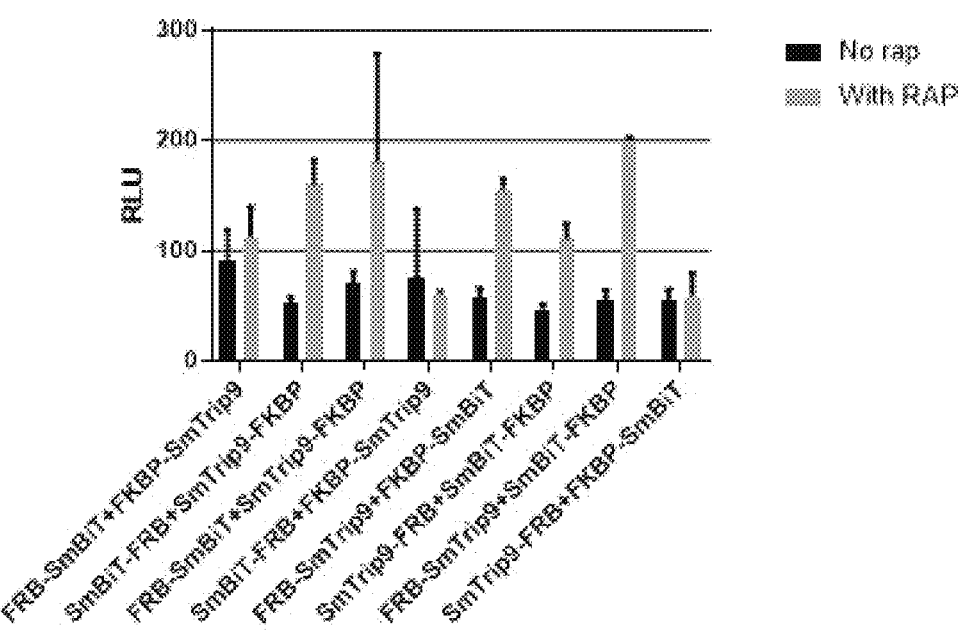

Experiments were conducted during development of embodiments herein to demonstrate the use of a tripartite complementation system in detecting protein-protein interactions (FIG. 13). Lysates containing FRB and FKBP fused to one each of SmTrip9 pep245 and SmTrip10 pep86 (FIG. 13A) or SmTrip9 pep245 and SmBIT (FIG. 13B) were added to purified LgTrip 2098 (SEQ ID NO: 31). Formation of the FRB/FKBP complex was induced with rapamycin and facilitated complementation of the tripartite system was monitored by luminescence.

Cell and lysate preparation. Cultures of each FRB-FKBP construct were grown overnight in LB+100 ug/ml ampicillin. Cultures were induced (30 µl in 3 ml of culture) in LB+0.1% rhamnose+0.15% glucose+100 ug/ml ampicillin and grow for 24 hours at 25° C. 200 µl of 10× Fastbreak Cell Lysis Reagent (Promega) was added to 2 ml of culture 0.001 U/ml RQ1 DNase. Cultures were incubated for 30 min at 4° C. on a rotating mixer and then spun at 3500 rpm for 30 min. at 4° C. Cleared lysate was removed and placed into new tubes, frozen, and stored at −70° C.

Assay. Lysates were thawed, diluted 1:10 into TBS+0.1% BSA, and appropriate lysates combined. The lysates were divided, and 30 nM rapamycin was added to one of the aliquots. 25 µl of each lysate was combined with 25 µl of LgTrip 2098 (SEQ ID NO: 31), diluted to 200 nM in TBS+0.01% BSA, and incubated for one hour. 50 µl of NanoGlo® Buffer+50 µM furimazine was added, and luminescence was read on GMM+.

Example 16

Random Library Preparation and Screening

A random library of variant LgTrip polypeptides (using template LgTrip 2098) (SEQ ID NO: 31) was generated and screened for complementation with the β9/β10 dipeptide (SEQ ID NO: 35) (pep263).

Template DNA from LgTrip 2098 (SEQ ID NO: 32) was diluted to 10 ug/ml in water. Diversify™ PCR Random Mutagenesis Kit (63070-ClonTech) was used to prepare a random library of mutants. Library amplification products were band isolated and purified using WIZARD SV Gel and PCR Clean-Up System (A9281; Promega), cloned into pF4Ag, transformed into KRX competent cells (Promega), and plated onto LB agarose plates. Colonies were picked and place into wells of a 96-well plates with LB+ampicillin, and samples were grown overnight at 37° C. with shaking. Overnight cultures were diluted 1:20 into induction media (LB+0.1% Rhamnose+0.15% glucose+100 ug/ml ampicillin), and cultures were grown for 2-6 hours at 37° C. 10 ul of cells were added to 250 ul of PLB lysis buffer (0.3×PLB, 25 mM HEPES pH 7.0, 0.001 U/ml DNase). 50 ul of cell lysate was combined with 50 ul of assay buffer (NanoGlo® buffer+50 uM Furimazine+0.2 nM of pep263). Plates were incubated for 5 minutes after reagent addition and then samples were read on ClarioStar luminometer. Clones that had improved luminescence compared to the template clone were selected for additional screening.

Approximately 6,000 LgTrip 2098-based variant clones were further screened, and favorable mutation sites were evaluated with site saturation mutagenesis. Favorable mutations following saturation mutagenesis were combined to derive the LgTrip clone LgTrip 3092 (SEQ ID NO: 19). Screening was repeated using LgTrip 3092 (SEQ ID NO: 19) as a template, and the resulting clone was LgTrip 3546 (SEQ ID NO: 51).

Example 17

Purification of LgTrip Clones 50 ml cultures of LgTrip mutants were induced in LB+0.1% Rhamnose+0.15% Glucose+amp. Cultures were spun and re-suspended in 4.5 ml of Hepes pH 7.5+0.001 U/ml DNase. 500 ul of FastBreak™ Cell Lysis Reagent (Promega; V8571) was added, and samples were incubated on a rotating mixer for 1 hour at 4° C. Samples were spun to clear lysate, and supernatant was transferred to a new tube. Using the HisLink™ Spin Protein Purification System, 500 ul of HisLink™ Protein Purification Resin (Promega; V8821) was added to the samples, incubated for 2 hours at 4° C. on a rotating mixer, washed with HisLink wash/binding buffer, and eluted with elution buffer. Slide-A-Lyzer dialysis columns were used to exchange buffer to TBS.

Example 18

Stability Comparison

Experiments were conducted during development of embodiments herein to compare the stability of activity of LgBiT (SEQ ID NO: 11) and LgTrip 2098 (SEQ ID NO: 31) over time (FIG. 14). Diluted purified LgTrip 2098 and LgBiT to 20 nM in TBS+0.01% BSA or in 0.3×PLB+25 mM HEPES pH 7.5. Aliquoted 100 µl of each sample into 200 µl thin walled PCR tubes. Incubated samples at 37° C. in thermal cycler, removed at various time-points, and placed on ice. Samples were equilibrated to room temperature and then diluted each sample to 0.2 nM (5 µl in 495 µl) in PLB lysis buffer (0.3×PLB+25 mM HEPES pH 7.5). 50 µl of each diluted sample was combined with 50 µl of 50 µM Furimazine+6 µM pep263 (SEQ ID NO: 35) in NanoGlo® buffer. Samples were incubated for 10 minutes and then read on GMM+. Calculated half-life using GraphPad Prism nonlinear regression (One-Phase Decay plateau set to zero).

Example 19

Stability of LgTrip in TBS+Minimal BSA Carrier

Figure 15A:
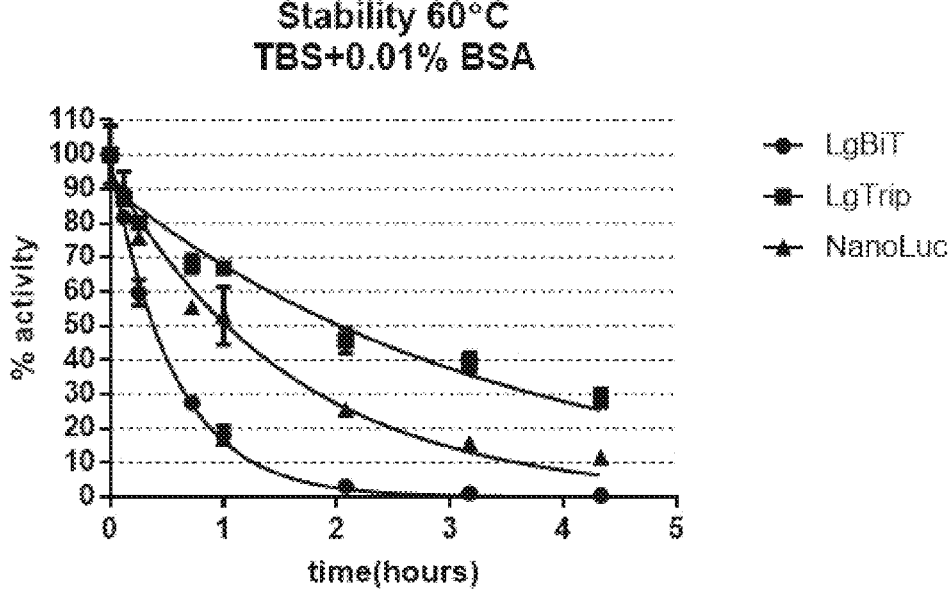
FIG. 15A-B. Graphs comparing stability of LgBIT (SEQ ID NO: 11), LgTrip 3546 (SEQ ID NO: 51), and NanoLuc (SEQ ID NO: 31) at 60° C.; (A) time course and (B) half-life.
Figure 15B:
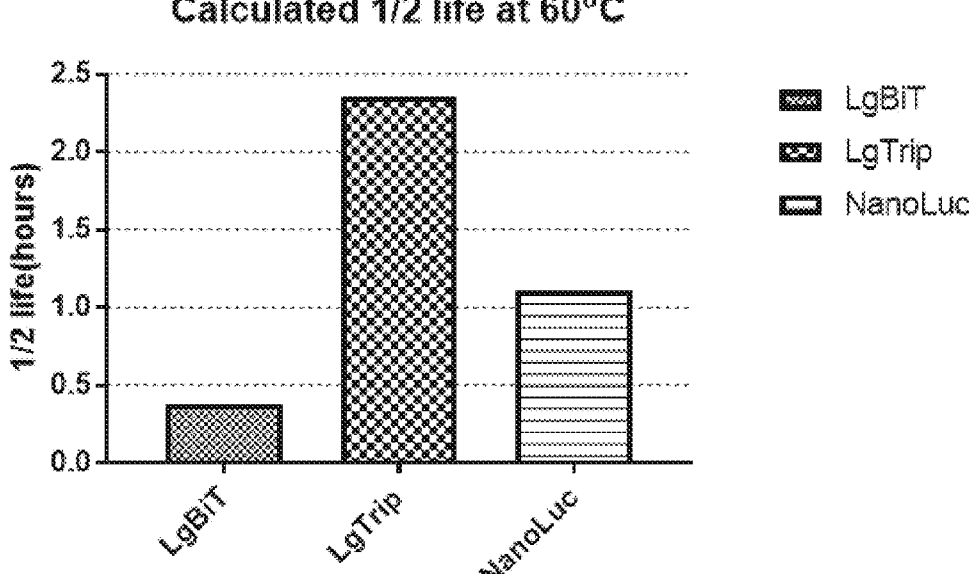

Experiments were conducted during development of embodiments herein to determine the stability of the activity of NanoLuc® (SEQ ID NO: 3), LgBiT (SEQ ID NO: 11), and LgTrip 3546 (SEQ ID NO: 51) in TBS and a minimal BSA carrier over time (FIG. 15). NanoLuc, LgBiT, and LgTrip 3546 were diluted to 20 nM in TBS+0.01% BSA. 100 µl of each were aliquoted into 200 µl thin walled PCR tubes. Samples were incubated at 60° C. in thermal cycler, removed at various time-points, and placed on ice. Samples were equilibrated to room temperature and diluted to 0.2 nM (5 µl in 495 µl) in PLB lysis buffer (0.3×PLB+25 mM HEPES pH 7.5). 50 µl of each diluted sample was combined with 50 µl of 50 µM Furimazine+6 µM pep263 (SEQ ID NO: 35) in NanoGlo® buffer. Samples were incubated for 10 minutes and then read on GMM+. Half-life was calculated using GraphPad Prism non-linear regression (One-Phase Decay plateau set to zero).

Example 20

Effect of Salt on Activity

Figure 16A:
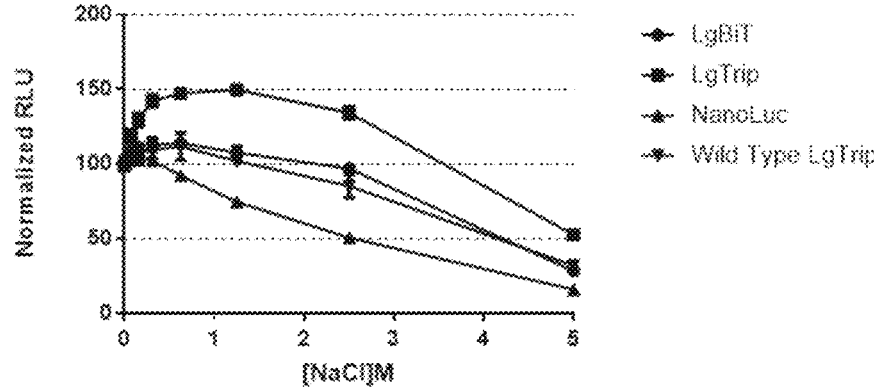
FIG. 16A-B. Graphs comparing LgBIT (SEQ ID NO: 11), NanoLuc (SEQ ID NO: 3), and LgTrip 3546 (SEQ ID NO: 51), and LgTrip 2098 (WT) (SEQ ID NO: 31) (A) in the presence NaCl and (B) after 26 hour exposure to NaCl.
Figure 16B:
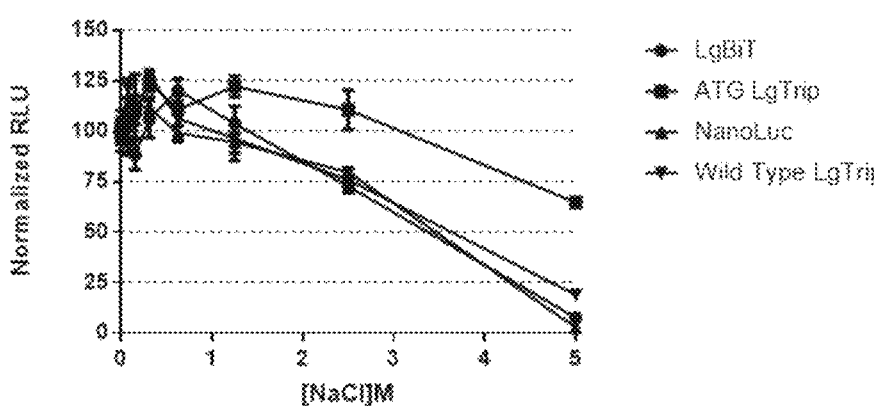

Experiments were conducted during development of embodiments herein to determine the effect of salt concentration on the activity of NanoLuc® (SEQ ID NO: 3), LgBIT (SEQ ID NO: 11) LgTrip 2098 (SEQ ID NO: 31) and LgTrip 3546 (SEQ ID NO: 51) (FIG. 16). To test activity in the presence of salt, each enzyme was diluted to 1 uM in TBS+0.01% BSA+0.01% Tergitol, and further diluted to 2 nM in TBS+0.01% BSA+0.01% Tergitol. 4 uM of pep 263 (SEQ ID NO: 35) was added to LgBiT, LgTrip 3546 (SEQ ID NO: 51), and LgTrip 2098 (SEQ ID NO: 31) and incubated for 30 minutes. A two-fold titration series was prepared for each, starting with 5M NaCl in 25 mM Tris pH 7.5+0.01% Tergitol. 10 uM furimazine was added to each sample of the titration series, and 5 ul of each enzyme or enzyme+pep263 (SEQ ID NO: 35) were combined with 45 ul of each substrate additive mixture. Plates were incubated for 3 minutes and then read on GMM+.

To test the effect of prolonged exposure to salt, each enzyme was diluted to 1 uM, and a two-fold titration series was prepared starting with 5M NaCl in 25 mM Tris pH 7.5+0.01% Tergitol. 2 ul of each enzyme was added to 198 ul of the NaCl titration (10 nM final of each enzyme). The "no" additive control was TBS+0.01% BSA+0.01% Tergitol. Samples were incubated for 26 hours. After incubation, samples were diluted 1:10,000 into TBS+0.01% BSA+0.01% Tergitol (10 ul in 990 two times). 4 uM pep263 (SEQ ID NO: 35) was added to LgTrip 2098 (SEQ ID NO: 31), LgTrip 3546 (SEQ ID NO: 51), and LgBIT (SEQ ID NO: 11) in the second dilution. 50 ul of each sample was combined with 50 ul of NanoGlo® buffer+50 uM Furimazine. Plates were incubated for 3 minutes and then read on GMM+.

Example 21

Effect of Urea on Activity

Figure 17A:
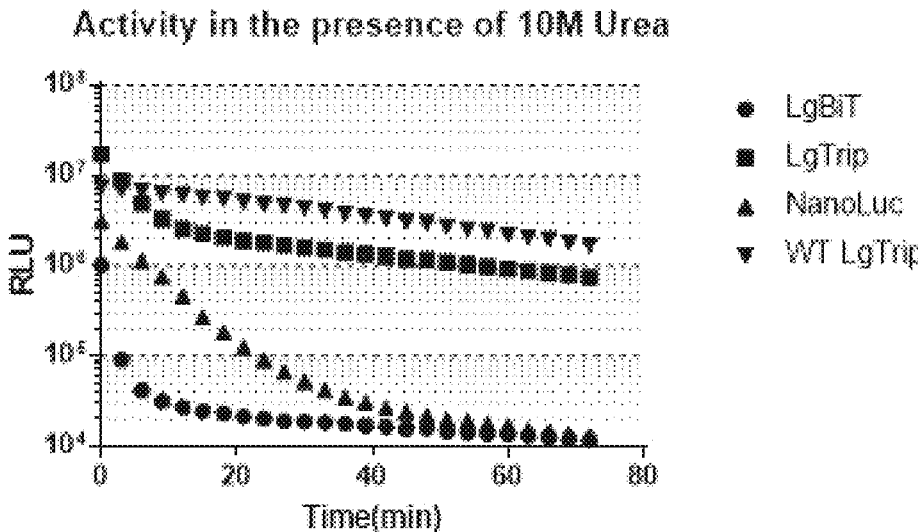
FIG. 17A-B. Graphs comparing LgBIT (SEQ ID NO: 11), NanoLuc (SEQ ID NO: 3), and LgTrip 3546 (SEQ ID NO: 51) and LgTrip 2098 (WT) (SEQ ID NO: 31) variants (A) in the presence urea and (B) after 26 hour exposure to urea.
Figure 17B:
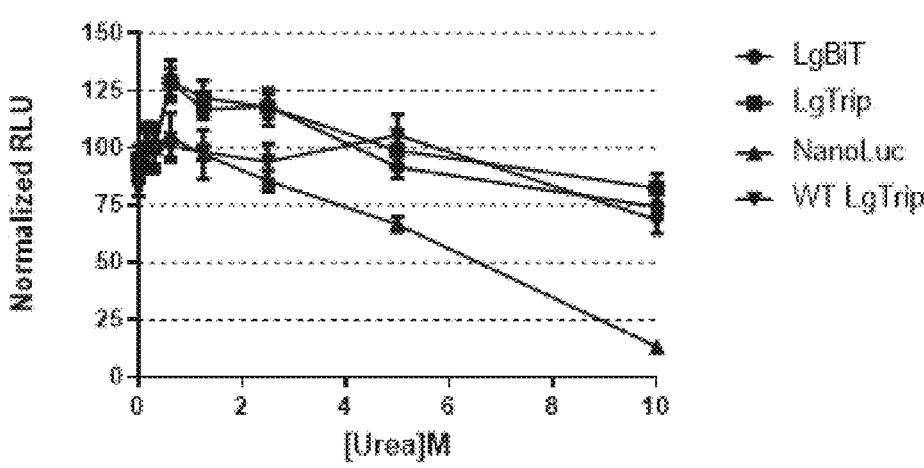

Experiments were conducted during development of embodiments herein to determine the effect of urea concentration on the activity of NanoLuc (SEQ ID NO: 3), LgBIT (SEQ ID NO: 11), LgTrip 2098 (SEQ ID NO: 31), and LgTrip 3546 (SEQ ID NO: 51) (FIG. 17).

To test activity in the presence of urea, each enzyme was diluted to 1 uM in TBS+0.01% BSA+0.01% Tergitol and further diluted to 2 nM in TBS+0.01% BSA+0.01% Tergitol. 4 uM of pep263 (SEQ ID NO: 35) was added to LgBIT (SEQ ID NO: 11), LgTrip 3546 (SEQ ID NO: 51), and LgTrip 2098 (SEQ ID NO: 31) and incubated for 30 minutes. A two-fold titration series was prepared for each, starting with 10M urea in 25 mM Tris pH 7.5+0.01% Tergitol. 10 uM furimazine was added to each sample of the titration series, and 5 ul of each enzyme or enzyme+pep263 (SEQ ID NO: 35) were combined with 45 ul of each substrate additive mixture. Plates were incubated for 3 minutes and then read on GMM+.

To test the effect of prolonged exposure to urea, each enzyme was diluted to 1 uM, and a two-fold titration series was prepared starting with 10M urea in 25 mM Tris pH 7.5+0.01% Tergitol. 2 ul of each enzyme was added to 198 ul of the urea titration (10 nM final of each enzyme). The "no" additive control was TBS+0.01% BSA+0.01% Tergitol. Samples were incubated for 26 hours. After incubation, samples were diluted 1:10,000 into TBS+0.01% BSA+0.01% Tergitol (10 ul in 990 ul two times). 4 uM pep263 (SEQ ID NO: 35) was added to LgTrip 2098 (SEQ ID NO: 31), LgTrip 3546 (SEQ ID NO: 51), and LgBIT (SEQ ID NO: 11) in the second dilution. 50 ul of each sample was combined with 50 ul of NanoGlo® buffer+50 uM Furimazine. Plates were incubated for 3 minutes and then read on GMM+.

The results demonstrate that NanoLuc and NanoBiT are more susceptible to inactivation by urea compared to LgTrip 3546, while LgTrip 2098 is the least effected by urea. The exposure results demonstrate that LgTrip 3546, LgTrip 2098, and LgBiT regain activity upon prolonged treatment with urea indicating that activity of these polypeptide may be negatively affected by contaminating proteins, and that denaturation of these contaminants enhances activity.

Example 22

Effect of pH on Activity

Experiments were conducted during development of embodiments herein to determine the effect of pH on the activity of NanoLuc® (SEQ ID NO: 3), LgBIT (SEQ ID NO: 11), LgTrip 2098 (WT) (SEQ ID NO: 31), and LgTrip 3546 (SEQ ID NO: 51) (FIG. 18).

A universal buffer was prepared containing 25 mM of each: NaCitrate, MES, PIPES, HEPES, TAPS, and Thiourea in 0.5% Tergitol. The buffer was divided into 8 aliquots of 20 ml, and NaOH or HCl was added to create a pH titration series.

To test effect of pH on activity, each enzyme was diluted to 1 uM and then diluted to 0.4 nM in 3 ml of TBS+0.01% BSA+0.01% Tergitol. 4 uM pep263 (SEQ ID NO: 35) was added to LgBiT, LgTrip 2098, and LgTrip 3546. Assay reagent for each pH buffer tested (Table 5) (20 ul of furimazine in 980 of buffer). 10 ul of each enzyme/peptide dilution was combined with 50 ul of assay reagent. Plates were incubated for 3 minutes and read on GMM+.

TABLE 5

| Buffers. | | |
|---|---|---|
| Component | MW(g/mol) | g |
| Na Citrate | 294.1 | 1.47 |
| MES | 195.24 | 0.98 |
| PIPES | 302.37 | 1.51 |
| Hepes | 238.3 | 1.19 |
| TAPS | 243.3 | 1.22 |
| Thiourea | 76.12 | 0.53 |

To test the effect of prolonged exposure varying pH, each enzyme was diluted to 1 uM in TBS+0.01% BSA+0.01% Tergitol, which was then diluted to 20 nM in each buffer. T=0 samples were mixed and then diluted 1:10 into 200 mM HEPES pH 7.5+0.01% BSA+0.01% Tergitol and stored at 4° C. T=8 samples were mixed and then diluted 1:10 into 200 mM HEPES pH 7.5+0.01% BSA+0.01% Tergitol store at 4° C. T=24 samples were mixed and then diluted 1:10 into 200 mM HEPES pH 7.5+0.01% BSA+0.01% Tergitol store at 4° C. To perform the assay, LgTrip and LgBiT were diluted 1:10 in TBS+0.01% BSA+0.01% Tergitol+4 uM SmTrip10 pep286 (SEQ ID NO: 35), and NanoLuc was diluted into TBS+0.01% BSA+0.01% Tergitol. 40 ul of each sample was diluted with 40 ul of NanoGlo® buffer+40 uM furimazine, incubated for 3 minutes, and then read on GMM+.

The results indicate that LgTrip is resistant to a wide pH range.

Example 23

Autoluminescence

Experiments were conducted during development of embodiments herein to compare the autoluminescence of LgBIT (SEQ ID NO: 11) and LgTrip 3546 (SEQ ID NO: 51). Each was diluted to 3 uM in DPBS+0.01% BSA. Three-fold serial dilutions were prepared of each in DPBS+0.01% BSA (300 ul to 700 ul) and placed in wells of a 96-well plate. The last row of the plate contained the furimazine controls (n=12). 50 ul of each titration (or controls) were combined with 50 ul of NanoGlo® buffer+50 uM furimazine, incubated for 3 minutes, and then read on GMM+. LgTrip (i.e., LgTrip 3546) exhibited significantly reduced autoluminescence compared to LgBiT (FIG. 19).

Example 24

Complementation of LgTrip with β9/β10 Dipeptide

Figure 20A:
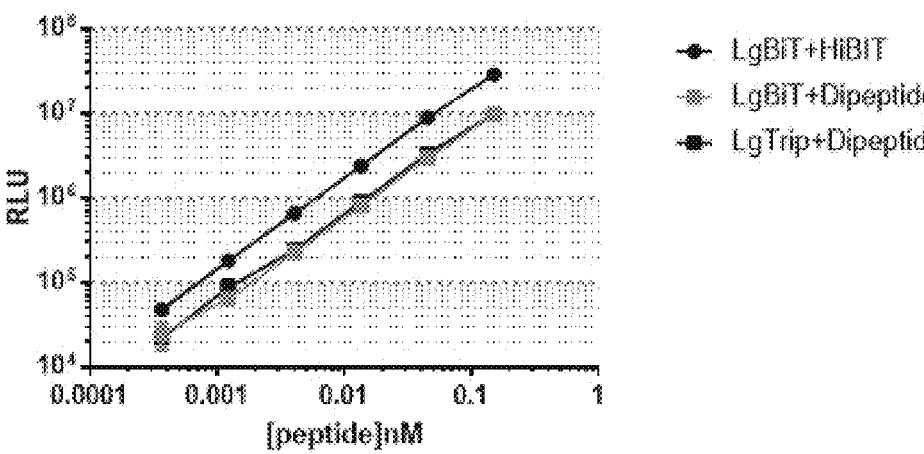
FIG. 20A-B. Graph comparing the luminescence of LgBIT (SEQ ID NO: 11)+SmTrip 10 pep86 (HiBiT; SEQ ID NO: 25), LgBIT (SEQ ID NO: 11)+pep263 (SEQ ID NO: 35) (β9/β10 dipeptide), and LgTrip 3546 (SEQ ID NO: 51)+pep263 (β9/β10 dipeptide) (SEQ ID NO: 35): (A) RLU and (B) signal/background (S/B).
Figure 20B:
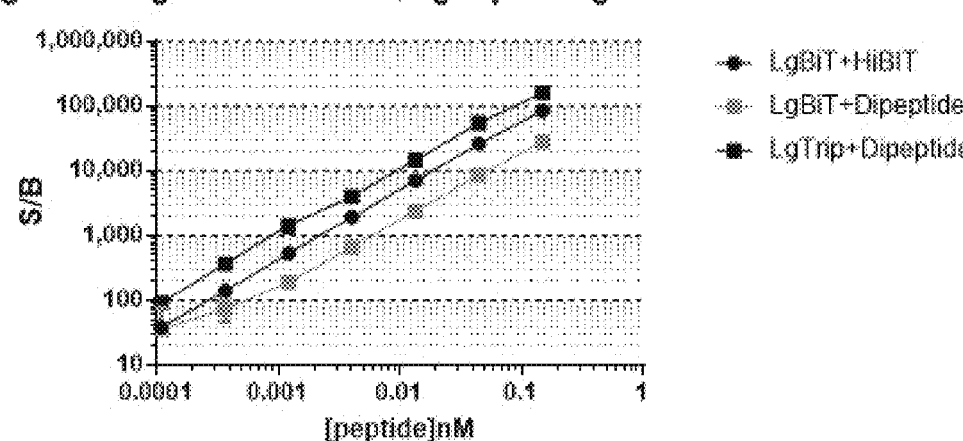

Experiments were conducted during development of embodiments herein to determine the capacity of a β9/β10 dipeptide (e.g., pep263) (SEQ ID NO: 35) to form a bioluminescent complex with either LgTrip 3546 (SEQ ID NO: 51) or LgBIT (SEQ ID NO: 11). The luminescence of such a complex was compared with the luminescence of complexes of LgTrip 3546 with β9/β10 dipeptide and LgBiT with either SmTrip10 pep86 (SmHiTrip; SEQ ID NO: 25) or the dipeptide, pep263 (SEQ ID NO: 35) (FIG. 20). SmTrip10 pep86 (SmHiTrip; SEQ ID NO: 25) and pep263 (SEQ ID NO: 35) were diluted to 2 nM in $H_2O$. A 3× dilution series was prepared of each peptide in TBS+0.01% BSA starting at 300 nM. Solutions of 200 nM LgTrip 3546 and LgBiT were prepared in NanoGlo® buffer+50 uM furimazine (NanoGlo® reagent). 50 ul of each titration were combined with 50 ul of each NanoGlo® reagent, and luminescence was read after a five minute incubation. Signal/background was calculated by dividing the amount of peptide dependent RLU by the background reading. Results demonstrate that the dipeptide has a $K_d$~2-3× higher than HiBiT which accounts for lower RLU at low peptide concentration. The background of LgBiT decreases signal to background. RLU values for LgBiT/dipeptide and LgTrip/dipeptide were equal.

Example 25

Comparison of LgTrip 2098 & LgTrip 3546 Complementation with SmTrip10 and SmTrip9

Figure 21A:
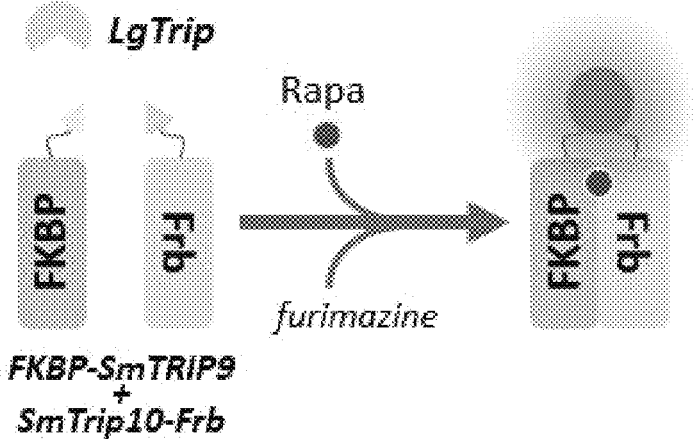
FIG. 21A-C. Facilitated complementation of LgTrip 2098 (SEQ ID NO: 31) and LgTrip 3546 (SEQ ID NO: 51), respectively with SmTrip10 pep86 (SEQ ID NO: 25) and SmTrip9 pep245 (SEQ ID NO: 23): (A) schematic of assay system, (B) RLU, and (C) signal/background (S/B).
Figure 21B:
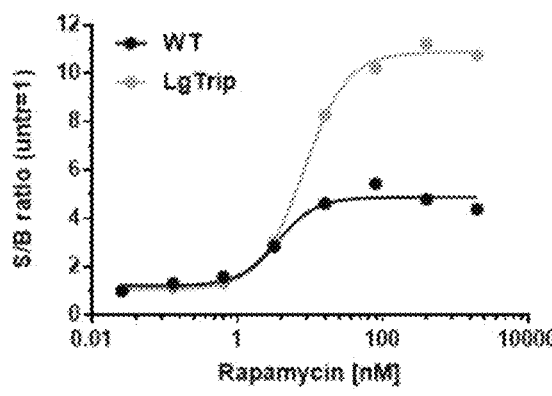
Figure 21C:
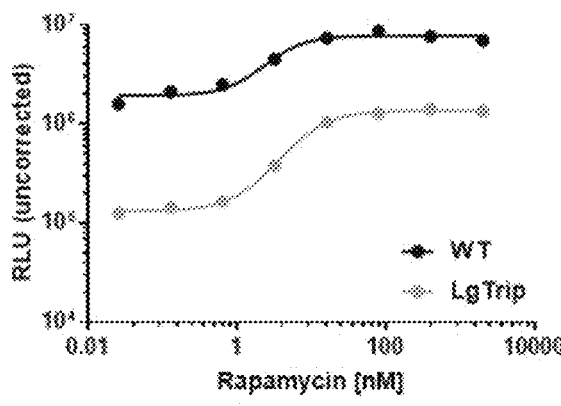

Experiments were conducted during development of embodiments herein to demonstrate complementation of LgTrip 2098 (SEQ ID NO: 31) & LgTrip 3546 (SEQ ID NO: 51), respectively, with SmTrip10 and SmTrip9 peptides, facilitated by the rapamycin-induced binding of SmTrip9 pep245-bound FKBP to SmTrip10 pep86-bound Frb (FIG. 21). FKBP-SmTrip9 pep245, SmTrip10 pep86-Frb, and LgTrip 3546 or LgTrip 2098 were transiently transfected into HEK293 cells (20,000 cells per well/96-well plate). Samples were exposed to serial dilutions of rapamycin (to induce FKBP/Frb complex formation) and 10 μM furimazine, and luminescence was measured. Results demonstrate that the affinity of SmTrip10 pep86 is ~10× lower for LgTrip 3546 compared to LgTrip 2098.

Example 26

Affinity of Various SmTrip10 Sequences

Figure 22:
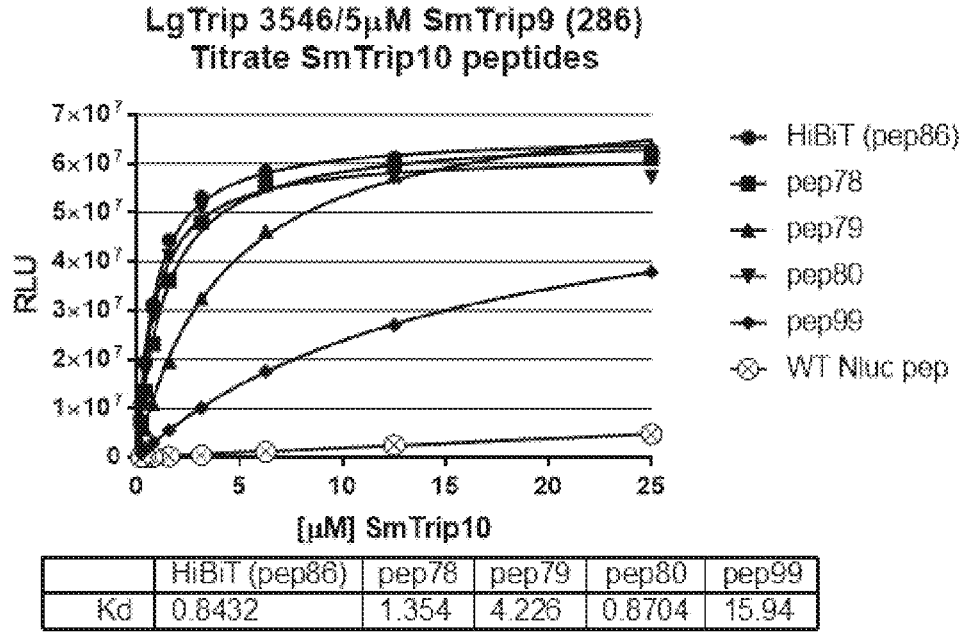
FIG. 22. Graph and table comparing the affinities of various SmTrip10 sequences for LgTrip 3546 (SEQ ID NO: 51) and SmTrip9 pep286 (SEQ ID NO: 37).

Experiments were conducted during development of embodiments herein forming luminescent complexes between various SmTrip10 pep286 (HiBIT; SEQ ID NO: 25) sequences and LgTrip 3546 (SEQ ID NO: 51)/SmTrip9 pep286 (SEQ ID NO: 37) (FIG. 22). Enzymes were diluted to 200 nM in TBS+0.01% BSA+0.01% Tergitol, serial dilutions (100 ul into 900 ul) were prepared in TBS+0.01% BSA+0.01% Tergitol (2× to make 2 nM), and 2 nM sample was diluted 1:10 into TBS+0.01% BSA+0.01% Tergitol (500 ul into 4.5 ml). A 2× dilution series was prepared of each SmTrip 10-like peptide in TBS+0.01% BSA+0.01% Tergitol+20 uM of SmTrip9 pep286 (SEQ ID NO: 37) starting at 100 uM. 50 ul of diluted LgTrip 3546 (SEQ ID NO: 51) was combined with 50 μl of the peptide titration and incubated for 10 minutes at room temperature. 100 μl of TBS+0.01% BSA+0.01% Tergitol+20 uM Furimazine was added to each sample, samples incubated for 10 minutes, and then read on GMM+.

Example 27

Inverse Dipeptide

Figure 23:
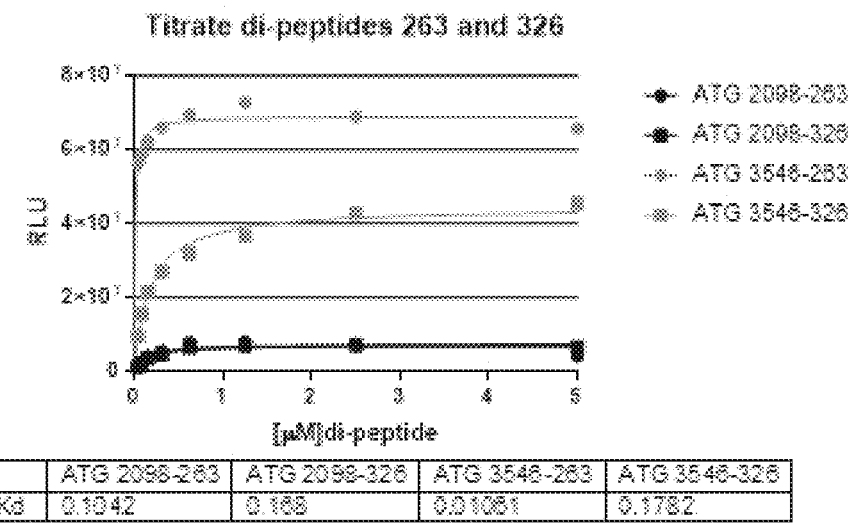
FIG. 23. Graph and table comparing the activation of LgTrip 2098 (SEQ ID NO: 31) and LgTrip 3546 (SEQ ID NO: 51) by standard-orientation (pep263) (SEQ ID NO: 35) and inverse-orientation (pep326) (SEQ ID NO: 179) dipeptides.

Experiments were conducted during development of embodiments herein to compare the capacity of dipeptides having opposite beta strand order (e.g., β9-β10 vs. β10-β9) to activate complement polypeptides (FIG. 23). LgTrip 3546 (SEQ ID NO: 51) and LgTrip 2098 (SEQ ID NO: 31) were diluted to 200 nM in TBS+0.01% BSA+0.01% Tergitol, and serial dilutions of each were prepared (100 ul into 900 ul) in TBS+0.01% BSA+0.01% Tergitol. The 2 nM sample was diluted 1:10 into TBS+0.01% BSA+0.01% Tergitol (500 ul into 4.5 ml). 20 uM stocks of each dipeptide (pep326 (SEQ ID NO: 179) and pep263 (SEQ ID NO: 35)) were prepared in TBS+0.01% BSA+0.01% Tergitol. 2× serial dilutions of each peptide were prepared TBS+0.01% BSA+0.01% Tergitol (250 ul in 250 ul). 50 ul diluted LgTrip 2098 and LgTrip 3546 was combined with 50 μl of the each peptide series and incubated at room temperature for 20 minutes. 100 ul of LCS (Live cell substrate; Promega Catalog No. N205) in TBS (20 uM) was added, and samples were incubated for 3 minutes and then read on GMM+.

Example 28

Figure 24:
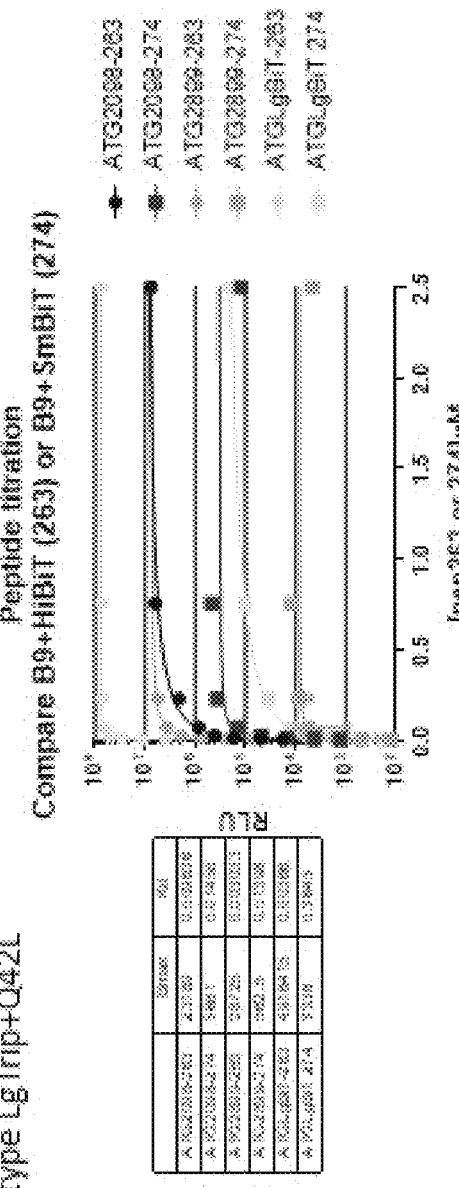
FIG. 24. Graph and table depicting activation of complement polypeptides by dipeptides comprising the HiBiT or SmBIT sequence. Dipeptide with HiBiT sequence pep263 (SEQ ID NO: 35) or Dipeptide with SmBiT sequence pep274 (SEQ ID NO: 147)

Comparison of Dipeptides Comprised of SmTrip9 (SEQ ID NO: 23) and Either SmHiTrip (SEQ ID NO: 25) or SmBIT (SEQ ID NO: 13) for the SmTrip10 Component Experiments were conducted during development of embodiments herein to compare the capacity of dipeptides comprising the SmHiTrip (SEQ ID NO:25) or SmBIT (SEQ ID NO:13) sequence to activate complement polypeptides (FIG. 24). LgBiT, LgTrip 2098, and LgTrip 2899 (SEQ ID NO: 364) were diluted to 200 nM into TBS+0.01% BSA. Polypeptides were further diluted 1:100 into NanoGlo® buffer+50 uM Furimazine (30 ul in 3 ml). Pep263 (SEQ ID NO: 35) and pep274 (SEQ ID NO: 147) were diluted into TBS+0.01% BSA to 5 uM. 50 ul of each LgBiT/LgTrip dilution were combined with 50 μl of peptide dilution, incubated 5 minutes, and then read on GMM+.

Example 29

Additions/Deletions of C-Terminus of LGTrip 3546

Experiments were conducted during development of embodiments herein to determine the effect of C-terminal additions/deletions and/or corresponding additions/deletions to peptide tags on complementation and luminescence (FIG. 25). Exemplary tested peptides and polypeptides are listed in Table 6.

TABLE 6

Peptide tags and polypeptide components comprising additions/deletions
SmTrip9   SmTrip10
LITPDGSMLFRVTINSVGWRLFKKIs
Note: SmTrip9 peptides contain additional
SSWKR sequence at their N-termini.

| LgTrip | C-term | SmTrip9 | ID | SmTrip10 | ID |
|---|---|---|---|---|---|
| ATG-3575 (aka LgTrip + GS) | --LITPDGS | MLFRVTINS | 292 | VSGWRLFKKIS | 86 |
| ATG-3572 (aka LgTrip + G) | --LITPDG | SMLFRVTINS | 291 | VSGWRLFKKIS | 86 |
| ATG-3573 (aka LgTrip - D) | --LITP | DGSMLFRVTINS | 293 | VSGWRLFKKIS | 86 |
| ATG-3574 (aka LgTrip - PD) | --LIT | PDGSMLFRVTINS | 294 | VSGWRLFKKIS | 86 |
| | | | | | |
| ATG-3575 (aka LgTrip + GS) | --LITPDGS | MLFRVTINSV | 297 | SGWRLFKKIS | 219 |
| ATG-3572 (aka LgTrip + G) | --LITPDG | SMLFRVTINSV | 296 | SGWRLFKKIS | 219 |
| ATG-3573 (aka LgTrip - D) | --LITP | DGSMLFRVTINSV | 298 | SGWRLFKKIS | 219 |
| ATG-3574 (aka LgTrip - PD) | --LIT | PDGSMLFRVTINSV | 299 | SGWRLFKKIS | 219 |
| | | | | | |
| ATG-3575 (aka LgTrip + GS) | --LITPDGS | MLFRVTINSVS | 302 | GWRLFKKIS | 206 |
| ATG-3572 (aka LgTrip + G) | --LITPDG | SMLFRVTINSVS | 301 | GWRLFKKIS | 206 |
| ATG-3573 (aka LgTrip - D) | --LITP | DGSMLFRVTINSVS | 303 | GWRLFKKIS | 206 |
| ATG-3574 (aka LgTrip - PD) | --LIT | PDGSMLFRVTINSVS | 304 | GWRLFKKIS | 206 |
| | | | | | |
| ATG-3575 (aka LgTrip + GS) | --LITPDGS | MLFRVTIN | 308 | SVSGWRLFKKIS | 157 |
| ATG-3572 (aka LgTrip + G) | --LITPDG | SMLFRVTIN | 307 | SVSGWRLFKKIS | 157 |
| ATG-3573 (aka LgTrip - D) | --LITP | DGSMLFRVTIN | 309 | SVSGWRLFKKIS | 157 |
| ATG-3574 (aka LgTrip - PD) | --LIT | PDGSMLFRVTIN | 310 | SVSGWRLFKKIS | 157 |
| | | | | | |
| ATG-3575 (aka LgTrip + GS) | --LITPDGS | MIFRVTI | 312 | NSVSGWRLFKKIS | 158 |
| ATG-3572 (aka LgTrip + G) | --LITPDG | SMLFRVTI | 311 | NSVSGWRLFKKIS | 158 |
| ATG-3573 (aka LgTrip - D) | --LITP | DGSMIFRVTI | 313 | NSVSGWRLFKKIS | 158 |
| ATG-3574 (aka LgTrip - PD) | --LIT | PDGSMLFRVTI | 314 | NSVSGWRLFKKIS | 158 |
| | | | | | |
| ATG-3546 (aka LgTrip) | --LITPD | GSMLFRVTINSV | 295 | SGWRLFKKIS | 219 |
| ATG-3546 (aka LgTrip) | --LITPD | GSMLFRVTINSVS | 300 | GWRLFKKIS | 206 |
| ATG-3546 (aka LgTrip) | --LITPD | GSMLFRVTIN | 305 | SVSGWRLFKKIS | 157 |
| ATG-3546 (aka LgTrip) | --LITPD | GSMLFRVTI | 306 | NSVSGWRLFKKIS | 158 |

Addition/deletion polypeptides were grown in 50 ml cultures, pelleted, and resuspended in 10 ml of 100 mm HEPES pH 7.5+0.001 U/ml DNase. 1 ml of Fastbreak Cell Lysis Reagent (Promega Corporation) and 1 ml of HisLink Resin (Promega Corporation) were added and incubated on a rotating shaker for 3 hours at 4° C. Resin was allowed to settle, and samples were washed 4× with 100 mM HEPES pH 7.5+10 mM Imidazole. Polypeptides were eluted twice into 500 ul HisLink Elution buffer. Thermo dialysis tubes were used to equilibrate to 1×TBS.

Enzymes were diluted to 200 nM in TBS+0.01% BSA+ 0.01% Tergitol, and serial dilutions were prepared (100 ul into 900 ul) in TBS+0.01% BSA+0.01% Tergitol. 2 nM samples were diluted 1:10 into TBS+0.01% BSA+0.01% Tergitol (500 ul into 4.5 ml). SmTrip9- and SmTrip10-like peptides were combined with a polypeptide complement according to Table 7 and incubated for 10 minutes at room temperature. 100 μl of TBS+0.01% BSA+0.01% Tergitol+ 20 uM furimazine was added, incubated for 10 minutes, and then read on GMM+.

TABLE 7

Polypeptide/peptide combinations tested.

| | SmTrip 9 | SmTrip10 |
|---|---|---|
| Group 1 | | |
| 3546 | 286 | 86 |
| 3575 | 292 | 86 |
| 3572 | 291 | 86 |
| 3573 | 293 | 86 |
| 3574 | 294 | 86 |

TABLE 7-continued

Polypeptide/peptide combinations tested.

| | SmTrip 9 | SmTrip10 |
|---|---|---|
| Group 2 | | |
| 3546 | 286 | 86 |
| 3575 | 297 | 219 |
| 3572 | 296 | 219 |
| 3573 | 298 | 219 |
| 3574 | 299 | 219 |

TABLE 7-continued

| Polypeptide/peptide combinations tested. | | |
| --- | --- | --- |
| | SmTrip 9 | SmTrip10 |
| Group 3 | | |
| 3546 | 286 | 86 |
| 3575 | 302 | 206 |
| 3572 | 302 | 206 |
| 3573 | 303 | 206 |
| 3574 | 304 | 206 |
| Group 4 | | |
| 3546 | 286 | 86 |
| 3575 | 312 | 158 |
| 3572 | 312 | 158 |
| 3573 | 312 | 158 |
| 3574 | 312 | 158 |
| Group 5 | | |
| 3546 | 286 | 86 |
| 3546 | 295 | 219 |
| 3546 | 300 | 206 |
| 3546 | 305 | 157 |
| 3546 | 306 | 158 |

Example 30

Polypeptide/Peptide and/or Peptide/Peptide Overlap

Figure 26A:
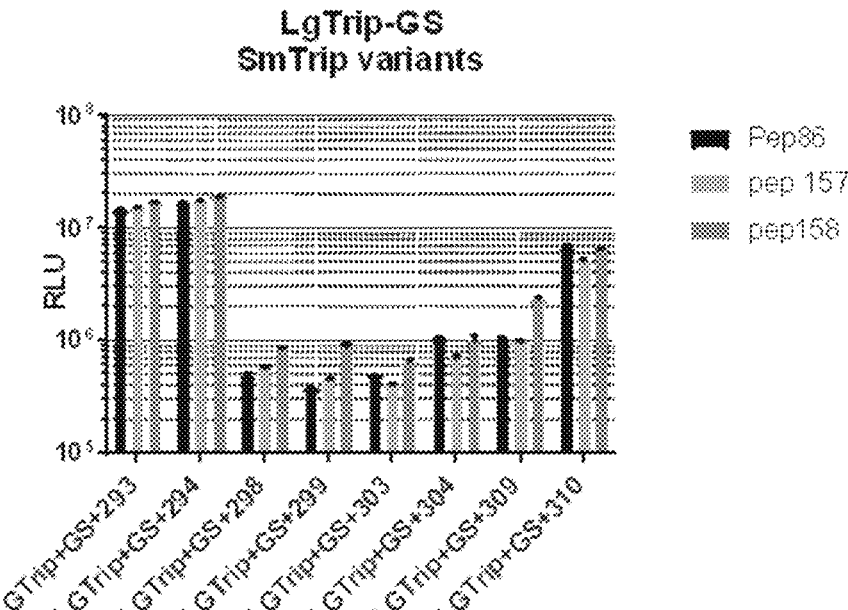
FIG. 26A-C. (A-C) Graphs depicting luminescence produced by polypeptide/peptide combinations having overlap (relative to a base luciferase sequence) between the polypeptide component and a peptide corresponding to the β9-strand or between the β9 and β10-like peptides.
Figure 26B:
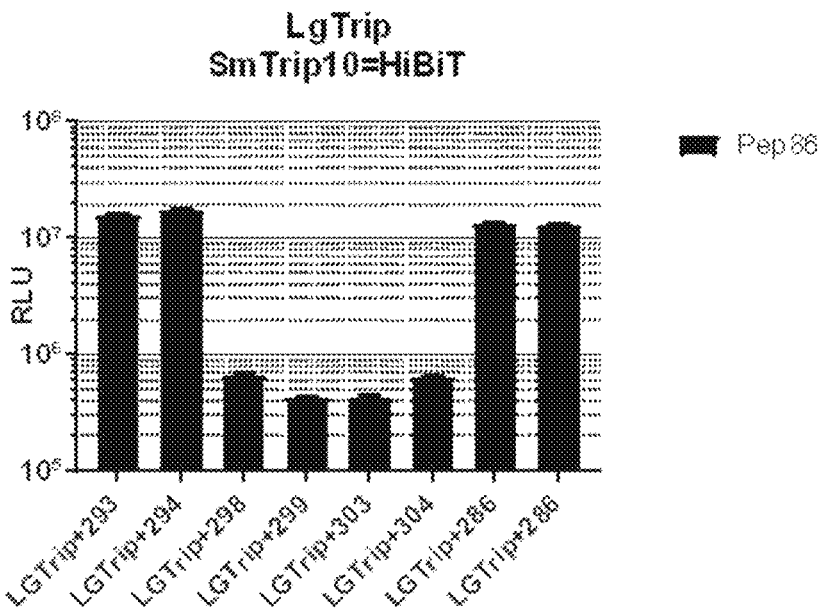
Figure 26C:
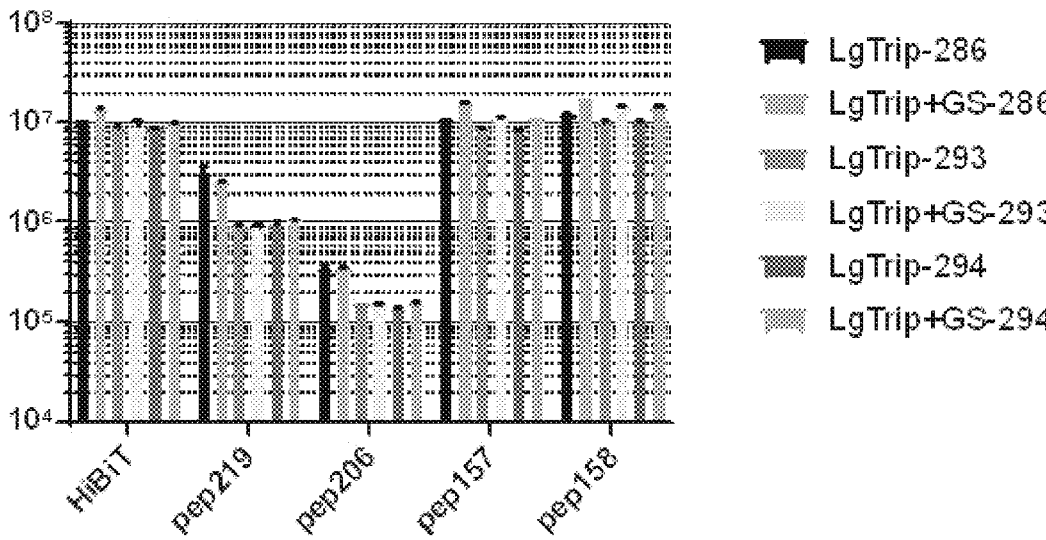

Experiments were conducted during development of embodiments herein to determine the sequence overlap between the polypeptide component and a peptide corresponding to the β-strand or between the two peptides (FIG. 26). In such experiments, a polypeptide component and peptide, or the two peptides, each comprise amino acids corresponding to the same amino acids in a base luciferase.

Polypeptides were diluted to 200 nM in TBS+0.01% BSA+0.01% Tergitol. Serial dilutions (100 ul into 900 ul) were prepared in TBS+0.01% BSA+0.01% Tergitol. 2 nM of each polypeptide sample were diluted 1:10 into TBS+0.01% BSA+0.01% Tergitol (500 into 4.5 ml). Polypeptides and peptides were combined, i.e., 50 ul of each LgTrip mutant with 50 μl of the peptide, according to Table 8. Reactions were incubated for 10 minutes at room temperature. Next, 100 μl of TBS+0.01% BSA+0.01% Tergitol+20 uM furimazine was added, and reactions were incubated for 10 more minutes prior to reading on a GMM+ luminometer.

TABLE 8

| Polypeptide/peptide combinations tested. | | |
| --- | --- | --- |
| | SmTrip9 | SmTrip10 |
| Group1 | | |
| 3546 | 286 | 86 |
| 3546 | 286 | 219 |
| 3546 | 286 | 206 |
| 3546 | 286 | 157 |
| 3546 | 286 | 158 |
| Group2 | | |
| 3575 | 286 | 86 |
| 3575 | 286 | 219 |
| 3575 | 286 | 206 |
| 3575 | 286 | 157 |
| 3575 | 286 | 158 |

TABLE 8-continued

| Polypeptide/peptide combinations tested. | | |
| --- | --- | --- |
| | SmTrip9 | SmTrip10 |
| Group3 | | |
| 3546 | 293 | 86 |
| 3546 | 293 | 219 |
| 3546 | 293 | 206 |
| 3546 | 293 | 157 |
| 3546 | 293 | 158 |
| Graup4 | | |
| 3575 | 293 | 86 |
| 3575 | 293 | 86 |
| 3575 | 293 | 86 |
| 3575 | 293 | 86 |
| 3575 | 293 | 86 |
| Group5 | | |
| 3546 | 294 | 86 |
| 3546 | 294 | 219 |
| 3546 | 294 | 206 |
| 3546 | 294 | 157 |
| 3546 | 294 | 158 |
| Group6 | | |
| 3575 | 294 | 86 |
| 3575 | 294 | 219 |
| 3575 | 294 | 206 |
| 3575 | 294 | 157 |
| 3575 | 294 | 158 |

Example 31

The Identity of the β9-Peptide Alters the Affinity of the β10-Peptide

Figure 27A:
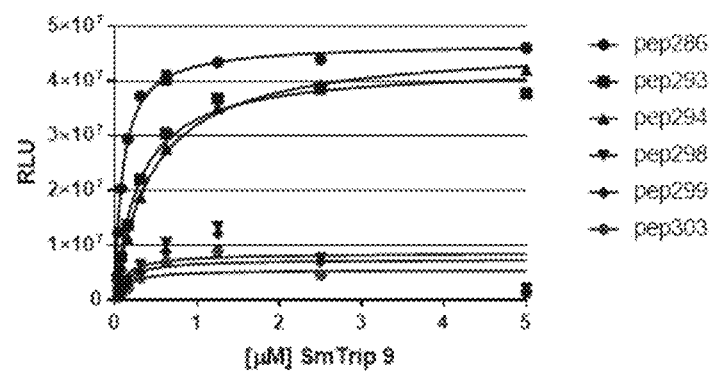
FIG. 27A-B. Figures and tables depicting luminescence resulting from (A) the titration of various β9-like peptides (SmTrip9 peptides) in the present of constant LgTrip 3546 (SEQ ID NO: 51) and SmTrip10 pep86 (SEQ ID NO: 25) concentrations, and (B) the titration of SmTrip10 pep86 (SEQ ID NO: 25) in the presence of constant concentrations of LgTrip 3546 (SEQ ID NO: 51) and various β9-like peptides (SmTrip9 peptides).
Figure 27B:
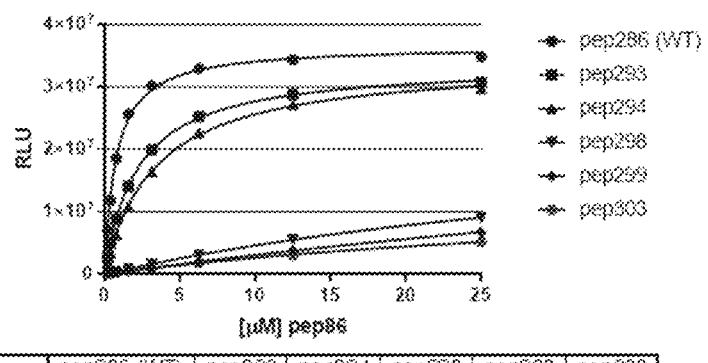

Experiments were conducted during development of embodiments herein to determine the sequence overlap between the polypeptide component and a peptide corresponding to the β-strand or between the two peptides (FIG. 27). These results show that the sequence of the β9 strand peptide (SmTrip9) can impact the affinity of the β10 strand peptide (SmTrip10). SmTrip9 titration LgTrip 3546 (SEQ ID NO: 51) was diluted to 200 nM in TBS+0.01% BSA+0.01% Tergitol, and serial dilutions were prepared (100 ul into 900 ul) in TBS+0.01% BSA+0.01% Tergitol. 2 nM polypeptide samples were diluted 1:10 into TBS+0.01% BSA+0.01% Tergitol (500 into 4.5 ml).

A 2× dilution series was prepared of each SmTrip9 peptide in TBS+0.01% BSA+0.01% Tergitol+100 uM of SmTrip10 pep86 (SEQ ID NO: 25) starting at 20 uM. 50 ul of diluted LgTrip 3546 (SEQ ID NO: 51) was combined with 50 ul of each peptide titration. Reactions were incubated for 10 minutes at room temperature. 100 μl of TBS+0.01% BSA+0.01% Tergitol+20 uM furimazine was added, the reaction was incubated for 10 more minutes, and read on a GMM+.

SmTrip 10 Titration

LgTrip 3546 (SEQ ID NO: 51) was diluted to 200 nM in TBS+0.01% BSA+0.01% Tergitol, and serial dilutions were prepared (100 ul into 900 ul) in TBS+0.01% BSA+0.01% Tergitol. 2 nM polypeptide samples were diluted 1:10 into TBS+0.01% BSA+0.01% Tergitol (500 into 4.5 ml).

A 2× dilution series was prepared of SmTrip10 pep86 (SEQ ID NO: 25) in TBS+0.01% BSA+0.01% Tergitol+20 uM of SmTrip9-like peptides starting at 100 uM. 50 ul of diluted LgTrip 3546 was combined with 50 ul of each peptide titration. Reactions were incubated for 10 minutes at room temperature. 100 μl of TBS+0.01% BSA+0.01% Tergitol+20 uM furimazine was added, reaction was incubated for 10 more minutes, and then read on GMM+.

Results (FIG. 27)

SmTrip 9 peptide variants were titrated in the presence of constant SmTrip10 ep86 (SEQ ID 15) (FIG. 27a), and then SmTrip10 pep86 was titrated in the presence of saturating amounts of each SmTrip9 variant peptide. (FIG. 27b) This shows that the affinity of the SmTrip10 sequence can be altered depending on the SmTrip9 sequence. The experiments demonstrate that identity of the β9-like peptide (e.g., SmTrip9) can influence the affinity of the β10-like peptide (e.g., SmTrip10) for the polypeptide component. SmTrip9 pep293 (SEQ ID NO: 154) and SmTrip9 pep294 (SEQ ID NO: 155) sequences have overlap with the C-terminus of LgTrip 3546 (SEQ ID NO: 51) and show a decrease in affinity compared to SmTrip9 pep286 (SEQ ID NO: 37) (no overlap), but also decrease affinity of SmTrip10 pep86 (SmHiTrip; SEQ ID NO: 25) for LgTrip 3546. SmTrip9 pep298 (SEQ ID NO: 158) and SmTrip9 pep299 (SEQ ID NO: 159) sequences overlap with the C-terminus of LgTrip 3546 and the N-terminus of SmTrip10 pep86 (SmHiTrip; SEQ ID NO: 25) and decrease the affinity of SmTrip10 pep86 (HiBiT) for or LgTrip 3546.

Example 32

Figure 28:
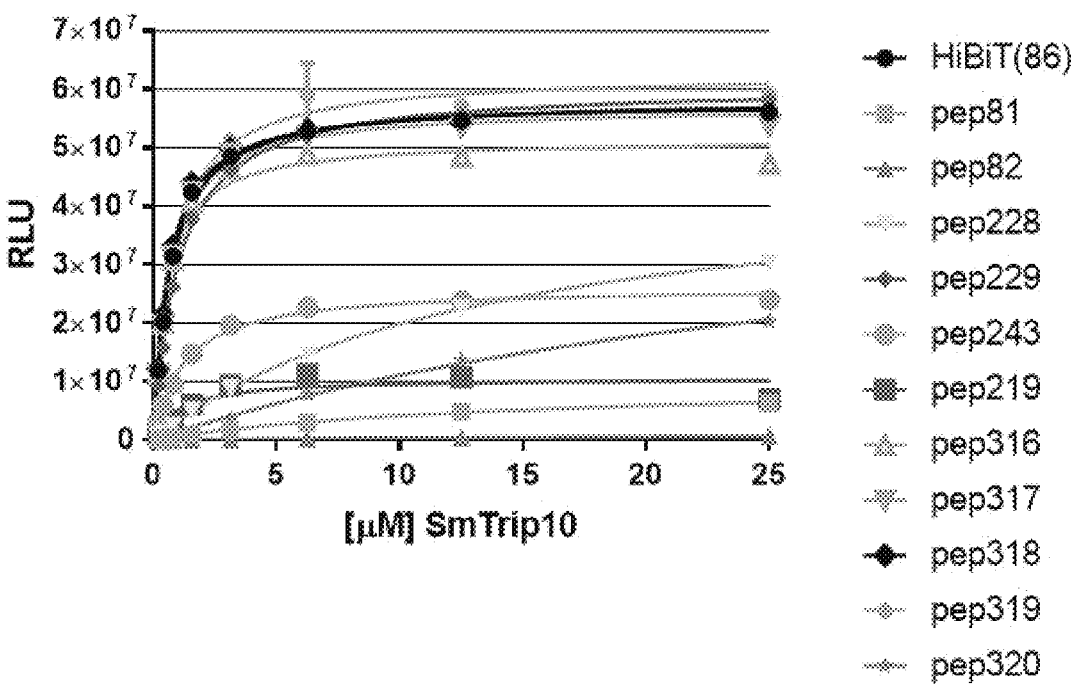
FIG. 28. Figure and table depicting luminescence resulting from the titration of various β10-like peptides (SmTrip 10 peptides) in the present of constant concentrations of LgTrip 3546 (SEQ ID NO: 51) and SmTrip9 pep286 (SEQ ID NO: 37).

Effect of β10-Peptide Identity on the Affinity of the β10 Peptide Component to the Polypeptide and β9-Peptide Experiments were conducted during development of embodiments herein to determine the how sequence overlaps or sequence gaps between the polypeptide component and a peptide corresponding to the β-strands or between the two peptides influence the affinity of the β10-like (e.g., SmTrip10) peptides (FIG. 28). LgTrip 3546 (SEQ ID NO: 51) was diluted to 200 nM in TBS+0.01% BSA+0.01% Tergitol, and serial dilutions were prepared (100 ul into 900 ul) in TBS+0.01% BSA+0.01% Tergitol. 2 nM polypeptide samples were diluted 1:10 into TBS+0.01% BSA+0.01% Tergitol (500 into 4.5 ml). A 2× dilution series was prepared of each SmTrip10-like peptide in TBS+0.01% BSA+0.01% Tergitol+20 uM of SmTrip9 pep286 (SEQ ID NO: 37) starting at 100 uM. 50 ul of diluted LgTrip 3546 was combined with 50 ul of each peptide titration. Reactions were incubated for 10 minutes at room temperature. 100 ul of TBS+0.01% BSA+0.01% Tergitol+20 uM furimazine was added, reaction was incubated for 10 more minutes, and then read on GMM+.

Example 33

Figure 29A:
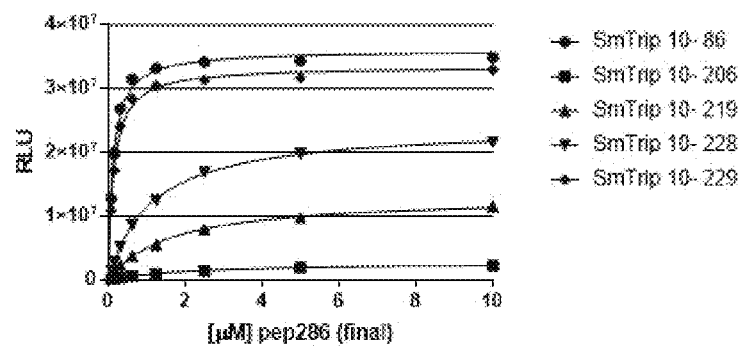
FIG. 29A-B. Figures and tables depicting titration of β9-like peptides (A) SmTrip9 pep286 (SEQ. ID 37) and (B) SmTrip9 pep287 (SEQ ID NO: 148) in the presence of constant concentration of various β10-like peptides (SmTrip10 peptides) and LgTrip 3546 (SEQ ID NO: 51) polypeptide component.
Figure 29B:
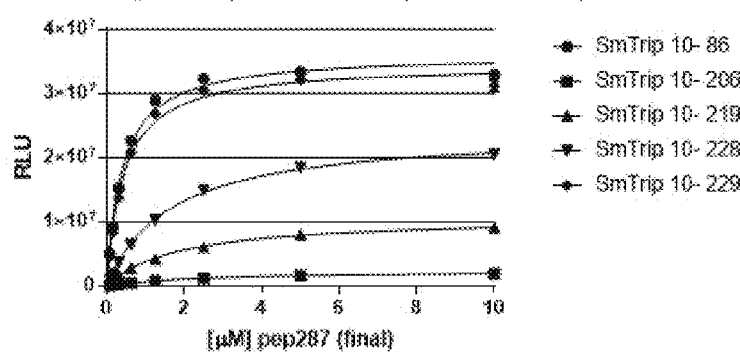

Measure of Affinity of β9-Like Peptides in the Presence of Various Saturating β10-Like Peptides Experiments were conducted during development of embodiments herein to determine the how the affinity of β9-like (e.g., SmTrip9) peptides are impacted in the presence of constant concentrations of various β10-like (e.g., SmTrip10) peptides with LgTrip 3546 (SEQ ID NO: 51) (FIG. 29). Polypeptide component LgTrip 3546 was diluted to 200 nM in TBS+0.01% BSA+0.01% Tergitol, serial dilutions were prepared (100 ul into 900 ul) in TBS+0.01% BSA+0.01% Tergitol (2× to make 2 nM), and 2 nM sample was diluted 1:10 into TBS+0.01% BSA+0.01% Tergitol (500 ul into 4.5 ml). A 2× dilution series was prepared of each β9-like peptide (SmTrip9 pep286 (SEQ ID NO: 37) and SmTrip9 pep287 (SEQ ID NO: 148)) in TBS+0.01% BSA+0.01% Tergitol+100 uM of each SmTrip10-like peptide starting at 20 uM. 50 ul of diluted LgTrip 3546 (SEQ ID NO: 51) was combined with 50 ul of each peptide titration. The reactions were incubated for 10 minutes at room temperature, 100 μl of TBS+0.01% BSA+0.01% Tergitol+20 uM furimazine was added, and the reactions were incubated for another 10 minutes and then read on GMM+.

Example 34

Figure 30:
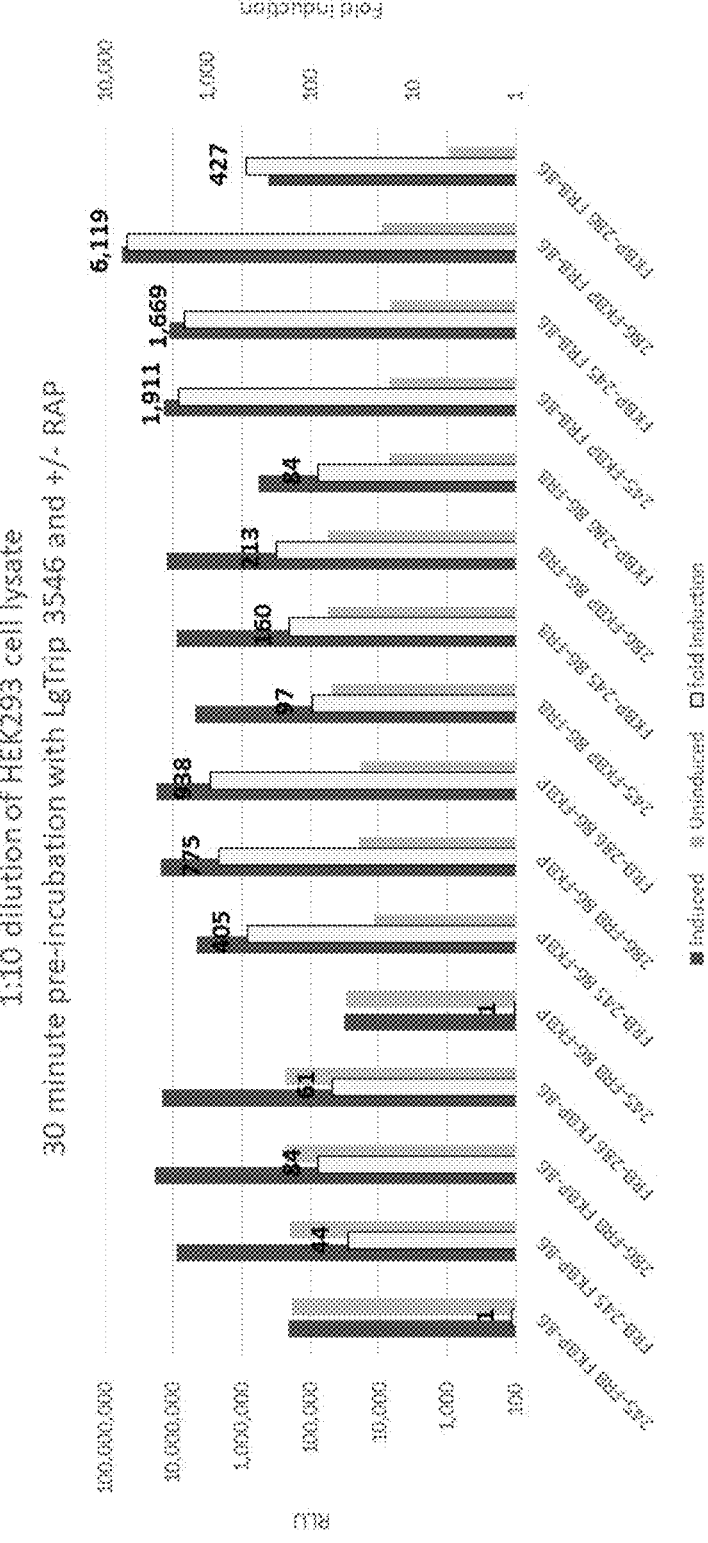
FIG. 30. Graph depicting the effect of construct orientation (β9-FKBP, FKBP-β9, β10-FKBP, FKBP-β10, β9-FRB, FRB-β9, β10-FRB, or FRB-β10) on facilitated complementation in HEK293 cells.

Effect of Construct Orientation on Facilitated Complementation in HEK293 Cells Experiments were conducted during development of embodiments herein to determine the effect the orientation of interaction elements (FRB and FKBP) relative to the peptide tags on complementation with LgTrip 3546 (SEQ ID NO: 51) (FIG. 30). Un-induced signal greater than 100,000 RLU is indicative of background contamination, which decreases the apparent fold-response.

HEK293 cells were grown overnight at 37° C. with 5% $CO_2$. Cells were transfected with 3 ug DNA (SmTrip9 pep245-FKBP, FKBP-SmTrip9 pep245, SmTrip10 pep86-FKBP, FKBP-SmTrip10 pep86, SmTrip9 pep245-FRB, FRB-SmTrip9 pep245, SmTrip10 pep86-FRB, or FRB-SmTrip10 pep86 construct) per well using FuGENE protocol. Cells were washed in DPBS. 1 ml DPBS was added, cells were frozen at −80 C for ~10 min, and thawed at room temperature. Lysates were cleared by centrifugation for 10 minutes, diluted 1:10 in TBS+200 nM LgTrip (+/−30 nM RAP), and incubated for 30 min at room temperature. 50 ul of each sample was combined with 50 ul of TBS+20 uM Furimazine, and luminescence was read at 5 minutes.

Example 35

Effect of Construct Orientation on Facilitated Complementation in *E. coli*

Figure 31:
FIG. 31. Graph depicting the effect of construct orientation (β9-FKBP, FKBP-β9, β10-FKBP, FKBP-β10, 9-FRB, FRB-β9, β10-FRB, or FRB-β10) on facilitated complementation in *E. coli* cells.

Experiments were conducted during development of embodiments herein to determine the effect the orientation of interaction elements (FRB and FKBP) relative to the peptide tags on complementation with LgTrip 3546 (SEQ ID NO: 51) (FIG. 31).

Overnight cultures of each construct were prepared in LB+100 ug/ml ampicillin. Cultures were diluted 1:100 into induction media (LB+amp+0.1% rhamnose+0.15% glucose, cells were grown for 20 hours at 25° C., and lysed with PLB lysis buffer (0.3×PLB, 25 mM Hepes pH 7.5, 0.001 U/ul Rq1 DNase; 250 ul of cells, 750 ul PLB) for 15 minutes. Cells were diluted 5× into $CO_2$ independent media+10% FBS that contains 200 nM LgTrip 3546 and +/−30 nM RAP. Reactions were incubated for 30 minutes at room temperature, combined with equal volumes of NanoGlo+50 uM furimazine (50 ul to 50 ul), incubated for 5 minutes, and then read on GMM+

Example 36

Kd Measurement for Various β10-Like Peptides

Figure 32:
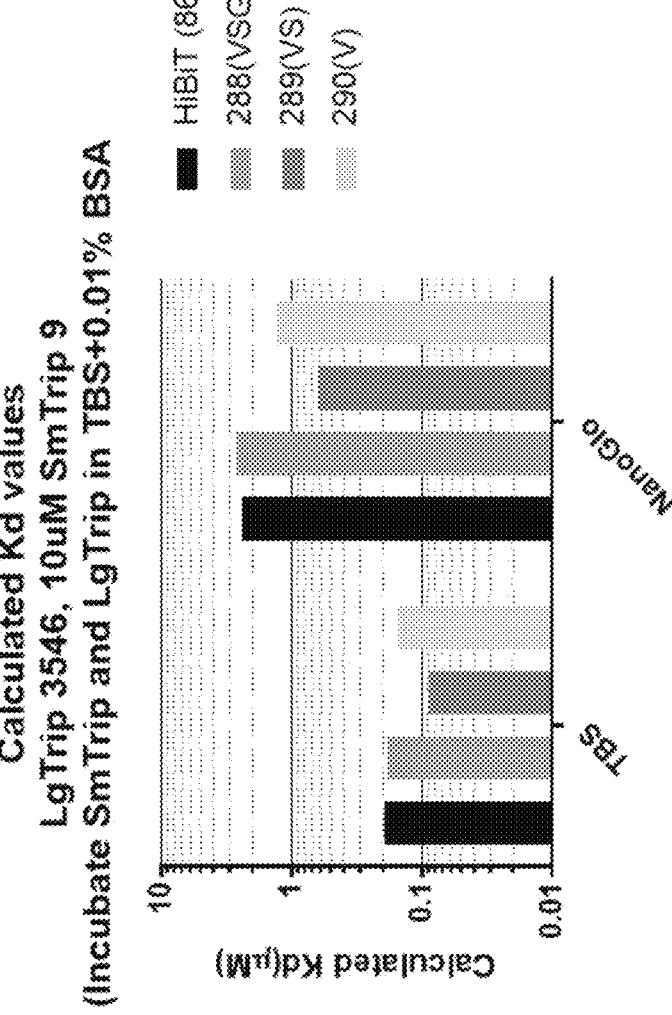
FIG. 32. Graph depicting calculated Kd values for various β10-like peptides with LgTrip 3546 (SEQ ID NO: 51) and SmTrip9 pep286 (SEQ ID NO: 37).

Experiments were conducted during development of embodiments herein to measure $K_d$ values for various β10-like peptides with LgTrip 3546 (SEQ ID NO: 51) and SmTrip9 pep286 (SEQ ID NO: 37) (FIG. 32). A solution was prepared of 20 uM SmTrip9 pep286 (SEQ ID NO: 37) in TBS+0.005%+0.01% BSA. 3× serial dilutions were prepared of SmTrip10 pep86 (SmHiTrip; SEQ ID NO: 25), SmTrip10 pep288 (SEQ ID NO: 149), SmTrip10 pep289 (SEQ ID NO: 150), and SmTrip10 pep290 (SEQ ID NO: 151) (150 ul in 350 ul TBS+0.01% BSA+286 solution starting at 100 uM). 20 nM LgTrip 3546 solutions were prepared in TBS+0.01% BSA, and then diluted 1:10 in TBS+0.01% BSA. 25 ul of each peptide solution was combined with 2.5 ul of the LgTrip 3546 solutions. Reactions were incubated for 10 minutes, 28 ul of TBS+20 uM LCS (Promega Catalog No. N205) was added, incubated for 10 minutes, and then read on GMM+. This experiment shows that the addition of either "V" or "VS" to the N-terminus of SEQ ID NO: 25 increases the affinity of the SmTrip10-like peptide compared to SmTrip10 pep86 (HiBiT).

Example 37

Effect of Polypeptide/β9 Split Site on Luciferase Light Output

Experiments were conducted during development of embodiments herein to analyze the effect of moving the split site between the polypeptide component and the SmTrip9-like peptide (FIG. 33). Polypeptide components with varied C-terminal extensions or deletions were diluted to 0.2 nM in TBS+0.01% BSA+0.01% Tergitol, and 50 uM SmTrip10 pep86 (SEQ ID NO: 25) was added to each. SmTrip9 pep286 (SEQ ID NO: 37) was added to 10 uM in the SmTrip10 pep86+LgTrip solutions, and samples were incubated for 10 minutes. TBS+0.01% BSA+0.01% Tergitol+20 uM furimazine detection reagent was added at 1:1, and luminescence was read. All synthetic SmTrip9 peptides contained the N-terminal solubility tag SSWKR.

Example 38

Figure 34:
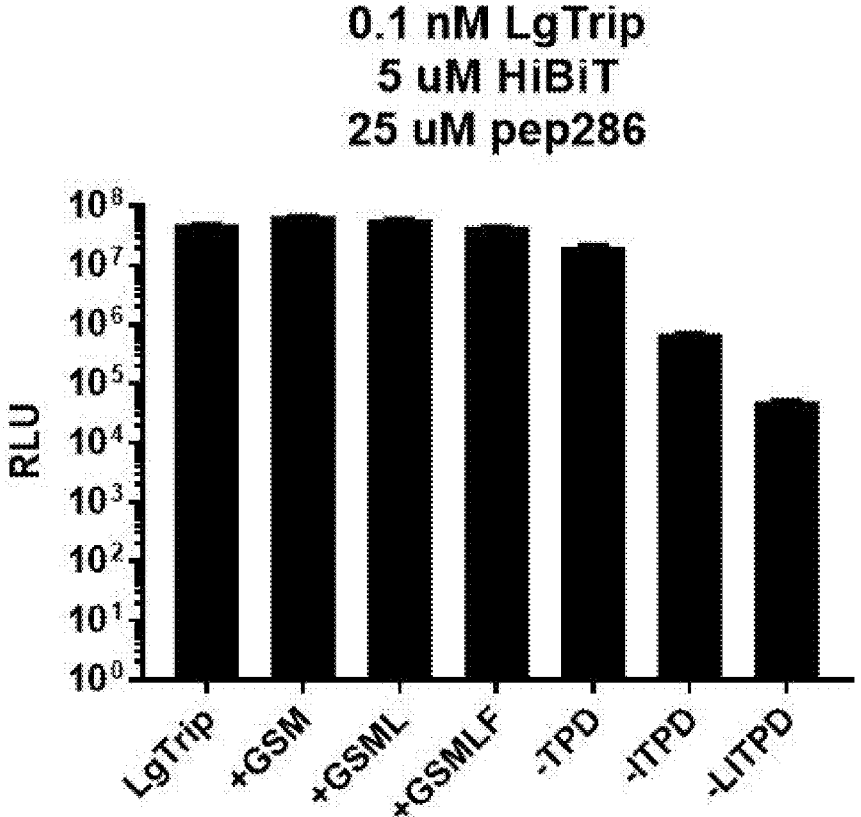
FIG. 34. Graph depicting luminescence from combinations of components with sequence gaps and/or overlaps between various LgTrip polypeptide components and SmTrip9 pep286 (SEQ ID NO: 37).

Effect of Sequence Gaps and Overlaps Between LgTrip C-Terminus and SmTrip9 Pep286 on Luciferase Light Output Experiments were conducted during development of embodiments herein to analyze the effect of gaps and/or overlaps between the polypeptide component and the SmTrip9-like peptide (FIG. 34). Polypeptide components with varied C-terminal extensions or deletions were diluted to 0.2 nM in TBS+0.01% BSA+0.01% Tergitol, and 50 uM SmTrip10 pep86 (SEQ ID NO: 25) was added to each. 10 uM of a SmTrip9 pep286 was added to SmTrip10 pep86+LgTrip solutions, and the reactions were incubated for 10 minutes. TBS+0.01% BSA+0.01% Tergitol+20 uM furimazine detection reagent was added at 1:1, and luminescence was read.

Example 39

Effect of SmTrip9 Sequence Gaps and Overlaps with LgTrip 3546 and SmTrip10 Pep 86 (HiBiT) on Luciferase Light Output Experiments were conducted during development of embodiments herein to analyze the effect of gaps and/or overlaps between the SmTrip9-like peptide and the polypeptide component (e.g., LgTrip) and/or SmTrip10-like peptide (FIG. 35). LgTrip 3546 (SEQ ID NO: 51) was diluted to 0.2 nM in TBS+0.01% BSA+0.01% Tergitol, and 50 uM SmTrip10 pep86 (SEQ ID NO: 25) was added to each. SmTrip9 pep286 (SEQ ID NO: 37) was added to 10 uM in SmTrip10 pep86+LgTrip solutions, and samples were incubated for 10 minutes. TBS+0.01% BSA+0.01% Tergitol+20 uM furimazine detection reagent was added at 1:1, and luminescence was read. All synthetic SmTrip9 peptides contained the N-terminal solubility tag, SSWKR.

Example 40

Biochemical Analysis (Kd and Bmax) of SmTrip9 Peptide Length Variants

Experiments were conducted during development of embodiments herein to analyze complementation of SmTrip9 peptides of different lengths with LgTrip 3546 (SEQ ID NO: 51) and SmTrip10 pep86 (SmHiTrip; SEQ ID NO: 15) (FIGS. 36-37).
SmTrip9 Titration (FIG. 36)

LgTrip 3546 (SEQ ID NO: 51) polypeptide was diluted to 0.2 nM in TBS+0.01% BSA+0.01% Tergitol. 100 uM SmTrip10 pep86 was prepared in TBS+0.01% BSA+0.01% Tergitol. 20 uM solutions of each SmTrip9-like peptide were added to the SmTrip10 pep86 solution. 2× serial dilutions were prepared of each SmTrip9 peptide solution using the SmTrip10 pep86 solution as a diluent. Peptide dilutions and LgTrip 3546 solution were combined 1:1 and incubated for 10 minutes. TBS+0.01% BSA+0.01% Tergitol+20 uM furimazine detection reagent was added (1:1), and luminescence was detected.
HiBIT (SmTrip10) Titration (FIG. 37)

LgTrip 3546 (SEQ ID NO: 51) polypeptide was diluted to 0.2 nM in TBS+0.01% BSA+0.01% Tergitol. 20 uM SmTrip9-like peptide solutions were prepared in TBS+0.01% BSA+0.01% Tergitol for each SmTrip9-like peptide to be tested. 100 uM solutions of SmTrip10 pep86 was added to each SmTrip9-like peptide solution. 2× serial dilutions were prepared of SmTrip10 pep86 using each SmTrip9-like peptide solution as a diluent. Peptide dilutions and LgTrip 3546 solution were combined, 1:1, and incubated for 10 minutes. TBS+0.01% BSA+0.01% Tergitol+20 uM furimazine detection reagent was added (1:1), and luminescence was detected.

Example 41

Biochemical Affinity and Bmax of SmTrip9 Pep286 Point Mutants

Experiments were conducted during development of embodiments herein to analyze the affinity of SmTrip9 pep286 (SEQ ID NO: 37) point mutants for LgTrip 3546 (SEQ ID NO: 51) and SmTrip10 pep86 (SmHiTrip; SEQ ID NO: 25). LgTrip 3546 polypeptide was diluted to 0.2 nM in TBS+0.01% BSA+0.01% Tergitol. 100 uM SmTrip10 pep86 was prepared in TBS+0.01% BSA+0.01% Tergitol. 20 uM solutions of each SmTrip9-like peptide were added to the SmTrip10 pep86 solution. 2× serial dilutions were prepared of each SmTrip9-like peptide solution using the SmTrip10 pep86 solution as a diluent. Equal volumes of peptide dilutions and LgTrip solution were combined and incubated for 10 minutes. TBS+0.01% BSA+0.01% Tergitol+20 uM furimazine detection reagent was added (1:1, vol:vol), and luminescence was detected (FIG. 38) to determine Kd and Bmax of each SmTrip9-like peptide.

Example 42

Effect of SmTrip9 Solubility Tags on Biochemical Affinity and Bmax

Experiments were conducted during development of embodiments herein to analyze the affinity of SmTrip9-like peptides with alternative solubility tags (FIG. 39). LgTrip 3546 (SEQ ID NO: 51) was diluted to 0.2 nM in TBS+0.01% BSA+0.01% Tergitol. 100 uM SmTrip10/pep86 solution was prepared in TBS+0.01% BSA+0.01% Tergitol. 20 uM solutions were prepared of each SmTrip9-like peptide in the SmTrip10 pep86 solution. 2× serial dilutions were prepared of each SmTrip9-like peptide using the SmTrip10 pep86 solution as a diluent. Equal volumes of peptide dilutions were combined with the LgTrip 3546 solution, and reactions were incubated for 10 minutes. TBS+0.01% BSA+0.01% Tergitol+20 uM furimazine detection reagent was added 1:1 vol:vol to the reactions, and luminescence was read after 10 minutes of incubation.

Example 43

C-Terminal Extension Sequences

Experiments were conducted during development of embodiments herein to analyze the affinity of SmTrip9-like peptides with C-terminal sequence extensions (FIG. 40).
SmTrip9 Peptide Titration LgTrip 3546 (SEQ ID NO: 51) polypeptide was diluted to 0.2 nM in TBS+0.01% BSA+0.01% Tergitol. 100 uM SmTrip10 pep86 was prepared in TBS+0.01% BSA+0.01% Tergitol. 20 uM solutions of each SmTrip9-like peptide were added to the SmTrip10 pep86 solution. 2× serial dilutions were prepared of each SmTrip9-like peptide solution using the SmTrip10 pep86 solution as a diluent. Peptide dilutions and LgTrip 3546 solution were combined 1:1 and incubated for 10 minutes. TBS+0.01% BSA+0.01% Tergitol+20 uM furimazine detection reagent was added (1:1), and luminescence was detected.
SmTrip 10 Pep 86 (HiBiT) Titration LgTrip 3546 (SEQ ID NO: 51) polypeptide was diluted to 0.2 nM in TBS+0.01% BSA+0.01% Tergitol. 20 uM SmTrip9-like peptide solutions were prepared in TBS+0.01% BSA+0.01% Tergitol for SmTrip9-like peptide to be tested. 100 uM solutions of SmTrip10 pep86 (SEQ ID NO: 25) was added each SmTrip9-like solution. 2× serial dilutions were prepared of SmTrip10 pep86 using each SmTrip9-like peptide solution as a diluent. Peptide dilutions and LgTrip 3546 solution were combined 1:1 and incubated for 10 minutes. TBS+0.01% BSA+0.01% Tergitol+20 uM furimazine detection reagent was added (1:1), and luminescence was detected.

Example 44

Figure 41:
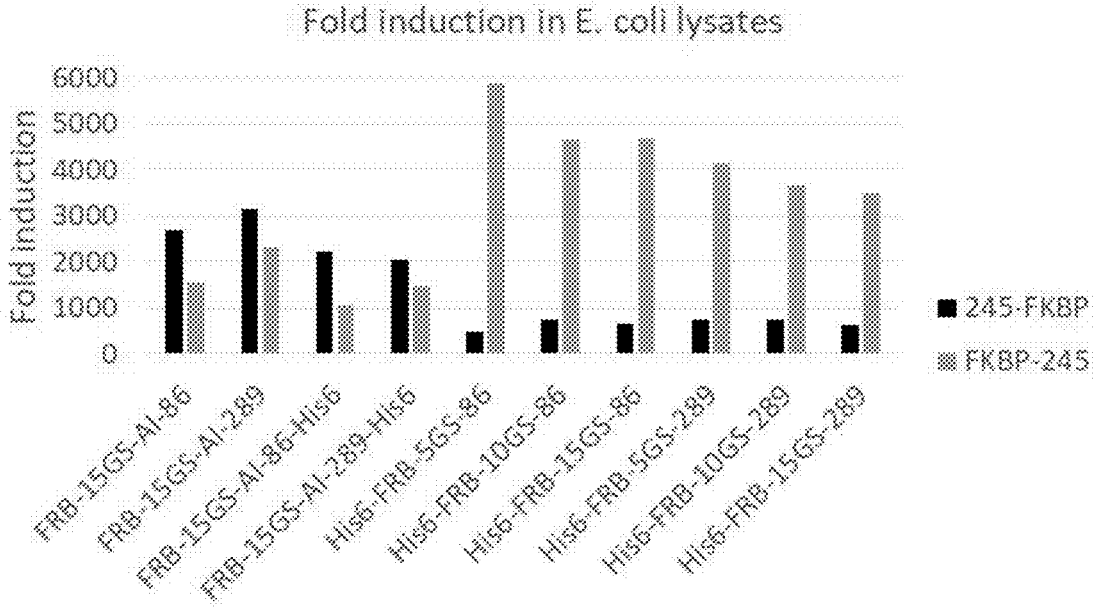
FIG. 41. Graph depicting the effect of FRB-β10 construct linker length (15, 10, or 5 Gly/Ser residues), linker composition (with or without Ala-Ile), hexahistidine tag inclusion, and β10 composition (SmTrip10 pep86 (SEQ ID NO: 25) or SmTrip10 pep289 (SEQ ID NO: 150)) on facilitated complementation in *E. coli* lysates with LgTrip 3546 (SEQ ID NO: 51).

Measurement of FRB-FKBP Facilitated Complementation Using FRB-SmTrip10 Variants and FKBP Fused SmTrip9 Pep245 in KRX *E. coli* Lysates Overnight cultures of FRB-SmTrip10 variants, FKBP-SmTrip9 pep245, and SmTrip9 pep245-FKBP were grown in LB+100 ug/ml ampicillin from glycerol stocks. Cells were diluted 1:100 in LB+0.15% glucose+0.1% rhamnose+Amp, and shook for 20 hours at 25° C. Cultures were diluted 1:4 in PLB and incubated 15 min at room temperature to lyse cells. SmTrip9/SmTrip10 peptide combinations were mixed 1:1 (vol:vol). Mixtures were diluted 1:5 into PLB+200 nM LgTrip 3546 (SEQ ID NO: 51) with or without 30 nM rapamycin, and reactions were incubated for 30 minutes at room temperature. Each reaction was combined with 50 ul of NanoGlo® buffer+50 uM Furimazine, and luminescence was measured at 5 minutes. Results for fold induction (+rap signal/−rap signal) are depicted in FIG. 41. FRB-SmTrip10 variant peptide constructs possessed varied linker lengths, linker content (with or without alanine-isoleucine), and either contained or lacked a hexahistidine tag.

Example 45

Figure 42:
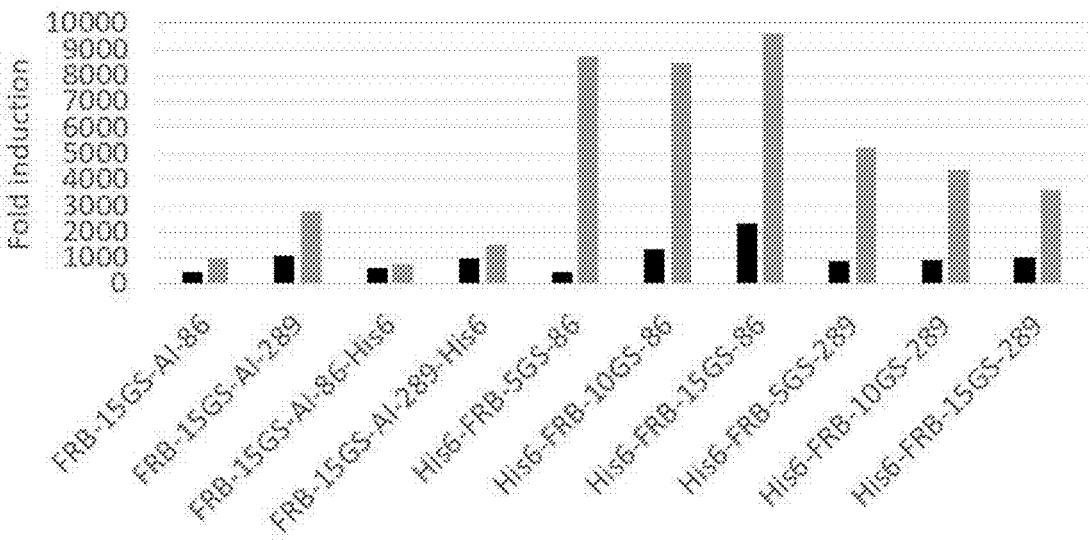
FIG. 42. Graph depicting the effect of FRB-β10 construct linker length (15, 10, or 5 Gly/Ser residues), linker composition (with or without Ala-Ile), hexahistidine tag inclusion, and β10 composition SmTrip10 pep86 (SEQ ID NO: 25) or SmTrip10 pep289 (SEQ ID NO: 150) on facilitated complementation in HEK lysates with LgTrip 3546 (SEQ ID NO: 51).
Figure 43:
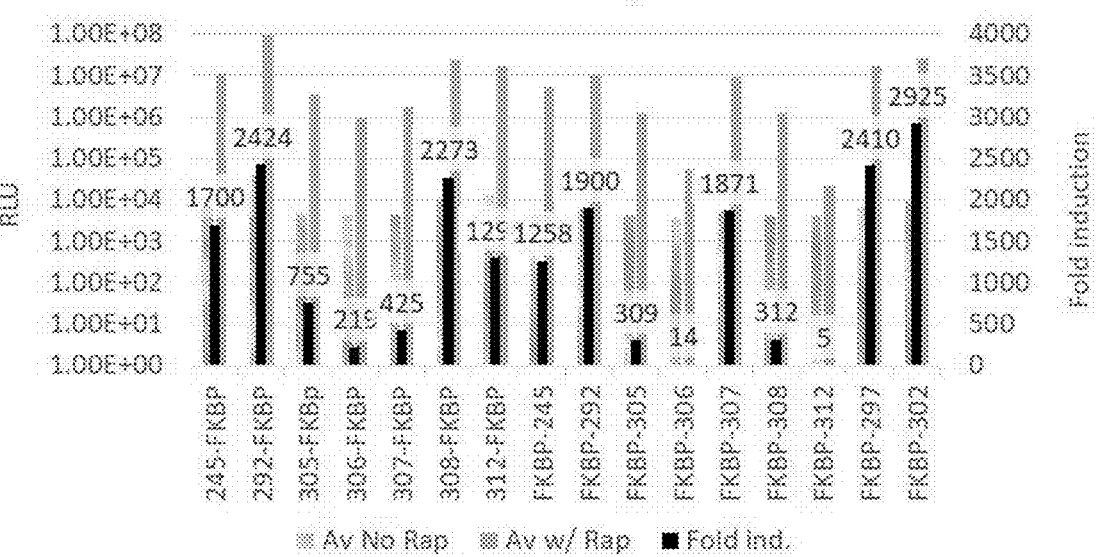
FIG. 43. Graph depicting the effect of β9 sequence truncations and extensions and construct orientation (β9-FKBP or FKBP-β9) on facilitated complementation with FRB-SmTrip10 pep86 (β10) (SEQ ID NO: 25) in *E. coli* lysates with LgTrip 3546 (SEQ ID NO: 51).
Figure 44:
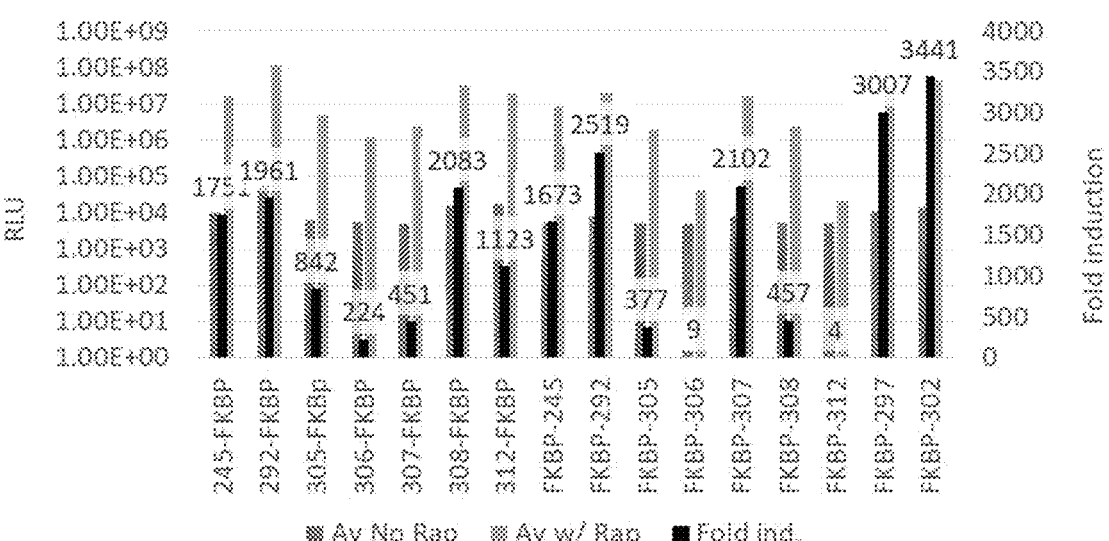
FIG. 44. Graph depicting the effect of β9 sequence truncations and extensions and construct orientation (β9-FKBP or FKBP-β9) on facilitated complementation with FRB-SmTrip10 pep289 (β10) (SEQ ID NO: 150) in *E. coli* lysates with LgTrip 3546 (SEQ ID NO: 51).

Measurement of FRB-FKBP Facilitated Complementation Using FRB-SmTrip10 Variants and FKBP Fused SmTrip9 Pep245 in HEK Lysates Overnight cultures of FRB-SmTrip10 variants, FKBP-SmTrip9 pep245, and SmTrip9 pep245-FKBP were grown at 37° C. with 5% $CO_2$. Cells were transfected with 1 ug DNA (FKBP or FRB construct) per well using FuGENE protocol. Cells were washed in 1 ml DPBS. 1 ml DPBS was added and cultures were frozen at −80° C. for 10 min. Cultures were thawed at room temperature to lyse cells. Lysates were cleared by centrifugation for 10 min and diluted 2-fold in PLB. SmTrip9/SmTrip10 peptide combinations were mixed 1:1 (vol:vol). Mixtures were diluted 1:5 into PLB+200 nM LgTrip 3546 (SEQ ID NO: 51) with or without 30 nM rapamycin, and reactions were incubated for 30 minutes at room temperature. Each reaction was combined with 50 ul of NanoGlo® buffer+50 uM Furimazine, and luminescence was measured at 5 minutes. Results for fold induction (+rap signal/−rap signal) are depicted in FIG. 42. FRB-SmTrip10 variant peptide constructs possessed varied linker lengths, linker content (with or without alanine-isoleucine), and either contained or lacked a hexahistidine tag.

Example 46

Measurement of FRB-FKBP Facilitated Complementation Using FRB-SmTrip10 Pep86 (HiBiT)/SmTrip10 Pep289 (VS-HiBiT) and SmTrip9 Sequences Fused to FKBP in Both Orientations in KRX *E. coli* Lysates Overnight cultures for FRB-SmTrip10 pep86 (HiBIT; SEQ ID NO: 25) or FRB-SmTrip10 pep289 (VS-HiBIT; SEQ ID NO: 150) and SmTrip9-like peptide sequences fused to FKBP were grown in LB+100 ug/ml ampicillin from glycerol stocks. Cells were diluted 1:100 in LB+0.15% glucose+0.1% rhamnose+Amp and shaken for 20 hours at 25° C. Cultures were diluted 1:4 in PLB and incubated 15 min at room temperature to lyse. SmTrip9/SmTrip10 peptide combinations were mixed 1:1 (vol:vol). Mixtures were diluted 1:5 into PLB+200 nM LgTrip 3546 (SEQ ID NO: 51) with or without 30 nM rapamycin, and reactions were incubated for 30 minutes at room temperature. Each reaction was combined with 50 ul of NanoGlo® buffer+50 uM Furimazine, and luminescence was measured at 5 minutes. Results are depicted in FIGS. 43-47.

Example 47

Measurement of FRB-FKBP Facilitated
Complementation Using FRB-SmTrip10 Pep86
(HiBiT)/SmTrip10 Pep289 (VS-HiBiT) and
SmTrip9 Sequences Fused to FKBP in Both
Orientations in HEK Lysates Overnight cultures for FRB-SmTrip10 pep86 (HiBIT; SEQ ID NO: 25) or FRB-SmTrip10 pep289 (VS-HiBiT; SEQ ID NO: 150) and SmTrip9-like peptide sequences fused to FKBP were grown at 37° C. with 5% CO₂. Cells were transfected with 1 ug DNA (FKBP or FRB construct) per well using FuGENE protocol. Cells were washed in 1 ml DPBS. 1 ml DPBS was added and cultures were frozen at −80° C. for 10 min. Cultures were thawed at room temperature to lyse cells. Lysates were cleared by centrifugation for 10 min, and diluted 2-fold in PLB. SmTrip9/SmTrip10 peptide combinations were mixed 1:1 (vol:vol). Mixtures were diluted 1:5 into PLB+200 nM LgTrip 3546 (SEQ ID NO: 51) with or without 30 nM rapamycin, and reactions were incubated for 30 minutes at room temperature. Each reaction was combined with 50 ul of NanoGlo® buffer+50 uM Furimazine, and luminescence was measured at 5 minutes. Results are depicted in FIGS. 48-50.

Example 48

Measurement of FRB-FKBP Facilitated
Complementation Using FRB-SmTrip10 Pep86
(HiBiT)/SmTrip10 Pep289 (VS-HiBiT) and
SmTrip9 Sequences Fused to FKBP in *E. coli*
Lysates Overnight cultures for FRB-SmTrip10 pep86 (HiBIT; SEQ ID NO: 25) or FRB-SmTrip10 pep289 (VS-HiBIT; SEQ ID NO: 150) and SmTrip9-like peptide sequences fused to FKBP were grown in LB+100 ug/ml ampicillin from glycerol stocks. Cells were diluted 1:100 in LB+0.15% glucose+0.1% rhamnose+Amp and shook for 20 hours at 25° C. Cultures were diluted 1:4 in PLB and incubated 15 min at room temperature to lyse. SmTrip9/SmTrip10 peptide combinations were mixed 1:1 (vol:vol). Mixtures were diluted 1:5 into PLB+200 nM LgTrip 3546 (SEQ ID NO: 51) with or without 30 nM rapamycin, and reactions were incubated for 30 minutes at room temperature. Each reaction was combined with 50 ul of NanoGlo® buffer+50 uM Furimazine, and luminescence was measured at 5 minutes. Results are depicted in FIGS. 57, 59, 60, 62-63, 66-67, and 70-71. In FIG. 57, ** indicates that alanine-isoleucine (AI) in the linker directly upstream of SmTrip9 peptides or SmTrip10 peptides has been removed. Alanine-isoleucine is absent from C-terminal FKBP or FRB fusions with SmTrip9 peptide or SmTrip10 peptides, respectively, in all subsequent figures.

Example 49

Measurement of FRB-FKBP Facilitated
Complementation Using FRB-SmTrip10 Pep86
(HiBiT)/SmTrip10 Pep289 (VS-HiBiT) and
SmTrip9 Sequences Fused to FKBP in HEK293
Lysates Overnight cultures for FRB-SmTrip10 pep86 (HiBIT; SEQ ID NO: 25) or FRB SmTrip10 pep289 (VS-HiBIT; SEQ ID NO: 150) and SmTrip9-like peptide sequences fused to FKBP were grown at 37° C. with 5% CO₂. Cells were transfected with 3 ug DNA (FKBP or FRB construct) per well using FuGENE protocol. Cells were washed in 1 ml DPBS. 1 ml DPBS was added and cultures were frozen at −80° C. for 10 min. Cultures were thawed at room temperature to lyse cells. Lysates were cleared by centrifugation for 10 min, and diluted 2-fold in PLB. SmTrip9/SmTrip10 peptide combinations were mixed 1:1 (vol:vol). Mixtures were diluted 1:5 into PLB+200 nM LgTrip 3546 (SEQ ID NO: 51) with or without 30 nM rapamycin, and reactions were incubated for 30 minutes at room temperature. Each reaction was combined with 50 ul of NanoGlo® buffer+50 uM Furimazine, and luminescence was measured at 5 minutes. Results are depicted in FIGS. 58, 61, 64-65, 68-69, and 72-73. In FIG. 58, ** indicates that alanine-isoleucine (AI) in the linker directly upstream of SmTrip9 peptides or SmTrip10 peptides has been removed. Alanine-isoleucine is absent from C-terminal FKBP or FRB fusions with SmTrip9 peptides or SmTrip10 peptides, respectively, in all subsequent figures.

Example 50

Biochemical Analysis (Kd and Bmax) of Varied
SmTrip9 Sequences

Results are depicted in FIGS. 74-76.
SmTrip9-like Peptide Titrations
    LgTrip 3546 (SEQ ID NO: 51) was diluted to 0.2 nM in TBS+0.01% BSA+0.01% Tergitol. 100 uM SmTrip10 pep86 (SmHiTrip; SEQ ID NO: 25) was prepared in TBS+0.01% BSA+0.01% Tergitol. 20 uM solutions were prepared of each SmTrip9-like peptide in the SmTrip10 pep86 solution. 2× serial dilutions of each SmTrip9-like peptide were prepared using the SmTrip10 pep86 solution as a diluent. Peptide dilutions were combined with LgTrip 3546 (SEQ ID NO: 51) solution, 1:1, and incubated for 10 minutes. TBS+0.01% BSA+0.01% Tergitol+20 uM Furimazine (Fz) detection reagent was added, 1:1. Luminescence was read at 10 min.
SmTrip 10 Pep86 (HiBiT) Titrations
    LgTrip 3546 (SEQ ID NO: 51) was diluted to 0.2 nM in TBS+0.01% BSA+0.01% Tergitol. 20 uM SmTrip9-like peptide solutions were prepared in TBS+0.01% BSA+0.01% Tergitol. SmTrip10 pep86 was added to 100 uM in each SmTrip9-like peptide solution. 2× serial dilutions of each SmTrip 10 pep86 (SEQ ID NO: 25) were prepared using the SmTrip9-like peptide solutions as a diluent. Peptide dilutions were combined with LgTrip 3546 (SEQ ID NO: 51) solution 1:1 and incubated for 10 minutes. TBS+0.01% BSA+0.01% Tergitol+20 uM Furimazine (Fz) detection reagent was added, 1:1. Luminescence was read at 10 min.

Example 51

Solubility of Synthetic SmTrip9 Peptides

Synthetic peptides were synthesized by Peptide2.0 with termini blocked (N-terminal acetylation and C-terminal amidation) unless otherwise noted. Peptides were dissolved in nuclease-free water to ~1 mM and mixed on rotator at 4° C. for 30 min. Following centrifugation for 10 min at top speed, peptides were diluted 1:50 in water and quantified on NanoDrop. Peptides were stored at −20° C. until use. Peptides were deemed soluble if they remained in solution after 3 freeze/thaw cycles in which peptides were thawed in a 22° C. water bath, kept at 4° C., and frozen at −20° C. Solubility of synthetic peptides is depicted in FIG. 77.

Example 52

Circularly Permuted LgBiT

SmTrip9 Pep286 Affinity and Bmax for SmTrip 10 Pep 86 (HiBiT)-LgTrip 3546 Fusions A fusion polypeptide comprising a SmTrip10 pep86 (SmHiTrip; SEQ ID NO: 25) sequence fused to the front of LgTrip 3546 (SEQ ID NO: 51) was generated and experiments were conducted to monitor complex formation and luminescence of the SmTrip10 pep86 HiBiT-LgTrip fusions with SmTrip9 pep286 (SEQ ID NO: 37) (FIG. 78).

Overnight cultures were grown in LB+100 ug/ml ampicillin from glycerol stocks. Cells were diluted 1:100 in LB+0.15% glucose+0.1% rhamnose+Amp and shaken for 20 hr at 25° C. 800 μl culture was lysed in FastBreak and each SmTrip10 pep86-LgTrip fusion was purified using the HisLink protocol. 2-fold SmTrip9 pep286 (SEQ ID NO: 37) serial dilutions starting at 10 uM were made in TBS+0.01% Tergitol+0.01% BSA containing 0.2 nM SmTrip10 pep86-LgTrip fusion (ATG 3745 (SEQ ID NO: 211) or ATG 3746 (SEQ ID NO: 213)). Reactions were pre-incubated for 10 minutes at room temperature. TBS+0.01% Tergitol+0.01% BSA with 20 uM Furimazine (Fz) was added to samples 1:1 (vol:vol). Luminescence was read on GloMax® luminometer at 10 min.

SmTrip9 Pep759 Affinity for Various SmTrip 10 Pep 86 (HiBIT)-LgTrip 3546 Fusions From pellets of induced cell culture, pellets were resuspended in ¹⁄₁₀ of the original culture volume (e.g. a 50 mL culture would be resuspended in 5 mL) using 1×TBS+0.01% BSA. A lysis buffer was prepared using 100 parts Fast Break® Buffer, 10 Parts RQ1 RNAse free DNAse, and 1 part 1 M DTT (e.g. 650 μL Fast Break® Buffer+65 μL RQ1 RNAse free DNAse, and 6.5 μL 1 M DTT or equivalent scaling). 1 part Lysis buffer was added to 9 parts cell suspension (e.g. 33.3 μL Lysis buffer+300 uL suspension) in a 15 mL tube. Incubated at 4° C. for 30 minutes while mixing (using a rotary shaker). A 4 μM solution of pep 759 was prepared in 1×TBS+0.01% BSA. 50 μL of 4 μM pep759 was added to 50 μL of each lysate in a 96 well plate in triplicate. 50 μL of each lysate was separately mixed with 50 μL of 1×TBS+0.01% BSA buffer in triplicate. NanoGlo® Reagent was prepared by mixing 100 parts NanoGlo® Buffer with 1 part Furimazine (e.g. 10 mL buffer+100 uL furimazine). 100 μL of NanoGlo® reagent was added to each well. Luminescence was measured using Glomax® Multi instrument kinetic cycles. Luminescence measurements were compared after about 29 minutes. Luminescence readings for samples with pep759 were divided by the corresponding measurement of the same lysate without pep759. Results are depicted in FIG. 78B. Two batches of cultures were used to generate data: one was from inductions of 50 mL cultures (the right side, ATG-4808 through and including ATG-4632) and the other was from inductions of 3 mL cultures (left side, starting with ATG-4815 through and including ATG-3746). Some constructs were present in both tests (ATG-2623, ATG-3745, ATG-3746, ATG-4632).

Example 53

Detergent Titration

Experiments were conducted during development of embodiments herein to determine the impact of various detergents on NanoLuc (SEQ ID NO: 3), LgBIT (SEQ ID NO: 11), and LgTrip 3546 (SEQ ID NO: 51) complexes with the dipeptide, pep263 (SEQ ID NO: 35).

Exposure Experiments 500 ul of 20 mM SDS or 2 mM CDTA or 5% Tergitol was added to a deep well plate. 3× serial dilutions were prepared of each detergent in TBS+0.01% BSA (150 ul in 350 ul). 100 ul of each dilution was combined with 100 ul of either 2 nM NanoLuc, LgBiT, or LgTrip, and samples were incubated for 18 hours. Samples were diluted 1:100 in TBS+0.01% BSA (5 ul in 495 ul). 50 ul of each sample was combined in triplicate with 50 ul of TBS+0.01% BSA+20 uM Furimazine (Fz) for NanoLuc or TBS+0.01% BSA+20 uM Furimazine (Fz)+2 uM pep263 for LgBiT and LgTrip. Luminescence of samples was read on GMM+ 3 minutes after reagent addition. Results of prolonged exposure to detergent on LgBiT, LgTrip 3546, and NanoLuc are depicted in FIG. 79.

Activity Experiments 20 ml of 20 uM Fz was prepared in TBS+0.01% BSA. 2 ml of 20 mM SDS and 2 mM of CDTA and 5% Tergitol were added to a deep well plate. 20 uM Fz was added to each sample (8 ul). 2× serial dilutions were prepared of each detergent in 20 uM Fz solution (1 ml to 1 ml). A solution of 400 pM NanoLuc in TBS+0.01% BSA was prepared. A solution of 400 pM LgBiT+1 uM pep263 (SEQ ID NO: 35) in TBS+0.01% BSA was prepared. A solution of 400 pM LgTrip 3546 (SEQ ID NO: 51)+1 uM pep263 (SEQ ID NO: 35) in TBS+0.01% BSA was prepared. 50 ul of each enzyme solution was combined with 50 μl of the detergent titrations, placed in luminometer, and read after a 3 minute incubation at RT. Results of LgBiT, LgTrip and NanoLuc activity in the presence of detergent are depicted in FIG. 80.

Example 54

Reversibility of FRB-FKBP Facilitated Complex Formation

Experiments were conducted during development of embodiments herein to demonstrate the reversibility of bioluminescent complex formation. Media was aspirated from a T75 growth flask of HEK293 cells. Cells were washed with 10 ml of DPBS and trypsinized by adding 3 ml of Tryple Express Trypsin. After a 3 minute incubation at 37° C., 10 ml of growth media (DMDM+10% FBS) was added to the flask, mixing cells with pipette. Cells were pelleted at 200 rpm for 5 minutes. Media was aspirated and replaced by fresh media. Cells were counted on a T20 cell counter and diluted to 200,000 cells/ml. 3 ml of the cell suspension was added to each well of a six well plate. Cells were grown overnight at 37° C. with 5% CO$_2$. To transfect the cells, DNA was diluted for each construct to a concentration of 100 ng/ul and 3.3 ug of DNA was added in a final volume of 155 ul of OptiMEM for each construct (FKBP-SmBIT, FRB-LgBIT, FRB-SmTrip10 pep86 (HiBiT), FKBP-SmTrip9 pep245). 9.9 ul of FugeneHd was added to the diluted DNA and incubated for 15 minutes. 150 ul of each DNA complex was then added to cells plated in a 6 well plate. Cells were grown overnight at 37° C. with 5% CO$_2$. After aspirating media, cells were washed once with DPBS (Life Technologies Cat. No. 14190) and then frozen in a fresh 1 ml of DPBS at −80° C. The samples were then thawed to lyse cells. FRB and FKBP constructs for NanoBIT (FKBP-SmBiT+FRB-LgBiT) and NanoTrip (FRB-SmTrip10 pep86 (HiBiT)+FKBP-SmTrip9 pep245+200 nM purified LgTrip 3546 (SEQ ID NO: 51)) were combined and incubated with 30 nM Rapamycin for 30 minutes. A dilution series of FK506 was prepared in DMSO starting at 10 mM. 3-fold serial dilutions were performed in DMSO (30 ul into 70 ul). 200 ul of each FRB-FKBP combination was aliquoted into 8 wells of a 96 well PCR tray. Upon addition of 2 ul of the FK506 dilution series, each sample was incubated at 37° C. for 6 hours. 50 ul of each sample was combined with 50 ul of TBS+0.01% BSA+20 uM Furimazine (Fz), incubated for 3 minutes, and read on GMM+. Results are depicted in FIG. 81.

Example 55

LgTrip/SmTrip9 Titration with SmTrip10 Peptides

Experiments were conducted during development of embodiments herein to analyze titrations of LgTrip 3546 (SEQ ID NO: 51) and SmTrip9 pep286 (SEQ ID NO: 37) with various SmTrip10 peptides. Data was normalized to SmTrip10 pep86 (HiBiT) values. SmTrip10 pep86 (HiBiT) is SmHiTrip10 (SEQ ID NO: 25).

Peptide stocks were diluted to 250 uM in water. A SmTrip9 pep286 (SEQ ID NO: 37) solution (10 uM in final reaction) was prepared in OptiMEM+10% FBS. A 2-fold serial dilution of each SmTrip10 peptide was performed in the OptiMEM solution containing SmTrip9 pep286. The highest concentration of the SmTrip10 peptide was 15 uM (final in reaction). A 10× stock (1 nM) of LgTrip 3546 (SEQ ID NO: 51) was prepared in OptiMEM+10% FBS, and 10 ul was added to 90 ul of each of the SmTrip10 peptide titrations. Samples were incubated for 30 minutes on an orbital shaker set to 500 rpm. 2 ml of detection reagent (OptiMEM+10% FBS+20 ul of 1M DTT+80 ul of 5 mM Furimazine) was prepared. 10 ul of detection reagent was added to each LgTrip 3546: peptide solution, and plates were placed on an orbital shaker. Plates were read at 5 minutes and 10 minutes. SmTrip10 pep86 (SmHiTrip; SEQ ID NO: 25) and SmTrip10 pep289 (SEQ ID NO: 150) were used as controls on each of the 4 plates. Results are depicted in the tables of FIGS. 82-83.

Example 56

Antares Constructs

Experiments were conducted during development of embodiments herein to demonstrate the complementation systems described herein in the context of the Antares BRET system comprising one or more CyOFP fluorescent proteins linked to a component of the systems described herein.

Samples were purified using HisLink Resin: 10 ml of 100 mM HEPES pH 7.5, 1 ml of FastBreak Cell Lysis Reagent and 50 u of DNase were added, and samples were placed on rotating mixer for 45 minutes and then spun at 7,000 rpm for 20 minutes. Next, 1 ml of HisLink resin was added to each sample, and samples were washed 3× with 5 ml of binding wash buffer, eluted with 300 ul of elution buffer, and dialyzed against TBS (2 hours, TBS replace, 2 more hours). Samples were diluted to 100 nM in TBS+0.01% BSA and then further diluted to 0.4 nM by adding 4 ul to 996 ul of TBS+0.01% BSA. 3× serial dilutions were prepared by transferring 300 ul to 700 ul. 10 ml of 2 uM dipeptide pep263 (SEQ ID NO: 35) was prepared in TBS+0.01% BSA. 10 ml of 400 pM SmTrip10 pep86 (SEQ ID NO: 25) was prepared in TBS+0.01% BSA. 10 ml of 1 uM SmTrip9 pep286 (SEQ ID NO: 37) and 10 uM SmTrip10 pep86 were prepared. 50 ul of each enzyme was combined with either TBS or dipeptide solution (all samples in triplicate on two plates). Antares fusions with LgBiT and LgTrip 3546 samples were combined with SmTrip9 pep286+SmTrip10 pep86. Samples were incubated for 1 hour at RT. 100 ul of 20 um furimazine was added in TBS+0.01% BSA+2 mM ATT. Plates were incubated for 3 minutes and then read on GMM+. Results are depicted in graphs of FIGS. 84-85.

Example 57

"Dark" Dipeptide 272

Experiments were conducted during development of embodiments herein to compare titration series with "Dark" dipeptide 272 (SEQ ID NO: 146) with LgBIT (SEQ ID NO: 11) and LgTrip 3546 (SEQ ID NO: 51) in the presence of 0.1 nM pep 263. LgBiT and LgTrip 3456 were diluted to 200 nM in TBS+0.01% BSA and +/−0.4 nM of dipeptide pep263 (SEQ ID NO: 35) and incubated for 10 minutes. A 3× dilution series of dipeptide pep272 was prepared starting at 40 nM (at this concentration, LgBiT showed inhibition at high concentrations, so Kd value could not be calculated; a new titration series was created starting at 4 nM pep272 for LgBiT to obtain a Kd value). 50 μl of the peptide dilution series was added to an assay plate followed by addition of 50 μl of the LgBiT and LgTrip 3546 dilutions. Samples were incubated for 1 hour at room temperature. After addition of 100 ul of NanoGlo+50 uM Furimazine (Fz), plates were incubated for 5 minutes and luminescence was read on GMM+. Results are depicted in FIG. 86.

Example 58

Comparison of Dark Dipeptides Pep272 and Pep273

LgBIT (SEQ ID NO: 11) and LgTrip 3546 (SEQ ID NO: 51) were diluted to 200 nM in TBS+0.01% BSA with +/−0.4 nM of dipeptide pep263 (SEQ ID NO: 35) or +/−0.4 nM didpeptide pep264 (SEQ ID NO: 299) and incubated for 10 minutes. 3× dilution series of didpeptide pep272 (SEQ ID NO: 146) and dipeptide pep273 (SEQ ID NO: 298) were prepared starting at 40 nM using the dipeptide pep263 dilution as a diluent for pep272 and the dipeptide pep264 dilution as a diluent for pep273. 50 ul of the LgBiT and LgTrip 3546 dilutions was combined with 50 μl of the pep272/273 titration series and incubated at room temperature for 2 hours. After addition of 100 ul of NanoGlo® buffer+50 uM Fz, plates were incubated at room temperature for 5 minutes, and luminescence was read on GMM+. Results are depicted in FIG. 87.

Example 59

DarkBiT Pep167

Solutions with 200 nM LgBIT (SEQ ID NO: 11) and LgTrip 3546 (SEQ ID NO: 51) were prepared. 0.2 nM SmTrip10 pep86 (SmHiTrip; SEQ ID NO: 25) was added to LgBiT solutions, and 1 uM of SmTrip9 pep286 (SEQ ID NO: 37) with 200 nM of SmTrip10 pep86 was added to LgTrip 3546 solutions. A dark bit (pep167) (SEQ ID NO: 300) titration was prepared starting at 12 uM in TBS+0.01% BSA. 50 μl of the dark bit titration was combined with 50 μl of the LgBiT or LgTrip 3546/pep167 dilutions and incubated for 1 hour. After addition of 100 ul of NanoGlo® buffer+50 uM Furimazine (Fz), plates were incubated 10 minutes, and luminescence was read on GMM+. Results are depicted in FIG. 88.

Example 60

FRB-FKBP Facilitated Complementation in *E. coli* Lysates with SmTrip9 Pep435/434 Variants Cultures were grown overnight in LB+100 ug/ml ampicillin from glycerol stocks, and cells were diluted 1:100 in LB+0.15% glucose+0.1% rhamnose+Amp. After 20 hr shaking at 25° C., cells were diluted 1:4 in PLB and incubated 15 min at room temperature to lyse. Lysates of SmTrip9/SmTrip10 peptide combinations of interest were mixed 1:1 vol:vol and diluted 1:5 in PLB+200 nM LgTrip 3546 (SEQ ID NO: 51) with or without 30 nM rapamycin. Samples were incubated for 30 minutes at room temperature and combined 1:1 (vol:vol) with NanoGlo® buffer containing 50 uM Furimazine. Luminescence was read at 5 minutes. Results are depicted in FIGS. 89-90.

Example 61

FRB-FKBP Facilitated Complementation

FRB-FKBP Facilitated Complementation in HEK Lysates with SmTrip9 Pep435 and Pep434 Variants 600,000 cells were added to each well of 6-well plates in DMEM+1% FBS. Cells were grown overnight at 37° C. with 5% $CO_2$ and transfected with 3 ug DNA (FKBP or FRB construct) per well using FuGENE protocol. Following overnight incubation at 37° C. with 5% $CO_2$, cells were washed with DPBS. After aspiration, 1 ml of fresh DPBS was added to each well and plates were frozen at −80° C. for ~10 min. Plates were thawed at room temperature to lyse cells and lysates were cleared by centrifuging 10 min and removing supernatant. Lysates were diluted 2-fold in PLB and SmTrip9/SmTrip10 peptide combinations of interest were mixed 1:1 (vol:vol). Mixtures were then diluted 1:5 in PLB+200 nM LgTrip 3546 (SEQ ID NO: 51) with or without 30 nM rapamycin. Samples were incubated for 30 minutes at room temperature and combined 1:1 vol:vol with NanoGlo® buffer containing 50 uM Furimazine. Luminescence was read at 5 minutes. Results are depicted in FIG. 91.

FRB-FKBP Assay Screen with SmTrip9s 823 and 840

Cultures of FKBP_SmTrip9 variants and FRB-SmTrip10s were grown overnight in LB+100 µg/ml ampicillin at 37° C. Cells were diluted 1:20 in LB with 0.15% glucose, 0.1% rhamnose, and 100 ug/ml ampicillin. Cultures were induced ~20 hr at 25° C. with shaking. PLB assay reagent was prepared with 444 nM LgTrip 3546, 90× diluted FRB-SmTrip10 culture, +/−35 nM Rapamycin. Ninety microliters of assay reagent was added to each well of 96-well assay plates. FKBP_SmTrip9 cultures were diluted 1:10 in PLB and 10 ul was added to assay plates. Samples were incubated 30 min at room temperature. One hundred microliters of NanoGlo containing 50 uM furimazine was added to assay plates wells and luminescence was read on GloMax after 5 minutes. Results are depicted in FIG. 92.

Example 62

Determination of Kd of Pep434 and Pep435 Variants

LgTrip 3546 (SEQ ID NO: 51) was diluted to 0.2 nM in TBS+0.01% BSA+0.01% Tergitol. 20 uM solutions of each SmTrip9-like peptides were prepared with 100 uM SmTrip10 pep86 (SEQ ID NO: 25) in TBS+0.01% BSA+0.01% Tergitol. 2-fold serial dilutions of each SmTrip9-like peptide were performed using the 100 uM SmTrip10 pep86 solution as a diluent. Peptide dilutions were combined with LgTrip 3546 solution 1:1 (vol:vol) and incubated 10 minutes. TBS+0.01% BSA+0.01% Tergitol+20 uM Furimazine (Fz) detection reagent was added to LgTrip/peptide solutions 1:1 vol:vol and luminescence was read at 10 min. Results are depicted in FIG. 93.

Example 63

Detection of CRISPR-Tagged Dipeptide-GAPDH Using LgTrip 3546

Experiments were conducted during development of embodiments herein to demonstrate that both LgTrip 2098 (SEQ ID NO: 31) and LgTrip 3546 (SEQ ID NO: 51) find use as bioluminescence reagents for detecting endogenously tagged GAPDH (Tagged with SmTrip10 pep86 (SmHiTrip; SEQ ID NO: 25).

HeLa cells were edited using CRISPR/Cas9 to express endogenous GAPDH C-terminal fusions to the indicated peptide. The edited HeLa cells were plated at a density of approximately 20,000 cells per well of a solid white assay plate in 100 µl of DMEM/10% FBS. Cells were then incubated in the presence of 100 µl of NanoGlo® HiBiT Lytic Buffer (Promega) containing NanoGlo® HiBiT Lytic Buffer and 200 nM of LgTrip for 10 min. Luminescence was recorded using a GloMax® Discover with 0.5s integration time. Relative cell numbers were determined using the CellTiter® Glo Luminescent Cell Viability Assay (Promega) according to manufacturer's protocol. Data are represented as average relative light units normalized to cell number, with variability expressed as standard deviation.

Results are depicted in FIG. 94.

Example 64

Site-Saturation Screen of SmTrip9

Experiments were conducted during development of embodiments herein to identify beneficial amino acid substitutions in SmTrip9.

Genetic site-saturation libraries were generated using primers with randomized codons at the indicated positions in SmTrip9. KRX *E. coli* was transformed with pooled genetic variants, plated onto LB+ampicillin agar, and grown overnight at 37° C. Individual colonies were picked and placed into 96-well culture plates containing LB+100 µg/ml ampicillin. Cultures were grown overnight at 37° C. with shaking. Cells were diluted 1:20 in LB with 0.15% glucose, 0.1% rhamnose, and 100 ug/ml ampicillin. Cultures were induced ~20 hr at 25° C. with shaking. Assay reagent was prepared by adding 444 nM LgTrip (SEQ ID NO: 51), 90× diluted FRB-VS-HiBIT culture, and +/−35 nM rapamycin to 25 mM HEPES with 0.3× Passive Lysis Buffer (PLB) and DNase. Ninety microliters of assay reagent was added to each well of 96-well assay plates. FKBP_SmTrip9 cultures were diluted 1:10 in PLB, and 10 ul was added to assay plates. Samples were incubated 30 min at room temperature. One hundred microliters of NanoGlo® buffer containing 50 uM furimazine was added to assay plates wells, and luminescence was read on GloMax® luminometer after 5 minutes. Results are depicted in FIGS. 100-112.

Example 65

FRB-FKBP Facilitated Complementation in *E. coli* Lysates with SmTrip9 Pep435/434 Variants Cultures of FKBP_SmTrip9 variants and FRB-SmTrip10s were grown overnight in LB+100 µg/ml ampicillin at 37° C. Cells were diluted 1:20 in LB with 0.15% glucose, 0.1% rhamnose, and 100 ug/ml ampicillin. Cultures were induced ~20 hr at 25° C. with shaking. Cultures were diluted 1:4 in PLB and incubated 15 min at room temperature to lyse cells. SmTrip9 and SmTrip10 dilutions were mixed 1:1 (vol:vol) for combinations of interest. Mixtures were diluted 1:5 into PLB+200 nM LgTrip, with or without 30 nM rapamycin. Samples were incubated 30 min at room temperature. Fifty microliters of NanoGlo® buffer containing 50 uM furimazine was added to assay plates wells, and luminescence was read on GloMax® luminometer after 5 minutes. Results are depicted in FIGS. 113-115.

Example 66

FRB-FKBP Facilitated Complementation Assay Screen with Combinational SmTrip9 Variants Cultures of FKBP_SmTrip9 variants and FRB-SmTrip10s were grown overnight in LB+100 µg/ml ampicillin at 37° C. Cells were diluted 1:20 in LB with 0.15% glucose, 0.1% rhamnose, and 100 ug/ml ampicillin. Cultures were induced ~20 hr at 25° C. with shaking. PLB assay reagent was prepared with 444 nM LgTrip, 90× diluted FRB-SmTrip10 culture, +/−35 nM Rapamycin. Ninety microliters of assay reagent was added to each well of 96-well assay plates. FKBP_SmTrip9 cultures were diluted 1:10 in PLB, and 10 ul was added to assay plates. Samples were incubated 30 min at room temperature. One hundred microliters of Nano-Glo® buffer containing 50 uM furimazine was added to assay plates wells, and luminescence was read on GloMax® luminometer after 5 minutes. Results are depicted in FIGS. 116-122.

Example 67

Determination of Kd and Bmax of SmTrip9 Synthetic Peptides

LgTrip was diluted to 0.2 nM in TBS+0.01% BSA+0.01% Tergitol and pep289 was added to 25 uM. This solution was used as the diluent for 5-fold serial dilution series of SmTrip9 peptides. Samples were equilibrated 10 min at room temperature and aliquoted into assay plates in triplicate. TBS+0.01% BSA+0.01% Tergitol containing 20 uM furimazine was added to samples in 1:1 vol:vol ratio. Plates were incubated 10 min, and luminescence was read. To determine VS-HiBiT Kd, the same protocol was followed, but with saturating SmTrip9 (25 uM) and titration of VS-HiBiT. Results are depicted in FIGS. 123-130.

Example 68

Determination of Solubility of Synthetic SmTrip9 Peptides

Synthetic peptides were ordered from Peptide2.0 with termini blocked (N-terminal acetylation and C-terminal amidation) unless otherwise noted. Peptides were dissolved in nuclease-free water and stored at −20° C. Stocks were thawed in 22° C. water bath, centrifuged, and kept at 4° C. until use. Results are depicted in FIG. 131.

Example 69

Biochemical Co-Titration of SmTrip9 Synthetic Peptides and Pep289

LgTrip was diluted to 200 nM in 25 mM HEPES with 0.3× Passive Lysis Buffer (PLB) and DNase. SmTrip9 peptides and pep289 were diluted to 100 uM and co-titrated serially 6-fold in PLB. Samples were incubated 10 minutes at room temperature. Most concentrated samples were diluted 50-100-fold in PLB. Samples were aliquoted in triplicate into assay plates and mixed 1:1 vol:vol with NanoGlo® buffer+50 uM furimazine. Luminescence was read after 10 minutes on ClarioStar or GloMax® instruments. Results are depicted in FIGS. 132-133.

Example 70

Biochemical Co-Titration of SmTrip9 and SmTrip 10 Synthetic Peptides

LgTrip was diluted to 200 nM in 25 mM HEPES with 0.3× Passive Lysis Buffer (PLB) and DNase. SmTrip9 and SmTrip10 peptides were diluted to 100 uM and co-titrated serially 6-fold in PLB. Samples were incubated 10 minutes at room temperature. Most concentrated samples were diluted 50-100-fold in PLB. Samples were aliquoted in triplicate into assay plates and mixed 1:1 vol:vol with NanoGlo® buffer+50 uM furimazine. Luminescence was read after 10 minutes on ClarioStar or GloMax® instruments. Results are depicted in FIG. 134.

Example 71

Biochemical Co-Titration of Pep521 and Alternative SmTrip 10 Synthetic Peptides

LgTrip was diluted to 200 nM in 25 mM HEPES with 0.3× Passive Lysis Buffer (PLB) and DNase. SmTrip10 peptides and pep521 were diluted to 100 uM and co-titrated serially 6-fold in PLB. Samples were incubated 10 minutes at room temperature. Most concentrated samples were diluted 50-100-fold in PLB. Samples were aliquoted in triplicate into assay plates and mixed 1:1 vol:vol with NanoGlo® buffer+50 uM furimazine. Luminescence was read after 10 minutes on ClarioStar or GloMax® instruments. Results are depicted in FIG. 135.

Example 72

Strand Removal (Purification) from LgTrip 3546 Template

A single colony from each clone was grown for 18 hours at 37° C. in LB+100 ug/ml ampicillin. The overnight culture was diluted 1:100 into 50 ml of Terrific Broth+0.1% Rhamnose+100 ug/ml ampicillin. After 48 hours of growth at 15° C., cells were pelleted and resuspended in 10 ml of 100 mM HEPES pH 7.5+0.001 U/ml DNase. 1 ml of FastBreak® Lysis Buffer was added to each sample, and then samples incubated on a rotating mixer at 4° C. for 1 hour. A cleared lysate was prepared by centrifugation of 7,000 RPM for 10 minutes.

Purification of the strands using the MagneHis purification system: 300 ul µl of MagneHis resin (Promega) was added to each sample, and then samples mixed 20 times and placed on a magnetic stand. The supernatant was removed, and the resin was washed two times with column wash buffer. Samples were eluted in 600 ul of elution buffer. Samples were then placed in a dialysis apparatus to exchange with TBS. Identification of the strand removal proteins was observed via SDS PAGE as depicted in FIG. 136.

Example 73

Strand Removal Proteins with Various Combinations of Peptides

200 µl of OptiMEM+10% FBS was added to multiple wells of a multi-well plate. Peptide combinations were added to a final concentration of 10 µM with each to be assayed separately with each strand removal protein. Each strand removal protein was diluted to 20 nM (2 nM for LgTrip 3546) in OptiMEM+10% FBS. 20 µl of each strand removal peptide was added to the designated peptide combination, samples e mixed, and 45 µl aliquoted in triplicate into wells of a white assay plate (Costar 3600). After 15-minute incubation at RT, 5 µl of detection reagent (100 uM Fz (Promega LCS N205)) was added to each sample. Samples were placed on an orbital shaker for 30 seconds, and then luminescence was measured every 2 minutes for 1 hour. Luminescence is reported as peak height of the kinetic read. Background is OptiMEM+10% FBS+detection reagent.

As demonstrated in FIG. 137, there was no signal over background for strand removal proteins 7, 8, 9, 10 when added as separate peptides. Two of the three peptide combinations gave ~2× signal over background ((8+9) dipeptide+7+10) or ((7+8) dipeptide+9+10). One of the 3 peptide combinations gave ~10× signal over background (((9+10) dipeptide+7+8) The two dipeptide combination of (10+9)+ (7+8) gave signal of ~4.5 logs over background. It is likely that the peptide combinations that gave the greatest signal have the highest affinity. Lower affinity combinations could produce light in a facilitated complementation assay. FIG. 137D demonstrates that peptides with alternative split sites (e.g., mid beta strand) are capable of forming a bioluminescent complex.

Example 74

Strands 6, 7, 8, 9, or 10 Removal (Purification) from LgTrip 3546 Template

400 µl of OptiMEM+10% FBS was added to multiple wells of a deep well 96-well plate. Peptide combinations were added to a final concentration of 10 µM each peptide to be assayed separately with either ATG-3929 or LgTrip. The peptide solutions were then divided. To one of the peptide aliquots, 20 ul of either 20 nM ATG-3929 or 2 nM LgTrip was added to the designated peptide combination, samples mixed, and 45 µl of the +/−peptide samples aliquoted in triplicate into wells of a white assay plate (Costar 3600). After a 15-minute incubation at RT, 5 µl of detection reagent (100 uM Fz in OptiMEM+10% FBS (Promega LCS N205)) was added to each sample. Samples were placed on an orbital shaker for 5 minutes. Background for each sample is OptiMEM+10% FBS+peptide dilutions+detection reagent.

As demonstrated in FIG. 138, sample ATG-3929 with strands (9+10)+(7+8)+6 shows ~2× signal over background. On the other hand, the sample with two peptides (6+7+8)+ (9+10) showed ~300× over background.

Note that spontaneous complementation is not visible for samples with more than 3 peptides. It is possible that the affinity is not high enough affinity of the peptides is not high enough to produce light. It is possible that if the peptides are brought together through facilitated complementation with a fusion partner that it would be possible to obtain signal.

Example 75

Dipeptide Titrations

Figure 139A:
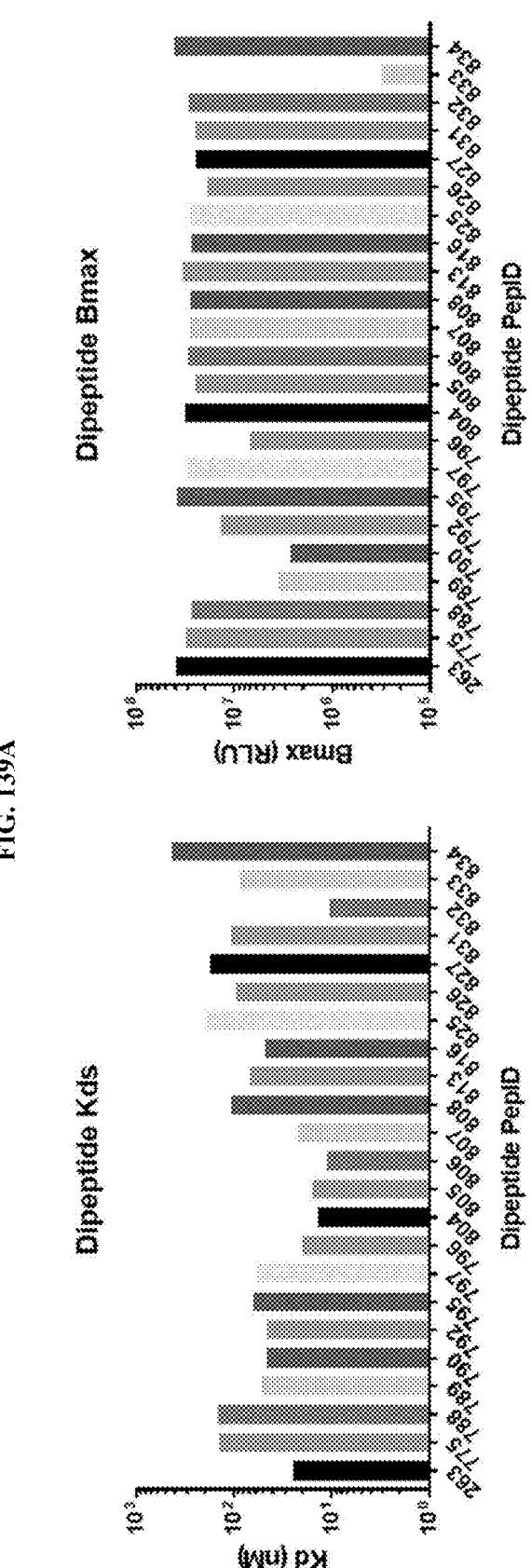
Figure 139C:
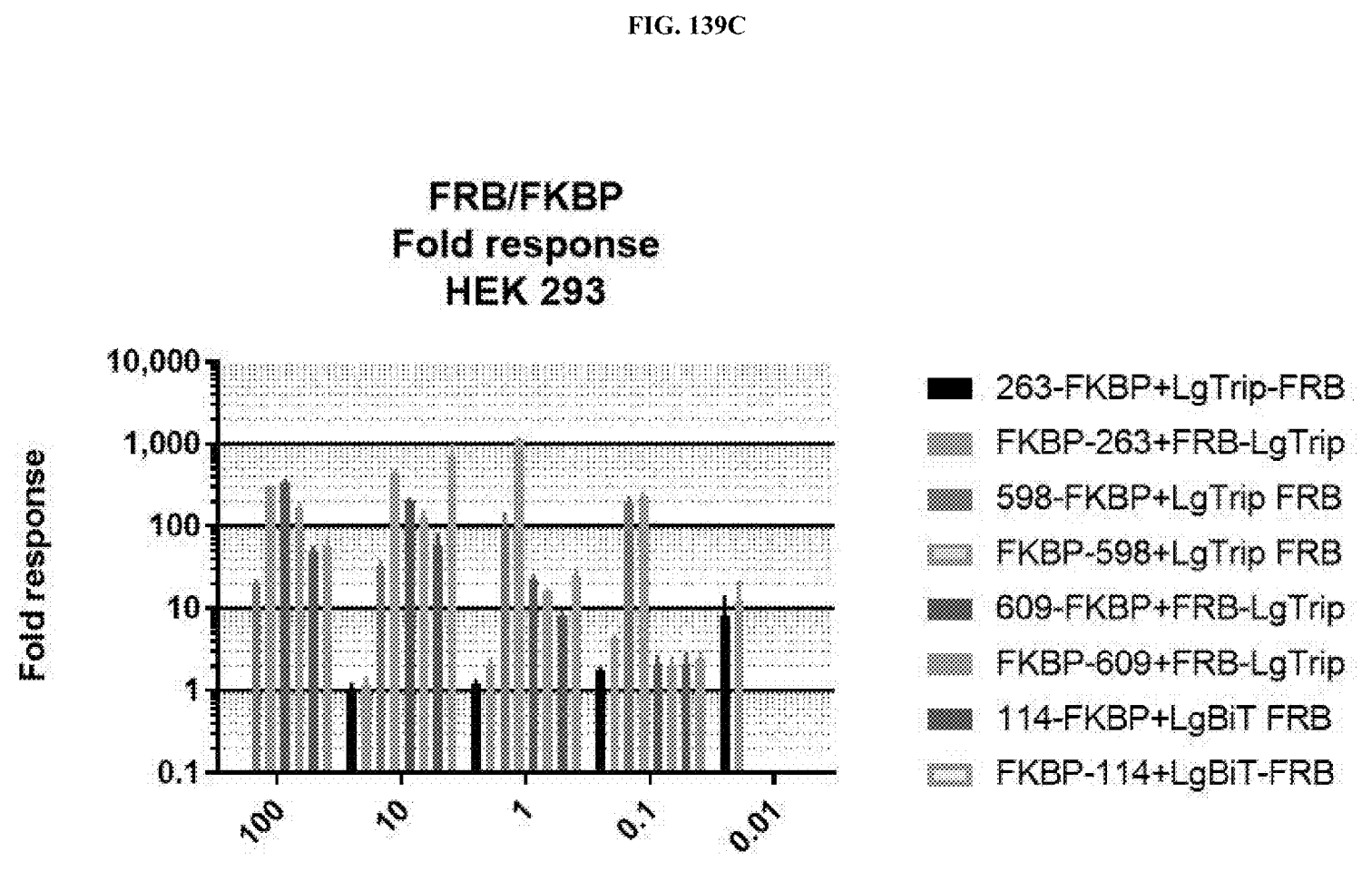
Figure 139D:
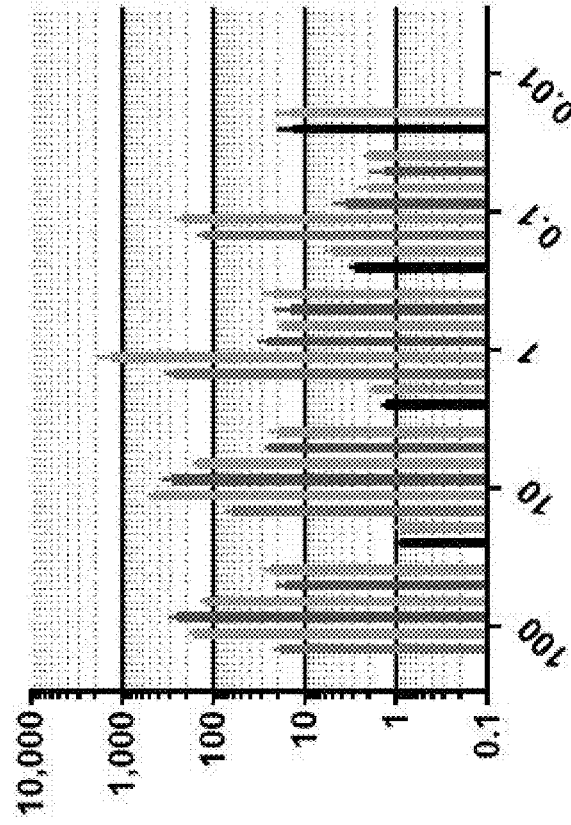
Figure 139E:
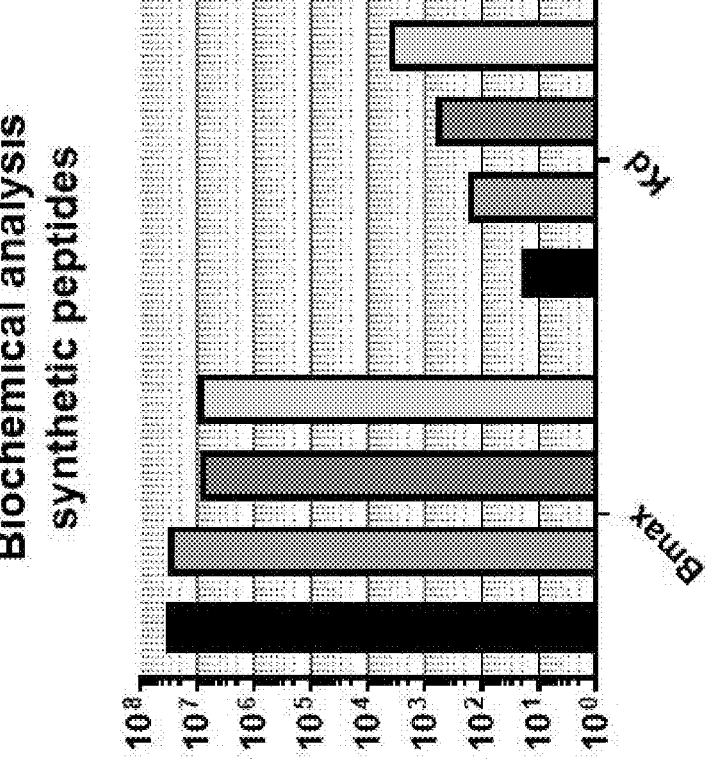

Dipeptides were diluted to 5 uM and diluted serially 5-fold using TBS+0.01% BSA+0.01% Tergitol with 0.2 nM of LgTrip as the diluent. Samples were incubated 10 minutes at room temperature and added to wells of assay plates in triplicate. One-to-one vol:vol of TBS+0.01% BSA+0.01% Tergitol with 20× diluted live cell substrate was added to samples and plates were read on a GloMax luminometer after 10 minutes. FIG. 139A-B demonstate the Kd and Bmax values from the dipeptide titrations.

Fold Response of Binary Nano Trip in Mammalian Cells

Growth media was removed from confluent flasks of cells. (HEK293 and Hela). Cells were washed with 10 ml of DPBS and then 3 ml of TrypLE Express trypsin was added to cells. Cells were incubated for 3 minutes at 37° C. 10 ml of growth media was added and then cells were spun at 200RCF for 5 minutes. Media was replaced and cells were resuspend in 10 ml of growth media. Cells were counted and diluted to 200,000/ml. 100 ul of cells were plated into each well of a white assay plates and grow overnight at 37° C. with $CO_2$. The next day 100 ng/ul DNA from FRB and FKBP fusions of LgTrip (3546) and various dipeptide in each orientation were combined. 263 samples started at 1:10 dilution in carrier DNA or 10 ng/ul. DNA samples were then diluted serially into carrier DNA (10 ul to 90 µl in 100 ng/ul carrier DNA) Next 20 ul of each DNA dilution was added to 83 ul of OptiMEM. Samples were mixed and then 6.6 ul of Viafect transfection reagent was added to each sample. Samples were incubated for 20 minutes at RT and then 5 ul of transfection complex was added to 6 wells of cells for each FRB-FKBP orientation. Plates were then grown overnight at 37° C. with $CO_2$. The next day Rapamycin (RAP) was added to 3 of the wells for each sample to a final concentration of 100 nM. Samples were placed on orbital shaker for 1 minute and then Incubated at 37 C for 30 minutes. After incubation, 100 ul of NanoGlo+50 uM Fz was added to each sample (+RAP and −RAP) and then samples were placed on orbital shaker for 5 minutes. Luminescent measurements were acquired using a Glomax Discover luminometer. Fold response was calculated by dividing RLU values from the +RAP sample by the RLU values from the −RAP samples. Results are depicted I FIG. 139C-E. Dipeptide fusions that have lower affinity to LgTrip produce a greater fold response compared to samples with higher affinity.

Example 76

Development of a Tripartite Quantitative Assay for Anti-TNFa Biologic Agents Using Tripartite Fusion Proteins Infliximab (Remicade), Adalimumab (Humira), and Etanercept (Enbrel) are TNFa inhibitors that all bind human TNFa and also all contain a human IgG1 Fc. A quantitative assay was developed for all 3 TNFa inhibitors by expressing and purifying SmTrip9- or SmTrip10-protein G and TNFa fusion proteins which serve as the binding components to the TNFa inhibitor (FIG. 140). The Protein G fusion protein will bind to the conserved IgG1 Fc region of the TNFa inhibitor. The Inhibitor will bind to the TNFa fusion protein bringing the SmTrip9 and SmTrip10 into close proximity. In the presence of LgTrip, the bioluminescent complex will form creating the signal that is proportional to the amount of TNFa inhibitor present. All reporter tag configurations were tested with SmTrip9 or SmTrip10 expressed on the N- or C-terminal of Protein G and TNFa with either a 4gly-ser or 15gly-ser linker. The optimal pairing resulting from screening all orientations was SmTrip9-15gly/ser-protein G with TNFa-15gly/ser-SmTrip10.

Methods for Making the Fusion Proteins

A fusion protein comprising of SmTrip9 pep521 (SEQ ID NO: 268) sequence followed by a linker of 15 glycine-serine repeat was fused to the N-terminus of Protein G was expressed and purified. A second fusion protein comprising of SmTrip10 pep289 (SEQ ID NO: 150) sequence was fused to the C terminus of human TNFa separated by a linker of 15 glycine-serine repeat was also expressed and purified. Streak plates from glycerol stocks of KRX transformed *E. coli* cells were created on LB plates with Ampicillin (100 ug/ml) and allowed to incubate overnight at 37° C. A single colony was inoculated into 3 mls of SOC media+AMP and incubated shaking (275 rpm) overnight at 37° C. The cells were lysed and the plasmid DNA was collected. Shuffle competent *E. coli* cells were transformed with 100 ng of plasmid DNA, spread onto pre-warmed selection plates, and allowed to incubate overnight at 30° C. A colony was selected and inoculated into a 50 ml volume of LB containing ampicillin. The cultures were incubated overnight at 37° C. shaking before being diluted 1:100 into 500 mL of LB medium containing ampicillin. These flasks were allowed to incubate at 37° C. while shaking until the OD600 reached 0.6-0.8. Cells were induced by addition of IPTG at a final concentration of 1 mM and allowed to incubate overnight at 25° C. while shaking. Cells were harvested, centrifuged, and resuspended in 50 mL extraction and lysis buffer at 4° C. with mixing. Three cycles of freeze/thaw were performed followed by addition of RQI DNase. The total lysate was transferred to a think 50 mL centrifuge tube and spun at 10,000×g for 30 minutes at 4° C. 20 mM Imidazole/350 mM NaCl was added prior to loading onto a nickel column. Fusion proteins were washed and eluted off the columns in a 5 step elution process with increasing imidazole. Samples were dialyzed against TBS and final stock proteins were stored in 50% glycerol in TBS at −20° C.

Example 77

Homogeneous Quantitative Analysis of TNFa Inhibitors Infliximab, Adalimumab, and Etanercept Using SmTrip9 Pep521-Protein G and TNFa-SmTrip10 Pep289 Fusion Proteins Experiments were conducted during development of embodiments herein to determine the ability of NanoTrip fusion proteins to quantitate TNFa inhibitors in a homogeneous assay. The results show that protein G and TNFa NanoTrip fusion proteins together with LgTrip display great sensitivity and range for quantitating infliximab, adalimumab, and etanercept.

A 2× stock of the TNFa inhibitors was generated in assay buffer, serially diluted 1:2 to create a dose response, and 50 ul/well was added to a non-binding surface treated, 96 well solid-white plate (Costar 3600). A 2× master mix of the purified LgTrip 3546 (SEQ ID NO: 51) (final concentration 1 uM)+SmTrip9 pep521-protein G (SEQ ID NO: 268) (final 10 nM)+TNFa-SmTrip10 pep289 (SEQ ID NO: 150) (final 10 nM) was created in assay buffer, and 50 ul/well added. Plates were allowed to incubate at room temperature for 90 minutes. A 5× stock of Nano-Glo® Live Cell Substrate in assay buffer, 25 ul/well added to the plate for a final concentration of 10 uM, allowed to incubate for ~5 minutes, and luminescence measured using a GloMax® Discover. Assay buffer consisted of Blocker BSA (10%) (Thermo) diluted in PBS (pH 7.0) to a final of 0.01% BSA in PBS. Samples were tested in triplicate/plate, and n=3 independent experiments run. Data as demonstrated in FIG. 141 was analyzed for limit of detection (LOD), limit of quantitation (LOQ), and upper limit of quantitation (ULOQ).

Example 78

Homogenous Quantitative Analysis of Infliximab in Complex Sample Matrices Such as Human Serum and Urine Experiments were conducted during development of embodiments herein to determine the ability of NanoTrip fusion proteins to quantitate infliximab in the presence of the complex sample matrices of normal human IgG depleted serum, normal pooled human AB serum, and pooled normal human urine in a homogenous assay. Results indicate that the NanoTrip system was largely unaffected by the presence of urine nor the presence of serum proteins with the exception of endogenous IgG as expected.

A 2× stock containing 20 nM Infliximab in presence of the human sample matrix to be tested was created by diluting with assay buffer, and 50 ul/well added to a non-binding surface treated, 96 well solid-white plate (Costar 3600). A 2× master mix of the purified LgTrip 3546 (SEQ ID NO: 51) (final concentration 1 uM)+SmTrip9 pep521-protein G (SEQ ID NO: 268) (final 10 nM)+TNFa-SmTrip10 pep289 (SEQ ID NO: 150) (final 10 nM) was created in assay buffer, and 50 ul/well added. Plates were allowed to incubate at room temperature for 90 minutes. A 5× stock of Nano-Glo® Live Cell Substrate in assay buffer, 25 ul/well added to the plate for a final concentration of 10 uM, allowed to incubate for ~5 minutes, and luminescence measured using a GloMax® Discover. Assay buffer consisted of Blocker BSA (10%) (Thermo) diluted in PBS (pH 7.0) to a final of 0.01% BSA in PBS. Samples were tested in triplicate. Data as demonstrated in FIG. 142 is displayed as signal/background.

Example 79

Kinetic Analysis of Signal Generation Via Facilitated Complementation of SmTrip9 Pep521-Protein G (SEQ ID NO: 268) and TNFa-SmTrip10 Pep289 (VS-HiBIT; SEQ ID NO: 150) Fusion Proteins with Purified LgTrip 3546 (SEQ ID NO: 51) in the Presence of 100 pM of Infliximab in a Solution Phase, Homogenous Assay Experiments were conducted during development of embodiments herein to determine the binding kinetics of the Protein G/TNFa NanoTrip system to quantitate 100 pM of Infliximab in a solution phase, homogenous assay. Results show that signal generation is immediate and sustained indicating rapid binding kinetics of the fusion proteins to infliximab as well as LgTrip to the SmTrip9 and SmTrip10 fusion proteins.

A 2× stock of Infliximab (100 pM final) was generated in assay buffer, and 50 ul/well added to a non-binding surface treated, 96 well solid-white plate (Costar 3600). A 2× master mix of the purified LgTrip 3546 (SEQ ID NO: 51) (final concentration 1 uM)+SmTrip9 pep521-protein G (SEQ ID NO: 268) (final 10 nM)+TNFa-SmTrip10 pep289 (SEQ ID NO: 150) (final 10 nM) was created in assay buffer, and 50 ul/well added. A 5× stock of Nano-Glo® Live Cell Substrate in assay buffer, and 25 ul/well added to the plate for a final concentration of 10 uM. All reagents were added, and the plate immediately placed on a GloMax® Discover to read luminescence over time. Assay buffer consisted of Blocker BSA (10%) (Thermo) diluted in PBS (pH 7.0) to a final of 0.01% BSA in PBS. Samples were tested in triplicate.

Results are depicted in FIG. 143.

Example 80

Testing SmTrip9-Protein G Variants for their Ability to Measure Infliximab Via Facilitated Complementation with TNFa-SmTrip10 Pep289 (VS-HiBIT; SEQ ID NO:150) Fusion Proteins Purified LgTrip 3546 (SEQ ID NO: 51) in a Solution Phase, Homogenous Assay Experiments were conducted during development of embodiments herein to determine the ability of other SmTrip9 variants expressed as a fusion proteins to protein G to measure Infliximab via facilitated complementation with TNFa-SmTrip10 pep289 (VS-HiBIT; SEQ ID NO: 150) fusion proteins purified LgTrip 3546 (SEQ ID NO: 51) in a solution phase, homogenous assay. Results show that all of the SmTrip9 pep(x)-Protein G variants tested were able to generate signal.

A 2× stock of Infliximab (10 nM final) was generated in assay buffer, and 50 ul/well added to a non-binding surface treated, 96 well solid-white plate (Costar 3600). A 2× master mix of the purified LgTrip 3546 (SEQ ID NO: 51) (final concentration 1 uM)+SmTrip9 pep(x)-Protein G (final 10 nM)+TNFa-SmTrip10 pep289 (SEQ ID NO: 150) (final 10 nM) was created in assay buffer, and 50 ul/well added. Plates were allowed to incubate at room temperature for 90 minutes. A 5× stock of Nano-Glo® Live Cell Substrate in assay buffer, 25 ul/well added to the plate for a final concentration of 10 uM, allowed to incubate for ~5 minutes, and luminescence was measured using a GloMax® Discover. Assay buffer consisted of Blocker BSA (10%) (Thermo) diluted in PBS (pH 7.0) to a final of 0.01% BSA in PBS. Samples were tested in triplicate. Results are depicted in FIG. 144.

Example 81

Homogeneous Quantitative Infliximab Testing SmTrip9 Pep(X)-Protein G Variants and TNFa-SmTrip10 Pep289 Fusion Proteins Experiments were conducted during development of embodiments herein to demonstrate the ability of different SmTrip9 pep(X)-Protein G variants to quantitate Infliximab via facilitated complementation with TNFa-SmTrip10 pep289 (VS-HiBIT; SEQ ID NO: 150) fusion proteins with purified LgTrip 3546 (SEQ ID NO: 51) in a solution phase, homogeneous assay. Results show that all SmTrip9 variants were able to quantitate infliximab.

A 2× stock of Infliximab (10 nM final) was generated in assay buffer, and 50 ul/well added to a non-binding surface treated, 96 well solid-white plate (Costar 3600). A 2× master mix of the purified LgTrip 3546 (SEQ ID NO: 51) (final concentration 1 uM)+SmTrip9 pep(x)-protein G (final 10 nM)+TNFa-SmTrip10 pep289 (SEQ ID NO: 150) (final 10 nM) was created in assay buffer, and 50 ul/well added. Plates were allowed to incubate at room temperature for 90 minutes. A 5× stock of Nano-Glo® Live Cell Substrate in assay buffer, 25 ul/well added to the plate for a final concentration of 10 uM, allowed to incubate for ~5 minutes, and luminescence was measured using a GloMax® Discover. Assay buffer consisted of Blocker BSA (10%) (Thermo) diluted in PBS (pH 7.0) to a final of 0.01% BSA in PBS. Samples were tested in triplicate.

Example 82

Development of a Tripartite Quantitative Assay for Anti-EGFR Biologic Agents Using Tripartite Fusion Proteins in a Cell-Based Assay We developed a quantitative, cell-based assay for panitumumab and cetuximab representing a phase separation or surface chemistry like assay. Using purified SmTrip9-Protein G fusion proteins that will bind to the conserved human IgG Fc region of the EGFR inhibitor, the Inhibitor will bind to the SmTrip10-EGFR fusion protein that is expressed on the cell surface bringing the SmTrip9 and SmTrip10 into close proximity. In the presence of LgTrip, the bioluminescent complex will form creating the signal that is proportional to the amount of EGFR inhibitor present. All reporter tag configurations were tested with SmTrip9 or SmTrip10 expressed on the N- or C-terminal of protein G or on the N terminal of EGFR with either a 4gly-ser or 15gly-ser linker. The optimal pairing resulting from screening all orientations was SmTrip9-4gly/ser-protein G with EGFR-15gly/ser-SmTrip10.

Results are depicted in FIG. 145.

Example 83

Quantitation of Panitumumab Via Facilitated Complementation with SmTrip9 Pep521-Protein G (SEQ ID NO: 268) Fusion Protein and SmTrip10 Pep289-EGFR (VS-HiBIT; SEQ ID NO:150) Expressing Cells with Purified LgTrip 3546 (SEQ ID NO: 51) in a Cell-Based Homogeneous Assay Experiments were conducted during development of embodiments herein to determine the ability of NanoTrip fusion proteins to quantitate the EGFR inhibitor panitumumab in a cell-based homogeneous assay. The results show that SmTrip9 pep521-protein G (SEQ ID NO: 268) purified protein, SmTrip10 pep289-EGFR (SEQ ID NO:150) expressing cells, and LgTrip 3546 (SEQ ID NO: 51) display great sensitivity and range for quantitating panitumumab.

HEK293 cells were maintained in growth medium (DMEM) supplemented with 10% fetal bovine serum (FBS, Hyclone) at 37° C./5% CO$_2$ in a humidified tissue culture incubator. Transient reverse transfection were performed by first diluting the expression construct for the SmTrip10 pep289-EGFR (VS-HiBIT; SEQ ID NO:150) into Opti-MEM containing carrier DNA (PGEM-3ZF(−)) at a mass ratio of 1:10. The transfection reagent:DNA complex was prepared by adding FuGENE HD transfection reagent at a ratio of 1:3 (mg DNA per mL FuGENE HD) followed by 15 minutes incubation at room temperature. The resulting transfection: DNA complex was then mixed with a HEK293 cell suspension ($2 \times 10^5$ cells/ml) in growth medium at a ratio of 1:20 (vol/vol), followed by incubation for 18-20 hours at 37° C./5% $CO_2$ in humidified tissue culture incubator.

HEK293 cells expressing the SmTrip10 pep289-EGFR (SEQ ID NO: 150) fusion protein were harvested using Trypsin-EDTA, washed in growth medium, and resuspended in Opti-MEM at a concentration of $4.5 \times 10^5$ cells/ml. 50 ul of cells/well (20,000 cells/well) are added to a non-binding surface, solid white 96 well plate (Costar 3600). A 4× stock of Panitumumab was generated in Opti-MEM, serially diluted in Opti-MEM to create dose response, and 25 ul/well added. A 4× master mix of the purified LgTrip 3546 (SEQ ID NO: 51) (final concentration 1 uM)+SmTrip9 pep521-protein G (SEQ ID NO: 268) (final 5 nM) was created in Opti-MEM, and 25 ul/well added. Plates were allowed to incubate for 1 hour at 37° C. A 5× stock of Nano-Glo® Live Cell Substrate in assay buffer, 25 ul/well added to the plate for a final concentration of 10 uM, and luminescence was measured on a GloMax® Discover. Samples were tested in triplicate. N=3 independent experiments.

Results are depicted in FIG. 146.

Example 84

Real-Time Binding Kinetic Analysis of Signal Generation Via Facilitated Complementation of SmTrip9 Pep521-Protein G (SEQ ID NO: 268) Purified Fusion Protein and SmTrip10 Pep289-EGFR (VS-HiBIT; SEQ ID NO:150) Expressing HEK293 Cells Paired with Purified LgTrip 3546 (SEQ ID NO: 51) in the Presence of Increasing Doses of Cetuximab in a Cell-Based Homogeneous Assay Experiments were conducted during development of embodiments herein to determine the binding kinetics of the Protein G/EGFR NanoTrip system to quantitate Cetuximab in a cell-based homogenous assay. Results show that the luminescent signal increases with time in accordance with the formation of the luciferase complex. Signal generation is also dose dependent.

HEK293 cells were maintained in growth medium (DMEM) supplemented with 10% fetal bovine serum (FBS, Hyclone) at 37° C./5% $CO_2$ in a humidified tissue culture incubator. Transient reverse transfection were performed by first diluting the expression construct for the SmTrip10 pep289-EGFR (VS-HiBIT; SEQ ID NO: 150) into Opti-MEM containing carrier DNA (PGEM-3ZF(−)) at a mass ratio of 1:10. The transfection reagent:DNA complex was prepared by adding FuGENE HD transfection reagent at a ratio of 1:3 (mg DNA per mL FuGENE HD) followed by 15 minutes incubation at room temperature. The resulting transfection: DNA complex was then mixed with a HEK293 cell suspension ($2 \times 10^5$ cells/ml) in growth medium at a ratio of 1:20 (vol/vol), followed by incubation for 18-20 hours at 37° C./5% $CO_2$ in humidified tissue culture incubator.

HEK293 cells expressing the SmTrip10 pep289-EGFR fusion protein were harvested using Trypsin-EDTA, washed in growth medium, and resuspended in Opti-MEM at a concentration of $4.5 \times 10^5$ cells/ml. 50 ul of cells/well (20,000 cells/well) were added to a non-binding surface, solid white 96 well plate (Costar 3600). A 4× stock of cetuximab was generated in Opti-MEM, and 25 ul/well added. A 4× master mix of the purified LgTrip 3546 (SEQ ID NO: 51) (final concentration 10 uM)+SmTrip9 pep521-protein G (SEQ ID NO: 268) (final 780 pM) was created in Opti-MEM, and 25 ul/well added. A 5× stock of Nano-Glo® Live Cell Substrate in assay buffer, and 25 ul/well added to the plate for a final concentration of 10 uM. All reagents were added, and the plate was immediately placed on a GloMax® Discover to read luminescence over time. Samples were tested in triplicate.

Results are depicted in FIG. 147.

Example 85

Testing SmTrip9-Protein G Variants for their Ability to Measure Panitumumab Via Facilitated Complementation with SmTrip10 Pep289-EGFR (VS-HiBIT; SEQ ID NO:150) Expressing Cell Paired with Purified LgTrip 3546 (SEQ ID NO: 51) in a Cell-Based Homogenous Assay Experiments were conducted during development of embodiments herein to determine the ability of other SmTrip9 variants expressed as a fusion proteins to protein G to measure Panitumumab via facilitated complementation with SmTrip10 pep289-EGFR (VS-HiBIT; SEQ ID NO: 150) expressing cells paired with purified LgTrip 3546 (SEQ ID NO: 51) in a cell-based homogenous assay. Results show that all of the SmTrip9 pep(x)-protein G variants tested were able to generate signal.

HEK293 cells were maintained in growth medium (DMEM) supplemented with 10% fetal bovine serum (FBS, Hyclone) at 37° C./5% $CO_2$ in a humidified tissue culture incubator. Transient reverse transfection were performed by first diluting the expression construct for the SmTrip10 pep289-EGFR (VS-HiBIT; SEQ ID NO:150) into Opti-MEM containing carrier DNA (PGEM-3ZF(−)) at a mass ratio of 1:10. The transfection reagent:DNA complex was prepared by adding FuGENE HD transfection reagent at a ratio of 1:3 (mg DNA per mL FuGENE HD) followed by 15 minutes incubation at room temperature. The resulting transfection: DNA complex was then mixed with a HEK293 cell suspension ($2 \times 10^5$ cells/ml) in growth medium at a ratio of 1:20 (vol/vol), followed by incubation for 18-20 hours at 37° C./5% $CO_2$ in humidified tissue culture incubator.

HEK293 cells expressing the SmTrip10 pep289-EGFR (SEQ ID NO: 150) fusion protein were harvested using Trypsin-EDTA, washed in growth medium, and resuspended in Opti-MEM at a concentration of $4.5 \times 10^5$ cells/ml. 50 ul of cells/well (20,000 cells/well) were added to a non-binding surface, solid white 96 well plate (Costar 3600). A 4× stock of Panitumumab (final 1 nM) was generated in Opti-MEM, and 25 ul/well added. A 4× master mix of the purified LgTrip 3546 (SEQ ID NO: 51) (final concentration 1 uM)+SmTrip9 pep(X)-protein G (final 10 nM) was created in Opti-MEM, and 25 ul/well added. Plates were allowed to incubate for 1 hour at 37 C. A 5× stock of Nano-Glo® Live Cell Substrate in assay buffer, 25 ul/well added to the plate for a final concentration of 10 uM, and luminescence was measured on a GloMax® Discover. Samples were tested in triplicate. N=3 independent experiments. Results are depicted in FIG. 148.

Example 86

Testing SmTrip9-Protein G Variants for their
Ability to Measure Panitumumab Via Facilitated
Complementation with SmTrip10 Pep289-EGFR
(VS-HiBIT; SEQ ID NO:150) Expressing Cell
Paired with Purified LgTrip 3546 (SEQ ID NO: 51)
in a Cell-Based Homogenous Assay Experiments were conducted during development of embodiments herein to determine the ability of other SmTrip9 variants expressed as a fusion proteins to protein G to measure panitumumab via facilitated complementation with SmTrip10 pep289-EGFR (VS-HiBIT; SEQ ID NO: 150) expressing cells paired with purified LgTrip 3546 (SEQ ID NO: 51) in a cell-based homogenous assay. Results show that all of the SmTrip9 pep(x)-protein G variants tested were able to quantitate panitumumab in a dose response analysis.

HEK293 cells were maintained in growth medium (DMEM) supplemented with 10% fetal bovine serum (FBS, Hyclone) at 37° C./5% $CO_2$ in a humidified tissue culture incubator. Transient reverse transfection were performed by first diluting the expression construct for the SmTrip10 pep289-EGFR (VS-HiBIT; SEQ ID NO:150) into Opti-MEM containing carrier DNA (PGEM-3ZF(–)) at a mass ratio of 1:10. The transfection reagent:DNA complex was prepared by adding FuGENE HD transfection reagent at a ratio of 1:3 (mg DNA per mL FuGENE HD) followed by 15 minutes incubation at room temperature. The resulting transfection: DNA complex was then mixed with a HEK293 cell suspension ($2×10^5$ cells/ml) in growth medium at a ratio of 1:20 (vol/vol), followed by incubation for 18-20 hours at 37° C./5% $CO_2$ in humidified tissue culture incubator.

HEK293 cells expressing the SmTrip10 pep289-EGFR (SEQ ID NO: 150) fusion protein were harvested using Trypsin-EDTA, washed in growth medium, and resuspended in Opti-MEM at a concentration of $4.5×10^5$ cells/ml. 50 ul of cells/well (20,000 cells/well) were added to a non-binding surface, solid white 96 well plate (Costar 3600). A 4× stock of Panitumumab (final 1 nM) was generated in Opti-MEM, and 25 ul/well added. A 4× master mix of the purified LgTrip 3546 (SEQ ID NO: 51) (final concentration 1 uM)+SmTrip9 pep(X)-protein G (final 10 nM) was created in Opti-MEM, and 25 ul/well added. Plates were allowed to incubate for 1 hour at 37° C. A 5× stock of Nano-Glo® Live Cell Substrate in assay buffer, 25 ul/well added to the plate for a final concentration of 10 uM, and luminescence was measured on a GloMax® Discover. Samples were tested in triplicate. Results are depicted in FIG. 149.

Example 87

Quantitation of Human IL-1Beta Using NanoTrip
Chemically Labeled-Paired Antibodies Experiments were conducted during development of embodiments herein to demonstrate the use of paired monoclonal antibodies that have been chemically conjugated with NanoTrip peptides to quantitation human IL-1beta. This model system consists of two monoclonal mouse antibodies that recognize IL-1beta at different epitopes. HaloTag-SmTrip9 pep521 (SEQ ID NO: 268) was chemically conjugated to one of the antibodies, and HaloTag-SmTrip10 pep289 (SEQ ID NO: 150) was chemically conjugated to the other antibody. In the presence of IL-1 beta, the two antibodies bind to the IL-1beta thus bringing the two tags in close proximity. Addition of LgTrip 3546 (SEQ ID NO: 51) completes the complementation, and a luminescent signal is generated.

HaloTag-SmTrip9 and HaloTag-SmTrip10 fusion proteins are expressed and purified. Anti-IL-1beta mouse monoclonal antibody clone 508A 4A2 (Thermo) is labeled with the HaloTag-SmTrip9 pep521 (SEQ ID NO: 268) and anti-IL-1beta mouse monoclonal antibody clone 508A 7G8 (Thermo) is labeled with the HaloTag-SmTrip10 pep289 (SEQ ID NO: 150). The unlabeled antibodies are prepped by first doing a buffer exchange into 10 mM $NaHCO_3$ (pH 8.5) using a Zeba column. Antibodies are then primed with a 20-fold excess of HaloTag® Succinimidyl Ester (04) Ligand (Promega) and allowed to incubate at room temperature for 2 hours. A buffer exchange is done 2× using Zeba columns to remove free linker. The primed antibodies are incubated with a 4-fold excess of HaloTag-SmTrip9 or HaloTag-SmTrip10 overnight at 4 C while mixing. HaloLink® Resin is used to remove any free HaloTag® fusion proteins.

A 2× stock of recombinant human IL-1beta was generated in assay buffer, serially diluted 1:2 to create a dose response, and 50 ul/well added to a non-binding surface treated, 96 well solid-white plate (Costar 3600). A 2× master mix of the purified LgTrip 3546 (SEQ ID NO: 51) (final concentration 1 uM)+SmTrip9 pep521 labeled 4A2 clone (SEQ ID NO: 268) (final 100 ng/ml)+SmTrip10 pep289 labeled 7G8 clone (SEQ ID NO: 150) (final 100 ng/ml) was created in assay buffer, and 50 ul/well added. A 5× stock of Nano-Glo® Live Cell Substrate in assay buffer, 25 ul/well added to the plate for a final concentration of 10 uM, and luminescence measured in real-time using a GloMax® Discover. Assay buffer consisted of Blocker BSA (10%) (Thermo) diluted in PBS (pH 7.0) to a final of 0.01% BSA in PBS. Samples were tested in triplicate. Data displayed is the signal that was read at the 20 minute time point.

Results are depicted in FIG. 150.

Example 88

Real-Time Binding Kinetics for Human Troponin
Using NanoTrip Chemically-Labeled Paired
Antibodies Experiments were conducted during development of embodiments herein to demonstrate the use of paired monoclonal antibodies that have been chemically conjugated with NanoTrip peptides to quantitation human Troponin. This model system consists of two monoclonal mouse antibodies that recognize Troponin at different epitopes. HaloTag-SmTrip9 pep521 (SEQ ID NO: 268) was chemically conjugated to one of the antibodies, and HaloTag-SmTrip10 pep289 (SEQ ID NO: 150) was chemically conjugated to the other antibody. In the presence of Troponin, the two antibodies bind to the Troponin thus bringing the two tags in close proximity. Addition of LgTrip 3546 (SEQ ID NO: 51) completes the complementation and a luminescent signal is generated.

HaloTag-SmTrip9 and HaloTag-SmTrip10 fusion proteins are expressed and purified. Anti-troponin mouse monoclonal antibody 10-T79C (Fitzgerald) is labeled with the HaloTag-SmTrip10 pep289 (SEQ ID NO: 150), and anti-troponin mouse monoclonal antibody 10-T79F (Fitzgerald) is labeled with the HaloTag-SmTrip9 pep521 (SEQ ID NO: 268). The unlabeled antibodies are prepped by first doing a buffer exchange into 10 mM $NaHCO_3$ (pH 8.5) using a Zeba column. Antibodies are then primed with a 20-fold excess of HaloTag® Succinimidyl Ester (04) Ligand (Promega) and allowed to incubate at room temperature for 2 hours. A buffer exchange is done 2× using Zeba columns to remove free linker. The primed antibodies are incubated with a 4-fold excess of HaloTag-SmTrip9 or HaloTag-SmTrip10 overnight at 4° C. while mixing. HaloLink® Resin is used to remove any free HaloTag® fusion proteins.

A 2× stock of recombinant human Troponin (final 1 ug/ml) was generated in assay buffer, and 50 ul/well added to a non-binding surface treated, 96 well solid-white plate (Costar 3600). A 2× master mix of the purified LgTrip 3546 (SEQ ID NO: 51) (final concentration 1 uM)+SmTrip9 pep521 labeled 10-T79F clone (SEQ ID NO: 268) (final 1 ug/ml)+SmTrip10 pep289 labeled 10-T79C clone (SEQ ID NO: 150) (final 1 ug/ml) was created in assay buffer, and 50 ul/well added. A 5× stock of Nano-Glo® Live Cell Substrate in assay buffer, 25 ul/well was added to the plate for a final concentration of 10 uM, and luminescence was measured in real-time using a GloMax® Discover. Assay buffer consisted of Blocker BSA (10%) (Thermo) diluted in PBS (pH 7.0) to a final of 0.01% BSA in PBS. Samples were tested in triplicate.

Results are depicted in FIG. 151.

Example 89

Translocation Assay

HiBiT exhibits a very high affinity for the LgBiT polypeptide ($K_D$=1 nM) and other similar complementary polypeptides. The strong interaction between the two fragments would drive complementation without any stimuli (FIG. 154), which would be unsuitable for a translocation assay. A study was conducted to determine the optimal affinity between two components (e.g., peptide and polypeptide) of a translocation assays. The optimal affinity was found to be in the range of 280 nM to 1300 nM. A quadruple mutations in LgBiT (E11K/144M/N135V/L150S), referred to as LgBiT*, reduces its interaction with HiBiT by ~1000 fold ($K_D$=1296 nM), rendering the HiBIT/LgBiT* pair well-suited for a translocation assay. Two different translocation assays were designed and tested.

A membrane translocation assay was developed to measure PKCα translocation from cytosol to the plasma membrane under PMA stimulus. PKCα was endogenously tagged with HiBiT at the C-terminus in Hela cells. The clones of edited cells were isolated, and the best clone with the highest luminescence signal was chosen to perform the assay. LgBiT*-membrane sensor was introduced to the clone using transfection method. Addition of PMA recruits PKCα-HiBiT to the plasma membrane, where HiBiT meets LgBiT* to produce light. Titration of PMA yielded 12- to 19-fold increase in response depending on the amount of LgBiT* transfected (FIG. 155).

A nuclear translocation assay was developed using measuring p65 movement from cytosol to the nucleus under TNFa stimulus. The nuclear translocation assay was set up similar to the membrane translocation assay. Specifically, p65 was endogenously tagged at the C-terminus in HeLa cells, and LgBiT*-nuclear sensor was introduced to p65-HiBiT cell line via transfection method. Treatment of TNFα promotes translocation of p65-HiBiT to the nucleus, where complementation occurs between HiBiT and LgBiT* to yield luminescence signal. Titration of TNFα resulted in 4-fold increase in response (FIG. 156A). The assay allows measurement of protein translocation in real time. As shown in FIG. 156B, it takes approximately 30 minutes for p65 to migrate to the nucleus upon stimulation of TNFa, which is consistent with findings in the literature.

Example 90

Comparison Kd and Bmax Values of LgBiT Mutants with HiBiT

A solution of HiBiT peptide was prepared starting at 1.22 uM in OptiMEM+10% FBS. Serially diluted the peptide dilution 3-fold into OptiMEM+10% FBS. (300 ul in 700 ul). Diluted purified LgBiT or LgBiT mutant into OptiMEM+10% FBS to a concentration of 2 nM. 90 ul of the peptide solution was combined with 10 µl of the LgBiT dilution (0.2 nM LgBiT final). Samples were incubated on an orbital shaker for 30 minutes, and then 11 ul of 100 uM furimazine in OptiMEM+10% FBS added. Samples were placed on an orbital shaker for 5 minutes, and then luminescence read using a GloMax Multi+luminometer. Bmax and Kd was calculated with GraphPad Prism using one site specific binding non-linear regression (FIG. 157A-B).

Example 91

Affinity of LgBiT Mutant Lysates for HiBIT

Grew 37° C. overnight cultures of LgBiT and each LgBiT mutant. Diluted each culture 1:100 into LB+0.1% Rhamnose and 0.15% glucose. Grew for 20 hours at 25° C. Lysates of each culture were prepared by diluting equal volumes of induced cultures with PLB lysis buffer. (PLB lysis buffer is 0.3×PLB+25 mM HEPES pH 7.5). Each lysate was then diluted 10,000× into PLB lysis buffer. A dilution series of synthetic HiBiT peptide starting at 300 nM was prepared into NanoGlo® Assay buffer+50 uM furimazine. 50 ul of each diluted lysate was combined with 50 µl of the peptide/NanoGlo® titration. Samples were incubated for 3 minutes, and then luminescence read samples on a GloMax® multi+luminometer (FIG. 158).

Sequences

The following polypeptide sequences each comprise an N-terminal methionine residue or corresponding ATG codon; polypeptide sequences lacking the N-terminal methionine residue or corresponding ATG codon are also within the scope herein and are incorporated herein by reference.

The following peptide sequences (and the peptide sequences of Table 1) each lack an N-terminal methionine residue; peptide sequences comprising an N-terminal methionine residue are also within the scope herein and are incorporated herein by reference.

Some embodiments described herein make reference to a His-tagged (or non-His-tagged) sequence within Table 1; alternative embodiments utilizing a non-His-tagged (or His-tagged) version of the sequence, either appearing in Table 1 or not listed, are within the scope herein.

TABLE 1

Exemplary peptide, dipeptide, and polypeptide sequences.

| SEQ ID NO | Name | Sequence |
|---|---|---|
| 1 | WT OgLuc | MFTLADFVGDWQQTAGYNQDQVLEQGGLSSLFQALGVSVTPIQ KVVLSGENGLKADIHVIIPYEGLSGFQMGLIEMIFKVVYPVDDH HFKIILHYGTLVIDGVTPNMIDYFGRPYPGIAVFDGKQITVTGTL WNGNKIYDERLINPDGSLLFRVTINGVTGWRLCENILA |
| 2 | WT OgLuc | atggtgtttaccttggcagatttcgttggagactggcaacagacagctggatacaaccaagatcaagtg ttagaacaaggaggattgtctagtctgttccaagccctgggagtgtcagtcaccccaatccagaaagtt gtgctgtctggggagaatgggttaaaagctgatattcatgtcatcatcccttacgagggactcagtggtt ttcaaatgggtctgattgaaatgatcttcaaagttgtttacccagtggatgatcatcatttcaagattattct ccattatggtacactcgttattgacggtgtgacaccaaacatgattgactactttggacgcccttaccctg gaattgctgtgtttgacggcaagcagatcacagttactggaactctgtggaacggcaacaagatctatg atgagcgcctgatcaacccagatggttcactcctcttccgcgttactatcaatggagtcaccggatggc gcctttgcgagaacattcttgcc |
| 3 | NanoLuc | MKHHHHHHAIAMVFTLEDFVGDWRQTAGYNLDQVLEQGGVSSLFQNLGVSVTPIQ RIVLSGENGLKIDIHVIIPYEGLSGDQMGQIEKIFKVVYPVDDHHFKVILHYGTLVIDGVT PNMIDYFGRPYEGIAVFDGKKITVTGTLWNGNKIIDERLINPDGSLLFRVTINGVTGWR LCERILAV |
| 4 | NanoLuc | atgaaacatcaccatcaccatcatgcgatcgccatggtcttcacactcgaagatttcgttggggactggcgac agacagccggctacaacctggaccaagtccttgaacagggaggtgtgtccagtttgtttcagaatctcggggt gtccgtaactccgatccaaaggattgtcctgagcggtgaaaatgggctgaagatcgacatccatgtcatcatc ccgtatgaaggtctgagcggcgaccaaatgggccagatcgaaaaaaattttttaaggtggtgtaccctgtggat gatcatcactttaaggtgatcctgcactatggcaccactgttgtaatcgacgggggttacgccgaacatgatcgact atttcggacggccgtatgaaggcatcgccgtgttcgacggcaaaaagatcactgtaacagggaccctgtggga acggcaacaaattatcgacgagcgcctgatcaacccccgacggctccctgctgttccgagtaaccatcaacg gagtgaccggctggcggctgtgcgaacgcattctggcggtt |
| 5 | WT OgLuc Lg | MFTLADFVGDWQQTAGYNQDQVLEQGGLSSLFQALGVSVTPIQ KVVLSGENGLKADIHVIIPYEGLSGFQMGLIEMIFKVVYPVDDH HFKIILHYGTLVIDGVTPNMIDYFGRPYPGIAVFDGKQITVTGTL WNGNKIYDERLINPD |
| 6 | WT OgLuc β9 | GSLLFRVTIN |
| 7 | WT OgLuc β10 | GVTGWRLCENILA |
| 8 | WT NanoLuc Lg | MVFTLEDFVGDWRQTAGYNLDQVLEQGGVSSLFQNLGVSVTPI QRIVLSGENGLKIDIHVIIPYEGLSGDQMGQIEKIFKVVYPVDDH HFKVILHYGTLVIDGVTPNMIDYFGRPYEGIAVFDGKKITVTGTL WNGNKIIDERLINPD |
| 9 | WT NanoLuc β9 | GSLLFRVTINV |
| 10 | WT NanoLuc β10 | GVTGWRLCERILA |
| 11 | LgBit | MVFTLEDFVGDWEQTAAYNLDQVLEQGGVSSLLQNLAVSVTPIQRIVRSGENALKIDI HVIIPYEGLSADQMAQIEEVFKVVYPVDDHHFKVILPYGTLVIDGVTPNMLNYFGRPYE GIAVFDGKKITVTGTLWNGNKIIDERLITPDGSMLFRVTINSHHHHHH |
| 12 | LgBit | atggtcttcacactcgaagatttcgttggggactgggaacagacagccgctacaacctggaccaagtccttg aacagggaggtgtgtccagtttgctgcagaatctcgccgtgtccgtaactccgatccaaaggattgtccggag cggtgaaaatgccctgaagatcgacatccatgtcatcatcccgtatgaaggtctgagcgccgaccaaatggc ccagatcgaagaggtgtttaaggtggtgtaccctgtggatgatcatcactttaaggtgatcctgccctatggca cactggtaatcgacggggttacgccgaacatgctgaactatttcggacggccgtatgaaggcatcgccgtgtt cgacggcaaaaagatcactgtaacagggaccctgtggaacggcaacaaaattatcgacgagcgcctgatca cccccgacggctccatgctgttccgagtaaccatcaacagccatcatcaccatcaccac |
| 13 | SmBit | VTGYRLFEEIL |
| 14 | SmBit | gtgaccggctaccggctgttcgaggagattctg |
| 15 | HiBit | VSGWRLFKKIS |
| 16 | HiBit | gtgagcggctggcggctgttcaagaagattagc |
| 17 | LgTrip 2098 | MVFTLEDFVGDWEQTAAYNLDQVLEQGGVSSLLQNLAVSVTPI QRIVRSGENALKIDIHVIIPYEGLSADQMAQIEEVFKVVYPVDDH HFKVILPYGTLVIDGVTPNMLNYFGRPYEGIAVFDGKKITVTGT LWNGNKIIDERLITPD |

TABLE 1-continued

Exemplary peptide, dipeptide, and polypeptide sequences.

| SEQ ID NO | Name | Sequence |
|---|---|---|
| 18 | LgTrip 2098 | atggtcttcacactcgaagatttcgttgggggactgggaacagacagccgcctacaacctggaccaagt<br>ccttgaacagggaggtgtgtccagtttgctgcagaatctcgccgtgtccgtaactccgatccaaaggat<br>tgtccggagcggtgaaaatgCcctgaagatcgacatccatgtcatcatcccgtatgaaggtctgagc<br>gccgaccaaatggcccagatcgaagaggtgtttaaggtggtgtaccctgtggatgatcatcactttaa<br>ggtgatcctgccctatggcacactggtaatcgacggggttacgccgaacatgctgaactatttcggac<br>ggccgtatgaaggcatcgccgtgttcgacggcaaaaagatcactgtaacagggaccctgtggaacg<br>gcaacaaaattatcgacgagcgcctgatcacccccgac |
| 19 | LgTrip 3092 His | MKHHHHHHVFTLDDFVGDWEQTAAYNLDQVLEQGGVSSLLQ<br>NLAVSVTPIMRIVRSGENALKIDIHVIIPYEGLSADQMAQIEEVFK<br>VVYPVDDHHFKVILPYGTLVIDGVTPNKLNYFGRPYEGIAVFDG<br>KKITVTGTLWNGNKIIDERLITPD |
| 20 | LgTrip 3092 His | atgaaacatcaccatcaccatcatgtcttcacactcgaagatttcgttgggggactgggaacagacagc<br>cgcctacaacctggaccaagtccttgaacagggaggtgtgtccagtttgctgcagaatctcgccgtgt<br>ccgtaactccgatccaaaggattgtccggagcggtgaaaatgccctgaagatcgacatccatgtcatc<br>atcccgtatgaaggtctgagcgccgaccaaatggcccagatcgaagaggtgtttaaggtggtgtacc<br>ctgtggatgatcatcactttaaggtgatcctgccctatggcacactggtaatcgacggggttacgccga<br>acatgctgaactatttcggacggccgtatgaaggcatcgccgtgttcgacggcaaaaagatcactgta<br>acagggaccctgtggaacggcaacaaaattatcgacgagcgcctgatcacccccgac |
| 21 | LgTrip 3092 | MVFTLDDFVGDWEQTAAYNLDQVLEQGGVSSLLQNLAVSVTPI<br>MRIVRSGENALKIDIHVIIPYEGLSADQMAQIEEVFKVVYPVDDH<br>HFKVILPYGTLVIDGVTPNKLNYFGRPYEGIAVFDGKKITVTGTL<br>WNGNKIIDERLITPD |
| 22 | LgTrip 3092 | atggtcttcacactcgacgatttcgttgggggactgggaacagacagccgcctacaacctggaccaagt<br>ccttgaacagggaggtgtgtccagtttgctgcagaatctcgccgtgtccgtaactccgatcatgatgat<br>tgtccggagcggtgaaaatgccctgaagatcgacatccatgtcatcatcccgtatgaaggtctgagcg<br>ccgaccaaatggcccagatcgaagaggtgtttaaggtggtgtaccctgtggatgatcatcactttaag<br>gtgatcctgccctatggcacactggtaatcgacggggttacgccgaacaagctgaactatttcggacg<br>gccgtatgaaggcatcgccgtgttcgacggcaaaaagatcactgtaacagggaccctgtggaacgg<br>caacaaaattatcgacgagcgcctgatcacccccgac |
| 23 | SmTrip9 | GSMLFRVTINS |
| 24 | SmTrip9 | ggctccatgctgttccgagtaaccatcaacagc |
| 25 | SmHiTrip10 | VSGWRLFKKIS |
| 26 | SmHiTrip10 | gtgagcggctggcggctgttcaagaagattagc |
| 27 | 5P-B9 | MVFTLEDFVGDWEQTAAYNLDQVLEQGGVSSLFQNLAVSVTPI<br>QRIVLSGENALKIDIHVIIPYEGLSADQMAQIEKIFKVVYPVDDH<br>HFKVILHYGTLVIDGVTPNMINYFGRPYEGIAVFDGKKITVTGTL<br>WNGNKIIDERLITPD |
| 28 | 5P-B9 | atggtcttcacactcgaagatttcgttgggggactgggaacagacagccgcctacaacctggaccaagt<br>ccttgaacagggaggtgtgtccagtttgtttcagaatctcgccgtgtccgtaactccgatccaaaggatt<br>gtcctgagcggtgaaaatgccctgaagatcgacatccatgtcatcatcccgtatgaaggtctgagcgc<br>cgaccaaatggcccagatcgaaaaaattttaaggtggtgtaccctgtggatgatcatcactttaaggtg<br>atcctgcactatggcacactggtaatcgacggggttacgccgaacatgatcaactatttcggacggcc<br>gtatgaaggcatcgccgtgttcgacggcaaaaagatcactgtaacagggaccctgtggaacggcaa<br>caaaattatcgacgagcgcctgatcacccccgac |
| 29 | 5P(147-157) | GSMLFRVTINV |
| 30 | 5P(147-157) | ggctccatgctgttccgagtaaccatcaac |
| 31 | LgTrip 2098 His | MKHHHHHHVFTLEDFVGDWEQTAAYNLDQVLEQGGVSSLLQ<br>NLAVSVTPIQRIVRSGENALKIDIHVIIPYEGLSADQMAQIEEVFK<br>VVYPVDDHHFKVILPYGTLVIDGVTPNMLNYFGRPYEGIAVFDG<br>KKITVTGTLWNGNKIIDERLITPD |
| 32 | LgTrip 2098 His | atgaaacatcaccatcaccatcatgtcttcacactcgaagatttcgttgggggactgggaacagacagc<br>cgcctacaacctggaccaagtccttgaacagggaggtgtgtccagtttgctgcagaatctcgccgtgt<br>ccgtaactccgatccaaaggattgtccggagcggtgaaaatgccctgaagatcgacatccatgtcatc<br>atcccgtatgaaggtctgagcgccgaccaaatggcccagatcgaagaggtgtttaaggtggtgtacc<br>ctgtggatgatcatcactttaaggtgatcctgccctatggcacactggtaatcgacggggttacgccga<br>acatgctgaactatttcggacggccgtatgaaggcatcgccgtgttcgacggcaaaaagatcactgta<br>acagggaccctgtggaacggcaacaaaattatcgacgagcgcctgatcacccccgac |

TABLE 1-continued

Exemplary peptide, dipeptide, and polypeptide sequences.

| SEQ ID NO | Name | Sequence |
|---|---|---|
| 35 | SmTrip9/10 Dipeptide (pep263) | GSMLFRVTINSVSGWRLFKKIS |
| 36 | SmTrip9/10 Dipeptide (pep263) | ggctccatgctgttccgagtaaccatcaacagcgtgagcggctggcggctgttcaagaagattagc |
| 37 | SmTrip9 + (pep286) | SSWKRGSMLFRVTINS |
| 38 | SmTrip9 + (pep286) | Agcagctggaagcgcggctccatgctgttccgagtaaccatcaacagc |
| 39 | LgTrip 3440 | MKHHHHHHVFTLDDFVGDWEQTAAYNLDQVLEQGGVSSLLQ<br>NLAVSVTPIMRIVRSGENALKIDIHVIIPYEGLSADQMAQIEEVFK<br>VVYPVDDHHFKVILPYGTLVIDGDTPNKLNYFGRPYDGIAVEDG<br>KKITVTGTLWNGNKIIDERLITPD |
| 40 | LgTrip 3440 | atgaaacatcaccatcaccatcatgtcttcacactcgacgatttcgttggggactgggaacagacagc<br>cgcctacaacctggaccaagtccttgaacagggaggtgtgtccagtttgctgcagaatctcgccgtgt<br>ccgtaactccgatcatgaggattgtccggagcggtgaaaatgccctgaagatcgacatccatgtcatc<br>atcccgtatgaaggtctgagcgccgaccaaatggcccagatcgaagaggtgtttaaggtggtgtacc<br>ctgtggatgatcatcactttaaggtgatcctgccctatggcacactggtaatcgacggggatacgccga<br>acaagctgaactatttcggacggccgtatgatggcatcgccgtgttcgacggcaaaaagatcactgta<br>acagggaccctgtggaacggcaacaaaattatcgacgagcgcctgatcacccccgac |
| 41 | LgTrip 3121 | MKHHHHHHVFTLDDFVGDWEQTAAYNLDQVLEQGGVSSLLQ<br>NLAVSVTPIMRIVRSGENALKIDIHVIIPYEGLSADQMAQIEEVFK<br>VVYPVDDHHFKVILPYGTLVIDGVTPSKLNYFGRPYEGIAVFDG<br>KKITVTGTLWNGNKIIDERLITPD |
| 42 | LgTrip 3121 | atgaaacatcaccatcaccatcatgtcttcacactcgacgatttcgttggggactgggaacagacagc<br>cgcctacaacctggaccaagtccttgaacagggaggtgtgtccagtttgctgcagaatctcgccgtgt<br>ccgtaactccgatcatgaggattgtccggagcggtgaaaatgccctgaagatcgacatccatgtcatc<br>atcccgtatgaaggtctgagcgccgaccaaatggcccagatcgaagaggtgtttaaggtggtgtacc<br>ctgtggatgatcatcactttaaggtgatcctgccctatggcacactggtaatcgacggggttacgccga<br>gcaagctgaactatttcggacggccgtatgaaggcatcgccgtgttcgacggcaaaaagatcactgt<br>aacagggaccctgtggaacggcaacaaaattatcgacgagcgcctgatcacccccgac |
| 43 | LgTrip 3482 | MKHHHHHHVFTLDDFVGDWEQTAAYNLDQVLEQGGVSSLLQ<br>NLAVSVTPIMRIVRSGENALKIDIHVIIPYEGLSADQMAQIEEVFK<br>VVYPVDDHHFKVILPYGTLVIDGVTPNKLNYFGRPYEGFAVFD<br>GKKITVTGTLWNGNKIIDERLITPD |
| 44 | LgTrip 3482 | atgaaacatcaccatcaccatcatgtcttcacactcgacgatttcgttggggactgggaacagacagc<br>cgcctacaacctggaccaagtccttgaacagggaggtgtgtccagtttgctgcagaatctcgccgtgt<br>ccgtaactccgatcatgaggattgtccggagcggtgaaaatgccctgaagatcgacatccatgtcatc<br>atcccgtatgaaggtctgagcgccgaccaaatggcccagatcgaagaggtgtttaaggtggtgtacc<br>ctgtggatgatcatcactttaaggtgatcctgccctatggcacactggtaatcgacggggttacgccga<br>acaagctgaactatttcggacggccgtatgaaggcttcgccgtgttcgacggcaaaaagatcactgta<br>acagggaccctgtggaacggcaacaaaattatcgacgagcgcctgatcacccccgac |
| 45 | LgTrip 3497 | MKHHHHHHVFTLDDFVGDWEQTAAYNLDQVLEQGGVSSLLQ<br>NLAVSVTPIMRIVRSGENALKIDIHVIIPYEGLSADQMAQIEEVFK<br>VVYPVDDHHFKVILPYGTLVIDGVTPNKLNYFGRPYEGIAVCDG<br>KKITVTGTLWNGNKIIDERLITPD |
| 46 | LgTrip 3497 | atgaaacatcaccatcaccatcatgtcttcacactcgacgatttcgttggggactgggaacagacagc<br>cgcctacaacctggaccaagtccttgaacagggaggtgtgtccagtttgctgcagaatctcgccgtgt<br>ccgtaactccgatcatgaggattgtccggagcggtgaaaatgccctgaagatcgacatccatgtcatc<br>atcccgtatgaaggtctgagcgccgaccaaatggcccagatcgaagaggtgtttaaggtggtgtacc<br>ctgtggatgatcatcactttaaggtgatcctgccctatggcacactggtaatcgacggggttacgccga<br>acaagctgaactatttcggacggccgtatgaaggcatcgccgtgtgcgacggcaaaaagatcactgt<br>aacagggaccctgtggaacggcaacaaaattatcgacgagcgcctgatcacccccgac |
| 47 | LgTrip 3125 | MKHHHHHHVFTLDDFVGDWEQTAAYNLDQVLEQGGVSSLLQ<br>NLAVSVTPIMRIVRSGENALKIDIHVIIPYEGLSADQMAQIEEVFK<br>VVYPVDDHHFKVILPYGTLVIDGVTPNKLNYFGRPYEGIAVFDG<br>KKISVTGTLWNGNKIIDERLITPD |
| 48 | LgTrip 3125 | atgaaacatcaccatcaccatcatgtcttcacactcgacgatttcgttggggactgggaacagacagc<br>cgcctacaacctggaccaagtccttgaacagggaggtgtgtccagtttgctgcagaatctcgccgtgt<br>ccgtaactccgatcatgaggattgtccggagcggtgaaaatgccctgaagatcgacatccatgtcatc |

TABLE 1-continued

Exemplary peptide, dipeptide, and polypeptide sequences.

| SEQ ID NO | Name | Sequence |
|---|---|---|
| | | atcccgtatgaaggtctgagcgccgaccaaatggcccagatcgaagaggtgtttaaggtggtgtacc ctgtggatgatcatcactttaaggtgatcctgccctatggcacactggtaatcgacggggttacgccga acaagctgaactatttcgggcggccgtatgaaggcatcgccgtgttcgacggcaaaaagatctctgta acagggaccctgtggaacggcaacaaaattatcgacgagcgcctgatcaccccgac |
| 49 | LgTrip 3118 | MKHHHHHHVFTLDDFVGDWEQTAAYNLDQVLEQGGVSSLLQ NLAVSVTPIMRIVRSGENALKIDIHVIIPYEGLSADQMAQIEEVFK VVYPVDDHHFKVILPYGTLVIDGVTPNKLNYFGRPYEGIAVFDG KKITATGTLWNGNKIIDERLITPD |
| 50 | LgTrip 3118 | atgaaacatcaccatcaccatcatgtcttcacactcgacgatttcgttggggactgggaacagacagc cgcctacaacctggaccaagtccttgaacagggaggtgtgtccagtttgctgcagaatctcgccgtgt ccgtaactccgatcatgaggattgtccggagcggtgaaaatgccctgaagatcgacatccatgtcatc atcccgtatgaaggtctgagcgccgaccaaatggcccagatcgaagaggtgtttaaggtggtgtacc ctgtggatgatcatcactttaaggtgatcctgccctatggcacactggtaatcgacggggttacgccga acaagctgaactatttcggacggccgtatgaaggcatcgccgtgttcgacggcaaaaagatcactgc aacagggaccctgtggaacggcaacaaaattatcgacgagcgcctgatcaccccgac |
| 51 | LgTrip 3546 | MKHHHHHHVFTLDDFVGDWEQTAAYNLDQVLEQGGVSSLLQ NLAVSVTPIMRIVRSGENALKIDIHVIIPYEGLSADQMAQIEEVFK VVYPVDDHHFKVILPYGTLVIDGVTPNKLNYFGRPYEGIAVFDG KKITTTGTLWNGNKIIDERLITPD |
| 52 | LgTrip 3546 | atgaaacatcaccatcaccatcatgtcttcacactcgacgatttcgttggggactgggaacagacagc cgcctacaacctggaccaagtccttgaacagggaggtgtgtccagtttgctgcagaatctcgccgtgt ccgtaactccgatcatgaggattgtccggagcggtgaaaatgccctgaagatcgacatccatgtcatc atcccgtatgaaggtctgagcgccgaccaaatggcccagatcgaagaggtgtttaaggtggtgtacc ctgtggatgatcatcactttaaggtgatcctgccctatggcacactggtaatcgacggggttacgccga acaagctgaactatttcggacggccgtatgaaggcatcgccgtgttcgacggcaaaaagatcactac cacagggaccctgtggaacggcaacaaaattatcgacgagcgcctgatcaccccgac |
| 53 | LgTrip 3546 + G (ATG 3572) | MVFTLDDFVGDWEQTAAYNLDQVLEQGGVSSLLQNLAVSVTPI MRIVRSGENALKIDIHVIIPYEGLSADQMAQIEEVFKVVYPVDDH HFKVILPYGTLVIDGVTPNKLNYFGRPYEGIAVFDGKKITTTGTL WNGNKIIDERLITPDG |
| 54 | LgTrip 3546 + G (ATG 3572) | atggtcttcacactcgacgatttcgttggggactgggaacagacagccgcctacaacctggaccaagt ccttgaacagggaggtgtgtccagtttgctgcagaatctcgccgtgtccgtaactccgatcatgaggat tgtccggagcggtgaaaatgccctgaagatcgacatccatgtcatcatcccgtatgaaggtctgagcg ccgaccaaatggcccagatcgaagaggtgtttaaggtggtgtaccctgtggatgatcatcactttaag gtgatcctgccctatggcacactggtaatcgacggggttacgccgaacaagctgaactatttcggacg gccgtatgaaggcatcgccgtgttcgacggcaaaaagatcactaccacagggaccctgtggaacgg caacaaaattatcgacgagcgcctgatcaccccgacggc |
| 55 | LgTrip 3546-D (ATG 3573) | MVFTLDDFVGDWEQTAAYNLDQVLEQGGVSSLLQNLAVSVTPI MRIVRSGENALKIDIHVIIPYEGLSADQMAQIEEVFKVVYPVDDH HFKVILPYGTLVIDGVTPNKLNYFGRPYEGIAVFDGKKITTTGTL WNGNKIIDERLITP |
| 56 | LgTrip 3546-D (ATG 3573) | atggtcttcacactcgacgatttcgttggggactgggaacagacagccgcctacaacctggaccaagt ccttgaacagggaggtgtgtccagtttgctgcagaatctcgccgtgtccgtaactccgatcatgaggat tgtccggagcggtgaaaatgccctgaagatcgacatccatgtcatcatcccgtatgaaggtctgagcg ccgaccaaatggcccagatcgaagaggtgtttaaggtggtgtaccctgtggatgatcatcactttaag gtgatcctgccctatggcacactggtaatcgacggggttacgccgaacaagctgaactatttcggacg gccgtatgaaggcatcgccgtgttcgacggcaaaaagatcactaccacagggaccctgtggaacgg caacaaaattatcgacgagcgcctgatcaccccc |
| 57 | LgTrip 3546-PD (ATG 3574) | MVFTLDDFVGDWEQTAAYNLDQVLEQGGVSSLLQNLAVSVTPI MRIVRSGENALKIDIHVIIPYEGLSADQMAQIEEVFKVVYPVDDH HFKVILPYGTLVIDGVTPNKLNYFGRPYEGIAVFDGKKITTTGTL WNGNKIIDERLIT |
| 58 | LgTrip 3546-PD (ATG 3574) | atggtcttcacactcgacgatttcgttggggactgggaacagacagccgcctacaacctggaccaagt ccttgaacagggaggtgtgtccagtttgctgcagaatctcgccgtgtccgtaactccgatcatgaggat tgtccggagcggtgaaaatgccctgaagatcgacatccatgtcatcatcccgtatgaaggtctgagcg ccgaccaaatggcccagatcgaagaggtgtttaaggtggtgtaccctgtggatgatcatcactttaag gtgatcctgccctatggcacactggtaatcgacggggttacgccgaacaagctgaactatttcggacg gccgtatgaaggcatcgccgtgttcgacggcaaaaagatcactaccacagggaccctgtggaacgg caacaaaattatcgacgagcgcctgatcacc |
| 59 | LgTrip 3546 + GS (ATG 3575) | MVFTLDDFVGDWEQTAAYNLDQVLEQGGVSSLLQNLAVSVTPI MRIVRSGENALKIDIHVIIPYEGLSADQMAQIEEVFKVVYPVDDH HFKVILPYGTLVIDGVTPNKLNYFGRPYEGIAVFDGKKITTTGTL WNGNKIIDERLITPDGS |

TABLE 1-continued

Exemplary peptide, dipeptide, and polypeptide sequences.

| SEQ ID NO | Name | Sequence |
|---|---|---|
| 60 | LgTrip 3546 + GS (ATG 3575) | atggtcttcacactcgacgatttcgttgggggactgggaacagacagccgcctacaacctggaccaagt ccttgaacagggaggtgtgtccagtttgctgcagaatctcgccgtgtccgtaactccgatcatgaggat tgtccggagcggtgaaaatgccctgaagatcgacatccatgtcatcatcccgtatgaaggtctgagcg ccgaccaaatggcccagatcgaagaggtgtttaaggtggtgtaccctgtggatgatcatcactttaag gtgatcctgccctatggcacactggtaatcgacgggggttacgccgaacaagctgaactatttcggacg gccgtatgaaggcatcgccgtgttcgacggcaaaaagatcactaccacagggaccctgtggaacgg caacaaaattatcgacgagcgcctgatcaccccgacggcagc |
| 61 | -V_LgBiT (ATG3618) | MFTLEDFVGDWEQTAAYNLDQVLEQGGVSSLLQNLAVSVTPIQ RIVRSGENALKIDIHVIIPYEGLSADQMAQIEEVFKVVYPVDDHH FKVILPYGTLVIDGVTPNMLNYFGRPYEGIAVFDGKKITVTGTL WNGNKIIDERLITPDGSMLFRVTINSHEIHHHH |
| 62 | -V_LgBiT (ATG3618) | atgttcacactcgaagatttcgttgggggactgggaacagacagccgcctacaacctggaccaagtcct tgaacagggaggtgtgtccagtttgctgcagaatctcgccgtgtccgtaactccgatccaaaggattgt ccggagcggtgaaaatgccctgaagatcgacatccatgtcatcatcccgtatgaaggtctgagcgcc gaccaaatggcccagatcgaagaggtgtttaaggtggtgtaccctgtggatgatcatcactttaaggtg atcctgccctatggcacactggtaatcgacgggggttacgccgaacatgctgaactatttcggacggcc gtatgaaggcatcgccgtgttcgacggcaaaaagatcactgtaacagggaccctgtggaacggcaa caaaattatcgacgagcgcctgatcaccccgacggctccatgctgttccgagtaaccatcaacagc catcatcaccatcaccactaa |
| 63 | -VF_LgBiT (ATG3619) | MTLEDFVGDWEQTAAYNLDQVLEQGGVSSLLQNLAVSVTPIQR IVRSGENALKIDIHVIIPYEGLSADQMAQIEEVFKVVYPVDDHHF KVILPYGTLVIDGVTPNMLNYFGRPYEGIAVFDGKKITVTGTLW NGNKIIDERLITPDGSMLFRVTINSHHHHHH |
| 64 | -VF_LgBiT (ATG3619) | atgacactcgaagatttcgttgggggactgggaacagacagccgcctacaacctggaccaagtccttg aacagggaggtgtgtccagtttgctgcagaatctcgccgtgtccgtaactccgatccaaaggattgtcc ggagcggtgaaaatgccctgaagatcgacatccatgtcatcatcccgtatgaaggtctgagcgccga ccaaatggcccagatcgaagaggtgtttaaggtggtgtaccctgtggatgatcatcactttaaggtgat cctgccctatggcacactggtaatcgacgggggttacgccgaacatgctgaactatttcggacggccgt atgaaggcatcgccgtgttcgacggcaaaaagatcactgtaacagggaccctgtggaacggcaaca aaattatcgacgagcgcctgatcaccccgacggctccatgctgttccgagtaaccatcaacagccat catcaccatcaccactaa |
| 65 | -VFT_LgBiT (ATG3620) | MLEDFVGDWEQTAAYNLDQVLEQGGVSSLLQNLAVSVTPIQRI VRSGENALKIDIHVIIPYEGLSADQMAQIEEVFKVVYPVDDHHF KVILPYGTLVIDGVTPNMLNYFGRPYEGIAVFDGKKITVTGTLW NGNKIIDERLITPDGSMLFRVTINSHHHHHH |
| 66 | -VFT_LgBiT (ATG3620) | atgctcgaagatttcgttgggggactgggaacagacagccgcctacaacctggaccaagtccttgaac agggaggtgtgtccagtttgctgcagaatctcgccgtgtccgtaactccgatccaaaggattgtccgg agcggtgaaaatgccctgaagatcgacatccatgtcatcatcccgtatgaaggtctgagcgccgacc aaatggcccagatcgaagaggtgtttaaggtggtgtaccctgtggatgatcatcactttaaggtgatcct gccctatggcacactggtaatcgacgggggttacgccgaacatgctgaactatttcggacggccgtatg aaggcatcgccgtgttcgacggcaaaaagatcactgtaacagggaccctgtggaacggcaacaaa ttatcgacgagcgcctgatcaccccgacggctccatgctgttccgagtaaccatcaacagccatcat caccatcaccactaa |
| 67 | -VFTL_LgBiT (ATG3621) | MEDFVGDWEQTAAYNLDQVLEQGGVSSLLQNLAVSVTPIQRIV RSGENALKIDIHVIIPYEGLSADQMAQIEEVFKVVYPVDDHHFK VILPYGTLVIDGVTPNMLNYFGRPYEGIAVFDGKKITVTGTLWN GNKIIDERLITPDGSMLFRVTINSHHHHHH |
| 68 | -VFTL_LgBiT (ATG3621) | atggaagatttcgttgggggactgggaacagacagccgcctacaacctggaccaagtccttgaacagg gaggtgtgtccagtttgctgcagaatctcgccgtgtccgtaactccgatccaaaggattgtccggagc ggtgaaaatgccctgaagatcgacatccatgtcatcatcccgtatgaaggtctgagcgccgaccaaat ggcccagatcgaagaggtgtttaaggtggtgtaccctgtggatgatcatcactttaaggtgatcctgcc ctatggcacactggtaatcgacgggggttacgccgaacatgctgaactatttcggacggccgtatgaag gcatcgccgtgttcgacggcaaaaagatcactgtaacagggaccctgtggaacggcaacaaaattat cgacgagcgcctgatcaccccgacggctccatgctgttccgagtaaccatcaacagccatcatcac catcaccactaa |
| 69 | (M)FKKIS-GSSG-LgBiT (ATG3632) | MFKKISGSSGVFTLEDFVGDWEQTAAYNLDQVLEQGGVSSLLQ NLAVSVTPIQRIVRSGENALKIDIHVIIPYEGLSADQMAQIEEVFK VVYPVDDHHFKVILPYGTLVIDGVTPNMLNYFGRPYEGIAVFDG KKITVTGTLWNGNKIIDERLITPDGSMLFRVTINSHHHHHH |
| 70 | (M)FKKIS-GSSG-LgBiT (ATG3632) | atgttcaagaagattagcggctcgagcggtgtgtcttcacactcgaagatttcgttgggggactgggaaca gacagccgcctacaacctggaccaagtccttgaacagggaggtgtgtccagtttgctgcagaatctc gccgtgtccgtaactccgatccaaaggattgtccggagcggtgaaaatgccctgaagatcgacatcc atgtcatcatcccgtatgaaggtctgagcgccgaccaaatggcccagatcgaagaggtgtttaaggtg |

TABLE 1-continued

Exemplary peptide, dipeptide, and polypeptide sequences.

| SEQ ID NO | Name | Sequence |
|---|---|---|
| | | gtgtaccctgtggatgatcatcactttaaggtgatcctgccctatggcacactggtaatcgacggggtta<br>cgccgaacatgctgaactatttcggacggccgtatgaaggcatcgccgtgttcgacggcaaaaagat<br>cactgtaacagggaccctgtggaacggcaacaaaattatcgacgagcgcctgatcacccccgacgg<br>ctccatgctgttccgagtaaccatcaacagccatcatcaccatcaccactaa |
| 71 | (M)KKIS-<br>GSSG-LgBiT<br>(ATG3633) | MKKISGSSGVFTLEDFVGDWEQTAAYNLDQVLEQGGVSSLLQN<br>LAVSVTPIQRIVRSGENALKIDIHVIIPYEGLSADQMAQIEEVFKV<br>VYPVDDHHFKVILPYGTLVIDGVTPNMLNYFGRPYEGIAVFDGK<br>KITVTGTLWNGNKIIDERLITPDGSMLFRVTINSHHHHHH |
| 72 | (M)KKIS-<br>GSSG-LgBiT<br>(ATG3633) | atgaagaagattagcggctcgagcggtgtcttcacactcgaagatttcgttggggactgggaacaga<br>cagccgcctacaacctggaccaagtccttgaacagggaggtgtgtccagtttgctgcagaatctcgcc<br>gtgtccgtaactccgatccaaaggattgtccggagcggtgaaaatgccctgaagatcgacatccatgt<br>catcatcccgtatgaaggtctgagcgccgaccaaatggcccagatcgaagaggtgtttaaggtggtgt<br>accctgtggatgatcatcactttaaggtgatcctgccctatggcacactggtaatcgacggggttacgc<br>cgaacatgctgaactatttcggacggccgtatgaaggcatcgccgtgttcgacggcaaaaagatcact<br>gtaacagggaccctgtggaacggcaacaaaattatcgacgagcgcctgatcacccccgacggctcc<br>atgctgttccgagtaaccatcaacagccatcatcaccatcaccactaa |
| 73 | (M)KIS-<br>GSSG-LgBiT<br>(ATG3634) | MKISGSSGVFTLEDFVGDWEQTAAYNLDQVLEQGGVSSLLQNL<br>AVSVTPIQRIVRSGENALKIDIHVIIPYEGLSADQMAQIEEVFKVV<br>YPVDDHHFKVILPYGTLVIDGVTPNMLNYFGRPYEGIAVFDGKK<br>ITVTGTLWNGNKIIDERLITPDGSMLFRVTINSHHHHHH |
| 74 | (M)KIS-<br>GSSG-LgBiT<br>(ATG3634) | atgaagattagcggctcgagcggtgtcttcacactcgaagatttcgttggggactgggaacagacag<br>ccgcctacaacctggaccaagtccttgaacagggaggtgtgtccagtttgctgcagaatctcgccgtg<br>tccgtaactccgatccaaaggattgtccggagcggtgaaaatgccctgaagatcgacatccatgtcat<br>catcccgtatgaaggtctgagcgccgaccaaatggcccagatcgaagaggtgtttaaggtggtgtac<br>cctgtggatgatcatcactttaaggtgatcctgccctatggcacactggtaatcgacggggttacgccg<br>aacatgctgaactatttcggacggccgtatgaaggcatcgccgtgttcgacggcaaaaagatcactgt<br>aacagggaccctgtggaacggcaacaaaattatcgacgagcgcctgatcacccccgacggctccat<br>gctgttccgagtaaccatcaacagccatcatcaccatcaccactaa |
| 75 | (M)IS-GSSG-<br>LgBiT<br>(ATG3635) | MISGSSGVFTLEDFVGDWEQTAAYNLDQVLEQGGVSSLLQNLA<br>VSVTPIQRIVRSGENALKIDIHVIIPYEGLSADQMAQIEEVFKVVY<br>PVDDHHFKVILPYGTLVIDGVTPNMLNYFGRPYEGIAVFDGKKI<br>TVTGTLWNGNKIIDERLITPDGSMLFRVTINSHHHHHH |
| 76 | (M)IS-GSSG-<br>LgBiT<br>(ATG3635) | atgattagcggctcgagcggtgtatcacactcgaagatttcgttggggactgggaacagacagccg<br>cctacaacctggaccaagtccttgaacagggaggtgtgtccagtttgctgcagaatctcgccgtgtcc<br>gtaactccgatccaaaggattgtccggagcggtgaaaatgccctgaagatcgacatccatgtcatcat<br>cccgtatgaaggtctgagcgccgaccaaatggcccagatcgaagaggtgtttaaggtggtgtaccct<br>gtggatgatcatcactttaaggtgatcctgccctatggcacactggtaatcgacggggttacgccgaac<br>atgctgaactatttcggacggccgtatgaaggcatcgccgtgttcgacggcaaaaagatcactgtaac<br>agggaccctgtggaacggcaacaaaattatcgacgagcgcctgatcacccccgacggctccatgct<br>gttccgagtaaccatcaacagccatcatcaccatcaccactaa |
| 77 | (M)S-GSSG-<br>LgBiT<br>(ATG3636) | MSGSSGVFTLEDFVGDWEQTAAYNLDQVLEQGGVSSLLQNLA<br>VSVTPIQRIVRSGENALKIDIHVIIPYEGLSADQMAQIEEVFKVVY<br>PVDDHHFKVILPYGTLVIDGVTPNMLNYFGRPYEGIAVFDGKKI<br>TVTGTLWNGNKIIDERLITPDGSMLFRVTINSHHHHHH |
| 78 | (M)S-GSSG-<br>LgBiT<br>(ATG3636) | atgagcggctcgagcggtgtcttcacactcgaagatttcgttggggactgggaacagacagccgcct<br>acaacctggaccaagtccttgaacagggaggtgtgtccagtttgctgcagaatctcgccgtgtccgta<br>actccgatccaaaggattgtccggagcggtgaaaatgccctgaagatcgacatccatgtcatcatccc<br>gtatgaaggtctgagcgccgaccaaatggcccagatcgaagaggtgtttaaggtggtgtaccctgtg<br>gatgatcatcactttaaggtgatcctgccctatggcacactggtaatcgacggggttacgccgaacatg<br>ctgaactatttcggacggccgtatgaaggcatcgccgtgttcgacggcaaaaagatcactgtaacag<br>ggaccctgtggaacggcaacaaaattatcgacgagcgcctgatcacccccgacggctccatgctgtt<br>ccgagtaaccatcaacagccatcatcaccatcaccactaa |
| 79 | LgTrip + GSM<br>(ATG3722) | MKHHHHHHVFTLDDFVGDWEQTAAYNLDQVLEQGGVSSLLQ<br>NLAVSVTPIMRIVRSGENALKIDIHVIIPYEGLSADQMAQIEEVFK<br>VVYPVDDHHFKVILPYGTLVIDGVTPNKLNYFGRPYEGIAVFDG<br>KKITTTGTLWNGNKIIDERLITPDGSM |
| 80 | LgTrip + GSM<br>(ATG3722) | atgaaacatcaccatcaccatcatgtcttcacactcgacgatttcgttggggactgggaacagacagc<br>cgcctacaacctggaccaagtccttgaacagggaggtgtgtccagtttgctgcagaatctcgccgtgt<br>cctaactccgatcatgaggattgtccggagcggtgaaaatgccctgaagatcgacatccatgtcatc<br>atcccgtatgaaggtctgagcgccgaccaaatggcccagatcgaagaggtgtttaaggtggtgtacc<br>ctgtggatgatcatcactttaaggtgatcctgccctatggcacactggtaatcgacggggttacgccga<br>acaagctgaactatttcggacggccgtatgaaggcatcgccgtgttcgacggcaaaaagatcactac<br>cacagggaccctgtggaacggcaacaaaattatcgacgagcgcctgatcacccccgacggcagca<br>tgtaa |

TABLE 1-continued

Exemplary peptide, dipeptide, and polypeptide sequences.

| SEQ ID NO | Name | Sequence |
|---|---|---|
| 81 | LgTrip + GSML (ATG3723) | MKHHHHHHVFTLDDFVGDWEQTAAYNLDQVLEQGGVSSLLQ NLAVSVTPIMRIVRSGENALKIDIHVIIPYEGLSADQMAQIEEVFK VVYPVDDHHFKVILPYGTLVIDGVTPNKLNYFGRPYEGIAVFDG KKITTTGTLWNGNKIIDERLITPDGSML |
| 82 | LgTrip + GSML (ATG3723) | atgaaacatcaccatcaccatcatgtcttcacactcgacgatttcgttggggactgggaacagacagc cgcctacaacctggaccaagtccttgaacagggaggtgtgtccagtttgctgcagaatctcgccgtgt ccgtaactccgatcatgaggattgtccggagcggtgaaaatgccctgaagatcgacatccatgtcatc atcccgtatgaaggtctgagcgccgaccaaatggcccagatcgaagaggtgtttaaggtggtgtacc ctgtggatgatcatcactttaaggtgatcctgccctatggcacactggtaatcgacggggttacgccga acaagctgaactatttcggacggccgtatgaaggcatcgccgtgttcgacggcaaaaagatcactac cacagggaccctgtggaacggcaacaaaattatcgacgagcgcctgatcaccccgacggcagca tgctgtaa |
| 83 | LgTrip + GSMLF (ATG3724) | MKHHHHHHVFTLDDFVGDWEQTAAYNLDQVLEQGGVSSLLQ NLAVSVTPIMRIVRSGENALKIDIHVIIPYEGLSADQMAQIEEVFK VVYPVDDHHFKVILPYGTLVIDGVTPNKLNYFGRPYEGIAVFDG KKITTTGTLWNGNKIIDERLITPDGSMLF |
| 84 | LgTrip + GSMLF (ATG3724) | atgaaacatcaccatcaccatcatgtcttcacactcgacgatttcgttggggactgggaacagacagc cgcctacaacctggaccaagtccttgaacagggaggtgtgtccagtttgctgcagaatctcgccgtgt ccgtaactccgatcatgaggattgtccggagcggtgaaaatgccctgaagatcgacatccatgtcatc atcccgtatgaaggtctgagcgccgaccaaatggcccagatcgaagaggtgtttaaggtggtgtacc ctgtggatgatcatcactttaaggtgatcctgccctatggcacactggtaatcgacggggttacgccga acaagctgaactatttcggacggccgtatgaaggcatcgccgtgttcgacggcaaaaagatcactac cacagggaccctgtggaacggcaacaaaattatcgacgagcgcctgatcaccccgacggcagca tgctgttctaa |
| 85 | LgTrip - TPD (ATG3725) | MKHHHHHHVFTLDDFVGDWEQTAAYNLDQVLEQGGVSSLLQ NLAVSVTPIMRIVRSGENALKIDIHVIIPYEGLSADQMAQIEEVFK VVYPVDDHHFKVILPYGTLVIDGVTPNKLNYFGRPYEGIAVFDG KKITTTGTLWNGNKIIDERLI |
| 86 | LgTrip - TPD (ATG3725) | atgaaacatcaccatcaccatcatgtcttcacactcgacgatttcgttggggactgggaacagacagc cgcctacaacctggaccaagtccttgaacagggaggtgtgtccagtttgctgcagaatctcgccgtgt ccgtaactccgatcatgaggattgtccggagcggtgaaaatgccctgaagatcgacatccatgtcatc atcccgtatgaaggtctgagcgccgaccaaatggcccagatcgaagaggtgtttaaggtggtgtacc ctgtggatgatcatcactttaaggtgatcctgccctatggcacactggtaatcgacggggttacgccga acaagctgaactatttcggacggccgtatgaaggcatcgccgtgttcgacggcaaaaagatcactac cacagggaccctgtggaacggcaacaaaattatcgacgagcgcctgatctaa |
| 87 | LgTrip - ITPD (ATG3726) | MKHHHHHHVFTLDDFVGDWEQTAAYNLDQVLEQGGVSSLLQ NLAVSVTPIMRIVRSGENALKIDIHVIIPYEGLSADQMAQIEEVFK VVYPVDDHHFKVILPYGTLVIDGVTPNKLNYFGRPYEGIAVFDG KKITTTGTLWNGNKIIDERL |
| 88 | LgTrip - ITPD (ATG3726) | atgaaacatcaccatcaccatcatgtcttcacactcgacgatttcgttggggactgggaacagacagc cgcctacaacctggaccaagtccttgaacagggaggtgtgtccagtttgctgcagaatctcgccgtgt ccgtaactccgatcatgaggattgtccggagcggtgaaaatgccctgaagatcgacatccatgtcatc atcccgtatgaaggtctgagcgccgaccaaatggcccagatcgaagaggtgtttaaggtggtgtacc ctgtggatgatcatcactttaaggtgatcctgccctatggcacactggtaatcgacggggttacgccga acaagctgaactatttcggacggccgtatgaaggcatcgccgtgttcgacggcaaaaagatcactac cacagggaccctgtggaacggcaacaaaattatcgacgagcgcctgtaa |
| 89 | LgTrip - LITPD (ATG3727) | MKHHHHHHVFTLDDFVGDWEQTAAYNLDQVLEQGGVSSLLQ NLAVSVTPIMRIVRSGENALKIDIHVIIPYEGLSADQMAQIEEVFK VVYPVDDHHFKVILPYGTLVIDGVTPNKLNYFGRPYEGIAVFDG KKITTTGTLWNGNKIIDER |
| 90 | LgTrip - LITPD (ATG3727) | atgaaacatcaccatcaccatcatgtcttcacactcgacgatttcgttggggactgggaacagacagc cgcctacaacctggaccaagtccttgaacagggaggtgtgtccagtttgctgcagaatctcgccgtgt ccgtaactccgatcatgaggattgtccggagcggtgaaaatgccctgaagatcgacatccatgtcatc atcccgtatgaaggtctgagcgccgaccaaatggcccagatcgaagaggtgtttaaggtggtgtacc ctgtggatgatcatcactttaaggtgatcctgccctatggcacactggtaatcgacggggttacgccga acaagctgaactatttcggacggccgtatgaaggcatcgccgtgttcgacggcaaaaagatcactac cacagggaccctgtggaacggcaacaaaattatcgacgagcgctaa |
| 91 | FRB-15GS-AI-86 (ATG1634) | MVAILWHEMWHEGLEEASRLYFGERNVKGMFEVLEPLHAMM ERGPQTLKETSFNQAYGRDLMEAQEWCRKYMKSGNVKDLTQA WDLYYHVFRRISGGSGGGGSGGSSSGGAIVSGWRLFKKIS |
| 92 | FRB-15GS-AI-86 (ATG1634) | atggtggccatcctctggcatgagatgtggcatgaaggcctggaagaggcatctcgtttgtactttggg gaaaggaacgtgaaaggcatgtttgaggtgctggagcccttgcatgctatgatggaacgggggcccc |

TABLE 1-continued

Exemplary peptide, dipeptide, and polypeptide sequences.

| SEQ ID NO | Name | Sequence |
|---|---|---|
| | | cagactctgaaggaaacatcctttaatcaggcctatggtcgagatttaatggaggcccaagagtggtg caggaagtacatgaaatcagggaatgtcaaggacctcacccaagcctgggacctctattatcatgtgtt ccgacgaatcagtggtggttcaggtggtggcgggagcggtggctcgagcagcggtggagcgatcg tgagcggctggcggctgttcaagaagattagctaa |
| 93 | FRB-15GS-AI-289 (ATG3586) | MVAILWHEMWHEGLEEASRLYFGERNVKGMFEVLEPLHAMM ERGPQTLKETSFNQAYGRDLMEAQEWCRKYMKSGNVKDLTQA WDLYYHVFRRISGGSGGGGSGGSSSGGAIVSVSGWRLFKKIS |
| 94 | FRB-15GS-AI-289 (ATG3586) | atggtggccatcctctggcatgagatgtggcatgaaggcctggaagaggcatctcgtttgtactttggg gaaaggaacgtgaaaggcatgtttgaggtgctggagcccttgcatgctatgatggaacggggcccc cagactctgaaggaaacatcctttaatcaggcctatggtcgagatttaatggaggcccaagagtggtg caggaagtacatgaaatcagggaatgtcaaggacctcacccaagcctgggacctctattatcatgtgtt ccgacgaatcagtggtggttcaggtggtggcgggagcggtggctcgagcagcggtggagcgatcg ttagcgttagcggctggcgcctgttcaagaagatcagctaa |
| 95 | FRB-15GS-AI-86-His6 (ATG3743) | MVAILWHEMWHEGLEEASRLYFGERNVKGMFEVLEPLHAMM ERGPQTLKETSFNQAYGRDLMEAQEWCRKYMKSGNVKDLTQA WDLYYHVFRRISGGSGGGGSGGSSSGGAIVSGWRLFKKISHHH HHH |
| 96 | FRB-15GS-AI-86-His6 (ATG3743) | atggtggccatcctctggcatgagatgtggcatgaaggcctggaagaggcatctcgtttgtactttggg gaaaggaacgtgaaaggcatgtttgaggtgctggagcccttgcatgctatgatggaacggggcccc cagactctgaaggaaacatcctttaatcaggcctatggtcgagatttaatggaggcccaagagtggtg caggaagtacatgaaatcagggaatgtcaaggacctcacccaagcctgggacctctattatcatgtgtt ccgacgaatcagtggtggttcaggtggtggcgggagcggtggctcgagcagcggtggagcgatcg tgagcggctggcggctgttcaagaagattagccatcatcaccatcaccactaa |
| 97 | FRB-15G5-AI-289-His6 (ATG3744) | MVAILWHEMWHEGLEEASRLYFGERNVKGMFEVLEPLHAMM ERGPQTLKETSFNQAYGRDLMEAQEWCRKYMKSGNVKDLTQA WDLYYHVFRRISGGSGGGGSGGSSSGGAIVSVSGWRLFKKISHH HHHH |
| 98 | FRB-15GS-AI-289-His6 (ATG3744) | atggtggccatcctctggcatgagatgtggcatgaaggcctggaagaggcatctcgtttgtactttggg gaaaggaacgtgaaaggcatgtttgaggtgctggagcccttgcatgctatgatggaacggggcccc cagactctgaaggaaacatcctttaatcaggcctatggtcgagatttaatggaggcccaagagtggtg caggaagtacatgaaatcagggaatgtcaaggacctcacccaagcctgggacctctattatcatgtgtt ccgacgaatcagtggtggttcaggtggtggcgggagcggtggctcgagcagcggtggagcgatcg ttagcgtgagcggctggcggctgttcaagaagattagccatcatcaccatcaccactaa |
| 99 | His6-FRB-SGS-86 (ATG3760) | MKHHHHHHVAILWHEMWHEGLEEASRLYFGERNVKGMFEVL EPLHAMMERGPQTLKETSFNQAYGRDLMEAQEWCRKYMKSG NVKDLTQAWDLYYHVFRRISGGSGGVSGWRLFKKIS |
| 100 | His6-FRB-SGS-86 (ATG3760) | atgaaacatcaccatcaccatcatgtggccatcctctggcatgagatgtggcatgaaggcctggaaga ggcatctcgtttgtactttggggaaaggaacgtgaaaggcatgtttgaggtgctggagcccttgcatgc tatgatggaacggggcccccagactctgaaggaaacatcctttaatcaggcctatggtcgagatttaat ggaggcccaagagtggtgcaggaagtacatgaaatcagggaatgtcaaggacctcacccaagcct gggacctctattatcatgtgttccgacgaatcagtggtggttcaggtggtgtgagcggctggcggctgt tcaagaagattagctaa |
| 101 | His6-FRB-10GS-86 (ATG3761) | MKHHHHHHVAILWHEMWHEGLEEASRLYFGERNVKGMFEVL EPLHAMMERGPQTLKETSFNQAYGRDLMEAQEWCRKYMKSG NVKDLTQAWDLYYHVFRRISGGSGGGGSGGVSGWRLFKKIS |
| 102 | His6-FRB-10GS-86 (ATG3761) | atgaaacatcaccatcaccatcatgtggccatcctctggcatgagatgtggcatgaaggcctggaaga ggcatctcgtttgtactttggggaaaggaacgtgaaaggcatgtttgaggtgctggagcccttgcatgc tatgatggaacggggcccccagactctgaaggaaacatcctttaatcaggcctatggtcgagatttaat ggaggcccaagagtggtgcaggaagtacatgaaatcagggaatgtcaaggacctcacccaagcct gggacctctattatcatgtgttccgacgaatcagtggtggttcaggtggtggcgggagcggtggcgtg agcggctggcggctgttcaagaagattagctaa |
| 103 | His6-FRB-15GS-86 (ATG3762) | MKHHHHHHVAILWHEMWHEGLEEASRLYFGERNVKGMFEVL EPLHAMMERGPQTLKETSFNQAYGRDLMEAQEWCRKYMKSG NVKDLTQAWDLYYHVFRRISGGSGGGGSGGSSSGGVSGWRLF KKIS |
| 104 | His6-FRB-15GS-86 (ATG3762) | atgaaacatcaccatcaccatcatgtggccatcctctggcatgagatgtggcatgaaggcctggaaga ggcatctcgtttgtactttggggaaaggaacgtgaaaggcatgtttgaggtgctggagcccttgcatgc tatgatggaacggggcccccagactctgaaggaaacatcctttaatcaggcctatggtcgagatttaat ggaggcccaagagtggtgcaggaagtacatgaaatcagggaatgtcaaggacctcacccaagcct gggacctctattatcatgtgttccgacgaatcagtggtggttcaggtggtggcgggagcggtggctcg agcagcggtggagtgagcggctggcggctgttcaagaagattagctaa |

TABLE 1-continued

Exemplary peptide, dipeptide, and polypeptide sequences.

| SEQ ID NO | Name | Sequence |
|---|---|---|
| 105 | His6-FRB-5GS-289 (ATG3763) | MKHHHHHHVAILWHEMWHEGLEEASRLYFGERNVKGMFEVL EPLHAMMERGPQTLKETSFNQAYGRDLMEAQEWCRKYMKSG NVKDLTQAWDLYYHVFRRISGGSGGGGSGGVSVSGWRLFKKIS |
| 106 | His6-FRB-5GS-289 (ATG3763) | atgaaacatcaccatcaccatcatgtggccatcctctggcatgagatgtggcatgaaggcctggaaga ggcatctcgtttgtactttggggaaaggaacgtgaaaggcatgtttgaggtgctggagcccttgcatgc tatgatggaacggggcccccagactctgaaggaaacatcctttaatcaggcctatggtcgagatttaat ggaggcccaagagtggtgcaggaagtacatgaaatcagggaatgtcaaggacctcacccaagcct gggacctctattatcatgtgttccgacgaatcagtggtggttcaggtggtgttagcgttagcggctggc gcctgttcaagaagatcagctaa |
| 107 | His6-FRB-10GS-289 (ATG3764) | MKHHHHHHVAILWHEMWHEGLEEASRLYFGERNVKGMFEVL EPLHAMMERGPQTLKETSFNQAYGRDLMEAQEWCRKYMKSG NVKDLTQAWDLYYHVFRRISGGSGGGGSGGVSVSGWRLFKKIS |
| 108 | His6-FRB-10GS-289 (ATG3764) | atgaaacatcaccatcaccatcatgtggccatcctctggcatgagatgtggcatgaaggcctggaaga ggcatctcgtttgtactttggggaaaggaacgtgaaaggcatgtttgaggtgctggagcccttgcatgc tatgatggaacggggcccccagactctgaaggaaacatcctttaatcaggcctatggtcgagatttaat ggaggcccaagagtggtgcaggaagtacatgaaatcagggaatgtcaaggacctcacccaagcct gggacctctattatcatgtgttccgacgaatcagtggtggttcaggtggtggcgggagcggtggcgtt agcgttagcggctggcgcctgttcaagaagatcagctaa |
| 109 | His6-FRB-15GS-289 (ATG3765) | MKHHHHHHVAILWHEMWHEGLEEASRLYFGERNVKGMFEVL EPLHAMMERGPQTLKETSFNQAYGRDLMEAQEWCRKYMKSG NVKDLTQAWDLYYHVFRRISGGSGGGGSGGSSSGGVSVSGWR LFKKIS |
| 110 | His6-FRB-15GS-289 (ATG3765) | atgaaacatcaccatcaccatcatgtggccatcctctggcatgagatgtggcatgaaggcctggaaga ggcatctcgtttgtactttggggaaaggaacgtgaaaggcatgtttgaggtgctggagcccttgcatgc tatgatggaacggggcccccagactctgaaggaaacatcctttaatcaggcctatggtcgagatttaat ggaggcccaagagtggtgcaggaagtacatgaaatcagggaatgtcaaggacctcacccaagcct gggacctctattatcatgtgttccgacgaatcagtggtggttcaggtggtggcgggagcggtggctcg agcggtggtagcggttagcggctggcgcctgttcaagaagatcagctaa |
| 111 | SmTrip9-FKBP fusion template (ATG780) | M-- GSMLFRVTINS-- SSSGGGGSGGGGSSGGGVQVETISPGDGRTFPKRGQTCVVHYTG MLEDGKKFDSSRDRNKPFKFMLGKQEVIRGWEEGVAQMSVGQ RAKLTISPDYAYGATGHPGIIPPHATLVFDVELLKLE |
| 112 | SmTrip9-FKBP fusion template (ATG780) | atgggctccatgctgttccgagtaaccatcaacagctcgagttcaggtggtggcgggagcggtggag ggagcagcggtggaggagtgcaggtggaaaccatctccccaggagacgggcgcaccttccccaa gcgcggccagacctgcgtggtgcactacaccgggatgcttgaagatggaaagaaatttgattcctcc cgggacagaaacaagccctttaagtttatgctaggcaagcaggaggtgatccgaggctgggaagaa ggggttgcccagatgagtgtgggtcagagagccaaactgactatatctccagattatgcctatggtgc cactgggcacccaggcatcatcccaccacatgccactctcgtcttcgatgtggagcttctaaaactggg aataa |
| 113 | FKBP-SmTrip9 fusion template (ATG777) | MGVQVETISPGDGRTFPKRGQTCVVHYTGMLEDGKKFDSSRDR NKPFKFMLGKQEVIRGWEEGVAQMSVGQRAKLTISPDYAYGA TGHPGIIPPHATLVFDVELLKLEGGSGGGGSGGSSSGGAI-- GSMLFRVTINS |
| 114 | FKBP-SmTrip9 fusion template (ATG777) | Atgggagtgcaggtggaaaccatctccccaggagacgggcgcaccttccccaagcgcggccaga cctgcgtggtgcactacaccgggatgcttgaagatggaaagaaatttgattcctcccgggacagaaa caagccctttaagtttatgctaggcaagcaggaggtgatccgaggctgggaagaaggggttgccca gatgagtgtgggtcagagagccaaactgactatatctccagattatgcctatggtgccactgggcacc caggcatcatcccaccacatgccactctcgtcttcgatgtggagcttctaaaactggaaggtggttcag gtggtggcgggagcggtggctcgagcagcggtggagcgatcggctccatgctgttccgagtaacca tcaacagc |
| 115 | LgBiT (ATG2623) | MVFTLEDFVGDWEQTAAYNLDQVLEQGGVSSLLQNLAVSVTPI QRIVRSGENALKIDIHVIIPYEGLSADQMAQIEEVFKVVYPVDDH HFKVILPYGTLVIDGVTPNMLNYFGRPYEGIAVFDGKKITVTGT LWNGNKIIDERLITPDGSMLFRVTINSHHHHHH |
| 116 | LgBiT (ATG2623) | atggtcttcacactcgaagatttcgttggggactgggaacagacagccgcctacaacctggaccaagt ccttgaacagggaggtgtgtccagtttgctgcagaatctcgccgtgtccgtaactccgatccaaaggat tgtccggagcggtgaaaatgccctgaagatcgacatccatgtcatcatcccgtatgaaggtctgagcg ccgacaaatggcccagatcgaagaggtgtttaaggtggtgtaccctgtggatgatcatcactttaag gtgatcctgccctatggcacactggtaatcgacggggttacgccgaacatgctgaactatttcggacg gccgtatgaaggcatcgccgtgttcgacggcaaaaagatcactgtaacagggaccctgtggaacgg caacaaaattatcgacgagcgcctgatcacccccgacggctccatgctgttccgagtaaccatcaaca gccatcatcaccatcaccactaa |

TABLE 1-continued

Exemplary peptide, dipeptide, and polypeptide sequences.

| SEQ ID NO | Name | Sequence |
|---|---|---|
| 133 | pep78 | NVSGWRLFKKISN |
| 134 | pep79 | NVTGYRLFKKISN |
| 135 | pep80 | VSGWRLFKKISN |
| 136 | pep81 | SGWRLFKKISN |
| 137 | pep82 | GWRLFKKISN |
| 138 | pep99 | VTGYRLFEKIS |
| 139 | pep219 | SGWRLFKKIS |
| 140 | pep225 | VSGWRL |
| 141 | pep226 | VSGWRLF |
| 142 | pep227 | VSGWRLFK |
| 143 | pep228 | VSGWRLFKK |
| 144 | pep229 | VSGWRLFKKI |
| 145 | pep243 | VSGWRLYKKIS |
| 146 | pep272 | GSMLFRVTINSVSGWALFKKIS |
| 147 | pep274 | GSMLFRVTINSVTGYRLFEEIL |
| 148 | pep287 (WT SmTrip9) + Cterm solubility tag | GSMLFRVTINSSSWKR |
| 149 | pep288 | VSGVSGWRLFKKIS |
| 150 | pep289 | VSVSGWRLFKKIS |
| 151 | pep290 | VVSGWRLFKKIS |
| 152 | pep291 | SSWKRSMLFRVTINS |
| 153 | pep292 | SSWKRMLFRVTINS |
| 154 | pep293 | SSWKRDGSMLFRVTINS |
| 155 | pep294 | SSWKRPDGSMLFRVTINS |
| 156 | pep296 | SSWKRSMLFRVTINSV |
| 157 | pep297 | SSWKRMLFRVTINSV |
| 158 | pep298 | SSWKRDGSMLFRVTINSV |
| 159 | pep299 | SSWKRPDGSMLFRVTINSV |
| 160 | pep301 | SSWKRSMLFRVTINSVS |
| 161 | pep302 | SSWKRMLFRVTINSVS |
| 162 | pep303 | SSWKRDGSMLFRVTINSVS |
| 163 | pep304 | SSWKRPDGSMLFRVTINSVS |
| 164 | pep305 | SSWKRGSMLFRVTIN |
| 165 | pep306 | SSWKRGSMLFRVTI |
| 166 | pep307 | SSWKRSMLFRVTIN |
| 167 | pep308 | SSWKRMLFRVTIN |
| 168 | pep309 | SSWKRDGSMLFRVTIN |

TABLE 1-continued

Exemplary peptide, dipeptide, and polypeptide sequences.

| SEQ ID NO | Name | Sequence |
|---|---|---|
| 169 | pep310 | SSWKRPDGSMLFRVTIN |
| 170 | pep311 | SSWKRSMLFRVTI |
| 171 | pep312 | SSWKRMLFRVTI |
| 172 | pep313 | SSWKRDGSMLFRVTI |
| 173 | pep314 | SSWKRPDGSMLFRVTI |
| 174 | pep316 | VSGWRLFKKISVFTL |
| 175 | pep317 | VSGWRLFKKISVFT |
| 176 | pep318 | VSGWRLFKKISVF |
| 177 | pep319 | VSGWRLFKKISV |
| 178 | pep320 | VSGWRLCKKIS |
| 179 | pep326 | VSGWRLFKKISGSMLFRVTINS |
| 180 | pep380 | SSWKRLFRVTINS |
| 181 | pep383 | SSWKRFRVTINS |
| 182 | pep386 | SSWKRRVTINS |
| 183 | pep389 | SSWKRTPDGSMLFRVTINS |
| 184 | pep392 | SSWKRITPDGSMLFRVTINS |
| 185 | pep395 | SSWKRLITPDGSMLFRVTINS |
| 186 | pep396 | SSRGSMLFRVTINSWK |
| 187 | pep397 | SKRGSMLFRVTINSWS |
| 188 | pep398 | SWRGSMLFRVTINS |
| 189 | pep400 | SSRGSMLFRVTIWK |
| 190 | pep401 | SSWKRGSMLYRVTINS |
| 191 | pep402 | SSWKRGSMLWRVTINS |
| 192 | pep403 | SSWKRGSMLHRVTINS |
| 193 | pep404 | SSWKRGSLLFRVTINS |
| 194 | pep405 | SSWKRGSKLFRVTINS |
| 195 | pep406 | SSWKRGSRLFRVTINS |
| 196 | pep407 | SSWKRGSFLFRVTINS |
| 197 | pep408 | SSWKRGSWLFRVTINS |
| 198 | pep409 | SSWKRGSMLFRVSINS |
| 199 | pep410 | SSWKRGSMLFRVQINS |
| 200 | pep411 | SSWKRGSMLFRVNINS |
| 201 | SmTrip9-286 with cysteine | SSWKRGSMLFRVTINSC |
| 202 | HiBit with cysteine | CVSGWRLFKKIS |
| 203 | SmTrip9-286 with azide | SSWKRGSMLFRVTINSK(Aza) |

TABLE 1-continued

Exemplary peptide, dipeptide, and polypeptide sequences.

| SEQ ID NO | Name | Sequence |
|---|---|---|
| 204 | HiBit with azide | (aza)KVSGWRLFKKIS |
| 205 | WT OgLuc dipeptide | GSLLFRVTINGVTGWRLCENILA |
| 206 | WTNanoLuc dipeptide | GSLLFRVTINVGVTGWRLCERILA |
| 207 | pep157 | SVSGWRLFKKIS |
| 208 | pep158 | NSVSGWRLFKKIS |
| 209 | pep206 | GWRLFKKIS |
| 210 | HiBiT-His-LgTrip3546 (ATG 3745) | Atggtgagcggctggcggctgttcaagaagattagccaccatcaccatcaccatcatcacttcacact cgacgatttcgttggggactgggaacagacagccgcctacaacctggaccaagtccttgaacaggg aggtgtgtccagtttgctgcagaatctcgccgtgtccgtaactccgatcatgaggattgtccggagcgg tgaaaatgccctgaagatcgacatccatgtcatcatcccgtatgaaggtctgagcgcgccgaccaaatgg cccagatcgaagaggtgtttaaggtggtgtaccctgtggatgatcatcactttaaggtgatcctgcccta tggcacactggtaatcgacggggttacgccgaacaagctgaactatttcggacggccgtatgaaggc atcgccgtgttcgacggcaaaaagatcactaccacagggaccctgtggaacggcaacaaaattatcg acgagcgcctgatcacccccgactaa |
| 211 | HiBiT-His-LgTrip3546 (ATG 3745) | MVSGWRLFKKISHHHHHHHHFTLDDFVGDWEQTAAYNLDQVL EQGGVSSLLQNLAVSVTPIMRIVRSGENALKIDIHVIIPYEGLSAD QMAQIEEVFKVVYPVDDHHFKVILPYGTLVIDGVTPNKLNYFG RPYEGIAVFDGKKITTTGTLWNGNKIIDERLITPD |
| 212 | His-HiBiT-GSSG-LgTrip3546 (ATG 3746) | Atgaaacatcaccatcaccatcatgtgagcggctggcggctgttcaagaagattagcggcagctccg gtttcacactcgacgatttcgttggggactgggaacagacagccgcctacaacctggaccaagtcctt gaacagggaggtgtgtccagtttgctgcagaatctcgccgtgtccgtaactccgatcatgaggattgtc cggagcggtgaaaatgccctgaagatcgacatccatgtcatcatcccgtatgaaggtctgagcgccg accaaatggcccagatcgaagaggtgtttaaggtggtgtaccctgtggatgatcatcactttaaggtga tcctgcccctatggcacactggtaatcgacggggttacgccgaacaagctgaactatttcggacggcc gtatgaaggcatcgccgtgttcgacggcaaaaagatcactaccacagggaccctgtggaacggcaa caaaattatcgacgagcgcctgatcacccccgactaa |
| 213 | His-HiBiT-GSSG-LgTrip3546 (ATG 3746) | MKHHHHHHVSGWRLFKKISGSSGFTLDDFVGDWEQTAAYNLD QVLEQGGVSSLLQNLAVSVTPIMRIVRSGENALKIDIHVIIPYEGL SADQMAQIEEVFKVVYPVDDHHFKVILPYGTLVIDGVTPNKLN YFGRPYEGIAVFDGKKITTTGTLWNGNKIIDERLITPD |
| 214 | FRB-15GS-86, no AI in linker (ATG3768) | Atggtggccatcctctggcatgagatgtggcatgaaggcctggaagaggcatctcgtttgtactttgg ggaaaggaacgtgaaaggcatgtttgaggtgctggagcccttgcatgctatgatggaacggggccc ccagactctgaaggaaacatcctttaatcaggcctatggtcgagatttaatggaggcccaagagtggt gcaggaagtacatgaaatcaggggaatgtcaaggacctcacccaagcctgggacctctattatcatgtg ttccgacgaatcagtggtggttcaggtggtggcggggagcggtggctcgagcagcggtggagtgagc ggctggcggctgttcaagaagattagctaa |
| 215 | FRB-15GS-86, no AI in linker (ATG3768) | MVAILWHEMWHEGLEEASRLYFGERNVKGMFEVLEPLHAMM ERGPQTLKETSFNQAYGRDLMEAQEWCRKYMKSGNVKDLTQA WDLYYHVFRRISGGSGGGGSGGSSSGGVSGWRLFKKIS |
| 216 | FRB-15GS-289 (ATG3769) | Atggtggccatcctctggcatgagatgtggcatgaaggcctggaagaggcatctcgtttgtactttgg ggaaaggaacgtgaaaggcatgtttgaggtgctggagcccttgcatgctatgatggaacggggccc ccagactctgaaggaaacatcctttaatcaggcctatggtcgagatttaatggaggcccaagagtggt gcaggaagtacatgaaatcaggggaatgtcaaggacctcacccaagcctgggacctctattatcatgtg ttccgacgaatcagtggtggttcaggtggtggcgggagcggtggctcgagcagcggtggagttagc gttagcggctggcgcctgttcaagaagatcagctaa |
| 217 | FRB-15GS-289 (ATG3769) | MVAILWHEMWHEGLEEASRLYFGERNVKGMFEVLEPLHAMM ERGPQTLKETSFNQAYGRDLMEAQEWCRKYMKSGNVKDLTQA WDLYYHVFRRISGGSGGGGSGGSSSGGVSVSGWRLFKKIS |
| 218 | FKBP-SmTrip9 fusion template, no AI in linker (ATG3770) | atggggagtgcaggtggaaaccatctcccccaggagacgggcgcaccttcccccaagcgcggccagac ctcgcgtggtgcactacaccgggatgcttgaagatgaaagaaatttgattcctcccgggacagaaac aagcccttttaagtttatgctaggcaagcaggaggtgatccgaggctgggaagaaggggttgcccag atgagtgtgggtcagagagccaaactgactatatctccagattatgcctatggtgccactgggcaccc aggcatcatcccaccacatgccactctcgtcttcgatgtggacttctaaaactggaaggtggttcagg tggtggcgggagcggtggctcgagcagcggtgga |

TABLE 1-continued

Exemplary peptide, dipeptide, and polypeptide sequences.

| SEQ ID NO | Name | Sequence |
|---|---|---|
| 219 | FKBP-SmTrip9 fusion template, no AI in linker (ATG3770) | MGVQVETISPGDGRTFPKRGQTCVVHYTGMLEDGKKFDSSRDR NKPFKFMLGKQEVIRGWEEGVAQMSVGQRAKLTISPDYAYGA TGHPGIIPPHATLVFDVELLKLEGGSGGGGSGGSSSGG |
| 220 | 295 | GSMLFRVTINSV |
| 221 | 300 | GSMLFRVTINSVS |
| 222 | 412 | MLFRVTINSVSG |
| 223 | 413 | MLFRVTINSVSGW |
| 224 | 415 | MLFRVTINSVSGWK |
| 225 | 416 | MLFRVTINSVSGWR |
| 226 | 418 | GSMLFRVTINSVSG |
| 227 | 419 | GSMLFRVTINSVSGW |
| 228 | 422 | GSMLFRVTINSVSGWR |
| 229 | 423 | GSMLFRVTINSVSGWK |
| 230 | 434 | GSMLFRVTIWK |
| 231 | 435 | GSMLFRVTINSWK |
| 232 | 477 | MLFRVTINSWK |
| 233 | 478 | MLFRVTINSWS |
| 234 | 479 | MLFRVTIWS |
| 235 | 480 | MLFRVTIWK |
| 236 | 481 | MLFRVKINS |
| 237 | 482 | GSMLFRVTINSWS |
| 238 | 483 | GSMLFRVKINS |
| 239 | 484 | GSMLFRVTIWS |
| 240 | 485 | MLFRVNINS |
| 241 | 486 | MLFRVWINS |
| 242 | 487 | LLFRVKINS |
| 243 | 488 | FLFRVTINS |
| 244 | 295 | SSWKRGSMLFRVTINSV |
| 245 | 300 | SSWKRGSMLFRVTINSVS |
| 246 | 412 | SSWKRMLFRVTINSVSG |
| 247 | 413 | SSWKRMLFRVTINSVSGW |
| 248 | 414 | SSWKRMLFRVTINSVSGWR |
| 249 | 415 | SSWKRMLFRVTINSVSGWK |
| 250 | 417 | MLFRVTINSVSGWK |
| 251 | 418 | SSWKRGSMLFRVTINSVSG |
| 252 | 419 | SSWKRGSMLFRVTINSVSGW |
| 253 | 420 | SSWKRGSMLFRVTINSVSGWR |

TABLE 1-continued

Exemplary peptide, dipeptide, and polypeptide sequences.

| SEQ ID NO | Name | Sequence |
|---|---|---|
| 254 | 421 | SSWKRGSMLFRVTINSVSGWK |
| 255 | 424 | SSWKRGSYLFRVTINS |
| 256 | 425 | SSWKRGSMLFRVKINS |
| 257 | 426 | SSWKRGSMLFRVRINS |
| 258 | 427 | SSWKRGSMLFRVWINS |
| 259 | 428 | SSKRGSMLFRVTIWSV |
| 260 | 429 | SSKRGSMLFRVTIWSVS |
| 261 | 430 | SSWRGSMLFRVTIKS |
| 262 | 431 | KRSSGSMLFRVTIWS |
| 263 | 432 | SSKRMLFRVTIWS |
| 264 | 433 | KRSSMLFRVTIWS |
| 265 | 445 | GSMKFRVTINSWK |
| 266 | 450 | GSMLFRKTINSWK |
| 267 | 455 | GSMLFRVTKNSWK |
| 268 | 521 | GKMLFRVTINSWK |
| 269 | 522 | GKMLFRVTIWK |
| 270 | 523 | GSMKFRVTINSWK |
| 271 | 524 | GSMKFRVTIWK |
| 272 | 525 | GRMLFRVTINSWK |
| 273 | 526 | GRMLFRVTIWK |
| 274 | 527 | GSMRFRVTINSWK |
| 275 | 528 | GSMRFRVTIWK |
| 276 | 529 | GDMLFRVTINSWK |
| 277 | 530 | GDMLFRVTIWK |
| 278 | 531 | GSMDFRVTINSWK |
| 279 | 532 | GSMDFRVTIWK |
| 280 | 533 | GEMLFRVTINSWK |
| 281 | 535 | GSMEFRVTINSWK |
| 282 | 536 | GSMEFRVTIWK |
| 283 | 538 | GSMLFRVTIWKVK |
| 284 | 539 | GSMLFRVTIWSVK |
| 285 | 540 | GSMLFRVTIWSK |
| 286 | 541 | GSMLFRVTIWKWK |
| 287 | 542 | GSMLFRVTIWKK |
| 288 | 245 | GSMLFRVTINS |
| 289 | 292.x | MLFRVTINS |
| 290 | 297.x | MLFVTINSV |

TABLE 1-continued

Exemplary peptide, dipeptide, and polypeptide sequences.

| SEQ ID NO | Name | Sequence |
|---|---|---|
| 291 | 302.x | MLFRVTINSVS |
| 292 | 305.x | GSMLFRVTIN |
| 293 | 306.x | GSMLFRVTI |
| 294 | 307.x | SMLFRVTIN |
| 295 | 308.x | MLFRVTIN |
| 296 | 312.x | MLFRVTI |
| 297 | 399 | SSKRGSMLFRVTIWS |
| 298 | 273 | GSMLFRVTINSGVSGWALFKKIS |
| 299 | 264 | GSMLFRVTINSGVSGWRLFKKIS |
| 300 | 167 | VSGWALFKKIS |
| 301 | 331 | GSMLFRVTINSVSGVSGWRLFKKIS |
| 302 | LgTrip 3546 (no His6) | MVFTLDDFVGDWEQTAAYNLDQVLEQGGVSSLLQNLAVSVTPI MRIVRSGENALKIDIHVIIPYEGLSADQMAQIEEVFKVVYPVDDH HFKVILPYGTLVIDGVTPNKLNYFGRPYEGIAVFDGKKITTTGTL WNGNKIIDERLITPD |
| 303 | LgTrip 3546 (no His6) | atggtcttcacactcgacgatttcgttggggactgggaacagacagccgcctacaacctggaccaagt ccttgaacagggaggtgtgtccagtttgctgcagaatctcgccgtgtccgtaactccgatcatgaggat tgtccggagcggtgaaaatgccctgaagatcgacatccatgtcatcatcccgtatgaaggtctgagcg ccgacaaatggcccagatcgaagaggtgtttaaggtggtgtaccctgtggatgatcatcactttaag gtgatcctgccctatggcacactggtaatcgacggggttacgccgaacaagctgaactatttcggacg gccgtatgaaggcatcgccgtgttcgacggcaaaaagatcactaccacagggaccctgtggaacgg caacaaaattatcgacgagcgcctgatcacccccgac |
| 304 | LgTrip 2098 (no His6) | MVFTLDDFVGDWEQTAAYNLDQVLEQGGVSSLLQNLAVSVTPI MRIVRSGENALKIDIHVIIPYEGLSADQMAQIEEVFKVVYPVDDH HFKVILPYGTLVIDGVTPNKLNYFGRPYEGIAVFDGKKITVTGTL WNGNKIIDERLITPD |
| 305 | LgTrip 2098 (no His6) | atggtcttcacactcgaagatttcgttggggactgggaacagacagccgcctacaacctggaccaagt ccttgaacagggaggtgtgtccagtttgctgcagaatctcgccgtgtccgtaactccgatccaaaggat tgtccggagcggtgaaaatgccctgaagatcgacatccatgtcatcatcccgtatgaaggtctgagcg ccgaccaaatggcccagatcgaagaggtgtttaaggtggtgtaccctgtggatgatcatcactttaag gtgatcctgccctatggcacactggtaatcgacggggttacgccgaacatgctgaactatttcggacg gccgtatgaaggcatcgccgtgttcgacggcaaaaagatcactgtaacagggaccctgtggaacgg caacaaaattatcgacgagcgcctgatcacccccgac |
| 306 | 157 | SVSGWRLFKKIS |
| 307 | 158 | NSVSGWRLFKKIS |
| 308 | 206 | GWRLFKKIS |
| 309 | 264 | GSMLFRVTINSGVSGWRLFKKIS |
| 310 | 489 | GSMLFRVTINSWK (N-term unblocked) |
| 311 | 490 | GSMLFRVTINSWK (C-term unblocked) |
| 312 | 491 | GSMLFRVTINSWK (Both unblocked) |
| 313 | 492 | GSMLFRVTINKWK |
| 314 | 493 | GSMLFRVTIKSWK |
| 315 | 494 | GSMLFRVTINRWK |
| 316 | 495 | GSMLFRVTIRSWK |
| 317 | 496 | GSMLFRVTINDWK |
| 318 | 497 | GSMLFRVTIDSWK |

TABLE 1-continued

Exemplary peptide, dipeptide, and polypeptide sequences.

| SEQ ID NO | Name | Sequence |
|---|---|---|
| 319 | 498 | GSMLFRVTINEWK |
| 320 | 499 | GSMLFRVTIESWK |
| 321 | 465 | GSMRFRVTINSWK (Both termini unblocked) |
| 322 | 466 | GSMDFRVTINSWK (Both termini unblocked) |
| 323 | 467 | GSMEFRVTINSWK (Both termini unblocked) |
| 324 | 468 | GSMLFRRTINSWK (Both termini unblocked) |
| 325 | 469 | GSMLFRDTINSWK (Both termini unblocked) |
| 326 | 470 | GSMLFRETINSWK (Both termini unblocked) |
| 327 | 472 | GSMLFRVTDNSWK (Both termini unblocked) |
| 328 | 473 | GSMLFRVTENSWK (Both termini unblocked) |
| 329 | 474 | GSMKFRVTINSWK (Both termini unblocked) |
| 330 | 475 | GSMLFRKTINSWK (Both termini unblocked) |
| 331 | 476 | GSMLFRVTKNSWK (Both termini unblocked) |
| 332 | 436 | GSMLFRVTINS (N-term unblocked) |
| 333 | 437 | GSMLFRVSINS (N-term unblocked) |
| 334 | 438 | GSMLFRVNINS (N-term unblocked) |
| 335 | 439 | GSKLFRVTINS (N-term unblocked) |
| 336 | 440 | GSRLFRVTINS (N-term unblocked) |
| 337 | 441 | GSMWFRVTINS (N-term unblocked) |
| 338 | 442 | GSMSFRVTINS (N-term unblocked) |
| 339 | 443 | GSMNFRVTINS (N-term unblocked) |
| 340 | 444 | GSMKFRVTINS (N-term unblocked) |
| 341 | 446 | GSMLFRWTINS (N-term unblocked) |
| 342 | 447 | GSMLFRSTINS (N-term unblocked) |
| 343 | 448 | GSMLFRNTINS (N-term unblocked) |
| 344 | 449 | GSMLFRKTINS (N-term unblocked) |
| 345 | 451 | GSMLFRVTWNS (N-term unblocked) |
| 346 | 452 | GSMLFRVTSNS (N-term unblocked) |
| 347 | 453 | GSMLFRVTNNS (N-term unblocked) |
| 348 | 454 | GSMLFRVTKNS (N-term unblocked) |
| 349 | 456 | GSMLFRVTIKS (N-term unblocked) |
| 350 | Antares ATG 3802 | MKHHHHHHVSKGEELIKENMRSKLYLEGSVNGHQFKCTHEGE GKPYEGKQTNRIKVVEGGPLPFAFDILATHFMYGSKVFIKYPAD LPDYFKQSFPEGFTWERVMVFEDGGVLTATQDTSLQDGELIYN VKVRGVNFPANGPVMQKKTLGWEPSTETMYPADGGLEGRCDK ALKLVGGGHLHVNFKTTYKSKKPVKMPGVHYVDRRLERIKEA DNETYVEQYEHAVARYSNLGGGFTLEDFVGDWRQTAGYNLDQ VLEQGGVSSLFQNLGVSVTPIQRIVLSGENGLKIDIHVIIPYEGLS GDQMGQIEKIFKVVYPVDDHHFKVILHYGTLVIDGVTPNMIDYF GRPYEGIAVFDGKKITVTGTLWNGNKIIDERLINPDGSLLFRVTI NGVTGWRLCERILARHELIKENMRSKLYLEGSVNGHQFKCTHE GEGKPYEGKQTNRIKVVEGGPLPFAFDILATHFMYGSKVFIKYP |

TABLE 1-continued

Exemplary peptide, dipeptide, and polypeptide sequences.

| SEQ ID NO | Name | Sequence |
|---|---|---|
| | | ADLPDYFKQSFPEGFTWERVMVFEDGGVLTATQDTSLQDGELI YNVKVRGVNFPANGPVMQKKTLGWEPSTETMYPADGGLEGRC DKALKLVGGGHLHVNFKTTYKSKKPVKMPGVHYVDRRLERIK EADNETYVEQYEHAVARYSNLGGGMDELYK |
| 351 | Antares ATG 3802 | atgaaacatcaccatcaccatcatgtgagcaagggagaagaacttataaaagaaaacatgcggtcta aactgtacctcgagggctccgtcaatgggcaccagtttaagtgtacccacgagggtgagggaaagc cctatgaggggaagcagacaaaccgcatcaaggtcgtcgaaggggggacccctcccgtttgcctttga tatcttggctactcactttatgtacggaagcaaagttttcataaagtatcctgccgaccttcctgattatttta aacagtcatttcccgagggttttcacatgggaaagggtcatggtgtttgaggatggaggcgtgctcact gcaactcaggacacctcactgcaggacggcgagctgatctacaatgtgaaggtccggggtgtaaact tccctgccaacgggcctgtaatgcagaagaagaccctgggatgggagccgtccaccgaaaccatgt accctgctgatggtgggctggagggccgatgtgacaaggctctgaagctcgttggaggtggtcatttg cacgtaaatttcaagacaacttacaagagcaaaaaacccgtaaaaatgcccgggggttcattacgttga cagaaggcttgaacgcataaaggaagctgataacgagacatacgtggagcagtacgagcacgccg ttgcccggtactcaaacctggggggtggcttacactggaggattttgtgggagattggagacagaca gccggctacaatctggatcaggtgctggaacaaggaggagtgtcttctctgtttcagaatctgggagt gagcgtgacacctatccagaggatcgtgctgtctggcgagaatggactgaagatcgatattcacgtga tcatcccctacgaaggcctgtctgtcggaccagatgggccagattgagaagatcttcaaagtggtgtat cctgtggacgatcaccacttcaaggtgatcctgcactacggcaccctggtgattgatggagtgacacc taacatgatcgactactcggaagaccttacgagggaatcgccgtgttcgacggaaagaagatcacc gtgacaggaacactgtggaatggaaacaagatcatcgacgagcggctgatcaaccctgatggatctc tgctgttcagagtgaccatcaacggagtgacaggatggagactgtgcgagagaattctggctagaca tgagctaatcaaggaaaatatgagaagtaagctatacttagagggtccgtcaacggtcaccagttta aatgcactcatgaaggtgaggggaaaccttatgaaggtaagcagactaatcgaataaaagtggtcga gggcggtcctctgccattcgctttcgatattctggccactcactttatgtatgggtctaaggtctttattaaa taccccgctgatttgccagactactttaaacagtccttccctgaaggattcacatgggagcgggtgatg gtgttcgaggatggaggccgttcttactgcaactcaggatacttccttgcaagacggggaactgatctac aacgttaaggtccgcggcgtcaatttcccagccaatggtccagtgatgcagaagaaaaccttgggtt gggagccctcaacggagacaatgtaccctgcgggacggcgggcttgagggtagatgtgataaggcat tgaaactcgtcggggggcggccacccttcatgtgaatttcaagactacatatataaaagtaaaaaaccagtc aagatgcctggagtgcactacgtggatcgtaggttggagaggataaaagaagccgacaacgaaact tatgtagagcaatatgagcacgccgtggctcgttattccaacttgggcggaggaatggatgaactgta caag |
| 352 | Antares (LgBiT) ATG 3803 | MKHHHHHHVSKGEELIKENMRSKLYLEGSVNGHQFKCTHEGE GKPYEGKQTNRIKVVEGGPLPFAFDILATHFMYGSKVFIKYPAD LPDYFKQSFPEGFTWERVMVFEDGGVLTATQDTSLQDGELIYN VKVRGVNFPANGPVMQKKTLGWEPSTETMYPADGGLEGRCDK ALKLVGGGHLHVNFKTTYKSKKPVKMPGVHYVDRRLERIKEA DNETYVEQYEHAVARYSNLGGGFTLEDFVGDWEQTAAYNLDQ VLEQGGVSSLLQNLAVSVTPIQRIVRSGENALKIDIHVIIPYEGLS ADQMAQIEEVFKVVYPVDDHHFKVILPYGTLVIDGVTPNMLNY FGRPYEGIAVFDGKKITVTGTLWNGNKIIDERLITPDGSMLFRVT INSRHELIKENMRSKLYLEGSVNGHQFKCTHEGEGKPYEGKQT NRIKVVEGGPLPFAFDILATHFMYGSKVFIKYPADLPDYFKQSFP EGFTWERVMVFEDGGVLTATQDTSLQDGELIYNVKVRGVNFPA NGPVMQKKTLGWEPSTETMYPADGGLEGRCDKALKLVGGGHL HVNFKTTYKSKKPVKMPGVHYVDRRLERIKEADNETYVEQYE HAVARYSNLGGGMDELYK |
| 353 | Antares (LgBiT) ATG 3803 | atgaaacatcaccatcaccatcatgtgagcaagggagaagaacttataaaagaaaacatgcggtcta aactgtacctcgagggctccgtcaatgggcaccagtttaagtgtacccacgagggtgagggaaagc cctatgaggggaagcagacaaaccgcatcaaggtcgtcgaaggggggacccctcccgtttgcctttga tatcttggctactcactttatgtacggaagcaaagttttcataaagtatcctgccgaccttcctgattatttta aacagtcatttcccgagggttttcacatgggaaagggtcatggtgtttgaggatggaggcgtgctcact gcaactcaggacacctcactgcaggacggcgagctgatctacaatgtgaaggtccggggtgtaaact tccctgccaacgggcctgtaatgcagaagaagaccctgggatgggagccgtccaccgaaaccatgt accctgctgatggtgggctggagggccgatgtgacaaggctctgaagctcgttggaggtggtcatttg cacgtaaatttcaagacaacttacaagagcaaaaaacccgtaaaaatgcccgggggttcattacgttga cagaaggcttgaacgcataaaggaagctgataacgagacatacgtggagcagtacgagcacgccg ttgcccggtactcaaacctggggggtggcttcacactcgaagatttcgttggggactgggaacagac agccgcctacaacctggaccaagtccttgaacaggaggtgtgtccagtttgctgcagaatctcgcc gtgtccgtaactccgatccaaaggattgtccggagcggtgaaaatgccctgaagatcgacatccatgt catcatccctatgaaggtcgagcgccgaccaaatggcccagatggcacactggtaatcgacggggtacgc cgaacatgctgaactattcggacggccgtatgaaggcatcgccgtgttcgacggcaaaaagatcact gtaacagggaccctgtggaacggcaacaaaattatcgacgagcgcctgatcacccccgacggctcc atgctgttccgagtaaccatcaacagcagacatgagctaatcaaggaaaatatgagaagtaagctata cttagagggggtccgtcaacggtcaccagtttaaatgcactcatgaaggtgagggggaaaccttatgaag gtaagcagactaatcgaataaaagtggtcgagggcggtcctctgccattcgctttcgatattctggcca ctcactttatgtatgggtctaaggtctttattaaataccccgctgatttgccagactactttaaacagtcctt ccctgaaggattcacatgggagcgggtgatggtgttcgaggatggaggcgttcttactgcaactcag gatacttccttgcaagacggggaactgatctacaacgttaaggtccgcggcgtcaatttcccagccaat |

TABLE 1-continued

Exemplary peptide, dipeptide, and polypeptide sequences.

| SEQ ID NO | Name | Sequence |
|---|---|---|

|  |  | ggtccagtgatgcagaagaaaaccttggggtgggagccctcaacggagacaatgtaccctgcggac<br>ggcgggcttgagggtagatgtgataaggcattgaaactcgtcgggggcggccaccttcatgtgaattt<br>caagactacatataaaagtaaaaaaccagtcaagatgcctggagtgcactacgtggatcgtaggttgg<br>agaggataaaagaagccgacaacgaaacttatgtagagcaatatgagcacgccgtggctcgttattc<br>caacttgggcggaggaatggatgaactgtacaag |
| 354 | Antares<br>(LgTrip 3546)<br>ATG 3804 | MKHHHHHVSKGEELIKENMRSKLYLEGSVNGHQFKCTHEGE<br>GKPYEGKQTNRIKVVEGGPLPFAFDILATHFMYGSKVFIKYPAD<br>LPDYFKQSFPEGFTWERVMVFEDGGVLTATQDTSLQDGELIYN<br>VKVRGVNFPANGPVMQKKTLGWEPSTETMYPADGGLEGRCDK<br>ALKLVGGGHLHVNFKTTYKSKKPVKMPGVHYVDRRLERIKEA<br>DNETYVEQYEHAVARYSNLGGGFTLDDFVGDWEQTAAYNLDQ<br>VLEQGGVSSLLQNLAVSVTPIMRIVRSGENALKIDIHVIIPYEGLS<br>ADQMAQIEEVFKVVYPVDDHHFKVILPYGTLVIDGVTPNKLNY<br>FGRPYEGIAVFDGKKITTTGTLWNGNKIIDERLITPDRHELIKEN<br>MRSKLYLEGSVNGHQFKCTHEGEGKPYEGKQTNRIKVVEGGPL<br>PFAFDILATHFMYGSKVFIKYPADLPDYFKQSFPEGFTWERVMV<br>FEDGGVLTATQDTSLQDGELIYNVKVRGVNFPANGPVMQKKTL<br>GWEPSTETMYPADGGLEGRCDKALKLVGGGHLHVNFKTTYKS<br>KKPVKMPGVHYVDRRLERIKEADNETYVEQYEHAVARYSNLG<br>GGMDELYK |
| 355 | Antares<br>(LgTrip 3546)<br>ATG 3804 | atgaaacatcaccatcaccatcatgtgagcaagggagaagaacttataaaagaaaacatgcggtcta<br>aactgtacctcgagggctccgtcaatgggcaccagtttaagtgtacccacgagggtgagggaaagc<br>cctatgaggggaagcagacaaaccgcatcaaggtcgtcgaaggggggacccctcccgtttgcctttga<br>tatcttggctactcactttatgtacggaagcaaagtttttcataaagtatcctgccgaccttcctgattattttta<br>aacagtcatttcccgagggtttcacatgggaaagggtcatggtgtttgaggatggaggcgtgctcact<br>gcaactcaggacacctcactgcaggacggcgagctgatctcaatgtgaaggtccggggtgtaaact<br>tccctgccaacgggcctgtaatgcagaagaagaccctgggatgggagccgtccaccgaaaccatgt<br>accctgctgatggtgggctggagggccgatgtgacaaggctctgaagctcgttggaggtggtcatttg<br>cacgtaaatttcaagacaacttacaagagcaaaaaacccgtaaaaatgcccgggggttcattacgttga<br>cagaaggcttgaacgcataaaggaagctgataacgagacatacgtgggagcagtacgagcacgccg<br>ttgcccggtactcaaacctggggggggtggcttcacactcgacgatttcgttggggactgggaacagac<br>agccgcctacaacctggaccaagtccttgaacaggaggtgtgtccagtttgctgcagaatctcgcc<br>gtgtccgtaactccgatcatgaggattgtccggagcggtgaaaatgccctgaagatcgacatccatgt<br>catcatcccgtatgaaggtctgagcgccgaccaaatggcccagatggtcgaagaggtgtttaaggtggtgt<br>accctgtggatgatcatcactttaaggtgatcctgccctatggcacactggtaatcgacggggttacgc<br>cgaacaagctgaactatttcggacggccgtatgaaggcatcgccgtgttcgacggcaaaaagatcac<br>taccacagggaccctgtggaacggcaacaaaattatcgacgagcgcctgatcacccccgacagaca<br>tgagctaatcaaggaaaatatgagaagtaagctatacttagagggtccgtcaacggtcaccagtttta<br>aatgcactcatgaaggtgaggggaaaccttatgaaggtaagcagactaatcgaataaaagtggtcga<br>gggcggtctctgccattcgctttcgatattctggccactcactttatgtatgggtctaaggtctttattaaa<br>taccccgctgatttgccagactactttaaacagtccttccctgaaggattcacatgggagcgggtgatg<br>gtgttcgaggatggaggcgttcttactgcaactcaggatacttccttgcaagacgggagctgatctac<br>aacgttaaggtccgcggcgtcaatttcccagccaatggtccagtgatgcagaagaaaaccttggggt<br>gggagccctcaacggagacaatgtaccctgcggacggcgggcttgagggtagatgtgataaggcat<br>tgaaactcgtcggggcggccaccttcatgtgaatttcaagactacatataaaagtaaaaaaccagtc<br>aagatgcctggagtgcactacgtggatcgtaggttggagaggataaaagaagccgacaacgaaact<br>tatgtagagcaatatgagcacgccgtggctcgttattccaacttgggcggaggaatggatgaactgta<br>caag |
| 356 | ATG 3815 | MKHHHHHFTLEDFVGDWEQTAAYNLDQVLEQGGVSSLLQNL<br>AVSVTPIQRIVRSGENALKIDIHVIIPYEGLSADQMAQIEEVFKVV<br>YPVDDHHFKVILPYGTLVIDGVTPNMLNYFGRPYEGIAVFDGKK<br>ITVTGTLWNGNKIIDERLITPDGSMLFRVTINSGGSGGSSGELIKE<br>NMRSKLYLEGSVNGHQFKCTHEGEGKPYEGKQTNRIKVVEGGP<br>LPFAFDILATHFMYGSKVFIKYPADLPDYFKQSFPEGFTWERVM<br>VFEDGGVLTATQDTSLQDGELIYNVKVRGVNFPANGPVMQKK<br>TLGWEPSTETMYPADGGLEGRCDKALKLVGGGHLHVNFKTTY<br>KSKKPVKMPGVHYVDRRLERIKEADNETYVEQYEHAVARYSN<br>LGGGMDELYK |
| 357 | ATG 3815 | atgaaacatcaccatcaccatcatttcacactcgaagatttcgttggggactgggaacagacagccgc<br>ctacaacctggaccaagtccttgaacagggaggtgtgtccagtttgctgcagaatctcgccgtgtccgt<br>aactccgatccaaaggattgtccggagcggtgaaaatgccctgaagatcgacatccatgtcatcatcc<br>cgtatgaaggtctgagcgccgaccaaatggcccagatcgaagaggtgtttaaggtggtgtaccctgt<br>ggatgatcatcactttaaggtgatcctgccctatggcacactggtaatcgacggggttacgccgaacat<br>gctgaactatttcggacggccgtatgaaggcatcgccgtgttcgacggcaaaaagatcactgtaaca<br>gggaccctgtggaacggcaacaaaattatcgacgagcgcctgatcacccccgacggctccatgctg<br>ttccgagtaaccatcaacagcggaggctcaggtggatcctcaggtgagctaatcaaggaaaatatga<br>gaagtaagctatacttagagggtccgtcaacggtcaccagtttaaatgcactcatgaaggtgaggg<br>aaaccttatgaaggtaagcagactaatcgaataaaagtggtcgagggcggtcctctgccattcgctttc<br>gatattctggccactcactttatgtatgggtctaaggtctttattaaataccccgctgatttgccagactact<br>ttaaacagtccttccctgaaggattcacatgggagcgggtgatggtgttcgaggatggaggcgttctta |

TABLE 1-continued

Exemplary peptide, dipeptide, and polypeptide sequences.

| SEQ ID NO | Name | Sequence |
|-----------|------|----------| ctgcaactcaggatacttccttgcaagacggggaactgatctacaacgttaaggtccgcggcgtcaat
ttcccagccaatggtccagtgatgcagaagaaaaccttggggtgggagccctcaacggagacaatgt
accctgcggacggcgggcttgagggtagatgtgataaggcattgaaactcgtcggggggcggccac
cttcatgtgaatttcaagactacatataaaagtaaaaaaaccagtcaagatgcctggagtgcactacgtg
gatcgtaggttggagaggataaaagaagccgacaacgaaacttatgtagagcaatatgagcacgcc
gtggctcgttattccaacttgggcggaggaatggatgaactgtacaag

358 ATG 3816

MKHHHHHHFTLEDFVGDWEQTAAYNLDQVLEQGGVSSLLQNL
AVSVTPIQRIVRSGENALKIDIHVIIPYEGLSADQMAQIEEVFKVV
YPVDDHHFKVILPYGTLVIDGVTPNMLNYFGRPYEGIAVFDGKK
ITVTGTLWNGNKIIDERLITPDGSMLFRVTINSRHELIKENMRSK
LYLEGSVNGHQFKCTHEGEGKPYEGKQTNRIKVVEGGPLPFAF
DILATHFMYGSKVFIKYPADLPDYFKQSFPEGFTWERVMVFEDG
GVLTATQDTSLQDGELIYNVKVRGVNFPANGPVMQKKTLGWE
PSTETMYPADGGLEGRCDKALKLVGGGHLHVNFKTTYKSKKP
VKMPGVHYVDRRLERIKEADNETYVEQYEHAVARYSNLGGGM
DELYK

359 ATG 3816

Atgaaacatcaccatcaccatcatttcacactcgaagatttcgttggggactgggaacagacagccg
cctacaacctggaccaagtccttgaacagggaggtgtgtccagtttgctgcagaatctcgccgtgtcc
gtaactccgatccaaaggattgtccggagcggtgaaaatgccctgaagatcgacatccatgtcatcat
cccgtatgaaggtctgagcgccgaccaaatggcccagatcgaagaggtgtttaaggtggtgtaccct
gtggatgatcatcactttaaggtgatcctgccctatggcacactggtaatcgacggggttacgccgaac
atgctgaactatttcggacggccgtatgaaggcatcgccgtgttcgacggcaaaaagatcactgtaac
agggaccctgtggaacggcaacaaaattatcgacgagcgcctgatcaccccgacggctccatgct
gttccgagtaaccatcaacagcagacatgagctaatcaaggaaaatatgagaagtaagctatacttag
aggggtccgtcaacggtcaccagtttaaatgcactcatgaaggtgagggggaaaccttatgaaggtaa
gcagactaatcgaataaaagtggtcgagggcggtcctctgccattcgctttcgatattctggccactca
ctttatgtatgggtctaaggtattattaaataccccgctgatttgccagactactttaaacagtccttccct
gaaggattcacatgggagcgggtgatggtgttcgaggatggaggcgttcttactgcaactcaggata
cttccttgcaagacggggaactgatctacaacgttaaggtccgcggcgtcaatttcccagccaatggt
ccagtgatgcagaagaaaaccttggggtgggagccctcaacggagacaatgtaccctgcggacggc
gggcttgagggtagatgtgataaggcattgaaactcgtcggggggcggccaccttcatgtgaatttca
agactacatataaaagtaaaaaaaccagtcaagatgcctggagtgcactacgtggatcgtaggttggag
aggataaaagaagccgacaacgaaacttatgtagagcaatatgagcacgccgtggctcgttattcca
acttgggcggaggaatggatgaactgtacaag

360 ATG 3817

MKHHHHHHFTLDDFVGDWEQTAAYNLDQVLEQGGVSSLLQN
LAVSVTPIMRIVRSGENALKIDIHVIIPYEGLSADQMAQIEEVFKV
VYPVDDHHFKVILPYGTLVIDGVTPNKLNYFGRPYEGIAVFDGK
KITTTGTLWNGNKIIDERLITPDGGSGGSSGELIKENMRSKLYLE
GSVNGHQFKCTHEGEGKPYEGKQTNRIKVVEGGPLPFAFDILAT
HFMYGSKVFIKYPADLPDYFKQSFPEGFTWERVMVFEDGGVLT
ATQDTSLQDGELIYNVKVRGVNFPANGPVMQKKTLGWEPSTET
MYPADGGLEGRCDKALKLVGGGHLHVNFKTTYKSKKPVKMP
GVHYVDRRLERIKEADNETYVEQYEHAVARYSNLGGGMDELY
K

361 ATG 3817

Atgaaacatcaccatcaccatcatttcacactcgacgatttcgttggggactgggaacagacagccg
cctacaacctggaccaagtccttgaacagggaggtgtgtccagtttgctgcagaatctcgccgtgtcc
gtaactccgatcatgaggattgtccggagcggtgaaaatgccctgaagatcgacatccatgtcatcat
cccgtatgaaggtctgagcgccgaccaaatggcccagatcgaagaggtgtttaaggtggtgtaccct
gtggatgatcatcactttaaggtgatcctgccctatggcacactggtaatcgacggcaaaaagatcactacca
aagctgaactatttcggacggccgtatgaaggcatcgccgtgttcgacggcaaaaagatcactacca
cagggaccctgtggaacggcaacaaaattatcgacgagcgcctgatcacccccgacggagctca
ggtggatcctcaggtgagctaatcaaggaaaatatgagaagtaagctatacttagaggggtccgtcaa
cggtcaccagtttaaatgcactcatgaaggtgagggggaaaccttatgaaggtaagcagactaatcgaa
taaaagtggtcgagggcggtcctctgccattcgctttcgatattctggccactcactttatgtatgggtct
aaggtctttattaaataccccgctgatttgccagactactttaaacagtccttccctgaaggattcacatg
ggagcgggtgatggtgttcgaggatggaggcgttcttactgcaactcaggatacttccttgcaagacg
gggaactgatctacaacgttaaggtccgcggcgtcaatttcccagccaatggtccagtgatgcagaa
gaaaaccttggggtgggagccctcaacggagacaatgtaccctgcggacggcgggcttgagggta
gatgtgataaggcattgaaactcgtcggggggcggccaccttcatgtgaatttcaagactacatataaaa
gtaaaaaaccagtcaagatgcctggagtgcactacgtggatcgtaggttggagaggataaaagaag
ccgacaacgaaacttatgtagagcaatatgagcacgccgtggctcgttattccaacttgggcggagg
aatggatgaactgtacaag TABLE 1-continued Exemplary peptide, dipeptide, and polypeptide sequences.

| SEQ ID NO | Name | Sequence |
|---|---|---|
| 362 | ATG 3818 | MKHHHHHHFTLDDFVGDWEQTAAYNLDQVLEQGGVSSLLQN LAVSVTPIMIRIVRSGENALKIDIHVIIPYEGLSADQMAQIEEVFKV VYPVDDHHFKVILPYGTLVIDGVTPNKLNYFGRPYEGIAVFDGK KITTTGTLWNGNKIIDERLITPDRHELIKENMRSKLYLEGSVNGH QFKCTHEGEGKPYEGKQTNRIKVVEGGPLPFAFDILATHFMYGS KVFIKYPADLPDYFKQSFPEGFTWERVMVFEDGGVLTATQDTS LQDGELIYNVKVRGVNFPANGPVMQKKTLGWEPSTETMYPAD GGLEGRCDKALKLVGGGHLHVNFKTTYKSKKPVKMPGVHYV DRRLERIKEADNETYVEQYEHAVARYSNLGGGMDELYK |
| 363 | ATG 3818 | Atgaaacatcaccatcaccatcatttcacactcgacgatttcgttggggactgggaacagacagccg cctacaacctggaccaagtccttgaacaggaggtgtgtccagtttgctgcagaatctcgccgtgtcc gtaactccgatcatgaggattgtccggagcggtgaaaatgccctgaagatcgacatccatgtcatcat cccgtatgaaggtctgagcgccgaccaaatggcccagatcgaagaggtgtttaaggtggtgtaccct gtggatgatcatcactttaaggtgatcctgccctatggcacactggtaatcgacggggttacgccgaac aagctgaactatttcggacggccgtatgaaggcatcgccgtgttcgacggcaaaaagatcactacca cagggaccctgtggaacggcaacaaaattatcgacgagcgcctgatcaccccgacagacatgag ctaatcaaggaaaatatgagaagtaagctatacttagaggggtccgtcaacggtcaccagtttaaatgc actcatgaaggtgaggggaaaccttatgaaggtaagcagactaatcgaataaaagtggtcgagggc ggtcctctgccattcgctttcgatattctggccactcactttatgtatgggtctaaggtcttttattaaataccc cgctgatttgccagactactttaaacagtccttccctgaaggattcacatgggagcgggtgatggtgtt cgaggatggaggcgttcttactgcaactcaggatacttccttgcaagacggggaactgatctacaacg ttaaggtccgcggcgtcaatttcccagccaatggtccagtgatgcagaagaaaaccttggggtggga gccctcaacggagacaatgtaccctgcggacggcgggcttgagggtagatgtgataaggcattgaa actcgtcgggggcggccaccttcatgtgaatttcaagactacatataaaagtaaaaaaccagtcaaga tgcctggagtgcactacgtggatcgtaggttggagaggataaaaagaagccgacaacgaaacttatgt agagcaatatgagcacgccgtggctcgttattccaacttgggcggaggaatggatgaactgtacaag |
| 364 | LgTrip 2899 (LgTrip 2098 + Q42L) | MKHHHHHHVFTLEDFVGDWEQTAAYNLDQVLEQGGVSSLLQ NLAVSVTPILRIVRSGENALKIDIHVIIPYEGLSADQMAQIEEVFK VVYPVDDHHFKVILPYGTLVIDGVTPNMLNYFGRPYEGIAVFDG KKITVTGTLWNGNKIIDERLITPD |
| 365 | LgTrip 2899 (LgTrip 2098 + Q42L) | atgaaacatcaccatcaccatcatgtcttcacactcgaagatttcgttggggactgggaacagaccgc cgcctacaacctggaccaagtccttgaacaggaggtgtgtccagtttgctgcagaatctcgccgtgt ccgtaactccgatcctaaggattgtccggagcggtgaaaatgccctgaagatcgacatccatgtcatc atcccgtatgaaggtctgagcgccgaccaaatggcccagatcgaagaggtgtttaaggtggtgtacc ctgtggatgatcatcactttaaggtgatcctgccctatggcacactggtaatcgacggggttacgccga acatgctgaactatttcggacggccgtatgaaggcatcgccgtgttcgacggcaaaaagatcactgta acagggaccctgtggaacggcaacaaaattatcgacgagcgcctgatcaccccgac |
| 820 | ATG-3930 | atgAAACATCACCATCACCATCATgtcTTCACACTCGACGATTTC GTTGGGGACTGGGAACAGACAGCCGCCTACAACCTGGACCA AGTCCTTGAACAGGGAGGTGTGTCCAGTTTGCTGCAGAATCT CGCCGTGTCCGTAACTCCGATCATGAGGATTGTCCGGAGCGG TGAAAATGCCCTGAAGATCGACATCCATGTCATCATCCCGTA TGAAGGTCTGAGCGCCGACCAAATGGCCCAGATCGAAGAGG TGTTTAAGGTGGTGTACCCTGTGGATGATCATCACTTTAAGG TGATCCTGCCCTATGGCACACTGGTAATCGACGGGGTTACGC CGAACAAGCTGAACTATTTCGGACGGCCGTATGAAGGCATCG CCGTGTTCGACGGCTAA |
| 821 | ATG-3930 | MKHHHHHHVFTLDDFVGDWEQTAAYNLDQVLEQGGVSSLLQ NLAVSVTPIMRIVRSGENALKIDIHVIIPYEGLSADQMAQIEEVFK VVYPVDDHHFKVILPYGTLVIDGVTPNKLNYFGRPYEGIAVFDG |
| 822 | SmTrip9-15GS-ProteinG (ATG 4002) | gggagctccGGTGGTGGCGGGAGCGGAGGTGGAGGctcgAGCGGT ATGACGTATAAGTTAATCCTTAATGGTAAAACATTGAAAGGC GAGACAACTACTGAAGCTGTTGATGCTGCTACTGCAGAAAAA GTCTTCAAACAATACGCTAACGACAACGGTGTTGACGGTGAA TGGACTTACGACGATGCGACGAAAACCTTTACGGTCACCGAA AAACCAGAAGTGATCGATGCGTCTGAATTAACACCAGCCGTG ACAACTTACAAACTTGTTATTAATGGTAAAACATTGAAAGGC GAAACAACTACTGAGGCTGTTGATGCTGCTACTGCAGAGAAG GTGTTCAAACAATATGCGAATGACAACGGTGTTGACGGTGAG TGGACTTACGACGATGCGACTAAGACCTTTACAGTTACTGAA AAACCAGAAGTGATCGATGCGTCTGAGTTAACACCAGCCGTG ACAACTTACAAACTTGTTATTAATGGTAAAACATTGAAAGGC GAAACAACTACTAAAGCAGTAGACGCAGAAACTGCGGAGAA GGCCTTCAAACAATACGCTAACGACAACGGTGTTGATGGTGT TTGGACTTATGATGATGCCACAAAAACCTTTACGGTAACTGA GCATCATCACCATCACCACTAA |

TABLE 1-continued

Exemplary peptide, dipeptide, and polypeptide sequences.

| SEQ ID NO | Name | Sequence |
|---|---|---|
| 823 | SmTrip9-15GS-ProteinG (ATG 4002) | GSSGGGGSGGGGSSGMTYKLILNGKTLKGETTTEAVDAATAEK VFKQYANDNGVDGEWTYDDATKTFTVTEKPEVIDASELTPAVT TYKLVINGKTLKGETTTEAVDAATAEKVFKQYANDNGVDGEW TYDDATKTFTVTEKPEVIDASELTPAVTTYKLVINGKTLKGETT TKAVDAETAEKAFKQYANDNGVDGVWTYDDATKTFTVTEHH HHHH |
| 830 | ATG-3929 | atgAAACATCACCATCACCATCATgtcTTCACACTCGACGATTTC GTTGGGGACTGGGAACAGACAGCCGCCTACAACCTGGACCA AGTCCTTGAACAGGGAGGTGTGTCCAGTTTGCTGCAGAATCT CGCCGTGTCCGTAACTCCGATCATGAGGATTGTCCGGAGCGG TGAAAATGCCCTGAAGATCGACATCCATGTCATCATCCCGTA TGAAGGTCTGAGCGCCGACCAAATGGCCCAGATCGAAGAGG TGTTTAAGGTGGTGTACCCTGTGGATGATCATCACTTTAAGG TGATCCTGCCCTATGGCACACTGGTAATCGACGGGGTTACGC CGAACAAGCTGAACTATTTCGGATAA |
| 831 | ATG-3929 | Mkhhhhhhvftlddfvgdweqtaaynldqvleqggvssllqnlavsvtpimrivrsgenalkidi hviipyeglsadqmaqieevfkvvypvddhhfkvilpygtlvidgvtpnklnyfg |
| 832 | ATG-3930 | atgAAACATCACCATCACCATCATgtcTTCACACTCGACGATTTC GTTGGGGACTGGGAACAGACAGCCGCCTACAACCTGGACCA AGTCCTTGAACAGGGAGGTGTGTCCAGTTTGCTGCAGAATCT CGCCGTGTCCGTAACTCCGATCATGAGGATTGTCCGGAGCGG TGAAAATGCCCTGAAGATCGACATCCATGTCATCATCCCGTA TGAAGGTCTGAGCGCCGACCAAATGGCCCAGATCGAAGAGG TGTTTAAGGTGGTGTACCCTGTGGATGATCATCACTTTAAGG TGATCCTGCCCTATGGCACACTGGTAATCGACGGGGTTACGC CGAACAAGCTGAACTATTTCGGACGGCCGTATGAAGGCATCG CCGTGTTCGACGGCTAA |
| 833 | ATG-3930 | Mkhhhhhhvftlddfvgdweqtaaynldqvleqggvssllqnlavsvtpimrivrsgenalkidi hviipyeglsadqmaqieevfkvvypvddhhfkvilpygtlvidgvtpnklnyfgrpyegiavfd g |
| 834 | ATG-3931 | atgAAACATCACCATCACCATCATgtcTTCACACTCGACGATTTC GTTGGGGACTGGGAACAGACAGCCGCCTACAACCTGGACCA AGTCCTTGAACAGGGAGGTGTGTCCAGTTTGCTGCAGAATCT CGCCGTGTCCGTAACTCCGATCATGAGGATTGTCCGGAGCGG TGAAAATGCCCTGAAGATCGACATCCATGTCATCATCCCGTA TGAAGGTCTGAGCGCCGACCAAATGGCCCAGATCGAAGAGG TGTTTAAGGTGGTGTACCCTGTGGATGATCATCACTTTAAGG TGATCCTGCCCTATGGCACACTGGTAATCGACGGGGTTACGC CGAACAAGCTGAACTATTTCGGACGGCCGTATGAAGGCATCG CCGTGTTCGACGGCAAAAAGATCACTACCACAGGGACCCTGT AA |
| 835 | ATG-3931 | Mkhhhhhhvftlddfvgdweqtaaynldqvleqggvssllqnlavsvtpimrivrsgenalkidi hviipyeglsadqmaqieevfkvvypvddhhfkvilpygtlvidgvtpnklnyfgrpyegiavfd gkkitttgtl |
| 836 | ATG-3932 | atgAAACATCACCATCACCATCATgtcTTCACACTCGACGATTTC GTTGGGGACTGGGAACAGACAGCCGCCTACAACCTGGACCA AGTCCTTGAACAGGGAGGTGTGTCCAGTTTGCTGCAGAATCT CGCCGTGTCCGTAACTCCGATCATGAGGATTGTCCGGAGCGG TGAAAATGCCCTGAAGATCGACATCCATGTCATCATCCCGTA TGAAGGTCTGAGCGCCGACCAAATGGCCCAGATCGAAGAGG TGTTTAAGGTGGTGTACCCTGTGGATGATCATCACTTTAAGG TGATCCTGCCCTATGGCACACTGGTAATCGACGGGGTTACGC CGAACAAGCTGAACTATTTCGGACGGCCGTATGAAGGCATCG CCGTGTTCGACGGCAAAAAGATCACTACCACAGGGACCCTGT GGAACGGCTAA |
| 837 | ATG-3932 | Mkhhhhhhvftlddfvgdweqtaaynldqvleqggvssllqnlavsvtpimrivrsgenalkidi hviipyeglsadqmaqieevfkvvypvddhhfkvilpygtlvidgvtpnklnyfgrpyegiavfd gkkitttgtlwng |

TABLE 1-continued

Exemplary peptide, dipeptide, and polypeptide sequences.

| SEQ ID NO | Name | Sequence |
|---|---|---|
| 838 | ATG-4808 | Atggtttccgtgagcggctggcggctgttcaagaagattagatcacactcgacgatttcgttgggga ctgggaacagacagccgcctacaacctggaccaagtccttgaacagggaggtgtgtccagtttgctg cagaatctcgccgtgtccgtaactccgatcatgaggattgtccggagcggtgaaaatgccctgaagat cgacatccatgtcatcatcccgtatgaaggtctgagcgccgaccaaatggcccagatcgaagaggtg tttaaggtggtgtaccctgtggatgatcatcactttaaggtgatcctgccctatggcacactggtaatcga cgggggttacgccgaacaagctgaactatttcggacggccgtatgaaggcatcgccgtgttcgacggc aaaaagatcactaccacagggaccctgtggaacggcaacaaaattatcgacgagcgcctgatcacc cccgactaa |
| 839 | ATG-4808 | Mvsvsgwrlfkkisftlddfvgdweqtaaynldqvleqggvssl|qnlaysvtpimrivrsgenal kidihviipyeglsadqmaqieevfkvvypvddhhfkvilpygtlvidgvtpnklnyfgrpyegi avfdgkkitttgtlwngnkiiderlitpd |
| 840 | ATG-4809 | Atggtttccgtgagcggctggcggctgttcaagaagattagcggcagctccggtttcacactcgacg atttcgttggggactgggaacagacagccgcctacaacctggaccaagtccttgaacagggaggtgt gtccagtttgctgcagaatctcgccgtgtccgtaactccgatcatgaggattgtccggagcggtgaaa atgccctgaagatcgacatccatgtcatcatcccgtatgaaggtctgagcgccgaccaaatggccca gatcgaagaggtgtttaaggtggtgtaccctgtggatgatcatcactttaaggtgatcctgccctatggc acactggtaatcgacgggggttacgccgaacaagctgaactatttcggacggccgtatgaaggcatcg ccgtgttcgacggcaaaaagatcactaccacagggaccctgtggaacggcaacaaaattatcgacg agcgcctgatcacccccgactaa |
| 841 | ATG-4809 | MVSVSGWRLFKKISGSSGFTLDDFVGDWEQTAAYNLDQVLEQ GGVSSLLQNLAVSVTPIMRIVRSGENALKIDIHVIIPYEGLSADQ MAQIEEVFKVVYPVDDHHFKVILPYGTLVIDGVTPNKLNYFGRP YEGIAVFDGKKITTTGTLWNGNKIIDERLITPD |
| 842 | ATG-4810 | Atggtttccgtgagcggctggcggctgttcaagaagattagcggctcgagcggtggctcgagcggtt tcacactcgacgatttcgttggggactgggaacagacagccgcctacaacctggaccaagtccttga acagggaggtgtgtccagtttgctgcagaatctcgccgtgtccgtaactccgatcatgaggattgtccg gagcggtgaaaatgccctgaagatcgacatccatgtcatcatcccgtatgaaggtctgagcgccgac caaatggcccagatcgaagaggtgtttaaggtggtgtaccctgtggatgatcatcactttaaggtgatc ctgccctatggcacactggtaatcgacgggggttacgccgaacaagctgaactatttcggacggccgt atgaaggcatcgccgtgttcgacggcaaaaagatcactaccacagggaccctgtggaacggcaaca aaattatcgacgagcgcctgatcacccccgactaa |
| 843 | ATG-4810 | MVSVSGWRLFKKISGSSGGSSGFTLDDFVGDWEQTAAYNLDQV LEQGGVSSLLQNLAVSVTPIMRIVRSGENALKIDIHVIIPYEGLSA DQMAQIEEVFKVVYPVDDHHFKVILPYGTLVIDGVTPNKLNYF GRPYEGIAVFDGKKITTTGTLWNGNKIIDERLITPD |
| 844 | ATG-4811 | Atggtttccgtgagcggctggcggctgttcaagaagattagcggctcgagcggtggctcgagcggt ggctcgagcggtttcacactcgacgatttcgttggggactgggaacagacagccgcctacaacctgg accaagtccttgaacagggaggtgtgtccagtttgctgcagaatctcgccgtgtccgtaactccgatca tgaggattgtccggagcggtgaaaatgccctgaagatcgacatccatgtcatcatcccgtatgaaggt ctgagcgccgaccaaatggcccagatcgaagaggtgtttaaggtggtgtaccctgtggatgatcatca ctttaaggtgatcctgccctatggcacactggtaatcgacgggggttacgccgaacaagctgaactattt cggacggccgtatgaaggcatcgccgtgttcgacggcaaaaagatcactaccacagggaccctgtg gaacggcaacaaaattatcgacgagcgcctgatcacccccgactaa |
| 845 | ATG-4811 | MVSVSGWRLFKKISGSSGGSSGGSSGFTLDDFVGDWEQTAAYN LDQVLEQGGVSSLLQNLAVSVTPIMRIVRSGENALKIDIHVIIPYE GLSADQMAQIEEVFKVVYPVDDHHFKVILPYGTLVIDGVTPNKL NYFGRPYEGIAVFDGKKITTTGTLWNGNKIIDERLITPD |
| 846 | ATG-4812 | Atggtttccgtgagcggctggcggctgttcaagaagattagcggctcgagcggtggctcgagcggt ggctcgagcggtggctcgagcggtttcacactcgacgatttcgttggggactgggaacagacagcc gcctacaacctggaccaagtccttgaacagggaggtgtgtccagtttgctgcagaatctcgccgtgtc cgtaactccgatcatgaggattgtccggagcggtgaaaatgccctgaagatcgacatccatgtcatca tcccgtatgaaggtctgagcgccgaccaaatggcccagatcgaagaggtgtttaaggtggtgtaccct gtggatgatcatcactttaaggtgatcctgccctatggcacactggtaatcgacgggggttacgccgaac aagctgaactatttcggacggccgtatgaaggcatcgccgtgttcgacggcaaaaagatcactacca cagggaccctgtggaacggcaacaaaattatcgacgagcgcctgatcacccccgactaa |
| 847 | ATG-4812 | MVSVSGWRLFKKISGSSGGSSGGSSGGSSGFTLDDFVGDWEQT AAYNLDQVLEQGGVSSLLQNLAVSVTPIMRIVRSGENALKIDIH VIIPYEGLSADQMAQIEEVFKVVYPVDDHHFKVILPYGTLVIDG VTPNKLNYFGRPYEGIAVFDGKKITTTGTLWNGNKIIDERLITPD |
| 848 | ATG-4813 | Atggtttccgtgagcggctggcggctgttcaagaagattagcggctcgagcggtggctcgagcggt ggctcgagcggtggctcgagcggtggctcgagcggtttcacactcgacgatttcgttggggactggg aacagacagccgcctacaacctggaccaagtccttgaacagggaggtgtgtccagtttgctgcagaa tctcgccgtgtccgtaactccgatcatgaggattgtccggagcggtgaaaatgccctgaagatcgaca tccatgtcatcatcccgtatgaaggtctgagcgccgaccaaatggcccagatcgaagaggtgtttaag |

TABLE 1-continued

Exemplary peptide, dipeptide, and polypeptide sequences.

| SEQ ID NO | Name | Sequence |
|---|---|---|
| | | gtggtgtaccctgtggatgatcatcactttaaggtgatcctgccctatggcacactggtaatcgacggg gttacgccgaacaagctgaactatttcggacggccgtatgaaggcatcgccgtgttcgacggcaaaa agatcactaccacagggaccctgtggaacggcaacaaaattatcgacgagcgcctgatcacccccg actaa |
| 849 | ATG-4813 | MVSVSGWRLFKKISGSSGGSSGGSSGGSSGGSSGFTLDDFVGD WEQTAAYNLDQVLEQGGVSSLLQNLAVSVTPIMRIVRSGENAL KIDIHVIIPYEGLSADQMAQIEEVFKVVYPVDDHHFKVILPYGTL VIDGVTPNKLNYFGRPYEGIAVFDGKKITTTGTLWNGNKIIDERL ITPD |
| 850 | ATG-4814 | Atggtgagcggctggcggctgttcaagaagattagcggctcgagcggtggctcgagcggtggctc gagcggtggctcgagcggtggctcgagcggtttcacactcgacgatttcgttgggggactgggaaca gacagccgcctacaacctggaccaagtccttgaacagggaggtgtgtccagtttgctgcagaatctc gccgtgtccgtaactccgatcatgaggattgtccggagcggtgaaaatgccctgaagatcgacatcc atgtcatcatcccgtatgaaggtctgagcgccgaccaaatggcccagatcgaagaggtgtttaaggtg gtgtaccctgtggatgatcatcactttaaggtgatcctgccctatggcacactggtaatcgacggggtta cgccgaacaagctgaactatttcggacggccgtatgaaggcatcgccgtgttcgacggcaaaaagat cactaccacagggaccctgtggaacggcaacaaaattatcgacgagcgcctgatcacccccgacta a |
| 851 | ATG-4814 | MVSGWRLFKKISGSSGGSSGGSSGGSSGGSSGFTLDDFVGDWE QTAAYNLDQVLEQGGVSSLLQNLAVSVTPIMRIVRSGENALKID IHVIIPYEGLSADQMAQIEEVFKVVYPVDDHHFKVILPYGTLVID GVTPNKLNYFGRPYEGIAVFDGKKITTTGTLWNGNKIIDERLITP D |
| 852 | ATG-4815 | Atggtcttcacactcgacgatttcgttgggggactgggaacagacagccgcctacaacctggaccaag tccttgaacagggaggtgtgtccagtttgctgcagaatctcgccgtgtccgtaactccgatcatgagga ttgtccggagcggtgaaaatgccctgaagatcgacatccatgtcatcatcccgtatgaaggtctgagc gccgaccaaatggcccagatcgaagaggtgtttaaggtggtgtaccctgtggatgatcatcactttaa ggtgatcctgccctatggcacactggtaatcgacggggtttcgtgagcggctggcggctgttcaa gaagattagctaa |
| 853 | ATG-4815 | MVFTLDDFVGDWEQTAAYNLDQVLEQGGVSSLLQNLAVSVTPI MRIVRSGENALKIDIHVIIPYEGLSADQMAQIEEVFKVVYPVDDH HFKVILPYGTLVIDGVTPNKLNYFGRPYEGIAVFDGKKITTTGTL WNGNKIIDERLITPDVSVSGWRLFKKIS |
| 854 | ATG-4816 | Atggtcttcacactcgacgatttcgttgggggactgggaacagacagccgcctacaacctggaccaag tccttgaacagggaggtgtgtccagtttgctgcagaatctcgccgtgtccgtaactccgatcatgagga ttgtccggagcggtgaaaatgccctgaagatcgacatccatgtcatcatcccgtatgaaggtctgagc gccgaccaaatggcccagatcgaagaggtgtttaaggtggtgtaccctgtggatgatcatcactttaa ggtgatcctgccctatggcacactggtaatcgacggggttacgccgaacaagctgaactatttcggac ggccgtatgaaggcatcgccgtgttcgacggcaaaaagatcactaccacagggaccctgtggaacg gcaacaaaattatcgacgagcgcctgatcacccccgacggctcgagcggtgtgtttccgtgagcggctg gcggctgttcaagaagattagctaa |
| 855 | ATG-4816 | MVFTLDDFVGDWEQTAAYNLDQVLEQGGVSSLLQNLAVSVTPI MRIVRSGENALKIDIHVIIPYEGLSADQMAQIEEVFKVVYPVDDH HFKVILPYGTLVIDGVTPNKLNYFGRPYEGIAVFDGKKITTTGTL WNGNKIIDERLITPDGSSGVSVSGWRLFKKIS |
| 856 | ATG-4817 | Atggtcttcacactcgacgatttcgttgggggactgggaacagacagccgcctacaacctggaccaag tccttgaacagggaggtgtgtccagtttgctgcagaatctcgccgtgtccgtaactccgatcatgagga ttgtccggagcggtgaaaatgccctgaagatcgacatccatgtcatcatcccgtatgaaggtctgagc gccgaccaaatggcccagatcgaagaggtgtttaaggtggtgtaccctgtggatgatcatcactttaa ggtgatcctgccctatggcacactggtaatcgacggggttacgccgaacaagctgaactatttcggac ggccgtatgaaggcatcgccgtgttcgacggcaaaaagatcactaccacagggaccctgtggaacg gcaacaaaattatcgacgagcgcctgatcacccccgacggctcgagcggtggctcgagcggtgtttc cgtgagcggctggcggctgttcaagaagattagctaa |
| 857 | ATG-4817 | MVFTLDDFVGDWEQTAAYNLDQVLEQGGVSSLLQNLAVSVTPI MRIVRSGENALKIDIHVIIPYEGLSADQMAQIEEVFKVVYPVDDH HFKVILPYGTLVIDGVTPNKLNYFGRPYEGIAVFDGKKITTTGTL WNGNKIIDERLITPDGSSGGSSGVSVSGWRLFKKIS |
| 858 | ATG-4818 | Atggtcttcacactcgacgatttcgttgggggactgggaacagacagccgcctacaacctggaccaag tccttgaacagggaggtgtgtccagtttgctgcagaatctcgccgtgtccgtaactccgatcatgagga ttgtccggagcggtgaaaatgccctgaagatcgacatccatgtcatcatcccgtatgaaggtctgagc gccgaccaaatggcccagatcgaagaggtgtttaaggtggtgtaccctgtggatgatcatcactttaa ggtgatcctgccctatggcacactggtaatcgacggggttacgccgaacaagctgaactatttcggac |

TABLE 1-continued

Exemplary peptide, dipeptide, and polypeptide sequences.

| SEQ ID NO | Name | Sequence |
|---|---|---| ggccgtatgaaggcatcgccgtgttcgacggcaaaaagatcactaccacagggaccctgtggaacg
gcaacaaaattatcgacgagcgcctgatcacccccgacggctcgagcggtggctcgagcggtgtga
gcggctggcggctgttcaagaagattagctaa 859  ATG-4818   MVFTLDDFVGDWEQTAAYNLDQVLEQGGVSSLLQNLAVSVTPI
MRIVRSGENALKIDIHVIIPYEGLSADQMAQIEEVFKVVYPVDDH
HFKVILPYGTLVIDGVTPNKLNYFGRPYEGIAVFDGKKITTTGTL
WNGNKIIDERLITPDGSSGGSSGVSGWRLFKKIS 860  ATG-4819   Atggtttccgtgagcggctggcggctgttcaagaagattagcttcacactcgacgatttcgttgggga
ctgggaacagacagccgcctacaacctggaccaagtccttgaacagggaggtgtgtccagtttgctg
cagaatctcgccgtgtccgtaactccgatcatgaggattgtccggagcggtgaaaatgccctgaagat
cgacatccatgtcatcatcccgtatgaaggtctgagcgccgaccaaatggcccagatcgaagaggtg
tttaaggtggtgtaccctgtggatgatcatcactttaaggtgatcctgccctatggcacactggtaatcga
cggggttacgccgaacaagctgaactatttcggacggccgtatgaaggcatcgccgtgttcgacggc
aaaaagatcactaccacagggaccctgtggaacggcaacaaaattatcgacgagcgcctgatcacc
cccgaccatcaccatcaccatcattaa 861  ATG-4819   MVSVSGWRLFKKISFTLDDFVGDWEQTAAYNLDQVLEQGGVS
SLLQNLAVSVTPIMRIVRSGENALKIDIHVIIPYEGLSADQMAQIE
EVFKVVYPVDDHHFKVILPYGTLVIDGVTPNKLNYFGRPYEGIA
VFDGKKITTTGTLWNGNKIIDERLITPDHHHHHH 862  ATG-4820   Atggtttccgtgagcggctggcggctgttcaagaagattagcggcagctccggtttcacactcgacg
atttcgttggggactgggaacagacagccgcctacaacctggaccaagtccttgaacagggaggtgt
gtccagtttgctgcagaatctcgccgtgtccgtaactccgatcatgaggattgtccggagcggtgaaa
atgccctgaagatcgacatccatgtcatcatcccgtatgaaggtctgagcgccgaccaaatggccca
gatcgaagaggtgtttaaggtggtgtaccctgtggatgatcatcactttaaggtgatcctgccctatggc
acactggtaatcgacggggttacgccgaacaagctgaactatttcggacggccgtatgaaggcatcg
ccgtgttcgacggcaaaaagatcactaccacagggaccctgtggaacggcaacaaaattatcgacg
agcgcctgatcacccccgaccatcaccatcaccatcattaa 863  ATG-4820   MVSVSGWRLFKKISGSSGFTLDDFVGDWEQTAAYNLDQVLEQ
GGVSSLLQNLAVSVTPIMRIVRSGENALKIDIHVIIPYEGLSADQ
MAQIEEVFKVVYPVDDHHFKVILPYGTLVIDGVTPNKLNYFGRP
YEGIAVFDGKKITTTGTLWNGNKIIDERLITPDHHHHHH 864  ATG-4821   Atggtttccgtgagcggctggcggctgttcaagaagattagcggctcgagcggtggctcgagcggtt
tcacactcgacgatttcgttggggactgggaacagacagccgcctacaacctggaccaagtccttga
acagggaggtgtgtccagtttgctgcagaatctcgccgtgtccgtaactccgatcatgaggattgtccg
gagcggtgaaaatgccctgaagatcgacatccatgtcatcatcccgtatgaaggtctgagcgccgac
caaatggcccagatcgaagaggtgtttaaggtggtgtaccctgtggatgatcatcactttaaggtgatc
ctgccctatggcacactggtaatcgacggggttacgccgaacaagctgaactatttcggacggccgt
atgaaggcatcgccgtgttcgacggcaaaaagatcactaccacagggaccctgtggaacggcaaca
aaattatcgacgagcgcctgatcacccccgaccatcaccatcaccatcattaa 865  ATG-4821   MVSVSGWRLFKKISGSSGGSSGFTLDDFVGDWEQTAAYNLDQV
LEQGGVSSLLQNLAVSVTPIMRIVRSGENALKIDIHVIIPYEGLSA
DQMAQIEEVFKVVYPVDDHHFKVILPYGTLVIDGVTPNKLNYF
GRPYEGIAVFDGKKITTTGTLWNGNKIIDERLITPDHHHHHH 866  ATG-4822   Atggtttccgtgagcggctggcggctgttcaagaagattagcggctcgagcggtggctcgagcggt
ggctcgagcggtttcacactcgacgatttcgttggggactgggaacagacagccgcctacaacctgg
accaagtccttgaacagggaggtgtgtccagtttgctgcagaatctcgccgtgtccgtaactccgatca
tgaggattgtccggagcggtgaaaatgccctgaagatcgacatccatgtcatcatcccgtatgaaggt
ctgagcgccgaccaaatggcccagatcgaagaggtgtttaaggtggtgtaccctgtggatgatcatca
ctttaaggtgatcctgccctatggcacactggtaatcgacggggttacgccgaacaagctgaactattt
cggacggccgtatgaaggcatcgccgtgttcgacggcaaaaagatcactaccacagggaccctgtg
gaacggcaacaaaattatcgacgagcgcctgatcacccccgaccatcaccatcaccatcattaa 867  ATG-4822   MVSVSGWRLFKKISGSSGGSSGGSSGFTLDDFVGDWEQTAAYN
LDQVLEQGGVSSLLQNLAVSVTPIMRIVRSGENALKIDIHVIIPYE
GLSADQMAQIEEVFKVVYPVDDHHFKVILPYGTLVIDGVTPNKL
NYFGRPYEGIAVFDGKKITTTGTLWNGNKIIDERLITPDHHHHH
H TABLE 1-continued Exemplary peptide, dipeptide, and polypeptide sequences.

| SEQ ID NO | Name | Sequence |
|---|---|---|
| 868 | ATG-4823 | Atggtttccgtgagcggctggcggctgttcaagaagattagcggctcgagcggtggctcgagcggt ggctcgagcggtggctcgagcggtttcacactcgacgatttcgttggggactgggaacagacagcc gcctacaacctggaccaagtccttgaacagggaggtgtgtccagtttgctgcagaatctcgccgtgtc cgtaactccgatcatgaggattgtccggagcggtgaaaatgccctgaagatcgacatccatgtcatca tcccgtatgaaggtctgagcgccgaccaaatggcccagatcgaagaggtgtttaaggtggtgtaccct gtggatgatcatcactttaaggtgatcctgccctatggcacactggtaatcgacggggttacgccgaac aagctgaactatttcggacggccgtatgaaggcatcgccgtgttcgacggcaaaaagatcactacca cagggaccctgtggaacggcaacaaaattatcgacgagcgcctgatcacccccgaccatcaccatc accatcattaa |
| 869 | ATG-4823 | MVSVSGWRLFKKISGSSGGSSGGSSGGSSGFTLDDFVGDWEQT AAYNLDQVLEQGGVSSLLQNLAVSVTPIMRIVRSGENALKIDIH VIIPYEGLSADQMAQIEEVFKVVYPVDDHHFKVILPYGTLVIDG VTPNKLNYFGRPYEGIAVFDGKKITTTGTLWNGNKIIDERLITPD HHHHHH |
| 870 | ATG-4824 | Atggtgagcggctggcggctgttcaagaagattagcggctcgagcggtggctcgagcggtggctc gagcggtggctcgagcggtggctcgagcggtttcacactcgacgatttcgttggggactgggaaca gacagccgcctacaacctggaccaagtccttgaacagggaggtgtgtccagtttgctgcagaatctc gccgtgtccgtaactccgatcatgaggattgtccggagcggtgaaaatgccctgaagatcgacatcc atgtcatcatcccgtatgaaggtctgagcgccgaccaaatggcccagatcgaagaggtgtttaaggtg gtgtaccctgtggatgatcatcactttaaggtgatcctgccctatggcacactggtaatcgacggggtta cgccgaacaagctgaactatttcggacggccgtatgaaggcatcgccgtgttcgacggcaaaaagat cactaccacagggaccctgtggaacggcaacaaaattatcgacgagcgcctgatcacccccgacca tcaccatcaccatcattaa |
| 871 | ATG-4824 | MVSGWRLFKKISGSSGGSSGGSSGGSSGGSSGFTLDDFVGDWE QTAAYNLDQVLEQGGVSSLLQNLAVSVTPIMRIVRSGENALKID IHVIIPYEGLSADQMAQIEEVFKVVYPVDDHHFKVILPYGTLVID GVTPNKLNYFGRPYEGIAVFDGKKITTTGTLWNGNKIIDERLITP DHHHHHH |
| 872 | ATG-4825 | Atggtttccgtgagcggctggcggctgttcaagaagattagcggctcgagcggtggctcgagcggt ggctcgagcggtggctcgagcggtttcacactcgacgatttcgttggggactgggaacagacagccgcctacaacctggaccaagtccttgaacagggaggtgtgtccagtttgctgcagaatctcgccgtgtccgtaactccgatcatgaggattgtccggagcggtgaaaatgccctgaagatcgacatccatgtcatcatcccgtatgaaggtctgagcgccgaccaaatggcccagatcgaagaggtgtttaaggtggtgtaccctgtggatgatcatcactttaaggtgatcctgccctatggcacactggtaatcgacgggggttacgccgaacaagctgaactatttcggacggccgtatgaaggcatcgccgtgttcgacggcaaaaagatcactaccacagggaccctgtggaacggcaacaaaattatcgacgagcgcctgatcacccccgaccatcaccatcaccatcattaa |
| 873 | ATG-4825 | MVSVSGWRLFKKISGSSGGSSGGSSGGSSGGSSGFTLDDFVGD WEQTAAYNLDQVLEQGGVSSLLQNLAVSVTPIMRIVRSGENAL KIDIHVIIPYEGLSADQMAQIEEVFKVVYPVDDHHFKVILPYGTL VIDGVTPNKLNYFGRPYEGIAVFDGKKITTTGTLWNGNKIIDERL ITPDHHHHHH |
| 874 | ATG-4826 | Atgaaacatcaccatcaccatcatgtcttcacactcgacgatttcgttggggactgggaacagacagc cgcctacaacctggaccaagtccttgaacagggaggtgtgtccagtttgctgcagaatctcgccgtgt ccgtaactccgatcatgaggattgtccggagcggtgaaaatgccctgaagatcgacatccatgtcatc atcccgtatgaaggtctgagcgccgaccaaatggcccagatcgaagaggtgtttaaggtggtgtacc ctgtggatgatcatcactttaaggtgatcctgccctatggcacactggtaatcgacggggttacgccga acaagctgaactatttcggacggccgtatgaaggcatcgccgtgttcgacggcaaaaagatcactac cacagggaccctgtggaacggcaacaaaattatcgacgagcgcctgatcacccccgacgtttccgtg agcggctggcggctgttcaagaagattagctaa |
| 875 | ATG-4826 | MKHHHHHHVFTLDDFVGDWEQTAAYNLDQVLEQGGVSSLLQ NLAVSVTPIMRIVRSGENALKIDIHVIIPYEGLSADQMAQIEEVFK VVYPVDDHHFKVILPYGTLVIDGVTPNKLNYFGRPYEGIAVFDG KKITTTGTLWNGNKIIDERLITPDVSVSGWRLFKKIS |
| 876 | ATG-4827 | Atgaaacatcaccatcaccatcatgtcttcacactcgacgatttcgttggggactgggaacagacagc cgcctacaacctggaccaagtccttgaacagggaggtgtgtccagtttgctgcagaatctcgccgtgt ccgtaactccgatcatgaggattgtccggagcggtgaaaatgccctgaagatcgacatccatgtcatc atcccgtatgaaggtctgagcgccgaccaaatggcccagatcgaagaggtgtttaaggtggtgtacc ctgtggatgatcatcactttaaggtgatcctgccctatggcacactggtaatcgacggggttacgccga acaagctgaactatttcggacggccgtatgaaggcatcgccgtgttcgacggcaaaaagatcactac cacagggaccctgtggaacggcaacaaaattatcgacgagcgcctgatcacccccgacggctcga gcggtgtttccgtgagcggctggcggctgttcaagaagattagctaa |

TABLE 1-continued

Exemplary peptide, dipeptide, and polypeptide sequences.

| SEQ ID NO | Name | Sequence |
|---|---|---|
| 877 | ATG-4827 | MKHHHHHHVFTLDDFVGDWEQTAAYNLDQVLEQGGVSSLLQ<br>NLAVSVTPIMRIVRSGENALKIDIHVIIPYEGLSADQMAQIEEVFK<br>VVYPVDDHHFKVILPYGTLVIDGVTPNKLNYFGRPYEGIAVFDG<br>KKITTTGTLWNGNKIIDERLITPDGSSGVSVSGWRLFKKIS |
| 878 | ATG-4828 | Atgaaacatcaccatcaccatcatgtcttcacactcgacgatttcgttggggactgggaacagacagc<br>cgcctacaacctggaccaagtccttgaacagggaggtgtgtccagtttgctgcagaatctcgccgtgt<br>ccgtaactccgatcatgaggattgtccggagcggtgaaaatgccctgaagatcgacatccatgtcatc<br>atcccgtatgaaggtctgagcgccgaccaaatggcccagatcgaagaggtgtttaaggtggtgtacc<br>ctgtggatgatcatcactttaaggtgatcctgccctatggcacactggtaatcgacgggttacgccga<br>acaagctgaactatttcggacggccgtatgaaggcatcgccgtgttcgacggcaaaaagatcactac<br>cacagggaccctgtggaacggcaacaaaattatcgacgagcgcctgatcaccccgacggctcga<br>gcggtggctcgagcggtgtgagcggctggcggctgttcaagaagattagctaa |
| 879 | ATG-4828 | MKHHHHHHVFTLDDFVGDWEQTAAYNLDQVLEQGGVSSLLQ<br>NLAVSVTPIMRIVRSGENALKIDIHVIIPYEGLSADQMAQIEEVFK<br>VVYPVDDHHFKVILPYGTLVIDGVTPNKLNYFGRPYEGIAVFDG<br>KKITTTGTLWNGNKIIDERLITPDGSSGGSSGVSGWRLFKKIS |
| 880 | ATG-4829 | Atgaaacatcaccatcaccatcatgtcttcacactcgacgatttcgttggggactgggaacagacagc<br>cgcctacaacctggaccaagtccttgaacagggaggtgtgtccagtttgctgcagaatctcgccgtgt<br>ccgtaactccgatcatgaggattgtccggagcggtgaaaatgccctgaagatcgacatccatgtcatc<br>atcccgtatgaaggtctgagcgccgaccaaatggcccagatcgaagaggtgtttaaggtggtgtacc<br>ctgtggatgatcatcactttaaggtgatcctgccctatggcacactggtaatcgacgggttacgccga<br>acaagctgaactatttcggacggccgtatgaaggcatcgccgtgttcgacggcaaaaagatcactac<br>cacagggaccctgtggaacggcaacaaaattatcgacgagcgcctgatcaccccgacggctcga<br>gcggtggctcgagcggtgtttccgtgagcggctggcggctgttcaagaagattagctaa |
| 881 | ATG-4829 | MKHHHHHHVFTLDDFVGDWEQTAAYNLDQVLEQGGVSSLLQ<br>NLAVSVTPIMRIVRSGENALKIDIHVIIPYEGLSADQMAQIEEVFK<br>VVYPVDDHHFKVILPYGTLVIDGVTPNKLNYFGRPYEGIAVFDG<br>KKITTTGTLWNGNKIIDERLITPDGSSGGSSGVSVSGWRLFKKIS |
| 882 | ATG-2623 | atggtcttcacactcgaagatttcgttggggactgggaacagacagccgcctacaacctggaccaagt<br>ccttgaacagggaggtgtgtccagtttgctgcagaatctcgccgtgtccgtaactccgatccaaaggat<br>tgtccggagcggtgaaaatgccctgaagatcgacatccatgtcatcatcccgtatgaaggtctgagcg<br>ccgaccaaatggcccagatcgaagaggtgtttaaggtggtgtaccctgtggatgatcatcactttaag<br>gtgatcctgccctatggcacactggtaatcgacgggggttacgccgaacatgctgaactatttcggacg<br>gccgtatgaaggcatcgccgtgttcgacggcaaaaagatcactgtaacagggaccctgtggaacgg<br>caacaaaattatcgacgagcgcctgatcaccccgacggctccatgctgttccgagtaaccatcaaca<br>gccatcatcaccatcaccactaa |
| 883 | ATG-2623 | MVFTLEDFVGDWEQTAAYNLDQVLEQGGVSSLLQNLAVSVTPI<br>QRIVRSGENALKIDIHVIIPYEGLSADQMAQIEEVFKVVYPVDDH<br>HFKVILPYGTLVIDGVTPNMLNYFGRPYEGIAVFDGKKITVTGT<br>LWNGNKIIDERLITPDGSMLFRVTINSHHHHHH |
| 884 | ATG-3745 | atggtgagcggctggcggctgttcaagaagattagccaccatcaccatcaccatcatcacttcacact<br>cgacgatttcgttggggactgggaacagacagccgcctacaacctggaccaagtccttgaacaggg<br>aggtgtgtccagtttgctgcagaatctcgccgtgtccgtaactccgatcatgaggattgtccggagcgg<br>tgaaaatgccctgaagatcgacatccatgtcatcatcccgtatgaaggtctgagcgccgaccaaatgg<br>cccagatcgaagaggtgtttaaggtggtgtaccctgtggatgatcatcactttaaggtgatcctgcccta<br>tggcacactggtaatcgacgggggttacgccgaacaagctgaactatttcggacggccgtatgaaggc<br>atcgccgtgttcgacggcaaaaagatcactaccacagggaccctgtggaacggcaacaaaattatcg<br>acgagcgcctgatcaccccgactaa |
| 885 | ATG-3745 | MVSGWRLFKKISHHHHHHHHFTLDDFVGDWEQTAAYNLDQVL<br>EQGGVSSLLQNLAVSVTPIMRIVRSGENALKIDIHVIIPYEGLSAD<br>QMAQIEEVFKVVYPVDDHHFKVILPYGTLVIDGVTPNKLNYFG<br>RPYEGIAVFDGKKITTTGTLWNGNKIIDERLITPD |
| 886 | ATG-3746 | atgaaacatcaccatcaccatcatgtgagcggctggcggctgttcaagaagattagcggcagctccg<br>gtttcacactcgacgatttcgttggggactgggaacagacagccgcctacaacctggaccaagtcctt<br>gaacagggaggtgtgtccagtttgctgcagaatctcgccgtgtccgtaactccgatcatgaggattgtc<br>cggagcggtgaaaatgccctgaagatcgacatccatgtcatcatcccgtatgaaggtctgagcgccg<br>accaaatggcccagatcgaagaggtgtttaaggtggtgtaccctgtggatgatcatcactttaaggtga<br>tcctgccctatggcacactggtaatcgacgggggttacgccgaacaagctgaactatttcggacggcc<br>gtatgaaggcatcgccgtgttcgacggcaaaaagatcactaccacagggaccctgtggaacggcaa<br>caaaattatcgacgagcgcctgatcaccccgactaa |
| 887 | ATG-3746 | MKHHHHHHVSGWRLFKKISGSSGFTLDDFVGDWEQTAAYNLD<br>QVLEQGGVSSLLQNLAVSVTPIMRIVRSGENALKIDIHVIIPYEGL<br>SADQMAQIEEVFKVVYPVDDHHFKVILPYGTLVIDGVTPNKLN<br>YFGRPYEGIAVFDGKKITTTGTLWNGNKIIDERLITPD |

TABLE 1-continued

Exemplary peptide, dipeptide, and polypeptide sequences.

| SEQ ID NO | Name | Sequence |
|---|---|---|
| 888 | ATG-4632 | atggtgagcggctggcggctgttcaagaagattagcggcagctccggtttccacactcgacgatttcgtt ggggactgggaacagacagccgcctacaacctggaccaagtccttgaacagggaggtgtgtccagt ttgctgcagaatctcgccgtgtccgtaactccgatcatgaggattgtccggagcggtgaaaatgccct gaagatcgacatccatgtcatcatcccgtatgaaggtctgagcgccgaccaaatggcccagatcgaa gaggtgtttaaggtggtgtaccctgtggatgatcatcactttaaggtgatcctgccctatggcacactgg taatcgacgggggttacgccgaacaagctgaactatttcggacggccgtatgaaggcatcgccgtgttc gacggcaaaaagatcactaccacagggaccctgtggaacggcaacaaaattatcgacgagcgcct gatcacccccgaccatcaccatcaccatcattaa |
| 889 | ATG-4632 | MVSGWRLFKKISGSSGFTLDDFVGDWEQTAAYNLDQVLEQGG VSSLLQNLAVSVTPIMRIVRSGENALKIDIHVIIPYEGLSADQMA QIEEVFKVVYPVDDHHFKVILPYGTLVIDGVTPNKLNYFGRPYE GIAVFDGKKITTTGTLWNGNKIIDERLITPDHHHHHH |
| 890 | ATG-2757 | atggtcttcacactcgaagatttcgttggggactgggaacagacagccgcctacaacctggaccaagt ccttgaacagggaggtgtgtccagtttgctgcagaatctcgccgtgtccgtaactccgatccaaaggat tgtccggagcggtgaaaatgccctgaagatcgacatccatgtcatcatcccgtatgaaggtctgagcg ccgaccaaatggcccagatcgaagaggtgtttaaggtggtgtaccctgtggatgatcatcactttaag gtgatcctgccctatggcacactggtaatcgacgggggttacgccgaacatgctgaactatttcggacg gccgtatgaaggcatcgccgtgttcgacggcaaaaagatcactgtaacagggaccctgtggaacga gaacaaaattatcgacgagcgcctgatcacccccgacggctccatgctgttccgagtaaccatcaac agccatcatcaccatcacccactaa |
| 891 | ATG-2757 | MVFTLEDFVGDWEQTAAYNLDQVLEQGGVSSLLQNLAVSVTPI QRIVRSGENALKIDIHVIIPYEGLSADQMAQIEEVFKVVYPVDDH HFKVILPYGTLVIDGVTPNMLNYFGRPYEGIAVFDGKKITVTGT LWNENKIIDERLITPDGSMLFRVTINSHHHHHH |
| 892 | ATG-2760 | atggtcttcacactcgaagatttcgttggggactgggaacagacagccgcctacaacctggaccaagt ccttgaacagggaggtgtgtccagtttgctgcagaatctcgccgtgtccgtaactccgatccaaaggat tgtccggagcggtgaaaatgccctgaagatcgacatccatgtcatcatcccgtatgaaggtctgagcg ccgaccaaatggcccagatcgaagaggtgtttaaggtggtgtaccctgtggatgatcatcactttaag gtgatcctgccctatggcacactggtaatcgacgggggttacgccgaacatgctgaactatttcggacg gccgtatgaaggcatcgccgtgttcgacggcaaaaagatcactgtaacagggaccctgtggaacgg cgttaaaaattatcgacgagcgcctgatcacccccgacggctccatgctgttccgagtaaccatcaaca gccatcatcaccatcaccactaa |
| 893 | ATG-2760 | MVFTLEDFVGDWEQTAAYNLDQVLEQGGVSSLLQNLAVSVTPI QRIVRSGENALKIDIHVIIPYEGLSADQMAQIEEVFKVVYPVDDH HFKVILPYGTLVIDGVTPNMLNYFGRPYEGIAVFDGKKITVTGT LWNGVKIIDERLITPDGSMLFRVTINSHHHHHH |
| 894 | ATG-3882 | atggtcttcacactcgaagatttcgttggggactgggaacagacagccgcctacaacctggaccaagt ccttgaacagggaggtgtgtccagtttgctgcagaatctcgccgtgtccgtaactccgatccaaaggat ggtccggagcggtgaaaatgccctgaagatcgacatccatgtcatcatcccgtatgaaggtctgagc gccgaccaaatggcccagatcgaagaggtgtttaaggtggtgtaccctgtggatgatcatcactttaa ggtgatcctgccctatggcacactggtaatcgacgggggttacgccgaacatgctgaactatttcggac ggccgtatgaaggcatcgccgtgttcgacggcaaaaagatcactgtaacagggaccctgtggaacg gcaacaaaattatcgacgagcgcctgatcacccccgacggctccatgctgttccgagtaaccatcaa cagccatcatcaccatcaccactaa |
| 895 | ATG-3882 | MVFTLEDFVGDWEQTAAYNLDQVLEQGGVSSLLQNLAVSVTPI QRMVRSGENALKIDIHVIIPYEGLSADQMAQIEEVFKVVYPVDD HHFKVILPYGTLVIDGVTPNMLNYFGRPYEGIAVFDGKKITVTG TLWNGNKIIDERLITPDGSMLFRVTINSHHHHHH |
| 896 | ATG-3901 | atggtcttcacactcgaagatttcgttggggactggaagcagacagccgcctacaacctggaccaagt ccttgaacagggaggtgtgtccagtttgctgcagaatctcgccgtgtccgtaactccgatccaaaggat ggtccggagcggtgaaaatgccctgaagatcgacatccatgtcatcatcccgtatgaaggtctgagc gccgaccaaatggcccagatcgaagaggtgtttaaggtggtgtaccctgtggatgatcatcactttaa ggtgatcctgccctatggcacactggtaatcgacgggggttacgccgaacatgctgaactatttcggac ggccgtatgaaggcatcgccgtgttcgacggcaaaaagatcactgtaacagggaccctgtggaacg gcaacaaaattatcgacgagcgcctgatcacccccgacggctccatgctgttccgagtaaccatcaa cagccatcatcaccatcaccactaa |
| 897 | ATG-3901 | MVFTLEDFVGDWKQTAAYNLDQVLEQGGVSSLLQNLAVSVTPI QRMVRSGENALKIDIHVIIPYEGLSADQMAQIEEVFKVVYPVDD HHFKVILPYGTLVIDGVTPNMLNYFGRPYEGIAVFDGKKITVTG TLWNGNKIIDERLITPDGSMLFRVTINSHHHHHH |
| 898 | ATG-3945 | atggtcttcacactcgaagatttcgttggggactggaagcagacagccgcctacaacctggaccaagt ccttgaacagggaggtgtgtccagtttgctgcagaatctcgccgtgtccgtaactccgatccaaaggat ggtccggagcggtgaaaatgccctgaagatcgacatccatgtcatcatcccgtatgaaggtctgagc |

TABLE 1-continued

Exemplary peptide, dipeptide, and polypeptide sequences.

| SEQ ID NO | Name | Sequence |
|---|---|---|
| | | gccgaccaaatggcccagatcgaagaggtgtttaaggtggtgtaccctgtggatgatcatcactttaa ggtgatcctgccctatggcacactggtaatcgacgggttacgccgaacatgctgaactatttcggac ggccgtatgaaggcatcgccgtgttcgacggcaaaaagatcactgtaacagggaccctgtggaacg acgtcaaaattatcgacgagcgcctgatcacccccgacggctccatgctgttccgagtaaccatcaac agccatcataccatcaccactaa |
| 899 | ATG-3945 | MVFTLEDFVGDWKQTAAYNLDQVLEQGGVSSLLQNLAVSVTPI QRMVRSGENALKIDIHVIIPYEGLSADQMAQIEEVFKVVYPVDD HHFKVILPYGTLVIDGVTPNMLNYFGRPYEGIAVFDGKKITVTG TLWNDVKIIDERLITPDGSMLFRVTINSHHHHHH |
| 890 | ATG-3984 | atggtcttcacactcgaagatttcgttgggggactggaagcagacagccgcctacaacctggaccaagt ccttgaacagggaggtgtgtccagtttgctgcagaatctcgccgtgtccgtaactccgatccaaaggat ggtccggagcggtgaaaatgccctgaagatcgacatccatgtcatcatcccgtatgaaggtctgagc gccgaccaaatggcccagatcgaagaggtgtttaaggtggtgtaccctgtggatgatcatcactttaa ggtgatcctgccctatggcacactggtaatcgacgggttacgccgaacatgctgaactatttcggac ggccgtatgaaggcatcgccgtgttcgacggcaaaaagatcactgtaacagggaccctgtggaacg acgtcaaaattatcgacgagcgcctgatcacccccgacggctccatgtccttccgagtaaccatcaac agccatcataccatcaccactaa |
| 891 | ATG-3984 | MVFTLEDFVGDWKQTAAYNLDQVLEQGGVSSLLQNLAVSVTPI QRMVRSGENALKIDIHVIIPYEGLSADQMAQIEEVFKVVYPVDD HHFKVILPYGTLVIDGVTPNMLNYFGRPYEGIAVFDGKKITVTG TLWNDVKIIDERLITPDGSMSFRVTINSHHHHHH |
| 892 | ATG-4147 | atggtcttcacactcgaagatttcgttgggggactggaagcagacagccgcctacaacctggaccaagt ccttgaacagggaggtgtgtccagtttgctgcagaatctcgccgtgtccgtaactccgatccaaaggat ggtccggagcggtgaaaatgccctgaagatcgacatccatgtcatcatcccgtatgaaggtctgagc gccgaccaaatggcccagatcgaagaggtgtttaaggtggtgtaccctgtggatgatcatcactttaa ggtgatcctgccctatggcacactggtaatcgacgggttacgccgaacatgctgaactatttcggac ggccgtatgaaggcatcgccgtgttcgacggcaaaaagatcactgtaacagggaccctgtggaacg gcaacaaaattatcgacgagcgcctgatcacccccgacggctccatgtccttccgagtaaccatcaac agccatcataccatcaccactaa |
| 893 | ATG-4147 | MVFTLEDFVGDWKQTAAYNLDQVLEQGGVSSLLQNLAVSVTPI QRMVRSGENALKIDIHVIIPYEGLSADQMAQIEEVFKVVYPVDD HHFKVILPYGTLVIDGVTPNMLNYFGRPYEGIAVFDGKKITVTG TLWNGNKIIDERLITPDGSMSFRVTINSHHHHHH |
| 894 | ATG-4166 | atggtcttcacactcgaagatttcgttgggggactggaagcagacagccgcctacaacctggaccaagt ccttgaacagggaggtgtgtccagtttgctgcagaatctcgccgtgtccgtaactccgatccaaaggat ggtccggagcggtgaaaatgccctgaagatcgacatccatgtcatcatcccgtatgaaggtctgagc gccgaccaaatggcccagatcgaagaggtgtttaaggtggtgtaccctgtggatgatcatcactttaa ggtgatcctgccctatggcacactggtaatcgacgggttacgccgaacatgctgaactatttcggac ggccgtatgaaggcatcgccgtgttcgacggcaaaaagatcactgtaacagggaccctgtggaacg gcgtcaaaattatcgacgagcgcctgatcacccccgacggctccatgtccttccgagtaaccatcaac agccatcataccatcaccactaa |
| 895 | ATG-4166 | MVFTLEDFVGDWKQTAAYNLDQVLEQGGVSSLLQNLAVSVTPI QRMVRSGENALKIDIHVIIPYEGLSADQMAQIEEVFKVVYPVDD HHFKVILPYGTLVIDGVTPNMLNYFGRPYEGIAVFDGKKITVTG TLWNGVKIIDERLITPDGSMSFRVTINSHHHHHH |

TABLE 9

Exemplary peptide sequences.

| Pep ID | SEQ ID NO. | Sequence |
|---|---|---|
| 86 | 824 | VSGWRLFKKIS |
| 229 | 825 | VSGWRLFKKI |
| 289 | 826 | VSVSGWRLFKKIS |
| 521 | 827 | GKMLFRVTINSWK |
| 543 | 366 | WNGNKIIDERLITPD |
| 544 | 367 | KKITTTGTLWNGR |

TABLE 9-continued

Exemplary peptide sequences.

| Pep ID | SEQ ID NO. | Sequence |
|---|---|---|
| 545 | 368 | RPYEGIAVFDGK |
| 591 | 369 | GKMLFRVTIWKVSVSGWRLFKKIS |
| 592 | 370 | GKMLFRVTIWKVSGWRLFKKIS |
| 593 | 371 | GSMKFRVTINSWKVSVSGWRLFKKIS |
| 594 | 372 | GSMKFRVTINSWKVSGWRLFKKIS |

TABLE 9-continued

Exemplary peptide sequences.

| Pep ID | SEQ ID NO. | Sequence |
|---|---|---|
| 595 | 373 | GSMKFRVTINSWKNVTGYRLFKKISN |
| 596 | 374 | GSMKFRVTINSWKVTGYRLFEKIS |
| 597 | 375 | GSMKFRVTIWKVSVSGWRLFKKIS |
| 598 | 376 | GSMKFRVTIWKVSGWRLFKKIS |
| 599 | 377 | GRMLFRVTINSWKVSVSGWRLFKKIS |
| 600 | 378 | GRMLFRVTINSWKVSGWRLFKKIS |
| 601 | 379 | GRMLFRVTIWKVSVSGWRLFKKIS |
| 602 | 380 | GRMLFRVTIWKVSGWRLFKKIS |
| 603 | 381 | GSMLFRVTINSVSVSGWRLFKKIS |
| 604 | 382 | GSMLFKVTINSVSGWRLFKKIS |
| 605 | 383 | GSMLFQVTINSVSGWRLFKKIS |
| 606 | 384 | GSMLFEVTINSVSGWRLFKKIS |
| 607 | 385 | GSMLFNVTINSVSGWRLFKKIS |
| 608 | 386 | GRPYEGIAVFDGKKITTTGTL |
| 609 | 387 | GSMKFRVTINSWKVTGYRLFEKES |
| 610 | 388 | GSMKFRVTINSWKVEGYRLFEKIS |
| 611 | 389 | KKITTTGTLWNGNKIIDERLITPD |
| 612 | 390 | WNGNKIIDERLITPDGSMLFRVTINS |
| 671 | 391 | GKMLFRVTIQKWK |
| 668 | 392 | GKMLFRVTIGKWK |
| 727 | 393 | GKMLFRVTIGRWK |
| 669 | 394 | GKMLFRVTIGNWK |
| 674 | 395 | GKMLFRVTIQNWK |
| 702 | 396 | GKMLFRVTIDKWK |
| 703 | 397 | GKMLFRVTIEKWK |
| 705 | 810 | EKMLFRVTIESWK |
| 724 | 811 | EKLLFRVTIESWK |
| 725 | 812 | EKLLFRVTIESYK |
| 730 | 398 | GKMLFRVTIERWK |
| 731 | 399 | GKMLFRVTIDRWK |
| 738 | 400 | DKMLFRVTIQKWK |
| 739 | 401 | DKMLFRVTIGKWK |
| 848 | 402 | DKMLFRVTIGRWK |
| 740 | 403 | DKMLFRVTIGNWK |
| 741 | 404 | DKMLFRVTIQNWK |
| 732 | 405 | DKMLFRVTIDKWK |
| 742 | 406 | DKMLFRVTIEKWK |
| 735 | 407 | DKMLFRVTIERWK |

TABLE 9-continued

Exemplary peptide sequences.

| Pep ID | SEQ ID NO. | Sequence |
|---|---|---|
| 733 | 408 | DKMLFRVTIDRWK |
| 759 | 816 | DKLLFTVTIEKYK |
| 798 | 409 | RPYEGIAVFDGKKITVTGTLWNGNKIIDERLITPD |
| 849 | 410 | EKMLFRVTIQKWK |
| 708 | 411 | EKMLFRVTIGKWK |
| 709 | 412 | EKMLFRVTIGRWK |
| 775 | 413 | DKMLFTVTIQKVSGWRLFKKIS |
| 788 | 414 | DKLLFTVTIEKVSGWRLFKKIS |
| 789 | 415 | DKLLFTVTIEKWKVSGWRLFKKIS |
| 790 | 416 | DKLLFTVTIEKYKVSGWRLFKKIS |
| 792 | 417 | DKLLFTVTIEKYKVSVSGWRLFKKIS |
| 795 | 418 | KKMLFRVTIQKVSGWRLFKKIS |
| 797 | 419 | KKMLFRVTIQKWKVSVSGWRLFKKIS |
| 796 | 420 | KKMLFRVTIQKWKVSGWRLFKKIS |
| 804 | 421 | DKLLFTVTIGKVSGWRLFKKIS |
| 805 | 422 | DKLLFTVTIGKYKVSGWRLFKKIS |
| 806 | 423 | DKLLFTVTIGKYKVSVSGWRLFKKIS |
| 807 | 424 | DKLLFTVTIGKWKVSVSGWRLFKKIS |
| 808 | 425 | DKLLFTVTIQKVSGWRLFKKIS |
| 813 | 426 | KKMLFTVTIQKVSGWRLFKKIS |
| 816 | 427 | KKLLFRVTIQKVSGWRLFKKIS |
| 825 | 428 | DKLLFTVTIEKVSGWRLFKKI |
| 826 | 429 | DKLLFTVTIEKYKVSVSGWRLFKKI |
| 827 | 430 | DRLLFTVTIERVSGWRLFKKIS |
| 831 | 431 | EKLLFTVTIEKVSGWRLFKKIS |
| 832 | 432 | KKLLFTVTIGKVSGWRLFKKIS |
| 833 | 433 | GSMRFRVTINSWRVTGYRLFERES |
| 834 | 434 | GSMKFRVTINSVTGYRLFEKES |
| 844 | 435 | KKITTTGTLWNGNKIID |
| 845 | 436 | ERLITPDGSMLFRVTINSVSGWRLFKKIS |
| 846 | 437 | GRPYEGIAVDFGKKITTTGTLWNGNKIIDERLITPDGSMLFRVTINSVSGWRLFKKIS |
| 847 | 438 | GVTPNKLNYFGRPYEGIAVDFGKKITTTGTLWNGNKIIDERLITPDGSMLFRVTINSVSGWRLFKKIS |
| 850 | 439 | EKMLFRVTIGNWK |
| 851 | 440 | EKMLFRVTIQNWK |
| 706 | 441 | EKMLFRVTIDKWK |
| 707 | 442 | EKMLFRVTIEKWK |

193

TABLE 9-continued

Exemplary peptide sequences.

| Pep ID | SEQ ID NO. | Sequence |
|---|---|---|
| 737 | 443 | EKMLFRVTIERWK |
| 736 | 444 | EKMLFRVTIDRWK |
| 760 | 445 | KKMLFRVTIQKWK |
| 852 | 446 | KKMLFRVTIGKWK |
| 853 | 447 | KKMLFRVTIGRWK |
| 854 | 448 | KKMLFRVTIGNWK |
| 855 | 449 | KKMLFRVTIQNWK |
| 856 | 450 | KKMLFRVTIDKWK |
| 857 | 451 | KKMLFRVTIEKWK |
| 858 | 452 | KKMLFRVTIERWK |
| 859 | 453 | KKMLFRVTIDRWK |
| 860 | 454 | RKMLFRVTIQKWK |
| 861 | 455 | RKMLFRVTIGKWK |
| 862 | 456 | RKMLFRVTIGRWK |
| 863 | 457 | RKMLFRVTIGNWK |
| 864 | 458 | RKMLFRVTIQNWK |
| 865 | 459 | RKMLFRVTIDKWK |
| 866 | 460 | RKMLFRVTIEKWK |
| 867 | 461 | RKMLFRVTIERWK |
| 868 | 462 | RKMLFRVTIDRWK |
| 656 | 463 | EQMLFRVTINSWK |
| 869 | 464 | SRMLFRVTINSWK |
| 533 | 465 | GEMLFRVTINSWK |
| 690 | 466 | GKMKFRVTINSWK |
| 678 | 467 | GKMLFRVKINSWK |
| 679 | 468 | GKMLFRVRINSWK |
| 681 | 469 | GKMLFRVDINSWK |
| 663 | 470 | GKMLFRVTIDSWK |
| 743 | 471 | GKMLFRVTINKWK |
| 714 | 472 | EKMLFKVTIQKWK |
| 870 | 473 | EKMLFTVTIQKWK |
| 871 | 474 | EKMLFKVTIDKWK |
| 872 | 475 | EKMLFTVTIDKWK |
| 873 | 476 | EKMLFKVTIGRWK |
| 744 | 477 | DKMLFKVTIQKWK |
| 745 | 478 | DKMLFTVTIQKWK |
| 874 | 479 | DKMLFKVTIDKWK |
| 875 | 480 | DKMLFTVTIDKWK |

194

TABLE 9-continued

Exemplary peptide sequences.

| Pep ID | SEQ ID NO. | Sequence |
|---|---|---|
| 876 | 481 | GKMLFKVTIEKWK |
| 877 | 482 | GKMLFTVTIEKWK |
| 748 | 483 | DKMLFKVTIGKWK |
| 749 | 484 | DKMLFTVTIGKWK |
| 878 | 485 | DKMLFKVTIGNWK |
| 879 | 486 | DKMLFKVTIQNWK |
| 781 | 487 | GKMLFKVTINKWK |
| 782 | 488 | GKMLFTVTINKWK |
| 752 | 489 | DKMLFKVTIEKWK |
| 753 | 490 | DKMLFTVTIEKWK |
| 750 | 491 | DKLLFKVTIGKWK |
| 786 | 492 | DKMLFTVTINKWK |
| 756 | 493 | DKLLFTVTIQKWK |
| 757 | 494 | DKLLFTVTIQKYK |
| 758 | 495 | DKLLFTVTIEKWK |
| 759 | 496 | DKLLFTVTIEKYK |
| 793 | 497 | DKLLFTVTIGKWK |
| 794 | 498 | DKLLFTVTIGKYK |
| 799 | 499 | DKLLFTVTINKWK |
| 800 | 500 | DKLLFTVTINKYK |
| 780 | 501 | GKMLFRVTINS |
| 765 | 502 | DKMLFTVTIQK |
| 779 | 503 | DKMLFKVTIQK |
| 820 | 504 | DKLLFTVTIGK |
| 819 | 505 | DKMLFTVTIGK |
| 822 | 506 | DKMLFTVTIEK |
| 821 | 507 | DKLLFTVTIEK |
| 627 | 508 | *DKMLFRVTINSWK |
| 628 | 509 | *EKMLFRVTINSWK |
| 629 | 510 | *RKMLFRVTINSWK |
| 630 | 511 | *KKMLFRVTINSWK |
| 631 | 512 | *HKMLFRVTINSWK |
| 632 | 513 | *GLMLFRVTINSWK |
| 633 | 514 | *GQMLFRVTINSWK |
| 634 | 515 | *GTMLFRVTINSWK |
| 635 | 516 | *GKLLFRVTINSWK |
| 636 | 517 | *GKMLFKVTINSWK |

195

TABLE 9-continued

Exemplary peptide sequences.

| Pep ID | SEQ ID NO. | Sequence |
|---|---|---|
| 637 | 518 | *GKMLFRVTIQSWK |
| 638 | 519 | *GKMLFRVTIDSWK |
| 639 | 520 | *GKMLFRVTIGSWK |
| 640 | 521 | *GKMLFRVTINTWK |
| 641 | 522 | *GKMLFRVTINNWK |
| 642 | 523 | *GKMLFRVTINQWK |
| 643 | 524 | *GKMLFRVTINPWK |
| 644 | 525 | *GKMLFRVTINKWK |
| 645 | 526 | *GKMLFRVTINSWQ |
| 646 | 527 | *GKMLFRVTINSWN |
| 647 | 528 | *GKMLFRVTINSWT |
| 648 | 529 | *GKMLFRVTINSWH |
| 649 | 530 | *GKMLFRVTINSWP |
| 650 | 531 | *GKMLFRVTINSWR |
| 677 | 532 | GKMKFRVTIDSWK |
| 680 | 533 | GKMLFRVEINSWK |
| 682 | 534 | GKMLFRVQINSWK |
| 683 | 535 | GKMKFRVKINSWK |
| 684 | 536 | GKMKFRVRINSWK |
| 685 | 537 | GKMKFRVEINSWK |
| 686 | 538 | GKMKFRVDINSWK |
| 687 | 539 | GKMKFRVQINSWK |
| 688 | 540 | GKMKFRVNINSWK |
| 689 | 541 | GKMKFRVSINSWK |
| 613 | 542 | GKMLFRVNINSWK |
| 614 | 543 | GKMLFRVSINSWK |
| 615 | 544 | GKMLFRVWINSWK |
| 616 | 545 | GKMSFRVTINSWK |
| 617 | 546 | GKMWFRVTINSWK |
| 618 | 547 | GKMNFRVTINSWK |
| 619 | 548 | GSMLFRVTINSYK |
| 620 | 549 | GKMLFRVTINSYK |
| 621 | 550 | GKMLFRVTIKSWK |
| 622 | 551 | GKMLFRVTIESWK |
| 716 | 552 | GKMKFRVTIQSWK |
| 717 | 553 | GKMKFRVTIESWK |
| 718 | 554 | GKMKFRVTIKSWK |
| 719 | 555 | GKMKFRVTIRSWK |

196

TABLE 9-continued

Exemplary peptide sequences.

| Pep ID | SEQ ID NO. | Sequence |
|---|---|---|
| 651 | 556 | RLMLFRVTINSWK |
| 652 | 557 | RQMLFRVTINSWK |
| 653 | 558 | KLMLFRVTINSWK |
| 654 | 559 | KQMLFRVTINSWK |
| 655 | 560 | ELMLFRVTINSWK |
| 657 | 561 | DLMLFRVTINSWK |
| 658 | 562 | DQMLFRVTINSWK |
| 659 | 563 | DKMLFRVTINSWK |
| 660 | 564 | EKMLFRVTINSWK |
| 661 | 565 | RKMLFRVTINSWK |
| 662 | 566 | KKMLFRVTINSWK |
| 665 | 567 | GKMLFRVTIGSWK |
| 667 | 568 | GKMLFRVTINKWK |
| 670 | 569 | GKMLFRVTISKWK |
| 671 | 570 | GKMLFRVTIQKWK |
| 672 | 571 | GKMLFRVTITKWK |
| 673 | 572 | GKMLFRVTIKKWK |
| 675 | 573 | GKMLFKVTINSWK |
| 676 | 574 | RLMLFRVTIGKWK |
| 701 | 575 | GKMLFRVTINRWK |
| 710 | 576 | EKMLFTVTIGKWK |
| 711 | 577 | EKLLFTVTIGKWK |
| 712 | 578 | EKMLFTVTIGRWK |
| 720 | 579 | EKMLFTVTIEKWK |
| 722 | 580 | DKMLFRVTIESWK |
| 726 | 581 | EKLLFRVTIGKYK |
| 746 | 582 | DKLLFKVTIQKWK |
| 747 | 583 | DKLLFKVTIQKYK |
| 751 | 584 | DKLLFKVTIGKYK |
| 754 | 585 | DKLLFKVTIEKWK |
| 755 | 586 | DKLLFKVTIEKYK |
| 761 | 587 | KKLLFRVTIQKWK |
| 762 | 588 | DRMLFRVTIQRWR |
| 766 | 589 | ERMLFRVTIGRWR |
| 768 | 590 | GRMLFRVTINRWR |
| 770 | 591 | DRMLFRVTIERWR |

TABLE 9-continued

Exemplary peptide sequences.

| Pep ID | SEQ ID NO. | Sequence |
|---|---|---|
| 783 | 592 | DKMLFKVTIQKYK |
| 784 | 593 | DKMLFRVTINKWK |

TABLE 9-continued

Exemplary peptide sequences.

| Pep ID | SEQ ID NO. | Sequence |
|---|---|---|
| 785 | 594 | DKMLFKVTIEKYK |
| 787 | 595 | DKMLFKVTINKWK |

*Terminus unblocked

TABLE 10

Exemplary luciferase base sequences

| Pep ID | SEQ ID NO. | Sequence |
|---|---|---|
| LgTrip 3546 - WT strand 9-HiBiT | 788 | MVFTLDDFVGDWEQTAAYNLDQVLEQGGVSSLLQNLAVSVTPIM RIVRSGENALKIDIHVIIPYEGLSADQMAQIEEVFKVVYPVDDHHF KVILPYGTLVIDGVTPNKLNYFGRPYEGIAVFDGKKITTTGTLWN GNKIIDERLITPDGSMLFRVTINSVSGWRLFKKIS |
| LgTrip 3546 - WT strand 9-SmBiT | 789 | MVFTLDDFVGDWEQTAAYNLDQVLEQGGVSSLLQNLAVSVTPIM RIVRSGENALKIDIHVIIPYEGLSADQMAQIEEVFKVVYPVDDHHF KVILPYGTLVIDGVTPNKLNYFGRPYEGIAVFDGKKITTTGTLWN GNKIIDERLITPDGSMLFRVTINSVTGYRLFEEIL |
| LgTrip 3546 (1-5) | 790 | MVFTLDDFVGDWEQTAAYNLDQVLEQGGVSSLLQNLAVSVTPIM RIVRSGENALKIDIHVIIPYEGLSADQMAQIEEVFKVVYPVDDHHF KVILPYGTLVID |
| LgTrip 3546 (1-6) | 791 | MVFTLDDFVGDWEQTAAYNLDQVLEQGGVSSLLQNLAVSVTPIM RIVRSGENALKIDIHVIIPYEGLSADQMAQIEEVFKVVYPVDDHHF KVILPYGTLVIDGVTPNKLNYFGRPYEGIAVFDG |
| LgTrip 3546 (1-7) | 792 | MVFTLDDFVGDWEQTAAYNLDQVLEQGGVSSLLQNLAVSVTPIM RIVRSGENALKIDIHVIIPYEGLSADQMAQIEEVFKVVYPVDDHHF KVILPYGTLVIDGVTPNKLNYFGRPYEGIAVFDGKKITTTGTL |
| LgTrip 3546 (1-8) | 793 | MVFTLDDFVGDWEQTAAYNLDQVLEQGGVSSLLQNLAVSVTPIM RIVRSGENALKIDIHVIIPYEGLSADQMAQIEEVFKVVYPVDDHHF KVILPYGTLVIDGVTPNKLNYFGRPYEGIAVFDGKKITTTGTLWN GNKIIDERLITPD |
| LgTrip 3546 (strands 6-8) - WT strand 9 - HiBiT | 794 | GVTPNKLNYFGRPYEGIAVFDGKKITTTGTLWNGNKIIDERLIT PDGSMLFRVTINSVSGWRLFKKIS |
| LgTrip 3546 (strands 7-8) - WT strand 9 - HiBiT | 795 | KKITTTGTLWNGNKIIDERLITPDGSMLFRVTINSVSGWRLFKKI S |
| LgTrip 3546 (strand 8) - WT strand 9 - HiBiT | 796 | WNGNKIIDERLITPDGSMLFRVTINSVSGWRLFKKIS |
| WT strand 9 - HiBiT | 797 | GSMLFRVTINSVSGWRLFKKIS |
| LgTrip 3546 (strands 6-8) - WT strand 9 - SmBiT | 798 | GVTPNKLNYFGRPYEGIAVFDGKKITTTGTLWNGNKIIDERLIT PDGSMLFRVTINSVTGYRLFEEIL |

TABLE 10-continued

| | | |
|---|---|---|
| Exemplary luciferase base sequences | | |

| Pep ID | SEQ ID NO. | Sequence |
|---|---|---|
| LgTrip 3546 (strands 7-strand 9 - SmBiT | 799 | KKITTTGTLWNGNKIIDERLITPDGSMLFRVTINSVTGYRLFEEIL |
| LgTrip 3546 (strand 8) - WT strand 9 - SmBiT | 800 | WNGNKIIDERLITPDGSMLFRVTINSVTGYRLFEEIL |
| WT strand 9 - SmBiT | 801 | GSMLFRVTINSVTGYRLFEEIL |
| β6-like | 817 | GVTPNKLNYFGRPYEGIAVFDG |
| β7-like | 818 | KKITTTGTL |
| β8-like | 819 | WNGNKIIDERLITPD |

TABLE 11

| | |
|---|---|
| Exemplary polypeptides | |

| Name | Polypeptide construct description |
|---|---|
| ATG-2623 | LgBiT-6His |
| ATG-3745 | HiBiT-8His-LgTrip |
| ATG-3746 | 6His-HiBiT-4GS-LgTrip |
| ATG-4632 | HiBiT-4GS-LgTrip-6His |
| ATG-4808 | VS-HiBiT-0GS-LgTrip |
| ATG-4809 | VS-HiBiT-4GS-LgTrip |
| ATG-4810 | VS-HiBIT-8GS-LgTrip |

TABLE 11-continued

| | |
|---|---|
| Exemplary polypeptides | |

| Name | Polypeptide construct description |
|---|---|
| ATG-4811 | VS-HiBiT-12GS-LgTrip |
| ATG-4812 | VS-HiBiT-16GS-LgTrip |
| ATG-4813 | VS-HiBiT-20GS-LgTrip |
| ATG-4814 | HiBIT-20GS-LgTrip |
| ATG-4815 | LgTrip-0GS-VS-HiBiT |
| ATG-4816 | LgTrip-4GS-VS-HiBiT |

The invention claimed is:

1. A composition comprising:

(a) a peptide comprising an amino acid sequence having 100% sequence identity with SEQ ID NO: 268, wherein the amino acid sequence is compared to the full length of SEQ ID NO: 268, wherein a bioluminescent signal produced in the presence of a coelenterazine substrate is capable of substantial increase when the peptide contacts a second peptide consisting of SEQ ID NO: 25 and a polypeptide complement consisting of SEQ ID NO: 17 when compared to a bioluminescent signal produced by (1) the peptide and the coelenterazine substrate alone or (2) the peptide, the coelenterazine substrate, and only one of the second peptide or the polypeptide complement;

(b) a nucleic acid comprising a sequence coding for the peptide of (a);

(c) a fusion protein comprising the peptide of (a) and additional amino acid sequence; or (d) a nucleic acid comprising a sequence coding for the fusion protein of (c).

2. The composition of claim 1, wherein the bioluminescent signal is substantially increased when the peptide associates with the second peptide and the polypeptide complement.

3. The composition of claim 1, wherein the peptide exhibits enhancement of one or more traits compared to a peptide of SEQ ID NO: 6 and/or SEQ ID NO: 9, wherein the traits are selected from: affinity for the second peptide and the polypeptide complement, expression, solubility, stability, and bioluminescent activity when combined with the second peptide and the polypeptide complement.

4. The composition of claim 1, wherein the additional amino acid sequence of the fusion is selected from the group consisting of a protein of interest, an interaction element, a co-localization element, and a binding moiety.

5. The composition of claim 4, wherein the additional amino acid sequence of the fusion is a binding moiety selected from the group consisting of antibody, antibody fragment, protein A, an Ig binding domain of protein A, protein G, an Ig binding domain of protein G, protein A/G, an Ig binding domain of protein A/G, protein L, an Ig binding domain of protein L, protein M, an Ig binding domain of protein M, peptide nucleic acid, DARPin, aptamer, affimer, a purified protein, and analyte binding domains of proteins.

6. The composition of claim 5, wherein the additional amino acid sequence of the fusion is a first interaction polypeptide that is configured to form a complex with a second interaction polypeptide upon contact of the first interaction polypeptide and the second interaction polypeptide.

7. The composition of claim 4, wherein the additional amino acid sequence of the fusion is a first co-localization polypeptide that is configured to co-localize within a cellular compartment, a cell, a tissue, or an organism within a with a second co-localization polypeptide.

8. The composition of claim 4, wherein the additional amino acid sequence of the fusion is a protein of interest and is a candidate drug target.

\* \* \* \* \*

SEQUENCE LISTING

```
<160> NUMBER OF SEQ ID NOS: 899

<210> SEQ ID NO 1
<211> LENGTH: 170
<212> TYPE: PRT
<213> ORGANISM: Oplophorus gracilirostris

<400> SEQUENCE: 1

Met Phe Thr Leu Ala Asp Phe Val Gly Asp Trp Gln Gln Thr Ala Gly
1               5                   10                  15

Tyr Asn Gln Asp Gln Val Leu Glu Gln Gly Gly Leu Ser Ser Leu Phe
            20                  25                  30

Gln Ala Leu Gly Val Ser Val Thr Pro Ile Gln Lys Val Val Leu Ser
        35                  40                  45

Gly Glu Asn Gly Leu Lys Ala Asp Ile His Val Ile Ile Pro Tyr Glu
    50                  55                  60

Gly Leu Ser Gly Phe Gln Met Gly Leu Ile Glu Met Ile Phe Lys Val
65                  70                  75                  80

Val Tyr Pro Val Asp Asp His His Phe Lys Ile Ile Leu His Tyr Gly
                85                  90                  95

Thr Leu Val Ile Asp Gly Val Thr Pro Asn Met Ile Asp Tyr Phe Gly
            100                 105                 110

Arg Pro Tyr Pro Gly Ile Ala Val Phe Asp Gly Lys Gln Ile Thr Val
```

-continued

```
          115              120              125
Thr Gly Thr Leu Trp Asn Gly Asn Lys Ile Tyr Asp Glu Arg Leu Ile
    130              135              140
Asn Pro Asp Gly Ser Leu Leu Phe Arg Val Thr Ile Asn Gly Val Thr
145              150              155              160
Gly Trp Arg Leu Cys Glu Asn Ile Leu Ala
                165              170
```

<210> SEQ ID NO 2
<211> LENGTH: 513
<212> TYPE: DNA
<213> ORGANISM: Oplophorus gracilirostris

<400> SEQUENCE: 2

```
atggtgttta ccttggcaga tttcgttgga gactggcaac agacagctgg atacaaccaa      60
gatcaagtgt tagaacaagg aggattgtct agtctgttcc aagccctggg agtgtcagtc     120
accccaatcc agaaagttgt gctgtctggg gagaatgggt taaaagctga tattcatgtc     180
atcatccctt acgagggact cagtggtttt caaatgggtc tgattgaaat gatcttcaaa     240
gttgtttacc cagtggatga tcatcatttc aagattattc tccattatgg tacactcgtt     300
attgacggtg tgacaccaaa catgattgac tactttggac gcccttaccc tggaattgct     360
gtgtttgacg gcaagcagat cacagttact ggaactctgt ggaacggcaa caagatctat     420
gatgagcgcc tgatcaaccc agatggttca ctcctcttcc gcgttactat caatggagtc     480
accggatggc gcctttgcga gaacattctt gcc                                  513
```

<210> SEQ ID NO 3
<211> LENGTH: 183
<212> TYPE: PRT
<213> ORGANISM: Artificial sequence
<220> FEATURE:
<223> OTHER INFORMATION: Synthetic

<400> SEQUENCE: 3

```
Met Lys His His His His His His Ala Ile Ala Met Val Phe Thr Leu
1               5                   10                  15
Glu Asp Phe Val Gly Asp Trp Arg Gln Thr Ala Gly Tyr Asn Leu Asp
                20                  25                  30
Gln Val Leu Glu Gln Gly Gly Val Ser Ser Leu Phe Gln Asn Leu Gly
            35                  40                  45
Val Ser Val Thr Pro Ile Gln Arg Ile Val Leu Ser Gly Glu Asn Gly
        50                  55                  60
Leu Lys Ile Asp Ile His Val Ile Ile Pro Tyr Glu Gly Leu Ser Gly
65                  70                  75                  80
Asp Gln Met Gly Gln Ile Glu Lys Ile Phe Lys Val Val Tyr Pro Val
                85                  90                  95
Asp Asp His His Phe Lys Val Ile Leu His Tyr Gly Thr Leu Val Ile
                100                 105                 110
Asp Gly Val Thr Pro Asn Met Ile Asp Tyr Phe Gly Arg Pro Tyr Glu
            115                 120                 125
Gly Ile Ala Val Phe Asp Gly Lys Lys Ile Thr Val Thr Gly Thr Leu
            130                 135                 140
Trp Asn Gly Asn Lys Ile Ile Asp Glu Arg Leu Ile Asn Pro Asp Gly
145                 150                 155                 160
Ser Leu Leu Phe Arg Val Thr Ile Asn Gly Val Thr Gly Trp Arg Leu
                165                 170                 175
```

Cys Glu Arg Ile Leu Ala Val
          180

<210> SEQ ID NO 4
<211> LENGTH: 549
<212> TYPE: DNA
<213> ORGANISM: Artificial sequence
<220> FEATURE:
<223> OTHER INFORMATION: Synthetic

<400> SEQUENCE: 4
atgaaacatc accatcacca tcatgcgatc gccatggtct tcacactcga agatttcgtt      60
ggggactggc gacagacagc cggctacaac ctggaccaag tccttgaaca gggaggtgtg     120
tccagtttgt ttcagaatct cggggtgtcc gtaactccga tccaaaggat tgtcctgagc     180
ggtgaaaatg ggctgaagat cgacatccat gtcatcatcc cgtatgaagg tctgagcggc     240
gaccaaatgg gccagatcga aaaaattttt aaggtggtgt accctgtgga tgatcatcac     300
tttaaggtga tcctgcacta tggcacactg gtaatcgacg gggttacgcc gaacatgatc     360
gactatttcg gacggccgta tgaaggcatc gccgtgttcg acggcaaaaa gatcactgta     420
acagggaccc tgtggaacgg caacaaaatt atcgacgagc gcctgatcaa ccccgacggc     480
tccctgctgt tccgagtaac catcaacgga gtgaccggct ggcggctgtg cgaacgcatt     540
ctggcggtt                                                            549

<210> SEQ ID NO 5
<211> LENGTH: 147
<212> TYPE: PRT
<213> ORGANISM: Artificial sequence
<220> FEATURE:
<223> OTHER INFORMATION: Synthetic

<400> SEQUENCE: 5

Met Phe Thr Leu Ala Asp Phe Val Gly Asp Trp Gln Gln Thr Ala Gly
1               5                   10                  15

Tyr Asn Gln Asp Gln Val Leu Glu Gln Gly Gly Leu Ser Ser Leu Phe
            20                  25                  30

Gln Ala Leu Gly Val Ser Val Thr Pro Ile Gln Lys Val Val Leu Ser
        35                  40                  45

Gly Glu Asn Gly Leu Lys Ala Asp Ile His Val Ile Ile Pro Tyr Glu
    50                  55                  60

Gly Leu Ser Gly Phe Gln Met Gly Leu Ile Glu Met Ile Phe Lys Val
65                  70                  75                  80

Val Tyr Pro Val Asp Asp His His Phe Lys Ile Ile Leu His Tyr Gly
                85                  90                  95

Thr Leu Val Ile Asp Gly Val Thr Pro Asn Met Ile Asp Tyr Phe Gly
            100                 105                 110

Arg Pro Tyr Pro Gly Ile Ala Val Phe Asp Gly Lys Gln Ile Thr Val
        115                 120                 125

Thr Gly Thr Leu Trp Asn Gly Asn Lys Ile Tyr Asp Glu Arg Leu Ile
    130                 135                 140

Asn Pro Asp
145

<210> SEQ ID NO 6
<211> LENGTH: 10
<212> TYPE: PRT
<213> ORGANISM: Artificial sequence -continued

```
<220> FEATURE:
<223> OTHER INFORMATION: Synthetic

<400> SEQUENCE: 6

Gly Ser Leu Leu Phe Arg Val Thr Ile Asn
1               5                   10

<210> SEQ ID NO 7
<211> LENGTH: 13
<212> TYPE: PRT
<213> ORGANISM: Artificial sequence
<220> FEATURE:
<223> OTHER INFORMATION: Synthetic

<400> SEQUENCE: 7

Gly Val Thr Gly Trp Arg Leu Cys Glu Asn Ile Leu Ala
1               5                   10

<210> SEQ ID NO 8
<211> LENGTH: 148
<212> TYPE: PRT
<213> ORGANISM: Artificial sequence
<220> FEATURE:
<223> OTHER INFORMATION: Synthetic

<400> SEQUENCE: 8

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp
145

<210> SEQ ID NO 9
<211> LENGTH: 11
<212> TYPE: PRT
<213> ORGANISM: Artificial sequence
<220> FEATURE:
<223> OTHER INFORMATION: Synthetic

<400> SEQUENCE: 9

Gly Ser Leu Leu Phe Arg Val Thr Ile Asn Val
1               5                   10

<210> SEQ ID NO 10
<211> LENGTH: 13
<212> TYPE: PRT
<213> ORGANISM: Artificial sequence
```

<220> FEATURE:
<223> OTHER INFORMATION: Synthetic

<400> SEQUENCE: 10

Gly Val Thr Gly Trp Arg Leu Cys Glu Arg Ile Leu Ala
1               5                   10

<210> SEQ ID NO 11
<211> LENGTH: 165
<212> TYPE: PRT
<213> ORGANISM: Artificial sequence
<220> FEATURE:
<223> OTHER INFORMATION: Synthetic

<400> SEQUENCE: 11

Met Val Phe Thr Leu Glu Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Gln Arg Ile Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Met Leu Asn Tyr Phe
                100                 105                 110

Gly Arg Pro Tyr Glu Gly Ile Ala Val Phe Asp Gly Lys Lys Ile Thr
            115                 120                 125

Val Thr Gly Thr Leu Trp Asn Gly Asn Lys Ile Ile Asp Glu Arg Leu
        130                 135                 140

Ile Thr Pro Asp Gly Ser Met Leu Phe Arg Val Thr Ile Asn Ser His
145                 150                 155                 160

His His His His His
                165

<210> SEQ ID NO 12
<211> LENGTH: 495
<212> TYPE: DNA
<213> ORGANISM: Artificial sequence
<220> FEATURE:
<223> OTHER INFORMATION: Synthetic

<400> SEQUENCE: 12
atggtcttca cactcgaaga tttcgttggg gactgggaac agacagccgc ctacaacctg      60
gaccaagtcc ttgaacaggg aggtgtgtcc agtttgctgc agaatctcgc cgtgtccgta     120
actccgatcc aaaggattgt ccggagcggt gaaaatgccc tgaagatcga catccatgtc     180
atcatcccgt atgaaggtct gagcgccgac caaatggccc agatcgaaga ggtgtttaag     240
gtggtgtacc ctgtggatga tcatcacttt aaggtgatcc tgccctatgg cacactggta     300
atcgacgggg ttacgccgaa catgctgaac tatttcggac ggccgtatga aggcatcgcc     360
gtgttcgacg gcaaaaagat cactgtaaca gggaccctgt ggaacggcaa caaaattatc     420
gacgagcgcc tgatcacccc cgacggctcc atgctgttcc gagtaaccat caacagccat     480
catcaccatc accac                                                      495

-continued

<210> SEQ ID NO 13
<211> LENGTH: 11
<212> TYPE: PRT
<213> ORGANISM: Artificial sequence
<220> FEATURE:
<223> OTHER INFORMATION: Synthetic

<400> SEQUENCE: 13

Val Thr Gly Tyr Arg Leu Phe Glu Glu Ile Leu
1               5                   10

<210> SEQ ID NO 14
<211> LENGTH: 33
<212> TYPE: DNA
<213> ORGANISM: Artificial sequence
<220> FEATURE:
<223> OTHER INFORMATION: Synthetic

<400> SEQUENCE: 14
gtgaccggct accggctgtt cgaggagatt ctg                                33

<210> SEQ ID NO 15
<211> LENGTH: 11
<212> TYPE: PRT
<213> ORGANISM: Artificial sequence
<220> FEATURE:
<223> OTHER INFORMATION: Synthetic

<400> SEQUENCE: 15

Val Ser Gly Trp Arg Leu Phe Lys Lys Ile Ser
1               5                   10

<210> SEQ ID NO 16
<211> LENGTH: 33
<212> TYPE: DNA
<213> ORGANISM: Artificial sequence
<220> FEATURE:
<223> OTHER INFORMATION: Synthetic

<400> SEQUENCE: 16
gtgagcggct ggcggctgtt caagaagatt agc                                33

<210> SEQ ID NO 17
<211> LENGTH: 148
<212> TYPE: PRT
<213> ORGANISM: Artificial sequence
<220> FEATURE:
<223> OTHER INFORMATION: Synthetic

<400> SEQUENCE: 17

Met Val Phe Thr Leu Glu Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Gln Arg Ile Val Arg
        35                  40                  45

Ser Gly Glu Asn Ala Leu Lys Ile Asp Ile His Val Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Met Leu Asn Tyr Phe

-continued

```
                100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Thr Pro Asp
145

<210> SEQ ID NO 18
<211> LENGTH: 444
<212> TYPE: DNA
<213> ORGANISM: Artificial sequence
<220> FEATURE:
<223> OTHER INFORMATION: Synthetic

<400> SEQUENCE: 18
atggtcttca cactcgaaga tttcgttggg gactgggaac agacagccgc ctacaacctg      60
gaccaagtcc ttgaacaggg aggtgtgtcc agtttgctgc agaatctcgc cgtgtccgta     120
actccgatcc aaaggattgt ccggagcggt gaaaatgccc tgaagatcga catccatgtc     180
atcatcccgt atgaaggtct gagcgccgac caaatggccc agatcgaaga ggtgtttaag     240
gtggtgtacc ctgtggatga tcatcacttt aaggtgatcc tgccctatgg cacactggta     300
atcgacgggg ttacgccgaa catgctgaac tatttcggac ggccgtatga aggcatcgcc     360
gtgttcgacg gcaaaaagat cactgtaaca gggaccctgt ggaacggcaa caaaattatc     420
gacgagcgcc tgatcacccc cgac                                             444

<210> SEQ ID NO 19
<211> LENGTH: 155
<212> TYPE: PRT
<213> ORGANISM: Artificial sequence
<220> FEATURE:
<223> OTHER INFORMATION: Synthetic

<400> SEQUENCE: 19

Met Lys His His His His His His Val Phe Thr Leu Asp Asp Phe Val
1               5                  10                  15

Gly Asp Trp Glu Gln Thr Ala Ala Tyr Asn Leu Asp Gln Val Leu Glu
            20                  25                  30

Gln Gly Gly Val Ser Ser Leu Leu Gln Asn Leu Ala Val Ser Val Thr
        35                  40                  45

Pro Ile Met Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
                85                  90                  95

Phe Lys Val Ile Leu Pro Tyr Gly Thr Leu Val Ile Asp Gly Val Thr
            100                 105                 110

Pro Asn Lys Leu Asn Tyr Phe Gly Arg Pro Tyr Glu Gly Ile Ala Val
        115                 120                 125

Phe Asp Gly Lys Lys Ile Thr Val Thr Gly Thr Leu Trp Asn Gly Asn
    130                 135                 140

Lys Ile Ile Asp Glu Arg Leu Ile Thr Pro Asp
145                 150                 155

<210> SEQ ID NO 20
```

<211> LENGTH: 465
<212> TYPE: DNA
<213> ORGANISM: Artificial sequence
<220> FEATURE:
<223> OTHER INFORMATION: Synthetic

<400> SEQUENCE: 20
atgaaacatc accatcacca tcatgtcttc acactcgaag atttcgttgg ggactgggaa      60
cagacagccg cctacaacct ggaccaagtc cttgaacagg gaggtgtgtc cagtttgctg     120
cagaatctcg ccgtgtccgt aactccgatc caaaggattg tccggagcgg tgaaaatgcc     180
ctgaagatcg acatccatgt catcatcccg tatgaaggtc tgagcgccga ccaaatggcc     240
cagatcgaag aggtgtttaa ggtggtgtac cctgtggatg atcatcactt taaggtgatc     300
ctgccctatg gcacactggt aatcgacggg gttacgccga acatgctgaa ctatttcgga     360
cggccgtatg aaggcatcgc cgtgttcgac ggcaaaaaga tcactgtaac agggaccctg     420
tggaacggca acaaaattat cgacgagcgc ctgatcaccc ccgac               465

<210> SEQ ID NO 21
<211> LENGTH: 148
<212> TYPE: PRT
<213> ORGANISM: Artificial sequence
<220> FEATURE:
<223> OTHER INFORMATION: Synthetic

<400> SEQUENCE: 21

Met Val Phe Thr Leu Asp Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Met Arg Ile Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Lys Leu Asn Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Thr Pro Asp
145

<210> SEQ ID NO 22
<211> LENGTH: 444
<212> TYPE: DNA
<213> ORGANISM: Artificial sequence
<220> FEATURE:
<223> OTHER INFORMATION: Synthetic

<400> SEQUENCE: 22
atggtcttca cactcgacga tttcgttggg gactgggaac agacagccgc ctacaacctg      60
gaccaagtcc ttgaacaggg aggtgtgtcc agtttgctgc agaatctcgc cgtgtccgta     120
actccgatca tgaggattgt ccggagcggt gaaaatgccc tgaagatcga catccatgtc     180

-continued

```
atcatcccgt atgaaggtct gagcgccgac caaatggccc agatcgaaga ggtgtttaag      240
gtggtgtacc ctgtggatga tcatcacttt aaggtgatcc tgccctatgg cacactggta      300
atcgacgggg ttacgccgaa caagctgaac tatttcggac ggccgtatga aggcatcgcc      360
gtgttcgacg gcaaaaagat cactgtaaca gggaccctgt ggaacggcaa caaaattatc      420
gacgagcgcc tgatcacccc cgac                                            444
```

```
<210> SEQ ID NO 23
<211> LENGTH: 11
<212> TYPE: PRT
<213> ORGANISM: Artificial sequence
<220> FEATURE:
<223> OTHER INFORMATION: Synthetic

<400> SEQUENCE: 23

Gly Ser Met Leu Phe Arg Val Thr Ile Asn Ser
1               5                   10

<210> SEQ ID NO 24
<211> LENGTH: 33
<212> TYPE: DNA
<213> ORGANISM: Artificial sequence
<220> FEATURE:
<223> OTHER INFORMATION: Synthetic

<400> SEQUENCE: 24
ggctccatgc tgttccgagt aaccatcaac agc                                   33

<210> SEQ ID NO 25
<211> LENGTH: 11
<212> TYPE: PRT
<213> ORGANISM: Artificial sequence
<220> FEATURE:
<223> OTHER INFORMATION: Synthetic

<400> SEQUENCE: 25

Val Ser Gly Trp Arg Leu Phe Lys Lys Ile Ser
1               5                   10

<210> SEQ ID NO 26
<211> LENGTH: 33
<212> TYPE: DNA
<213> ORGANISM: Artificial sequence
<220> FEATURE:
<223> OTHER INFORMATION: Synthetic

<400> SEQUENCE: 26
gtgagcggct ggcggctgtt caagaagatt agc                                   33

<210> SEQ ID NO 27
<211> LENGTH: 148
<212> TYPE: PRT
<213> ORGANISM: Artificial sequence
<220> FEATURE:
<223> OTHER INFORMATION: Synthetic

<400> SEQUENCE: 27

Met Val Phe Thr Leu Glu Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Phe Gln Asn Leu Ala Val Ser Val Thr Pro Ile Gln Arg Ile Val Leu
        35                  40                  45
```

```
Ser Gly Glu Asn Ala Leu Lys Ile Asp Ile His Val Ile Ile Pro Tyr
    50                  55                  60
```

```
Glu Gly Leu Ser Ala Asp Gln Met Ala Gln Ile Glu Lys Ile Phe Lys
65                  70                  75                  80
```

```
Val Val Tyr Pro Val Asp Asp His His Phe Lys Val Ile Leu His Tyr
                85                  90                  95
```

```
Gly Thr Leu Val Ile Asp Gly Val Thr Pro Asn Met Ile Asn Tyr Phe
            100                 105                 110
```

```
Gly Arg Pro Tyr Glu Gly Ile Ala Val Phe Asp Gly Lys Lys Ile Thr
            115                 120                 125
```

```
Val Thr Gly Thr Leu Trp Asn Gly Asn Lys Ile Ile Asp Glu Arg Leu
    130                 135                 140
```

```
Ile Thr Pro Asp
145
```

```
<210> SEQ ID NO 28
<211> LENGTH: 444
<212> TYPE: DNA
<213> ORGANISM: Artificial sequence
<220> FEATURE:
<223> OTHER INFORMATION: Synthetic

<400> SEQUENCE: 28
atggtcttca cactcgaaga tttcgttggg gactgggaac agacagccgc ctacaacctg      60
gaccaagtcc ttgaacaggg aggtgtgtcc agtttgtttc agaatctcgc cgtgtccgta     120
actccgatcc aaaggattgt cctgagcggt gaaaatgccc tgaagatcga catccatgtc     180
atcatcccgt atgaaggtct gagcgccgac caaatggccc agatcgaaaa aattttttaag    240 gtggtgtacc ctgtggatga tcatcacttt aaggtgatcc tgcactatgg cacactggta     300
atcgacgggg ttacgccgaa catgatcaac tatttcggac ggccgtatga aggcatcgcc     360
gtgttcgacg gcaaaaagat cactgtaaca gggaccctgt ggaacggcaa caaaattatc     420
gacgagcgcc tgatcacccc cgac                                           444
```

```
<210> SEQ ID NO 29
<211> LENGTH: 11
<212> TYPE: PRT
<213> ORGANISM: Artificial sequence
<220> FEATURE:
<223> OTHER INFORMATION: Synthetic

<400> SEQUENCE: 29

Gly Ser Met Leu Phe Arg Val Thr Ile Asn Val
1               5                   10
```

```
<210> SEQ ID NO 30
<211> LENGTH: 30
<212> TYPE: DNA
<213> ORGANISM: Artificial sequence
<220> FEATURE:
<223> OTHER INFORMATION: Synthetic

<400> SEQUENCE: 30
ggctccatgc tgttccgagt aaccatcaac                                      30
```

```
<210> SEQ ID NO 31
<211> LENGTH: 155
<212> TYPE: PRT
<213> ORGANISM: Artificial sequence
<220> FEATURE:
```

<223> OTHER INFORMATION: Synthetic

<400> SEQUENCE: 31

Met Lys His His His His His His Val Phe Thr Leu Glu Asp Phe Val
1               5                   10                  15

Gly Asp Trp Glu Gln Thr Ala Ala Tyr Asn Leu Asp Gln Val Leu Glu
                20                  25                  30

Gln Gly Gly Val Ser Ser Leu Leu Gln Asn Leu Ala Val Ser Val Thr
            35                  40                  45

Pro Ile Gln Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
                85                  90                  95

Phe Lys Val Ile Leu Pro Tyr Gly Thr Leu Val Ile Asp Gly Val Thr
            100                 105                 110

Pro Asn Met Leu Asn Tyr Phe Gly Arg Pro Tyr Glu Gly Ile Ala Val
            115                 120                 125

Phe Asp Gly Lys Lys Ile Thr Val Thr Gly Thr Leu Trp Asn Gly Asn
    130                 135                 140

Lys Ile Ile Asp Glu Arg Leu Ile Thr Pro Asp
145                 150                 155

<210> SEQ ID NO 32
<211> LENGTH: 465
<212> TYPE: DNA
<213> ORGANISM: Artificial sequence
<220> FEATURE:
<223> OTHER INFORMATION: Synthetic

<400> SEQUENCE: 32
atgaaacatc accatcacca tcatgtcttc acactcgaag atttcgttgg ggactgggaa        60
cagacagccg cctacaacct ggaccaagtc cttgaacagg gaggtgtgtc cagtttgctg       120
cagaatctcg ccgtgtccgt aactccgatc caaaggattg tccggagcgg tgaaaatgcc       180
ctgaagatcg acatccatgt catcatcccg tatgaaggtc tgagcgccga ccaaatggcc       240
cagatcgaag aggtgtttaa ggtggtgtac cctgtggatg atcatcactt taaggtgatc       300
ctgccctatg gcacactggt aatcgacggg gttacgccga acatgctgaa ctatttcgga       360
cggccgtatg aaggcatcgc cgtgttcgac ggcaaaaaga tcactgtaac agggaccctg       420
tggaacggca acaaaattat cgacgagcgc ctgatcaccc ccgac                       465

<210> SEQ ID NO 33

<400> SEQUENCE: 33

000

<210> SEQ ID NO 34

<400> SEQUENCE: 34

000

<210> SEQ ID NO 35
<211> LENGTH: 22
<212> TYPE: PRT
<213> ORGANISM: Artificial sequence -continued
<220> FEATURE:
<223> OTHER INFORMATION: Synthetic

<400> SEQUENCE: 35

Gly Ser Met Leu Phe Arg Val Thr Ile Asn Ser Val Ser Gly Trp Arg
1               5                   10                  15

Leu Phe Lys Lys Ile Ser
            20

<210> SEQ ID NO 36
<211> LENGTH: 66
<212> TYPE: DNA
<213> ORGANISM: Artificial sequence
<220> FEATURE:
<223> OTHER INFORMATION: Synthetic

<400> SEQUENCE: 36
ggctccatgc tgttccgagt aaccatcaac agcgtgagcg ctggcggct gttcaagaag      60 attagc                                                                66

<210> SEQ ID NO 37
<211> LENGTH: 16
<212> TYPE: PRT
<213> ORGANISM: Artificial sequence
<220> FEATURE:
<223> OTHER INFORMATION: Synthetic

<400> SEQUENCE: 37

Ser Ser Trp Lys Arg Gly Ser Met Leu Phe Arg Val Thr Ile Asn Ser
1               5                   10                  15

<210> SEQ ID NO 38
<211> LENGTH: 48
<212> TYPE: DNA
<213> ORGANISM: Artificial sequence
<220> FEATURE:
<223> OTHER INFORMATION: Synthetic

<400> SEQUENCE: 38
agcagctgga agcgcggctc catgctgttc cgagtaacca tcaacagc                  48

<210> SEQ ID NO 39
<211> LENGTH: 155
<212> TYPE: PRT
<213> ORGANISM: Artificial sequence
<220> FEATURE:
<223> OTHER INFORMATION: Synthetic

<400> SEQUENCE: 39

Met Lys His His His His His His Val Phe Thr Leu Asp Asp Phe Val
1               5                   10                  15

Gly Asp Trp Glu Gln Thr Ala Ala Tyr Asn Leu Asp Gln Val Leu Glu
            20                  25                  30

Gln Gly Gly Val Ser Ser Leu Leu Gln Asn Leu Ala Val Ser Val Thr
        35                  40                  45

Pro Ile Met Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
                85                  90                  95

Phe Lys Val Ile Leu Pro Tyr Gly Thr Leu Val Ile Asp Gly Asp Thr

```
                100              105              110
Pro Asn Lys Leu Asn Tyr Phe Gly Arg Pro Tyr Asp Gly Ile Ala Val
        115              120              125

Phe Asp Gly Lys Lys Ile Thr Val Thr Gly Thr Leu Trp Asn Gly Asn
    130              135              140

Lys Ile Ile Asp Glu Arg Leu Ile Thr Pro Asp
145              150              155
```

<210> SEQ ID NO 40
<211> LENGTH: 465
<212> TYPE: DNA
<213> ORGANISM: Artificial sequence
<220> FEATURE:
<223> OTHER INFORMATION: Synthetic

<400> SEQUENCE: 40

```
atgaaacatc accatcacca tcatgtcttc acactcgacg atttcgttgg ggactgggaa      60
cagacagccg cctacaacct ggaccaagtc cttgaacagg aggtgtgtc cagtttgctg     120 cagaatctcg ccgtgtccgt aactccgatc atgaggattg tccggagcgg tgaaaatgcc     180
ctgaagatcg acatccatgt catcatcccg tatgaaggtc tgagcgccga ccaaatggcc     240
cagatcgaag aggtgtttaa ggtggtgtac cctgtggatg atcatcactt taaggtgatc     300
ctgccctatg gcacactggt aatcgacggg gatacgccga caagctgaa ctatttcgga     360 cggccgtatg atggcatcgc cgtgttcgac ggcaaaaaga tcactgtaac agggaccctg     420
tggaacggca acaaaattat cgacgagcgc ctgatcaccc ccgac                    465
```

<210> SEQ ID NO 41
<211> LENGTH: 155
<212> TYPE: PRT
<213> ORGANISM: Artificial sequence
<220> FEATURE:
<223> OTHER INFORMATION: Synthetic

<400> SEQUENCE: 41

```
Met Lys His His His His His His Val Phe Thr Leu Asp Asp Phe Val
1               5                10               15

Gly Asp Trp Glu Gln Thr Ala Ala Tyr Asn Leu Asp Gln Val Leu Glu
            20               25               30

Gln Gly Gly Val Ser Ser Leu Leu Gln Asn Leu Ala Val Ser Val Thr
            35               40               45

Pro Ile Met Arg Ile Val Arg Ser Gly Glu Asn Ala Leu Lys Ile Asp
    50               55               60

Ile His Val Ile Ile Pro Tyr Glu Gly Leu Ser Ala Asp Gln Met Ala
65               70               75               80

Gln Ile Glu Glu Val Phe Lys Val Val Tyr Pro Val Asp Asp His His
            85               90               95

Phe Lys Val Ile Leu Pro Tyr Gly Thr Leu Val Ile Asp Gly Val Thr
            100              105              110

Pro Ser Lys Leu Asn Tyr Phe Gly Arg Pro Tyr Glu Gly Ile Ala Val
        115              120              125

Phe Asp Gly Lys Lys Ile Thr Val Thr Gly Thr Leu Trp Asn Gly Asn
    130              135              140

Lys Ile Ile Asp Glu Arg Leu Ile Thr Pro Asp
145              150              155
```

<210> SEQ ID NO 42

```
<211> LENGTH: 465
<212> TYPE: DNA
<213> ORGANISM: Artificial sequence
<220> FEATURE:
<223> OTHER INFORMATION: Synthetic

<400> SEQUENCE: 42
atgaaacatc accatcacca tcatgtcttc acactcgacg atttcgttgg ggactgggaa        60
cagacagccg cctacaacct ggaccaagtc cttgaacagg gaggtgtgtc cagtttgctg       120
cagaatctcg ccgtgtccgt aactccgatc atgaggattg tccggagcgg tgaaaatgcc       180
ctgaagatcg acatccatgt catcatcccg tatgaaggtc tgagcgccga ccaaatggcc       240
cagatcgaag aggtgtttaa ggtggtgtac cctgtggatg atcatcactt taaggtgatc       300
ctgccctatg gcacactggt aatcgacggg gttacgccga gcaagctgaa ctatttcgga       360
cggccgtatg aaggcatcgc cgtgttcgac ggcaaaaaga tcactgtaac agggaccctg       420
tggaacggca acaaaattat cgacgagcgc ctgatcaccc ccgac                       465

<210> SEQ ID NO 43
<211> LENGTH: 155
<212> TYPE: PRT
<213> ORGANISM: Artificial sequence
<220> FEATURE:
<223> OTHER INFORMATION: Synthetic

<400> SEQUENCE: 43

Met Lys His His His His His His Val Phe Thr Leu Asp Asp Phe Val
1               5                   10                  15

Gly Asp Trp Glu Gln Thr Ala Ala Tyr Asn Leu Asp Gln Val Leu Glu
                20                  25                  30

Gln Gly Gly Val Ser Ser Leu Leu Gln Asn Leu Ala Val Ser Val Thr
            35                  40                  45

Pro Ile Met Arg Ile Val Arg Ser Gly Glu Asn Ala Leu Lys Ile Asp
        50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
                85                  90                  95

Phe Lys Val Ile Leu Pro Tyr Gly Thr Leu Val Ile Asp Gly Val Thr
                100                 105                 110

Pro Asn Lys Leu Asn Tyr Phe Gly Arg Pro Tyr Glu Gly Phe Ala Val
            115                 120                 125

Phe Asp Gly Lys Lys Ile Thr Val Thr Gly Thr Leu Trp Asn Gly Asn
        130                 135                 140

Lys Ile Ile Asp Glu Arg Leu Ile Thr Pro Asp
145                 150                 155

<210> SEQ ID NO 44
<211> LENGTH: 465
<212> TYPE: DNA
<213> ORGANISM: Artificial sequence
<220> FEATURE:
<223> OTHER INFORMATION: Synthetic

<400> SEQUENCE: 44
atgaaacatc accatcacca tcatgtcttc acactcgacg atttcgttgg ggactgggaa        60
cagacagccg cctacaacct ggaccaagtc cttgaacagg gaggtgtgtc cagtttgctg       120
cagaatctcg ccgtgtccgt aactccgatc atgaggattg tccggagcgg tgaaaatgcc       180
```

```
ctgaagatcg acatccatgt catcatcccg tatgaaggtc tgagcgccga ccaaatggcc      240
cagatcgaag aggtgtttaa ggtggtgtac cctgtggatg atcatcactt taaggtgatc      300
ctgccctatg gcacactggt aatcgacggg gttacgccga acaagctgaa ctatttcgga      360
cggccgtatg aaggcttcgc cgtgttcgac ggcaaaaaga tcactgtaac agggaccctg      420
tggaacggca acaaaattat cgacgagcgc ctgatcaccc ccgac                     465
```

<210> SEQ ID NO 45
<211> LENGTH: 155
<212> TYPE: PRT
<213> ORGANISM: Artificial sequence
<220> FEATURE:
<223> OTHER INFORMATION: Synthetic

<400> SEQUENCE: 45

```
Met Lys His His His His His His Val Phe Thr Leu Asp Asp Phe Val
1               5                   10                  15

Gly Asp Trp Glu Gln Thr Ala Ala Tyr Asn Leu Asp Gln Val Leu Glu
            20                  25                  30

Gln Gly Gly Val Ser Ser Leu Leu Gln Asn Leu Ala Val Ser Val Thr
        35                  40                  45

Pro Ile Met Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
                85                  90                  95

Phe Lys Val Ile Leu Pro Tyr Gly Thr Leu Val Ile Asp Gly Val Thr
            100                 105                 110

Pro Asn Lys Leu Asn Tyr Phe Gly Arg Pro Tyr Glu Gly Ile Ala Val
        115                 120                 125

Cys Asp Gly Lys Lys Ile Thr Val Thr Gly Thr Leu Trp Asn Gly Asn
    130                 135                 140

Lys Ile Ile Asp Glu Arg Leu Ile Thr Pro Asp
145                 150                 155
```

<210> SEQ ID NO 46
<211> LENGTH: 465
<212> TYPE: DNA
<213> ORGANISM: Artificial sequence
<220> FEATURE:
<223> OTHER INFORMATION: Synthetic

<400> SEQUENCE: 46

```
atgaaacatc accatcacca tcatgtcttc acactcgacg atttcgttgg ggactgggaa       60
cagacagccg cctacaacct ggaccaagtc cttgaacagg gaggtgtgtc cagtttgctg      120
cagaatctcg ccgtgtccgt aactccgatc atgaggattg tccggagcgg tgaaaatgcc      180
ctgaagatcg acatccatgt catcatcccg tatgaaggtc tgagcgccga ccaaatggcc      240
cagatcgaag aggtgtttaa ggtggtgtac cctgtggatg atcatcactt taaggtgatc      300
ctgccctatg gcacactggt aatcgacggg gttacgccga acaagctgaa ctatttcgga      360
cggccgtatg aaggcatcgc cgtgtgcgac ggcaaaaaga tcactgtaac agggaccctg      420
tggaacggca acaaaattat cgacgagcgc ctgatcaccc ccgac                     465
```

<210> SEQ ID NO 47

```
<211> LENGTH: 155
<212> TYPE: PRT
<213> ORGANISM: Artificial sequence
<220> FEATURE:
<223> OTHER INFORMATION: Synthetic

<400> SEQUENCE: 47

Met Lys His His His His His His Val Phe Thr Leu Asp Asp Phe Val
1               5                   10                  15

Gly Asp Trp Glu Gln Thr Ala Ala Tyr Asn Leu Asp Gln Val Leu Glu
            20                  25                  30

Gln Gly Gly Val Ser Ser Leu Leu Gln Asn Leu Ala Val Ser Val Thr
        35                  40                  45

Pro Ile Met Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
            85                  90                  95

Phe Lys Val Ile Leu Pro Tyr Gly Thr Leu Val Ile Asp Gly Val Thr
            100                 105                 110

Pro Asn Lys Leu Asn Tyr Phe Gly Arg Pro Tyr Glu Gly Ile Ala Val
        115                 120                 125

Phe Asp Gly Lys Lys Ile Ser Val Thr Gly Thr Leu Trp Asn Gly Asn
    130                 135                 140

Lys Ile Ile Asp Glu Arg Leu Ile Thr Pro Asp
145                 150                 155

<210> SEQ ID NO 48
<211> LENGTH: 465
<212> TYPE: DNA
<213> ORGANISM: Artificial sequence
<220> FEATURE:
<223> OTHER INFORMATION: Synthetic

<400> SEQUENCE: 48
atgaaacatc accatcacca tcatgtcttc acactcgacg atttcgttgg ggactgggaa      60
cagacagccg cctacaacct ggaccaagtc cttgaacagg gaggtgtgtc cagtttgctg     120
cagaatctcg ccgtgtccgt aactccgatc atgaggattg tccggagcgg tgaaaatgcc     180
ctgaagatcg acatccatgt catcatcccg tatgaaggtc tgagcgccga ccaaatggcc     240
cagatcgaag aggtgtttaa ggtggtgtac cctgtggatg atcatcactt taaggtgatc     300
ctgccctatg gcacactggt aatcgacggg gttacgccga caagctgaa ctatttcggg      360 cggccgtatg aaggcatcgc cgtgttcgac ggcaaaaaga tctctgtaac agggaccctg     420
tggaacggca caaaattat cgacgagcgc ctgatcaccc ccgac                      465

<210> SEQ ID NO 49
<211> LENGTH: 155
<212> TYPE: PRT
<213> ORGANISM: Artificial sequence
<220> FEATURE:
<223> OTHER INFORMATION: Synthetic

<400> SEQUENCE: 49

Met Lys His His His His His His Val Phe Thr Leu Asp Asp Phe Val
1               5                   10                  15

Gly Asp Trp Glu Gln Thr Ala Ala Tyr Asn Leu Asp Gln Val Leu Glu
            20                  25                  30
```

```
Gln Gly Gly Val Ser Ser Leu Leu Gln Asn Leu Ala Val Ser Val Thr
        35                  40                  45

Pro Ile Met Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
                85                  90                  95

Phe Lys Val Ile Leu Pro Tyr Gly Thr Leu Val Ile Asp Gly Val Thr
               100                 105                 110

Pro Asn Lys Leu Asn Tyr Phe Gly Arg Pro Tyr Glu Gly Ile Ala Val
               115                 120                 125

Phe Asp Gly Lys Lys Ile Thr Ala Thr Gly Thr Leu Trp Asn Gly Asn
    130                 135                 140

Lys Ile Ile Asp Glu Arg Leu Ile Thr Pro Asp
145                 150                 155
```

<210> SEQ ID NO 50
<211> LENGTH: 465
<212> TYPE: DNA
<213> ORGANISM: Artificial sequence
<220> FEATURE:
<223> OTHER INFORMATION: Synthetic

<400> SEQUENCE: 50

```
atgaaacatc accatcacca tcatgtcttc acactcgacg atttcgttgg ggactgggaa      60
cagacagccg cctacaacct ggaccaagtc cttgaacagg gaggtgtgtc cagtttgctg     120
cagaatctcg ccgtgtccgt aactccgatc atgaggattg tccggagcgg tgaaaatgcc     180
ctgaagatcg acatccatgt catcatcccg tatgaaggtc tgagcgccga ccaaatggcc     240
cagatcgaag aggtgtttaa ggtggtgtac cctgtggatg atcatcactt taaggtgatc     300
ctgccctatg gcacactggt aatcgacggg gttacgccga acaagctgaa ctatttcgga     360
cggccgtatg aaggcatcgc cgtgttcgac ggcaaaaaga tcactgcaac agggaccctg     420
tggaacggca acaaaattat cgacgagcgc ctgatcaccc ccgac                     465
```

<210> SEQ ID NO 51
<211> LENGTH: 155
<212> TYPE: PRT
<213> ORGANISM: Artificial sequence
<220> FEATURE:
<223> OTHER INFORMATION: Synthetic

<400> SEQUENCE: 51

```
Met Lys His His His His His His Val Phe Thr Leu Asp Asp Phe Val
1                   5                   10                  15

Gly Asp Trp Glu Gln Thr Ala Ala Tyr Asn Leu Asp Gln Val Leu Glu
                20                  25                  30

Gln Gly Gly Val Ser Ser Leu Leu Gln Asn Leu Ala Val Ser Val Thr
        35                  40                  45

Pro Ile Met Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
                85                  90                  95
```

```
Phe Lys Val Ile Leu Pro Tyr Gly Thr Leu Val Ile Asp Gly Val Thr
            100                 105                 110

Pro Asn Lys Leu Asn Tyr Phe Gly Arg Pro Tyr Glu Gly Ile Ala Val
        115                 120                 125

Phe Asp Gly Lys Lys Ile Thr Thr Thr Gly Thr Leu Trp Asn Gly Asn
    130                 135                 140

Lys Ile Ile Asp Glu Arg Leu Ile Thr Pro Asp
145                 150                 155
```

```
<210> SEQ ID NO 52
<211> LENGTH: 465
<212> TYPE: DNA
<213> ORGANISM: Artificial sequence
<220> FEATURE:
<223> OTHER INFORMATION: Synthetic

<400> SEQUENCE: 52
atgaaacatc accatcacca tcatgtcttc acactcgacg atttcgttgg ggactgggaa      60
cagacagccg cctacaacct ggaccaagtc cttgaacagg gaggtgtgtc cagtttgctg     120
cagaatctcg ccgtgtccgt aactccgatc atgaggattg tccggagcgg tgaaaatgcc     180
ctgaagatcg acatccatgt catcatcccg tatgaaggtc tgagcgccga ccaaatggcc     240
cagatcgaag aggtgtttaa ggtggtgtac cctgtggatg atcatcactt taaggtgatc     300
ctgccctatg gcacactggt aatcgacggg gttacgccga caagctgaa ctatttcgga     360 cggccgtatg aaggcatcgc cgtgttcgac ggcaaaaaga tcactaccac agggaccctg     420
tggaacggca caaaaattat cgacgagcgc ctgatcaccc ccgac                     465
```

```
<210> SEQ ID NO 53
<211> LENGTH: 149
<212> TYPE: PRT
<213> ORGANISM: Artificial sequence
<220> FEATURE:
<223> OTHER INFORMATION: Synthetic

<400> SEQUENCE: 53

Met Val Phe Thr Leu Asp Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Met Arg Ile Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Lys Leu Asn Tyr Phe
            100                 105                 110

Gly Arg Pro Tyr Glu Gly Ile Ala Val Phe Asp Gly Lys Lys Ile Thr
        115                 120                 125

Thr Thr Gly Thr Leu Trp Asn Gly Asn Lys Ile Ile Asp Glu Arg Leu
    130                 135                 140

Ile Thr Pro Asp Gly
145
```

```
<210> SEQ ID NO 54
<211> LENGTH: 447
<212> TYPE: DNA
<213> ORGANISM: Artificial sequence
<220> FEATURE:
<223> OTHER INFORMATION: Synthetic

<400> SEQUENCE: 54
atggtcttca cactcgacga tttcgttggg gactgggaac agacagccgc ctacaacctg      60
gaccaagtcc ttgaacaggg aggtgtgtcc agtttgctgc agaatctcgc cgtgtccgta     120
actccgatca tgaggattgt ccggagcggt gaaaatgccc tgaagatcga catccatgtc     180
atcatcccgt atgaaggtct gagcgccgac caaatggccc agatcgaaga ggtgtttaag     240
gtggtgtacc ctgtggatga tcatcacttt aaggtgatcc tgccctatgg cacactggta     300
atcgacgggg ttacgccgaa caagctgaac tatttcggac ggccgtatga aggcatcgcc     360
gtgttcgacg gcaaaaagat cactaccaca gggaccctgt ggaacggcaa caaaattatc     420
gacgagcgcc tgatcacccc cgacggc                                         447

<210> SEQ ID NO 55
<211> LENGTH: 147
<212> TYPE: PRT
<213> ORGANISM: Artificial sequence
<220> FEATURE:
<223> OTHER INFORMATION: Synthetic

<400> SEQUENCE: 55

Met Val Phe Thr Leu Asp Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Met Arg Ile Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Lys Leu Asn Tyr Phe
            100                 105                 110

Gly Arg Pro Tyr Glu Gly Ile Ala Val Phe Asp Gly Lys Lys Ile Thr
        115                 120                 125

Thr Thr Gly Thr Leu Trp Asn Gly Asn Lys Ile Ile Asp Glu Arg Leu
    130                 135                 140

Ile Thr Pro
145

<210> SEQ ID NO 56
<211> LENGTH: 441
<212> TYPE: DNA
<213> ORGANISM: Artificial sequence
<220> FEATURE:
<223> OTHER INFORMATION: Synthetic

<400> SEQUENCE: 56
atggtcttca cactcgacga tttcgttggg gactgggaac agacagccgc ctacaacctg      60
gaccaagtcc ttgaacaggg aggtgtgtcc agtttgctgc agaatctcgc cgtgtccgta     120
```
actccgatca tgaggattgt ccggagcggt gaaaatgccc tgaagatcga catccatgtc          180
atcatcccgt atgaaggtct gagcgccgac caaatggccc agatcgaaga ggtgtttaag          240
gtggtgtacc ctgtggatga tcatcacttt aaggtgatcc tgccctatgg cacactggta          300
atcgacgggg ttacgccgaa caagctgaac tatttcggac ggccgtatga aggcatcgcc          360
gtgttcgacg gcaaaaagat cactaccaca gggaccctgt ggaacggcaa caaaattatc          420
gacgagcgcc tgatcacccc c                                                     441

<210> SEQ ID NO 57
<211> LENGTH: 146
<212> TYPE: PRT
<213> ORGANISM: Artificial sequence
<220> FEATURE:
<223> OTHER INFORMATION: Synthetic

<400> SEQUENCE: 57

Met Val Phe Thr Leu Asp Asp Phe Val Gly Asp Trp Glu Gln Thr Ala
1               5                   10                  15

Ala Tyr Asn Leu Asp Gln Val Leu Glu Gln Gly Gly Val Ser Ser Leu
                20                  25                  30

Leu Gln Asn Leu Ala Val Ser Val Thr Pro Ile Met Arg Ile Val Arg
            35                  40                  45

Ser Gly Glu Asn Ala Leu Lys Ile Asp Ile His Val Ile Pro Tyr
        50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Lys Leu Asn Tyr Phe
            100                 105                 110

Gly Arg Pro Tyr Glu Gly Ile Ala Val Phe Asp Gly Lys Lys Ile Thr
        115                 120                 125

Thr Thr Gly Thr Leu Trp Asn Gly Asn Lys Ile Ile Asp Glu Arg Leu
    130                 135                 140

Ile Thr
145

<210> SEQ ID NO 58
<211> LENGTH: 438
<212> TYPE: DNA
<213> ORGANISM: Artificial sequence
<220> FEATURE:
<223> OTHER INFORMATION: Synthetic

<400> SEQUENCE: 58
atggtcttca cactcgacga tttcgttggg gactgggaac agacagccgc ctacaacctg           60
gaccaagtcc ttgaacaggg aggtgtgtcc agtttgctgc agaatctcgc cgtgtccgta          120
actccgatca tgaggattgt ccggagcggt gaaaatgccc tgaagatcga catccatgtc          180
atcatcccgt atgaaggtct gagcgccgac caaatggccc agatcgaaga ggtgtttaag          240
gtggtgtacc ctgtggatga tcatcacttt aaggtgatcc tgccctatgg cacactggta          300
atcgacgggg ttacgccgaa caagctgaac tatttcggac ggccgtatga aggcatcgcc          360
gtgttcgacg gcaaaaagat cactaccaca gggaccctgt ggaacggcaa caaaattatc          420
gacgagcgcc tgatcacc                                                        438

```
<210> SEQ ID NO 59
<211> LENGTH: 150
<212> TYPE: PRT
<213> ORGANISM: Artificial sequence
<220> FEATURE:
<223> OTHER INFORMATION: Synthetic

<400> SEQUENCE: 59

Met Val Phe Thr Leu Asp Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Met Arg Ile Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Lys Leu Asn Tyr Phe
            100                 105                 110

Gly Arg Pro Tyr Glu Gly Ile Ala Val Phe Asp Gly Lys Lys Ile Thr
        115                 120                 125

Thr Thr Gly Thr Leu Trp Asn Gly Asn Lys Ile Ile Asp Glu Arg Leu
    130                 135                 140

Ile Thr Pro Asp Gly Ser
145                 150

<210> SEQ ID NO 60
<211> LENGTH: 450
<212> TYPE: DNA
<213> ORGANISM: Artificial sequence
<220> FEATURE:
<223> OTHER INFORMATION: Synthetic

<400> SEQUENCE: 60
atggtcttca cactcgacga tttcgttggg gactgggaac agacagccgc ctacaacctg      60
gaccaagtcc ttgaacaggg aggtgtgtcc agtttgctgc agaatctcgc cgtgtccgta     120
actccgatca tgaggattgt ccggagcggt gaaaatgccc tgaagatcga catccatgtc     180
atcatcccgt atgaaggtct gagcgccgac caaatggccc agatcgaaga ggtgtttaag     240
gtggtgtacc ctgtggatga tcatcacttt aaggtgatcc tgccctatgg cacactggta     300
atcgacgggg ttacgccgaa caagctgaac tatttcggac ggccgtatga aggcatcgcc     360
gtgttcgacg gcaaaaagat cactaccaca gggaccctgt ggaacggcaa caaaattatc     420
gacgagcgcc tgatcacccc cgacggcagc                                      450

<210> SEQ ID NO 61
<211> LENGTH: 164
<212> TYPE: PRT
<213> ORGANISM: Artificial sequence
<220> FEATURE:
<223> OTHER INFORMATION: Synthetic

<400> SEQUENCE: 61

Met Phe Thr Leu Glu Asp Phe Val Gly Asp Trp Glu Gln Thr Ala Ala
1               5                   10                  15

Tyr Asn Leu Asp Gln Val Leu Glu Gln Gly Gly Val Ser Ser Leu Leu
```

```
                20              25              30

Gln Asn Leu Ala Val Ser Val Thr Pro Ile Gln Arg Ile Val Arg Ser
        35              40              45

Gly Glu Asn Ala Leu Lys Ile Asp Ile His Val Ile Ile Pro Tyr Glu
    50              55              60

Gly Leu Ser Ala Asp Gln Met Ala Gln Ile Glu Glu Val Phe Lys Val
65              70              75              80

Val Tyr Pro Val Asp Asp His His Phe Lys Val Ile Leu Pro Tyr Gly
                85              90              95

Thr Leu Val Ile Asp Gly Val Thr Pro Asn Met Leu Asn Tyr Phe Gly
            100             105             110

Arg Pro Tyr Glu Gly Ile Ala Val Phe Asp Gly Lys Lys Ile Thr Val
        115             120             125

Thr Gly Thr Leu Trp Asn Gly Asn Lys Ile Ile Asp Glu Arg Leu Ile
        130             135             140

Thr Pro Asp Gly Ser Met Leu Phe Arg Val Thr Ile Asn Ser His His
145             150             155             160

His His His His
```

```
<210> SEQ ID NO 62
<211> LENGTH: 495
<212> TYPE: DNA
<213> ORGANISM: Artificial sequence
<220> FEATURE:
<223> OTHER INFORMATION: Synthetic

<400> SEQUENCE: 62
atgttcacac tcgaagattt cgttggggac tgggaacaga cagccgccta caacctggac     60
caagtccttg aacagggagg tgtgtccagt ttgctgcaga atctcgccgt gtccgtaact    120
ccgatccaaa ggattgtccg gagcggtgaa aatgccctga agatcgacat ccatgtcatc    180
atcccgtatg aaggtctgag cgccgaccaa atggcccaga tcgaagaggt gtttaaggtg    240
gtgtaccctg tggatgatca tcactttaag gtgatcctgc cctatggcac actggtaatc    300
gacggggtta cgccgaacat gctgaactat ttcggacggc cgtatgaagg catcgccgtg    360
ttcgacggca aaaagatcac tgtaacaggg accctgtgga cggcaacaa aattatcgac     420 gagcgcctga tcaccccga cggctccatg ctgttccgag taaccatcaa cagccatcat    480
caccatcacc actaa                                                     495
```

```
<210> SEQ ID NO 63
<211> LENGTH: 163
<212> TYPE: PRT
<213> ORGANISM: Artificial sequence
<220> FEATURE:
<223> OTHER INFORMATION: Synthetic

<400> SEQUENCE: 63

Met Thr Leu Glu Asp Phe Val Gly Asp Trp Glu Gln Thr Ala Ala Tyr
1               5               10              15

Asn Leu Asp Gln Val Leu Glu Gln Gly Gly Val Ser Ser Leu Leu Gln
            20              25              30

Asn Leu Ala Val Ser Val Thr Pro Ile Gln Arg Ile Val Arg Ser Gly
        35              40              45

Glu Asn Ala Leu Lys Ile Asp Ile His Val Ile Ile Pro Tyr Glu Gly
    50              55              60

Leu Ser Ala Asp Gln Met Ala Gln Ile Glu Glu Val Phe Lys Val Val
```

```
65              70              75              80

Tyr Pro Val Asp Asp His His Phe Lys Val Ile Leu Pro Tyr Gly Thr
                85              90              95

Leu Val Ile Asp Gly Val Thr Pro Asn Met Leu Asn Tyr Phe Gly Arg
                100             105             110

Pro Tyr Glu Gly Ile Ala Val Phe Asp Gly Lys Lys Ile Thr Val Thr
            115             120             125

Gly Thr Leu Trp Asn Gly Asn Lys Ile Ile Asp Glu Arg Leu Ile Thr
        130             135             140

Pro Asp Gly Ser Met Leu Phe Arg Val Thr Ile Asn Ser His His His
145             150             155             160

His His His
```

```
<210> SEQ ID NO 64
<211> LENGTH: 492
<212> TYPE: DNA
<213> ORGANISM: Artificial sequence
<220> FEATURE:
<223> OTHER INFORMATION: Synthetic

<400> SEQUENCE: 64
atgacactcg aagatttcgt tggggactgg aacagacag ccgcctacaa cctggaccaa       60
gtccttgaac agggaggtgt gtccagtttg ctgcagaatc tcgccgtgtc cgtaactccg      120
atccaaagga ttgtccggag cggtgaaaat gccctgaaga tcgacatcca tgtcatcatc      180
ccgtatgaag gtctgagcgc cgaccaaatg gcccagatcg aagaggtgtt taaggtggtg      240
taccctgtgg atgatcatca ctttaaggtg atcctgccct atggcacact ggtaatcgac      300
ggggttacgc cgaacatgct gaactatttc ggacggccgt atgaaggcat cgccgtgttc      360
gacggcaaaa agatcactgt aacagggacc ctgtggaacg gcaacaaaat tatcgacgag      420
cgcctgatca cccccgacgg ctccatgctg ttccgagtaa ccatcaacag ccatcatcac      480
catcaccact aa                                                          492
```

```
<210> SEQ ID NO 65
<211> LENGTH: 162
<212> TYPE: PRT
<213> ORGANISM: Artificial sequence
<220> FEATURE:
<223> OTHER INFORMATION: Synthetic

<400> SEQUENCE: 65

Met Leu Glu Asp Phe Val Gly Asp Trp Glu Gln Thr Ala Ala Tyr Asn
1               5               10              15

Leu Asp Gln Val Leu Glu Gln Gly Gly Val Ser Ser Leu Leu Gln Asn
                20              25              30

Leu Ala Val Ser Val Thr Pro Ile Gln Arg Ile Val Arg Ser Gly Glu
            35              40              45

Asn Ala Leu Lys Ile Asp Ile His Val Ile Ile Pro Tyr Glu Gly Leu
        50              55              60

Ser Ala Asp Gln Met Ala Gln Ile Glu Glu Val Phe Lys Val Val Tyr
65              70              75              80

Pro Val Asp Asp His His Phe Lys Val Ile Leu Pro Tyr Gly Thr Leu
                85              90              95

Val Ile Asp Gly Val Thr Pro Asn Met Leu Asn Tyr Phe Gly Arg Pro
                100             105             110

Tyr Glu Gly Ile Ala Val Phe Asp Gly Lys Lys Ile Thr Val Thr Gly
```

-continued

```
                115                 120                 125
Thr Leu Trp Asn Gly Asn Lys Ile Ile Asp Glu Arg Leu Ile Thr Pro
    130                 135                 140
Asp Gly Ser Met Leu Phe Arg Val Thr Ile Asn Ser His His His His
145                 150                 155                 160
His His
```

<210> SEQ ID NO 66
<211> LENGTH: 489
<212> TYPE: DNA
<213> ORGANISM: Artificial sequence
<220> FEATURE:
<223> OTHER INFORMATION: Synthetic

<400> SEQUENCE: 66

```
atgctcgaag atttcgttgg ggactgggaa cagacagccg cctacaacct ggaccaagtc      60
cttgaacagg gaggtgtgtc cagtttgctg cagaatctcg ccgtgtccgt aactccgatc     120
caaaggattg tccggagcgg tgaaaatgcc ctgaagatcg acatccatgt catcatcccg     180
tatgaaggtc tgagcgccga ccaaatggcc cagatcgaag aggtgtttaa ggtggtgtac     240
cctgtggatg atcatcactt taaggtgatc ctgccctatg gcacactggt aatcgacggg     300
gttacgccga acatgctgaa ctatttcgga cggccgtatg aaggcatcgc cgtgttcgac     360
ggcaaaaaga tcactgtaac agggaccctg tggaacggca acaaaattat cgacgagcgc     420 ctgatcacc ccgacggctc catgctgttc cgagtaacca tcaacagcca tcatcaccat     480
caccactaa                                                            489
```

<210> SEQ ID NO 67
<211> LENGTH: 161
<212> TYPE: PRT
<213> ORGANISM: Artificial sequence
<220> FEATURE:
<223> OTHER INFORMATION: Synthetic

<400> SEQUENCE: 67

```
Met Glu Asp Phe Val Gly Asp Trp Glu Gln Thr Ala Ala Tyr Asn Leu
1               5                   10                  15
Asp Gln Val Leu Glu Gln Gly Gly Val Ser Ser Leu Leu Gln Asn Leu
            20                  25                  30
Ala Val Ser Val Thr Pro Ile Gln Arg Ile Val Arg Ser Gly Glu Asn
            35                  40                  45
Ala Leu Lys Ile Asp Ile His Val Ile Ile Pro Tyr Glu Gly Leu Ser
        50                  55                  60
Ala Asp Gln Met Ala Gln Ile Glu Glu Val Phe Lys Val Val Tyr Pro
65                  70                  75                  80
Val Asp Asp His His Phe Lys Val Ile Leu Pro Tyr Gly Thr Leu Val
                85                  90                  95
Ile Asp Gly Val Thr Pro Asn Met Leu Asn Tyr Phe Gly Arg Pro Tyr
            100                 105                 110
Glu Gly Ile Ala Val Phe Asp Gly Lys Lys Ile Thr Val Thr Gly Thr
            115                 120                 125
Leu Trp Asn Gly Asn Lys Ile Ile Asp Glu Arg Leu Ile Thr Pro Asp
        130                 135                 140
Gly Ser Met Leu Phe Arg Val Thr Ile Asn Ser His His His His His
145                 150                 155                 160
His
```

<210> SEQ ID NO 68
<211> LENGTH: 486
<212> TYPE: DNA
<213> ORGANISM: Artificial sequence
<220> FEATURE:
<223> OTHER INFORMATION: Synthetic

<400> SEQUENCE: 68
atggaagatt cgttggggga ctgggaacag acagccgcct acaacctgga ccaagtcctt      60
gaacagggag gtgtgtccag tttgctgcag aatctcgccg tgtccgtaac tccgatccaa     120
aggattgtcc ggagcggtga aaatgccctg aagatcgaca tccatgtcat catcccgtat     180
gaaggtctga gcgccgacca aatggcccag atcgaagagg tgtttaaggt ggtgtaccct     240
gtggatgatc atcactttaa ggtgatcctg ccctatggca cactggtaat cgacgggggtt     300 acgccgaaca tgctgaacta tttcggacgg ccgtatgaag gcatcgccgt gttcgacggc     360
aaaaagatca ctgtaacagg gaccctgtgg aacggcaaca aaattatcga cgagcgcctg     420
atcacccccg acggctccat gctgttccga gtaaccatca acagccatca tcaccatcac     480
cactaa                                                                486

<210> SEQ ID NO 69
<211> LENGTH: 174
<212> TYPE: PRT
<213> ORGANISM: Artificial sequence
<220> FEATURE:
<223> OTHER INFORMATION: Synthetic

<400> SEQUENCE: 69

Met Phe Lys Lys Ile Ser Gly Ser Ser Gly Val Phe Thr Leu Glu Asp
1               5                   10                  15

Phe Val Gly Asp Trp Glu Gln Thr Ala Ala Tyr Asn Leu Asp Gln Val
                20                  25                  30

Leu Glu Gln Gly Gly Val Ser Ser Leu Leu Gln Asn Leu Ala Val Ser
            35                  40                  45

Val Thr Pro Ile Gln Arg Ile Val Arg Ser Gly Glu Asn Ala Leu Lys
        50                  55                  60

Ile Asp Ile His Val Ile Ile Pro Tyr Glu Gly Leu Ser Ala Asp Gln
65                  70                  75                  80

Met Ala Gln Ile Glu Glu Val Phe Lys Val Val Tyr Pro Val Asp Asp
                85                  90                  95

His His Phe Lys Val Ile Leu Pro Tyr Gly Thr Leu Val Ile Asp Gly
                100                 105                 110

Val Thr Pro Asn Met Leu Asn Tyr Phe Gly Arg Pro Tyr Glu Gly Ile
            115                 120                 125

Ala Val Phe Asp Gly Lys Lys Ile Thr Val Thr Gly Thr Leu Trp Asn
        130                 135                 140

Gly Asn Lys Ile Ile Asp Glu Arg Leu Ile Thr Pro Asp Gly Ser Met
145                 150                 155                 160

Leu Phe Arg Val Thr Ile Asn Ser His His His His His
                165                 170

<210> SEQ ID NO 70
<211> LENGTH: 525
<212> TYPE: DNA
<213> ORGANISM: Artificial sequence
<220> FEATURE:
<223> OTHER INFORMATION: Synthetic

<400> SEQUENCE: 70
atgttcaaga agattagcgg ctcgagcggt gtcttcacac tcgaagattt cgttggggac        60
tgggaacaga cagccgccta caacctggac caagtccttg aacagggagg tgtgtccagt       120
ttgctgcaga atctcgccgt gtccgtaact ccgatccaaa ggattgtccg gagcggtgaa       180
aatgccctga agatcgacat ccatgtcatc atcccgtatg aaggtctgag cgccgaccaa       240
atggcccaga tcgaagaggt gtttaaggtg gtgtaccctg tggatgatca tcactttaag       300
gtgatcctgc cctatggcac actggtaatc gacggggtta cgccgaacat gctgaactat       360
ttcggacggc cgtatgaagg catcgccgtg ttcgacggca aaaagatcac tgtaacaggg       420
accctgtgga acggcaacaa aattatcgac gagcgcctga tcaccccga cggctccatg       480 ctgttccgag taaccatcaa cagccatcat caccatcacc actaa                       525

<210> SEQ ID NO 71
<211> LENGTH: 173
<212> TYPE: PRT
<213> ORGANISM: Artificial sequence
<220> FEATURE:
<223> OTHER INFORMATION: Synthetic

<400> SEQUENCE: 71

Met Lys Lys Ile Ser Gly Ser Ser Gly Val Phe Thr Leu Glu Asp Phe
1               5                   10                  15

Val Gly Asp Trp Glu Gln Thr Ala Ala Tyr Asn Leu Asp Gln Val Leu
                20                  25                  30

Glu Gln Gly Gly Val Ser Ser Leu Leu Gln Asn Leu Ala Val Ser Val
            35                  40                  45

Thr Pro Ile Gln Arg Ile Val Arg Ser Gly Glu Asn Ala Leu Lys Ile
        50                  55                  60

Asp Ile His Val Ile Ile Pro Tyr Glu Gly Leu Ser Ala Asp Gln Met
65                  70                  75                  80

Ala Gln Ile Glu Glu Val Phe Lys Val Val Tyr Pro Val Asp Asp His
                85                  90                  95

His Phe Lys Val Ile Leu Pro Tyr Gly Thr Leu Val Ile Asp Gly Val
                100                 105                 110

Thr Pro Asn Met Leu Asn Tyr Phe Gly Arg Pro Tyr Glu Gly Ile Ala
            115                 120                 125

Val Phe Asp Gly Lys Lys Ile Thr Val Thr Gly Thr Leu Trp Asn Gly
        130                 135                 140

Asn Lys Ile Ile Asp Glu Arg Leu Ile Thr Pro Asp Gly Ser Met Leu
145                 150                 155                 160

Phe Arg Val Thr Ile Asn Ser His His His His His
                165                 170

<210> SEQ ID NO 72
<211> LENGTH: 522
<212> TYPE: DNA
<213> ORGANISM: Artificial sequence
<220> FEATURE:
<223> OTHER INFORMATION: Synthetic

<400> SEQUENCE: 72
atgaagaaga ttagcggctc gagcggtgtc ttcacactcg aagatttcgt tggggactgg        60
gaacagacag ccgcctacaa cctggaccaa gtccttgaac agggaggtgt gtccagtttg       120
ctgcagaatc tcgccgtgtc cgtaactccg atccaaagga ttgtccggag cggtgaaaat       180

-continued

```
gccctgaaga tcgacatcca tgtcatcatc ccgtatgaag gtctgagcgc cgaccaaatg      240
gcccagatcg aagaggtgtt taaggtggtg taccctgtgg atgatcatca ctttaaggtg      300
atcctgccct atggcacact ggtaatcgac ggggttacgc cgaacatgct gaactatttc      360
ggacggccgt atgaaggcat cgccgtgttc gacggcaaaa agatcactgt aacagggacc      420
ctgtggaacg gcaacaaaat tatcgacgag cgcctgatca cccccgacgg ctccatgctg      480
ttccgagtaa ccatcaacag ccatcatcac catcaccact aa                         522
```

```
<210> SEQ ID NO 73
<211> LENGTH: 172
<212> TYPE: PRT
<213> ORGANISM: Artificial sequence
<220> FEATURE:
<223> OTHER INFORMATION: Synthetic

<400> SEQUENCE: 73

Met Lys Ile Ser Gly Ser Ser Gly Val Phe Thr Leu Glu Asp Phe Val
1               5                   10                  15

Gly Asp Trp Glu Gln Thr Ala Ala Tyr Asn Leu Asp Gln Val Leu Glu
            20                  25                  30

Gln Gly Gly Val Ser Ser Leu Leu Gln Asn Leu Ala Val Ser Val Thr
        35                  40                  45

Pro Ile Gln Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
            85                  90                  95

Phe Lys Val Ile Leu Pro Tyr Gly Thr Leu Val Ile Asp Gly Val Thr
            100                 105                 110

Pro Asn Met Leu Asn Tyr Phe Gly Arg Pro Tyr Glu Gly Ile Ala Val
        115                 120                 125

Phe Asp Gly Lys Lys Ile Thr Val Thr Gly Thr Leu Trp Asn Gly Asn
    130                 135                 140

Lys Ile Ile Asp Glu Arg Leu Ile Thr Pro Asp Gly Ser Met Leu Phe
145                 150                 155                 160

Arg Val Thr Ile Asn Ser His His His His His His
            165                 170
```

```
<210> SEQ ID NO 74
<211> LENGTH: 519
<212> TYPE: DNA
<213> ORGANISM: Artificial sequence
<220> FEATURE:
<223> OTHER INFORMATION: Synthetic

<400> SEQUENCE: 74
atgaagatta gcggctcgag cggtgtcttc acactcgaag atttcgttgg ggactgggaa       60
cagacagccg cctacaacct ggaccaagtc cttgaacagg gaggtgtgtc cagtttgctg      120
cagaatctcg ccgtgtccgt aactccgatc caaaggattg tccggagcgg tgaaaatgcc      180
ctgaagatcg acatccatgt catcatcccg tatgaaggtc tgagcgccga ccaaatggcc      240
cagatcgaag aggtgtttaa ggtggtgtac cctgtggatg atcatcactt taaggtgatc      300
ctgccctatg gcacactggt aatcgacggg gttacgccga acatgctgaa ctatttcgga      360
cggccgtatg aaggcatcgc cgtgttcgac ggcaaaaaga tcactgtaac agggaccctg      420
```
tggaacggca acaaaattat cgacgagcgc ctgatcaccc ccgacggctc catgctgttc        480
cgagtaacca tcaacagcca tcatcaccat caccactaa                              519

<210> SEQ ID NO 75
<211> LENGTH: 171
<212> TYPE: PRT
<213> ORGANISM: Artificial sequence
<220> FEATURE:
<223> OTHER INFORMATION: Synthetic

<400> SEQUENCE: 75

Met Ile Ser Gly Ser Ser Gly Val Phe Thr Leu Glu Asp Phe Val Gly
1               5                   10                  15

Asp Trp Glu Gln Thr Ala Ala Tyr Asn Leu Asp Gln Val Leu Glu Gln
            20                  25                  30

Gly Gly Val Ser Ser Leu Leu Gln Asn Leu Ala Val Ser Val Thr Pro
        35                  40                  45

Ile Gln Arg Ile Val Arg Ser Gly Glu Asn Ala Leu Lys Ile Asp Ile
    50                  55                  60

His Val Ile Ile Pro Tyr Glu Gly Leu Ser Ala Asp Gln Met Ala Gln
65                  70                  75                  80

Ile Glu Glu Val Phe Lys Val Val Tyr Pro Val Asp Asp His His Phe
                85                  90                  95

Lys Val Ile Leu Pro Tyr Gly Thr Leu Val Ile Asp Gly Val Thr Pro
            100                 105                 110

Asn Met Leu Asn Tyr Phe Gly Arg Pro Tyr Glu Gly Ile Ala Val Phe
        115                 120                 125

Asp Gly Lys Lys Ile Thr Val Thr Gly Thr Leu Trp Asn Gly Asn Lys
    130                 135                 140

Ile Ile Asp Glu Arg Leu Ile Thr Pro Asp Gly Ser Met Leu Phe Arg
145                 150                 155                 160

Val Thr Ile Asn Ser His His His His His His
            165                 170

<210> SEQ ID NO 76
<211> LENGTH: 516
<212> TYPE: DNA
<213> ORGANISM: Artificial sequence
<220> FEATURE:
<223> OTHER INFORMATION: Synthetic

<400> SEQUENCE: 76
atgattagcg gctcgagcgg tgtcttcaca ctcgaagatt tcgttgggga ctgggaacag        60
acagccgcct acaacctgga ccaagtcctt gaacagggag gtgtgtccag tttgctgcag       120
aatctcgccg tgtccgtaac tccgatccaa aggattgtcc ggagcggtga aaatgccctg       180
aagatcgaca tccatgtcat catcccgtat gaaggtctga gcgccgacca atggcccag        240 atcgaagagg tgtttaaggt ggtgtaccct gtggatgatc atcactttaa ggtgatcctg       300
ccctatggca cactggtaat cgacggggtt acgccgaaca tgctgaacta tttcggacgg       360
ccgtatgaag catcgccgt gttcgacggc aaaaagatca ctgtaacagg accctgtgg        420 aacggcaaca aaattatcga cgagcgcctg atcacccccg acggctccat gctgttccga       480
gtaaccatca acagccatca tcaccatcac cactaa                                 516

<210> SEQ ID NO 77
<211> LENGTH: 170

<212> TYPE: PRT
<213> ORGANISM: Artificial sequence
<220> FEATURE:
<223> OTHER INFORMATION: Synthetic

<400> SEQUENCE: 77

Met Ser Gly Ser Ser Gly Val Phe Thr Leu Glu Asp Phe Val Gly Asp
1               5                   10                  15

Trp Glu Gln Thr Ala Ala Tyr Asn Leu Asp Gln Val Leu Glu Gln Gly
                20                  25                  30

Gly Val Ser Ser Leu Leu Gln Asn Leu Ala Val Ser Val Thr Pro Ile
            35                  40                  45

Gln Arg Ile Val Arg Ser Gly Glu Asn Ala Leu Lys Ile Asp Ile His
        50                  55                  60

Val Ile Ile Pro Tyr Glu Gly Leu Ser Ala Asp Gln Met Ala Gln Ile
65                  70                  75                  80

Glu Glu Val Phe Lys Val Val Tyr Pro Val Asp Asp His His Phe Lys
                85                  90                  95

Val Ile Leu Pro Tyr Gly Thr Leu Val Ile Asp Gly Val Thr Pro Asn
            100                 105                 110

Met Leu Asn Tyr Phe Gly Arg Pro Tyr Glu Gly Ile Ala Val Phe Asp
        115                 120                 125

Gly Lys Lys Ile Thr Val Thr Gly Thr Leu Trp Asn Gly Asn Lys Ile
    130                 135                 140

Ile Asp Glu Arg Leu Ile Thr Pro Asp Gly Ser Met Leu Phe Arg Val
145                 150                 155                 160

Thr Ile Asn Ser His His His His His His
                165                 170

<210> SEQ ID NO 78
<211> LENGTH: 513
<212> TYPE: DNA
<213> ORGANISM: Artificial sequence
<220> FEATURE:
<223> OTHER INFORMATION: Synthetic

<400> SEQUENCE: 78
atgagcggct cgagcggtgt cttcacactc gaagatttcg ttggggactg ggaacagaca      60
gccgcctaca acctggacca agtccttgaa cagggaggtg tgtccagttt gctgcagaat     120
ctcgccgtgt ccgtaactcc gatccaaagg attgtccgga gcggtgaaaa tgccctgaag     180
atcgacatcc atgtcatcat cccgtatgaa ggtctgagcg ccgaccaaat ggcccagatc     240
gaagaggtgt ttaaggtggt gtaccctgtg gatgatcatc actttaaggt gatcctgccc     300
tatggcacac tggtaatcga cggggttacg ccgaacatgc tgaactattt cggacggccg     360
tatgaaggca tcgccgtgtt cgacggcaaa aagatcactg taacagggac cctgtggaac     420
ggcaacaaaa ttatcgacga gcgcctgatc accccgacg gctccatgct gttccgagta     480
accatcaaca gccatcatca ccatcaccac taa                                  513

<210> SEQ ID NO 79
<211> LENGTH: 158
<212> TYPE: PRT
<213> ORGANISM: Artificial sequence
<220> FEATURE:
<223> OTHER INFORMATION: Synthetic

<400> SEQUENCE: 79

Met Lys His His His His His His Val Phe Thr Leu Asp Asp Phe Val

```
1               5                   10                  15
Gly Asp Trp Glu Gln Thr Ala Ala Tyr Asn Leu Asp Gln Val Leu Glu
            20                  25                  30

Gln Gly Gly Val Ser Ser Leu Leu Gln Asn Leu Ala Val Ser Val Thr
            35                  40                  45

Pro Ile Met Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
            85                  90                  95

Phe Lys Val Ile Leu Pro Tyr Gly Thr Leu Val Ile Asp Gly Val Thr
            100                 105                 110

Pro Asn Lys Leu Asn Tyr Phe Gly Arg Pro Tyr Glu Gly Ile Ala Val
            115                 120                 125

Phe Asp Gly Lys Lys Ile Thr Thr Thr Gly Thr Leu Trp Asn Gly Asn
    130                 135                 140

Lys Ile Ile Asp Glu Arg Leu Ile Thr Pro Asp Gly Ser Met
145                 150                 155
```

<210> SEQ ID NO 80
<211> LENGTH: 477
<212> TYPE: DNA
<213> ORGANISM: Artificial sequence
<220> FEATURE:
<223> OTHER INFORMATION: Synthetic

<400> SEQUENCE: 80

```
atgaaacatc accatcacca tcatgtcttc acactcgacg atttcgttgg ggactgggaa      60
cagacagccg cctacaacct ggaccaagtc cttgaacagg gaggtgtgtc cagtttgctg     120
cagaatctcg ccgtgtccgt aactccgatc atgaggattg tccggagcgg tgaaaatgcc     180
ctgaagatcg acatccatgt catcatcccg tatgaaggtc tgagcgccga ccaaatggcc     240
cagatcgaag aggtgtttaa ggtggtgtac cctgtggatg atcatcactt taaggtgatc     300
ctgccctatg gcacactggt aatcgacggg gttacgccga caagctgaa ctatttcgga     360 cggccgtatg aaggcatcgc cgtgttcgac ggcaaaaaga tcactaccac agggaccctg     420
tggaacggca acaaaattat cgacgagcgc ctgatcaccc ccgacggcag catgtaa       477
```

<210> SEQ ID NO 81
<211> LENGTH: 159
<212> TYPE: PRT
<213> ORGANISM: Artificial sequence
<220> FEATURE:
<223> OTHER INFORMATION: Synthetic

<400> SEQUENCE: 81

```
Met Lys His His His His His His Val Phe Thr Leu Asp Asp Phe Val
1               5                   10                  15

Gly Asp Trp Glu Gln Thr Ala Ala Tyr Asn Leu Asp Gln Val Leu Glu
            20                  25                  30

Gln Gly Gly Val Ser Ser Leu Leu Gln Asn Leu Ala Val Ser Val Thr
            35                  40                  45

Pro Ile Met Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80
```

```
Gln Ile Glu Glu Val Phe Lys Val Val Tyr Pro Val Asp Asp His His
            85                  90                  95

Phe Lys Val Ile Leu Pro Tyr Gly Thr Leu Val Ile Asp Gly Val Thr
                100                 105                 110

Pro Asn Lys Leu Asn Tyr Phe Gly Arg Pro Tyr Glu Gly Ile Ala Val
            115                 120                 125

Phe Asp Gly Lys Lys Ile Thr Thr Thr Gly Thr Leu Trp Asn Gly Asn
    130                 135                 140

Lys Ile Ile Asp Glu Arg Leu Ile Thr Pro Asp Gly Ser Met Leu
145                 150                 155
```

<210> SEQ ID NO 82
<211> LENGTH: 480
<212> TYPE: DNA
<213> ORGANISM: Artificial sequence
<220> FEATURE:
<223> OTHER INFORMATION: Synthetic

<400> SEQUENCE: 82

```
atgaaacatc accatcacca tcatgtcttc acactcgacg atttcgttgg ggactgggaa      60
cagacagccg cctacaacct ggaccaagtc cttgaacagg gaggtgtgtc cagtttgctg     120
cagaatctcg ccgtgtccgt aactccgatc atgaggattg tccggagcgg tgaaaatgcc     180
ctgaagatcg acatccatgt catcatcccg tatgaaggtc tgagcgccga ccaaatggcc     240
cagatcgaag aggtgtttaa ggtggtgtac cctgtggatg atcatcactt taaggtgatc     300
ctgccctatg gcacactggt aatcgacggg gttacgccga acaagctgaa ctatttcgga     360
cggccgtatg aaggcatcgc cgtgttcgac ggcaaaaaga tcactaccac agggaccctg     420
tggaacggca acaaaattat cgacgagcgc ctgatcaccc ccgacggcag catgctgtaa     480
```

<210> SEQ ID NO 83
<211> LENGTH: 160
<212> TYPE: PRT
<213> ORGANISM: Artificial sequence
<220> FEATURE:
<223> OTHER INFORMATION: Synthetic

<400> SEQUENCE: 83

```
Met Lys His His His His His His Val Phe Thr Leu Asp Asp Phe Val
1               5                   10                  15

Gly Asp Trp Glu Gln Thr Ala Ala Tyr Asn Leu Asp Gln Val Leu Glu
                20                  25                  30

Gln Gly Gly Val Ser Ser Leu Leu Gln Asn Leu Ala Val Ser Val Thr
            35                  40                  45

Pro Ile Met Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
            85                  90                  95

Phe Lys Val Ile Leu Pro Tyr Gly Thr Leu Val Ile Asp Gly Val Thr
                100                 105                 110

Pro Asn Lys Leu Asn Tyr Phe Gly Arg Pro Tyr Glu Gly Ile Ala Val
            115                 120                 125

Phe Asp Gly Lys Lys Ile Thr Thr Thr Gly Thr Leu Trp Asn Gly Asn
    130                 135                 140
```

```
Lys Ile Ile Asp Glu Arg Leu Ile Thr Pro Asp Gly Ser Met Leu Phe
145             150             155             160
```

<210> SEQ ID NO 84
<211> LENGTH: 483
<212> TYPE: DNA
<213> ORGANISM: Artificial sequence
<220> FEATURE:
<223> OTHER INFORMATION: Synthetic

<400> SEQUENCE: 84

```
atgaaacatc accatcacca tcatgtcttc acactcgacg atttcgttgg ggactgggaa      60
cagacagccg cctacaacct ggaccaagtc cttgaacagg gaggtgtgtc cagtttgctg     120
cagaatctcg ccgtgtccgt aactccgatc atgaggattg tccggagcgg tgaaaatgcc     180
ctgaagatcg acatccatgt catcatcccg tatgaaggtc tgagcgccga ccaaatggcc     240
cagatcgaag aggtgtttaa ggtggtgtac cctgtggatg atcatcactt taaggtgatc     300
ctgccctatg gcacactggt aatcgacggg gttacgccga caagctgaa ctatttcgga     360 cggccgtatg aaggcatcgc cgtgttcgac ggcaaaaaga tcactaccac agggaccctg     420
tggaacggca acaaaattat cgacgagcgc ctgatcaccc ccgacggcag catgctgttc     480
taa                                                                   483
```

<210> SEQ ID NO 85
<211> LENGTH: 152
<212> TYPE: PRT
<213> ORGANISM: Artificial sequence
<220> FEATURE:
<223> OTHER INFORMATION: Synthetic

<400> SEQUENCE: 85

```
Met Lys His His His His His His Val Phe Thr Leu Asp Asp Phe Val
1               5               10              15

Gly Asp Trp Glu Gln Thr Ala Ala Tyr Asn Leu Asp Gln Val Leu Glu
            20              25              30

Gln Gly Gly Val Ser Ser Leu Leu Gln Asn Leu Ala Val Ser Val Thr
        35              40              45

Pro Ile Met Arg Ile Val Arg Ser Gly Glu Asn Ala Leu Lys Ile Asp
    50              55              60

Ile His Val Ile Ile Pro Tyr Glu Gly Leu Ser Ala Asp Gln Met Ala
65              70              75              80

Gln Ile Glu Glu Val Phe Lys Val Val Tyr Pro Val Asp Asp His His
            85              90              95

Phe Lys Val Ile Leu Pro Tyr Gly Thr Leu Val Ile Asp Gly Val Thr
            100             105             110

Pro Asn Lys Leu Asn Tyr Phe Gly Arg Pro Tyr Glu Gly Ile Ala Val
            115             120             125

Phe Asp Gly Lys Lys Ile Thr Thr Thr Gly Thr Leu Trp Asn Gly Asn
    130             135             140

Lys Ile Ile Asp Glu Arg Leu Ile
145             150
```

<210> SEQ ID NO 86
<211> LENGTH: 459
<212> TYPE: DNA
<213> ORGANISM: Artificial sequence
<220> FEATURE:
<223> OTHER INFORMATION: Synthetic

<400> SEQUENCE: 86
atgaaacatc accatcacca tcatgtcttc acactcgacg atttcgttgg ggactgggaa      60
cagacagccg cctacaacct ggaccaagtc cttgaacagg gaggtgtgtc cagtttgctg     120
cagaatctcg ccgtgtccgt aactccgatc atgaggattg tccggagcgg tgaaaatgcc     180
ctgaagatcg acatccatgt catcatcccg tatgaaggtc tgagcgccga ccaaatggcc     240
cagatcgaag aggtgtttaa ggtggtgtac cctgtggatg atcatcactt taaggtgatc     300 ctgcccctatg gcacactggt aatcgacggg gttacgccga acaagctgaa ctatttcgga     360
cggccgtatg aaggcatcgc cgtgttcgac ggcaaaaaga tcactaccac agggaccctg     420
tggaacggca acaaaattat cgacgagcgc ctgatctaa                            459

<210> SEQ ID NO 87
<211> LENGTH: 151
<212> TYPE: PRT
<213> ORGANISM: Artificial sequence
<220> FEATURE:
<223> OTHER INFORMATION: Synthetic

<400> SEQUENCE: 87

Met Lys His His His His His His Val Phe Thr Leu Asp Asp Phe Val
1               5                   10                  15

Gly Asp Trp Glu Gln Thr Ala Ala Tyr Asn Leu Asp Gln Val Leu Glu
            20                  25                  30

Gln Gly Gly Val Ser Ser Leu Leu Gln Asn Leu Ala Val Ser Val Thr
        35                  40                  45

Pro Ile Met Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
                85                  90                  95

Phe Lys Val Ile Leu Pro Tyr Gly Thr Leu Val Ile Asp Gly Val Thr
            100                 105                 110

Pro Asn Lys Leu Asn Tyr Phe Gly Arg Pro Tyr Glu Gly Ile Ala Val
            115                 120                 125

Phe Asp Gly Lys Lys Ile Thr Thr Thr Gly Thr Leu Trp Asn Gly Asn
    130                 135                 140

Lys Ile Ile Asp Glu Arg Leu
145                 150

<210> SEQ ID NO 88
<211> LENGTH: 456
<212> TYPE: DNA
<213> ORGANISM: Artificial sequence
<220> FEATURE:
<223> OTHER INFORMATION: Synthetic

<400> SEQUENCE: 88
atgaaacatc accatcacca tcatgtcttc acactcgacg atttcgttgg ggactgggaa      60
cagacagccg cctacaacct ggaccaagtc cttgaacagg gaggtgtgtc cagtttgctg     120
cagaatctcg ccgtgtccgt aactccgatc atgaggattg tccggagcgg tgaaaatgcc     180
ctgaagatcg acatccatgt catcatcccg tatgaaggtc tgagcgccga ccaaatggcc     240
cagatcgaag aggtgtttaa ggtggtgtac cctgtggatg atcatcactt taaggtgatc     300 ctgcccctatg gcacactggt aatcgacggg gttacgccga acaagctgaa ctatttcgga     360

-continued

```
cggccgtatg aaggcatcgc cgtgttcgac ggcaaaaaga tcactaccac agggaccctg       420
tggaacggca acaaaattat cgacgagcgc ctgtaa                                 456
```

<210> SEQ ID NO 89
<211> LENGTH: 150
<212> TYPE: PRT
<213> ORGANISM: Artificial sequence
<220> FEATURE:
<223> OTHER INFORMATION: Synthetic

<400> SEQUENCE: 89

```
Met Lys His His His His His His Val Phe Thr Leu Asp Asp Phe Val
1               5                   10                  15

Gly Asp Trp Glu Gln Thr Ala Ala Tyr Asn Leu Asp Gln Val Leu Glu
            20                  25                  30

Gln Gly Gly Val Ser Ser Leu Leu Gln Asn Leu Ala Val Ser Val Thr
        35                  40                  45

Pro Ile Met Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
                85                  90                  95

Phe Lys Val Ile Leu Pro Tyr Gly Thr Leu Val Ile Asp Gly Val Thr
            100                 105                 110

Pro Asn Lys Leu Asn Tyr Phe Gly Arg Pro Tyr Glu Gly Ile Ala Val
        115                 120                 125

Phe Asp Gly Lys Lys Ile Thr Thr Thr Gly Thr Leu Trp Asn Gly Asn
    130                 135                 140

Lys Ile Ile Asp Glu Arg
145                 150
```

<210> SEQ ID NO 90
<211> LENGTH: 453
<212> TYPE: DNA
<213> ORGANISM: Artificial sequence
<220> FEATURE:
<223> OTHER INFORMATION: Synthetic

<400> SEQUENCE: 90

```
atgaaacatc accatcacca tcatgtcttc acactcgacg atttcgttgg ggactgggaa        60
cagacagccg cctacaacct ggaccaagtc cttgaacagg gaggtgtgtc cagtttgctg       120
cagaatctcg ccgtgtccgt aactccgatc atgaggattg tccggagcgg tgaaaatgcc       180
ctgaagatcg acatccatgt catcatcccg tatgaaggtc tgagcgccga ccaaatggcc       240
cagatcgaag aggtgtttaa ggtggtgtac cctgtggatg atcatcactt taaggtgatc       300
ctgccctatg gcacactggt aatcgacggg gttacgccga caagctgaa ctatttcgga        360 cggccgtatg aaggcatcgc cgtgttcgac ggcaaaaaga tcactaccac agggaccctg       420
tggaacggca acaaaattat cgacgagcgc taa                                    453
```

<210> SEQ ID NO 91
<211> LENGTH: 123
<212> TYPE: PRT
<213> ORGANISM: Artificial sequence
<220> FEATURE:
<223> OTHER INFORMATION: Synthetic

```
<400> SEQUENCE: 91

Met Val Ala Ile Leu Trp His Glu Met Trp His Glu Gly Leu Glu Glu
1               5                   10                  15

Ala Ser Arg Leu Tyr Phe Gly Glu Arg Asn Val Lys Gly Met Phe Glu
                20                  25                  30

Val Leu Glu Pro Leu His Ala Met Met Glu Arg Gly Pro Gln Thr Leu
            35                  40                  45

Lys Glu Thr Ser Phe Asn Gln Ala Tyr Gly Arg Asp Leu Met Glu Ala
        50                  55                  60

Gln Glu Trp Cys Arg Lys Tyr Met Lys Ser Gly Asn Val Lys Asp Leu
65                  70                  75                  80

Thr Gln Ala Trp Asp Leu Tyr Tyr His Val Phe Arg Arg Ile Ser Gly
                85                  90                  95

Gly Ser Gly Gly Gly Gly Ser Gly Gly Ser Ser Ser Gly Gly Ala Ile
            100                 105                 110

Val Ser Gly Trp Arg Leu Phe Lys Lys Ile Ser
        115                 120
```

```
<210> SEQ ID NO 92
<211> LENGTH: 372
<212> TYPE: DNA
<213> ORGANISM: Artificial sequence
<220> FEATURE:
<223> OTHER INFORMATION: Synthetic

<400> SEQUENCE: 92
atggtggcca tcctctggca tgagatgtgg catgaaggcc tggaagaggc atctcgtttg       60
tactttgggg aaaggaacgt gaaaggcatg tttgaggtgc tggagccctt gcatgctatg      120
atggaacggg gcccccagac tctgaaggaa acatccttta atcaggccta tggtcgagat      180
ttaatggagg cccaagagtg gtgcaggaag tacatgaaat cagggaatgt caaggacctc      240
acccaagcct gggacctcta ttatcatgtg ttccgacgaa tcagtggtgg ttcaggtggt      300
ggcgggagcg gtggctcgag cagcggtgga gcgatcgtga gcggctggcg gctgttcaag      360
aagattagct aa                                                          372
```

```
<210> SEQ ID NO 93
<211> LENGTH: 125
<212> TYPE: PRT
<213> ORGANISM: Artificial sequence
<220> FEATURE:
<223> OTHER INFORMATION: Synthetic

<400> SEQUENCE: 93

Met Val Ala Ile Leu Trp His Glu Met Trp His Glu Gly Leu Glu Glu
1               5                   10                  15

Ala Ser Arg Leu Tyr Phe Gly Glu Arg Asn Val Lys Gly Met Phe Glu
                20                  25                  30

Val Leu Glu Pro Leu His Ala Met Met Glu Arg Gly Pro Gln Thr Leu
            35                  40                  45

Lys Glu Thr Ser Phe Asn Gln Ala Tyr Gly Arg Asp Leu Met Glu Ala
        50                  55                  60

Gln Glu Trp Cys Arg Lys Tyr Met Lys Ser Gly Asn Val Lys Asp Leu
65                  70                  75                  80

Thr Gln Ala Trp Asp Leu Tyr Tyr His Val Phe Arg Arg Ile Ser Gly
                85                  90                  95

Gly Ser Gly Gly Gly Gly Ser Gly Gly Ser Ser Ser Gly Gly Ala Ile
```

```
                100               105               110
Val Ser Val Ser Gly Trp Arg Leu Phe Lys Lys Ile Ser
        115               120               125

<210> SEQ ID NO 94
<211> LENGTH: 378
<212> TYPE: DNA
<213> ORGANISM: Artificial sequence
<220> FEATURE:
<223> OTHER INFORMATION: Synthetic

<400> SEQUENCE: 94
atggtggcca tcctctggca tgagatgtgg catgaaggcc tggaagaggc atctcgtttg      60
tactttgggg aaaggaacgt gaaaggcatg tttgaggtgc tggagcccct tgcatgctatg    120 atggaacggg gcccccagac tctgaaggaa acatccttta atcaggccta tggtcgagat     180
ttaatggagg cccaagagtg gtgcaggaag tacatgaaat cagggaatgt caaggacctc     240
acccaagcct gggacctcta ttatcatgtg ttccgacgaa tcagtggtgg ttcaggtggt     300
ggcgggagcg gtggctcgag cagcggtgga gcgatcgtta gcgttagcgg ctggcgcctg     360
ttcaagaaga tcagctaa                                                    378

<210> SEQ ID NO 95
<211> LENGTH: 129
<212> TYPE: PRT
<213> ORGANISM: Artificial sequence
<220> FEATURE:
<223> OTHER INFORMATION: Synthetic

<400> SEQUENCE: 95

Met Val Ala Ile Leu Trp His Glu Met Trp His Glu Gly Leu Glu Glu
1               5                   10                  15

Ala Ser Arg Leu Tyr Phe Gly Glu Arg Asn Val Lys Gly Met Phe Glu
            20                  25                  30

Val Leu Glu Pro Leu His Ala Met Met Glu Arg Gly Pro Gln Thr Leu
        35                  40                  45

Lys Glu Thr Ser Phe Asn Gln Ala Tyr Gly Arg Asp Leu Met Glu Ala
    50                  55                  60

Gln Glu Trp Cys Arg Lys Tyr Met Lys Ser Gly Asn Val Lys Asp Leu
65                  70                  75                  80

Thr Gln Ala Trp Asp Leu Tyr Tyr His Val Phe Arg Arg Ile Ser Gly
                85                  90                  95

Gly Ser Gly Gly Gly Gly Ser Gly Gly Ser Ser Ser Gly Gly Ala Ile
            100                 105                 110

Val Ser Gly Trp Arg Leu Phe Lys Lys Ile Ser His His His His
        115                 120                 125

His

<210> SEQ ID NO 96
<211> LENGTH: 390
<212> TYPE: DNA
<213> ORGANISM: Artificial sequence
<220> FEATURE:
<223> OTHER INFORMATION: Synthetic

<400> SEQUENCE: 96
atggtggcca tcctctggca tgagatgtgg catgaaggcc tggaagaggc atctcgtttg      60
tactttgggg aaaggaacgt gaaaggcatg tttgaggtgc tggagcccct tgcatgctatg    120
```
atggaacggg gcccccagac tctgaaggaa acatccttta atcaggccta tggtcgagat        180
ttaatggagg cccaagagtg gtgcaggaag tacatgaaat cagggaatgt caaggacctc        240
acccaagcct gggacctcta ttatcatgtg ttccgacgaa tcagtggtgg ttcaggtggt        300
ggcgggagcg gtggctcgag cagcggtgga gcgatcgtga gcggctggcg gctgttcaag        360
aagattagcc atcatcacca tcaccactaa        390

<210> SEQ ID NO 97
<211> LENGTH: 131
<212> TYPE: PRT
<213> ORGANISM: Artificial sequence
<220> FEATURE:
<223> OTHER INFORMATION: Synthetic

<400> SEQUENCE: 97

Met Val Ala Ile Leu Trp His Glu Met Trp His Glu Gly Leu Glu Glu
1               5                   10                  15

Ala Ser Arg Leu Tyr Phe Gly Glu Arg Asn Val Lys Gly Met Phe Glu
            20                  25                  30

Val Leu Glu Pro Leu His Ala Met Met Glu Arg Gly Pro Gln Thr Leu
        35                  40                  45

Lys Glu Thr Ser Phe Asn Gln Ala Tyr Gly Arg Asp Leu Met Glu Ala
    50                  55                  60

Gln Glu Trp Cys Arg Lys Tyr Met Lys Ser Gly Asn Val Lys Asp Leu
65                  70                  75                  80

Thr Gln Ala Trp Asp Leu Tyr Tyr His Val Phe Arg Arg Ile Ser Gly
                85                  90                  95

Gly Ser Gly Gly Gly Gly Ser Gly Gly Ser Ser Ser Gly Gly Ala Ile
            100                 105                 110

Val Ser Val Ser Gly Trp Arg Leu Phe Lys Lys Ile Ser His His His
        115                 120                 125

His His His
    130

<210> SEQ ID NO 98
<211> LENGTH: 396
<212> TYPE: DNA
<213> ORGANISM: Artificial sequence
<220> FEATURE:
<223> OTHER INFORMATION: Synthetic

<400> SEQUENCE: 98
atggtggcca tcctctggca tgagatgtgg catgaaggcc tggaagaggc atctcgtttg         60
tactttgggg aaaggaacgt gaaaggcatg tttgaggtgc tggagccctt gcatgctatg        120
atggaacggg gcccccagac tctgaaggaa acatccttta atcaggccta tggtcgagat        180
ttaatggagg cccaagagtg gtgcaggaag tacatgaaat cagggaatgt caaggacctc        240
acccaagcct gggacctcta ttatcatgtg ttccgacgaa tcagtggtgg ttcaggtggt        300
ggcgggagcg gtggctcgag cagcggtgga gcgatcgtta gcgtgagcgg ctggcggctg        360
ttcaagaaga ttagccatca tcaccatcac cactaa        396

<210> SEQ ID NO 99
<211> LENGTH: 118
<212> TYPE: PRT
<213> ORGANISM: Artificial sequence
<220> FEATURE:
<223> OTHER INFORMATION: Synthetic

<400> SEQUENCE: 99

```
Met Lys His His His His His His Val Ala Ile Leu Trp His Glu Met
1               5                   10                  15

Trp His Glu Gly Leu Glu Glu Ala Ser Arg Leu Tyr Phe Gly Glu Arg
                20                  25                  30

Asn Val Lys Gly Met Phe Glu Val Leu Glu Pro Leu His Ala Met Met
            35                  40                  45

Glu Arg Gly Pro Gln Thr Leu Lys Glu Thr Ser Phe Asn Gln Ala Tyr
        50                  55                  60

Gly Arg Asp Leu Met Glu Ala Gln Glu Trp Cys Arg Lys Tyr Met Lys
65                  70                  75                  80

Ser Gly Asn Val Lys Asp Leu Thr Gln Ala Trp Asp Leu Tyr Tyr His
                85                  90                  95

Val Phe Arg Arg Ile Ser Gly Gly Ser Gly Gly Val Ser Gly Trp Arg
            100                 105                 110

Leu Phe Lys Lys Ile Ser
        115
```

<210> SEQ ID NO 100
<211> LENGTH: 357
<212> TYPE: DNA
<213> ORGANISM: Artificial sequence
<220> FEATURE:
<223> OTHER INFORMATION: Synthetic

<400> SEQUENCE: 100

```
atgaaacatc accatcacca tcatgtggcc atcctctggc atgagatgtg gcatgaaggc      60
ctggaagagg catctcgttt gtactttggg aaaggaacg tgaaaggcat gtttgaggtg     120
ctggagccct tgcatgctat gatggaacgg ggcccccaga ctctgaagga aacatccttt     180
aatcaggcct atggtcgaga tttaatggag gcccaagagt ggtgcaggaa gtacatgaaa     240
tcagggaatg tcaaggacct cacccaagcc tgggacctct attatcatgt gttccgacga     300
atcagtggtg gttcaggtgg tgtgagcggc tggcggctgt tcaagaagat tagctaa      357
```

<210> SEQ ID NO 101
<211> LENGTH: 123
<212> TYPE: PRT
<213> ORGANISM: Artificial sequence
<220> FEATURE:
<223> OTHER INFORMATION: Synthetic

<400> SEQUENCE: 101

```
Met Lys His His His His His His Val Ala Ile Leu Trp His Glu Met
1               5                   10                  15

Trp His Glu Gly Leu Glu Glu Ala Ser Arg Leu Tyr Phe Gly Glu Arg
                20                  25                  30

Asn Val Lys Gly Met Phe Glu Val Leu Glu Pro Leu His Ala Met Met
            35                  40                  45

Glu Arg Gly Pro Gln Thr Leu Lys Glu Thr Ser Phe Asn Gln Ala Tyr
        50                  55                  60

Gly Arg Asp Leu Met Glu Ala Gln Glu Trp Cys Arg Lys Tyr Met Lys
65                  70                  75                  80

Ser Gly Asn Val Lys Asp Leu Thr Gln Ala Trp Asp Leu Tyr Tyr His
                85                  90                  95

Val Phe Arg Arg Ile Ser Gly Gly Ser Gly Gly Gly Gly Ser Gly Gly
            100                 105                 110
```

Val Ser Gly Trp Arg Leu Phe Lys Lys Ile Ser
        115                 120

<210> SEQ ID NO 102
<211> LENGTH: 372
<212> TYPE: DNA
<213> ORGANISM: Artificial sequence
<220> FEATURE:
<223> OTHER INFORMATION: Synthetic

<400> SEQUENCE: 102
atgaaacatc accatcacca tcatgtggcc atcctctggc atgagatgtg gcatgaaggc        60
ctggaagagg catctcgttt gtactttggg gaaaggaacg tgaaaggcat gtttgaggtg       120
ctggagccct tgcatgctat gatggaacgg ggcccccaga ctctgaagga aacatccttt       180
aatcaggcct atggtcgaga tttaatggag gcccaagagt ggtgcaggaa gtacatgaaa       240
tcagggaatg tcaaggacct cacccaagcc tgggacctct attatcatgt gttccgacga       300
atcagtggtg gttcaggtgg tggcgggagc ggtggcgtga cggctggcg gctgttcaag        360 aagattagct aa                                                          372

<210> SEQ ID NO 103
<211> LENGTH: 128
<212> TYPE: PRT
<213> ORGANISM: Artificial sequence
<220> FEATURE:
<223> OTHER INFORMATION: Synthetic

<400> SEQUENCE: 103

Met Lys His His His His His His Val Ala Ile Leu Trp His Glu Met
1               5                   10                  15

Trp His Glu Gly Leu Glu Glu Ala Ser Arg Leu Tyr Phe Gly Glu Arg
            20                  25                  30

Asn Val Lys Gly Met Phe Glu Val Leu Glu Pro Leu His Ala Met Met
        35                  40                  45

Glu Arg Gly Pro Gln Thr Leu Lys Glu Thr Ser Phe Asn Gln Ala Tyr
    50                  55                  60

Gly Arg Asp Leu Met Glu Ala Gln Glu Trp Cys Arg Lys Tyr Met Lys
65                  70                  75                  80

Ser Gly Asn Val Lys Asp Leu Thr Gln Ala Trp Asp Leu Tyr Tyr His
                85                  90                  95

Val Phe Arg Arg Ile Ser Gly Gly Ser Gly Gly Gly Ser Gly Gly
            100                 105                 110

Ser Ser Ser Gly Gly Val Ser Gly Trp Arg Leu Phe Lys Lys Ile Ser
        115                 120                 125

<210> SEQ ID NO 104
<211> LENGTH: 387
<212> TYPE: DNA
<213> ORGANISM: Artificial sequence
<220> FEATURE:
<223> OTHER INFORMATION: Synthetic

<400> SEQUENCE: 104
atgaaacatc accatcacca tcatgtggcc atcctctggc atgagatgtg gcatgaaggc        60
ctggaagagg catctcgttt gtactttggg gaaaggaacg tgaaaggcat gtttgaggtg       120
ctggagccct tgcatgctat gatggaacgg ggcccccaga ctctgaagga aacatccttt       180
aatcaggcct atggtcgaga tttaatggag gcccaagagt ggtgcaggaa gtacatgaaa       240

-continued

--- tcagggaatg tcaaggacct cacccaagcc tgggacctct attatcatgt gttccgacga      300
atcagtggtg gttcaggtgg tggcgggagc ggtggctcga gcagcggtgg agtgagcggc      360
tggcggctgt tcaagaagat tagctaa                                          387

<210> SEQ ID NO 105
<211> LENGTH: 120
<212> TYPE: PRT
<213> ORGANISM: Artificial sequence
<220> FEATURE:
<223> OTHER INFORMATION: Synthetic

<400> SEQUENCE: 105

Met Lys His His His His His His Val Ala Ile Leu Trp His Glu Met
1               5                   10                  15

Trp His Glu Gly Leu Glu Glu Ala Ser Arg Leu Tyr Phe Gly Glu Arg
            20                  25                  30

Asn Val Lys Gly Met Phe Glu Val Leu Glu Pro Leu His Ala Met Met
        35                  40                  45

Glu Arg Gly Pro Gln Thr Leu Lys Glu Thr Ser Phe Asn Gln Ala Tyr
    50                  55                  60

Gly Arg Asp Leu Met Glu Ala Gln Glu Trp Cys Arg Lys Tyr Met Lys
65                  70                  75                  80

Ser Gly Asn Val Lys Asp Leu Thr Gln Ala Trp Asp Leu Tyr Tyr His
                85                  90                  95

Val Phe Arg Arg Ile Ser Gly Gly Ser Gly Gly Val Ser Val Ser Gly
            100                 105                 110

Trp Arg Leu Phe Lys Lys Ile Ser
            115                 120

<210> SEQ ID NO 106
<211> LENGTH: 363
<212> TYPE: DNA
<213> ORGANISM: Artificial sequence
<220> FEATURE:
<223> OTHER INFORMATION: Synthetic

<400> SEQUENCE: 106
atgaaacatc accatcacca tcatgtggcc atcctctggc atgagatgtg gcatgaaggc       60
ctggaagagg catctcgttt gtactttggg gaaaggaacg tgaaaggcat gtttgaggtg      120
ctggagccct tgcatgctat gatggaacgg ggcccccaga ctctgaagga aacatccttt      180
aatcaggcct atggtcgaga tttaatggag gcccaagagt ggtgcaggaa gtacatgaaa      240
tcagggaatg tcaaggacct cacccaagcc tgggacctct attatcatgt gttccgacga      300
atcagtggtg gttcaggtgg tgttagcgtt agcggctggc gcctgttcaa gaagatcagc      360
taa                                                                    363

<210> SEQ ID NO 107
<211> LENGTH: 125
<212> TYPE: PRT
<213> ORGANISM: Artificial sequence
<220> FEATURE:
<223> OTHER INFORMATION: Synthetic

<400> SEQUENCE: 107

Met Lys His His His His His His Val Ala Ile Leu Trp His Glu Met
1               5                   10                  15

Trp His Glu Gly Leu Glu Glu Ala Ser Arg Leu Tyr Phe Gly Glu Arg
            20                  25                  30

-continued

```
Asn Val Lys Gly Met Phe Glu Val Leu Glu Pro Leu His Ala Met Met
        35                  40                  45

Glu Arg Gly Pro Gln Thr Leu Lys Glu Thr Ser Phe Asn Gln Ala Tyr
    50                  55                  60

Gly Arg Asp Leu Met Glu Ala Gln Glu Trp Cys Arg Lys Tyr Met Lys
65                  70                  75                  80

Ser Gly Asn Val Lys Asp Leu Thr Gln Ala Trp Asp Leu Tyr Tyr His
                85                  90                  95

Val Phe Arg Arg Ile Ser Gly Gly Ser Gly Gly Gly Gly Ser Gly Gly
            100                 105                 110

Val Ser Val Ser Gly Trp Arg Leu Phe Lys Lys Ile Ser
        115                 120                 125
```

```
<210> SEQ ID NO 108
<211> LENGTH: 378
<212> TYPE: DNA
<213> ORGANISM: Artificial sequence
<220> FEATURE:
<223> OTHER INFORMATION: Synthetic

<400> SEQUENCE: 108
atgaaacatc accatcacca tcatgtggcc atcctctggc atgagatgtg gcatgaaggc      60
ctggaagagg catctcgttt gtactttggg gaaaggaacg tgaaaggcat gtttgaggtg     120
ctggagccct tgcatgctat gatggaacgg ggccccagaa ctctgaagga aacatccttt     180
aatcaggcct atggtcgaga tttaatggag gcccaagagt ggtgcaggaa gtacatgaaa     240
tcagggaatg tcaaggacct cacccaagcc tgggacctct attatcatgt gttccgacga     300
atcagtggtg gttcaggtgg tggcgggagc ggtggcgtta cgttagcggg ctggcgcctg     360
ttcaagaaga tcagctaa                                                   378
```

```
<210> SEQ ID NO 109
<211> LENGTH: 130
<212> TYPE: PRT
<213> ORGANISM: Artificial sequence
<220> FEATURE:
<223> OTHER INFORMATION: Synthetic

<400> SEQUENCE: 109

Met Lys His His His His His His Val Ala Ile Leu Trp His Glu Met
1               5                   10                  15

Trp His Glu Gly Leu Glu Glu Ala Ser Arg Leu Tyr Phe Gly Glu Arg
            20                  25                  30

Asn Val Lys Gly Met Phe Glu Val Leu Glu Pro Leu His Ala Met Met
        35                  40                  45

Glu Arg Gly Pro Gln Thr Leu Lys Glu Thr Ser Phe Asn Gln Ala Tyr
    50                  55                  60

Gly Arg Asp Leu Met Glu Ala Gln Glu Trp Cys Arg Lys Tyr Met Lys
65                  70                  75                  80

Ser Gly Asn Val Lys Asp Leu Thr Gln Ala Trp Asp Leu Tyr Tyr His
                85                  90                  95

Val Phe Arg Arg Ile Ser Gly Gly Ser Gly Gly Gly Gly Ser Gly Gly
            100                 105                 110

Ser Ser Ser Gly Gly Val Ser Val Ser Gly Trp Arg Leu Phe Lys Lys
        115                 120                 125

Ile Ser
    130
```

-continued

<210> SEQ ID NO 110
<211> LENGTH: 393
<212> TYPE: DNA
<213> ORGANISM: Artificial sequence
<220> FEATURE:
<223> OTHER INFORMATION: Synthetic

<400> SEQUENCE: 110
atgaaacatc accatcacca tcatgtggcc atcctctggc atgagatgtg gcatgaaggc      60
ctggaagagg catctcgttt gtactttggg gaaaggaacg tgaaaggcat gtttgaggtg     120
ctggagccct tgcatgctat gatggaacgg ggcccccaga ctctgaagga aacatccttt     180
aatcaggcct atggtcgaga tttaatggag gcccaagagt ggtgcaggaa gtacatgaaa     240
tcagggaatg tcaaggacct cacccaagcc tgggacctct attatcatgt gttccgacga     300
atcagtggtg gttcaggtgg tggcgggagc ggtggctcga gcagcggtgg agttagcgtt     360
agcggctggc gcctgttcaa gaagatcagc taa                                  393

<210> SEQ ID NO 111
<211> LENGTH: 134
<212> TYPE: PRT
<213> ORGANISM: Artificial sequence
<220> FEATURE:
<223> OTHER INFORMATION: Synthetic

<400> SEQUENCE: 111

Met Gly Ser Met Leu Phe Arg Val Thr Ile Asn Ser Ser Ser Ser Gly
1               5                   10                  15

Gly Gly Gly Ser Gly Gly Gly Ser Ser Gly Gly Gly Val Gln Val Glu
                20                  25                  30

Thr Ile Ser Pro Gly Asp Gly Arg Thr Phe Pro Lys Arg Gly Gln Thr
            35                  40                  45

Cys Val Val His Tyr Thr Gly Met Leu Glu Asp Gly Lys Lys Phe Asp
        50                  55                  60

Ser Ser Arg Asp Arg Asn Lys Pro Phe Lys Phe Met Leu Gly Lys Gln
65                  70                  75                  80

Glu Val Ile Arg Gly Trp Glu Glu Gly Val Ala Gln Met Ser Val Gly
                85                  90                  95

Gln Arg Ala Lys Leu Thr Ile Ser Pro Asp Tyr Ala Tyr Gly Ala Thr
                100                 105                 110

Gly His Pro Gly Ile Ile Pro Pro His Ala Thr Leu Val Phe Asp Val
            115                 120                 125

Glu Leu Leu Lys Leu Glu
        130

<210> SEQ ID NO 112
<211> LENGTH: 405
<212> TYPE: DNA
<213> ORGANISM: Artificial sequence
<220> FEATURE:
<223> OTHER INFORMATION: Synthetic

<400> SEQUENCE: 112
atgggctcca tgctgttccg agtaaccatc aacagctcga gttcaggtgg tggcgggagc      60
ggtggaggga gcagcggtgg aggagtgcag gtggaaacca tctccccag agacgggcgc     120 accttcccca gcgcggcca gacctgcgtg gtgcactaca ccgggatgct tgaagatgga     180
aagaaatttg attcctcccg ggacagaaac aagccctta agtttatgct aggcaagcag     240

-continued

```
gaggtgatcc gaggctggga agaagggggtt gcccagatga gtgtgggtca gagagccaaa      300
ctgactatat ctccagatta tgcctatggt gccactgggc acccaggcat catcccacca      360
catgccactc tcgtcttcga tgtggagctt ctaaaactgg aataa                      405
```

<210> SEQ ID NO 113
<211> LENGTH: 136
<212> TYPE: PRT
<213> ORGANISM: Artificial sequence
<220> FEATURE:
<223> OTHER INFORMATION: Synthetic

<400> SEQUENCE: 113

```
Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu Gly Gly Ser Gly
            100                 105                 110

Gly Gly Gly Ser Gly Gly Ser Ser Ser Gly Gly Ala Ile Gly Ser Met
        115                 120                 125

Leu Phe Arg Val Thr Ile Asn Ser
    130                 135
```

<210> SEQ ID NO 114
<211> LENGTH: 408
<212> TYPE: DNA
<213> ORGANISM: Artificial sequence
<220> FEATURE:
<223> OTHER INFORMATION: Synthetic

<400> SEQUENCE: 114

```
atgggagtgc aggtggaaac catctcccca ggagacgggc gcaccttccc caagcgcggc       60
cagacctgcg tggtgcacta caccgggatg cttgaagatg gaaagaaatt tgattcctcc      120
cgggacagaa acaagccctt taagtttatg ctaggcaagc aggaggtgat ccgaggctgg      180
gaagaagggg ttgcccagat gagtgtgggt cagagagcca aactgactat atctccagat      240
tatgcctatg gtgccactgg gcacccaggc atcatcccac acatgccac tctcgtcttc       300 gatgtggagc ttctaaaact ggaaggtggt tcaggtggtg gcgggagcgg tggctcgagc      360
agcggtggag cgatcggctc catgctgttc cgagtaacca tcaacagc                   408
```

<210> SEQ ID NO 115
<211> LENGTH: 165
<212> TYPE: PRT
<213> ORGANISM: Artificial sequence
<220> FEATURE:
<223> OTHER INFORMATION: Synthetic

<400> SEQUENCE: 115

```
Met Val Phe Thr Leu Glu Asp Phe Val Gly Asp Trp Glu Gln Thr Ala
```

-continued

```
1               5                    10                   15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Gln Arg Ile Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Met Leu Asn Tyr Phe
            100                 105                 110

Gly Arg Pro Tyr Glu Gly Ile Ala Val Phe Asp Gly Lys Lys Ile Thr
            115                 120                 125

Val Thr Gly Thr Leu Trp Asn Gly Asn Lys Ile Ile Asp Glu Arg Leu
        130                 135                 140

Ile Thr Pro Asp Gly Ser Met Leu Phe Arg Val Thr Ile Asn Ser His
145                 150                 155                 160

His His His His His
                165
```

```
<210> SEQ ID NO 116
<211> LENGTH: 498
<212> TYPE: DNA
<213> ORGANISM: Artificial sequence
<220> FEATURE:
<223> OTHER INFORMATION: Synthetic

<400> SEQUENCE: 116
atggtcttca cactcgaaga tttcgttggg gactgggaac agacagccgc ctacaacctg      60
gaccaagtcc ttgaacaggg aggtgtgtcc agtttgctgc agaatctcgc cgtgtccgta     120
actccgatcc aaaggattgt ccggagcggt gaaaatgccc tgaagatcga catccatgtc     180
atcatcccgt atgaaggtct gagcgccgac caaatggccc agatcgaaga ggtgtttaag     240
gtggtgtacc ctgtggatga tcatcacttt aaggtgatcc tgccctatgg cacactggta     300
atcgacgggg ttacgccgaa catgctgaac tatttcggac ggccgtatga aggcatcgcc     360
gtgttcgacg gcaaaaagat cactgtaaca gggaccctgt ggaacggcaa caaaattatc     420
gacgagcgcc tgatcacccc cgacggctcc atgctgttcc gagtaaccat caacagccat     480
catcaccatc accactaa                                                    498
```

```
<210> SEQ ID NO 117

<400> SEQUENCE: 117

000

<210> SEQ ID NO 118

<400> SEQUENCE: 118

000

<210> SEQ ID NO 119

<400> SEQUENCE: 119
```

-continued

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133
<211> LENGTH: 13
<212> TYPE: PRT
<213> ORGANISM: Artificial sequence
<220> FEATURE:
<223> OTHER INFORMATION: Synthetic

<400> SEQUENCE: 133

Asn Val Ser Gly Trp Arg Leu Phe Lys Lys Ile Ser Asn
1               5                   10

<210> SEQ ID NO 134
<211> LENGTH: 13
<212> TYPE: PRT
<213> ORGANISM: Artificial sequence
<220> FEATURE:
<223> OTHER INFORMATION: Synthetic

<400> SEQUENCE: 134

Asn Val Thr Gly Tyr Arg Leu Phe Lys Lys Ile Ser Asn
1               5                   10

<210> SEQ ID NO 135
<211> LENGTH: 12
<212> TYPE: PRT
<213> ORGANISM: Artificial sequence
<220> FEATURE:
<223> OTHER INFORMATION: Synthetic

<400> SEQUENCE: 135

Val Ser Gly Trp Arg Leu Phe Lys Lys Ile Ser Asn
1               5                   10

<210> SEQ ID NO 136
<211> LENGTH: 11
<212> TYPE: PRT
<213> ORGANISM: Artificial sequence
<220> FEATURE:
<223> OTHER INFORMATION: Synthetic

<400> SEQUENCE: 136

Ser Gly Trp Arg Leu Phe Lys Lys Ile Ser Asn
1               5                   10

<210> SEQ ID NO 137
<211> LENGTH: 10
<212> TYPE: PRT
<213> ORGANISM: Artificial sequence
<220> FEATURE:
<223> OTHER INFORMATION: Synthetic

<400> SEQUENCE: 137

Gly Trp Arg Leu Phe Lys Lys Ile Ser Asn
1               5                   10

<210> SEQ ID NO 138
<211> LENGTH: 11
<212> TYPE: PRT
<213> ORGANISM: Artificial sequence
<220> FEATURE:
<223> OTHER INFORMATION: Synthetic

<400> SEQUENCE: 138

Val Thr Gly Tyr Arg Leu Phe Glu Lys Ile Ser
1               5                   10

<210> SEQ ID NO 139
<211> LENGTH: 10
<212> TYPE: PRT
<213> ORGANISM: Artificial sequence
<220> FEATURE:
<223> OTHER INFORMATION: Synthetic

<400> SEQUENCE: 139

Ser Gly Trp Arg Leu Phe Lys Lys Ile Ser
1               5                   10

<210> SEQ ID NO 140
<211> LENGTH: 6
<212> TYPE: PRT
<213> ORGANISM: Artificial sequence
<220> FEATURE:
<223> OTHER INFORMATION: Synthetic

<400> SEQUENCE: 140

Val Ser Gly Trp Arg Leu
1               5

<210> SEQ ID NO 141
<211> LENGTH: 7
<212> TYPE: PRT
<213> ORGANISM: Artificial sequence
<220> FEATURE:
<223> OTHER INFORMATION: Synthetic

<400> SEQUENCE: 141

Val Ser Gly Trp Arg Leu Phe
1               5

<210> SEQ ID NO 142
<211> LENGTH: 8
<212> TYPE: PRT
<213> ORGANISM: Artificial sequence
<220> FEATURE:
<223> OTHER INFORMATION: Synthetic

<400> SEQUENCE: 142

Val Ser Gly Trp Arg Leu Phe Lys
1               5

<210> SEQ ID NO 143
<211> LENGTH: 9
<212> TYPE: PRT
<213> ORGANISM: Artificial sequence
<220> FEATURE:
<223> OTHER INFORMATION: Synthetic

<400> SEQUENCE: 143

Val Ser Gly Trp Arg Leu Phe Lys Lys
1               5

```
<210> SEQ ID NO 144
<211> LENGTH: 10
<212> TYPE: PRT
<213> ORGANISM: Artificial sequence
<220> FEATURE:
<223> OTHER INFORMATION: Synthetic

<400> SEQUENCE: 144

Val Ser Gly Trp Arg Leu Phe Lys Lys Ile
1               5                   10

<210> SEQ ID NO 145
<211> LENGTH: 11
<212> TYPE: PRT
<213> ORGANISM: Artificial sequence
<220> FEATURE:
<223> OTHER INFORMATION: Synthetic

<400> SEQUENCE: 145

Val Ser Gly Trp Arg Leu Tyr Lys Lys Ile Ser
1               5                   10

<210> SEQ ID NO 146
<211> LENGTH: 22
<212> TYPE: PRT
<213> ORGANISM: Artificial sequence
<220> FEATURE:
<223> OTHER INFORMATION: Synthetic

<400> SEQUENCE: 146

Gly Ser Met Leu Phe Arg Val Thr Ile Asn Ser Val Ser Gly Trp Ala
1               5                   10                  15

Leu Phe Lys Lys Ile Ser
            20

<210> SEQ ID NO 147
<211> LENGTH: 22
<212> TYPE: PRT
<213> ORGANISM: Artificial sequence
<220> FEATURE:
<223> OTHER INFORMATION: Synthetic

<400> SEQUENCE: 147

Gly Ser Met Leu Phe Arg Val Thr Ile Asn Ser Val Thr Gly Tyr Arg
1               5                   10                  15

Leu Phe Glu Glu Ile Leu
            20

<210> SEQ ID NO 148
<211> LENGTH: 16
<212> TYPE: PRT
<213> ORGANISM: Artificial sequence
<220> FEATURE:
<223> OTHER INFORMATION: Synthetic

<400> SEQUENCE: 148

Gly Ser Met Leu Phe Arg Val Thr Ile Asn Ser Ser Ser Trp Lys Arg
1               5                   10                  15

<210> SEQ ID NO 149
<211> LENGTH: 14
<212> TYPE: PRT
<213> ORGANISM: Artificial sequence
<220> FEATURE:
<223> OTHER INFORMATION: Synthetic

<400> SEQUENCE: 149
```

-continued

```
Val Ser Gly Val Ser Gly Trp Arg Leu Phe Lys Lys Ile Ser
1               5               10

<210> SEQ ID NO 150
<211> LENGTH: 13
<212> TYPE: PRT
<213> ORGANISM: Artificial sequence
<220> FEATURE:
<223> OTHER INFORMATION: Synthetic

<400> SEQUENCE: 150

Val Ser Val Ser Gly Trp Arg Leu Phe Lys Lys Ile Ser
1               5               10

<210> SEQ ID NO 151
<211> LENGTH: 12
<212> TYPE: PRT
<213> ORGANISM: Artificial sequence
<220> FEATURE:
<223> OTHER INFORMATION: Synthetic

<400> SEQUENCE: 151

Val Val Ser Gly Trp Arg Leu Phe Lys Lys Ile Ser
1               5               10

<210> SEQ ID NO 152
<211> LENGTH: 15
<212> TYPE: PRT
<213> ORGANISM: Artificial sequence
<220> FEATURE:
<223> OTHER INFORMATION: Synthetic

<400> SEQUENCE: 152

Ser Ser Trp Lys Arg Ser Met Leu Phe Arg Val Thr Ile Asn Ser
1               5               10                  15

<210> SEQ ID NO 153
<211> LENGTH: 14
<212> TYPE: PRT
<213> ORGANISM: Artificial sequence
<220> FEATURE:
<223> OTHER INFORMATION: Synthetic

<400> SEQUENCE: 153

Ser Ser Trp Lys Arg Met Leu Phe Arg Val Thr Ile Asn Ser
1               5               10

<210> SEQ ID NO 154
<211> LENGTH: 17
<212> TYPE: PRT
<213> ORGANISM: Artificial sequence
<220> FEATURE:
<223> OTHER INFORMATION: Synthetic

<400> SEQUENCE: 154

Ser Ser Trp Lys Arg Asp Gly Ser Met Leu Phe Arg Val Thr Ile Asn
1               5               10                  15

Ser

<210> SEQ ID NO 155
<211> LENGTH: 18
<212> TYPE: PRT
<213> ORGANISM: Artificial sequence
<220> FEATURE:
<223> OTHER INFORMATION: Synthetic
```

<400> SEQUENCE: 155

Ser Ser Trp Lys Arg Pro Asp Gly Ser Met Leu Phe Arg Val Thr Ile
1               5                   10                  15

Asn Ser

<210> SEQ ID NO 156
<211> LENGTH: 16
<212> TYPE: PRT
<213> ORGANISM: Artificial sequence
<220> FEATURE:
<223> OTHER INFORMATION: Synthetic

<400> SEQUENCE: 156

Ser Ser Trp Lys Arg Ser Met Leu Phe Arg Val Thr Ile Asn Ser Val
1               5                   10                  15

<210> SEQ ID NO 157
<211> LENGTH: 15
<212> TYPE: PRT
<213> ORGANISM: Artificial sequence
<220> FEATURE:
<223> OTHER INFORMATION: Synthetic

<400> SEQUENCE: 157

Ser Ser Trp Lys Arg Met Leu Phe Arg Val Thr Ile Asn Ser Val
1               5                   10                  15

<210> SEQ ID NO 158
<211> LENGTH: 18
<212> TYPE: PRT
<213> ORGANISM: Artificial sequence
<220> FEATURE:
<223> OTHER INFORMATION: Synthetic

<400> SEQUENCE: 158

Ser Ser Trp Lys Arg Asp Gly Ser Met Leu Phe Arg Val Thr Ile Asn
1               5                   10                  15

Ser Val

<210> SEQ ID NO 159
<211> LENGTH: 19
<212> TYPE: PRT
<213> ORGANISM: Artificial sequence
<220> FEATURE:
<223> OTHER INFORMATION: Synthetic

<400> SEQUENCE: 159

Ser Ser Trp Lys Arg Pro Asp Gly Ser Met Leu Phe Arg Val Thr Ile
1               5                   10                  15

Asn Ser Val

<210> SEQ ID NO 160
<211> LENGTH: 17
<212> TYPE: PRT
<213> ORGANISM: Artificial sequence
<220> FEATURE:
<223> OTHER INFORMATION: Synthetic

<400> SEQUENCE: 160

Ser Ser Trp Lys Arg Ser Met Leu Phe Arg Val Thr Ile Asn Ser Val
1               5                   10                  15

Ser

-continued

```
<210> SEQ ID NO 161
<211> LENGTH: 16
<212> TYPE: PRT
<213> ORGANISM: Artificial sequence
<220> FEATURE:
<223> OTHER INFORMATION: Synthetic

<400> SEQUENCE: 161

Ser Ser Trp Lys Arg Met Leu Phe Arg Val Thr Ile Asn Ser Val Ser
1               5                   10                  15

<210> SEQ ID NO 162
<211> LENGTH: 19
<212> TYPE: PRT
<213> ORGANISM: Artificial sequence
<220> FEATURE:
<223> OTHER INFORMATION: Synthetic

<400> SEQUENCE: 162

Ser Ser Trp Lys Arg Asp Gly Ser Met Leu Phe Arg Val Thr Ile Asn
1               5                   10                  15

Ser Val Ser

<210> SEQ ID NO 163
<211> LENGTH: 20
<212> TYPE: PRT
<213> ORGANISM: Artificial sequence
<220> FEATURE:
<223> OTHER INFORMATION: Synthetic

<400> SEQUENCE: 163

Ser Ser Trp Lys Arg Pro Asp Gly Ser Met Leu Phe Arg Val Thr Ile
1               5                   10                  15

Asn Ser Val Ser
            20

<210> SEQ ID NO 164
<211> LENGTH: 15
<212> TYPE: PRT
<213> ORGANISM: Artificial sequence
<220> FEATURE:
<223> OTHER INFORMATION: Synthetic

<400> SEQUENCE: 164

Ser Ser Trp Lys Arg Gly Ser Met Leu Phe Arg Val Thr Ile Asn
1               5                   10                  15

<210> SEQ ID NO 165
<211> LENGTH: 14
<212> TYPE: PRT
<213> ORGANISM: Artificial sequence
<220> FEATURE:
<223> OTHER INFORMATION: Synthetic

<400> SEQUENCE: 165

Ser Ser Trp Lys Arg Gly Ser Met Leu Phe Arg Val Thr Ile
1               5                   10

<210> SEQ ID NO 166
<211> LENGTH: 14
<212> TYPE: PRT
<213> ORGANISM: Artificial sequence
<220> FEATURE:
<223> OTHER INFORMATION: Synthetic

<400> SEQUENCE: 166
```

```
Ser Ser Trp Lys Arg Ser Met Leu Phe Arg Val Thr Ile Asn
1               5                   10

<210> SEQ ID NO 167
<211> LENGTH: 13
<212> TYPE: PRT
<213> ORGANISM: Artificial sequence
<220> FEATURE:
<223> OTHER INFORMATION: Synthetic

<400> SEQUENCE: 167

Ser Ser Trp Lys Arg Met Leu Phe Arg Val Thr Ile Asn
1               5                   10

<210> SEQ ID NO 168
<211> LENGTH: 16
<212> TYPE: PRT
<213> ORGANISM: Artificial sequence
<220> FEATURE:
<223> OTHER INFORMATION: Synthetic

<400> SEQUENCE: 168

Ser Ser Trp Lys Arg Asp Gly Ser Met Leu Phe Arg Val Thr Ile Asn
1               5                   10                  15

<210> SEQ ID NO 169
<211> LENGTH: 17
<212> TYPE: PRT
<213> ORGANISM: Artificial sequence
<220> FEATURE:
<223> OTHER INFORMATION: Synthetic

<400> SEQUENCE: 169

Ser Ser Trp Lys Arg Pro Asp Gly Ser Met Leu Phe Arg Val Thr Ile
1               5                   10                  15

Asn

<210> SEQ ID NO 170
<211> LENGTH: 13
<212> TYPE: PRT
<213> ORGANISM: Artificial sequence
<220> FEATURE:
<223> OTHER INFORMATION: Synthetic

<400> SEQUENCE: 170

Ser Ser Trp Lys Arg Ser Met Leu Phe Arg Val Thr Ile
1               5                   10

<210> SEQ ID NO 171
<211> LENGTH: 12
<212> TYPE: PRT
<213> ORGANISM: Artificial sequence
<220> FEATURE:
<223> OTHER INFORMATION: Synthetic

<400> SEQUENCE: 171

Ser Ser Trp Lys Arg Met Leu Phe Arg Val Thr Ile
1               5                   10

<210> SEQ ID NO 172
<211> LENGTH: 15
<212> TYPE: PRT
<213> ORGANISM: Artificial sequence
<220> FEATURE:
<223> OTHER INFORMATION: Synthetic

<400> SEQUENCE: 172
```

```
Ser Ser Trp Lys Arg Asp Gly Ser Met Leu Phe Arg Val Thr Ile
1               5                   10                  15

<210> SEQ ID NO 173
<211> LENGTH: 16
<212> TYPE: PRT
<213> ORGANISM: Artificial sequence
<220> FEATURE:
<223> OTHER INFORMATION: Synthetic

<400> SEQUENCE: 173

Ser Ser Trp Lys Arg Pro Asp Gly Ser Met Leu Phe Arg Val Thr Ile
1               5                   10                  15

<210> SEQ ID NO 174
<211> LENGTH: 15
<212> TYPE: PRT
<213> ORGANISM: Artificial sequence
<220> FEATURE:
<223> OTHER INFORMATION: Synthetic

<400> SEQUENCE: 174

Val Ser Gly Trp Arg Leu Phe Lys Lys Ile Ser Val Phe Thr Leu
1               5                   10                  15

<210> SEQ ID NO 175
<211> LENGTH: 14
<212> TYPE: PRT
<213> ORGANISM: Artificial sequence
<220> FEATURE:
<223> OTHER INFORMATION: Synthetic

<400> SEQUENCE: 175

Val Ser Gly Trp Arg Leu Phe Lys Lys Ile Ser Val Phe Thr
1               5                   10

<210> SEQ ID NO 176
<211> LENGTH: 13
<212> TYPE: PRT
<213> ORGANISM: Artificial sequence
<220> FEATURE:
<223> OTHER INFORMATION: Synthetic

<400> SEQUENCE: 176

Val Ser Gly Trp Arg Leu Phe Lys Lys Ile Ser Val Phe
1               5                   10

<210> SEQ ID NO 177
<211> LENGTH: 12
<212> TYPE: PRT
<213> ORGANISM: Artificial sequence
<220> FEATURE:
<223> OTHER INFORMATION: Synthetic

<400> SEQUENCE: 177

Val Ser Gly Trp Arg Leu Phe Lys Lys Ile Ser Val
1               5                   10

<210> SEQ ID NO 178
<211> LENGTH: 11
<212> TYPE: PRT
<213> ORGANISM: Artificial sequence
<220> FEATURE:
<223> OTHER INFORMATION: Synthetic

<400> SEQUENCE: 178
```

```
Val Ser Gly Trp Arg Leu Cys Lys Lys Ile Ser
1               5                   10

<210> SEQ ID NO 179
<211> LENGTH: 22
<212> TYPE: PRT
<213> ORGANISM: Artificial sequence
<220> FEATURE:
<223> OTHER INFORMATION: Synthetic

<400> SEQUENCE: 179

Val Ser Gly Trp Arg Leu Phe Lys Lys Ile Ser Gly Ser Met Leu Phe
1               5                   10                  15

Arg Val Thr Ile Asn Ser
            20

<210> SEQ ID NO 180
<211> LENGTH: 13
<212> TYPE: PRT
<213> ORGANISM: Artificial sequence
<220> FEATURE:
<223> OTHER INFORMATION: Synthetic

<400> SEQUENCE: 180

Ser Ser Trp Lys Arg Leu Phe Arg Val Thr Ile Asn Ser
1               5                   10

<210> SEQ ID NO 181
<211> LENGTH: 12
<212> TYPE: PRT
<213> ORGANISM: Artificial sequence
<220> FEATURE:
<223> OTHER INFORMATION: Synthetic

<400> SEQUENCE: 181

Ser Ser Trp Lys Arg Phe Arg Val Thr Ile Asn Ser
1               5                   10

<210> SEQ ID NO 182
<211> LENGTH: 11
<212> TYPE: PRT
<213> ORGANISM: Artificial sequence
<220> FEATURE:
<223> OTHER INFORMATION: Synthetic

<400> SEQUENCE: 182

Ser Ser Trp Lys Arg Arg Val Thr Ile Asn Ser
1               5                   10

<210> SEQ ID NO 183
<211> LENGTH: 19
<212> TYPE: PRT
<213> ORGANISM: Artificial sequence
<220> FEATURE:
<223> OTHER INFORMATION: Synthetic

<400> SEQUENCE: 183

Ser Ser Trp Lys Arg Thr Pro Asp Gly Ser Met Leu Phe Arg Val Thr
1               5                   10                  15

Ile Asn Ser

<210> SEQ ID NO 184
<211> LENGTH: 20
<212> TYPE: PRT
<213> ORGANISM: Artificial sequence
<220> FEATURE:
```

```
<223> OTHER INFORMATION: Synthetic

<400> SEQUENCE: 184

Ser Ser Trp Lys Arg Ile Thr Pro Asp Gly Ser Met Leu Phe Arg Val
1               5                   10                  15

Thr Ile Asn Ser
            20

<210> SEQ ID NO 185
<211> LENGTH: 21
<212> TYPE: PRT
<213> ORGANISM: Artificial sequence
<220> FEATURE:
<223> OTHER INFORMATION: Synthetic

<400> SEQUENCE: 185

Ser Ser Trp Lys Arg Leu Ile Thr Pro Asp Gly Ser Met Leu Phe Arg
1               5                   10                  15

Val Thr Ile Asn Ser
            20

<210> SEQ ID NO 186
<211> LENGTH: 16
<212> TYPE: PRT
<213> ORGANISM: Artificial sequence
<220> FEATURE:
<223> OTHER INFORMATION: Synthetic

<400> SEQUENCE: 186

Ser Ser Arg Gly Ser Met Leu Phe Arg Val Thr Ile Asn Ser Trp Lys
1               5                   10                  15

<210> SEQ ID NO 187
<211> LENGTH: 16
<212> TYPE: PRT
<213> ORGANISM: Artificial sequence
<220> FEATURE:
<223> OTHER INFORMATION: Synthetic

<400> SEQUENCE: 187

Ser Lys Arg Gly Ser Met Leu Phe Arg Val Thr Ile Asn Ser Trp Ser
1               5                   10                  15

<210> SEQ ID NO 188
<211> LENGTH: 14
<212> TYPE: PRT
<213> ORGANISM: Artificial sequence
<220> FEATURE:
<223> OTHER INFORMATION: Synthetic

<400> SEQUENCE: 188

Ser Trp Arg Gly Ser Met Leu Phe Arg Val Thr Ile Asn Ser
1               5                   10

<210> SEQ ID NO 189
<211> LENGTH: 14
<212> TYPE: PRT
<213> ORGANISM: Artificial sequence
<220> FEATURE:
<223> OTHER INFORMATION: Synthetic

<400> SEQUENCE: 189

Ser Ser Arg Gly Ser Met Leu Phe Arg Val Thr Ile Trp Lys
1               5                   10
```

<210> SEQ ID NO 190
<211> LENGTH: 16
<212> TYPE: PRT
<213> ORGANISM: Artificial sequence
<220> FEATURE:
<223> OTHER INFORMATION: Synthetic

<400> SEQUENCE: 190

Ser Ser Trp Lys Arg Gly Ser Met Leu Tyr Arg Val Thr Ile Asn Ser
1               5                   10                  15

<210> SEQ ID NO 191
<211> LENGTH: 16
<212> TYPE: PRT
<213> ORGANISM: Artificial sequence
<220> FEATURE:
<223> OTHER INFORMATION: Synthetic

<400> SEQUENCE: 191

Ser Ser Trp Lys Arg Gly Ser Met Leu Trp Arg Val Thr Ile Asn Ser
1               5                   10                  15

<210> SEQ ID NO 192
<211> LENGTH: 16
<212> TYPE: PRT
<213> ORGANISM: Artificial sequence
<220> FEATURE:
<223> OTHER INFORMATION: Synthetic

<400> SEQUENCE: 192

Ser Ser Trp Lys Arg Gly Ser Met Leu His Arg Val Thr Ile Asn Ser
1               5                   10                  15

<210> SEQ ID NO 193
<211> LENGTH: 16
<212> TYPE: PRT
<213> ORGANISM: Artificial sequence
<220> FEATURE:
<223> OTHER INFORMATION: Synthetic

<400> SEQUENCE: 193

Ser Ser Trp Lys Arg Gly Ser Leu Leu Phe Arg Val Thr Ile Asn Ser
1               5                   10                  15

<210> SEQ ID NO 194
<211> LENGTH: 16
<212> TYPE: PRT
<213> ORGANISM: Artificial sequence
<220> FEATURE:
<223> OTHER INFORMATION: Synthetic

<400> SEQUENCE: 194

Ser Ser Trp Lys Arg Gly Ser Lys Leu Phe Arg Val Thr Ile Asn Ser
1               5                   10                  15

<210> SEQ ID NO 195
<211> LENGTH: 16
<212> TYPE: PRT
<213> ORGANISM: Artificial sequence
<220> FEATURE:
<223> OTHER INFORMATION: Synthetic

<400> SEQUENCE: 195

Ser Ser Trp Lys Arg Gly Ser Arg Leu Phe Arg Val Thr Ile Asn Ser
1               5                   10                  15

<210> SEQ ID NO 196

-continued

```
<211> LENGTH: 16
<212> TYPE: PRT
<213> ORGANISM: Artificial sequence
<220> FEATURE:
<223> OTHER INFORMATION: Synthetic

<400> SEQUENCE: 196

Ser Ser Trp Lys Arg Gly Ser Phe Leu Phe Arg Val Thr Ile Asn Ser
1               5                   10                  15

<210> SEQ ID NO 197
<211> LENGTH: 16
<212> TYPE: PRT
<213> ORGANISM: Artificial sequence
<220> FEATURE:
<223> OTHER INFORMATION: Synthetic

<400> SEQUENCE: 197

Ser Ser Trp Lys Arg Gly Ser Trp Leu Phe Arg Val Thr Ile Asn Ser
1               5                   10                  15

<210> SEQ ID NO 198
<211> LENGTH: 16
<212> TYPE: PRT
<213> ORGANISM: Artificial sequence
<220> FEATURE:
<223> OTHER INFORMATION: Synthetic

<400> SEQUENCE: 198

Ser Ser Trp Lys Arg Gly Ser Met Leu Phe Arg Val Ser Ile Asn Ser
1               5                   10                  15

<210> SEQ ID NO 199
<211> LENGTH: 16
<212> TYPE: PRT
<213> ORGANISM: Artificial sequence
<220> FEATURE:
<223> OTHER INFORMATION: Synthetic

<400> SEQUENCE: 199

Ser Ser Trp Lys Arg Gly Ser Met Leu Phe Arg Val Gln Ile Asn Ser
1               5                   10                  15

<210> SEQ ID NO 200
<211> LENGTH: 16
<212> TYPE: PRT
<213> ORGANISM: Artificial sequence
<220> FEATURE:
<223> OTHER INFORMATION: Synthetic

<400> SEQUENCE: 200

Ser Ser Trp Lys Arg Gly Ser Met Leu Phe Arg Val Asn Ile Asn Ser
1               5                   10                  15

<210> SEQ ID NO 201
<211> LENGTH: 17
<212> TYPE: PRT
<213> ORGANISM: Artificial sequence
<220> FEATURE:
<223> OTHER INFORMATION: Synthetic

<400> SEQUENCE: 201

Ser Ser Trp Lys Arg Gly Ser Met Leu Phe Arg Val Thr Ile Asn Ser
1               5                   10                  15

Cys
```

-continued

```
<210> SEQ ID NO 202
<211> LENGTH: 12
<212> TYPE: PRT
<213> ORGANISM: Artificial sequence
<220> FEATURE:
<223> OTHER INFORMATION: Synthetic

<400> SEQUENCE: 202

Cys Val Ser Gly Trp Arg Leu Phe Lys Lys Ile Ser
1               5                   10

<210> SEQ ID NO 203
<211> LENGTH: 17
<212> TYPE: PRT
<213> ORGANISM: Artificial sequence
<220> FEATURE:
<223> OTHER INFORMATION: Synthetic

<400> SEQUENCE: 203

Ser Ser Trp Lys Arg Gly Ser Met Leu Phe Arg Val Thr Ile Asn Ser
1               5                   10                  15

Lys

<210> SEQ ID NO 204
<211> LENGTH: 12
<212> TYPE: PRT
<213> ORGANISM: Artificial sequence
<220> FEATURE:
<223> OTHER INFORMATION: Synthetic

<400> SEQUENCE: 204

Lys Val Ser Gly Trp Arg Leu Phe Lys Lys Ile Ser
1               5                   10

<210> SEQ ID NO 205
<211> LENGTH: 23
<212> TYPE: PRT
<213> ORGANISM: Artificial sequence
<220> FEATURE:
<223> OTHER INFORMATION: Synthetic

<400> SEQUENCE: 205

Gly Ser Leu Leu Phe Arg Val Thr Ile Asn Gly Val Thr Gly Trp Arg
1               5                   10                  15

Leu Cys Glu Asn Ile Leu Ala
            20

<210> SEQ ID NO 206
<211> LENGTH: 24
<212> TYPE: PRT
<213> ORGANISM: Artificial sequence
<220> FEATURE:
<223> OTHER INFORMATION: Synthetic

<400> SEQUENCE: 206

Gly Ser Leu Leu Phe Arg Val Thr Ile Asn Val Gly Val Thr Gly Trp
1               5                   10                  15

Arg Leu Cys Glu Arg Ile Leu Ala
            20

<210> SEQ ID NO 207
<211> LENGTH: 12
<212> TYPE: PRT
<213> ORGANISM: Artificial sequence
<220> FEATURE:
<223> OTHER INFORMATION: Synthetic
```

-continued

<400> SEQUENCE: 207

Ser Val Ser Gly Trp Arg Leu Phe Lys Lys Ile Ser
1               5                   10

<210> SEQ ID NO 208
<211> LENGTH: 13
<212> TYPE: PRT
<213> ORGANISM: Artificial sequence
<220> FEATURE:
<223> OTHER INFORMATION: Synthetic

<400> SEQUENCE: 208

Asn Ser Val Ser Gly Trp Arg Leu Phe Lys Lys Ile Ser
1               5                   10

<210> SEQ ID NO 209
<211> LENGTH: 9
<212> TYPE: PRT
<213> ORGANISM: Artificial sequence
<220> FEATURE:
<223> OTHER INFORMATION: Synthetic

<400> SEQUENCE: 209

Gly Trp Arg Leu Phe Lys Lys Ile Ser
1               5

<210> SEQ ID NO 210
<211> LENGTH: 501
<212> TYPE: DNA
<213> ORGANISM: Artificial sequence
<220> FEATURE:
<223> OTHER INFORMATION: Synthetic

<400> SEQUENCE: 210
atggtgagcg gctggcggct gttcaagaag attagccacc atcaccatca ccatcatcac      60
ttcacactcg acgatttcgt tggggactgg aacagacag ccgcctacaa cctggaccaa      120
gtccttgaac agggaggtgt gtccagtttg ctgcagaatc tcgccgtgtc cgtaactccg      180
atcatgagga ttgtccggag cggtgaaaat gccctgaaga tcgacatcca tgtcatcatc      240
ccgtatgaag gtctgagcgc cgaccaaatg gcccagatcg aagaggtgtt taaggtggtg      300
taccctgtgg atgatcatca ctttaaggtg atcctgccct atggcacact ggtaatcgac      360
ggggttacgc cgaacaagct gaactatttc ggacggccgt atgaaggcat cgccgtgttc      420
gacggcaaaa agatcactac cacagggacc ctgtggaacg gcaacaaaat tatcgacgag      480
cgcctgatca ccccgacta a                                                 501

<210> SEQ ID NO 211
<211> LENGTH: 166
<212> TYPE: PRT
<213> ORGANISM: Artificial sequence
<220> FEATURE:
<223> OTHER INFORMATION: Synthetic

<400> SEQUENCE: 211

Met Val Ser Gly Trp Arg Leu Phe Lys Lys Ile Ser His His His His
1               5                   10                  15

His His His His Phe Thr Leu Asp Asp Phe Val Gly Asp Trp Glu Gln
                20                  25                  30

Thr Ala Ala Tyr Asn Leu Asp Gln Val Leu Glu Gln Gly Gly Val Ser
        35                  40                  45

```
Ser Leu Leu Gln Asn Leu Ala Val Ser Val Thr Pro Ile Met Arg Ile
    50                  55                  60

Val Arg Ser Gly Glu Asn Ala Leu Lys Ile Asp Ile His Val Ile Ile
65                  70                  75                  80

Pro Tyr Glu Gly Leu Ser Ala Asp Gln Met Ala Gln Ile Glu Glu Val
                85                  90                  95

Phe Lys Val Val Tyr Pro Val Asp Asp His His Phe Lys Val Ile Leu
                100                 105                 110

Pro Tyr Gly Thr Leu Val Ile Asp Gly Val Thr Pro Asn Lys Leu Asn
            115                 120                 125

Tyr Phe Gly Arg Pro Tyr Glu Gly Ile Ala Val Phe Asp Gly Lys Lys
    130                 135                 140

Ile Thr Thr Thr Gly Thr Leu Trp Asn Gly Asn Lys Ile Ile Asp Glu
145                 150                 155                 160

Arg Leu Ile Thr Pro Asp
                165
```

<210> SEQ ID NO 212
<211> LENGTH: 510
<212> TYPE: DNA
<213> ORGANISM: Artificial sequence
<220> FEATURE:
<223> OTHER INFORMATION: Synthetic

<400> SEQUENCE: 212

```
atgaaacatc accatcacca tcatgtgagc ggctggcggc tgttcaagaa gattagcggc      60
agctccggtt tcacactcga cgatttcgtt ggggactggg aacagacagc cgcctacaac     120
ctggaccaag tccttgaaca gggaggtgtg tccagtttgc tgcagaatct cgccgtgtcc     180
gtaactccga tcatgaggat tgtccggagc ggtgaaaatg ccctgaagat cgacatccat     240
gtcatcatcc cgtatgaagg tctgagcgcc gaccaaatgg cccagatcga agaggtgttt     300
aaggtggtgt accctgtgga tgatcatcac tttaaggtga tcctgcccta tggcacactg     360
gtaatcgacg gggttacgcc gaacaagctg aactatttcg gacggccgta tgaaggcatc     420
gccgtgttcg acggcaaaaa gatcactacc acagggaccc tgtggaacgg caacaaaatt     480
atcgacgagc gcctgatcac ccccgactaa                                      510
```

<210> SEQ ID NO 213
<211> LENGTH: 169
<212> TYPE: PRT
<213> ORGANISM: Artificial sequence
<220> FEATURE:
<223> OTHER INFORMATION: Synthetic

<400> SEQUENCE: 213

```
Met Lys His His His His His His Val Ser Gly Trp Arg Leu Phe Lys
1                   5                   10                  15

Lys Ile Ser Gly Ser Ser Gly Phe Thr Leu Asp Asp Phe Val Gly Asp
                20                  25                  30

Trp Glu Gln Thr Ala Ala Tyr Asn Leu Asp Gln Val Leu Glu Gln Gly
            35                  40                  45

Gly Val Ser Ser Leu Leu Gln Asn Leu Ala Val Ser Val Thr Pro Ile
    50                  55                  60

Met Arg Ile Val Arg Ser Gly Glu Asn Ala Leu Lys Ile Asp Ile His
65                  70                  75                  80

Val Ile Ile Pro Tyr Glu Gly Leu Ser Ala Asp Gln Met Ala Gln Ile
                85                  90                  95
```

-continued

```
Glu Glu Val Phe Lys Val Val Tyr Pro Val Asp Asp His His Phe Lys
            100             105             110

Val Ile Leu Pro Tyr Gly Thr Leu Val Ile Asp Gly Val Thr Pro Asn
            115             120             125

Lys Leu Asn Tyr Phe Gly Arg Pro Tyr Glu Gly Ile Ala Val Phe Asp
            130             135             140

Gly Lys Lys Ile Thr Thr Thr Gly Thr Leu Trp Asn Gly Asn Lys Ile
145             150             155             160

Ile Asp Glu Arg Leu Ile Thr Pro Asp
                165
```

```
<210> SEQ ID NO 214
<211> LENGTH: 366
<212> TYPE: DNA
<213> ORGANISM: Artificial sequence
<220> FEATURE:
<223> OTHER INFORMATION: Synthetic

<400> SEQUENCE: 214
atggtggcca tcctctggca tgagatgtgg catgaaggcc tggaagaggc atctcgtttg      60
tactttgggg aaaggaacgt gaaaggcatg tttgaggtgc tggagccctt gcatgctatg     120
atggaacggg gcccccagac tctgaaggaa acatccttta atcaggccta tggtcgagat     180
ttaatggagg cccaagagtg gtgcaggaag tacatgaaat cagggaatgt caaggacctc     240
acccaagcct gggacctcta ttatcatgtg ttccgacgaa tcagtggtgg ttcaggtggt     300
ggcgggagcg gtggctcgag cagcggtgga gtgagcggct ggcggctgtt caagaagatt     360
agctaa                                                                366
```

```
<210> SEQ ID NO 215
<211> LENGTH: 121
<212> TYPE: PRT
<213> ORGANISM: Artificial sequence
<220> FEATURE:
<223> OTHER INFORMATION: Synthetic

<400> SEQUENCE: 215

Met Val Ala Ile Leu Trp His Glu Met Trp His Glu Gly Leu Glu Glu
1               5               10              15

Ala Ser Arg Leu Tyr Phe Gly Glu Arg Asn Val Lys Gly Met Phe Glu
            20              25              30

Val Leu Glu Pro Leu His Ala Met Met Glu Arg Gly Pro Gln Thr Leu
            35              40              45

Lys Glu Thr Ser Phe Asn Gln Ala Tyr Gly Arg Asp Leu Met Glu Ala
            50              55              60

Gln Glu Trp Cys Arg Lys Tyr Met Lys Ser Gly Asn Val Lys Asp Leu
65              70              75              80

Thr Gln Ala Trp Asp Leu Tyr Tyr His Val Phe Arg Arg Ile Ser Gly
                85              90              95

Gly Ser Gly Gly Gly Gly Ser Gly Gly Ser Ser Ser Gly Gly Val Ser
            100             105             110

Gly Trp Arg Leu Phe Lys Lys Ile Ser
            115             120
```

```
<210> SEQ ID NO 216
<211> LENGTH: 372
<212> TYPE: DNA
<213> ORGANISM: Artificial sequence
```

<220> FEATURE:
<223> OTHER INFORMATION: Synthetic

<400> SEQUENCE: 216
atggtggcca tcctctggca tgagatgtgg catgaaggcc tggaagaggc atctcgtttg      60
tactttgggg aaaggaacgt gaaaggcatg tttgaggtgc tggagccctt gcatgctatg     120
atggaacggg gcccccagac tctgaaggaa acatcctta atcaggccta tggtcgagat      180
ttaatggagg cccaagagtg gtgcaggaag tacatgaaat cagggaatgt caaggacctc     240
acccaagcct gggacctcta ttatcatgtg ttccgacgaa tcagtggtgg ttcaggtggt     300
ggcgggagcg tggctcgag cagcggtgga gttagcgtta gcggctggcg cctgttcaag       360
aagatcagct aa                                                         372

<210> SEQ ID NO 217
<211> LENGTH: 123
<212> TYPE: PRT
<213> ORGANISM: Artificial sequence
<220> FEATURE:
<223> OTHER INFORMATION: Synthetic

<400> SEQUENCE: 217

Met Val Ala Ile Leu Trp His Glu Met Trp His Glu Gly Leu Glu Glu
1               5                   10                  15

Ala Ser Arg Leu Tyr Phe Gly Glu Arg Asn Val Lys Gly Met Phe Glu
            20                  25                  30

Val Leu Glu Pro Leu His Ala Met Met Glu Arg Gly Pro Gln Thr Leu
        35                  40                  45

Lys Glu Thr Ser Phe Asn Gln Ala Tyr Gly Arg Asp Leu Met Glu Ala
    50                  55                  60

Gln Glu Trp Cys Arg Lys Tyr Met Lys Ser Gly Asn Val Lys Asp Leu
65                  70                  75                  80

Thr Gln Ala Trp Asp Leu Tyr Tyr His Val Phe Arg Arg Ile Ser Gly
                85                  90                  95

Gly Ser Gly Gly Gly Gly Ser Gly Gly Ser Ser Ser Gly Gly Val Ser
            100                 105                 110

Val Ser Gly Trp Arg Leu Phe Lys Lys Ile Ser
            115                 120

<210> SEQ ID NO 218
<211> LENGTH: 369
<212> TYPE: DNA
<213> ORGANISM: Artificial sequence
<220> FEATURE:
<223> OTHER INFORMATION: Synthetic

<400> SEQUENCE: 218
atgggagtgc aggtggaaac catctcccca ggagacgggc gcaccttccc caagcgcggc      60
cagacctgcg tggtgcacta caccgggatg cttgaagatg aaagaaatt tgattcctcc      120 cgggacagaa acaagccctt taagtttatg ctaggcaagc aggaggtgat ccgaggctgg     180
gaagaagggg ttgcccagat gagtgtgggt cagagagcca aactgactat atctccagat     240
tatgcctatg gtgccactgg gcacccaggc atcatcccac cacatgccac tctcgtcttc     300
gatgtggagc ttctaaaact ggaaggtggt tcaggtggtg cgggagcgg tggctcgagc       360 agcggtgga                                                             369

<210> SEQ ID NO 219

<211> LENGTH: 123
<212> TYPE: PRT
<213> ORGANISM: Artificial sequence
<220> FEATURE:
<223> OTHER INFORMATION: Synthetic

<400> SEQUENCE: 219

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu Gly Gly Ser Gly
            100                 105                 110

Gly Gly Gly Ser Gly Gly Ser Ser Ser Gly Gly
        115                 120

<210> SEQ ID NO 220
<211> LENGTH: 12
<212> TYPE: PRT
<213> ORGANISM: Artificial sequence
<220> FEATURE:
<223> OTHER INFORMATION: Synthetic

<400> SEQUENCE: 220

Gly Ser Met Leu Phe Arg Val Thr Ile Asn Ser Val
1               5                   10

<210> SEQ ID NO 221
<211> LENGTH: 13
<212> TYPE: PRT
<213> ORGANISM: Artificial sequence
<220> FEATURE:
<223> OTHER INFORMATION: Synthetic

<400> SEQUENCE: 221

Gly Ser Met Leu Phe Arg Val Thr Ile Asn Ser Val Ser
1               5                   10

<210> SEQ ID NO 222
<211> LENGTH: 12
<212> TYPE: PRT
<213> ORGANISM: Artificial sequence
<220> FEATURE:
<223> OTHER INFORMATION: Synthetic

<400> SEQUENCE: 222

Met Leu Phe Arg Val Thr Ile Asn Ser Val Ser Gly
1               5                   10

<210> SEQ ID NO 223
<211> LENGTH: 13
<212> TYPE: PRT
<213> ORGANISM: Artificial sequence
<220> FEATURE:
<223> OTHER INFORMATION: Synthetic

<400> SEQUENCE: 223

Met Leu Phe Arg Val Thr Ile Asn Ser Val Ser Gly Trp
1               5                   10

<210> SEQ ID NO 224
<211> LENGTH: 14
<212> TYPE: PRT
<213> ORGANISM: Artificial sequence
<220> FEATURE:
<223> OTHER INFORMATION: Synthetic

<400> SEQUENCE: 224

Met Leu Phe Arg Val Thr Ile Asn Ser Val Ser Gly Trp Lys
1               5                   10

<210> SEQ ID NO 225
<211> LENGTH: 14
<212> TYPE: PRT
<213> ORGANISM: Artificial sequence
<220> FEATURE:
<223> OTHER INFORMATION: Synthetic

<400> SEQUENCE: 225

Met Leu Phe Arg Val Thr Ile Asn Ser Val Ser Gly Trp Arg
1               5                   10

<210> SEQ ID NO 226
<211> LENGTH: 14
<212> TYPE: PRT
<213> ORGANISM: Artificial sequence
<220> FEATURE:
<223> OTHER INFORMATION: Synthetic

<400> SEQUENCE: 226

Gly Ser Met Leu Phe Arg Val Thr Ile Asn Ser Val Ser Gly
1               5                   10

<210> SEQ ID NO 227
<211> LENGTH: 15
<212> TYPE: PRT
<213> ORGANISM: Artificial sequence
<220> FEATURE:
<223> OTHER INFORMATION: Synthetic

<400> SEQUENCE: 227

Gly Ser Met Leu Phe Arg Val Thr Ile Asn Ser Val Ser Gly Trp
1               5                   10                  15

<210> SEQ ID NO 228
<211> LENGTH: 16
<212> TYPE: PRT
<213> ORGANISM: Artificial sequence
<220> FEATURE:
<223> OTHER INFORMATION: Synthetic

<400> SEQUENCE: 228

Gly Ser Met Leu Phe Arg Val Thr Ile Asn Ser Val Ser Gly Trp Arg
1               5                   10                  15

<210> SEQ ID NO 229
<211> LENGTH: 16
<212> TYPE: PRT
<213> ORGANISM: Artificial sequence
<220> FEATURE:
<223> OTHER INFORMATION: Synthetic

<400> SEQUENCE: 229

```
Gly Ser Met Leu Phe Arg Val Thr Ile Asn Ser Val Ser Gly Trp Lys
1               5                   10                  15

<210> SEQ ID NO 230
<211> LENGTH: 11
<212> TYPE: PRT
<213> ORGANISM: Artificial sequence
<220> FEATURE:
<223> OTHER INFORMATION: Synthetic

<400> SEQUENCE: 230

Gly Ser Met Leu Phe Arg Val Thr Ile Trp Lys
1               5                   10

<210> SEQ ID NO 231
<211> LENGTH: 13
<212> TYPE: PRT
<213> ORGANISM: Artificial sequence
<220> FEATURE:
<223> OTHER INFORMATION: Synthetic

<400> SEQUENCE: 231

Gly Ser Met Leu Phe Arg Val Thr Ile Asn Ser Trp Lys
1               5                   10

<210> SEQ ID NO 232
<211> LENGTH: 11
<212> TYPE: PRT
<213> ORGANISM: Artificial sequence
<220> FEATURE:
<223> OTHER INFORMATION: Synthetic

<400> SEQUENCE: 232

Met Leu Phe Arg Val Thr Ile Asn Ser Trp Lys
1               5                   10

<210> SEQ ID NO 233
<211> LENGTH: 11
<212> TYPE: PRT
<213> ORGANISM: Artificial sequence
<220> FEATURE:
<223> OTHER INFORMATION: Synthetic

<400> SEQUENCE: 233

Met Leu Phe Arg Val Thr Ile Asn Ser Trp Ser
1               5                   10

<210> SEQ ID NO 234
<211> LENGTH: 9
<212> TYPE: PRT
<213> ORGANISM: Artificial sequence
<220> FEATURE:
<223> OTHER INFORMATION: Synthetic

<400> SEQUENCE: 234

Met Leu Phe Arg Val Thr Ile Trp Ser
1               5

<210> SEQ ID NO 235
<211> LENGTH: 9
<212> TYPE: PRT
<213> ORGANISM: Artificial sequence
<220> FEATURE:
<223> OTHER INFORMATION: Synthetic

<400> SEQUENCE: 235
```

```
Met Leu Phe Arg Val Thr Ile Trp Lys
1               5

<210> SEQ ID NO 236
<211> LENGTH: 9
<212> TYPE: PRT
<213> ORGANISM: Artificial sequence
<220> FEATURE:
<223> OTHER INFORMATION: Synthetic

<400> SEQUENCE: 236

Met Leu Phe Arg Val Lys Ile Asn Ser
1               5

<210> SEQ ID NO 237
<211> LENGTH: 13
<212> TYPE: PRT
<213> ORGANISM: Artificial sequence
<220> FEATURE:
<223> OTHER INFORMATION: Synthetic

<400> SEQUENCE: 237

Gly Ser Met Leu Phe Arg Val Thr Ile Asn Ser Trp Ser
1               5                   10

<210> SEQ ID NO 238
<211> LENGTH: 11
<212> TYPE: PRT
<213> ORGANISM: Artificial sequence
<220> FEATURE:
<223> OTHER INFORMATION: Synthetic

<400> SEQUENCE: 238

Gly Ser Met Leu Phe Arg Val Lys Ile Asn Ser
1               5                   10

<210> SEQ ID NO 239
<211> LENGTH: 11
<212> TYPE: PRT
<213> ORGANISM: Artificial sequence
<220> FEATURE:
<223> OTHER INFORMATION: Synthetic

<400> SEQUENCE: 239

Gly Ser Met Leu Phe Arg Val Thr Ile Trp Ser
1               5                   10

<210> SEQ ID NO 240
<211> LENGTH: 9
<212> TYPE: PRT
<213> ORGANISM: Artificial sequence
<220> FEATURE:
<223> OTHER INFORMATION: Synthetic

<400> SEQUENCE: 240

Met Leu Phe Arg Val Asn Ile Asn Ser
1               5

<210> SEQ ID NO 241
<211> LENGTH: 9
<212> TYPE: PRT
<213> ORGANISM: Artificial sequence
<220> FEATURE:
<223> OTHER INFORMATION: Synthetic

<400> SEQUENCE: 241

Met Leu Phe Arg Val Trp Ile Asn Ser
```

```
1               5

<210> SEQ ID NO 242
<211> LENGTH: 9
<212> TYPE: PRT
<213> ORGANISM: Artificial sequence
<220> FEATURE:
<223> OTHER INFORMATION: Synthetic

<400> SEQUENCE: 242

Leu Leu Phe Arg Val Lys Ile Asn Ser
1               5

<210> SEQ ID NO 243
<211> LENGTH: 9
<212> TYPE: PRT
<213> ORGANISM: Artificial sequence
<220> FEATURE:
<223> OTHER INFORMATION: Synthetic

<400> SEQUENCE: 243

Phe Leu Phe Arg Val Thr Ile Asn Ser
1               5

<210> SEQ ID NO 244
<211> LENGTH: 17
<212> TYPE: PRT
<213> ORGANISM: Artificial sequence
<220> FEATURE:
<223> OTHER INFORMATION: Synthetic

<400> SEQUENCE: 244

Ser Ser Trp Lys Arg Gly Ser Met Leu Phe Arg Val Thr Ile Asn Ser
1               5                   10                  15

Val

<210> SEQ ID NO 245
<211> LENGTH: 18
<212> TYPE: PRT
<213> ORGANISM: Artificial sequence
<220> FEATURE:
<223> OTHER INFORMATION: Synthetic

<400> SEQUENCE: 245

Ser Ser Trp Lys Arg Gly Ser Met Leu Phe Arg Val Thr Ile Asn Ser
1               5                   10                  15

Val Ser

<210> SEQ ID NO 246
<211> LENGTH: 17
<212> TYPE: PRT
<213> ORGANISM: Artificial sequence
<220> FEATURE:
<223> OTHER INFORMATION: Synthetic

<400> SEQUENCE: 246

Ser Ser Trp Lys Arg Met Leu Phe Arg Val Thr Ile Asn Ser Val Ser
1               5                   10                  15

Gly

<210> SEQ ID NO 247
<211> LENGTH: 18
<212> TYPE: PRT
<213> ORGANISM: Artificial sequence
<220> FEATURE:
```

<223> OTHER INFORMATION: Synthetic

<400> SEQUENCE: 247

Ser Ser Trp Lys Arg Met Leu Phe Arg Val Thr Ile Asn Ser Val Ser
1               5                   10                  15

Gly Trp

<210> SEQ ID NO 248
<211> LENGTH: 19
<212> TYPE: PRT
<213> ORGANISM: Artificial sequence
<220> FEATURE:
<223> OTHER INFORMATION: Synthetic

<400> SEQUENCE: 248

Ser Ser Trp Lys Arg Met Leu Phe Arg Val Thr Ile Asn Ser Val Ser
1               5                   10                  15

Gly Trp Arg

<210> SEQ ID NO 249
<211> LENGTH: 19
<212> TYPE: PRT
<213> ORGANISM: Artificial sequence
<220> FEATURE:
<223> OTHER INFORMATION: Synthetic

<400> SEQUENCE: 249

Ser Ser Trp Lys Arg Met Leu Phe Arg Val Thr Ile Asn Ser Val Ser
1               5                   10                  15

Gly Trp Lys

<210> SEQ ID NO 250
<211> LENGTH: 14
<212> TYPE: PRT
<213> ORGANISM: Artificial sequence
<220> FEATURE:
<223> OTHER INFORMATION: Synthetic

<400> SEQUENCE: 250

Met Leu Phe Arg Val Thr Ile Asn Ser Val Ser Gly Trp Lys
1               5                   10

<210> SEQ ID NO 251
<211> LENGTH: 19
<212> TYPE: PRT
<213> ORGANISM: Artificial sequence
<220> FEATURE:
<223> OTHER INFORMATION: Synthetic

<400> SEQUENCE: 251

Ser Ser Trp Lys Arg Gly Ser Met Leu Phe Arg Val Thr Ile Asn Ser
1               5                   10                  15

Val Ser Gly

<210> SEQ ID NO 252
<211> LENGTH: 20
<212> TYPE: PRT
<213> ORGANISM: Artificial sequence
<220> FEATURE:
<223> OTHER INFORMATION: Synthetic

<400> SEQUENCE: 252

Ser Ser Trp Lys Arg Gly Ser Met Leu Phe Arg Val Thr Ile Asn Ser
1               5                   10                  15

```
Val Ser Gly Trp
            20

<210> SEQ ID NO 253
<211> LENGTH: 21
<212> TYPE: PRT
<213> ORGANISM: Artificial sequence
<220> FEATURE:
<223> OTHER INFORMATION: Synthetic

<400> SEQUENCE: 253

Ser Ser Trp Lys Arg Gly Ser Met Leu Phe Arg Val Thr Ile Asn Ser
1               5                   10                  15

Val Ser Gly Trp Arg
            20

<210> SEQ ID NO 254
<211> LENGTH: 21
<212> TYPE: PRT
<213> ORGANISM: Artificial sequence
<220> FEATURE:
<223> OTHER INFORMATION: Synthetic

<400> SEQUENCE: 254

Ser Ser Trp Lys Arg Gly Ser Met Leu Phe Arg Val Thr Ile Asn Ser
1               5                   10                  15

Val Ser Gly Trp Lys
            20

<210> SEQ ID NO 255
<211> LENGTH: 16
<212> TYPE: PRT
<213> ORGANISM: Artificial sequence
<220> FEATURE:
<223> OTHER INFORMATION: Synthetic

<400> SEQUENCE: 255

Ser Ser Trp Lys Arg Gly Ser Tyr Leu Phe Arg Val Thr Ile Asn Ser
1               5                   10                  15

<210> SEQ ID NO 256
<211> LENGTH: 16
<212> TYPE: PRT
<213> ORGANISM: Artificial sequence
<220> FEATURE:
<223> OTHER INFORMATION: Synthetic

<400> SEQUENCE: 256

Ser Ser Trp Lys Arg Gly Ser Met Leu Phe Arg Val Lys Ile Asn Ser
1               5                   10                  15

<210> SEQ ID NO 257
<211> LENGTH: 16
<212> TYPE: PRT
<213> ORGANISM: Artificial sequence
<220> FEATURE:
<223> OTHER INFORMATION: Synthetic

<400> SEQUENCE: 257

Ser Ser Trp Lys Arg Gly Ser Met Leu Phe Arg Val Arg Ile Asn Ser
1               5                   10                  15

<210> SEQ ID NO 258
<211> LENGTH: 16
<212> TYPE: PRT
```

<213> ORGANISM: Artificial sequence
<220> FEATURE:
<223> OTHER INFORMATION: Synthetic

<400> SEQUENCE: 258

Ser Ser Trp Lys Arg Gly Ser Met Leu Phe Arg Val Trp Ile Asn Ser
1               5                   10                  15

<210> SEQ ID NO 259
<211> LENGTH: 16
<212> TYPE: PRT
<213> ORGANISM: Artificial sequence
<220> FEATURE:
<223> OTHER INFORMATION: Synthetic

<400> SEQUENCE: 259

Ser Ser Lys Arg Gly Ser Met Leu Phe Arg Val Thr Ile Trp Ser Val
1               5                   10                  15

<210> SEQ ID NO 260
<211> LENGTH: 17
<212> TYPE: PRT
<213> ORGANISM: Artificial sequence
<220> FEATURE:
<223> OTHER INFORMATION: Synthetic

<400> SEQUENCE: 260

Ser Ser Lys Arg Gly Ser Met Leu Phe Arg Val Thr Ile Trp Ser Val
1               5                   10                  15

Ser

<210> SEQ ID NO 261
<211> LENGTH: 15
<212> TYPE: PRT
<213> ORGANISM: Artificial sequence
<220> FEATURE:
<223> OTHER INFORMATION: Synthetic

<400> SEQUENCE: 261

Ser Ser Trp Arg Gly Ser Met Leu Phe Arg Val Thr Ile Lys Ser
1               5                   10                  15

<210> SEQ ID NO 262
<211> LENGTH: 15
<212> TYPE: PRT
<213> ORGANISM: Artificial sequence
<220> FEATURE:
<223> OTHER INFORMATION: Synthetic

<400> SEQUENCE: 262

Lys Arg Ser Ser Gly Ser Met Leu Phe Arg Val Thr Ile Trp Ser
1               5                   10                  15

<210> SEQ ID NO 263
<211> LENGTH: 13
<212> TYPE: PRT
<213> ORGANISM: Artificial sequence
<220> FEATURE:
<223> OTHER INFORMATION: Synthetic

<400> SEQUENCE: 263

Ser Ser Lys Arg Met Leu Phe Arg Val Thr Ile Trp Ser
1               5                   10

<210> SEQ ID NO 264
<211> LENGTH: 13

-continued

```
<212> TYPE: PRT
<213> ORGANISM: Artificial sequence
<220> FEATURE:
<223> OTHER INFORMATION: Synthetic

<400> SEQUENCE: 264

Lys Arg Ser Ser Met Leu Phe Arg Val Thr Ile Trp Ser
1               5                   10

<210> SEQ ID NO 265
<211> LENGTH: 13
<212> TYPE: PRT
<213> ORGANISM: Artificial sequence
<220> FEATURE:
<223> OTHER INFORMATION: Synthetic

<400> SEQUENCE: 265

Gly Ser Met Lys Phe Arg Val Thr Ile Asn Ser Trp Lys
1               5                   10

<210> SEQ ID NO 266
<211> LENGTH: 13
<212> TYPE: PRT
<213> ORGANISM: Artificial sequence
<220> FEATURE:
<223> OTHER INFORMATION: Synthetic

<400> SEQUENCE: 266

Gly Ser Met Leu Phe Arg Lys Thr Ile Asn Ser Trp Lys
1               5                   10

<210> SEQ ID NO 267
<211> LENGTH: 13
<212> TYPE: PRT
<213> ORGANISM: Artificial sequence
<220> FEATURE:
<223> OTHER INFORMATION: Synthetic

<400> SEQUENCE: 267

Gly Ser Met Leu Phe Arg Val Thr Lys Asn Ser Trp Lys
1               5                   10

<210> SEQ ID NO 268
<211> LENGTH: 13
<212> TYPE: PRT
<213> ORGANISM: Artificial sequence
<220> FEATURE:
<223> OTHER INFORMATION: Synthetic

<400> SEQUENCE: 268

Gly Lys Met Leu Phe Arg Val Thr Ile Asn Ser Trp Lys
1               5                   10

<210> SEQ ID NO 269
<211> LENGTH: 11
<212> TYPE: PRT
<213> ORGANISM: Artificial sequence
<220> FEATURE:
<223> OTHER INFORMATION: Synthetic

<400> SEQUENCE: 269

Gly Lys Met Leu Phe Arg Val Thr Ile Trp Lys
1               5                   10

<210> SEQ ID NO 270
<211> LENGTH: 13
<212> TYPE: PRT
```

-continued

```
<213> ORGANISM: Artificial sequence
<220> FEATURE:
<223> OTHER INFORMATION: Synthetic

<400> SEQUENCE: 270

Gly Ser Met Lys Phe Arg Val Thr Ile Asn Ser Trp Lys
1               5                   10

<210> SEQ ID NO 271
<211> LENGTH: 11
<212> TYPE: PRT
<213> ORGANISM: Artificial sequence
<220> FEATURE:
<223> OTHER INFORMATION: Synthetic

<400> SEQUENCE: 271

Gly Ser Met Lys Phe Arg Val Thr Ile Trp Lys
1               5                   10

<210> SEQ ID NO 272
<211> LENGTH: 13
<212> TYPE: PRT
<213> ORGANISM: Artificial sequence
<220> FEATURE:
<223> OTHER INFORMATION: Synthetic

<400> SEQUENCE: 272

Gly Arg Met Leu Phe Arg Val Thr Ile Asn Ser Trp Lys
1               5                   10

<210> SEQ ID NO 273
<211> LENGTH: 11
<212> TYPE: PRT
<213> ORGANISM: Artificial sequence
<220> FEATURE:
<223> OTHER INFORMATION: Synthetic

<400> SEQUENCE: 273

Gly Arg Met Leu Phe Arg Val Thr Ile Trp Lys
1               5                   10

<210> SEQ ID NO 274
<211> LENGTH: 13
<212> TYPE: PRT
<213> ORGANISM: Artificial sequence
<220> FEATURE:
<223> OTHER INFORMATION: Synthetic

<400> SEQUENCE: 274

Gly Ser Met Arg Phe Arg Val Thr Ile Asn Ser Trp Lys
1               5                   10

<210> SEQ ID NO 275
<211> LENGTH: 11
<212> TYPE: PRT
<213> ORGANISM: Artificial sequence
<220> FEATURE:
<223> OTHER INFORMATION: Synthetic

<400> SEQUENCE: 275

Gly Ser Met Arg Phe Arg Val Thr Ile Trp Lys
1               5                   10

<210> SEQ ID NO 276
<211> LENGTH: 13
<212> TYPE: PRT
<213> ORGANISM: Artificial sequence
```

```
<220> FEATURE:
<223> OTHER INFORMATION: Synthetic

<400> SEQUENCE: 276

Gly Asp Met Leu Phe Arg Val Thr Ile Asn Ser Trp Lys
1               5                   10

<210> SEQ ID NO 277
<211> LENGTH: 11
<212> TYPE: PRT
<213> ORGANISM: Artificial sequence
<220> FEATURE:
<223> OTHER INFORMATION: Synthetic

<400> SEQUENCE: 277

Gly Asp Met Leu Phe Arg Val Thr Ile Trp Lys
1               5                   10

<210> SEQ ID NO 278
<211> LENGTH: 13
<212> TYPE: PRT
<213> ORGANISM: Artificial sequence
<220> FEATURE:
<223> OTHER INFORMATION: Synthetic

<400> SEQUENCE: 278

Gly Ser Met Asp Phe Arg Val Thr Ile Asn Ser Trp Lys
1               5                   10

<210> SEQ ID NO 279
<211> LENGTH: 11
<212> TYPE: PRT
<213> ORGANISM: Artificial sequence
<220> FEATURE:
<223> OTHER INFORMATION: Synthetic

<400> SEQUENCE: 279

Gly Ser Met Asp Phe Arg Val Thr Ile Trp Lys
1               5                   10

<210> SEQ ID NO 280
<211> LENGTH: 13
<212> TYPE: PRT
<213> ORGANISM: Artificial sequence
<220> FEATURE:
<223> OTHER INFORMATION: Synthetic

<400> SEQUENCE: 280

Gly Glu Met Leu Phe Arg Val Thr Ile Asn Ser Trp Lys
1               5                   10

<210> SEQ ID NO 281
<211> LENGTH: 13
<212> TYPE: PRT
<213> ORGANISM: Artificial sequence
<220> FEATURE:
<223> OTHER INFORMATION: Synthetic

<400> SEQUENCE: 281

Gly Ser Met Glu Phe Arg Val Thr Ile Asn Ser Trp Lys
1               5                   10

<210> SEQ ID NO 282
<211> LENGTH: 11
<212> TYPE: PRT
<213> ORGANISM: Artificial sequence
<220> FEATURE:
```

<223> OTHER INFORMATION: Synthetic

<400> SEQUENCE: 282

Gly Ser Met Glu Phe Arg Val Thr Ile Trp Lys
1               5                   10

<210> SEQ ID NO 283
<211> LENGTH: 13
<212> TYPE: PRT
<213> ORGANISM: Artificial sequence
<220> FEATURE:
<223> OTHER INFORMATION: Synthetic

<400> SEQUENCE: 283

Gly Ser Met Leu Phe Arg Val Thr Ile Trp Lys Val Lys
1               5                   10

<210> SEQ ID NO 284
<211> LENGTH: 13
<212> TYPE: PRT
<213> ORGANISM: Artificial sequence
<220> FEATURE:
<223> OTHER INFORMATION: Synthetic

<400> SEQUENCE: 284

Gly Ser Met Leu Phe Arg Val Thr Ile Trp Ser Val Lys
1               5                   10

<210> SEQ ID NO 285
<211> LENGTH: 12
<212> TYPE: PRT
<213> ORGANISM: Artificial sequence
<220> FEATURE:
<223> OTHER INFORMATION: Synthetic

<400> SEQUENCE: 285

Gly Ser Met Leu Phe Arg Val Thr Ile Trp Ser Lys
1               5                   10

<210> SEQ ID NO 286
<211> LENGTH: 13
<212> TYPE: PRT
<213> ORGANISM: Artificial sequence
<220> FEATURE:
<223> OTHER INFORMATION: Synthetic

<400> SEQUENCE: 286

Gly Ser Met Leu Phe Arg Val Thr Ile Trp Lys Trp Lys
1               5                   10

<210> SEQ ID NO 287
<211> LENGTH: 12
<212> TYPE: PRT
<213> ORGANISM: Artificial sequence
<220> FEATURE:
<223> OTHER INFORMATION: Synthetic

<400> SEQUENCE: 287

Gly Ser Met Leu Phe Arg Val Thr Ile Trp Lys Lys
1               5                   10

<210> SEQ ID NO 288
<211> LENGTH: 11
<212> TYPE: PRT
<213> ORGANISM: Artificial sequence
<220> FEATURE:
<223> OTHER INFORMATION: Synthetic

<400> SEQUENCE: 288

Gly Ser Met Leu Phe Arg Val Thr Ile Asn Ser
1               5                   10

<210> SEQ ID NO 289
<211> LENGTH: 9
<212> TYPE: PRT
<213> ORGANISM: Artificial sequence
<220> FEATURE:
<223> OTHER INFORMATION: Synthetic

<400> SEQUENCE: 289

Met Leu Phe Arg Val Thr Ile Asn Ser
1               5

<210> SEQ ID NO 290
<211> LENGTH: 9
<212> TYPE: PRT
<213> ORGANISM: Artificial sequence
<220> FEATURE:
<223> OTHER INFORMATION: Synthetic

<400> SEQUENCE: 290

Met Leu Phe Val Thr Ile Asn Ser Val
1               5

<210> SEQ ID NO 291
<211> LENGTH: 11
<212> TYPE: PRT
<213> ORGANISM: Artificial sequence
<220> FEATURE:
<223> OTHER INFORMATION: Synthetic

<400> SEQUENCE: 291

Met Leu Phe Arg Val Thr Ile Asn Ser Val Ser
1               5                   10

<210> SEQ ID NO 292
<211> LENGTH: 10
<212> TYPE: PRT
<213> ORGANISM: Artificial sequence
<220> FEATURE:
<223> OTHER INFORMATION: Synthetic

<400> SEQUENCE: 292

Gly Ser Met Leu Phe Arg Val Thr Ile Asn
1               5                   10

<210> SEQ ID NO 293
<211> LENGTH: 9
<212> TYPE: PRT
<213> ORGANISM: Artificial sequence
<220> FEATURE:
<223> OTHER INFORMATION: Synthetic

<400> SEQUENCE: 293

Gly Ser Met Leu Phe Arg Val Thr Ile
1               5

<210> SEQ ID NO 294
<211> LENGTH: 9
<212> TYPE: PRT
<213> ORGANISM: Artificial sequence
<220> FEATURE:
<223> OTHER INFORMATION: Synthetic -continued

```
<400> SEQUENCE: 294

Ser Met Leu Phe Arg Val Thr Ile Asn
1               5

<210> SEQ ID NO 295
<211> LENGTH: 8
<212> TYPE: PRT
<213> ORGANISM: Artificial sequence
<220> FEATURE:
<223> OTHER INFORMATION: Synthetic

<400> SEQUENCE: 295

Met Leu Phe Arg Val Thr Ile Asn
1               5

<210> SEQ ID NO 296
<211> LENGTH: 7
<212> TYPE: PRT
<213> ORGANISM: Artificial sequence
<220> FEATURE:
<223> OTHER INFORMATION: Synthetic

<400> SEQUENCE: 296

Met Leu Phe Arg Val Thr Ile
1               5

<210> SEQ ID NO 297
<211> LENGTH: 15
<212> TYPE: PRT
<213> ORGANISM: Artificial sequence
<220> FEATURE:
<223> OTHER INFORMATION: Synthetic

<400> SEQUENCE: 297

Ser Ser Lys Arg Gly Ser Met Leu Phe Val Thr Ile Trp Ser
1               5                   10                  15

<210> SEQ ID NO 298
<211> LENGTH: 23
<212> TYPE: PRT
<213> ORGANISM: Artificial sequence
<220> FEATURE:
<223> OTHER INFORMATION: Synthetic

<400> SEQUENCE: 298

Gly Ser Met Leu Phe Arg Val Thr Ile Asn Ser Gly Val Ser Gly Trp
1               5                   10                  15

Ala Leu Phe Lys Lys Ile Ser
            20

<210> SEQ ID NO 299
<211> LENGTH: 23
<212> TYPE: PRT
<213> ORGANISM: Artificial sequence
<220> FEATURE:
<223> OTHER INFORMATION: Synthetic

<400> SEQUENCE: 299

Gly Ser Met Leu Phe Arg Val Thr Ile Asn Ser Gly Val Ser Gly Trp
1               5                   10                  15

Arg Leu Phe Lys Lys Ile Ser
            20

<210> SEQ ID NO 300
<211> LENGTH: 11
```

```
<212> TYPE: PRT
<213> ORGANISM: Artificial sequence
<220> FEATURE:
<223> OTHER INFORMATION: Synthetic

<400> SEQUENCE: 300

Val Ser Gly Trp Ala Leu Phe Lys Lys Ile Ser
1               5                   10

<210> SEQ ID NO 301
<211> LENGTH: 25
<212> TYPE: PRT
<213> ORGANISM: Artificial sequence
<220> FEATURE:
<223> OTHER INFORMATION: Synthetic

<400> SEQUENCE: 301

Gly Ser Met Leu Phe Arg Val Thr Ile Asn Ser Val Ser Gly Val Ser
1               5                   10                  15

Gly Trp Arg Leu Phe Lys Lys Ile Ser
            20                  25

<210> SEQ ID NO 302
<211> LENGTH: 148
<212> TYPE: PRT
<213> ORGANISM: Artificial sequence
<220> FEATURE:
<223> OTHER INFORMATION: Synthetic

<400> SEQUENCE: 302

Met Val Phe Thr Leu Asp Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Met Arg Ile Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Lys Leu Asn Tyr Phe
            100                 105                 110

Gly Arg Pro Tyr Glu Gly Ile Ala Val Phe Asp Gly Lys Lys Ile Thr
        115                 120                 125

Thr Thr Gly Thr Leu Trp Asn Gly Asn Lys Ile Ile Asp Glu Arg Leu
    130                 135                 140

Ile Thr Pro Asp
145

<210> SEQ ID NO 303
<211> LENGTH: 444
<212> TYPE: DNA
<213> ORGANISM: Artificial sequence
<220> FEATURE:
<223> OTHER INFORMATION: Synthetic

<400> SEQUENCE: 303
atggtcttca cactcgacga tttcgttggg gactgggaac agacagccgc ctacaacctg      60
gaccaagtcc ttgaacaggg aggtgtgtcc agtttgctgc agaatctcgc cgtgtccgta     120
```

```
actccgatca tgaggattgt ccggagcggt gaaaatgccc tgaagatcga catccatgtc        180
atcatcccgt atgaaggtct gagcgccgac caaatggccc agatcgaaga ggtgtttaag        240
gtggtgtacc ctgtggatga tcatcacttt aaggtgatcc tgccctatgg cacactggta        300
atcgacgggg ttacgccgaa caagctgaac tatttcggac ggccgtatga aggcatcgcc        360
gtgttcgacg gcaaaaagat cactaccaca gggaccctgt ggaacggcaa caaaattatc        420
gacgagcgcc tgatcacccc cgac                                              444
```

<210> SEQ ID NO 304
<211> LENGTH: 148
<212> TYPE: PRT
<213> ORGANISM: Artificial sequence
<220> FEATURE:
<223> OTHER INFORMATION: Synthetic

<400> SEQUENCE: 304

```
Met Val Phe Thr Leu Asp Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Met Arg Ile Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Lys Leu Asn Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Thr Pro Asp
145
```

<210> SEQ ID NO 305
<211> LENGTH: 444
<212> TYPE: DNA
<213> ORGANISM: Artificial sequence
<220> FEATURE:
<223> OTHER INFORMATION: Synthetic

<400> SEQUENCE: 305

```
atggtcttca cactcgaaga tttcgttggg gactgggaac agacagccgc ctacaacctg         60
gaccaagtcc ttgaacaggg aggtgtgtcc agtttgctgc agaatctcgc cgtgtccgta        120
actccgatcc aaaggattgt ccggagcggt gaaaatgccc tgaagatcga catccatgtc        180
atcatcccgt atgaaggtct gagcgccgac caaatggccc agatcgaaga ggtgtttaag        240
gtggtgtacc ctgtggatga tcatcacttt aaggtgatcc tgccctatgg cacactggta        300
atcgacgggg ttacgccgaa catgctgaac tatttcggac ggccgtatga aggcatcgcc        360
gtgttcgacg gcaaaaagat cactgtaaca gggaccctgt ggaacggcaa caaaattatc        420
gacgagcgcc tgatcacccc cgac                                              444
```

-continued

```
<210> SEQ ID NO 306
<211> LENGTH: 12
<212> TYPE: PRT
<213> ORGANISM: Artificial sequence
<220> FEATURE:
<223> OTHER INFORMATION: Synthetic

<400> SEQUENCE: 306

Ser Val Ser Gly Trp Arg Leu Phe Lys Lys Ile Ser
1               5                   10

<210> SEQ ID NO 307
<211> LENGTH: 13
<212> TYPE: PRT
<213> ORGANISM: Artificial sequence
<220> FEATURE:
<223> OTHER INFORMATION: Synthetic

<400> SEQUENCE: 307

Asn Ser Val Ser Gly Trp Arg Leu Phe Lys Lys Ile Ser
1               5                   10

<210> SEQ ID NO 308
<211> LENGTH: 9
<212> TYPE: PRT
<213> ORGANISM: Artificial sequence
<220> FEATURE:
<223> OTHER INFORMATION: Synthetic

<400> SEQUENCE: 308

Gly Trp Arg Leu Phe Lys Lys Ile Ser
1               5

<210> SEQ ID NO 309
<211> LENGTH: 23
<212> TYPE: PRT
<213> ORGANISM: Artificial sequence
<220> FEATURE:
<223> OTHER INFORMATION: Synthetic

<400> SEQUENCE: 309

Gly Ser Met Leu Phe Arg Val Thr Ile Asn Ser Gly Val Ser Gly Trp
1               5                   10                  15

Arg Leu Phe Lys Lys Ile Ser
            20

<210> SEQ ID NO 310
<211> LENGTH: 13
<212> TYPE: PRT
<213> ORGANISM: Artificial sequence
<220> FEATURE:
<223> OTHER INFORMATION: Synthetic

<400> SEQUENCE: 310

Gly Ser Met Leu Phe Arg Val Thr Ile Asn Ser Trp Lys
1               5                   10

<210> SEQ ID NO 311
<211> LENGTH: 13
<212> TYPE: PRT
<213> ORGANISM: Artificial sequence
<220> FEATURE:
<223> OTHER INFORMATION: Synthetic

<400> SEQUENCE: 311

Gly Ser Met Leu Phe Arg Val Thr Ile Asn Ser Trp Lys
```

-continued

```
1               5                    10

<210> SEQ ID NO 312
<211> LENGTH: 13
<212> TYPE: PRT
<213> ORGANISM: Artificial sequence
<220> FEATURE:
<223> OTHER INFORMATION: Synthetic

<400> SEQUENCE: 312

Gly Ser Met Leu Phe Arg Val Thr Ile Asn Ser Trp Lys
1               5                    10

<210> SEQ ID NO 313
<211> LENGTH: 13
<212> TYPE: PRT
<213> ORGANISM: Artificial sequence
<220> FEATURE:
<223> OTHER INFORMATION: Synthetic

<400> SEQUENCE: 313

Gly Ser Met Leu Phe Arg Val Thr Ile Asn Lys Trp Lys
1               5                    10

<210> SEQ ID NO 314
<211> LENGTH: 13
<212> TYPE: PRT
<213> ORGANISM: Artificial sequence
<220> FEATURE:
<223> OTHER INFORMATION: Synthetic

<400> SEQUENCE: 314

Gly Ser Met Leu Phe Arg Val Thr Ile Lys Ser Trp Lys
1               5                    10

<210> SEQ ID NO 315
<211> LENGTH: 13
<212> TYPE: PRT
<213> ORGANISM: Artificial sequence
<220> FEATURE:
<223> OTHER INFORMATION: Synthetic

<400> SEQUENCE: 315

Gly Ser Met Leu Phe Arg Val Thr Ile Asn Arg Trp Lys
1               5                    10

<210> SEQ ID NO 316
<211> LENGTH: 13
<212> TYPE: PRT
<213> ORGANISM: Artificial sequence
<220> FEATURE:
<223> OTHER INFORMATION: Synthetic

<400> SEQUENCE: 316

Gly Ser Met Leu Phe Arg Val Thr Ile Arg Ser Trp Lys
1               5                    10

<210> SEQ ID NO 317
<211> LENGTH: 13
<212> TYPE: PRT
<213> ORGANISM: Artificial sequence
<220> FEATURE:
<223> OTHER INFORMATION: Synthetic

<400> SEQUENCE: 317

Gly Ser Met Leu Phe Arg Val Thr Ile Asn Asp Trp Lys
1               5                    10
```

-continued

```
<210> SEQ ID NO 318
<211> LENGTH: 13
<212> TYPE: PRT
<213> ORGANISM: Artificial sequence
<220> FEATURE:
<223> OTHER INFORMATION: Synthetic

<400> SEQUENCE: 318

Gly Ser Met Leu Phe Arg Val Thr Ile Asp Ser Trp Lys
1               5                   10

<210> SEQ ID NO 319
<211> LENGTH: 13
<212> TYPE: PRT
<213> ORGANISM: Artificial sequence
<220> FEATURE:
<223> OTHER INFORMATION: Synthetic

<400> SEQUENCE: 319

Gly Ser Met Leu Phe Arg Val Thr Ile Asn Glu Trp Lys
1               5                   10

<210> SEQ ID NO 320
<211> LENGTH: 13
<212> TYPE: PRT
<213> ORGANISM: Artificial sequence
<220> FEATURE:
<223> OTHER INFORMATION: Synthetic

<400> SEQUENCE: 320

Gly Ser Met Leu Phe Arg Val Thr Ile Glu Ser Trp Lys
1               5                   10

<210> SEQ ID NO 321
<211> LENGTH: 13
<212> TYPE: PRT
<213> ORGANISM: Artificial sequence
<220> FEATURE:
<223> OTHER INFORMATION: Synthetic

<400> SEQUENCE: 321

Gly Ser Met Arg Phe Arg Val Thr Ile Asn Ser Trp Lys
1               5                   10

<210> SEQ ID NO 322
<211> LENGTH: 13
<212> TYPE: PRT
<213> ORGANISM: Artificial sequence
<220> FEATURE:
<223> OTHER INFORMATION: Synthetic

<400> SEQUENCE: 322

Gly Ser Met Asp Phe Arg Val Thr Ile Asn Ser Trp Lys
1               5                   10

<210> SEQ ID NO 323
<211> LENGTH: 13
<212> TYPE: PRT
<213> ORGANISM: Artificial sequence
<220> FEATURE:
<223> OTHER INFORMATION: Synthetic

<400> SEQUENCE: 323

Gly Ser Met Glu Phe Arg Val Thr Ile Asn Ser Trp Lys
1               5                   10
```

```
<210> SEQ ID NO 324
<211> LENGTH: 13
<212> TYPE: PRT
<213> ORGANISM: Artificial sequence
<220> FEATURE:
<223> OTHER INFORMATION: Synthetic

<400> SEQUENCE: 324

Gly Ser Met Leu Phe Arg Arg Thr Ile Asn Ser Trp Lys
1               5                   10

<210> SEQ ID NO 325
<211> LENGTH: 13
<212> TYPE: PRT
<213> ORGANISM: Artificial sequence
<220> FEATURE:
<223> OTHER INFORMATION: Synthetic

<400> SEQUENCE: 325

Gly Ser Met Leu Phe Arg Asp Thr Ile Asn Ser Trp Lys
1               5                   10

<210> SEQ ID NO 326
<211> LENGTH: 13
<212> TYPE: PRT
<213> ORGANISM: Artificial sequence
<220> FEATURE:
<223> OTHER INFORMATION: Synthetic

<400> SEQUENCE: 326

Gly Ser Met Leu Phe Arg Glu Thr Ile Asn Ser Trp Lys
1               5                   10

<210> SEQ ID NO 327
<211> LENGTH: 13
<212> TYPE: PRT
<213> ORGANISM: Artificial sequence
<220> FEATURE:
<223> OTHER INFORMATION: Synthetic

<400> SEQUENCE: 327

Gly Ser Met Leu Phe Arg Val Thr Asp Asn Ser Trp Lys
1               5                   10

<210> SEQ ID NO 328
<211> LENGTH: 13
<212> TYPE: PRT
<213> ORGANISM: Artificial sequence
<220> FEATURE:
<223> OTHER INFORMATION: Synthetic

<400> SEQUENCE: 328

Gly Ser Met Leu Phe Arg Val Thr Glu Asn Ser Trp Lys
1               5                   10

<210> SEQ ID NO 329
<211> LENGTH: 13
<212> TYPE: PRT
<213> ORGANISM: Artificial sequence
<220> FEATURE:
<223> OTHER INFORMATION: Synthetic

<400> SEQUENCE: 329

Gly Ser Met Lys Phe Arg Val Thr Ile Asn Ser Trp Lys
1               5                   10
```

-continued

```
<210> SEQ ID NO 330
<211> LENGTH: 13
<212> TYPE: PRT
<213> ORGANISM: Artificial sequence
<220> FEATURE:
<223> OTHER INFORMATION: Synthetic

<400> SEQUENCE: 330

Gly Ser Met Leu Phe Arg Lys Thr Ile Asn Ser Trp Lys
1               5                   10

<210> SEQ ID NO 331
<211> LENGTH: 13
<212> TYPE: PRT
<213> ORGANISM: Artificial sequence
<220> FEATURE:
<223> OTHER INFORMATION: Synthetic

<400> SEQUENCE: 331

Gly Ser Met Leu Phe Arg Val Thr Lys Asn Ser Trp Lys
1               5                   10

<210> SEQ ID NO 332
<211> LENGTH: 11
<212> TYPE: PRT
<213> ORGANISM: Artificial sequence
<220> FEATURE:
<223> OTHER INFORMATION: Synthetic

<400> SEQUENCE: 332

Gly Ser Met Leu Phe Arg Val Thr Ile Asn Ser
1               5                   10

<210> SEQ ID NO 333
<211> LENGTH: 11
<212> TYPE: PRT
<213> ORGANISM: Artificial sequence
<220> FEATURE:
<223> OTHER INFORMATION: Synthetic

<400> SEQUENCE: 333

Gly Ser Met Leu Phe Arg Val Ser Ile Asn Ser
1               5                   10

<210> SEQ ID NO 334
<211> LENGTH: 11
<212> TYPE: PRT
<213> ORGANISM: Artificial sequence
<220> FEATURE:
<223> OTHER INFORMATION: Synthetic

<400> SEQUENCE: 334

Gly Ser Met Leu Phe Arg Val Asn Ile Asn Ser
1               5                   10

<210> SEQ ID NO 335
<211> LENGTH: 11
<212> TYPE: PRT
<213> ORGANISM: Artificial sequence
<220> FEATURE:
<223> OTHER INFORMATION: Synthetic

<400> SEQUENCE: 335

Gly Ser Lys Leu Phe Arg Val Thr Ile Asn Ser
1               5                   10

<210> SEQ ID NO 336
```

```
<211> LENGTH: 11
<212> TYPE: PRT
<213> ORGANISM: Artificial sequence
<220> FEATURE:
<223> OTHER INFORMATION: Synthetic

<400> SEQUENCE: 336

Gly Ser Arg Leu Phe Arg Val Thr Ile Asn Ser
1               5                   10

<210> SEQ ID NO 337
<211> LENGTH: 11
<212> TYPE: PRT
<213> ORGANISM: Artificial sequence
<220> FEATURE:
<223> OTHER INFORMATION: Synthetic

<400> SEQUENCE: 337

Gly Ser Met Trp Phe Arg Val Thr Ile Asn Ser
1               5                   10

<210> SEQ ID NO 338
<211> LENGTH: 11
<212> TYPE: PRT
<213> ORGANISM: Artificial sequence
<220> FEATURE:
<223> OTHER INFORMATION: Synthetic

<400> SEQUENCE: 338

Gly Ser Met Ser Phe Arg Val Thr Ile Asn Ser
1               5                   10

<210> SEQ ID NO 339
<211> LENGTH: 11
<212> TYPE: PRT
<213> ORGANISM: Artificial sequence
<220> FEATURE:
<223> OTHER INFORMATION: Synthetic

<400> SEQUENCE: 339

Gly Ser Met Asn Phe Arg Val Thr Ile Asn Ser
1               5                   10

<210> SEQ ID NO 340
<211> LENGTH: 11
<212> TYPE: PRT
<213> ORGANISM: Artificial sequence
<220> FEATURE:
<223> OTHER INFORMATION: Synthetic

<400> SEQUENCE: 340

Gly Ser Met Lys Phe Arg Val Thr Ile Asn Ser
1               5                   10

<210> SEQ ID NO 341
<211> LENGTH: 11
<212> TYPE: PRT
<213> ORGANISM: Artificial sequence
<220> FEATURE:
<223> OTHER INFORMATION: Synthetic

<400> SEQUENCE: 341

Gly Ser Met Leu Phe Arg Trp Thr Ile Asn Ser
1               5                   10

<210> SEQ ID NO 342
<211> LENGTH: 11
```

```
<212> TYPE: PRT
<213> ORGANISM: Artificial sequence
<220> FEATURE:
<223> OTHER INFORMATION: Synthetic

<400> SEQUENCE: 342

Gly Ser Met Leu Phe Arg Ser Thr Ile Asn Ser
1               5                   10

<210> SEQ ID NO 343
<211> LENGTH: 11
<212> TYPE: PRT
<213> ORGANISM: Artificial sequence
<220> FEATURE:
<223> OTHER INFORMATION: Synthetic

<400> SEQUENCE: 343

Gly Ser Met Leu Phe Arg Asn Thr Ile Asn Ser
1               5                   10

<210> SEQ ID NO 344
<211> LENGTH: 11
<212> TYPE: PRT
<213> ORGANISM: Artificial sequence
<220> FEATURE:
<223> OTHER INFORMATION: Synthetic

<400> SEQUENCE: 344

Gly Ser Met Leu Phe Arg Lys Thr Ile Asn Ser
1               5                   10

<210> SEQ ID NO 345
<211> LENGTH: 11
<212> TYPE: PRT
<213> ORGANISM: Artificial sequence
<220> FEATURE:
<223> OTHER INFORMATION: Synthetic

<400> SEQUENCE: 345

Gly Ser Met Leu Phe Arg Val Thr Trp Asn Ser
1               5                   10

<210> SEQ ID NO 346
<211> LENGTH: 11
<212> TYPE: PRT
<213> ORGANISM: Artificial sequence
<220> FEATURE:
<223> OTHER INFORMATION: Synthetic

<400> SEQUENCE: 346

Gly Ser Met Leu Phe Arg Val Thr Ser Asn Ser
1               5                   10

<210> SEQ ID NO 347
<211> LENGTH: 11
<212> TYPE: PRT
<213> ORGANISM: Artificial sequence
<220> FEATURE:
<223> OTHER INFORMATION: Synthetic

<400> SEQUENCE: 347

Gly Ser Met Leu Phe Arg Val Thr Asn Asn Ser
1               5                   10

<210> SEQ ID NO 348
<211> LENGTH: 11
<212> TYPE: PRT
```

```
<213> ORGANISM: Artificial sequence
<220> FEATURE:
<223> OTHER INFORMATION: Synthetic

<400> SEQUENCE: 348

Gly Ser Met Leu Phe Arg Val Thr Lys Asn Ser
1               5                   10

<210> SEQ ID NO 349
<211> LENGTH: 11
<212> TYPE: PRT
<213> ORGANISM: Artificial sequence
<220> FEATURE:
<223> OTHER INFORMATION: Synthetic

<400> SEQUENCE: 349

Gly Ser Met Leu Phe Arg Val Thr Ile Lys Ser
1               5                   10

<210> SEQ ID NO 350
<211> LENGTH: 634
<212> TYPE: PRT
<213> ORGANISM: Artificial sequence
<220> FEATURE:
<223> OTHER INFORMATION: Synthetic

<400> SEQUENCE: 350

Met Lys His His His His His His Val Ser Lys Gly Glu Glu Leu Ile
1               5                   10                  15

Lys Glu Asn Met Arg Ser Lys Leu Tyr Leu Glu Gly Ser Val Asn Gly
            20                  25                  30

His Gln Phe Lys Cys Thr His Glu Gly Glu Gly Lys Pro Tyr Glu Gly
        35                  40                  45

Lys Gln Thr Asn Arg Ile Lys Val Val Glu Gly Gly Pro Leu Pro Phe
    50                  55                  60

Ala Phe Asp Ile Leu Ala Thr His Phe Met Tyr Gly Ser Lys Val Phe
65                  70                  75                  80

Ile Lys Tyr Pro Ala Asp Leu Pro Asp Tyr Phe Lys Gln Ser Phe Pro
                85                  90                  95

Glu Gly Phe Thr Trp Glu Arg Val Met Val Phe Glu Asp Gly Gly Val
            100                 105                 110

Leu Thr Ala Thr Gln Asp Thr Ser Leu Gln Asp Gly Glu Leu Ile Tyr
        115                 120                 125

Asn Val Lys Val Arg Gly Val Asn Phe Pro Ala Asn Gly Pro Val Met
    130                 135                 140

Gln Lys Lys Thr Leu Gly Trp Glu Pro Ser Thr Glu Thr Met Tyr Pro
145                 150                 155                 160

Ala Asp Gly Gly Leu Glu Gly Arg Cys Asp Lys Ala Leu Lys Leu Val
                165                 170                 175

Gly Gly Gly His Leu His Val Asn Phe Lys Thr Thr Tyr Lys Ser Lys
            180                 185                 190

Lys Pro Val Lys Met Pro Gly Val His Tyr Val Asp Arg Arg Leu Glu
        195                 200                 205

Arg Ile Lys Glu Ala Asp Asn Glu Thr Tyr Val Glu Gln Tyr Glu His
    210                 215                 220

Ala Val Ala Arg Tyr Ser Asn Leu Gly Gly Gly Phe Thr Leu Glu Asp
225                 230                 235                 240

Phe Val Gly Asp Trp Arg Gln Thr Ala Gly Tyr Asn Leu Asp Gln Val
                245                 250                 255
```

```
Leu Glu Gln Gly Gly Val Ser Ser Leu Phe Gln Asn Leu Gly Val Ser
        260                 265                 270

Val Thr Pro Ile Gln Arg Ile Val Leu Ser Gly Glu Asn Gly Leu Lys
        275                 280                 285

Ile Asp Ile His Val Ile Ile Pro Tyr Glu Gly Leu Ser Gly Asp Gln
        290                 295                 300

Met Gly Gln Ile Glu Lys Ile Phe Lys Val Val Tyr Pro Val Asp Asp
305                 310                 315                 320

His His Phe Lys Val Ile Leu His Tyr Gly Thr Leu Val Ile Asp Gly
                325                 330                 335

Val Thr Pro Asn Met Ile Asp Tyr Phe Gly Arg Pro Tyr Glu Gly Ile
                340                 345                 350

Ala Val Phe Asp Gly Lys Lys Ile Thr Val Thr Gly Thr Leu Trp Asn
                355                 360                 365

Gly Asn Lys Ile Ile Asp Glu Arg Leu Ile Asn Pro Asp Gly Ser Leu
        370                 375                 380

Leu Phe Arg Val Thr Ile Asn Gly Val Thr Gly Trp Arg Leu Cys Glu
385                 390                 395                 400

Arg Ile Leu Ala Arg His Glu Leu Ile Lys Glu Asn Met Arg Ser Lys
                405                 410                 415

Leu Tyr Leu Glu Gly Ser Val Asn Gly His Gln Phe Lys Cys Thr His
                420                 425                 430

Glu Gly Glu Gly Lys Pro Tyr Glu Gly Lys Gln Thr Asn Arg Ile Lys
                435                 440                 445

Val Val Glu Gly Gly Pro Leu Pro Phe Ala Phe Asp Ile Leu Ala Thr
        450                 455                 460

His Phe Met Tyr Gly Ser Lys Val Phe Ile Lys Tyr Pro Ala Asp Leu
465                 470                 475                 480

Pro Asp Tyr Phe Lys Gln Ser Phe Pro Glu Gly Phe Thr Trp Glu Arg
                485                 490                 495

Val Met Val Phe Glu Asp Gly Gly Val Leu Thr Ala Thr Gln Asp Thr
                500                 505                 510

Ser Leu Gln Asp Gly Glu Leu Ile Tyr Asn Val Lys Val Arg Gly Val
                515                 520                 525

Asn Phe Pro Ala Asn Gly Pro Val Met Gln Lys Lys Thr Leu Gly Trp
        530                 535                 540

Glu Pro Ser Thr Glu Thr Met Tyr Pro Ala Asp Gly Gly Leu Glu Gly
545                 550                 555                 560

Arg Cys Asp Lys Ala Leu Lys Leu Val Gly Gly Gly His Leu His Val
                565                 570                 575

Asn Phe Lys Thr Thr Tyr Lys Ser Lys Lys Pro Val Lys Met Pro Gly
                580                 585                 590

Val His Tyr Val Asp Arg Arg Leu Glu Arg Ile Lys Glu Ala Asp Asn
                595                 600                 605

Glu Thr Tyr Val Glu Gln Tyr Glu His Ala Val Ala Arg Tyr Ser Asn
        610                 615                 620

Leu Gly Gly Gly Met Asp Glu Leu Tyr Lys
625                 630
```

<210> SEQ ID NO 351
<211> LENGTH: 1902
<212> TYPE: DNA
<213> ORGANISM: Artificial sequence
<220> FEATURE:

<223> OTHER INFORMATION: Synthetic

<400> SEQUENCE: 351

```
atgaaacatc accatcacca tcatgtgagc aagggagaag aacttataaa agaaaacatg    60
cggtctaaac tgtacctcga gggctccgtc aatgggcacc agtttaagtg tacccacgag   120
ggtgagggaa agccctatga ggggaagcag acaaaccgca tcaaggtcgt cgaaggggga   180
cccctcccgt ttgcctttga tatcttggct actcacttta tgtacggaag caaagttttc   240
ataaagtatc ctgccgacct tcctgattat tttaaacagt catttcccga gggtttcaca   300
tgggaaaggg tcatggtgtt tgaggatgga ggcgtgctca ctgcaactca ggacacctca   360
ctgcaggacg gcgagctgat ctacaatgtg aaggtccggg gtgtaaactt ccctgccaac   420
gggcctgtaa tgcagaagaa gaccctggga tgggagccgt ccaccgaaac catgtaccct   480
gctgatggtg ggctggaggg ccgatgtgac aaggctctga agctcgttgg aggtggtcat   540
ttgcacgtaa atttcaagac aacttacaag agcaaaaaac ccgtaaaaat gcccgggtt    600 cattacgttg acagaaggct tgaacgcata aaggaagctg ataacgagac atacgtggag   660
cagtacgagc acgccgttgc ccggtactca aacctggggg gtggctttac actggaggat   720
tttgtgggag attggagaca gacagccggc tacaatctgg atcaggtgct ggaacaagga   780
ggagtgtctt ctctgtttca gaatctggga gtgagcgtga cacctatcca gaggatcgtg   840
ctgtctggcg agaatggact gaagatcgat attcacgtga tcatccccta cgaaggcctg   900
tctggagacc agatgggcca gattgagaag atcttcaaag tggtgtatcc tgtggacgat   960
caccacttca aggtgatcct gcactacggc accctggtg ttgatggagt gacacctaac  1020
atgatcgact acttcggaag accttacgag ggaatcgccg tgttcgacgg aaagaagatc  1080
accgtgacag gaacactgtg gaatggaaac aagatcatcg acgagcggct gatcaaccct  1140
gatggatctc tgctgttcag agtgaccatc aacggagtga caggatggag actgtgcgag  1200
agaattctgg ctagacatga gctaatcaag gaaaatatga gaagtaagct atacttagag  1260
gggtccgtca acggtcacca gtttaaatgc actcatgaag gtgaggggaa accttatgaa  1320
ggtaagcaga ctaatcgaat aaaagtggtc gagggcggtc ctctgccatt cgctttcgat  1380
attctggcca ctcactttat gtatgggtct aaggtcttta ttaaatacccc cgctgatttg  1440 ccagactact ttaaacagtc cttccctgaa ggattcacat gggagcgggt gatggtgttc  1500
gaggatggag gcgttcttac tgcaactcag gatacttcct tgcaagacgg ggaactgatc  1560
tacaacgtta aggtccgcgg cgtcaatttc ccagccaatg gtccagtgat gcagaagaaa  1620
accttggggt gggagccctc aacggagaca atgtaccctg cggacggcgg gcttgagggt  1680
agatgtgata aggcattgaa actcgtcggg ggcggccacc ttcatgtgaa tttcaagact  1740
acatataaaa gtaaaaaacc agtcaagatg cctggagtgc actacgtgga tcgtaggttg  1800
gagaggataa aagaagccga caacgaaact tatgtagagc aatatgagca cgccgtggct  1860
cgttattcca acttgggcgg aggaatggat gaactgtaca ag                    1902
```

<210> SEQ ID NO 352
<211> LENGTH: 622
<212> TYPE: PRT
<213> ORGANISM: Artificial sequence
<220> FEATURE:
<223> OTHER INFORMATION: Synthetic

<400> SEQUENCE: 352

Met Lys His His His His His His Val Ser Lys Gly Glu Glu Leu Ile

-continued

```
1                5                10               15

Lys Glu Asn Met Arg Ser Lys Leu Tyr Leu Glu Gly Ser Val Asn Gly
            20              25              30

His Gln Phe Lys Cys Thr His Glu Gly Glu Gly Lys Pro Tyr Glu Gly
            35              40              45

Lys Gln Thr Asn Arg Ile Lys Val Val Glu Gly Gly Pro Leu Pro Phe
    50              55              60

Ala Phe Asp Ile Leu Ala Thr His Phe Met Tyr Gly Ser Lys Val Phe
65              70              75              80

Ile Lys Tyr Pro Ala Asp Leu Pro Asp Tyr Phe Lys Gln Ser Phe Pro
                85              90              95

Glu Gly Phe Thr Trp Glu Arg Val Met Val Phe Glu Asp Gly Gly Val
            100             105             110

Leu Thr Ala Thr Gln Asp Thr Ser Leu Gln Asp Gly Glu Leu Ile Tyr
            115             120             125

Asn Val Lys Val Arg Gly Val Asn Phe Pro Ala Asn Gly Pro Val Met
    130             135             140

Gln Lys Lys Thr Leu Gly Trp Glu Pro Ser Thr Glu Thr Met Tyr Pro
145             150             155             160

Ala Asp Gly Gly Leu Glu Gly Arg Cys Asp Lys Ala Leu Lys Leu Val
            165             170             175

Gly Gly Gly His Leu His Val Asn Phe Lys Thr Thr Tyr Lys Ser Lys
            180             185             190

Lys Pro Val Lys Met Pro Gly Val His Tyr Val Asp Arg Arg Leu Glu
            195             200             205

Arg Ile Lys Glu Ala Asp Asn Glu Thr Tyr Val Glu Gln Tyr Glu His
    210             215             220

Ala Val Ala Arg Tyr Ser Asn Leu Gly Gly Gly Phe Thr Leu Glu Asp
225             230             235             240

Phe Val Gly Asp Trp Glu Gln Thr Ala Ala Tyr Asn Leu Asp Gln Val
            245             250             255

Leu Glu Gln Gly Gly Val Ser Ser Leu Leu Gln Asn Leu Ala Val Ser
            260             265             270

Val Thr Pro Ile Gln Arg Ile Val Arg Ser Gly Glu Asn Ala Leu Lys
            275             280             285

Ile Asp Ile His Val Ile Ile Pro Tyr Glu Gly Leu Ser Ala Asp Gln
    290             295             300

Met Ala Gln Ile Glu Glu Val Phe Lys Val Val Tyr Pro Val Asp Asp
305             310             315             320

His His Phe Lys Val Ile Leu Pro Tyr Gly Thr Leu Val Ile Asp Gly
            325             330             335

Val Thr Pro Asn Met Leu Asn Tyr Phe Gly Arg Pro Tyr Glu Gly Ile
            340             345             350

Ala Val Phe Asp Gly Lys Lys Ile Thr Val Thr Gly Thr Leu Trp Asn
            355             360             365

Gly Asn Lys Ile Ile Asp Glu Arg Leu Ile Thr Pro Asp Gly Ser Met
    370             375             380

Leu Phe Arg Val Thr Ile Asn Ser Arg His Glu Leu Ile Lys Glu Asn
385             390             395             400

Met Arg Ser Lys Leu Tyr Leu Glu Gly Ser Val Asn Gly His Gln Phe
            405             410             415

Lys Cys Thr His Glu Gly Glu Gly Lys Pro Tyr Glu Gly Lys Gln Thr
            420             425             430
```

```
Asn Arg Ile Lys Val Val Glu Gly Gly Pro Leu Pro Phe Ala Phe Asp
        435                 440                 445

Ile Leu Ala Thr His Phe Met Tyr Gly Ser Lys Val Phe Ile Lys Tyr
    450                 455                 460

Pro Ala Asp Leu Pro Asp Tyr Phe Lys Gln Ser Phe Pro Glu Gly Phe
465                 470                 475                 480

Thr Trp Glu Arg Val Met Val Phe Glu Asp Gly Gly Val Leu Thr Ala
                485                 490                 495

Thr Gln Asp Thr Ser Leu Gln Asp Gly Glu Leu Ile Tyr Asn Val Lys
                500                 505                 510

Val Arg Gly Val Asn Phe Pro Ala Asn Gly Pro Val Met Gln Lys Lys
        515                 520                 525

Thr Leu Gly Trp Glu Pro Ser Thr Glu Thr Met Tyr Pro Ala Asp Gly
    530                 535                 540

Gly Leu Glu Gly Arg Cys Asp Lys Ala Leu Lys Leu Val Gly Gly Gly
545                 550                 555                 560

His Leu His Val Asn Phe Lys Thr Thr Tyr Lys Ser Lys Lys Pro Val
                565                 570                 575

Lys Met Pro Gly Val His Tyr Val Asp Arg Arg Leu Glu Arg Ile Lys
                580                 585                 590

Glu Ala Asp Asn Glu Thr Tyr Val Glu Gln Tyr Glu His Ala Val Ala
        595                 600                 605

Arg Tyr Ser Asn Leu Gly Gly Gly Met Asp Glu Leu Tyr Lys
        610                 615                 620
```

```
<210> SEQ ID NO 353
<211> LENGTH: 1866
<212> TYPE: DNA
<213> ORGANISM: Artificial sequence
<220> FEATURE:
<223> OTHER INFORMATION: Synthetic

<400> SEQUENCE: 353
atgaaacatc accatcacca tcatgtgagc aagggagaag aacttataaa agaaaacatg     60
cggtctaaac tgtacctcga gggctccgtc aatgggcacc agtttaagtg tacccacgag    120
ggtgagggaa agccctatga ggggaagcag acaaaccgca tcaaggtcgt cgaagggggga   180 cccctcccgt ttgcctttga tatcttggct actcacttta tgtacggaag caaagttttc    240
ataaagtatc ctgccgacct tcctgattat tttaaacagt catttcccga gggtttcaca    300
tgggaaaggg tcatggtgtt tgaggatgga ggcgtgctca ctgcaactca ggacacctca    360
ctgcaggacg gcgagctgat ctacaatgtg aaggtccggg gtgtaaactt ccctgccaac    420
gggcctgtaa tgcagaagaa gaccctggga tgggagccgt ccaccgaaac catgtaccct    480
gctgatggtg gctggagggg ccgatgtgac aaggctctga agctcgttgg aggtggtcat    540
ttgcacgtaa atttcaagac aacttacaag agcaaaaaac ccgtaaaaat gcccggggtt    600
cattacgttg acagaaggct tgaacgcata aaggaagctg ataacgagac atacgtggag    660
cagtacgagc acgccgttgc ccggtactca aacctggggg gtggcttcac actcgaagat    720
ttcgttgggg actgggaaca gacagccgcc tacaacctgg accaagtcct tgaacaggga    780
ggtgtgtcca gtttgctgca gaatctcgcc gtgtccgtaa ctccgatcca aaggattgtc    840
cggagcggtg aaaatgccct gaagatcgac atccatgtca tcatcccgta tgaaggtctg    900
agcgccgacc aaatggccca gatcgaagag gtgtttaagg tggtgtaccc tgtggatgat    960
```

-continued

```
catcacttta aggtgatcct gccctatggc acactggtaa tcgacggggt tacgccgaac    1020
atgctgaact atttcggacg gccgtatgaa ggcatcgccg tgttcgacgg caaaaagatc    1080
actgtaacag ggaccctgtg gaacggcaac aaaattatcg acgagcgcct gatcaccccc    1140
gacggctcca tgctgttccg agtaaccatc aacagcagac atgagctaat caaggaaaat    1200
atgagaagta agctatactt agaggggtcc gtcaacggtc accagtttaa atgcactcat    1260
gaaggtgagg ggaaacctta tgaaggtaag cagactaatc gaataaaagt ggtcgagggc    1320
ggtcctctgc cattcgcttt cgatattctg gccactcact ttatgtatgg gtctaaggtc    1380
tttattaaat accccgctga tttgccagac tactttaaac agtccttccc tgaaggattc    1440
acatgggagc gggtgatggt gttcgaggat ggaggcgttc ttactgcaac tcaggatact    1500
tccttgcaag acggggaact gatctacaac gttaaggtcc gcggcgtcaa tttcccagcc    1560
aatggtccag tgatgcagaa gaaaaccttg gggtgggagc cctcaacgga gacaatgtac    1620
cctgcggacg gcgggcttga gggtagatgt gataaggcat tgaaactcgt cgggggcggc    1680
caccttcatg tgaatttcaa gactacatat aaaagtaaaa aaccagtcaa gatgcctgga    1740
gtgcactacg tggatcgtag gttggagagg ataaaagaag ccgacaacga aacttatgta    1800
gagcaatatg agcacgccgt ggctcgttat tccaacttgg gcggaggaat ggatgaactg    1860
tacaag                                                             1866
```

<210> SEQ ID NO 354
<211> LENGTH: 611
<212> TYPE: PRT
<213> ORGANISM: Artificial sequence
<220> FEATURE:
<223> OTHER INFORMATION: Synthetic

<400> SEQUENCE: 354

```
Met Lys His His His His His His Val Ser Lys Gly Glu Glu Leu Ile
1               5                   10                  15

Lys Glu Asn Met Arg Ser Lys Leu Tyr Leu Glu Gly Ser Val Asn Gly
            20                  25                  30

His Gln Phe Lys Cys Thr His Glu Gly Glu Gly Lys Pro Tyr Glu Gly
        35                  40                  45

Lys Gln Thr Asn Arg Ile Lys Val Val Glu Gly Gly Pro Leu Pro Phe
    50                  55                  60

Ala Phe Asp Ile Leu Ala Thr His Phe Met Tyr Gly Ser Lys Val Phe
65                  70                  75                  80

Ile Lys Tyr Pro Ala Asp Leu Pro Asp Tyr Phe Lys Gln Ser Phe Pro
                85                  90                  95

Glu Gly Phe Thr Trp Glu Arg Val Met Val Phe Glu Asp Gly Gly Val
            100                 105                 110

Leu Thr Ala Thr Gln Asp Thr Ser Leu Gln Asp Gly Glu Leu Ile Tyr
        115                 120                 125

Asn Val Lys Val Arg Gly Val Asn Phe Pro Ala Asn Gly Pro Val Met
    130                 135                 140

Gln Lys Lys Thr Leu Gly Trp Glu Pro Ser Thr Glu Thr Met Tyr Pro
145                 150                 155                 160

Ala Asp Gly Gly Leu Glu Gly Arg Cys Asp Lys Ala Leu Lys Leu Val
                165                 170                 175

Gly Gly Gly His Leu His Val Asn Phe Lys Thr Thr Tyr Lys Ser Lys
            180                 185                 190

Lys Pro Val Lys Met Pro Gly Val His Tyr Val Asp Arg Arg Leu Glu
```

-continued

```
              195                200                205

Arg Ile Lys Glu Ala Asp Asn Glu Thr Tyr Val Glu Gln Tyr Glu His
    210                215                220

Ala Val Ala Arg Tyr Ser Asn Leu Gly Gly Gly Phe Thr Leu Asp Asp
225                230                235                240

Phe Val Gly Asp Trp Glu Gln Thr Ala Ala Tyr Asn Leu Asp Gln Val
                245                250                255

Leu Glu Gln Gly Gly Val Ser Ser Leu Leu Gln Asn Leu Ala Val Ser
                260                265                270

Val Thr Pro Ile Met Arg Ile Val Arg Ser Gly Glu Asn Ala Leu Lys
                275                280                285

Ile Asp Ile His Val Ile Ile Pro Tyr Glu Gly Leu Ser Ala Asp Gln
    290                295                300

Met Ala Gln Ile Glu Glu Val Phe Lys Val Val Tyr Pro Val Asp Asp
305                310                315                320

His His Phe Lys Val Ile Leu Pro Tyr Gly Thr Leu Val Ile Asp Gly
                325                330                335

Val Thr Pro Asn Lys Leu Asn Tyr Phe Gly Arg Pro Tyr Glu Gly Ile
                340                345                350

Ala Val Phe Asp Gly Lys Lys Ile Thr Thr Thr Gly Thr Leu Trp Asn
                355                360                365

Gly Asn Lys Ile Ile Asp Glu Arg Leu Ile Thr Pro Asp Arg His Glu
    370                375                380

Leu Ile Lys Glu Asn Met Arg Ser Lys Leu Tyr Leu Glu Gly Ser Val
385                390                395                400

Asn Gly His Gln Phe Lys Cys Thr His Glu Gly Glu Gly Lys Pro Tyr
                405                410                415

Glu Gly Lys Gln Thr Asn Arg Ile Lys Val Val Glu Gly Gly Pro Leu
                420                425                430

Pro Phe Ala Phe Asp Ile Leu Ala Thr His Phe Met Tyr Gly Ser Lys
                435                440                445

Val Phe Ile Lys Tyr Pro Ala Asp Leu Pro Asp Tyr Phe Lys Gln Ser
    450                455                460

Phe Pro Glu Gly Phe Thr Trp Glu Arg Val Met Val Phe Glu Asp Gly
465                470                475                480

Gly Val Leu Thr Ala Thr Gln Asp Thr Ser Leu Gln Asp Gly Glu Leu
                485                490                495

Ile Tyr Asn Val Lys Val Arg Gly Val Asn Phe Pro Ala Asn Gly Pro
                500                505                510

Val Met Gln Lys Lys Thr Leu Gly Trp Glu Pro Ser Thr Glu Thr Met
                515                520                525

Tyr Pro Ala Asp Gly Gly Leu Glu Gly Arg Cys Asp Lys Ala Leu Lys
    530                535                540

Leu Val Gly Gly Gly His Leu His Val Asn Phe Lys Thr Thr Tyr Lys
545                550                555                560

Ser Lys Lys Pro Val Lys Met Pro Gly Val His Tyr Val Asp Arg Arg
                565                570                575

Leu Glu Arg Ile Lys Glu Ala Asp Asn Glu Thr Tyr Val Glu Gln Tyr
                580                585                590

Glu His Ala Val Ala Arg Tyr Ser Asn Leu Gly Gly Gly Met Asp Glu
    595                600                605

Leu Tyr Lys
    610
```

```
<210> SEQ ID NO 355
<211> LENGTH: 1833
<212> TYPE: DNA
<213> ORGANISM: Artificial sequence
<220> FEATURE:
<223> OTHER INFORMATION: Synthetic

<400> SEQUENCE: 355
atgaaacatc accatcacca tcatgtgagc aagggagaag aacttataaa agaaaacatg      60
cggtctaaac tgtacctcga gggctccgtc aatgggcacc agtttaagtg tacccacgag     120
ggtgagggaa agccctatga ggggaagcag acaaaccgca tcaaggtcgt cgaaggggga     180
cccctcccgt ttgcctttga tatcttggct actcacttta tgtacggaag caaagttttc     240
ataaagtatc ctgccgacct tcctgattat tttaaacagt catttcccga gggttttcaca    300 tgggaaaggg tcatggtgtt tgaggatgga ggcgtgctca ctgcaactca ggacacctca     360
ctgcaggacg gcgagctgat ctacaatgtg aaggtccggg gtgtaaactt ccctgccaac     420
gggcctgtaa tgcagaagaa gaccctggga tgggagccgt ccaccgaaac catgtaccct     480
gctgatggtg ggctggaggg ccgatgtgac aaggctctga agctcgttgg aggtggtcat     540
ttgcacgtaa atttcaagac aacttacaag agcaaaaaac ccgtaaaaat gcccgggggtt    600 cattacgttg acagaaggct tgaacgcata aaggaagctg ataacgagac atacgtggag     660
cagtacgagc acgccgttgc ccggtactca aacctggggg gtggcttcac actcgacgat     720
ttcgttgggg actgggaaca gacagccgcc tacaacctgg accaagtcct tgaacaggga     780
ggtgtgtcca gtttgctgca gaatctcgcc gtgtccgtaa ctccgatcat gaggattgtc     840
cggagcggtg aaaatgccct gaagatcgac atccatgtca tcatcccgta tgaaggtctg     900
agcgccgacc aaatggccca gatcgaagag gtgtttaagg tggtgtaccc tgtggatgat     960
catcacttta aggtgatcct gcccctatggc acactggtaa tcgacggggt tacgccgaac    1020
aagctgaact atttcggacg gccgtatgaa ggcatcgccg tgttcgacgg caaaaagatc    1080
actaccacag ggaccctgtg gaacggcaac aaaattatcg acgagcgcct gatcacccccc   1140 gacagacatg agctaatcaa ggaaaatatg agaagtaagc tatacttaga ggggtccgtc    1200
aacggtcacc agtttaaatg cactcatgaa ggtgagggga aaccttatga aggtaagcag    1260
actaatcgaa taaagtggt cgagggcggt cctctgccat tcgctttcga tattctggcc    1320 actcactttta tgtatgggtc taaggtcttt attaaatacc ccgctgattt gccagactac    1380
tttaaacagt ccttccctga aggattcaca tgggagcggg tgatggtgtt cgaggatgga    1440
ggcgttctta ctgcaactca ggatacttcc ttgcaagacg gggaactgat ctacaacgtt    1500
aaggtccgcg gcgtcaattt cccagccaat ggtccagtga tgcagaagaa aaccttgggg    1560
tgggagccct caacggagac aatgtaccct gcggacggcg ggcttgaggg tagatgtgat    1620
aaggcattga aactcgtcgg gggcggccac cttcatgtga atttcaagac tacatataaa    1680
agtaaaaaac cagtcaagat gcctggagtg cactacgtgg atcgtaggtt ggagaggata    1740
aaagaagccg acaacgaaac ttatgtagag caatatgagc acgccgtggc tcgttattcc    1800
aacttgggcg gaggaatgga tgaactgtac aag                                 1833
```

```
<210> SEQ ID NO 356
<211> LENGTH: 401
<212> TYPE: PRT
<213> ORGANISM: Artificial sequence
<220> FEATURE:
```

-continued

<223> OTHER INFORMATION: Synthetic

<400> SEQUENCE: 356

```
Met Lys His His His His His Phe Thr Leu Glu Asp Phe Val Gly
1               5                   10                  15

Asp Trp Glu Gln Thr Ala Ala Tyr Asn Leu Asp Gln Val Leu Glu Gln
            20                  25                  30

Gly Gly Val Ser Ser Leu Leu Gln Asn Leu Ala Val Ser Val Thr Pro
            35                  40                  45

Ile Gln Arg Ile Val Arg Ser Gly Glu Asn Ala Leu Lys Ile Asp Ile
    50                  55                  60

His Val Ile Ile Pro Tyr Glu Gly Leu Ser Ala Asp Gln Met Ala Gln
65                  70                  75                  80

Ile Glu Glu Val Phe Lys Val Val Tyr Pro Val Asp Asp His His Phe
                85                  90                  95

Lys Val Ile Leu Pro Tyr Gly Thr Leu Val Ile Asp Gly Val Thr Pro
            100                 105                 110

Asn Met Leu Asn Tyr Phe Gly Arg Pro Tyr Glu Gly Ile Ala Val Phe
            115                 120                 125

Asp Gly Lys Lys Ile Thr Val Thr Gly Thr Leu Trp Asn Gly Asn Lys
    130                 135                 140

Ile Ile Asp Glu Arg Leu Ile Thr Pro Asp Gly Ser Met Leu Phe Arg
145                 150                 155                 160

Val Thr Ile Asn Ser Gly Gly Ser Gly Gly Ser Ser Gly Glu Leu Ile
            165                 170                 175

Lys Glu Asn Met Arg Ser Lys Leu Tyr Leu Glu Gly Ser Val Asn Gly
            180                 185                 190

His Gln Phe Lys Cys Thr His Glu Gly Glu Gly Lys Pro Tyr Glu Gly
            195                 200                 205

Lys Gln Thr Asn Arg Ile Lys Val Val Glu Gly Gly Pro Leu Pro Phe
    210                 215                 220

Ala Phe Asp Ile Leu Ala Thr His Phe Met Tyr Gly Ser Lys Val Phe
225                 230                 235                 240

Ile Lys Tyr Pro Ala Asp Leu Pro Asp Tyr Phe Lys Gln Ser Phe Pro
            245                 250                 255

Glu Gly Phe Thr Trp Glu Arg Val Met Val Phe Glu Asp Gly Gly Val
            260                 265                 270

Leu Thr Ala Thr Gln Asp Thr Ser Leu Gln Asp Gly Glu Leu Ile Tyr
            275                 280                 285

Asn Val Lys Val Arg Gly Val Asn Phe Pro Ala Asn Gly Pro Val Met
    290                 295                 300

Gln Lys Lys Thr Leu Gly Trp Glu Pro Ser Thr Glu Thr Met Tyr Pro
305                 310                 315                 320

Ala Asp Gly Gly Leu Glu Gly Arg Cys Asp Lys Ala Leu Lys Leu Val
            325                 330                 335

Gly Gly Gly His Leu His Val Asn Phe Lys Thr Thr Tyr Lys Ser Lys
            340                 345                 350

Lys Pro Val Lys Met Pro Gly Val His Tyr Val Asp Arg Arg Leu Glu
            355                 360                 365

Arg Ile Lys Glu Ala Asp Asn Glu Thr Tyr Val Glu Gln Tyr Glu His
    370                 375                 380

Ala Val Ala Arg Tyr Ser Asn Leu Gly Gly Gly Met Asp Glu Leu Tyr
385                 390                 395                 400
```

Lys

<210> SEQ ID NO 357
<211> LENGTH: 1203
<212> TYPE: DNA
<213> ORGANISM: Artificial sequence
<220> FEATURE:
<223> OTHER INFORMATION: Synthetic

<400> SEQUENCE: 357
atgaaacatc accatcacca tcatttcaca ctcgaagatt tcgttgggga ctgggaacag        60
acagccgcct acaacctgga ccaagtcctt gaacagggag gtgtgtccag tttgctgcag       120
aatctcgccg tgtccgtaac tccgatccaa aggattgtcc ggagcggtga aaatgccctg       180
aagatcgaca tccatgtcat catcccgtat gaaggtctga gcgccgacca aatggcccag       240
atcgaagagg tgtttaaggt ggtgtaccct gtggatgatc atcactttaa ggtgatcctg       300
ccctatggca cactggtaat cgacgggggtt acgccgaaca tgctgaacta tttcggacgg       360
ccgtatgaag gcatcgccgt gttcgacggc aaaaagatca ctgtaacagg gaccctgtgg       420
aacggcaaca aaattatcga cgagcgcctg atcacccccg acggctccat gctgttccga       480
gtaaccatca cagcggagg ctcaggtgga tcctcaggtg agctaatcaa ggaaaatatg       540
agaagtaagc tatacttaga ggggtccgtc aacggtcacc agtttaaatg cactcatgaa       600 ggtgaggga aaccttatga aggtaagcag actaatcgaa taaaagtggt cgagggcggt       660
cctctgccat tcgctttcga tattctggcc actcacttta tgtatgggtc taaggtcttt       720
attaaatacc ccgctgattt gccagactac tttaaacagt ccttccctga aggattcaca       780
tgggagcggg tgatggtgtt cgaggatgga ggcgttctta ctgcaactca ggatacttcc       840
ttgcaagacg gggaactgat ctacaacgtt aaggtccgcg gcgtcaattt cccagccaat       900
ggtccagtga tgcagaagaa aaccttgggg tgggagccct caacggagac aatgtaccct       960
gcggacggcg ggcttgaggg tagatgtgat aaggcattga aactcgtcgg gggcggccac      1020
cttcatgtga atttcaagac tacatataaa agtaaaaaac cagtcaagat gcctggagtg      1080
cactacgtgg atcgtaggtt ggagaggata aaagaagccg acaacgaaac ttatgtagag      1140
caatatgagc acgccgtggc tcgttattcc aacttgggcg gaggaatgga tgaactgtac      1200
aag                                                                     1203

<210> SEQ ID NO 358
<211> LENGTH: 395
<212> TYPE: PRT
<213> ORGANISM: Artificial sequence
<220> FEATURE:
<223> OTHER INFORMATION: Synthetic

<400> SEQUENCE: 358

Met Lys His His His His His His Phe Thr Leu Glu Asp Phe Val Gly
1               5                   10                  15

Asp Trp Glu Gln Thr Ala Ala Tyr Asn Leu Asp Gln Val Leu Glu Gln
            20                  25                  30

Gly Gly Val Ser Ser Leu Leu Gln Asn Leu Ala Val Ser Val Thr Pro
        35                  40                  45

Ile Gln Arg Ile Val Arg Ser Gly Glu Asn Ala Leu Lys Ile Asp Ile
    50                  55                  60

His Val Ile Ile Pro Tyr Glu Gly Leu Ser Ala Asp Gln Met Ala Gln
65                  70                  75                  80

-continued

```
Ile Glu Glu Val Phe Lys Val Val Tyr Pro Val Asp Asp His His Phe
                85              90                  95

Lys Val Ile Leu Pro Tyr Gly Thr Leu Val Ile Asp Gly Val Thr Pro
            100             105             110

Asn Met Leu Asn Tyr Phe Gly Arg Pro Tyr Glu Gly Ile Ala Val Phe
            115             120             125

Asp Gly Lys Lys Ile Thr Val Thr Gly Thr Leu Trp Asn Gly Asn Lys
    130             135             140

Ile Ile Asp Glu Arg Leu Ile Thr Pro Asp Gly Ser Met Leu Phe Arg
145             150             155                 160

Val Thr Ile Asn Ser Arg His Glu Leu Ile Lys Glu Asn Met Arg Ser
            165             170             175

Lys Leu Tyr Leu Glu Gly Ser Val Asn Gly His Gln Phe Lys Cys Thr
            180             185             190

His Glu Gly Glu Gly Lys Pro Tyr Glu Gly Lys Gln Thr Asn Arg Ile
            195             200             205

Lys Val Val Glu Gly Gly Pro Leu Pro Phe Ala Phe Asp Ile Leu Ala
    210             215             220

Thr His Phe Met Tyr Gly Ser Lys Val Phe Ile Lys Tyr Pro Ala Asp
225             230             235                 240

Leu Pro Asp Tyr Phe Lys Gln Ser Phe Pro Glu Gly Phe Thr Trp Glu
            245             250             255

Arg Val Met Val Phe Glu Asp Gly Gly Val Leu Thr Ala Thr Gln Asp
            260             265             270

Thr Ser Leu Gln Asp Gly Glu Leu Ile Tyr Asn Val Lys Val Arg Gly
            275             280             285

Val Asn Phe Pro Ala Asn Gly Pro Val Met Gln Lys Lys Thr Leu Gly
    290             295             300

Trp Glu Pro Ser Thr Glu Thr Met Tyr Pro Ala Asp Gly Gly Leu Glu
305             310             315                 320

Gly Arg Cys Asp Lys Ala Leu Lys Leu Val Gly Gly Gly His Leu His
            325             330             335

Val Asn Phe Lys Thr Thr Tyr Lys Ser Lys Lys Pro Val Lys Met Pro
            340             345             350

Gly Val His Tyr Val Asp Arg Arg Leu Glu Arg Ile Lys Glu Ala Asp
            355             360             365

Asn Glu Thr Tyr Val Glu Gln Tyr Glu His Ala Val Ala Arg Tyr Ser
    370             375             380

Asn Leu Gly Gly Gly Met Asp Glu Leu Tyr Lys
385             390             395
```

```
<210> SEQ ID NO 359
<211> LENGTH: 1185
<212> TYPE: DNA
<213> ORGANISM: Artificial sequence
<220> FEATURE:
<223> OTHER INFORMATION: Synthetic

<400> SEQUENCE: 359
atgaaacatc accatcacca tcatttcaca ctcgaagatt tcgttgggga ctgggaacag      60
acagccgcct acaacctgga ccaagtcctt gaacagggag gtgtgtccag tttgctgcag     120
aatctcgccg tgtccgtaac tccgatccaa aggattgtcc ggagcggtga aaatgccctg     180
aagatcgaca tccatgtcat catcccgtat gaaggtctga cgccgaccaa atggcccag      240 atcgaagagg tgtttaaggt ggtgtaccct gtggatgatc atcactttaa ggtgatcctg     300
```

```
ccctatggca cactggtaat cgacgggggtt acgccgaaca tgctgaacta tttcggacgg      360
ccgtatgaag gcatcgccgt gttcgacggc aaaaagatca ctgtaacagg gaccctgtgg      420
aacggcaaca aaattatcga cgagcgcctg atcaccccg acggctccat gctgttccga      480
gtaaccatca acagcagaca tgagctaatc aaggaaaata tgagaagtaa gctatactta      540
gaggggtccg tcaacggtca ccagtttaaa tgcactcatg aaggtgaggg gaaaccttat      600
gaaggtaagc agactaatcg aataaaagtg gtcgagggcg gtcctctgcc attcgctttc      660
gatattctgg ccactcactt tatgtatggg tctaaggtct ttattaaata ccccgctgat      720
ttgccagact actttaaaca gtccttccct gaaggattca catgggagcg ggtgatggtg      780
ttcgaggatg gaggcgttct tactgcaact caggatactt ccttgcaaga cggggaactg      840
atctacaacg ttaaggtccg cggcgtcaat ttcccagcca atggtccagt gatgcagaag      900
aaaaccttgg ggtgggagcc ctcaacggag acaatgtacc ctgcggacgg cgggcttgag      960
ggtagatgtg ataaggcatt gaaactcgtc gggggcggcc accttcatgt gaatttcaag     1020
actacatata aaagtaaaaa accagtcaag atgcctggag tgcactacgt ggatcgtagg     1080
ttggagagga taaagaaagc cgacaacgaa acttatgtag agcaatatga gcacgccgtg     1140
gctcgttatt ccaacttggg cggaggaatg gatgaactgt acaag                     1185
```

```
<210> SEQ ID NO 360
<211> LENGTH: 390
<212> TYPE: PRT
<213> ORGANISM: Artificial sequence
<220> FEATURE:
<223> OTHER INFORMATION: Synthetic

<400> SEQUENCE: 360

Met Lys His His His His His His Phe Thr Leu Asp Asp Phe Val Gly
1               5                   10                  15

Asp Trp Glu Gln Thr Ala Ala Tyr Asn Leu Asp Gln Val Leu Glu Gln
            20                  25                  30

Gly Gly Val Ser Ser Leu Leu Gln Asn Leu Ala Val Ser Val Thr Pro
        35                  40                  45

Ile Met Arg Ile Val Arg Ser Gly Glu Asn Ala Leu Lys Ile Asp Ile
    50                  55                  60

His Val Ile Ile Pro Tyr Glu Gly Leu Ser Ala Asp Gln Met Ala Gln
65                  70                  75                  80

Ile Glu Glu Val Phe Lys Val Val Tyr Pro Val Asp Asp His His Phe
                85                  90                  95

Lys Val Ile Leu Pro Tyr Gly Thr Leu Val Ile Asp Gly Val Thr Pro
            100                 105                 110

Asn Lys Leu Asn Tyr Phe Gly Arg Pro Tyr Glu Gly Ile Ala Val Phe
            115                 120                 125

Asp Gly Lys Lys Ile Thr Thr Thr Gly Thr Leu Trp Asn Gly Asn Lys
        130                 135                 140

Ile Ile Asp Glu Arg Leu Ile Thr Pro Asp Gly Gly Ser Gly Gly Ser
145                 150                 155                 160

Ser Gly Glu Leu Ile Lys Glu Asn Met Arg Ser Lys Leu Tyr Leu Glu
                165                 170                 175

Gly Ser Val Asn Gly His Gln Phe Lys Cys Thr His Glu Gly Glu Gly
            180                 185                 190

Lys Pro Tyr Glu Gly Lys Gln Thr Asn Arg Ile Lys Val Val Glu Gly
        195                 200                 205
```

```
Gly Pro Leu Pro Phe Ala Phe Asp Ile Leu Ala Thr His Phe Met Tyr
    210                 215                 220

Gly Ser Lys Val Phe Ile Lys Tyr Pro Ala Asp Leu Pro Asp Tyr Phe
225                 230                 235                 240

Lys Gln Ser Phe Pro Glu Gly Phe Thr Trp Glu Arg Val Met Val Phe
                245                 250                 255

Glu Asp Gly Gly Val Leu Thr Ala Thr Gln Asp Thr Ser Leu Gln Asp
                260                 265                 270

Gly Glu Leu Ile Tyr Asn Val Lys Val Arg Gly Val Asn Phe Pro Ala
            275                 280                 285

Asn Gly Pro Val Met Gln Lys Lys Thr Leu Gly Trp Glu Pro Ser Thr
    290                 295                 300

Glu Thr Met Tyr Pro Ala Asp Gly Gly Leu Glu Gly Arg Cys Asp Lys
305                 310                 315                 320

Ala Leu Lys Leu Val Gly Gly Gly His Leu His Val Asn Phe Lys Thr
                325                 330                 335

Thr Tyr Lys Ser Lys Lys Pro Val Lys Met Pro Gly Val His Tyr Val
                340                 345                 350

Asp Arg Arg Leu Glu Arg Ile Lys Glu Ala Asp Asn Glu Thr Tyr Val
            355                 360                 365

Glu Gln Tyr Glu His Ala Val Ala Arg Tyr Ser Asn Leu Gly Gly Gly
    370                 375                 380

Met Asp Glu Leu Tyr Lys
385                 390
```

```
<210> SEQ ID NO 361
<211> LENGTH: 1170
<212> TYPE: DNA
<213> ORGANISM: Artificial sequence
<220> FEATURE:
<223> OTHER INFORMATION: Synthetic

<400> SEQUENCE: 361
atgaaacatc accatcacca tcatttcaca ctcgacgatt tcgttgggga ctgggaacag     60
acagccgcct acaacctgga ccaagtcctt gaacagggag gtgtgtccag tttgctgcag    120
aatctcgccg tgtccgtaac tccgatcatg aggattgtcc ggagcggtga aaatgccctg    180
aagatcgaca tccatgtcat catcccgtat gaaggtctga gcgccgacca aatggcccag    240
atcgaagagg tgtttaaggt ggtgtaccct gtggatgatc atcactttaa ggtgatcctg    300
ccctatggca cactggtaat cgacgggggt acgccgaaca agctgaacta tttcggacgg    360
ccgtatgaag gcatcgccgt gttcgacggc aaaaagatca ctaccacagg gaccctgtgg    420
aacggcaaca aaattatcga cgagcgcctg atcaccccg acggaggctc aggtggatcc    480
tcaggtgagc taatcaagga aaatatgaga agtaagctat acttagaggg gtccgtcaac    540
ggtcaccagt ttaaatgcac tcatgaaggt gaggggaaac cttatgaagg taagcagact    600
aatcgaataa aagtggtcga gggcggtcct ctgccattcg ctttcgatat tctggccact    660
cactttatgt atgggtctaa ggtctttatt aaatacccccg ctgatttgcc agactacttt    720
aaacagtcct ccctgaagg attcacatgg agcgggtga tggtgttcga ggatggaggc    780
gttcttactg caactcagga tacttccttg caagacgggg aactgatcta caacgttaag    840
gtccgcggcg tcaatttccc agccaatggt ccagtgatgc agaagaaaac cttggggtgg    900
gagccctcaa cggagacaat gtaccctgcg gacggcgggc ttgagggtag atgtgataag    960
```

-continued

```
gcattgaaac tcgtcggggg cggccacctt catgtgaatt tcaagactac atataaaagt   1020
aaaaaaccag tcaagatgcc tggagtgcac tacgtggatc gtaggttgga gaggataaaa   1080
gaagccgaca acgaaactta tgtagagcaa tatgagcacg ccgtggctcg ttattccaac   1140
ttgggcggag gaatggatga actgtacaag                                    1170
```

```
<210> SEQ ID NO 362
<211> LENGTH: 384
<212> TYPE: PRT
<213> ORGANISM: Artificial sequence
<220> FEATURE:
<223> OTHER INFORMATION: Synthetic

<400> SEQUENCE: 362

Met Lys His His His His His His Phe Thr Leu Asp Asp Phe Val Gly
1               5                   10                  15

Asp Trp Glu Gln Thr Ala Ala Tyr Asn Leu Asp Gln Val Leu Glu Gln
                20                  25                  30

Gly Gly Val Ser Ser Leu Leu Gln Asn Leu Ala Val Ser Val Thr Pro
            35                  40                  45

Ile Met Arg Ile Val Arg Ser Gly Glu Asn Ala Leu Lys Ile Asp Ile
        50                  55                  60

His Val Ile Ile Pro Tyr Glu Gly Leu Ser Ala Asp Gln Met Ala Gln
65                  70                  75                  80

Ile Glu Glu Val Phe Lys Val Val Tyr Pro Val Asp Asp His His Phe
                85                  90                  95

Lys Val Ile Leu Pro Tyr Gly Thr Leu Val Ile Asp Gly Val Thr Pro
            100                 105                 110

Asn Lys Leu Asn Tyr Phe Gly Arg Pro Tyr Glu Gly Ile Ala Val Phe
        115                 120                 125

Asp Gly Lys Lys Ile Thr Thr Thr Gly Thr Leu Trp Asn Gly Asn Lys
        130                 135                 140

Ile Ile Asp Glu Arg Leu Ile Thr Pro Asp Arg His Glu Leu Ile Lys
145                 150                 155                 160

Glu Asn Met Arg Ser Lys Leu Tyr Leu Glu Gly Ser Val Asn Gly His
                165                 170                 175

Gln Phe Lys Cys Thr His Glu Gly Glu Gly Lys Pro Tyr Glu Gly Lys
            180                 185                 190

Gln Thr Asn Arg Ile Lys Val Val Glu Gly Gly Pro Leu Pro Phe Ala
        195                 200                 205

Phe Asp Ile Leu Ala Thr His Phe Met Tyr Gly Ser Lys Val Phe Ile
        210                 215                 220

Lys Tyr Pro Ala Asp Leu Pro Asp Tyr Phe Lys Gln Ser Phe Pro Glu
225                 230                 235                 240

Gly Phe Thr Trp Glu Arg Val Met Val Phe Glu Asp Gly Gly Val Leu
                245                 250                 255

Thr Ala Thr Gln Asp Thr Ser Leu Gln Asp Gly Glu Leu Ile Tyr Asn
            260                 265                 270

Val Lys Val Arg Gly Val Asn Phe Pro Ala Asn Gly Pro Val Met Gln
        275                 280                 285

Lys Lys Thr Leu Gly Trp Glu Pro Ser Thr Glu Thr Met Tyr Pro Ala
        290                 295                 300

Asp Gly Gly Leu Glu Gly Arg Cys Asp Lys Ala Leu Lys Leu Val Gly
305                 310                 315                 320

Gly Gly His Leu His Val Asn Phe Lys Thr Thr Tyr Lys Ser Lys Lys
```

```
                 325                 330                 335
Pro Val Lys Met Pro Gly Val His Tyr Val Asp Arg Arg Leu Glu Arg
             340                 345                 350

Ile Lys Glu Ala Asp Asn Glu Thr Tyr Val Glu Gln Tyr Glu His Ala
             355                 360                 365

Val Ala Arg Tyr Ser Asn Leu Gly Gly Gly Met Asp Glu Leu Tyr Lys
         370                 375                 380
```

<210> SEQ ID NO 363
<211> LENGTH: 1152
<212> TYPE: DNA
<213> ORGANISM: Artificial sequence
<220> FEATURE:
<223> OTHER INFORMATION: Synthetic

<400> SEQUENCE: 363

```
atgaaacatc accatcacca tcatttcaca ctcgacgatt tcgttgggga ctgggaacag      60
acagccgcct acaacctgga ccaagtcctt gaacagggag gtgtgtccag tttgctgcag     120
aatctcgccg tgtccgtaac tccgatcatg aggattgtcc ggagcggtga aaatgccctg     180
aagatcgaca tccatgtcat catcccgtat gaaggtctga gcgccgacca aatggcccag     240
atcgaagagg tgtttaaggt ggtgtaccct gtggatgatc atcactttaa ggtgatcctg     300
ccctatggca cactggtaat cgacgggggt acgccgaaca agctgaacta tttcggacgg     360
ccgtatgaag gcatcgccgt gttcgacggc aaaaagatca ctaccacagg gaccctgtgg     420
aacggcaaca aaattatcga cgagcgcctg atcacccccg acagacatga gctaatcaag     480
gaaaatatga gaagtaagct atacttagag gggtccgtca acggtcacca gtttaaatgc     540
actcatgaag gtgaggggaa accttatgaa ggtaagcaga ctaatcgaat aaaagtggtc     600
gagggcggtc tctgccatt cgctttcgat attctggcca ctcactttat gtatgggtct     660
aaggtcttta ttaaataccc cgctgatttg ccagactact ttaaacagtc cttccctgaa     720
ggattcacat gggagcgggt gatggtgttc gaggatggag gcgttcttac tgcaactcag     780
gatacttcct tgcaagacgg ggaactgatc tacaacgtta aggtccgcgg cgtcaatttc     840
ccagccaatg gtccagtgat gcagaagaaa accttggggt gggagccctc aacggagaca     900
atgtaccctg cggacggcgg gcttgagggt agatgtgata aggcattgaa actcgtcggg     960
ggcggccacc ttcatgtgaa tttcaagact acatataaaa gtaaaaaacc agtcaagatg    1020
cctggagtgc actacgtgga tcgtaggttg gagaggataa aagaagccga caacgaaact    1080
tatgtagagc aatatgagca cgccgtggct cgttattcca acttgggcgg aggaatggat    1140
gaactgtaca ag                                                        1152
```

<210> SEQ ID NO 364
<211> LENGTH: 155
<212> TYPE: PRT
<213> ORGANISM: Artificial sequence
<220> FEATURE:
<223> OTHER INFORMATION: Synthetic

<400> SEQUENCE: 364

```
Met Lys His His His His His His Val Phe Thr Leu Glu Asp Phe Val
1               5                   10                  15

Gly Asp Trp Glu Gln Thr Ala Ala Tyr Asn Leu Asp Gln Val Leu Glu
             20                  25                  30

Gln Gly Gly Val Ser Ser Leu Leu Gln Asn Leu Ala Val Ser Val Thr
         35                  40                  45
```

-continued

```
Pro Ile Leu Arg Ile Val Arg Ser Gly Glu Asn Ala Leu Lys Ile Asp
    50              55              60

Ile His Val Ile Ile Pro Tyr Glu Gly Leu Ser Ala Asp Gln Met Ala
65              70              75              80

Gln Ile Glu Glu Val Phe Lys Val Val Tyr Pro Val Asp Asp His His
            85              90              95

Phe Lys Val Ile Leu Pro Tyr Gly Thr Leu Val Ile Asp Gly Val Thr
            100             105             110

Pro Asn Met Leu Asn Tyr Phe Gly Arg Pro Tyr Glu Gly Ile Ala Val
        115             120             125

Phe Asp Gly Lys Lys Ile Thr Val Thr Gly Thr Leu Trp Asn Gly Asn
    130             135             140

Lys Ile Ile Asp Glu Arg Leu Ile Thr Pro Asp
145             150             155
```

```
<210> SEQ ID NO 365
<211> LENGTH: 465
<212> TYPE: DNA
<213> ORGANISM: Artificial sequence
<220> FEATURE:
<223> OTHER INFORMATION: Synthetic

<400> SEQUENCE: 365
atgaaacatc accatcacca tcatgtcttc acactcgaag atttcgttgg ggactgggaa      60
cagaccgccg cctacaacct ggaccaagtc cttgaacagg gaggtgtgtc cagtttgctg     120
cagaatctcg ccgtgtccgt aactccgatc ctaaggattg tccggagcgg tgaaaatgcc     180
ctgaagatcg acatccatgt catcatcccg tatgaaggtc tgagcgccga ccaaatggcc     240
cagatcgaag aggtgtttaa ggtggtgtac cctgtggatg atcatcactt taaggtgatc     300
ctgccctatg gcacactggt aatcgacggg gttacgccga acatgctgaa ctatttcgga     360
cggccgtatg aaggcatcgc cgtgttcgac ggcaaaaaga tcactgtaac agggaccctg     420
tggaacggca acaaaattat cgacgagcgc ctgatcaccc ccgac                     465
```

```
<210> SEQ ID NO 366
<211> LENGTH: 15
<212> TYPE: PRT
<213> ORGANISM: Artificial sequence
<220> FEATURE:
<223> OTHER INFORMATION: Synthetic

<400> SEQUENCE: 366

Trp Asn Gly Asn Lys Ile Ile Asp Glu Arg Leu Ile Thr Pro Asp
1               5               10              15
```

```
<210> SEQ ID NO 367
<211> LENGTH: 13
<212> TYPE: PRT
<213> ORGANISM: Artificial sequence
<220> FEATURE:
<223> OTHER INFORMATION: Synthetic

<400> SEQUENCE: 367

Lys Lys Ile Thr Thr Thr Gly Thr Leu Trp Asn Gly Arg
1               5               10
```

```
<210> SEQ ID NO 368
<211> LENGTH: 12
<212> TYPE: PRT
<213> ORGANISM: Artificial sequence
```

<220> FEATURE:
<223> OTHER INFORMATION: Synthetic

<400> SEQUENCE: 368

Arg Pro Tyr Glu Gly Ile Ala Val Phe Asp Gly Lys
1               5                   10

<210> SEQ ID NO 369
<211> LENGTH: 24
<212> TYPE: PRT
<213> ORGANISM: Artificial sequence
<220> FEATURE:
<223> OTHER INFORMATION: Synthetic

<400> SEQUENCE: 369

Gly Lys Met Leu Phe Arg Val Thr Ile Trp Lys Val Ser Val Ser Gly
1               5                   10                  15

Trp Arg Leu Phe Lys Lys Ile Ser
            20

<210> SEQ ID NO 370
<211> LENGTH: 22
<212> TYPE: PRT
<213> ORGANISM: Artificial sequence
<220> FEATURE:
<223> OTHER INFORMATION: Synthetic

<400> SEQUENCE: 370

Gly Lys Met Leu Phe Arg Val Thr Ile Trp Lys Val Ser Gly Trp Arg
1               5                   10                  15

Leu Phe Lys Lys Ile Ser
            20

<210> SEQ ID NO 371
<211> LENGTH: 26
<212> TYPE: PRT
<213> ORGANISM: Artificial sequence
<220> FEATURE:
<223> OTHER INFORMATION: Synthetic

<400> SEQUENCE: 371

Gly Ser Met Lys Phe Arg Val Thr Ile Asn Ser Trp Lys Val Ser Val
1               5                   10                  15

Ser Gly Trp Arg Leu Phe Lys Lys Ile Ser
            20                  25

<210> SEQ ID NO 372
<211> LENGTH: 24
<212> TYPE: PRT
<213> ORGANISM: Artificial sequence
<220> FEATURE:
<223> OTHER INFORMATION: Synthetic

<400> SEQUENCE: 372

Gly Ser Met Lys Phe Arg Val Thr Ile Asn Ser Trp Lys Val Ser Gly
1               5                   10                  15

Trp Arg Leu Phe Lys Lys Ile Ser
            20

<210> SEQ ID NO 373
<211> LENGTH: 26
<212> TYPE: PRT
<213> ORGANISM: Artificial sequence
<220> FEATURE:
<223> OTHER INFORMATION: Synthetic

<400> SEQUENCE: 373

Gly Ser Met Lys Phe Arg Val Thr Ile Asn Ser Trp Lys Asn Val Thr
1               5                   10                  15

Gly Tyr Arg Leu Phe Lys Lys Ile Ser Asn
            20                  25

<210> SEQ ID NO 374
<211> LENGTH: 24
<212> TYPE: PRT
<213> ORGANISM: Artificial sequence
<220> FEATURE:
<223> OTHER INFORMATION: Synthetic

<400> SEQUENCE: 374

Gly Ser Met Lys Phe Arg Val Thr Ile Asn Ser Trp Lys Val Thr Gly
1               5                   10                  15

Tyr Arg Leu Phe Glu Lys Ile Ser
            20

<210> SEQ ID NO 375
<211> LENGTH: 24
<212> TYPE: PRT
<213> ORGANISM: Artificial sequence
<220> FEATURE:
<223> OTHER INFORMATION: Synthetic

<400> SEQUENCE: 375

Gly Ser Met Lys Phe Arg Val Thr Ile Trp Lys Val Ser Val Ser Gly
1               5                   10                  15

Trp Arg Leu Phe Lys Lys Ile Ser
            20

<210> SEQ ID NO 376
<211> LENGTH: 22
<212> TYPE: PRT
<213> ORGANISM: Artificial sequence
<220> FEATURE:
<223> OTHER INFORMATION: Synthetic

<400> SEQUENCE: 376

Gly Ser Met Lys Phe Arg Val Thr Ile Trp Lys Val Ser Gly Trp Arg
1               5                   10                  15

Leu Phe Lys Lys Ile Ser
            20

<210> SEQ ID NO 377
<211> LENGTH: 26
<212> TYPE: PRT
<213> ORGANISM: Artificial sequence
<220> FEATURE:
<223> OTHER INFORMATION: Synthetic

<400> SEQUENCE: 377

Gly Arg Met Leu Phe Arg Val Thr Ile Asn Ser Trp Lys Val Ser Val
1               5                   10                  15

Ser Gly Trp Arg Leu Phe Lys Lys Ile Ser
            20                  25

<210> SEQ ID NO 378
<211> LENGTH: 24
<212> TYPE: PRT
<213> ORGANISM: Artificial sequence
<220> FEATURE:

-continued

```
<223> OTHER INFORMATION: Synthetic

<400> SEQUENCE: 378

Gly Arg Met Leu Phe Arg Val Thr Ile Asn Ser Trp Lys Val Ser Gly
1               5                   10                  15

Trp Arg Leu Phe Lys Lys Ile Ser
            20

<210> SEQ ID NO 379
<211> LENGTH: 24
<212> TYPE: PRT
<213> ORGANISM: Artificial sequence
<220> FEATURE:
<223> OTHER INFORMATION: Synthetic

<400> SEQUENCE: 379

Gly Arg Met Leu Phe Arg Val Thr Ile Trp Lys Val Ser Val Ser Gly
1               5                   10                  15

Trp Arg Leu Phe Lys Lys Ile Ser
            20

<210> SEQ ID NO 380
<211> LENGTH: 22
<212> TYPE: PRT
<213> ORGANISM: Artificial sequence
<220> FEATURE:
<223> OTHER INFORMATION: Synthetic

<400> SEQUENCE: 380

Gly Arg Met Leu Phe Arg Val Thr Ile Trp Lys Val Ser Gly Trp Arg
1               5                   10                  15

Leu Phe Lys Lys Ile Ser
            20

<210> SEQ ID NO 381
<211> LENGTH: 24
<212> TYPE: PRT
<213> ORGANISM: Artificial sequence
<220> FEATURE:
<223> OTHER INFORMATION: Synthetic

<400> SEQUENCE: 381

Gly Ser Met Leu Phe Arg Val Thr Ile Asn Ser Val Ser Val Ser Gly
1               5                   10                  15

Trp Arg Leu Phe Lys Lys Ile Ser
            20

<210> SEQ ID NO 382
<211> LENGTH: 22
<212> TYPE: PRT
<213> ORGANISM: Artificial sequence
<220> FEATURE:
<223> OTHER INFORMATION: Synthetic

<400> SEQUENCE: 382

Gly Ser Met Leu Phe Lys Val Thr Ile Asn Ser Val Ser Gly Trp Arg
1               5                   10                  15

Leu Phe Lys Lys Ile Ser
            20

<210> SEQ ID NO 383
<211> LENGTH: 22
<212> TYPE: PRT
<213> ORGANISM: Artificial sequence
```

-continued

```
<220> FEATURE:
<223> OTHER INFORMATION: Synthetic

<400> SEQUENCE: 383

Gly Ser Met Leu Phe Gln Val Thr Ile Asn Ser Val Ser Gly Trp Arg
1               5                   10                  15

Leu Phe Lys Lys Ile Ser
            20

<210> SEQ ID NO 384
<211> LENGTH: 22
<212> TYPE: PRT
<213> ORGANISM: Artificial sequence
<220> FEATURE:
<223> OTHER INFORMATION: Synthetic

<400> SEQUENCE: 384

Gly Ser Met Leu Phe Glu Val Thr Ile Asn Ser Val Ser Gly Trp Arg
1               5                   10                  15

Leu Phe Lys Lys Ile Ser
            20

<210> SEQ ID NO 385
<211> LENGTH: 22
<212> TYPE: PRT
<213> ORGANISM: Artificial sequence
<220> FEATURE:
<223> OTHER INFORMATION: Synthetic

<400> SEQUENCE: 385

Gly Ser Met Leu Phe Asn Val Thr Ile Asn Ser Val Ser Gly Trp Arg
1               5                   10                  15

Leu Phe Lys Lys Ile Ser
            20

<210> SEQ ID NO 386
<211> LENGTH: 21
<212> TYPE: PRT
<213> ORGANISM: Artificial sequence
<220> FEATURE:
<223> OTHER INFORMATION: Synthetic

<400> SEQUENCE: 386

Gly Arg Pro Tyr Glu Gly Ile Ala Val Phe Asp Gly Lys Lys Ile Thr
1               5                   10                  15

Thr Thr Gly Thr Leu
            20

<210> SEQ ID NO 387
<211> LENGTH: 24
<212> TYPE: PRT
<213> ORGANISM: Artificial sequence
<220> FEATURE:
<223> OTHER INFORMATION: Synthetic

<400> SEQUENCE: 387

Gly Ser Met Lys Phe Arg Val Thr Ile Asn Ser Trp Lys Val Thr Gly
1               5                   10                  15

Tyr Arg Leu Phe Glu Lys Glu Ser
            20

<210> SEQ ID NO 388
<211> LENGTH: 24
<212> TYPE: PRT
```

<213> ORGANISM: Artificial sequence
<220> FEATURE:
<223> OTHER INFORMATION: Synthetic

<400> SEQUENCE: 388

Gly Ser Met Lys Phe Arg Val Thr Ile Asn Ser Trp Lys Val Glu Gly
1               5                   10                  15

Tyr Arg Leu Phe Glu Lys Ile Ser
            20

<210> SEQ ID NO 389
<211> LENGTH: 24
<212> TYPE: PRT
<213> ORGANISM: Artificial sequence
<220> FEATURE:
<223> OTHER INFORMATION: Synthetic

<400> SEQUENCE: 389

Lys Lys Ile Thr Thr Thr Gly Thr Leu Trp Asn Gly Asn Lys Ile Ile
1               5                   10                  15

Asp Glu Arg Leu Ile Thr Pro Asp
            20

<210> SEQ ID NO 390
<211> LENGTH: 26
<212> TYPE: PRT
<213> ORGANISM: Artificial sequence
<220> FEATURE:
<223> OTHER INFORMATION: Synthetic

<400> SEQUENCE: 390

Trp Asn Gly Asn Lys Ile Ile Asp Glu Arg Leu Ile Thr Pro Asp Gly
1               5                   10                  15

Ser Met Leu Phe Arg Val Thr Ile Asn Ser
            20                  25

<210> SEQ ID NO 391
<211> LENGTH: 13
<212> TYPE: PRT
<213> ORGANISM: Artificial sequence
<220> FEATURE:
<223> OTHER INFORMATION: Synthetic

<400> SEQUENCE: 391

Gly Lys Met Leu Phe Arg Val Thr Ile Gln Lys Trp Lys
1               5                   10

<210> SEQ ID NO 392
<211> LENGTH: 13
<212> TYPE: PRT
<213> ORGANISM: Artificial sequence
<220> FEATURE:
<223> OTHER INFORMATION: Synthetic

<400> SEQUENCE: 392

Gly Lys Met Leu Phe Arg Val Thr Ile Gly Lys Trp Lys
1               5                   10

<210> SEQ ID NO 393
<211> LENGTH: 13
<212> TYPE: PRT
<213> ORGANISM: Artificial sequence
<220> FEATURE:
<223> OTHER INFORMATION: Synthetic

<400> SEQUENCE: 393

```
Gly Lys Met Leu Phe Arg Val Thr Ile Gly Arg Trp Lys
1               5                   10

<210> SEQ ID NO 394
<211> LENGTH: 13
<212> TYPE: PRT
<213> ORGANISM: Artificial sequence
<220> FEATURE:
<223> OTHER INFORMATION: Synthetic

<400> SEQUENCE: 394

Gly Lys Met Leu Phe Arg Val Thr Ile Gly Asn Trp Lys
1               5                   10

<210> SEQ ID NO 395
<211> LENGTH: 13
<212> TYPE: PRT
<213> ORGANISM: Artificial sequence
<220> FEATURE:
<223> OTHER INFORMATION: Synthetic

<400> SEQUENCE: 395

Gly Lys Met Leu Phe Arg Val Thr Ile Gln Asn Trp Lys
1               5                   10

<210> SEQ ID NO 396
<211> LENGTH: 13
<212> TYPE: PRT
<213> ORGANISM: Artificial sequence
<220> FEATURE:
<223> OTHER INFORMATION: Synthetic

<400> SEQUENCE: 396

Gly Lys Met Leu Phe Arg Val Thr Ile Asp Lys Trp Lys
1               5                   10

<210> SEQ ID NO 397
<211> LENGTH: 13
<212> TYPE: PRT
<213> ORGANISM: Artificial sequence
<220> FEATURE:
<223> OTHER INFORMATION: Synthetic

<400> SEQUENCE: 397

Gly Lys Met Leu Phe Arg Val Thr Ile Glu Lys Trp Lys
1               5                   10

<210> SEQ ID NO 398
<211> LENGTH: 13
<212> TYPE: PRT
<213> ORGANISM: Artificial sequence
<220> FEATURE:
<223> OTHER INFORMATION: Synthetic

<400> SEQUENCE: 398

Gly Lys Met Leu Phe Arg Val Thr Ile Glu Arg Trp Lys
1               5                   10

<210> SEQ ID NO 399
<211> LENGTH: 13
<212> TYPE: PRT
<213> ORGANISM: Artificial sequence
<220> FEATURE:
<223> OTHER INFORMATION: Synthetic

<400> SEQUENCE: 399
```

```
Gly Lys Met Leu Phe Arg Val Thr Ile Asp Arg Trp Lys
1               5                   10

<210> SEQ ID NO 400
<211> LENGTH: 13
<212> TYPE: PRT
<213> ORGANISM: Artificial sequence
<220> FEATURE:
<223> OTHER INFORMATION: Synthetic

<400> SEQUENCE: 400

Asp Lys Met Leu Phe Arg Val Thr Ile Gln Lys Trp Lys
1               5                   10

<210> SEQ ID NO 401
<211> LENGTH: 13
<212> TYPE: PRT
<213> ORGANISM: Artificial sequence
<220> FEATURE:
<223> OTHER INFORMATION: Synthetic

<400> SEQUENCE: 401

Asp Lys Met Leu Phe Arg Val Thr Ile Gly Lys Trp Lys
1               5                   10

<210> SEQ ID NO 402
<211> LENGTH: 13
<212> TYPE: PRT
<213> ORGANISM: Artificial sequence
<220> FEATURE:
<223> OTHER INFORMATION: Synthetic

<400> SEQUENCE: 402

Asp Lys Met Leu Phe Arg Val Thr Ile Gly Arg Trp Lys
1               5                   10

<210> SEQ ID NO 403
<211> LENGTH: 13
<212> TYPE: PRT
<213> ORGANISM: Artificial sequence
<220> FEATURE:
<223> OTHER INFORMATION: Synthetic

<400> SEQUENCE: 403

Asp Lys Met Leu Phe Arg Val Thr Ile Gly Asn Trp Lys
1               5                   10

<210> SEQ ID NO 404
<211> LENGTH: 13
<212> TYPE: PRT
<213> ORGANISM: Artificial sequence
<220> FEATURE:
<223> OTHER INFORMATION: Synthetic

<400> SEQUENCE: 404

Asp Lys Met Leu Phe Arg Val Thr Ile Gln Asn Trp Lys
1               5                   10

<210> SEQ ID NO 405
<211> LENGTH: 13
<212> TYPE: PRT
<213> ORGANISM: Artificial sequence
<220> FEATURE:
<223> OTHER INFORMATION: Synthetic

<400> SEQUENCE: 405

Asp Lys Met Leu Phe Arg Val Thr Ile Asp Lys Trp Lys
```

```
1               5                   10
```

```
<210> SEQ ID NO 406
<211> LENGTH: 13
<212> TYPE: PRT
<213> ORGANISM: Artificial sequence
<220> FEATURE:
<223> OTHER INFORMATION: Synthetic

<400> SEQUENCE: 406

Asp Lys Met Leu Phe Arg Val Thr Ile Glu Lys Trp Lys
1               5                   10

<210> SEQ ID NO 407
<211> LENGTH: 13
<212> TYPE: PRT
<213> ORGANISM: Artificial sequence
<220> FEATURE:
<223> OTHER INFORMATION: Synthetic

<400> SEQUENCE: 407

Asp Lys Met Leu Phe Arg Val Thr Ile Glu Arg Trp Lys
1               5                   10

<210> SEQ ID NO 408
<211> LENGTH: 13
<212> TYPE: PRT
<213> ORGANISM: Artificial sequence
<220> FEATURE:
<223> OTHER INFORMATION: Synthetic

<400> SEQUENCE: 408

Asp Lys Met Leu Phe Arg Val Thr Ile Asp Arg Trp Lys
1               5                   10

<210> SEQ ID NO 409
<211> LENGTH: 35
<212> TYPE: PRT
<213> ORGANISM: Artificial sequence
<220> FEATURE:
<223> OTHER INFORMATION: Synthetic

<400> SEQUENCE: 409

Arg Pro Tyr Glu Gly Ile Ala Val Phe Asp Gly Lys Lys Ile Thr Val
1               5                   10                  15

Thr Gly Thr Leu Trp Asn Gly Asn Lys Ile Ile Asp Glu Arg Leu Ile
            20                  25                  30

Thr Pro Asp
        35

<210> SEQ ID NO 410
<211> LENGTH: 13
<212> TYPE: PRT
<213> ORGANISM: Artificial sequence
<220> FEATURE:
<223> OTHER INFORMATION: Synthetic

<400> SEQUENCE: 410

Glu Lys Met Leu Phe Arg Val Thr Ile Gln Lys Trp Lys
1               5                   10

<210> SEQ ID NO 411
<211> LENGTH: 13
<212> TYPE: PRT
<213> ORGANISM: Artificial sequence
<220> FEATURE:
```

-continued

<223> OTHER INFORMATION: Synthetic

<400> SEQUENCE: 411

Glu Lys Met Leu Phe Arg Val Thr Ile Gly Lys Trp Lys
1               5                   10

<210> SEQ ID NO 412
<211> LENGTH: 13
<212> TYPE: PRT
<213> ORGANISM: Artificial sequence
<220> FEATURE:
<223> OTHER INFORMATION: Synthetic

<400> SEQUENCE: 412

Glu Lys Met Leu Phe Arg Val Thr Ile Gly Arg Trp Lys
1               5                   10

<210> SEQ ID NO 413
<211> LENGTH: 22
<212> TYPE: PRT
<213> ORGANISM: Artificial sequence
<220> FEATURE:
<223> OTHER INFORMATION: Synthetic

<400> SEQUENCE: 413

Asp Lys Met Leu Phe Thr Val Thr Ile Gln Lys Val Ser Gly Trp Arg
1               5                   10                  15

Leu Phe Lys Lys Ile Ser
            20

<210> SEQ ID NO 414
<211> LENGTH: 22
<212> TYPE: PRT
<213> ORGANISM: Artificial sequence
<220> FEATURE:
<223> OTHER INFORMATION: Synthetic

<400> SEQUENCE: 414

Asp Lys Leu Leu Phe Thr Val Thr Ile Glu Lys Val Ser Gly Trp Arg
1               5                   10                  15

Leu Phe Lys Lys Ile Ser
            20

<210> SEQ ID NO 415
<211> LENGTH: 24
<212> TYPE: PRT
<213> ORGANISM: Artificial sequence
<220> FEATURE:
<223> OTHER INFORMATION: Synthetic

<400> SEQUENCE: 415

Asp Lys Leu Leu Phe Thr Val Thr Ile Glu Lys Trp Lys Val Ser Gly
1               5                   10                  15

Trp Arg Leu Phe Lys Lys Ile Ser
            20

<210> SEQ ID NO 416
<211> LENGTH: 24
<212> TYPE: PRT
<213> ORGANISM: Artificial sequence
<220> FEATURE:
<223> OTHER INFORMATION: Synthetic

<400> SEQUENCE: 416

Asp Lys Leu Leu Phe Thr Val Thr Ile Glu Lys Tyr Lys Val Ser Gly

-continued

```
1              5              10             15

Trp Arg Leu Phe Lys Lys Ile Ser
            20

<210> SEQ ID NO 417
<211> LENGTH: 26
<212> TYPE: PRT
<213> ORGANISM: Artificial sequence
<220> FEATURE:
<223> OTHER INFORMATION: Synthetic

<400> SEQUENCE: 417

Asp Lys Leu Leu Phe Thr Val Thr Ile Glu Lys Tyr Lys Val Ser Val
1              5              10             15

Ser Gly Trp Arg Leu Phe Lys Lys Ile Ser
            20             25

<210> SEQ ID NO 418
<211> LENGTH: 22
<212> TYPE: PRT
<213> ORGANISM: Artificial sequence
<220> FEATURE:
<223> OTHER INFORMATION: Synthetic

<400> SEQUENCE: 418

Lys Lys Met Leu Phe Arg Val Thr Ile Gln Lys Val Ser Gly Trp Arg
1              5              10             15

Leu Phe Lys Lys Ile Ser
            20

<210> SEQ ID NO 419
<211> LENGTH: 26
<212> TYPE: PRT
<213> ORGANISM: Artificial sequence
<220> FEATURE:
<223> OTHER INFORMATION: Synthetic

<400> SEQUENCE: 419

Lys Lys Met Leu Phe Arg Val Thr Ile Gln Lys Trp Lys Val Ser Val
1              5              10             15

Ser Gly Trp Arg Leu Phe Lys Lys Ile Ser
            20             25

<210> SEQ ID NO 420
<211> LENGTH: 24
<212> TYPE: PRT
<213> ORGANISM: Artificial sequence
<220> FEATURE:
<223> OTHER INFORMATION: Synthetic

<400> SEQUENCE: 420

Lys Lys Met Leu Phe Arg Val Thr Ile Gln Lys Trp Lys Val Ser Gly
1              5              10             15

Trp Arg Leu Phe Lys Lys Ile Ser
            20

<210> SEQ ID NO 421
<211> LENGTH: 22
<212> TYPE: PRT
<213> ORGANISM: Artificial sequence
<220> FEATURE:
<223> OTHER INFORMATION: Synthetic

<400> SEQUENCE: 421
```

```
Asp Lys Leu Leu Phe Thr Val Thr Ile Gly Lys Val Ser Gly Trp Arg
1               5                   10                  15

Leu Phe Lys Lys Ile Ser
            20

<210> SEQ ID NO 422
<211> LENGTH: 24
<212> TYPE: PRT
<213> ORGANISM: Artificial sequence
<220> FEATURE:
<223> OTHER INFORMATION: Synthetic

<400> SEQUENCE: 422

Asp Lys Leu Leu Phe Thr Val Thr Ile Gly Lys Tyr Lys Val Ser Gly
1               5                   10                  15

Trp Arg Leu Phe Lys Lys Ile Ser
            20

<210> SEQ ID NO 423
<211> LENGTH: 26
<212> TYPE: PRT
<213> ORGANISM: Artificial sequence
<220> FEATURE:
<223> OTHER INFORMATION: Synthetic

<400> SEQUENCE: 423

Asp Lys Leu Leu Phe Thr Val Thr Ile Gly Lys Tyr Lys Val Ser Val
1               5                   10                  15

Ser Gly Trp Arg Leu Phe Lys Lys Ile Ser
            20                  25

<210> SEQ ID NO 424
<211> LENGTH: 26
<212> TYPE: PRT
<213> ORGANISM: Artificial sequence
<220> FEATURE:
<223> OTHER INFORMATION: Synthetic

<400> SEQUENCE: 424

Asp Lys Leu Leu Phe Thr Val Thr Ile Gly Lys Trp Lys Val Ser Val
1               5                   10                  15

Ser Gly Trp Arg Leu Phe Lys Lys Ile Ser
            20                  25

<210> SEQ ID NO 425
<211> LENGTH: 22
<212> TYPE: PRT
<213> ORGANISM: Artificial sequence
<220> FEATURE:
<223> OTHER INFORMATION: Synthetic

<400> SEQUENCE: 425

Asp Lys Leu Leu Phe Thr Val Thr Ile Gln Lys Val Ser Gly Trp Arg
1               5                   10                  15

Leu Phe Lys Lys Ile Ser
            20

<210> SEQ ID NO 426
<211> LENGTH: 22
<212> TYPE: PRT
<213> ORGANISM: Artificial sequence
<220> FEATURE:
<223> OTHER INFORMATION: Synthetic

<400> SEQUENCE: 426
```

```
Lys Lys Met Leu Phe Thr Val Thr Ile Gln Lys Val Ser Gly Trp Arg
1               5                   10                  15

Leu Phe Lys Lys Ile Ser
          20

<210> SEQ ID NO 427
<211> LENGTH: 22
<212> TYPE: PRT
<213> ORGANISM: Artificial sequence
<220> FEATURE:
<223> OTHER INFORMATION: Synthetic

<400> SEQUENCE: 427

Lys Lys Leu Leu Phe Arg Val Thr Ile Gln Lys Val Ser Gly Trp Arg
1               5                   10                  15

Leu Phe Lys Lys Ile Ser
          20

<210> SEQ ID NO 428
<211> LENGTH: 21
<212> TYPE: PRT
<213> ORGANISM: Artificial sequence
<220> FEATURE:
<223> OTHER INFORMATION: Synthetic

<400> SEQUENCE: 428

Asp Lys Leu Leu Phe Thr Val Thr Ile Glu Lys Val Ser Gly Trp Arg
1               5                   10                  15

Leu Phe Lys Lys Ile
          20

<210> SEQ ID NO 429
<211> LENGTH: 25
<212> TYPE: PRT
<213> ORGANISM: Artificial sequence
<220> FEATURE:
<223> OTHER INFORMATION: Synthetic

<400> SEQUENCE: 429

Asp Lys Leu Leu Phe Thr Val Thr Ile Glu Lys Tyr Lys Val Ser Val
1               5                   10                  15

Ser Gly Trp Arg Leu Phe Lys Lys Ile
          20                  25

<210> SEQ ID NO 430
<211> LENGTH: 22
<212> TYPE: PRT
<213> ORGANISM: Artificial sequence
<220> FEATURE:
<223> OTHER INFORMATION: Synthetic

<400> SEQUENCE: 430

Asp Arg Leu Leu Phe Thr Val Thr Ile Glu Arg Val Ser Gly Trp Arg
1               5                   10                  15

Leu Phe Lys Lys Ile Ser
          20

<210> SEQ ID NO 431
<211> LENGTH: 22
<212> TYPE: PRT
<213> ORGANISM: Artificial sequence
<220> FEATURE:
<223> OTHER INFORMATION: Synthetic
```

-continued

```
<400> SEQUENCE: 431

Glu Lys Leu Leu Phe Thr Val Thr Ile Glu Lys Val Ser Gly Trp Arg
1               5                   10                  15

Leu Phe Lys Lys Ile Ser
            20

<210> SEQ ID NO 432
<211> LENGTH: 22
<212> TYPE: PRT
<213> ORGANISM: Artificial sequence
<220> FEATURE:
<223> OTHER INFORMATION: Synthetic

<400> SEQUENCE: 432

Lys Lys Leu Leu Phe Thr Val Thr Ile Gly Lys Val Ser Gly Trp Arg
1               5                   10                  15

Leu Phe Lys Lys Ile Ser
            20

<210> SEQ ID NO 433
<211> LENGTH: 24
<212> TYPE: PRT
<213> ORGANISM: Artificial sequence
<220> FEATURE:
<223> OTHER INFORMATION: Synthetic

<400> SEQUENCE: 433

Gly Ser Met Arg Phe Arg Val Thr Ile Asn Ser Trp Arg Val Thr Gly
1               5                   10                  15

Tyr Arg Leu Phe Glu Arg Glu Ser
            20

<210> SEQ ID NO 434
<211> LENGTH: 22
<212> TYPE: PRT
<213> ORGANISM: Artificial sequence
<220> FEATURE:
<223> OTHER INFORMATION: Synthetic

<400> SEQUENCE: 434

Gly Ser Met Lys Phe Arg Val Thr Ile Asn Ser Val Thr Gly Tyr Arg
1               5                   10                  15

Leu Phe Glu Lys Glu Ser
            20

<210> SEQ ID NO 435
<211> LENGTH: 17
<212> TYPE: PRT
<213> ORGANISM: Artificial sequence
<220> FEATURE:
<223> OTHER INFORMATION: Synthetic

<400> SEQUENCE: 435

Lys Lys Ile Thr Thr Thr Gly Thr Leu Trp Asn Gly Asn Lys Ile Ile
1               5                   10                  15

Asp

<210> SEQ ID NO 436
<211> LENGTH: 29
<212> TYPE: PRT
<213> ORGANISM: Artificial sequence
<220> FEATURE:
<223> OTHER INFORMATION: Synthetic
```

<400> SEQUENCE: 436

Glu Arg Leu Ile Thr Pro Asp Gly Ser Met Leu Phe Arg Val Thr Ile
1               5                   10                  15

Asn Ser Val Ser Gly Trp Arg Leu Phe Lys Lys Ile Ser
            20                  25

<210> SEQ ID NO 437
<211> LENGTH: 58
<212> TYPE: PRT
<213> ORGANISM: Artificial sequence
<220> FEATURE:
<223> OTHER INFORMATION: Synthetic

<400> SEQUENCE: 437

Gly Arg Pro Tyr Glu Gly Ile Ala Val Asp Phe Gly Lys Lys Ile Thr
1               5                   10                  15

Thr Thr Gly Thr Leu Trp Asn Gly Asn Lys Ile Ile Asp Glu Arg Leu
            20                  25                  30

Ile Thr Pro Asp Gly Ser Met Leu Phe Arg Val Thr Ile Asn Ser Val
        35                  40                  45

Ser Gly Trp Arg Leu Phe Lys Lys Ile Ser
    50                  55

<210> SEQ ID NO 438
<211> LENGTH: 68
<212> TYPE: PRT
<213> ORGANISM: Artificial sequence
<220> FEATURE:
<223> OTHER INFORMATION: Synthetic

<400> SEQUENCE: 438

Gly Val Thr Pro Asn Lys Leu Asn Tyr Phe Gly Arg Pro Tyr Glu Gly
1               5                   10                  15

Ile Ala Val Asp Phe Gly Lys Lys Ile Thr Thr Thr Gly Thr Leu Trp
            20                  25                  30

Asn Gly Asn Lys Ile Ile Asp Glu Arg Leu Ile Thr Pro Asp Gly Ser
        35                  40                  45

Met Leu Phe Arg Val Thr Ile Asn Ser Val Ser Gly Trp Arg Leu Phe
    50                  55                  60

Lys Lys Ile Ser
65

<210> SEQ ID NO 439
<211> LENGTH: 13
<212> TYPE: PRT
<213> ORGANISM: Artificial sequence
<220> FEATURE:
<223> OTHER INFORMATION: Synthetic

<400> SEQUENCE: 439

Glu Lys Met Leu Phe Arg Val Thr Ile Gly Asn Trp Lys
1               5                   10

<210> SEQ ID NO 440
<211> LENGTH: 13
<212> TYPE: PRT
<213> ORGANISM: Artificial sequence
<220> FEATURE:
<223> OTHER INFORMATION: Synthetic

<400> SEQUENCE: 440

Glu Lys Met Leu Phe Arg Val Thr Ile Gln Asn Trp Lys

-continued

```
1               5               10

<210> SEQ ID NO 441
<211> LENGTH: 13
<212> TYPE: PRT
<213> ORGANISM: Artificial sequence
<220> FEATURE:
<223> OTHER INFORMATION: Synthetic

<400> SEQUENCE: 441

Glu Lys Met Leu Phe Arg Val Thr Ile Asp Lys Trp Lys
1               5               10

<210> SEQ ID NO 442
<211> LENGTH: 13
<212> TYPE: PRT
<213> ORGANISM: Artificial sequence
<220> FEATURE:
<223> OTHER INFORMATION: Synthetic

<400> SEQUENCE: 442

Glu Lys Met Leu Phe Arg Val Thr Ile Glu Lys Trp Lys
1               5               10

<210> SEQ ID NO 443
<211> LENGTH: 13
<212> TYPE: PRT
<213> ORGANISM: Artificial sequence
<220> FEATURE:
<223> OTHER INFORMATION: Synthetic

<400> SEQUENCE: 443

Glu Lys Met Leu Phe Arg Val Thr Ile Glu Arg Trp Lys
1               5               10

<210> SEQ ID NO 444
<211> LENGTH: 13
<212> TYPE: PRT
<213> ORGANISM: Artificial sequence
<220> FEATURE:
<223> OTHER INFORMATION: Synthetic

<400> SEQUENCE: 444

Glu Lys Met Leu Phe Arg Val Thr Ile Asp Arg Trp Lys
1               5               10

<210> SEQ ID NO 445
<211> LENGTH: 13
<212> TYPE: PRT
<213> ORGANISM: Artificial sequence
<220> FEATURE:
<223> OTHER INFORMATION: Synthetic

<400> SEQUENCE: 445

Lys Lys Met Leu Phe Arg Val Thr Ile Gln Lys Trp Lys
1               5               10

<210> SEQ ID NO 446
<211> LENGTH: 13
<212> TYPE: PRT
<213> ORGANISM: Artificial sequence
<220> FEATURE:
<223> OTHER INFORMATION: Synthetic

<400> SEQUENCE: 446

Lys Lys Met Leu Phe Arg Val Thr Ile Gly Lys Trp Lys
1               5               10
```

```
<210> SEQ ID NO 447
<211> LENGTH: 13
<212> TYPE: PRT
<213> ORGANISM: Artificial sequence
<220> FEATURE:
<223> OTHER INFORMATION: Synthetic

<400> SEQUENCE: 447

Lys Lys Met Leu Phe Arg Val Thr Ile Gly Arg Trp Lys
1               5                   10

<210> SEQ ID NO 448
<211> LENGTH: 13
<212> TYPE: PRT
<213> ORGANISM: Artificial sequence
<220> FEATURE:
<223> OTHER INFORMATION: Synthetic

<400> SEQUENCE: 448

Lys Lys Met Leu Phe Arg Val Thr Ile Gly Asn Trp Lys
1               5                   10

<210> SEQ ID NO 449
<211> LENGTH: 13
<212> TYPE: PRT
<213> ORGANISM: Artificial sequence
<220> FEATURE:
<223> OTHER INFORMATION: Synthetic

<400> SEQUENCE: 449

Lys Lys Met Leu Phe Arg Val Thr Ile Gln Asn Trp Lys
1               5                   10

<210> SEQ ID NO 450
<211> LENGTH: 13
<212> TYPE: PRT
<213> ORGANISM: Artificial sequence
<220> FEATURE:
<223> OTHER INFORMATION: Synthetic

<400> SEQUENCE: 450

Lys Lys Met Leu Phe Arg Val Thr Ile Asp Lys Trp Lys
1               5                   10

<210> SEQ ID NO 451
<211> LENGTH: 13
<212> TYPE: PRT
<213> ORGANISM: Artificial sequence
<220> FEATURE:
<223> OTHER INFORMATION: Synthetic

<400> SEQUENCE: 451

Lys Lys Met Leu Phe Arg Val Thr Ile Glu Lys Trp Lys
1               5                   10

<210> SEQ ID NO 452
<211> LENGTH: 13
<212> TYPE: PRT
<213> ORGANISM: Artificial sequence
<220> FEATURE:
<223> OTHER INFORMATION: Synthetic

<400> SEQUENCE: 452

Lys Lys Met Leu Phe Arg Val Thr Ile Glu Arg Trp Lys
1               5                   10
```

-continued

```
<210> SEQ ID NO 453
<211> LENGTH: 13
<212> TYPE: PRT
<213> ORGANISM: Artificial sequence
<220> FEATURE:
<223> OTHER INFORMATION: Synthetic

<400> SEQUENCE: 453

Lys Lys Met Leu Phe Arg Val Thr Ile Asp Arg Trp Lys
1               5                   10

<210> SEQ ID NO 454
<211> LENGTH: 13
<212> TYPE: PRT
<213> ORGANISM: Artificial sequence
<220> FEATURE:
<223> OTHER INFORMATION: Synthetic

<400> SEQUENCE: 454

Arg Lys Met Leu Phe Arg Val Thr Ile Gln Lys Trp Lys
1               5                   10

<210> SEQ ID NO 455
<211> LENGTH: 13
<212> TYPE: PRT
<213> ORGANISM: Artificial sequence
<220> FEATURE:
<223> OTHER INFORMATION: Synthetic

<400> SEQUENCE: 455

Arg Lys Met Leu Phe Arg Val Thr Ile Gly Lys Trp Lys
1               5                   10

<210> SEQ ID NO 456
<211> LENGTH: 13
<212> TYPE: PRT
<213> ORGANISM: Artificial sequence
<220> FEATURE:
<223> OTHER INFORMATION: Synthetic

<400> SEQUENCE: 456

Arg Lys Met Leu Phe Arg Val Thr Ile Gly Arg Trp Lys
1               5                   10

<210> SEQ ID NO 457
<211> LENGTH: 13
<212> TYPE: PRT
<213> ORGANISM: Artificial sequence
<220> FEATURE:
<223> OTHER INFORMATION: Synthetic

<400> SEQUENCE: 457

Arg Lys Met Leu Phe Arg Val Thr Ile Gly Asn Trp Lys
1               5                   10

<210> SEQ ID NO 458
<211> LENGTH: 13
<212> TYPE: PRT
<213> ORGANISM: Artificial sequence
<220> FEATURE:
<223> OTHER INFORMATION: Synthetic

<400> SEQUENCE: 458

Arg Lys Met Leu Phe Arg Val Thr Ile Gln Asn Trp Lys
1               5                   10
```

<210> SEQ ID NO 459
<211> LENGTH: 13
<212> TYPE: PRT
<213> ORGANISM: Artificial sequence
<220> FEATURE:
<223> OTHER INFORMATION: Synthetic

<400> SEQUENCE: 459

Arg Lys Met Leu Phe Arg Val Thr Ile Asp Lys Trp Lys
1               5                   10

<210> SEQ ID NO 460
<211> LENGTH: 13
<212> TYPE: PRT
<213> ORGANISM: Artificial sequence
<220> FEATURE:
<223> OTHER INFORMATION: Synthetic

<400> SEQUENCE: 460

Arg Lys Met Leu Phe Arg Val Thr Ile Glu Lys Trp Lys
1               5                   10

<210> SEQ ID NO 461
<211> LENGTH: 13
<212> TYPE: PRT
<213> ORGANISM: Artificial sequence
<220> FEATURE:
<223> OTHER INFORMATION: Synthetic

<400> SEQUENCE: 461

Arg Lys Met Leu Phe Arg Val Thr Ile Glu Arg Trp Lys
1               5                   10

<210> SEQ ID NO 462
<211> LENGTH: 13
<212> TYPE: PRT
<213> ORGANISM: Artificial sequence
<220> FEATURE:
<223> OTHER INFORMATION: Synthetic

<400> SEQUENCE: 462

Arg Lys Met Leu Phe Arg Val Thr Ile Asp Arg Trp Lys
1               5                   10

<210> SEQ ID NO 463
<211> LENGTH: 13
<212> TYPE: PRT
<213> ORGANISM: Artificial sequence
<220> FEATURE:
<223> OTHER INFORMATION: Synthetic

<400> SEQUENCE: 463

Glu Gln Met Leu Phe Arg Val Thr Ile Asn Ser Trp Lys
1               5                   10

<210> SEQ ID NO 464
<211> LENGTH: 13
<212> TYPE: PRT
<213> ORGANISM: Artificial sequence
<220> FEATURE:
<223> OTHER INFORMATION: Synthetic

<400> SEQUENCE: 464

Ser Arg Met Leu Phe Arg Val Thr Ile Asn Ser Trp Lys
1               5                   10

<210> SEQ ID NO 465

```
<211> LENGTH: 13
<212> TYPE: PRT
<213> ORGANISM: Artificial sequence
<220> FEATURE:
<223> OTHER INFORMATION: Synthetic

<400> SEQUENCE: 465

Gly Glu Met Leu Phe Arg Val Thr Ile Asn Ser Trp Lys
1               5                   10

<210> SEQ ID NO 466
<211> LENGTH: 13
<212> TYPE: PRT
<213> ORGANISM: Artificial sequence
<220> FEATURE:
<223> OTHER INFORMATION: Synthetic

<400> SEQUENCE: 466

Gly Lys Met Lys Phe Arg Val Thr Ile Asn Ser Trp Lys
1               5                   10

<210> SEQ ID NO 467
<211> LENGTH: 13
<212> TYPE: PRT
<213> ORGANISM: Artificial sequence
<220> FEATURE:
<223> OTHER INFORMATION: Synthetic

<400> SEQUENCE: 467

Gly Lys Met Leu Phe Arg Val Lys Ile Asn Ser Trp Lys
1               5                   10

<210> SEQ ID NO 468
<211> LENGTH: 13
<212> TYPE: PRT
<213> ORGANISM: Artificial sequence
<220> FEATURE:
<223> OTHER INFORMATION: Synthetic

<400> SEQUENCE: 468

Gly Lys Met Leu Phe Arg Val Arg Ile Asn Ser Trp Lys
1               5                   10

<210> SEQ ID NO 469
<211> LENGTH: 13
<212> TYPE: PRT
<213> ORGANISM: Artificial sequence
<220> FEATURE:
<223> OTHER INFORMATION: Synthetic

<400> SEQUENCE: 469

Gly Lys Met Leu Phe Arg Val Asp Ile Asn Ser Trp Lys
1               5                   10

<210> SEQ ID NO 470
<211> LENGTH: 13
<212> TYPE: PRT
<213> ORGANISM: Artificial sequence
<220> FEATURE:
<223> OTHER INFORMATION: Synthetic

<400> SEQUENCE: 470

Gly Lys Met Leu Phe Arg Val Thr Ile Asp Ser Trp Lys
1               5                   10

<210> SEQ ID NO 471
<211> LENGTH: 13
```

```
<212> TYPE: PRT
<213> ORGANISM: Artificial sequence
<220> FEATURE:
<223> OTHER INFORMATION: Synthetic

<400> SEQUENCE: 471

Gly Lys Met Leu Phe Arg Val Thr Ile Asn Lys Trp Lys
1               5                   10

<210> SEQ ID NO 472
<211> LENGTH: 13
<212> TYPE: PRT
<213> ORGANISM: Artificial sequence
<220> FEATURE:
<223> OTHER INFORMATION: Synthetic

<400> SEQUENCE: 472

Glu Lys Met Leu Phe Lys Val Thr Ile Gln Lys Trp Lys
1               5                   10

<210> SEQ ID NO 473
<211> LENGTH: 13
<212> TYPE: PRT
<213> ORGANISM: Artificial sequence
<220> FEATURE:
<223> OTHER INFORMATION: Synthetic

<400> SEQUENCE: 473

Glu Lys Met Leu Phe Thr Val Thr Ile Gln Lys Trp Lys
1               5                   10

<210> SEQ ID NO 474
<211> LENGTH: 13
<212> TYPE: PRT
<213> ORGANISM: Artificial sequence
<220> FEATURE:
<223> OTHER INFORMATION: Synthetic

<400> SEQUENCE: 474

Glu Lys Met Leu Phe Lys Val Thr Ile Asp Lys Trp Lys
1               5                   10

<210> SEQ ID NO 475
<211> LENGTH: 13
<212> TYPE: PRT
<213> ORGANISM: Artificial sequence
<220> FEATURE:
<223> OTHER INFORMATION: Synthetic

<400> SEQUENCE: 475

Glu Lys Met Leu Phe Thr Val Thr Ile Asp Lys Trp Lys
1               5                   10

<210> SEQ ID NO 476
<211> LENGTH: 13
<212> TYPE: PRT
<213> ORGANISM: Artificial sequence
<220> FEATURE:
<223> OTHER INFORMATION: Synthetic

<400> SEQUENCE: 476

Glu Lys Met Leu Phe Lys Val Thr Ile Gly Arg Trp Lys
1               5                   10

<210> SEQ ID NO 477
<211> LENGTH: 13
<212> TYPE: PRT
```

-continued

```
<213> ORGANISM: Artificial sequence
<220> FEATURE:
<223> OTHER INFORMATION: Synthetic

<400> SEQUENCE: 477

Asp Lys Met Leu Phe Lys Val Thr Ile Gln Lys Trp Lys
1               5                   10

<210> SEQ ID NO 478
<211> LENGTH: 13
<212> TYPE: PRT
<213> ORGANISM: Artificial sequence
<220> FEATURE:
<223> OTHER INFORMATION: Synthetic

<400> SEQUENCE: 478

Asp Lys Met Leu Phe Thr Val Thr Ile Gln Lys Trp Lys
1               5                   10

<210> SEQ ID NO 479
<211> LENGTH: 13
<212> TYPE: PRT
<213> ORGANISM: Artificial sequence
<220> FEATURE:
<223> OTHER INFORMATION: Synthetic

<400> SEQUENCE: 479

Asp Lys Met Leu Phe Lys Val Thr Ile Asp Lys Trp Lys
1               5                   10

<210> SEQ ID NO 480
<211> LENGTH: 13
<212> TYPE: PRT
<213> ORGANISM: Artificial sequence
<220> FEATURE:
<223> OTHER INFORMATION: Synthetic

<400> SEQUENCE: 480

Asp Lys Met Leu Phe Thr Val Thr Ile Asp Lys Trp Lys
1               5                   10

<210> SEQ ID NO 481
<211> LENGTH: 13
<212> TYPE: PRT
<213> ORGANISM: Artificial sequence
<220> FEATURE:
<223> OTHER INFORMATION: Synthetic

<400> SEQUENCE: 481

Gly Lys Met Leu Phe Lys Val Thr Ile Glu Lys Trp Lys
1               5                   10

<210> SEQ ID NO 482
<211> LENGTH: 13
<212> TYPE: PRT
<213> ORGANISM: Artificial sequence
<220> FEATURE:
<223> OTHER INFORMATION: Synthetic

<400> SEQUENCE: 482

Gly Lys Met Leu Phe Thr Val Thr Ile Glu Lys Trp Lys
1               5                   10

<210> SEQ ID NO 483
<211> LENGTH: 13
<212> TYPE: PRT
<213> ORGANISM: Artificial sequence
```

-continued

```
<220> FEATURE:
<223> OTHER INFORMATION: Synthetic

<400> SEQUENCE: 483

Asp Lys Met Leu Phe Lys Val Thr Ile Gly Lys Trp Lys
1               5                   10

<210> SEQ ID NO 484
<211> LENGTH: 13
<212> TYPE: PRT
<213> ORGANISM: Artificial sequence
<220> FEATURE:
<223> OTHER INFORMATION: Synthetic

<400> SEQUENCE: 484

Asp Lys Met Leu Phe Thr Val Thr Ile Gly Lys Trp Lys
1               5                   10

<210> SEQ ID NO 485
<211> LENGTH: 13
<212> TYPE: PRT
<213> ORGANISM: Artificial sequence
<220> FEATURE:
<223> OTHER INFORMATION: Synthetic

<400> SEQUENCE: 485

Asp Lys Met Leu Phe Lys Val Thr Ile Gly Asn Trp Lys
1               5                   10

<210> SEQ ID NO 486
<211> LENGTH: 13
<212> TYPE: PRT
<213> ORGANISM: Artificial sequence
<220> FEATURE:
<223> OTHER INFORMATION: Synthetic

<400> SEQUENCE: 486

Asp Lys Met Leu Phe Lys Val Thr Ile Gln Asn Trp Lys
1               5                   10

<210> SEQ ID NO 487
<211> LENGTH: 13
<212> TYPE: PRT
<213> ORGANISM: Artificial sequence
<220> FEATURE:
<223> OTHER INFORMATION: Synthetic

<400> SEQUENCE: 487

Gly Lys Met Leu Phe Lys Val Thr Ile Asn Lys Trp Lys
1               5                   10

<210> SEQ ID NO 488
<211> LENGTH: 13
<212> TYPE: PRT
<213> ORGANISM: Artificial sequence
<220> FEATURE:
<223> OTHER INFORMATION: Synthetic

<400> SEQUENCE: 488

Gly Lys Met Leu Phe Thr Val Thr Ile Asn Lys Trp Lys
1               5                   10

<210> SEQ ID NO 489
<211> LENGTH: 13
<212> TYPE: PRT
<213> ORGANISM: Artificial sequence
<220> FEATURE:
```

-continued

```
<223> OTHER INFORMATION: Synthetic

<400> SEQUENCE: 489

Asp Lys Met Leu Phe Lys Val Thr Ile Glu Lys Trp Lys
1               5                   10

<210> SEQ ID NO 490
<211> LENGTH: 13
<212> TYPE: PRT
<213> ORGANISM: Artificial sequence
<220> FEATURE:
<223> OTHER INFORMATION: Synthetic

<400> SEQUENCE: 490

Asp Lys Met Leu Phe Thr Val Thr Ile Glu Lys Trp Lys
1               5                   10

<210> SEQ ID NO 491
<211> LENGTH: 13
<212> TYPE: PRT
<213> ORGANISM: Artificial sequence
<220> FEATURE:
<223> OTHER INFORMATION: Synthetic

<400> SEQUENCE: 491

Asp Lys Leu Leu Phe Lys Val Thr Ile Gly Lys Trp Lys
1               5                   10

<210> SEQ ID NO 492
<211> LENGTH: 13
<212> TYPE: PRT
<213> ORGANISM: Artificial sequence
<220> FEATURE:
<223> OTHER INFORMATION: Synthetic

<400> SEQUENCE: 492

Asp Lys Met Leu Phe Thr Val Thr Ile Asn Lys Trp Lys
1               5                   10

<210> SEQ ID NO 493
<211> LENGTH: 13
<212> TYPE: PRT
<213> ORGANISM: Artificial sequence
<220> FEATURE:
<223> OTHER INFORMATION: Synthetic

<400> SEQUENCE: 493

Asp Lys Leu Leu Phe Thr Val Thr Ile Gln Lys Trp Lys
1               5                   10

<210> SEQ ID NO 494
<211> LENGTH: 13
<212> TYPE: PRT
<213> ORGANISM: Artificial sequence
<220> FEATURE:
<223> OTHER INFORMATION: Synthetic

<400> SEQUENCE: 494

Asp Lys Leu Leu Phe Thr Val Thr Ile Gln Lys Tyr Lys
1               5                   10

<210> SEQ ID NO 495
<211> LENGTH: 13
<212> TYPE: PRT
<213> ORGANISM: Artificial sequence
<220> FEATURE:
<223> OTHER INFORMATION: Synthetic
```

<400> SEQUENCE: 495

Asp Lys Leu Leu Phe Thr Val Thr Ile Glu Lys Trp Lys
1               5                   10

<210> SEQ ID NO 496
<211> LENGTH: 13
<212> TYPE: PRT
<213> ORGANISM: Artificial sequence
<220> FEATURE:
<223> OTHER INFORMATION: Synthetic

<400> SEQUENCE: 496

Asp Lys Leu Leu Phe Thr Val Thr Ile Glu Lys Tyr Lys
1               5                   10

<210> SEQ ID NO 497
<211> LENGTH: 13
<212> TYPE: PRT
<213> ORGANISM: Artificial sequence
<220> FEATURE:
<223> OTHER INFORMATION: Synthetic

<400> SEQUENCE: 497

Asp Lys Leu Leu Phe Thr Val Thr Ile Gly Lys Trp Lys
1               5                   10

<210> SEQ ID NO 498
<211> LENGTH: 13
<212> TYPE: PRT
<213> ORGANISM: Artificial sequence
<220> FEATURE:
<223> OTHER INFORMATION: Synthetic

<400> SEQUENCE: 498

Asp Lys Leu Leu Phe Thr Val Thr Ile Gly Lys Tyr Lys
1               5                   10

<210> SEQ ID NO 499
<211> LENGTH: 13
<212> TYPE: PRT
<213> ORGANISM: Artificial sequence
<220> FEATURE:
<223> OTHER INFORMATION: Synthetic

<400> SEQUENCE: 499

Asp Lys Leu Leu Phe Thr Val Thr Ile Asn Lys Trp Lys
1               5                   10

<210> SEQ ID NO 500
<211> LENGTH: 13
<212> TYPE: PRT
<213> ORGANISM: Artificial sequence
<220> FEATURE:
<223> OTHER INFORMATION: Synthetic

<400> SEQUENCE: 500

Asp Lys Leu Leu Phe Thr Val Thr Ile Asn Lys Tyr Lys
1               5                   10

<210> SEQ ID NO 501
<211> LENGTH: 11
<212> TYPE: PRT
<213> ORGANISM: Artificial sequence
<220> FEATURE:
<223> OTHER INFORMATION: Synthetic

```
<400> SEQUENCE: 501

Gly Lys Met Leu Phe Arg Val Thr Ile Asn Ser
1               5                   10

<210> SEQ ID NO 502
<211> LENGTH: 11
<212> TYPE: PRT
<213> ORGANISM: Artificial sequence
<220> FEATURE:
<223> OTHER INFORMATION: Synthetic

<400> SEQUENCE: 502

Asp Lys Met Leu Phe Thr Val Thr Ile Gln Lys
1               5                   10

<210> SEQ ID NO 503
<211> LENGTH: 11
<212> TYPE: PRT
<213> ORGANISM: Artificial sequence
<220> FEATURE:
<223> OTHER INFORMATION: Synthetic

<400> SEQUENCE: 503

Asp Lys Met Leu Phe Lys Val Thr Ile Gln Lys
1               5                   10

<210> SEQ ID NO 504
<211> LENGTH: 11
<212> TYPE: PRT
<213> ORGANISM: Artificial sequence
<220> FEATURE:
<223> OTHER INFORMATION: Synthetic

<400> SEQUENCE: 504

Asp Lys Leu Leu Phe Thr Val Thr Ile Gly Lys
1               5                   10

<210> SEQ ID NO 505
<211> LENGTH: 11
<212> TYPE: PRT
<213> ORGANISM: Artificial sequence
<220> FEATURE:
<223> OTHER INFORMATION: Synthetic

<400> SEQUENCE: 505

Asp Lys Met Leu Phe Thr Val Thr Ile Gly Lys
1               5                   10

<210> SEQ ID NO 506
<211> LENGTH: 11
<212> TYPE: PRT
<213> ORGANISM: Artificial sequence
<220> FEATURE:
<223> OTHER INFORMATION: Synthetic

<400> SEQUENCE: 506

Asp Lys Met Leu Phe Thr Val Thr Ile Glu Lys
1               5                   10

<210> SEQ ID NO 507
<211> LENGTH: 11
<212> TYPE: PRT
<213> ORGANISM: Artificial sequence
<220> FEATURE:
<223> OTHER INFORMATION: Synthetic

<400> SEQUENCE: 507
```

```
Asp Lys Leu Leu Phe Thr Val Thr Ile Glu Lys
1               5                   10

<210> SEQ ID NO 508
<211> LENGTH: 13
<212> TYPE: PRT
<213> ORGANISM: Artificial sequence
<220> FEATURE:
<223> OTHER INFORMATION: Synthetic

<400> SEQUENCE: 508

Asp Lys Met Leu Phe Arg Val Thr Ile Asn Ser Trp Lys
1               5                   10

<210> SEQ ID NO 509
<211> LENGTH: 13
<212> TYPE: PRT
<213> ORGANISM: Artificial sequence
<220> FEATURE:
<223> OTHER INFORMATION: Synthetic

<400> SEQUENCE: 509

Glu Lys Met Leu Phe Arg Val Thr Ile Asn Ser Trp Lys
1               5                   10

<210> SEQ ID NO 510
<211> LENGTH: 13
<212> TYPE: PRT
<213> ORGANISM: Artificial sequence
<220> FEATURE:
<223> OTHER INFORMATION: Synthetic

<400> SEQUENCE: 510

Arg Lys Met Leu Phe Arg Val Thr Ile Asn Ser Trp Lys
1               5                   10

<210> SEQ ID NO 511
<211> LENGTH: 13
<212> TYPE: PRT
<213> ORGANISM: Artificial sequence
<220> FEATURE:
<223> OTHER INFORMATION: Synthetic

<400> SEQUENCE: 511

Lys Lys Met Leu Phe Arg Val Thr Ile Asn Ser Trp Lys
1               5                   10

<210> SEQ ID NO 512
<211> LENGTH: 13
<212> TYPE: PRT
<213> ORGANISM: Artificial sequence
<220> FEATURE:
<223> OTHER INFORMATION: Synthetic

<400> SEQUENCE: 512

His Lys Met Leu Phe Arg Val Thr Ile Asn Ser Trp Lys
1               5                   10

<210> SEQ ID NO 513
<211> LENGTH: 13
<212> TYPE: PRT
<213> ORGANISM: Artificial sequence
<220> FEATURE:
<223> OTHER INFORMATION: Synthetic

<400> SEQUENCE: 513
```

-continued

```
Gly Leu Met Leu Phe Arg Val Thr Ile Asn Ser Trp Lys
1               5                   10

<210> SEQ ID NO 514
<211> LENGTH: 13
<212> TYPE: PRT
<213> ORGANISM: Artificial sequence
<220> FEATURE:
<223> OTHER INFORMATION: Synthetic

<400> SEQUENCE: 514

Gly Gln Met Leu Phe Arg Val Thr Ile Asn Ser Trp Lys
1               5                   10

<210> SEQ ID NO 515
<211> LENGTH: 13
<212> TYPE: PRT
<213> ORGANISM: Artificial sequence
<220> FEATURE:
<223> OTHER INFORMATION: Synthetic

<400> SEQUENCE: 515

Gly Thr Met Leu Phe Arg Val Thr Ile Asn Ser Trp Lys
1               5                   10

<210> SEQ ID NO 516
<211> LENGTH: 13
<212> TYPE: PRT
<213> ORGANISM: Artificial sequence
<220> FEATURE:
<223> OTHER INFORMATION: Synthetic

<400> SEQUENCE: 516

Gly Lys Leu Leu Phe Arg Val Thr Ile Asn Ser Trp Lys
1               5                   10

<210> SEQ ID NO 517
<211> LENGTH: 13
<212> TYPE: PRT
<213> ORGANISM: Artificial sequence
<220> FEATURE:
<223> OTHER INFORMATION: Synthetic

<400> SEQUENCE: 517

Gly Lys Met Leu Phe Lys Val Thr Ile Asn Ser Trp Lys
1               5                   10

<210> SEQ ID NO 518
<211> LENGTH: 13
<212> TYPE: PRT
<213> ORGANISM: Artificial sequence
<220> FEATURE:
<223> OTHER INFORMATION: Synthetic

<400> SEQUENCE: 518

Gly Lys Met Leu Phe Arg Val Thr Ile Gln Ser Trp Lys
1               5                   10

<210> SEQ ID NO 519
<211> LENGTH: 13
<212> TYPE: PRT
<213> ORGANISM: Artificial sequence
<220> FEATURE:
<223> OTHER INFORMATION: Synthetic

<400> SEQUENCE: 519

Gly Lys Met Leu Phe Arg Val Thr Ile Asp Ser Trp Lys
```

-continued

```
1               5                   10

<210> SEQ ID NO 520
<211> LENGTH: 13
<212> TYPE: PRT
<213> ORGANISM: Artificial sequence
<220> FEATURE:
<223> OTHER INFORMATION: Synthetic

<400> SEQUENCE: 520

Gly Lys Met Leu Phe Arg Val Thr Ile Gly Ser Trp Lys
1               5                   10

<210> SEQ ID NO 521
<211> LENGTH: 13
<212> TYPE: PRT
<213> ORGANISM: Artificial sequence
<220> FEATURE:
<223> OTHER INFORMATION: Synthetic

<400> SEQUENCE: 521

Gly Lys Met Leu Phe Arg Val Thr Ile Asn Thr Trp Lys
1               5                   10

<210> SEQ ID NO 522
<211> LENGTH: 13
<212> TYPE: PRT
<213> ORGANISM: Artificial sequence
<220> FEATURE:
<223> OTHER INFORMATION: Synthetic

<400> SEQUENCE: 522

Gly Lys Met Leu Phe Arg Val Thr Ile Asn Asn Trp Lys
1               5                   10

<210> SEQ ID NO 523
<211> LENGTH: 13
<212> TYPE: PRT
<213> ORGANISM: Artificial sequence
<220> FEATURE:
<223> OTHER INFORMATION: Synthetic

<400> SEQUENCE: 523

Gly Lys Met Leu Phe Arg Val Thr Ile Asn Gln Trp Lys
1               5                   10

<210> SEQ ID NO 524
<211> LENGTH: 13
<212> TYPE: PRT
<213> ORGANISM: Artificial sequence
<220> FEATURE:
<223> OTHER INFORMATION: Synthetic

<400> SEQUENCE: 524

Gly Lys Met Leu Phe Arg Val Thr Ile Asn Pro Trp Lys
1               5                   10

<210> SEQ ID NO 525
<211> LENGTH: 13
<212> TYPE: PRT
<213> ORGANISM: Artificial sequence
<220> FEATURE:
<223> OTHER INFORMATION: Synthetic

<400> SEQUENCE: 525

Gly Lys Met Leu Phe Arg Val Thr Ile Asn Lys Trp Lys
1               5                   10
```

-continued

```
<210> SEQ ID NO 526
<211> LENGTH: 13
<212> TYPE: PRT
<213> ORGANISM: Artificial sequence
<220> FEATURE:
<223> OTHER INFORMATION: Synthetic

<400> SEQUENCE: 526

Gly Lys Met Leu Phe Arg Val Thr Ile Asn Ser Trp Gln
1               5                   10

<210> SEQ ID NO 527
<211> LENGTH: 13
<212> TYPE: PRT
<213> ORGANISM: Artificial sequence
<220> FEATURE:
<223> OTHER INFORMATION: Synthetic

<400> SEQUENCE: 527

Gly Lys Met Leu Phe Arg Val Thr Ile Asn Ser Trp Asn
1               5                   10

<210> SEQ ID NO 528
<211> LENGTH: 13
<212> TYPE: PRT
<213> ORGANISM: Artificial sequence
<220> FEATURE:
<223> OTHER INFORMATION: Synthetic

<400> SEQUENCE: 528

Gly Lys Met Leu Phe Arg Val Thr Ile Asn Ser Trp Thr
1               5                   10

<210> SEQ ID NO 529
<211> LENGTH: 13
<212> TYPE: PRT
<213> ORGANISM: Artificial sequence
<220> FEATURE:
<223> OTHER INFORMATION: Synthetic

<400> SEQUENCE: 529

Gly Lys Met Leu Phe Arg Val Thr Ile Asn Ser Trp His
1               5                   10

<210> SEQ ID NO 530
<211> LENGTH: 13
<212> TYPE: PRT
<213> ORGANISM: Artificial sequence
<220> FEATURE:
<223> OTHER INFORMATION: Synthetic

<400> SEQUENCE: 530

Gly Lys Met Leu Phe Arg Val Thr Ile Asn Ser Trp Pro
1               5                   10

<210> SEQ ID NO 531
<211> LENGTH: 13
<212> TYPE: PRT
<213> ORGANISM: Artificial sequence
<220> FEATURE:
<223> OTHER INFORMATION: Synthetic

<400> SEQUENCE: 531

Gly Lys Met Leu Phe Arg Val Thr Ile Asn Ser Trp Arg
1               5                   10
```

```
<210> SEQ ID NO 532
<211> LENGTH: 13
<212> TYPE: PRT
<213> ORGANISM: Artificial sequence
<220> FEATURE:
<223> OTHER INFORMATION: Synthetic

<400> SEQUENCE: 532

Gly Lys Met Lys Phe Arg Val Thr Ile Asp Ser Trp Lys
1               5                   10

<210> SEQ ID NO 533
<211> LENGTH: 13
<212> TYPE: PRT
<213> ORGANISM: Artificial sequence
<220> FEATURE:
<223> OTHER INFORMATION: Synthetic

<400> SEQUENCE: 533

Gly Lys Met Leu Phe Arg Val Glu Ile Asn Ser Trp Lys
1               5                   10

<210> SEQ ID NO 534
<211> LENGTH: 13
<212> TYPE: PRT
<213> ORGANISM: Artificial sequence
<220> FEATURE:
<223> OTHER INFORMATION: Synthetic

<400> SEQUENCE: 534

Gly Lys Met Leu Phe Arg Val Gln Ile Asn Ser Trp Lys
1               5                   10

<210> SEQ ID NO 535
<211> LENGTH: 13
<212> TYPE: PRT
<213> ORGANISM: Artificial sequence
<220> FEATURE:
<223> OTHER INFORMATION: Synthetic

<400> SEQUENCE: 535

Gly Lys Met Lys Phe Arg Val Lys Ile Asn Ser Trp Lys
1               5                   10

<210> SEQ ID NO 536
<211> LENGTH: 13
<212> TYPE: PRT
<213> ORGANISM: Artificial sequence
<220> FEATURE:
<223> OTHER INFORMATION: Synthetic

<400> SEQUENCE: 536

Gly Lys Met Lys Phe Arg Val Arg Ile Asn Ser Trp Lys
1               5                   10

<210> SEQ ID NO 537
<211> LENGTH: 13
<212> TYPE: PRT
<213> ORGANISM: Artificial sequence
<220> FEATURE:
<223> OTHER INFORMATION: Synthetic

<400> SEQUENCE: 537

Gly Lys Met Lys Phe Arg Val Glu Ile Asn Ser Trp Lys
1               5                   10
```

```
<210> SEQ ID NO 538
<211> LENGTH: 13
<212> TYPE: PRT
<213> ORGANISM: Artificial sequence
<220> FEATURE:
<223> OTHER INFORMATION: Synthetic

<400> SEQUENCE: 538

Gly Lys Met Lys Phe Arg Val Asp Ile Asn Ser Trp Lys
1               5                   10

<210> SEQ ID NO 539
<211> LENGTH: 13
<212> TYPE: PRT
<213> ORGANISM: Artificial sequence
<220> FEATURE:
<223> OTHER INFORMATION: Synthetic

<400> SEQUENCE: 539

Gly Lys Met Lys Phe Arg Val Gln Ile Asn Ser Trp Lys
1               5                   10

<210> SEQ ID NO 540
<211> LENGTH: 13
<212> TYPE: PRT
<213> ORGANISM: Artificial sequence
<220> FEATURE:
<223> OTHER INFORMATION: Synthetic

<400> SEQUENCE: 540

Gly Lys Met Lys Phe Arg Val Asn Ile Asn Ser Trp Lys
1               5                   10

<210> SEQ ID NO 541
<211> LENGTH: 13
<212> TYPE: PRT
<213> ORGANISM: Artificial sequence
<220> FEATURE:
<223> OTHER INFORMATION: Synthetic

<400> SEQUENCE: 541

Gly Lys Met Lys Phe Arg Val Ser Ile Asn Ser Trp Lys
1               5                   10

<210> SEQ ID NO 542
<211> LENGTH: 13
<212> TYPE: PRT
<213> ORGANISM: Artificial sequence
<220> FEATURE:
<223> OTHER INFORMATION: Synthetic

<400> SEQUENCE: 542

Gly Lys Met Leu Phe Arg Val Asn Ile Asn Ser Trp Lys
1               5                   10

<210> SEQ ID NO 543
<211> LENGTH: 13
<212> TYPE: PRT
<213> ORGANISM: Artificial sequence
<220> FEATURE:
<223> OTHER INFORMATION: Synthetic

<400> SEQUENCE: 543

Gly Lys Met Leu Phe Arg Val Ser Ile Asn Ser Trp Lys
1               5                   10

<210> SEQ ID NO 544
```

-continued

```
<211> LENGTH: 13
<212> TYPE: PRT
<213> ORGANISM: Artificial sequence
<220> FEATURE:
<223> OTHER INFORMATION: Synthetic

<400> SEQUENCE: 544

Gly Lys Met Leu Phe Arg Val Trp Ile Asn Ser Trp Lys
1               5                   10

<210> SEQ ID NO 545
<211> LENGTH: 13
<212> TYPE: PRT
<213> ORGANISM: Artificial sequence
<220> FEATURE:
<223> OTHER INFORMATION: Synthetic

<400> SEQUENCE: 545

Gly Lys Met Ser Phe Arg Val Thr Ile Asn Ser Trp Lys
1               5                   10

<210> SEQ ID NO 546
<211> LENGTH: 13
<212> TYPE: PRT
<213> ORGANISM: Artificial sequence
<220> FEATURE:
<223> OTHER INFORMATION: Synthetic

<400> SEQUENCE: 546

Gly Lys Met Trp Phe Arg Val Thr Ile Asn Ser Trp Lys
1               5                   10

<210> SEQ ID NO 547
<211> LENGTH: 13
<212> TYPE: PRT
<213> ORGANISM: Artificial sequence
<220> FEATURE:
<223> OTHER INFORMATION: Synthetic

<400> SEQUENCE: 547

Gly Lys Met Asn Phe Arg Val Thr Ile Asn Ser Trp Lys
1               5                   10

<210> SEQ ID NO 548
<211> LENGTH: 13
<212> TYPE: PRT
<213> ORGANISM: Artificial sequence
<220> FEATURE:
<223> OTHER INFORMATION: Synthetic

<400> SEQUENCE: 548

Gly Ser Met Leu Phe Arg Val Thr Ile Asn Ser Tyr Lys
1               5                   10

<210> SEQ ID NO 549
<211> LENGTH: 13
<212> TYPE: PRT
<213> ORGANISM: Artificial sequence
<220> FEATURE:
<223> OTHER INFORMATION: Synthetic

<400> SEQUENCE: 549

Gly Lys Met Leu Phe Arg Val Thr Ile Asn Ser Tyr Lys
1               5                   10

<210> SEQ ID NO 550
<211> LENGTH: 13
```

```
<212> TYPE: PRT
<213> ORGANISM: Artificial sequence
<220> FEATURE:
<223> OTHER INFORMATION: Synthetic

<400> SEQUENCE: 550

Gly Lys Met Leu Phe Arg Val Thr Ile Lys Ser Trp Lys
1               5                   10

<210> SEQ ID NO 551
<211> LENGTH: 13
<212> TYPE: PRT
<213> ORGANISM: Artificial sequence
<220> FEATURE:
<223> OTHER INFORMATION: Synthetic

<400> SEQUENCE: 551

Gly Lys Met Leu Phe Arg Val Thr Ile Glu Ser Trp Lys
1               5                   10

<210> SEQ ID NO 552
<211> LENGTH: 13
<212> TYPE: PRT
<213> ORGANISM: Artificial sequence
<220> FEATURE:
<223> OTHER INFORMATION: Synthetic

<400> SEQUENCE: 552

Gly Lys Met Lys Phe Arg Val Thr Ile Gln Ser Trp Lys
1               5                   10

<210> SEQ ID NO 553
<211> LENGTH: 13
<212> TYPE: PRT
<213> ORGANISM: Artificial sequence
<220> FEATURE:
<223> OTHER INFORMATION: Synthetic

<400> SEQUENCE: 553

Gly Lys Met Lys Phe Arg Val Thr Ile Glu Ser Trp Lys
1               5                   10

<210> SEQ ID NO 554
<211> LENGTH: 13
<212> TYPE: PRT
<213> ORGANISM: Artificial sequence
<220> FEATURE:
<223> OTHER INFORMATION: Synthetic

<400> SEQUENCE: 554

Gly Lys Met Lys Phe Arg Val Thr Ile Lys Ser Trp Lys
1               5                   10

<210> SEQ ID NO 555
<211> LENGTH: 13
<212> TYPE: PRT
<213> ORGANISM: Artificial sequence
<220> FEATURE:
<223> OTHER INFORMATION: Synthetic

<400> SEQUENCE: 555

Gly Lys Met Lys Phe Arg Val Thr Ile Arg Ser Trp Lys
1               5                   10

<210> SEQ ID NO 556
<211> LENGTH: 13
<212> TYPE: PRT
```

-continued

<213> ORGANISM: Artificial sequence
<220> FEATURE:
<223> OTHER INFORMATION: Synthetic

<400> SEQUENCE: 556

Arg Leu Met Leu Phe Arg Val Thr Ile Asn Ser Trp Lys
1               5                   10

<210> SEQ ID NO 557
<211> LENGTH: 13
<212> TYPE: PRT
<213> ORGANISM: Artificial sequence
<220> FEATURE:
<223> OTHER INFORMATION: Synthetic

<400> SEQUENCE: 557

Arg Gln Met Leu Phe Arg Val Thr Ile Asn Ser Trp Lys
1               5                   10

<210> SEQ ID NO 558
<211> LENGTH: 13
<212> TYPE: PRT
<213> ORGANISM: Artificial sequence
<220> FEATURE:
<223> OTHER INFORMATION: Synthetic

<400> SEQUENCE: 558

Lys Leu Met Leu Phe Arg Val Thr Ile Asn Ser Trp Lys
1               5                   10

<210> SEQ ID NO 559
<211> LENGTH: 13
<212> TYPE: PRT
<213> ORGANISM: Artificial sequence
<220> FEATURE:
<223> OTHER INFORMATION: Synthetic

<400> SEQUENCE: 559

Lys Gln Met Leu Phe Arg Val Thr Ile Asn Ser Trp Lys
1               5                   10

<210> SEQ ID NO 560
<211> LENGTH: 13
<212> TYPE: PRT
<213> ORGANISM: Artificial sequence
<220> FEATURE:
<223> OTHER INFORMATION: Synthetic

<400> SEQUENCE: 560

Glu Leu Met Leu Phe Arg Val Thr Ile Asn Ser Trp Lys
1               5                   10

<210> SEQ ID NO 561
<211> LENGTH: 13
<212> TYPE: PRT
<213> ORGANISM: Artificial sequence
<220> FEATURE:
<223> OTHER INFORMATION: Synthetic

<400> SEQUENCE: 561

Asp Leu Met Leu Phe Arg Val Thr Ile Asn Ser Trp Lys
1               5                   10

<210> SEQ ID NO 562
<211> LENGTH: 13
<212> TYPE: PRT
<213> ORGANISM: Artificial sequence -continued

```
<220> FEATURE:
<223> OTHER INFORMATION: Synthetic

<400> SEQUENCE: 562

Asp Gln Met Leu Phe Arg Val Thr Ile Asn Ser Trp Lys
1               5                   10

<210> SEQ ID NO 563
<211> LENGTH: 13
<212> TYPE: PRT
<213> ORGANISM: Artificial sequence
<220> FEATURE:
<223> OTHER INFORMATION: Synthetic

<400> SEQUENCE: 563

Asp Lys Met Leu Phe Arg Val Thr Ile Asn Ser Trp Lys
1               5                   10

<210> SEQ ID NO 564
<211> LENGTH: 13
<212> TYPE: PRT
<213> ORGANISM: Artificial sequence
<220> FEATURE:
<223> OTHER INFORMATION: Synthetic

<400> SEQUENCE: 564

Glu Lys Met Leu Phe Arg Val Thr Ile Asn Ser Trp Lys
1               5                   10

<210> SEQ ID NO 565
<211> LENGTH: 13
<212> TYPE: PRT
<213> ORGANISM: Artificial sequence
<220> FEATURE:
<223> OTHER INFORMATION: Synthetic

<400> SEQUENCE: 565

Arg Lys Met Leu Phe Arg Val Thr Ile Asn Ser Trp Lys
1               5                   10

<210> SEQ ID NO 566
<211> LENGTH: 13
<212> TYPE: PRT
<213> ORGANISM: Artificial sequence
<220> FEATURE:
<223> OTHER INFORMATION: Synthetic

<400> SEQUENCE: 566

Lys Lys Met Leu Phe Arg Val Thr Ile Asn Ser Trp Lys
1               5                   10

<210> SEQ ID NO 567
<211> LENGTH: 13
<212> TYPE: PRT
<213> ORGANISM: Artificial sequence
<220> FEATURE:
<223> OTHER INFORMATION: Synthetic

<400> SEQUENCE: 567

Gly Lys Met Leu Phe Arg Val Thr Ile Gly Ser Trp Lys
1               5                   10

<210> SEQ ID NO 568
<211> LENGTH: 13
<212> TYPE: PRT
<213> ORGANISM: Artificial sequence
<220> FEATURE:
```

<223> OTHER INFORMATION: Synthetic

<400> SEQUENCE: 568

Gly Lys Met Leu Phe Arg Val Thr Ile Asn Lys Trp Lys
1               5               10

<210> SEQ ID NO 569
<211> LENGTH: 13
<212> TYPE: PRT
<213> ORGANISM: Artificial sequence
<220> FEATURE:
<223> OTHER INFORMATION: Synthetic

<400> SEQUENCE: 569

Gly Lys Met Leu Phe Arg Val Thr Ile Ser Lys Trp Lys
1               5               10

<210> SEQ ID NO 570
<211> LENGTH: 13
<212> TYPE: PRT
<213> ORGANISM: Artificial sequence
<220> FEATURE:
<223> OTHER INFORMATION: Synthetic

<400> SEQUENCE: 570

Gly Lys Met Leu Phe Arg Val Thr Ile Gln Lys Trp Lys
1               5               10

<210> SEQ ID NO 571
<211> LENGTH: 13
<212> TYPE: PRT
<213> ORGANISM: Artificial sequence
<220> FEATURE:
<223> OTHER INFORMATION: Synthetic

<400> SEQUENCE: 571

Gly Lys Met Leu Phe Arg Val Thr Ile Thr Lys Trp Lys
1               5               10

<210> SEQ ID NO 572
<211> LENGTH: 13
<212> TYPE: PRT
<213> ORGANISM: Artificial sequence
<220> FEATURE:
<223> OTHER INFORMATION: Synthetic

<400> SEQUENCE: 572

Gly Lys Met Leu Phe Arg Val Thr Ile Lys Lys Trp Lys
1               5               10

<210> SEQ ID NO 573
<211> LENGTH: 13
<212> TYPE: PRT
<213> ORGANISM: Artificial sequence
<220> FEATURE:
<223> OTHER INFORMATION: Synthetic

<400> SEQUENCE: 573

Gly Lys Met Leu Phe Lys Val Thr Ile Asn Ser Trp Lys
1               5               10

<210> SEQ ID NO 574
<211> LENGTH: 13
<212> TYPE: PRT
<213> ORGANISM: Artificial sequence
<220> FEATURE:
<223> OTHER INFORMATION: Synthetic

<400> SEQUENCE: 574

Arg Leu Met Leu Phe Arg Val Thr Ile Gly Lys Trp Lys
1               5                   10

<210> SEQ ID NO 575
<211> LENGTH: 13
<212> TYPE: PRT
<213> ORGANISM: Artificial sequence
<220> FEATURE:
<223> OTHER INFORMATION: Synthetic

<400> SEQUENCE: 575

Gly Lys Met Leu Phe Arg Val Thr Ile Asn Arg Trp Lys
1               5                   10

<210> SEQ ID NO 576
<211> LENGTH: 13
<212> TYPE: PRT
<213> ORGANISM: Artificial sequence
<220> FEATURE:
<223> OTHER INFORMATION: Synthetic

<400> SEQUENCE: 576

Glu Lys Met Leu Phe Thr Val Thr Ile Gly Lys Trp Lys
1               5                   10

<210> SEQ ID NO 577
<211> LENGTH: 13
<212> TYPE: PRT
<213> ORGANISM: Artificial sequence
<220> FEATURE:
<223> OTHER INFORMATION: Synthetic

<400> SEQUENCE: 577

Glu Lys Leu Leu Phe Thr Val Thr Ile Gly Lys Trp Lys
1               5                   10

<210> SEQ ID NO 578
<211> LENGTH: 13
<212> TYPE: PRT
<213> ORGANISM: Artificial sequence
<220> FEATURE:
<223> OTHER INFORMATION: Synthetic

<400> SEQUENCE: 578

Glu Lys Met Leu Phe Thr Val Thr Ile Gly Arg Trp Lys
1               5                   10

<210> SEQ ID NO 579
<211> LENGTH: 13
<212> TYPE: PRT
<213> ORGANISM: Artificial sequence
<220> FEATURE:
<223> OTHER INFORMATION: Synthetic

<400> SEQUENCE: 579

Glu Lys Met Leu Phe Thr Val Thr Ile Glu Lys Trp Lys
1               5                   10

<210> SEQ ID NO 580
<211> LENGTH: 13
<212> TYPE: PRT
<213> ORGANISM: Artificial sequence
<220> FEATURE:
<223> OTHER INFORMATION: Synthetic -continued

```
<400> SEQUENCE: 580

Asp Lys Met Leu Phe Arg Val Thr Ile Glu Ser Trp Lys
1               5                   10

<210> SEQ ID NO 581
<211> LENGTH: 13
<212> TYPE: PRT
<213> ORGANISM: Artificial sequence
<220> FEATURE:
<223> OTHER INFORMATION: Synthetic

<400> SEQUENCE: 581

Glu Lys Leu Leu Phe Arg Val Thr Ile Gly Lys Tyr Lys
1               5                   10

<210> SEQ ID NO 582
<211> LENGTH: 13
<212> TYPE: PRT
<213> ORGANISM: Artificial sequence
<220> FEATURE:
<223> OTHER INFORMATION: Synthetic

<400> SEQUENCE: 582

Asp Lys Leu Leu Phe Lys Val Thr Ile Gln Lys Trp Lys
1               5                   10

<210> SEQ ID NO 583
<211> LENGTH: 13
<212> TYPE: PRT
<213> ORGANISM: Artificial sequence
<220> FEATURE:
<223> OTHER INFORMATION: Synthetic

<400> SEQUENCE: 583

Asp Lys Leu Leu Phe Lys Val Thr Ile Gln Lys Tyr Lys
1               5                   10

<210> SEQ ID NO 584
<211> LENGTH: 13
<212> TYPE: PRT
<213> ORGANISM: Artificial sequence
<220> FEATURE:
<223> OTHER INFORMATION: Synthetic

<400> SEQUENCE: 584

Asp Lys Leu Leu Phe Lys Val Thr Ile Gly Lys Tyr Lys
1               5                   10

<210> SEQ ID NO 585
<211> LENGTH: 13
<212> TYPE: PRT
<213> ORGANISM: Artificial sequence
<220> FEATURE:
<223> OTHER INFORMATION: Synthetic

<400> SEQUENCE: 585

Asp Lys Leu Leu Phe Lys Val Thr Ile Glu Lys Trp Lys
1               5                   10

<210> SEQ ID NO 586
<211> LENGTH: 13
<212> TYPE: PRT
<213> ORGANISM: Artificial sequence
<220> FEATURE:
<223> OTHER INFORMATION: Synthetic

<400> SEQUENCE: 586
```

Asp Lys Leu Leu Phe Lys Val Thr Ile Glu Lys Tyr Lys
1               5                   10

<210> SEQ ID NO 587
<211> LENGTH: 13
<212> TYPE: PRT
<213> ORGANISM: Artificial sequence
<220> FEATURE:
<223> OTHER INFORMATION: Synthetic

<400> SEQUENCE: 587

Lys Lys Leu Leu Phe Arg Val Thr Ile Gln Lys Trp Lys
1               5                   10

<210> SEQ ID NO 588
<211> LENGTH: 13
<212> TYPE: PRT
<213> ORGANISM: Artificial sequence
<220> FEATURE:
<223> OTHER INFORMATION: Synthetic

<400> SEQUENCE: 588

Asp Arg Met Leu Phe Arg Val Thr Ile Gln Arg Trp Arg
1               5                   10

<210> SEQ ID NO 589
<211> LENGTH: 13
<212> TYPE: PRT
<213> ORGANISM: Artificial sequence
<220> FEATURE:
<223> OTHER INFORMATION: Synthetic

<400> SEQUENCE: 589

Glu Arg Met Leu Phe Arg Val Thr Ile Gly Arg Trp Arg
1               5                   10

<210> SEQ ID NO 590
<211> LENGTH: 13
<212> TYPE: PRT
<213> ORGANISM: Artificial sequence
<220> FEATURE:
<223> OTHER INFORMATION: Synthetic

<400> SEQUENCE: 590

Gly Arg Met Leu Phe Arg Val Thr Ile Asn Arg Trp Arg
1               5                   10

<210> SEQ ID NO 591
<211> LENGTH: 13
<212> TYPE: PRT
<213> ORGANISM: Artificial sequence
<220> FEATURE:
<223> OTHER INFORMATION: Synthetic

<400> SEQUENCE: 591

Asp Arg Met Leu Phe Arg Val Thr Ile Glu Arg Trp Arg
1               5                   10

<210> SEQ ID NO 592
<211> LENGTH: 13
<212> TYPE: PRT
<213> ORGANISM: Artificial sequence
<220> FEATURE:
<223> OTHER INFORMATION: Synthetic

<400> SEQUENCE: 592

-continued

```
Asp Lys Met Leu Phe Lys Val Thr Ile Gln Lys Tyr Lys
1               5                   10

<210> SEQ ID NO 593
<211> LENGTH: 13
<212> TYPE: PRT
<213> ORGANISM: Artificial sequence
<220> FEATURE:
<223> OTHER INFORMATION: Synthetic

<400> SEQUENCE: 593

Asp Lys Met Leu Phe Arg Val Thr Ile Asn Lys Trp Lys
1               5                   10

<210> SEQ ID NO 594
<211> LENGTH: 13
<212> TYPE: PRT
<213> ORGANISM: Artificial sequence
<220> FEATURE:
<223> OTHER INFORMATION: Synthetic

<400> SEQUENCE: 594

Asp Lys Met Leu Phe Lys Val Thr Ile Glu Lys Tyr Lys
1               5                   10

<210> SEQ ID NO 595
<211> LENGTH: 13
<212> TYPE: PRT
<213> ORGANISM: Artificial sequence
<220> FEATURE:
<223> OTHER INFORMATION: Synthetic

<400> SEQUENCE: 595

Asp Lys Met Leu Phe Lys Val Thr Ile Asn Lys Trp Lys
1               5                   10

<210> SEQ ID NO 596
<211> LENGTH: 13
<212> TYPE: PRT
<213> ORGANISM: Artificial sequence
<220> FEATURE:
<223> OTHER INFORMATION: Synthetic

<400> SEQUENCE: 596

Glu Lys Leu Leu Phe Thr Val Thr Ile Glu Lys Tyr Lys
1               5                   10

<210> SEQ ID NO 597
<211> LENGTH: 13
<212> TYPE: PRT
<213> ORGANISM: Artificial sequence
<220> FEATURE:
<223> OTHER INFORMATION: Synthetic

<400> SEQUENCE: 597

Gly Lys Leu Leu Phe Thr Val Thr Ile Glu Lys Tyr Lys
1               5                   10

<210> SEQ ID NO 598
<211> LENGTH: 20
<212> TYPE: DNA
<213> ORGANISM: Artificial sequence
<220> FEATURE:
<223> OTHER INFORMATION: Synthetic

<400> SEQUENCE: 598
aagtcgagaa ccatgaccac                                          20
```

-continued

```
<210> SEQ ID NO 599
<211> LENGTH: 20
<212> TYPE: DNA
<213> ORGANISM: Artificial sequence
<220> FEATURE:
<223> OTHER INFORMATION: Synthetic

<400> SEQUENCE: 599
cgccgcgtcc gccgaagttg                                              20

<210> SEQ ID NO 600

<400> SEQUENCE: 600

000

<210> SEQ ID NO 601

<400> SEQUENCE: 601

000

<210> SEQ ID NO 602

<400> SEQUENCE: 602

000

<210> SEQ ID NO 603

<400> SEQUENCE: 603

000

<210> SEQ ID NO 604

<400> SEQUENCE: 604

000

<210> SEQ ID NO 605

<400> SEQUENCE: 605

000

<210> SEQ ID NO 606

<400> SEQUENCE: 606

000

<210> SEQ ID NO 607

<400> SEQUENCE: 607

000

<210> SEQ ID NO 608

<400> SEQUENCE: 608

000

<210> SEQ ID NO 609
```

```
<400> SEQUENCE: 609

000

<210> SEQ ID NO 610

<400> SEQUENCE: 610

000

<210> SEQ ID NO 611

<400> SEQUENCE: 611

000

<210> SEQ ID NO 612

<400> SEQUENCE: 612

000

<210> SEQ ID NO 613

<400> SEQUENCE: 613

000

<210> SEQ ID NO 614

<400> SEQUENCE: 614

000

<210> SEQ ID NO 615

<400> SEQUENCE: 615

000

<210> SEQ ID NO 616

<400> SEQUENCE: 616

000

<210> SEQ ID NO 617

<400> SEQUENCE: 617

000

<210> SEQ ID NO 618

<400> SEQUENCE: 618

000

<210> SEQ ID NO 619

<400> SEQUENCE: 619

000

<210> SEQ ID NO 620

<400> SEQUENCE: 620
```

-continued

```
000

<210> SEQ ID NO 621

<400> SEQUENCE: 621

000

<210> SEQ ID NO 622

<400> SEQUENCE: 622

000

<210> SEQ ID NO 623

<400> SEQUENCE: 623

000

<210> SEQ ID NO 624

<400> SEQUENCE: 624

000

<210> SEQ ID NO 625

<400> SEQUENCE: 625

000

<210> SEQ ID NO 626

<400> SEQUENCE: 626

000

<210> SEQ ID NO 627

<400> SEQUENCE: 627

000

<210> SEQ ID NO 628

<400> SEQUENCE: 628

000

<210> SEQ ID NO 629

<400> SEQUENCE: 629

000

<210> SEQ ID NO 630

<400> SEQUENCE: 630

000

<210> SEQ ID NO 631

<400> SEQUENCE: 631

000
```

-continued

```
<210> SEQ ID NO 632

<400> SEQUENCE: 632

000

<210> SEQ ID NO 633

<400> SEQUENCE: 633

000

<210> SEQ ID NO 634

<400> SEQUENCE: 634

000

<210> SEQ ID NO 635

<400> SEQUENCE: 635

000

<210> SEQ ID NO 636

<400> SEQUENCE: 636

000

<210> SEQ ID NO 637

<400> SEQUENCE: 637

000

<210> SEQ ID NO 638

<400> SEQUENCE: 638

000

<210> SEQ ID NO 639

<400> SEQUENCE: 639

000

<210> SEQ ID NO 640

<400> SEQUENCE: 640

000

<210> SEQ ID NO 641

<400> SEQUENCE: 641

000

<210> SEQ ID NO 642

<400> SEQUENCE: 642

000

<210> SEQ ID NO 643
```

-continued

<400> SEQUENCE: 643

000

<210> SEQ ID NO 644

<400> SEQUENCE: 644

000

<210> SEQ ID NO 645

<400> SEQUENCE: 645

000

<210> SEQ ID NO 646

<400> SEQUENCE: 646

000

<210> SEQ ID NO 647

<400> SEQUENCE: 647

000

<210> SEQ ID NO 648

<400> SEQUENCE: 648

000

<210> SEQ ID NO 649

<400> SEQUENCE: 649

000

<210> SEQ ID NO 650

<400> SEQUENCE: 650

000

<210> SEQ ID NO 651

<400> SEQUENCE: 651

000

<210> SEQ ID NO 652

<400> SEQUENCE: 652

000

<210> SEQ ID NO 653

<400> SEQUENCE: 653

000

<210> SEQ ID NO 654

<400> SEQUENCE: 654

000

<210> SEQ ID NO 655

<400> SEQUENCE: 655

000

<210> SEQ ID NO 656

<400> SEQUENCE: 656

000

<210> SEQ ID NO 657

<400> SEQUENCE: 657

000

<210> SEQ ID NO 658

<400> SEQUENCE: 658

000

<210> SEQ ID NO 659

<400> SEQUENCE: 659

000

<210> SEQ ID NO 660

<400> SEQUENCE: 660

000

<210> SEQ ID NO 661

<400> SEQUENCE: 661

000

<210> SEQ ID NO 662

<400> SEQUENCE: 662

000

<210> SEQ ID NO 663

<400> SEQUENCE: 663

000

<210> SEQ ID NO 664

<400> SEQUENCE: 664

000

<210> SEQ ID NO 665

<400> SEQUENCE: 665

000

```
<210> SEQ ID NO 666

<400> SEQUENCE: 666

000

<210> SEQ ID NO 667

<400> SEQUENCE: 667

000

<210> SEQ ID NO 668

<400> SEQUENCE: 668

000

<210> SEQ ID NO 669

<400> SEQUENCE: 669

000

<210> SEQ ID NO 670

<400> SEQUENCE: 670

000

<210> SEQ ID NO 671

<400> SEQUENCE: 671

000

<210> SEQ ID NO 672

<400> SEQUENCE: 672

000

<210> SEQ ID NO 673

<400> SEQUENCE: 673

000

<210> SEQ ID NO 674

<400> SEQUENCE: 674

000

<210> SEQ ID NO 675

<400> SEQUENCE: 675

000

<210> SEQ ID NO 676

<400> SEQUENCE: 676

000
```

-continued

```
<210> SEQ ID NO 677

<400> SEQUENCE: 677

000

<210> SEQ ID NO 678

<400> SEQUENCE: 678

000

<210> SEQ ID NO 679

<400> SEQUENCE: 679

000

<210> SEQ ID NO 680

<400> SEQUENCE: 680

000

<210> SEQ ID NO 681

<400> SEQUENCE: 681

000

<210> SEQ ID NO 682

<400> SEQUENCE: 682

000

<210> SEQ ID NO 683

<400> SEQUENCE: 683

000

<210> SEQ ID NO 684

<400> SEQUENCE: 684

000

<210> SEQ ID NO 685

<400> SEQUENCE: 685

000

<210> SEQ ID NO 686

<400> SEQUENCE: 686

000

<210> SEQ ID NO 687

<400> SEQUENCE: 687

000

<210> SEQ ID NO 688
```

-continued

```
<400> SEQUENCE: 688

000

<210> SEQ ID NO 689

<400> SEQUENCE: 689

000

<210> SEQ ID NO 690

<400> SEQUENCE: 690

000

<210> SEQ ID NO 691

<400> SEQUENCE: 691

000

<210> SEQ ID NO 692

<400> SEQUENCE: 692

000

<210> SEQ ID NO 693

<400> SEQUENCE: 693

000

<210> SEQ ID NO 694

<400> SEQUENCE: 694

000

<210> SEQ ID NO 695

<400> SEQUENCE: 695

000

<210> SEQ ID NO 696

<400> SEQUENCE: 696

000

<210> SEQ ID NO 697

<400> SEQUENCE: 697

000

<210> SEQ ID NO 698

<400> SEQUENCE: 698

000

<210> SEQ ID NO 699

<400> SEQUENCE: 699
```

-continued

000

<210> SEQ ID NO 700

<400> SEQUENCE: 700

000

<210> SEQ ID NO 701

<400> SEQUENCE: 701

000

<210> SEQ ID NO 702

<400> SEQUENCE: 702

000

<210> SEQ ID NO 703

<400> SEQUENCE: 703

000

<210> SEQ ID NO 704

<400> SEQUENCE: 704

000

<210> SEQ ID NO 705

<400> SEQUENCE: 705

000

<210> SEQ ID NO 706

<400> SEQUENCE: 706

000

<210> SEQ ID NO 707

<400> SEQUENCE: 707

000

<210> SEQ ID NO 708

<400> SEQUENCE: 708

000

<210> SEQ ID NO 709

<400> SEQUENCE: 709

000

<210> SEQ ID NO 710

<400> SEQUENCE: 710

000

-continued

```
<210> SEQ ID NO 711

<400> SEQUENCE: 711

000

<210> SEQ ID NO 712

<400> SEQUENCE: 712

000

<210> SEQ ID NO 713

<400> SEQUENCE: 713

000

<210> SEQ ID NO 714

<400> SEQUENCE: 714

000

<210> SEQ ID NO 715

<400> SEQUENCE: 715

000

<210> SEQ ID NO 716

<400> SEQUENCE: 716

000

<210> SEQ ID NO 717

<400> SEQUENCE: 717

000

<210> SEQ ID NO 718

<400> SEQUENCE: 718

000

<210> SEQ ID NO 719

<400> SEQUENCE: 719

000

<210> SEQ ID NO 720

<400> SEQUENCE: 720

000

<210> SEQ ID NO 721

<400> SEQUENCE: 721

000

<210> SEQ ID NO 722
```

<400> SEQUENCE: 722

000

<210> SEQ ID NO 723

<400> SEQUENCE: 723

000

<210> SEQ ID NO 724

<400> SEQUENCE: 724

000

<210> SEQ ID NO 725

<400> SEQUENCE: 725

000

<210> SEQ ID NO 726

<400> SEQUENCE: 726

000

<210> SEQ ID NO 727

<400> SEQUENCE: 727

000

<210> SEQ ID NO 728

<400> SEQUENCE: 728

000

<210> SEQ ID NO 729

<400> SEQUENCE: 729

000

<210> SEQ ID NO 730

<400> SEQUENCE: 730

000

<210> SEQ ID NO 731

<400> SEQUENCE: 731

000

<210> SEQ ID NO 732

<400> SEQUENCE: 732

000

<210> SEQ ID NO 733

<400> SEQUENCE: 733

-continued

```
000

<210> SEQ ID NO 734

<400> SEQUENCE: 734

000

<210> SEQ ID NO 735

<400> SEQUENCE: 735

000

<210> SEQ ID NO 736

<400> SEQUENCE: 736

000

<210> SEQ ID NO 737

<400> SEQUENCE: 737

000

<210> SEQ ID NO 738

<400> SEQUENCE: 738

000

<210> SEQ ID NO 739

<400> SEQUENCE: 739

000

<210> SEQ ID NO 740

<400> SEQUENCE: 740

000

<210> SEQ ID NO 741

<400> SEQUENCE: 741

000

<210> SEQ ID NO 742

<400> SEQUENCE: 742

000

<210> SEQ ID NO 743

<400> SEQUENCE: 743

000

<210> SEQ ID NO 744

<400> SEQUENCE: 744

000
```

-continued

```
<210> SEQ ID NO 745

<400> SEQUENCE: 745

000

<210> SEQ ID NO 746

<400> SEQUENCE: 746

000

<210> SEQ ID NO 747

<400> SEQUENCE: 747

000

<210> SEQ ID NO 748

<400> SEQUENCE: 748

000

<210> SEQ ID NO 749

<400> SEQUENCE: 749

000

<210> SEQ ID NO 750

<400> SEQUENCE: 750

000

<210> SEQ ID NO 751

<400> SEQUENCE: 751

000

<210> SEQ ID NO 752

<400> SEQUENCE: 752

000

<210> SEQ ID NO 753

<400> SEQUENCE: 753

000

<210> SEQ ID NO 754

<400> SEQUENCE: 754

000

<210> SEQ ID NO 755

<400> SEQUENCE: 755

000
```

```
<210> SEQ ID NO 756

<400> SEQUENCE: 756

000

<210> SEQ ID NO 757

<400> SEQUENCE: 757

000

<210> SEQ ID NO 758

<400> SEQUENCE: 758

000

<210> SEQ ID NO 759

<400> SEQUENCE: 759

000

<210> SEQ ID NO 760

<400> SEQUENCE: 760

000

<210> SEQ ID NO 761

<400> SEQUENCE: 761

000

<210> SEQ ID NO 762

<400> SEQUENCE: 762

000

<210> SEQ ID NO 763

<400> SEQUENCE: 763

000

<210> SEQ ID NO 764

<400> SEQUENCE: 764

000

<210> SEQ ID NO 765

<400> SEQUENCE: 765

000

<210> SEQ ID NO 766

<400> SEQUENCE: 766

000

<210> SEQ ID NO 767
```

-continued

<400> SEQUENCE: 767

000

<210> SEQ ID NO 768

<400> SEQUENCE: 768

000

<210> SEQ ID NO 769

<400> SEQUENCE: 769

000

<210> SEQ ID NO 770

<400> SEQUENCE: 770

000

<210> SEQ ID NO 771

<400> SEQUENCE: 771

000

<210> SEQ ID NO 772

<400> SEQUENCE: 772

000

<210> SEQ ID NO 773

<400> SEQUENCE: 773

000

<210> SEQ ID NO 774

<400> SEQUENCE: 774

000

<210> SEQ ID NO 775

<400> SEQUENCE: 775

000

<210> SEQ ID NO 776

<400> SEQUENCE: 776

000

<210> SEQ ID NO 777

<400> SEQUENCE: 777

000

<210> SEQ ID NO 778

<400> SEQUENCE: 778

-continued

000

<210> SEQ ID NO 779

<400> SEQUENCE: 779

000

<210> SEQ ID NO 780

<400> SEQUENCE: 780

000

<210> SEQ ID NO 781

<400> SEQUENCE: 781

000

<210> SEQ ID NO 782

<400> SEQUENCE: 782

000

<210> SEQ ID NO 783

<400> SEQUENCE: 783

000

<210> SEQ ID NO 784

<400> SEQUENCE: 784

000

<210> SEQ ID NO 785

<400> SEQUENCE: 785

000

<210> SEQ ID NO 786

<400> SEQUENCE: 786

000

<210> SEQ ID NO 787

<400> SEQUENCE: 787

000

<210> SEQ ID NO 788
<211> LENGTH: 170
<212> TYPE: PRT
<213> ORGANISM: Artificial sequence
<220> FEATURE:
<223> OTHER INFORMATION: Synthetic

<400> SEQUENCE: 788

Met Val Phe Thr Leu Asp Asp Phe Val Gly Asp Trp Glu Gln Thr Ala
1               5                   10                  15

Ala Tyr Asn Leu Asp Gln Val Leu Glu Gln Gly Gly Val Ser Ser Leu

-continued

```
                20                  25                  30

Leu Gln Asn Leu Ala Val Ser Val Thr Pro Ile Met Arg Ile Val Arg
            35                  40                  45

Ser Gly Glu Asn Ala Leu Lys Ile Asp Ile His Val Ile Ile Pro Tyr
        50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Lys Leu Asn Tyr Phe
            100                 105                 110

Gly Arg Pro Tyr Glu Gly Ile Ala Val Phe Asp Gly Lys Lys Ile Thr
        115                 120                 125

Thr Thr Gly Thr Leu Trp Asn Gly Asn Lys Ile Ile Asp Glu Arg Leu
        130                 135                 140

Ile Thr Pro Asp Gly Ser Met Leu Phe Arg Val Thr Ile Asn Ser Val
145                 150                 155                 160

Ser Gly Trp Arg Leu Phe Lys Lys Ile Ser
                165                 170
```

```
<210> SEQ ID NO 789
<211> LENGTH: 170
<212> TYPE: PRT
<213> ORGANISM: Artificial sequence
<220> FEATURE:
<223> OTHER INFORMATION: Synthetic

<400> SEQUENCE: 789
```

```
Met Val Phe Thr Leu Asp Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Met Arg Ile Val Arg
            35                  40                  45

Ser Gly Glu Asn Ala Leu Lys Ile Asp Ile His Val Ile Ile Pro Tyr
        50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Lys Leu Asn Tyr Phe
            100                 105                 110

Gly Arg Pro Tyr Glu Gly Ile Ala Val Phe Asp Gly Lys Lys Ile Thr
        115                 120                 125

Thr Thr Gly Thr Leu Trp Asn Gly Asn Lys Ile Ile Asp Glu Arg Leu
        130                 135                 140

Ile Thr Pro Asp Gly Ser Met Leu Phe Arg Val Thr Ile Asn Ser Val
145                 150                 155                 160

Thr Gly Tyr Arg Leu Phe Glu Glu Ile Leu
                165                 170
```

```
<210> SEQ ID NO 790
<211> LENGTH: 102
<212> TYPE: PRT
<213> ORGANISM: Artificial sequence
<220> FEATURE:
<223> OTHER INFORMATION: Synthetic
```

-continued

<400> SEQUENCE: 790

Met Val Phe Thr Leu Asp Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Met Arg Ile Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp
            100

<210> SEQ ID NO 791
<211> LENGTH: 124
<212> TYPE: PRT
<213> ORGANISM: Artificial sequence
<220> FEATURE:
<223> OTHER INFORMATION: Synthetic

<400> SEQUENCE: 791

Met Val Phe Thr Leu Asp Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Met Arg Ile Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Lys Leu Asn Tyr Phe
            100                 105                 110

Gly Arg Pro Tyr Glu Gly Ile Ala Val Phe Asp Gly
        115                 120

<210> SEQ ID NO 792
<211> LENGTH: 133
<212> TYPE: PRT
<213> ORGANISM: Artificial sequence
<220> FEATURE:
<223> OTHER INFORMATION: Synthetic

<400> SEQUENCE: 792

Met Val Phe Thr Leu Asp Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Met Arg Ile Val Arg
        35                  40                  45

Ser Gly Glu Asn Ala Leu Lys Ile Asp Ile His Val Ile Ile Pro Tyr
    50                  55                  60

```
Glu Gly Leu Ser Ala Asp Gln Met Ala Gln Ile Glu Glu Val Phe Lys
65              70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Lys Leu Asn Tyr Phe
            100                 105                 110

Gly Arg Pro Tyr Glu Gly Ile Ala Val Phe Asp Gly Lys Lys Ile Thr
        115                 120                 125

Thr Thr Gly Thr Leu
    130
```

<210> SEQ ID NO 793
<211> LENGTH: 148
<212> TYPE: PRT
<213> ORGANISM: Artificial sequence
<220> FEATURE:
<223> OTHER INFORMATION: Synthetic

<400> SEQUENCE: 793

```
Met Val Phe Thr Leu Asp Asp Phe Val Gly Asp Trp Glu Gln Thr Ala
1               5                   10                  15

Ala Tyr Asn Leu Asp Gln Val Leu Glu Gln Gly Gly Val Ser Ser Leu
                20                  25                  30

Leu Gln Asn Leu Ala Val Ser Val Thr Pro Ile Met Arg Ile Val Arg
            35                  40                  45

Ser Gly Glu Asn Ala Leu Lys Ile Asp Ile His Val Ile Ile Pro Tyr
        50                  55                  60

Glu Gly Leu Ser Ala Asp Gln Met Ala Gln Ile Glu Glu Val Phe Lys
65              70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Lys Leu Asn Tyr Phe
            100                 105                 110

Gly Arg Pro Tyr Glu Gly Ile Ala Val Phe Asp Gly Lys Lys Ile Thr
        115                 120                 125

Thr Thr Gly Thr Leu Trp Asn Gly Asn Lys Ile Ile Asp Glu Arg Leu
    130                 135                 140

Ile Thr Pro Asp
145
```

<210> SEQ ID NO 794
<211> LENGTH: 68
<212> TYPE: PRT
<213> ORGANISM: Artificial sequence
<220> FEATURE:
<223> OTHER INFORMATION: Synthetic

<400> SEQUENCE: 794

```
Gly Val Thr Pro Asn Lys Leu Asn Tyr Phe Gly Arg Pro Tyr Glu Gly
1               5                   10                  15

Ile Ala Val Phe Asp Gly Lys Lys Ile Thr Thr Thr Gly Thr Leu Trp
                20                  25                  30

Asn Gly Asn Lys Ile Ile Asp Glu Arg Leu Ile Thr Pro Asp Gly Ser
            35                  40                  45

Met Leu Phe Arg Val Thr Ile Asn Ser Val Ser Gly Trp Arg Leu Phe
        50                  55                  60

Lys Lys Ile Ser
```

65

```
<210> SEQ ID NO 795
<211> LENGTH: 46
<212> TYPE: PRT
<213> ORGANISM: Artificial sequence
<220> FEATURE:
<223> OTHER INFORMATION: Synthetic

<400> SEQUENCE: 795

Lys Lys Ile Thr Thr Thr Gly Thr Leu Trp Asn Gly Asn Lys Ile Ile
1               5                   10                  15

Asp Glu Arg Leu Ile Thr Pro Asp Gly Ser Met Leu Phe Arg Val Thr
            20                  25                  30

Ile Asn Ser Val Ser Gly Trp Arg Leu Phe Lys Lys Ile Ser
        35                  40                  45

<210> SEQ ID NO 796
<211> LENGTH: 37
<212> TYPE: PRT
<213> ORGANISM: Artificial sequence
<220> FEATURE:
<223> OTHER INFORMATION: Synthetic

<400> SEQUENCE: 796

Trp Asn Gly Asn Lys Ile Ile Asp Glu Arg Leu Ile Thr Pro Asp Gly
1               5                   10                  15

Ser Met Leu Phe Arg Val Thr Ile Asn Ser Val Ser Gly Trp Arg Leu
            20                  25                  30

Phe Lys Lys Ile Ser
        35

<210> SEQ ID NO 797
<211> LENGTH: 22
<212> TYPE: PRT
<213> ORGANISM: Artificial sequence
<220> FEATURE:
<223> OTHER INFORMATION: Synthetic

<400> SEQUENCE: 797

Gly Ser Met Leu Phe Arg Val Thr Ile Asn Ser Val Ser Gly Trp Arg
1               5                   10                  15

Leu Phe Lys Lys Ile Ser
            20

<210> SEQ ID NO 798
<211> LENGTH: 68
<212> TYPE: PRT
<213> ORGANISM: Artificial sequence
<220> FEATURE:
<223> OTHER INFORMATION: Synthetic

<400> SEQUENCE: 798

Gly Val Thr Pro Asn Lys Leu Asn Tyr Phe Gly Arg Pro Tyr Glu Gly
1               5                   10                  15

Ile Ala Val Phe Asp Gly Lys Lys Ile Thr Thr Thr Gly Thr Leu Trp
            20                  25                  30

Asn Gly Asn Lys Ile Ile Asp Glu Arg Leu Ile Thr Pro Asp Gly Ser
        35                  40                  45

Met Leu Phe Arg Val Thr Ile Asn Ser Val Thr Gly Tyr Arg Leu Phe
    50                  55                  60

Glu Glu Ile Leu
```

65

<210> SEQ ID NO 799
<211> LENGTH: 46
<212> TYPE: PRT
<213> ORGANISM: Artificial sequence
<220> FEATURE:
<223> OTHER INFORMATION: Synthetic

<400> SEQUENCE: 799

Lys Lys Ile Thr Thr Thr Gly Thr Leu Trp Asn Gly Asn Lys Ile Ile
1               5                   10                  15

Asp Glu Arg Leu Ile Thr Pro Asp Gly Ser Met Leu Phe Arg Val Thr
                20                  25                  30

Ile Asn Ser Val Thr Gly Tyr Arg Leu Phe Glu Glu Ile Leu
            35                  40                  45

<210> SEQ ID NO 800
<211> LENGTH: 37
<212> TYPE: PRT
<213> ORGANISM: Artificial sequence
<220> FEATURE:
<223> OTHER INFORMATION: Synthetic

<400> SEQUENCE: 800

Trp Asn Gly Asn Lys Ile Ile Asp Glu Arg Leu Ile Thr Pro Asp Gly
1               5                   10                  15

Ser Met Leu Phe Arg Val Thr Ile Asn Ser Val Thr Gly Tyr Arg Leu
                20                  25                  30

Phe Glu Glu Ile Leu
        35

<210> SEQ ID NO 801
<211> LENGTH: 22
<212> TYPE: PRT
<213> ORGANISM: Artificial sequence
<220> FEATURE:
<223> OTHER INFORMATION: Synthetic

<400> SEQUENCE: 801

Gly Ser Met Leu Phe Arg Val Thr Ile Asn Ser Val Thr Gly Tyr Arg
1               5                   10                  15

Leu Phe Glu Glu Ile Leu
            20

<210> SEQ ID NO 802

<400> SEQUENCE: 802

000

<210> SEQ ID NO 803

<400> SEQUENCE: 803

000

<210> SEQ ID NO 804

<400> SEQUENCE: 804

000

<210> SEQ ID NO 805

```
<400> SEQUENCE: 805

000

<210> SEQ ID NO 806

<400> SEQUENCE: 806

000

<210> SEQ ID NO 807

<400> SEQUENCE: 807

000

<210> SEQ ID NO 808

<400> SEQUENCE: 808

000

<210> SEQ ID NO 809

<400> SEQUENCE: 809

000

<210> SEQ ID NO 810
<211> LENGTH: 13
<212> TYPE: PRT
<213> ORGANISM: Artificial sequence
<220> FEATURE:
<223> OTHER INFORMATION: Synthetic

<400> SEQUENCE: 810

Glu Lys Met Leu Phe Arg Val Thr Ile Glu Ser Trp Lys
1               5                   10

<210> SEQ ID NO 811
<211> LENGTH: 13
<212> TYPE: PRT
<213> ORGANISM: Artificial sequence
<220> FEATURE:
<223> OTHER INFORMATION: Synthetic

<400> SEQUENCE: 811

Glu Lys Leu Leu Phe Arg Val Thr Ile Glu Ser Trp Lys
1               5                   10

<210> SEQ ID NO 812
<211> LENGTH: 13
<212> TYPE: PRT
<213> ORGANISM: Artificial sequence
<220> FEATURE:
<223> OTHER INFORMATION: Synthetic

<400> SEQUENCE: 812

Glu Lys Leu Leu Phe Arg Val Thr Ile Glu Ser Tyr Lys
1               5                   10

<210> SEQ ID NO 813

<400> SEQUENCE: 813

000
```

<210> SEQ ID NO 814

<400> SEQUENCE: 814

000

<210> SEQ ID NO 815

<400> SEQUENCE: 815

000

<210> SEQ ID NO 816
<211> LENGTH: 13
<212> TYPE: PRT
<213> ORGANISM: Artificial sequence
<220> FEATURE:
<223> OTHER INFORMATION: Synthetic

<400> SEQUENCE: 816

Asp Lys Leu Leu Phe Thr Val Thr Ile Glu Lys Tyr Lys
1               5                   10

<210> SEQ ID NO 817
<211> LENGTH: 22
<212> TYPE: PRT
<213> ORGANISM: Artificial sequence
<220> FEATURE:
<223> OTHER INFORMATION: Synthetic

<400> SEQUENCE: 817

Gly Val Thr Pro Asn Lys Leu Asn Tyr Phe Gly Arg Pro Tyr Glu Gly
1               5                   10                  15

Ile Ala Val Phe Asp Gly
            20

<210> SEQ ID NO 818
<211> LENGTH: 9
<212> TYPE: PRT
<213> ORGANISM: Artificial sequence
<220> FEATURE:
<223> OTHER INFORMATION: Synthetic

<400> SEQUENCE: 818

Lys Lys Ile Thr Thr Thr Gly Thr Leu
1               5

<210> SEQ ID NO 819
<211> LENGTH: 15
<212> TYPE: PRT
<213> ORGANISM: Artificial sequence
<220> FEATURE:
<223> OTHER INFORMATION: Synthetic

<400> SEQUENCE: 819

Trp Asn Gly Asn Lys Ile Ile Asp Glu Arg Leu Ile Thr Pro Asp
1               5                   10                  15

<210> SEQ ID NO 820
<211> LENGTH: 396
<212> TYPE: DNA
<213> ORGANISM: Artificial sequence
<220> FEATURE:
<223> OTHER INFORMATION: Synthetic

<400> SEQUENCE: 820

-continued

```
atgaaacatc accatcacca tcatgtcttc acactcgacg atttcgttgg ggactgggaa        60
cagacagccg cctacaacct ggaccaagtc cttgaacagg gaggtgtgtc cagtttgctg       120
cagaatctcg ccgtgtccgt aactccgatc atgaggattg tccggagcgg tgaaaatgcc       180
ctgaagatcg acatccatgt catcatcccg tatgaaggtc tgagcgccga ccaaatggcc       240
cagatcgaag aggtgtttaa ggtggtgtac cctgtggatg atcatcactt taaggtgatc       300
ctgccctatg gcacactggt aatcgacggg gttacgccga acaagctgaa ctatttcgga       360
cggccgtatg aaggcatcgc cgtgttcgac ggctaa                                 396
```

```
<210> SEQ ID NO 821
<211> LENGTH: 131
<212> TYPE: PRT
<213> ORGANISM: Artificial sequence
<220> FEATURE:
<223> OTHER INFORMATION: Synthetic

<400> SEQUENCE: 821

Met Lys His His His His His His Val Phe Thr Leu Asp Asp Phe Val
1               5                   10                  15

Gly Asp Trp Glu Gln Thr Ala Ala Tyr Asn Leu Asp Gln Val Leu Glu
            20                  25                  30

Gln Gly Gly Val Ser Ser Leu Leu Gln Asn Leu Ala Val Ser Val Thr
        35                  40                  45

Pro Ile Met Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
                85                  90                  95

Phe Lys Val Ile Leu Pro Tyr Gly Thr Leu Val Ile Asp Gly Val Thr
            100                 105                 110

Pro Asn Lys Leu Asn Tyr Phe Gly Arg Pro Tyr Glu Gly Ile Ala Val
            115                 120                 125

Phe Asp Gly
    130
```

```
<210> SEQ ID NO 822
<211> LENGTH: 654
<212> TYPE: DNA
<213> ORGANISM: Artificial sequence
<220> FEATURE:
<223> OTHER INFORMATION: Synthetic

<400> SEQUENCE: 822
gggagctccg gtggtggcgg gagcggaggt ggaggctcga gcggtatgac gtataagtta        60
atccttaatg gtaaaacatt gaaaggcgag acaactactg aagctgttga tgctgctact       120
gcagaaaaag tcttcaaaca atacgctaac gacaacggtg ttgacggtga atggacttac       180
gacgatgcga cgaaaacctt tacggtcacc gaaaaaccag aagtgatcga tgcgtctgaa       240
ttaacaccag ccgtgacaac ttacaaactt gttattaatg gtaaaacatt gaaaggcgaa       300
acaactactg aggctgttga tgctgctact gcagagaagt gttcaaaca atatgcgaat       360 gacaacggtg ttgacggtga gtggacttac gacgatgcga ctaagacctt tacagttact       420
gaaaaaccag aagtgatcga tgcgtctgag ttaacaccag ccgtgacaac ttacaaactt       480
gttattaatg gtaaaacatt gaaaggcgaa acaactacta aagcagtaga cgcagaaact       540
```

```
gcggagaagg ccttcaaaca atacgctaac gacaacggtg ttgatggtgt ttggacttat    600
gatgatgcca caaaaacctt tacggtaact gagcatcatc accatcacca ctaa          654
```

```
<210> SEQ ID NO 823
<211> LENGTH: 217
<212> TYPE: PRT
<213> ORGANISM: Artificial sequence
<220> FEATURE:
<223> OTHER INFORMATION: Synthetic

<400> SEQUENCE: 823

Gly Ser Ser Gly Gly Gly Gly Ser Gly Gly Gly Gly Ser Ser Gly Met
1               5                   10                  15

Thr Tyr Lys Leu Ile Leu Asn Gly Lys Thr Leu Lys Gly Glu Thr Thr
            20                  25                  30

Thr Glu Ala Val Asp Ala Ala Thr Ala Glu Lys Val Phe Lys Gln Tyr
        35                  40                  45

Ala Asn Asp Asn Gly Val Asp Gly Glu Trp Thr Tyr Asp Asp Ala Thr
    50                  55                  60

Lys Thr Phe Thr Val Thr Glu Lys Pro Glu Val Ile Asp Ala Ser Glu
65                  70                  75                  80

Leu Thr Pro Ala Val Thr Thr Tyr Lys Leu Val Ile Asn Gly Lys Thr
                85                  90                  95

Leu Lys Gly Glu Thr Thr Thr Glu Ala Val Asp Ala Ala Thr Ala Glu
            100                 105                 110

Lys Val Phe Lys Gln Tyr Ala Asn Asp Asn Gly Val Asp Gly Glu Trp
            115                 120                 125

Thr Tyr Asp Asp Ala Thr Lys Thr Phe Thr Val Thr Glu Lys Pro Glu
    130                 135                 140

Val Ile Asp Ala Ser Glu Leu Thr Pro Ala Val Thr Thr Tyr Lys Leu
145                 150                 155                 160

Val Ile Asn Gly Lys Thr Leu Lys Gly Glu Thr Thr Thr Lys Ala Val
                165                 170                 175

Asp Ala Glu Thr Ala Glu Lys Ala Phe Lys Gln Tyr Ala Asn Asp Asn
            180                 185                 190

Gly Val Asp Gly Val Trp Thr Tyr Asp Asp Ala Thr Lys Thr Phe Thr
            195                 200                 205

Val Thr Glu His His His His His His
    210                 215
```

```
<210> SEQ ID NO 824
<211> LENGTH: 11
<212> TYPE: PRT
<213> ORGANISM: Artificial sequence
<220> FEATURE:
<223> OTHER INFORMATION: Synthetic

<400> SEQUENCE: 824

Val Ser Gly Trp Arg Leu Phe Lys Lys Ile Ser
1               5                   10
```

```
<210> SEQ ID NO 825
<211> LENGTH: 10
<212> TYPE: PRT
<213> ORGANISM: Artificial sequence
<220> FEATURE:
<223> OTHER INFORMATION: Synthetic

<400> SEQUENCE: 825
```

Val Ser Gly Trp Arg Leu Phe Lys Lys Ile
1               5                   10

<210> SEQ ID NO 826
<211> LENGTH: 13
<212> TYPE: PRT
<213> ORGANISM: Artificial sequence
<220> FEATURE:
<223> OTHER INFORMATION: Synthetic

<400> SEQUENCE: 826

Val Ser Val Ser Gly Trp Arg Leu Phe Lys Lys Ile Ser
1               5                   10

<210> SEQ ID NO 827
<211> LENGTH: 13
<212> TYPE: PRT
<213> ORGANISM: Artificial sequence
<220> FEATURE:
<223> OTHER INFORMATION: Synthetic

<400> SEQUENCE: 827

Gly Lys Met Leu Phe Arg Val Thr Ile Asn Ser Trp Lys
1               5                   10

<210> SEQ ID NO 828

<400> SEQUENCE: 828

000

<210> SEQ ID NO 829

<400> SEQUENCE: 829

000

<210> SEQ ID NO 830
<211> LENGTH: 363
<212> TYPE: DNA
<213> ORGANISM: Artificial sequence
<220> FEATURE:
<223> OTHER INFORMATION: Synthetic

<400> SEQUENCE: 830
atgaaacatc accatcacca tcatgtcttc acactcgacg atttcgttgg ggactgggaa        60
cagacagccg cctacaacct ggaccaagtc cttgaacagg gaggtgtgtc cagtttgctg       120
cagaatctcg ccgtgtccgt aactccgatc atgaggattg tccggagcgg tgaaaatgcc       180
ctgaagatcg acatccatgt catcatcccg tatgaaggtc tgagcgccga ccaaatggcc       240
cagatcgaag aggtgtttaa ggtggtgtac cctgtggatg atcatcactt taaggtgatc       300 ctgcccatg gcacactggt aatcgacggg gttacgccga acaagctgaa ctatttcgga        360
taa                                                                     363

<210> SEQ ID NO 831
<211> LENGTH: 120
<212> TYPE: PRT
<213> ORGANISM: Artificial sequence
<220> FEATURE:
<223> OTHER INFORMATION: Synthetic

<400> SEQUENCE: 831

Met Lys His His His His His His Val Phe Thr Leu Asp Asp Phe Val
1               5                   10                  15

-continued

```
Gly Asp Trp Glu Gln Thr Ala Ala Tyr Asn Leu Asp Gln Val Leu Glu
        20                  25                  30

Gln Gly Gly Val Ser Ser Leu Leu Gln Asn Leu Ala Val Ser Val Thr
        35                  40                  45

Pro Ile Met Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
                85                  90                  95

Phe Lys Val Ile Leu Pro Tyr Gly Thr Leu Val Ile Asp Gly Val Thr
            100                 105                 110

Pro Asn Lys Leu Asn Tyr Phe Gly
        115                 120
```

```
<210> SEQ ID NO 832
<211> LENGTH: 396
<212> TYPE: DNA
<213> ORGANISM: Artificial sequence
<220> FEATURE:
<223> OTHER INFORMATION: Synthetic

<400> SEQUENCE: 832
atgaaacatc accatcacca tcatgtcttc acactcgacg atttcgttgg ggactgggaa      60
cagacagccg cctacaacct ggaccaagtc cttgaacagg gaggtgtgtc cagtttgctg     120
cagaatctcg ccgtgtccgt aactccgatc atgaggattg tccggagcgg tgaaaatgcc     180
ctgaagatcg acatccatgt catcatcccg tatgaaggtc tgagcgccga ccaaatggcc     240
cagatcgaag aggtgtttaa ggtggtgtac cctgtggatg atcatcactt taaggtgatc     300
ctgccctatg gcacactggt aatcgacggg gttacgccga acaagctgaa ctatttcgga     360
cggccgtatg aaggcatcgc cgtgttcgac ggctaa                               396
```

```
<210> SEQ ID NO 833
<211> LENGTH: 131
<212> TYPE: PRT
<213> ORGANISM: Artificial sequence
<220> FEATURE:
<223> OTHER INFORMATION: Synthetic

<400> SEQUENCE: 833

Met Lys His His His His His His Val Phe Thr Leu Asp Asp Phe Val
1               5                   10                  15

Gly Asp Trp Glu Gln Thr Ala Ala Tyr Asn Leu Asp Gln Val Leu Glu
        20                  25                  30

Gln Gly Gly Val Ser Ser Leu Leu Gln Asn Leu Ala Val Ser Val Thr
        35                  40                  45

Pro Ile Met Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
                85                  90                  95

Phe Lys Val Ile Leu Pro Tyr Gly Thr Leu Val Ile Asp Gly Val Thr
            100                 105                 110

Pro Asn Lys Leu Asn Tyr Phe Gly Arg Pro Tyr Glu Gly Ile Ala Val
        115                 120                 125
```

```
Phe Asp Gly
    130

<210> SEQ ID NO 834
<211> LENGTH: 423
<212> TYPE: DNA
<213> ORGANISM: Artificial sequence
<220> FEATURE:
<223> OTHER INFORMATION: Synthetic

<400> SEQUENCE: 834
atgaaacatc accatcacca tcatgtcttc acactcgacg atttcgttgg ggactgggaa      60
cagacagccg cctacaacct ggaccaagtc cttgaacagg gaggtgtgtc cagtttgctg     120
cagaatctcg ccgtgtccgt aactccgatc atgaggattg tccggagcgg tgaaaatgcc     180
ctgaagatcg acatccatgt catcatcccg tatgaaggtc tgagcgccga ccaaatggcc     240
cagatcgaag aggtgtttaa ggtggtgtac cctgtggatg atcatcactt taaggtgatc     300 ctgcccctatg gcacactggt aatcgacggg gttacgccga acaagctgaa ctatttcgga     360
cggccgtatg aaggcatcgc cgtgttcgac ggcaaaaaga tcactaccac agggaccctg     420
taa                                                                   423

<210> SEQ ID NO 835
<211> LENGTH: 140
<212> TYPE: PRT
<213> ORGANISM: Artificial sequence
<220> FEATURE:
<223> OTHER INFORMATION: Synthetic

<400> SEQUENCE: 835

Met Lys His His His His His His Val Phe Thr Leu Asp Asp Phe Val
1               5                   10                  15

Gly Asp Trp Glu Gln Thr Ala Ala Tyr Asn Leu Asp Gln Val Leu Glu
            20                  25                  30

Gln Gly Gly Val Ser Ser Leu Leu Gln Asn Leu Ala Val Ser Val Thr
        35                  40                  45

Pro Ile Met Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
                85                  90                  95

Phe Lys Val Ile Leu Pro Tyr Gly Thr Leu Val Ile Asp Gly Val Thr
            100                 105                 110

Pro Asn Lys Leu Asn Tyr Phe Gly Arg Pro Tyr Glu Gly Ile Ala Val
        115                 120                 125

Phe Asp Gly Lys Lys Ile Thr Thr Thr Gly Thr Leu
    130                 135                 140

<210> SEQ ID NO 836
<211> LENGTH: 432
<212> TYPE: DNA
<213> ORGANISM: Artificial sequence
<220> FEATURE:
<223> OTHER INFORMATION: Synthetic

<400> SEQUENCE: 836
atgaaacatc accatcacca tcatgtcttc acactcgacg atttcgttgg ggactgggaa      60
```

```
cagacagccg cctacaacct ggaccaagtc cttgaacagg gaggtgtgtc cagtttgctg      120
cagaatctcg ccgtgtccgt aactccgatc atgaggattg tccggagcgg tgaaaatgcc      180
ctgaagatcg acatccatgt catcatcccg tatgaaggtc tgagcgccga ccaaatggcc      240
cagatcgaag aggtgtttaa ggtggtgtac cctgtggatg atcatcactt taaggtgatc      300
ctgccctatg gcacactggt aatcgacggg gttacgccga caagctgaa ctatttcgga      360 cggccgtatg aaggcatcgc cgtgttcgac ggcaaaaaga tcactaccac agggaccctg      420
tggaacggct aa                                                         432
```

<210> SEQ ID NO 837
<211> LENGTH: 143
<212> TYPE: PRT
<213> ORGANISM: Artificial sequence
<220> FEATURE:
<223> OTHER INFORMATION: Synthetic

<400> SEQUENCE: 837

```
Met Lys His His His His His His Val Phe Thr Leu Asp Asp Phe Val
1               5                   10                  15

Gly Asp Trp Glu Gln Thr Ala Ala Tyr Asn Leu Asp Gln Val Leu Glu
            20                  25                  30

Gln Gly Gly Val Ser Ser Leu Leu Gln Asn Leu Ala Val Ser Val Thr
        35                  40                  45

Pro Ile Met Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
                85                  90                  95

Phe Lys Val Ile Leu Pro Tyr Gly Thr Leu Val Ile Asp Gly Val Thr
            100                 105                 110

Pro Asn Lys Leu Asn Tyr Phe Gly Arg Pro Tyr Glu Gly Ile Ala Val
        115                 120                 125

Phe Asp Gly Lys Lys Ile Thr Thr Thr Gly Thr Leu Trp Asn Gly
    130                 135                 140
```

<210> SEQ ID NO 838
<211> LENGTH: 483
<212> TYPE: DNA
<213> ORGANISM: Artificial sequence
<220> FEATURE:
<223> OTHER INFORMATION: Synthetic

<400> SEQUENCE: 838

```
atggtttccg tgagcggctg gcggctgttc aagaagatta gcttcacact cgacgatttc       60
gttggggact gggaacagac agccgcctac aacctggacc aagtccttga acagggaggt      120
gtgtccagtt tgctgcagaa tctcgccgtg tccgtaactc cgatcatgag gattgtccgg      180
agcggtgaaa atgccctgaa gatcgacatc catgtcatca tcccgtatga aggtctgagc      240
gccgaccaaa tggcccagat cgaagaggtg tttaaggtgg tgtaccctgt ggatgatcat      300
cactttaagg tgatcctgcc ctatggcaca ctggtaatcg acggggttac gccgaacaag      360
ctgaactatt tcggacggcc gtatgaaggc atcgccgtgt cgacggcaa aaagatcact      420 accacaggga ccctgtggaa cggcaacaaa attatcgacg agcgcctgat cacccccgac      480
taa                                                                   483
```

<210> SEQ ID NO 839
<211> LENGTH: 160
<212> TYPE: PRT
<213> ORGANISM: Artificial sequence
<220> FEATURE:
<223> OTHER INFORMATION: Synthetic

<400> SEQUENCE: 839

Met Val Ser Val Ser Gly Trp Arg Leu Phe Lys Lys Ile Ser Phe Thr
1               5                   10                  15

Leu Asp Asp Phe Val Gly Asp Trp Glu Gln Thr Ala Ala Tyr Asn Leu
                20                  25                  30

Asp Gln Val Leu Glu Gln Gly Gly Val Ser Ser Leu Leu Gln Asn Leu
            35                  40                  45

Ala Val Ser Val Thr Pro Ile Met Arg Ile Val Arg Ser Gly Glu Asn
    50                  55                  60

Ala Leu Lys Ile Asp Ile His Val Ile Ile Pro Tyr Glu Gly Leu Ser
65                  70                  75                  80

Ala Asp Gln Met Ala Gln Ile Glu Glu Val Phe Lys Val Val Tyr Pro
                85                  90                  95

Val Asp Asp His His Phe Lys Val Ile Leu Pro Tyr Gly Thr Leu Val
            100                 105                 110

Ile Asp Gly Val Thr Pro Asn Lys Leu Asn Tyr Phe Gly Arg Pro Tyr
            115                 120                 125

Glu Gly Ile Ala Val Phe Asp Gly Lys Lys Ile Thr Thr Thr Gly Thr
        130                 135                 140

Leu Trp Asn Gly Asn Lys Ile Ile Asp Glu Arg Leu Ile Thr Pro Asp
145                 150                 155                 160

<210> SEQ ID NO 840
<211> LENGTH: 495
<212> TYPE: DNA
<213> ORGANISM: Artificial sequence
<220> FEATURE:
<223> OTHER INFORMATION: Synthetic

<400> SEQUENCE: 840
atggtttccg tgagcggctg gcggctgttc aagaagatta gcggcagctc cggtttcaca        60
ctcgacgatt tcgttgggga ctgggaacag acagccgcct acaacctgga ccaagtcctt       120
gaacagggag gtgtgtccag tttgctgcag aatctcgccg tgtccgtaac tccgatcatg       180
aggattgtcc ggagcggtga aaatgccctg aagatcgaca tccatgtcat catcccgtat       240
gaaggtctga gcgccgacca aatggcccag atcgaagagg tgtttaaggt ggtgtaccct       300
gtggatgatc atcactttaa ggtgatcctg ccctatggca cactggtaat cgacggggtt       360
acgccgaaca agctgaacta tttcggacgg ccgtatgaag gcatcgccgt gttcgacggc       420
aaaaagatca ctaccacagg gaccctgtgg aacggcaaca aaattatcga cgagcgcctg       480
atcacccccg actaa                                                        495

<210> SEQ ID NO 841
<211> LENGTH: 164
<212> TYPE: PRT
<213> ORGANISM: Artificial sequence
<220> FEATURE:
<223> OTHER INFORMATION: Synthetic

<400> SEQUENCE: 841

Met Val Ser Val Ser Gly Trp Arg Leu Phe Lys Lys Ile Ser Gly Ser

```
1               5                    10                   15

Ser Gly Phe Thr Leu Asp Asp Phe Val Gly Asp Trp Glu Gln Thr Ala
            20                   25                   30

Ala Tyr Asn Leu Asp Gln Val Leu Glu Gln Gly Gly Val Ser Ser Leu
            35                   40                   45

Leu Gln Asn Leu Ala Val Ser Val Thr Pro Ile Met Arg Ile Val Arg
       50                   55                   60

Ser Gly Glu Asn Ala Leu Lys Ile Asp Ile His Val Ile Ile Pro Tyr
65                   70                   75                   80

Glu Gly Leu Ser Ala Asp Gln Met Ala Gln Ile Glu Glu Val Phe Lys
                85                   90                   95

Val Val Tyr Pro Val Asp Asp His His Phe Lys Val Ile Leu Pro Tyr
            100                  105                  110

Gly Thr Leu Val Ile Asp Gly Val Thr Pro Asn Lys Leu Asn Tyr Phe
            115                  120                  125

Gly Arg Pro Tyr Glu Gly Ile Ala Val Phe Asp Gly Lys Lys Ile Thr
       130                  135                  140

Thr Thr Gly Thr Leu Trp Asn Gly Asn Lys Ile Ile Asp Glu Arg Leu
145                  150                  155                  160

Ile Thr Pro Asp
```

```
<210> SEQ ID NO 842
<211> LENGTH: 507
<212> TYPE: DNA
<213> ORGANISM: Artificial sequence
<220> FEATURE:
<223> OTHER INFORMATION: Synthetic

<400> SEQUENCE: 842
atggtttccg tgagcggctg gcggctgttc aagaagatta gcggctcgag cggtggctcg      60
agcggtttca cactcgacga tttcgttggg gactgggaac agacagccgc ctacaacctg     120
gaccaagtcc ttgaacaggg aggtgtgtcc agtttgctgc agaatctcgc cgtgtccgta     180
actccgatca tgaggattgt ccggagcggt gaaaatgccc tgaagatcga catccatgtc     240
atcatcccgt atgaaggtct gagcgccgac caaatggccc agatcgaaga ggtgtttaag     300
gtggtgtacc ctgtggatga tcatcacttt aaggtgatcc tgccctatgg cacactggta     360
atcgacgggg ttacgccgaa caagctgaac tatttcggac ggccgtatga aggcatcgcc     420
gtgttcgacg gcaaaaagat cactaccaca gggaccctgt ggaacggcaa caaaattatc     480
gacgagcgcc tgatcacccc cgactaa                                         507
```

```
<210> SEQ ID NO 843
<211> LENGTH: 168
<212> TYPE: PRT
<213> ORGANISM: Artificial sequence
<220> FEATURE:
<223> OTHER INFORMATION: Synthetic

<400> SEQUENCE: 843

Met Val Ser Val Ser Gly Trp Arg Leu Phe Lys Lys Ile Ser Gly Ser
1               5                    10                   15

Ser Gly Gly Ser Ser Gly Phe Thr Leu Asp Asp Phe Val Gly Asp Trp
            20                   25                   30

Glu Gln Thr Ala Ala Tyr Asn Leu Asp Gln Val Leu Glu Gln Gly Gly
            35                   40                   45

Val Ser Ser Leu Leu Gln Asn Leu Ala Val Ser Val Thr Pro Ile Met
```

-continued

```
      50                    55                    60

Arg Ile Val Arg Ser Gly Glu Asn Ala Leu Lys Ile Asp Ile His Val
65                    70                    75                    80

Ile Ile Pro Tyr Glu Gly Leu Ser Ala Asp Gln Met Ala Gln Ile Glu
                      85                    90                    95

Glu Val Phe Lys Val Val Tyr Pro Val Asp Asp His His Phe Lys Val
                     100                   105                   110

Ile Leu Pro Tyr Gly Thr Leu Val Ile Asp Gly Val Thr Pro Asn Lys
                 115                   120                   125

Leu Asn Tyr Phe Gly Arg Pro Tyr Glu Gly Ile Ala Val Phe Asp Gly
             130                   135                   140

Lys Lys Ile Thr Thr Thr Gly Thr Leu Trp Asn Gly Asn Lys Ile Ile
145                   150                   155                   160

Asp Glu Arg Leu Ile Thr Pro Asp
                 165
```

```
<210> SEQ ID NO 844
<211> LENGTH: 519
<212> TYPE: DNA
<213> ORGANISM: Artificial sequence
<220> FEATURE:
<223> OTHER INFORMATION: Synthetic

<400> SEQUENCE: 844
atggtttccg tgagcggctg gcggctgttc aagaagatta gcggctcgag cggtggctcg      60
agcggtggct cgagcggttt cacactcgac gatttcgttg gggactggga acagacagcc     120
gcctacaacc tggaccaagt ccttgaacag ggaggtgtgt ccagtttgct gcagaatctc     180
gccgtgtccg taactccgat catgaggatt gtccggagcg gtgaaaatgc cctgaagatc     240
gacatccatg tcatcatccc gtatgaaggt ctgagcgccg accaaatggc ccagatcgaa     300
gaggtgttta aggtggtgta ccctgtggat gatcatcact ttaaggtgat cctgccctat     360
ggcacactgg taatcgacgg ggttacgccg aacaagctga actatttcgg acggccgtat     420
gaaggcatcg ccgtgttcga cggcaaaaag atcactacca cagggaccct gtggaacggc     480
aacaaaatta tcgacgagcg cctgatcacc cccgactaa                            519
```

```
<210> SEQ ID NO 845
<211> LENGTH: 172
<212> TYPE: PRT
<213> ORGANISM: Artificial sequence
<220> FEATURE:
<223> OTHER INFORMATION: Synthetic

<400> SEQUENCE: 845

Met Val Ser Val Ser Gly Trp Arg Leu Phe Lys Lys Ile Ser Gly Ser
1                     5                    10                    15

Ser Gly Gly Ser Ser Gly Gly Ser Ser Gly Phe Thr Leu Asp Asp Phe
                      20                    25                    30

Val Gly Asp Trp Glu Gln Thr Ala Ala Tyr Asn Leu Asp Gln Val Leu
                 35                    40                    45

Glu Gln Gly Gly Val Ser Ser Leu Leu Gln Asn Leu Ala Val Ser Val
             50                    55                    60

Thr Pro Ile Met Arg Ile Val Arg Ser Gly Glu Asn Ala Leu Lys Ile
65                    70                    75                    80

Asp Ile His Val Ile Ile Pro Tyr Glu Gly Leu Ser Ala Asp Gln Met
                      85                    90                    95
```

```
Ala Gln Ile Glu Glu Val Phe Lys Val Val Tyr Pro Val Asp Asp His
            100                 105                 110

His Phe Lys Val Ile Leu Pro Tyr Gly Thr Leu Val Ile Asp Gly Val
        115                 120                 125

Thr Pro Asn Lys Leu Asn Tyr Phe Gly Arg Pro Tyr Glu Gly Ile Ala
    130                 135                 140

Val Phe Asp Gly Lys Lys Ile Thr Thr Thr Gly Thr Leu Trp Asn Gly
145                 150                 155                 160

Asn Lys Ile Ile Asp Glu Arg Leu Ile Thr Pro Asp
                165                 170
```

<210> SEQ ID NO 846
<211> LENGTH: 531
<212> TYPE: DNA
<213> ORGANISM: Artificial sequence
<220> FEATURE:
<223> OTHER INFORMATION: Synthetic

<400> SEQUENCE: 846

```
atggtttccg tgagcggctg gcggctgttc aagaagatta gcggctcgag cggtggctcg      60
agcggtggct cgagcggtgg ctcgagcggt ttcacactcg acgatttcgt tggggactgg     120
gaacagacag ccgcctacaa cctggaccaa gtccttgaac agggaggtgt gtccagtttg     180
ctgcagaatc tcgccgtgtc cgtaactccg atcatgagga ttgtccggag cggtgaaaat     240
gccctgaaga tcgacatcca tgtcatcatc ccgtatgaag gtctgagcgc cgaccaaatg     300
gcccagatcg aagaggtgtt taaggtggtg taccctgtgg atgatcatca ctttaaggtg     360
atcctgccct atggcacact ggtaatcgac ggggttacgc cgaacaagct gaactatttc     420
ggacggccgt atgaaggcat cgccgtgttc gacggcaaaa agatcactac cacagggacc     480
ctgtggaacg gcaacaaaat tatcgacgag cgcctgatca ccccgactaa                531
```

<210> SEQ ID NO 847
<211> LENGTH: 176
<212> TYPE: PRT
<213> ORGANISM: Artificial sequence
<220> FEATURE:
<223> OTHER INFORMATION: Synthetic

<400> SEQUENCE: 847

```
Met Val Ser Val Ser Gly Trp Arg Leu Phe Lys Lys Ile Ser Gly Ser
1               5                   10                  15

Ser Gly Gly Ser Ser Gly Gly Ser Ser Gly Gly Ser Ser Gly Phe Thr
            20                  25                  30

Leu Asp Asp Phe Val Gly Asp Trp Glu Gln Thr Ala Ala Tyr Asn Leu
        35                  40                  45

Asp Gln Val Leu Glu Gln Gly Gly Val Ser Ser Leu Leu Gln Asn Leu
    50                  55                  60

Ala Val Ser Val Thr Pro Ile Met Arg Ile Val Arg Ser Gly Glu Asn
65                  70                  75                  80

Ala Leu Lys Ile Asp Ile His Val Ile Ile Pro Tyr Glu Gly Leu Ser
                85                  90                  95

Ala Asp Gln Met Ala Gln Ile Glu Glu Val Phe Lys Val Val Tyr Pro
            100                 105                 110

Val Asp Asp His His Phe Lys Val Ile Leu Pro Tyr Gly Thr Leu Val
        115                 120                 125

Ile Asp Gly Val Thr Pro Asn Lys Leu Asn Tyr Phe Gly Arg Pro Tyr
    130                 135                 140
```

```
Glu Gly Ile Ala Val Phe Asp Gly Lys Lys Ile Thr Thr Thr Gly Thr
145                 150                 155                 160

Leu Trp Asn Gly Asn Lys Ile Ile Asp Glu Arg Leu Ile Thr Pro Asp
                165                 170                 175

<210> SEQ ID NO 848
<211> LENGTH: 543
<212> TYPE: DNA
<213> ORGANISM: Artificial sequence
<220> FEATURE:
<223> OTHER INFORMATION: Synthetic

<400> SEQUENCE: 848
atggtttccg tgagcggctg gcggctgttc aagaagatta gcggctcgag cggtggctcg        60
agcggtggct cgagcggtgg ctcgagcggt ggctcgagcg gtttcacact cgacgatttc       120
gttggggact gggaacagac agccgcctac aacctggacc aagtccttga acaggaggt       180 gtgtccagtt tgctgcagaa tctcgccgtg tccgtaactc cgatcatgag gattgtccgg       240
agcggtgaaa atgccctgaa gatcgacatc catgtcatca tcccgtatga aggtctgagc       300
gccgaccaaa tggcccagat cgaagaggtg tttaaggtgg tgtaccctgt ggatgatcat       360
cactttaagg tgatcctgcc ctatggcaca ctggtaatcg acggggttac gccgaacaag       420
ctgaactatt tcggacggcc gtatgaaggc atcgccgtgt tcgacggcaa aaagatcact       480
accacaggga ccctgtggaa cggcaacaaa attatcgacg agcgcctgat cacccccgac       540
taa                                                                      543

<210> SEQ ID NO 849
<211> LENGTH: 180
<212> TYPE: PRT
<213> ORGANISM: Artificial sequence
<220> FEATURE:
<223> OTHER INFORMATION: Synthetic

<400> SEQUENCE: 849

Met Val Ser Val Ser Gly Trp Arg Leu Phe Lys Lys Ile Ser Gly Ser
1               5                   10                  15

Ser Gly Gly Ser Ser Gly Gly Ser Ser Gly Gly Ser Ser Gly Gly Ser
                20                  25                  30

Ser Gly Phe Thr Leu Asp Asp Phe Val Gly Asp Trp Glu Gln Thr Ala
            35                  40                  45

Ala Tyr Asn Leu Asp Gln Val Leu Glu Gln Gly Gly Val Ser Ser Leu
        50                  55                  60

Leu Gln Asn Leu Ala Val Ser Val Thr Pro Ile Met Arg Ile Val Arg
65                  70                  75                  80

Ser Gly Glu Asn Ala Leu Lys Ile Asp Ile His Val Ile Ile Pro Tyr
                85                  90                  95

Glu Gly Leu Ser Ala Asp Gln Met Ala Gln Ile Glu Glu Val Phe Lys
            100                 105                 110

Val Val Tyr Pro Val Asp Asp His His Phe Lys Val Ile Leu Pro Tyr
        115                 120                 125

Gly Thr Leu Val Ile Asp Gly Val Thr Pro Asn Lys Leu Asn Tyr Phe
    130                 135                 140

Gly Arg Pro Tyr Glu Gly Ile Ala Val Phe Asp Gly Lys Lys Ile Thr
145                 150                 155                 160

Thr Thr Gly Thr Leu Trp Asn Gly Asn Lys Ile Ile Asp Glu Arg Leu
                165                 170                 175
```

Ile Thr Pro Asp
            180

<210> SEQ ID NO 850
<211> LENGTH: 537
<212> TYPE: DNA
<213> ORGANISM: Artificial sequence
<220> FEATURE:
<223> OTHER INFORMATION: Synthetic

<400> SEQUENCE: 850
atggtgagcg gctggcggct gttcaagaag attagcggct cgagcggtgg ctcgagcggt      60
ggctcgagcg gtggctcgag cggtggctcg agcggtttca cactcgacga tttcgttggg     120
gactgggaac agacagccgc ctacaacctg gaccaagtcc ttgaacaggg aggtgtgtcc     180
agtttgctgc agaatctcgc cgtgtccgta actccgatca tgaggattgt ccggagcggt     240
gaaaatgccc tgaagatcga catccatgtc atcatcccgt atgaaggtct gagcgccgac     300
caaatggccc agatcgaaga ggtgtttaag gtggtgtacc ctgtggatga tcatcacttt     360
aaggtgatcc tgccctatgg cacactggta atcgacgggg ttacgccgaa caagctgaac     420
tatttcggac ggccgtatga aggcatcgcc gtgttcgacg gcaaaaagat cactaccaca     480
gggaccctgt ggaacggcaa caaaattatc gacgagcgcc tgatcacccc cgactaa       537

<210> SEQ ID NO 851
<211> LENGTH: 178
<212> TYPE: PRT
<213> ORGANISM: Artificial sequence
<220> FEATURE:
<223> OTHER INFORMATION: Synthetic

<400> SEQUENCE: 851

Met Val Ser Gly Trp Arg Leu Phe Lys Lys Ile Ser Gly Ser Ser Gly
1               5                   10                  15

Gly Ser Ser Gly Gly Ser Ser Gly Gly Ser Ser Gly Gly Ser Ser Gly
            20                  25                  30

Phe Thr Leu Asp Asp Phe Val Gly Asp Trp Glu Gln Thr Ala Ala Tyr
        35                  40                  45

Asn Leu Asp Gln Val Leu Glu Gln Gly Gly Val Ser Ser Leu Leu Gln
    50                  55                  60

Asn Leu Ala Val Ser Val Thr Pro Ile Met Arg Ile Val Arg Ser Gly
65                  70                  75                  80

Glu Asn Ala Leu Lys Ile Asp Ile His Val Ile Ile Pro Tyr Glu Gly
                85                  90                  95

Leu Ser Ala Asp Gln Met Ala Gln Ile Glu Glu Val Phe Lys Val Val
            100                 105                 110

Tyr Pro Val Asp Asp His His Phe Lys Val Ile Leu Pro Tyr Gly Thr
        115                 120                 125

Leu Val Ile Asp Gly Val Thr Pro Asn Lys Leu Asn Tyr Phe Gly Arg
    130                 135                 140

Pro Tyr Glu Gly Ile Ala Val Phe Asp Gly Lys Lys Ile Thr Thr Thr
145                 150                 155                 160

Gly Thr Leu Trp Asn Gly Asn Lys Ile Ile Asp Glu Arg Leu Ile Thr
                165                 170                 175

Pro Asp

<210> SEQ ID NO 852

-continued

```
<211> LENGTH: 486
<212> TYPE: DNA
<213> ORGANISM: Artificial sequence
<220> FEATURE:
<223> OTHER INFORMATION: Synthetic

<400> SEQUENCE: 852
atggtcttca cactcgacga tttcgttggg gactgggaac agacagccgc ctacaacctg        60
gaccaagtcc ttgaacaggg aggtgtgtcc agtttgctgc agaatctcgc cgtgtccgta       120
actccgatca tgaggattgt ccggagcggt gaaaatgccc tgaagatcga catccatgtc       180
atcatcccgt atgaaggtct gagcgccgac caaatggccc agatcgaaga ggtgtttaag       240
gtggtgtacc ctgtggatga tcatcacttt aaggtgatcc tgccctatgg cacactggta       300
atcgacgggg ttacgccgaa caagctgaac tatttcggac ggccgtatga aggcatcgcc       360
gtgttcgacg gcaaaaagat cactaccaca gggaccctgt ggaacggcaa caaaattatc       420
gacgagcgcc tgatcacccc cgacgtttcc gtgagcggct ggcggctgtt caagaagatt       480
agctaa                                                                   486

<210> SEQ ID NO 853
<211> LENGTH: 161
<212> TYPE: PRT
<213> ORGANISM: Artificial sequence
<220> FEATURE:
<223> OTHER INFORMATION: Synthetic

<400> SEQUENCE: 853

Met Val Phe Thr Leu Asp Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Met Arg Ile Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Lys Leu Asn Tyr Phe
            100                 105                 110

Gly Arg Pro Tyr Glu Gly Ile Ala Val Phe Asp Gly Lys Lys Ile Thr
        115                 120                 125

Thr Thr Gly Thr Leu Trp Asn Gly Asn Lys Ile Ile Asp Glu Arg Leu
    130                 135                 140

Ile Thr Pro Asp Val Ser Val Ser Gly Trp Arg Leu Phe Lys Lys Ile
145                 150                 155                 160

Ser

<210> SEQ ID NO 854
<211> LENGTH: 498
<212> TYPE: DNA
<213> ORGANISM: Artificial sequence
<220> FEATURE:
<223> OTHER INFORMATION: Synthetic

<400> SEQUENCE: 854
atggtcttca cactcgacga tttcgttggg gactgggaac agacagccgc ctacaacctg        60
```

-continued

```
gaccaagtcc ttgaacaggg aggtgtgtcc agtttgctgc agaatctcgc cgtgtccgta    120
actccgatca tgaggattgt ccggagcggt gaaaatgccc tgaagatcga catccatgtc    180
atcatcccgt atgaaggtct gagcgccgac caaatggccc agatcgaaga ggtgtttaag    240
gtggtgtacc ctgtggatga tcatcacttt aaggtgatcc tgccctatgg cacactggta    300
atcgacgggg ttacgccgaa caagctgaac tatttcggac ggccgtatga aggcatcgcc    360
gtgttcgacg gcaaaaagat cactaccaca gggaccctgt ggaacggcaa caaaattatc    420
gacgagcgcc tgatcacccc cgacggctcg agcggtgttt ccgtgagcgg ctggcggctg    480
ttcaagaaga ttagctaa                                                  498
```

```
<210> SEQ ID NO 855
<211> LENGTH: 165
<212> TYPE: PRT
<213> ORGANISM: Artificial sequence
<220> FEATURE:
<223> OTHER INFORMATION: Synthetic

<400> SEQUENCE: 855

Met Val Phe Thr Leu Asp Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Met Arg Ile Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Lys Leu Asn Tyr Phe
            100                 105                 110

Gly Arg Pro Tyr Glu Gly Ile Ala Val Phe Asp Gly Lys Lys Ile Thr
        115                 120                 125

Thr Thr Gly Thr Leu Trp Asn Gly Asn Lys Ile Ile Asp Glu Arg Leu
    130                 135                 140

Ile Thr Pro Asp Gly Ser Ser Gly Val Ser Val Ser Gly Trp Arg Leu
145                 150                 155                 160

Phe Lys Lys Ile Ser
                165
```

```
<210> SEQ ID NO 856
<211> LENGTH: 510
<212> TYPE: DNA
<213> ORGANISM: Artificial sequence
<220> FEATURE:
<223> OTHER INFORMATION: Synthetic

<400> SEQUENCE: 856
atggtcttca cactcgacga tttcgttggg gactgggaac agacagccgc ctacaacctg     60
gaccaagtcc ttgaacaggg aggtgtgtcc agtttgctgc agaatctcgc cgtgtccgta    120
actccgatca tgaggattgt ccggagcggt gaaaatgccc tgaagatcga catccatgtc    180
atcatcccgt atgaaggtct gagcgccgac caaatggccc agatcgaaga ggtgtttaag    240
gtggtgtacc ctgtggatga tcatcacttt aaggtgatcc tgccctatgg cacactggta    300
```

-continued

```
atcgacgggg ttacgccgaa caagctgaac tatttcggac ggccgtatga aggcatcgcc      360
gtgttcgacg gcaaaaagat cactaccaca gggaccctgt ggaacggcaa caaaattatc      420
gacgagcgcc tgatcacccc cgacggctcg agcggtggct cgagcggtgt ttccgtgagc      480
ggctggcggc tgttcaagaa gattagctaa                                       510
```

```
<210> SEQ ID NO 857
<211> LENGTH: 169
<212> TYPE: PRT
<213> ORGANISM: Artificial sequence
<220> FEATURE:
<223> OTHER INFORMATION: Synthetic

<400> SEQUENCE: 857

Met Val Phe Thr Leu Asp Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Met Arg Ile Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Lys Leu Asn Tyr Phe
            100                 105                 110

Gly Arg Pro Tyr Glu Gly Ile Ala Val Phe Asp Gly Lys Lys Ile Thr
        115                 120                 125

Thr Thr Gly Thr Leu Trp Asn Gly Asn Lys Ile Ile Asp Glu Arg Leu
    130                 135                 140

Ile Thr Pro Asp Gly Ser Ser Gly Gly Ser Ser Gly Val Ser Val Ser
145                 150                 155                 160

Gly Trp Arg Leu Phe Lys Lys Ile Ser
                165
```

```
<210> SEQ ID NO 858
<211> LENGTH: 504
<212> TYPE: DNA
<213> ORGANISM: Artificial sequence
<220> FEATURE:
<223> OTHER INFORMATION: Synthetic

<400> SEQUENCE: 858
atggtcttca cactcgacga tttcgttggg gactgggaac agacagccgc ctacaacctg       60
gaccaagtcc ttgaacaggg aggtgtgtcc agtttgctgc agaatctcgc cgtgtccgta      120
actccgatca tgaggattgt ccggagcggt gaaaatgccc tgaagatcga catccatgtc      180
atcatcccgt atgaaggtct gagcgccgac caaatggccc agatcgaaga ggtgtttaag      240
gtggtgtacc ctgtggatga tcatcacttt aaggtgatcc tgccctatgg cacactggta      300
atcgacgggg ttacgccgaa caagctgaac tatttcggac ggccgtatga aggcatcgcc      360
gtgttcgacg gcaaaaagat cactaccaca gggaccctgt ggaacggcaa caaaattatc      420
gacgagcgcc tgatcacccc cgacggctcg agcggtggct cgagcggtgt gagcggctgg      480
cggctgttca agaagattag ctaa                                             504
```

<210> SEQ ID NO 859
<211> LENGTH: 167
<212> TYPE: PRT
<213> ORGANISM: Artificial sequence
<220> FEATURE:
<223> OTHER INFORMATION: Synthetic

<400> SEQUENCE: 859

```
Met Val Phe Thr Leu Asp Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Met Arg Ile Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Lys Leu Asn Tyr Phe
            100                 105                 110

Gly Arg Pro Tyr Glu Gly Ile Ala Val Phe Asp Gly Lys Lys Ile Thr
        115                 120                 125

Thr Thr Gly Thr Leu Trp Asn Gly Asn Lys Ile Ile Asp Glu Arg Leu
    130                 135                 140

Ile Thr Pro Asp Gly Ser Ser Gly Gly Ser Ser Gly Val Ser Gly Trp
145                 150                 155                 160

Arg Leu Phe Lys Lys Ile Ser
                165
```

<210> SEQ ID NO 860
<211> LENGTH: 501
<212> TYPE: DNA
<213> ORGANISM: Artificial sequence
<220> FEATURE:
<223> OTHER INFORMATION: Synthetic

<400> SEQUENCE: 860

```
atggtttccg tgagcggctg gcggctgttc aagaagatta gcttcacact cgacgatttc        60
gttggggact gggaacagac agccgcctac aacctggacc aagtccttga acagggaggt       120
gtgtccagtt tgctgcagaa tctcgccgtg tccgtaactc cgatcatgag gattgtccgg       180
agcggtgaaa atgccctgaa gatcgacatc catgtcatca tcccgtatga aggtctgagc       240
gccgaccaaa tggcccagat cgaagaggtg tttaaggtgg tgtaccctgt ggatgatcat       300
cactttaagg tgatcctgcc ctatggcaca ctggtaatcg acggggttac gccgaacaag       360
ctgaactatt tcggacggcc gtatgaaggc atcgccgtgt tcgacggcaa aaagatcact       420
accacaggga ccctgtggaa cggcaacaaa attatcgacg agcgcctgat cacccccgac       480
catcaccatc accatcatta a                                                 501
```

<210> SEQ ID NO 861
<211> LENGTH: 166
<212> TYPE: PRT
<213> ORGANISM: Artificial sequence
<220> FEATURE:
<223> OTHER INFORMATION: Synthetic

<400> SEQUENCE: 861

Met Val Ser Val Ser Gly Trp Arg Leu Phe Lys Lys Ile Ser Phe Thr
1               5                   10                  15

Leu Asp Asp Phe Val Gly Asp Trp Glu Gln Thr Ala Ala Tyr Asn Leu
            20                  25                  30

Asp Gln Val Leu Glu Gln Gly Gly Val Ser Ser Leu Leu Gln Asn Leu
            35                  40                  45

Ala Val Ser Val Thr Pro Ile Met Arg Ile Val Arg Ser Gly Glu Asn
        50                  55                  60

Ala Leu Lys Ile Asp Ile His Val Ile Ile Pro Tyr Glu Gly Leu Ser
65                  70                  75                  80

Ala Asp Gln Met Ala Gln Ile Glu Glu Val Phe Lys Val Val Tyr Pro
                85                  90                  95

Val Asp Asp His His Phe Lys Val Ile Leu Pro Tyr Gly Thr Leu Val
            100                 105                 110

Ile Asp Gly Val Thr Pro Asn Lys Leu Asn Tyr Phe Gly Arg Pro Tyr
            115                 120                 125

Glu Gly Ile Ala Val Phe Asp Gly Lys Lys Ile Thr Thr Thr Gly Thr
    130                 135                 140

Leu Trp Asn Gly Asn Lys Ile Ile Asp Glu Arg Leu Ile Thr Pro Asp
145                 150                 155                 160

His His His His His His
            165

<210> SEQ ID NO 862
<211> LENGTH: 513
<212> TYPE: DNA
<213> ORGANISM: Artificial sequence
<220> FEATURE:
<223> OTHER INFORMATION: Synthetic

<400> SEQUENCE: 862
atggtttccg tgagcggctg gcggctgttc aagaagatta gcggcagctc cggtttcaca      60
ctcgacgatt tcgttgggga ctgggaacag acagccgcct acaacctgga ccaagtcctt     120
gaacagggag gtgtgtccag tttgctgcag aatctcgccg tgtccgtaac tccgatcatg     180
aggattgtcc ggagcggtga aaatgccctg aagatcgaca tccatgtcat catcccgtat     240
gaaggtctga gcgccgacca aatggcccag atcgaagagg tgtttaaggt ggtgtaccct     300
gtggatgatc atcactttaa ggtgatcctg ccctatggca cactggtaat cgacggggtt     360
acgccgaaca agctgaacta tttcggacgg ccgtatgaag gcatcgccgt gttcgacggc     420
aaaaagatca ctaccacagg gaccctgtgg aacggcaaca aaattatcga cgagcgcctg     480
atcacccccg accatcacca tcaccatcat taa                                   513

<210> SEQ ID NO 863
<211> LENGTH: 170
<212> TYPE: PRT
<213> ORGANISM: Artificial sequence
<220> FEATURE:
<223> OTHER INFORMATION: Synthetic

<400> SEQUENCE: 863

Met Val Ser Val Ser Gly Trp Arg Leu Phe Lys Lys Ile Ser Gly Ser
1               5                   10                  15

Ser Gly Phe Thr Leu Asp Asp Phe Val Gly Asp Trp Glu Gln Thr Ala
            20                  25                  30

-continued

```
Ala Tyr Asn Leu Asp Gln Val Leu Glu Gln Gly Gly Val Ser Ser Leu
        35                  40                  45

Leu Gln Asn Leu Ala Val Ser Val Thr Pro Ile Met Arg Ile Val Arg
        50                  55                  60

Ser Gly Glu Asn Ala Leu Lys Ile Asp Ile His Val Ile Ile Pro Tyr
65                  70                  75                  80

Glu Gly Leu Ser Ala Asp Gln Met Ala Gln Ile Glu Glu Val Phe Lys
                85                  90                  95

Val Val Tyr Pro Val Asp Asp His His Phe Lys Val Ile Leu Pro Tyr
                100                 105                 110

Gly Thr Leu Val Ile Asp Gly Val Thr Pro Asn Lys Leu Asn Tyr Phe
                115                 120                 125

Gly Arg Pro Tyr Glu Gly Ile Ala Val Phe Asp Gly Lys Lys Ile Thr
        130                 135                 140

Thr Thr Gly Thr Leu Trp Asn Gly Asn Lys Ile Ile Asp Glu Arg Leu
145                 150                 155                 160

Ile Thr Pro Asp His His His His His His
                165                 170
```

<210> SEQ ID NO 864
<211> LENGTH: 525
<212> TYPE: DNA
<213> ORGANISM: Artificial sequence
<220> FEATURE:
<223> OTHER INFORMATION: Synthetic

<400> SEQUENCE: 864

```
atggtttccg tgagcggctg gcggctgttc aagaagatta gcggctcgag cggtggctcg      60
agcggtttca cactcgacga tttcgttggg gactgggaac agacagccgc ctacaacctg     120
gaccaagtcc ttgaacaggg aggtgtgtcc agtttgctgc agaatctcgc cgtgtccgta     180
actccgatca tgaggattgt ccggagcggt gaaaatgccc tgaagatcga catccatgtc     240
atcatcccgt atgaaggtct gagcgccgac caaatggccc agatcgaaga ggtgtttaag     300
gtggtgtacc ctgtggatga tcatcacttt aaggtgatcc tgccctatgg cacactggta     360
atcgacgggg ttacgccgaa caagctgaac tatttcggac ggccgtatga aggcatcgcc     420
gtgttcgacg gcaaaaagat cactaccaca gggaccctgt ggaacggcaa caaaattatc     480
gacgagcgcc tgatcacccc cgaccatcac catcaccatc attaa                     525
```

<210> SEQ ID NO 865
<211> LENGTH: 174
<212> TYPE: PRT
<213> ORGANISM: Artificial sequence
<220> FEATURE:
<223> OTHER INFORMATION: Synthetic

<400> SEQUENCE: 865

```
Met Val Ser Val Ser Gly Trp Arg Leu Phe Lys Lys Ile Ser Gly Ser
1               5                   10                  15

Ser Gly Gly Ser Ser Gly Phe Thr Leu Asp Asp Phe Val Gly Asp Trp
                20                  25                  30

Glu Gln Thr Ala Ala Tyr Asn Leu Asp Gln Val Leu Glu Gln Gly Gly
        35                  40                  45

Val Ser Ser Leu Leu Gln Asn Leu Ala Val Ser Val Thr Pro Ile Met
        50                  55                  60

Arg Ile Val Arg Ser Gly Glu Asn Ala Leu Lys Ile Asp Ile His Val
```

-continued

```
65                  70                  75                  80
Ile Ile Pro Tyr Glu Gly Leu Ser Ala Asp Gln Met Ala Gln Ile Glu
                85                  90                  95

Glu Val Phe Lys Val Val Tyr Pro Val Asp Asp His His Phe Lys Val
                100                 105                 110

Ile Leu Pro Tyr Gly Thr Leu Val Ile Asp Gly Val Thr Pro Asn Lys
                115                 120                 125

Leu Asn Tyr Phe Gly Arg Pro Tyr Glu Gly Ile Ala Val Phe Asp Gly
        130                 135                 140

Lys Lys Ile Thr Thr Thr Gly Thr Leu Trp Asn Gly Asn Lys Ile Ile
145                 150                 155                 160

Asp Glu Arg Leu Ile Thr Pro Asp His His His His His
                165                 170
```

<210> SEQ ID NO 866
<211> LENGTH: 537
<212> TYPE: DNA
<213> ORGANISM: Artificial sequence
<220> FEATURE:
<223> OTHER INFORMATION: Synthetic

<400> SEQUENCE: 866

```
atggtttccg tgagcggctg gcggctgttc aagaagatta gcggctcgag cggtggctcg      60
agcggtggct cgagcggttt cacactcgac gatttcgttg gggactggga acagacagcc     120
gcctacaacc tggaccaagt ccttgaacag ggaggtgtgt ccagtttgct gcagaatctc     180
gccgtgtccg taactccgat catgaggatt gtccggagcg gtgaaaatgc cctgaagatc     240
gacatccatg tcatcatccc gtatgaaggt ctgagcgccg accaaatggc ccagatcgaa     300
gaggtgttta aggtggtgta ccctgtggat gatcatcact ttaaggtgat cctgccctat     360
ggcacactgg taatcgacgg ggttacgccg aacaagctga actatttcgg acggccgtat     420
gaaggcatcg ccgtgttcga cggcaaaaag atcactacca cagggaccct gtggaacggc     480
aacaaaatta tcgacgagcg cctgatcacc cccgaccatc accatcacca tcattaa      537
```

<210> SEQ ID NO 867
<211> LENGTH: 178
<212> TYPE: PRT
<213> ORGANISM: Artificial sequence
<220> FEATURE:
<223> OTHER INFORMATION: Synthetic

<400> SEQUENCE: 867

```
Met Val Ser Val Ser Gly Trp Arg Leu Phe Lys Lys Ile Ser Gly Ser
1               5                   10                  15

Ser Gly Gly Ser Ser Gly Gly Ser Ser Gly Phe Thr Leu Asp Asp Phe
                20                  25                  30

Val Gly Asp Trp Glu Gln Thr Ala Ala Tyr Asn Leu Asp Gln Val Leu
        35                  40                  45

Glu Gln Gly Gly Val Ser Ser Leu Leu Gln Asn Leu Ala Val Ser Val
        50                  55                  60

Thr Pro Ile Met Arg Ile Val Arg Ser Gly Glu Asn Ala Leu Lys Ile
65                  70                  75                  80

Asp Ile His Val Ile Ile Pro Tyr Glu Gly Leu Ser Ala Asp Gln Met
                85                  90                  95

Ala Gln Ile Glu Glu Val Phe Lys Val Val Tyr Pro Val Asp Asp His
                100                 105                 110
```

```
His Phe Lys Val Ile Leu Pro Tyr Gly Thr Leu Val Ile Asp Gly Val
        115                 120                 125

Thr Pro Asn Lys Leu Asn Tyr Phe Gly Arg Pro Tyr Glu Gly Ile Ala
    130                 135                 140

Val Phe Asp Gly Lys Lys Ile Thr Thr Thr Gly Thr Leu Trp Asn Gly
145                 150                 155                 160

Asn Lys Ile Ile Asp Glu Arg Leu Ile Thr Pro Asp His His His His
                165                 170                 175

His His
```

```
<210> SEQ ID NO 868
<211> LENGTH: 549
<212> TYPE: DNA
<213> ORGANISM: Artificial sequence
<220> FEATURE:
<223> OTHER INFORMATION: Synthetic

<400> SEQUENCE: 868
atggtttccg tgagcggctg gcggctgttc aagaagatta gcggctcgag cggtggctcg      60
agcggtggct cgagcggtgg ctcgagcggt ttcacactcg acgatttcgt tggggactgg     120
gaacagacag ccgcctacaa cctggaccaa gtccttgaac agggaggtgt gtccagtttg     180
ctgcagaatc tcgccgtgtc cgtaactccg atcatgagga ttgtccggag cggtgaaaat     240
gccctgaaga tcgacatcca tgtcatcatc ccgtatgaag tctgagcgc cgaccaaatg      300 gcccagatcg aagaggtgtt taaggtggtg taccctgtgg atgatcatca ctttaaggtg     360
atcctgccct atggcacact ggtaatcgac ggggttacgc cgaacaagct gaactatttc     420
ggacggccgt atgaaggcat cgccgtgttc gacggcaaaa agatcactac cacagggacc     480
ctgtggaacg gcaacaaaat tatcgacgag cgcctgatca cccccgacca tcaccatcac     540
catcattaa                                                             549
```

```
<210> SEQ ID NO 869
<211> LENGTH: 182
<212> TYPE: PRT
<213> ORGANISM: Artificial sequence
<220> FEATURE:
<223> OTHER INFORMATION: Synthetic

<400> SEQUENCE: 869

Met Val Ser Val Ser Gly Trp Arg Leu Phe Lys Lys Ile Ser Gly Ser
1               5                   10                  15

Ser Gly Gly Ser Ser Gly Gly Ser Ser Gly Gly Ser Ser Gly Phe Thr
            20                  25                  30

Leu Asp Asp Phe Val Gly Asp Trp Glu Gln Thr Ala Ala Tyr Asn Leu
        35                  40                  45

Asp Gln Val Leu Glu Gln Gly Gly Val Ser Ser Leu Leu Gln Asn Leu
    50                  55                  60

Ala Val Ser Val Thr Pro Ile Met Arg Ile Val Arg Ser Gly Glu Asn
65                  70                  75                  80

Ala Leu Lys Ile Asp Ile His Val Ile Ile Pro Tyr Glu Gly Leu Ser
                85                  90                  95

Ala Asp Gln Met Ala Gln Ile Glu Glu Val Phe Lys Val Val Tyr Pro
            100                 105                 110

Val Asp Asp His His Phe Lys Val Ile Leu Pro Tyr Gly Thr Leu Val
        115                 120                 125

Ile Asp Gly Val Thr Pro Asn Lys Leu Asn Tyr Phe Gly Arg Pro Tyr
```

-continued

```
           130              135              140

Glu Gly Ile Ala Val Phe Asp Gly Lys Lys Ile Thr Thr Thr Gly Thr
145                  150              155                  160

Leu Trp Asn Gly Asn Lys Ile Ile Asp Glu Arg Leu Ile Thr Pro Asp
                 165              170                  175

His His His His His His
             180

<210> SEQ ID NO 870
<211> LENGTH: 555
<212> TYPE: DNA
<213> ORGANISM: Artificial sequence
<220> FEATURE:
<223> OTHER INFORMATION: Synthetic

<400> SEQUENCE: 870
atggtgagcg gctggcggct gttcaagaag attagcggct cgagcggtgg ctcgagcggt     60
ggctcgagcg gtggctcgag cggtggctcg agcggtttca cactcgacga tttcgttggg    120
gactgggaac agacagccgc ctacaacctg gaccaagtcc ttgaacaggg aggtgtgtcc    180
agtttgctgc agaatctcgc cgtgtccgta actccgatca tgaggattgt ccggagcggt    240
gaaaatgccc tgaagatcga catccatgtc atcatcccgt atgaaggtct gagcgccgac    300
caaatggccc agatcgaaga ggtgtttaag gtggtgtacc ctgtggatga tcatcacttt    360
aaggtgatcc tgccctatgg cacactggta atcgacgggg ttacgccgaa caagctgaac    420
tatttcggac ggccgtatga aggcatcgcc gtgttcgacg gcaaaaagat cactaccaca    480
gggaccctgt ggaacggcaa caaaattatc gacgagcgcc tgatcacccc cgaccatcac    540
catcaccatc attaa                                                     555

<210> SEQ ID NO 871
<211> LENGTH: 184
<212> TYPE: PRT
<213> ORGANISM: Artificial sequence
<220> FEATURE:
<223> OTHER INFORMATION: Synthetic

<400> SEQUENCE: 871

Met Val Ser Gly Trp Arg Leu Phe Lys Lys Ile Ser Gly Ser Ser Gly
1               5                  10                  15

Gly Ser Ser Gly Gly Ser Ser Gly Gly Ser Ser Gly Gly Ser Ser Gly
             20                  25                  30

Phe Thr Leu Asp Asp Phe Val Gly Asp Trp Glu Gln Thr Ala Ala Tyr
         35                  40                  45

Asn Leu Asp Gln Val Leu Glu Gln Gly Gly Val Ser Ser Leu Leu Gln
     50                  55                  60

Asn Leu Ala Val Ser Val Thr Pro Ile Met Arg Ile Val Arg Ser Gly
65                  70                  75                  80

Glu Asn Ala Leu Lys Ile Asp Ile His Val Ile Ile Pro Tyr Glu Gly
                 85                  90                  95

Leu Ser Ala Asp Gln Met Ala Gln Ile Glu Glu Val Phe Lys Val Val
             100                 105                 110

Tyr Pro Val Asp Asp His His Phe Lys Val Ile Leu Pro Tyr Gly Thr
         115                 120                 125

Leu Val Ile Asp Gly Val Thr Pro Asn Lys Leu Asn Tyr Phe Gly Arg
     130                 135                 140

Pro Tyr Glu Gly Ile Ala Val Phe Asp Gly Lys Lys Ile Thr Thr Thr
```

```
145           150           155           160

Gly Thr Leu Trp Asn Gly Asn Lys Ile Ile Asp Glu Arg Leu Ile Thr
          165           170           175

Pro Asp His His His His His His
          180

<210> SEQ ID NO 872
<211> LENGTH: 561
<212> TYPE: DNA
<213> ORGANISM: Artificial sequence
<220> FEATURE:
<223> OTHER INFORMATION: Synthetic

<400> SEQUENCE: 872
atggtttccg tgagcggctg gcggctgttc aagaagatta gcggctcgag cggtggctcg       60
agcggtggct cgagcggtgg ctcgagcggt ggctcgagcg gtttcacact cgacgatttc      120
gttggggact gggaacagac agccgcctac aacctggacc aagtccttga acagggaggt      180
gtgtccagtt tgctgcagaa tctcgccgtg tccgtaactc cgatcatgag gattgtccgg      240
agcggtgaaa atgccctgaa gatcgacatc catgtcatca tcccgtatga aggtctgagc      300
gccgaccaaa tggcccagat cgaagaggtg tttaaggtgg tgtaccctgt ggatgatcat      360
cactttaagg tgatcctgcc ctatggcaca ctggtaatcg acggggttac gccgaacaag      420
ctgaactatt tcggacggcc gtatgaaggc atcgccgtgt tcgacggcaa aaagatcact      480
accacaggga ccctgtggaa cggcaacaaa attatcgacg agcgcctgat cacccccgac      540
catcaccatc accatcatta a                                                561

<210> SEQ ID NO 873
<211> LENGTH: 186
<212> TYPE: PRT
<213> ORGANISM: Artificial sequence
<220> FEATURE:
<223> OTHER INFORMATION: Synthetic

<400> SEQUENCE: 873

Met Val Ser Val Ser Gly Trp Arg Leu Phe Lys Lys Ile Ser Gly Ser
1               5                   10                  15

Ser Gly Gly Ser Ser Gly Gly Ser Ser Gly Gly Ser Ser Gly Gly Ser
            20                  25                  30

Ser Gly Phe Thr Leu Asp Asp Phe Val Gly Asp Trp Glu Gln Thr Ala
        35                  40                  45

Ala Tyr Asn Leu Asp Gln Val Leu Glu Gln Gly Gly Val Ser Ser Leu
    50                  55                  60

Leu Gln Asn Leu Ala Val Ser Val Thr Pro Ile Met Arg Ile Val Arg
65                  70                  75                  80

Ser Gly Glu Asn Ala Leu Lys Ile Asp Ile His Val Ile Ile Pro Tyr
                85                  90                  95

Glu Gly Leu Ser Ala Asp Gln Met Ala Gln Ile Glu Glu Val Phe Lys
            100                 105                 110

Val Val Tyr Pro Val Asp Asp His His Phe Lys Val Ile Leu Pro Tyr
        115                 120                 125

Gly Thr Leu Val Ile Asp Gly Val Thr Pro Asn Lys Leu Asn Tyr Phe
        130                 135                 140

Gly Arg Pro Tyr Glu Gly Ile Ala Val Phe Asp Gly Lys Lys Ile Thr
145                 150                 155                 160

Thr Thr Gly Thr Leu Trp Asn Gly Asn Lys Ile Ile Asp Glu Arg Leu
```

```
                  165                 170                 175
Ile Thr Pro Asp His His His His His His
                  180                 185

<210> SEQ ID NO 874
<211> LENGTH: 507
<212> TYPE: DNA
<213> ORGANISM: Artificial sequence
<220> FEATURE:
<223> OTHER INFORMATION: Synthetic

<400> SEQUENCE: 874
atgaaacatc accatcacca tcatgtcttc acactcgacg atttcgttgg ggactgggaa      60
cagacagccg cctacaacct ggaccaagtc cttgaacagg gaggtgtgtc cagtttgctg     120
cagaatctcg ccgtgtccgt aactccgatc atgaggattg tccggagcgg tgaaaatgcc     180
ctgaagatcg acatccatgt catcatcccg tatgaaggtc tgagcgccga ccaaatggcc     240
cagatcgaag aggtgtttaa ggtggtgtac cctgtggatg atcatcactt taaggtgatc     300
ctgccctatg gcacactggt aatcgacggg gttacgccga caagctgaa ctatttcgga     360 cggccgtatg aaggcatcgc cgtgttcgac ggcaaaaaga tcactaccac agggaccctg     420
tggaacggca acaaaattat cgacgagcgc ctgatcaccc ccgacgtttc cgtgagcggc     480
tggcggctgt tcaagaagat tagctaa                                        507

<210> SEQ ID NO 875
<211> LENGTH: 168
<212> TYPE: PRT
<213> ORGANISM: Artificial sequence
<220> FEATURE:
<223> OTHER INFORMATION: Synthetic

<400> SEQUENCE: 875

Met Lys His His His His His His Val Phe Thr Leu Asp Asp Phe Val
1               5                   10                  15

Gly Asp Trp Glu Gln Thr Ala Ala Tyr Asn Leu Asp Gln Val Leu Glu
                20                  25                  30

Gln Gly Gly Val Ser Ser Leu Leu Gln Asn Leu Ala Val Ser Val Thr
            35                  40                  45

Pro Ile Met Arg Ile Val Arg Ser Gly Glu Asn Ala Leu Lys Ile Asp
        50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
                85                  90                  95

Phe Lys Val Ile Leu Pro Tyr Gly Thr Leu Val Ile Asp Gly Val Thr
                100                 105                 110

Pro Asn Lys Leu Asn Tyr Phe Gly Arg Pro Tyr Glu Gly Ile Ala Val
        115                 120                 125

Phe Asp Gly Lys Lys Ile Thr Thr Thr Gly Thr Leu Trp Asn Gly Asn
        130                 135                 140

Lys Ile Ile Asp Glu Arg Leu Ile Thr Pro Asp Val Ser Val Ser Gly
145                 150                 155                 160

Trp Arg Leu Phe Lys Lys Ile Ser
                165

<210> SEQ ID NO 876
<211> LENGTH: 519
```

<212> TYPE: DNA
<213> ORGANISM: Artificial sequence
<220> FEATURE:
<223> OTHER INFORMATION: Synthetic

<400> SEQUENCE: 876

```
atgaaacatc accatcacca tcatgtcttc acactcgacg atttcgttgg ggactgggaa      60
cagacagccg cctacaacct ggaccaagtc cttgaacagg gaggtgtgtc cagtttgctg     120
cagaatctcg ccgtgtccgt aactccgatc atgaggattg tccggagcgg tgaaaatgcc     180
ctgaagatcg acatccatgt catcatcccg tatgaaggtc tgagcgccga ccaaatggcc     240
cagatcgaag aggtgtttaa ggtggtgtac cctgtggatg atcatcactt taaggtgatc     300
ctgccctatg gcacactggt aatcgacggg gttacgccga acaagctgaa ctatttcgga     360
cggccgtatg aaggcatcgc cgtgttcgac ggcaaaaaga tcactaccac agggaccctg     420
tggaacggca acaaaattat cgacgagcgc ctgatcaccc ccgacggctc gagcggtgtt     480
tccgtgagcg gctggcggct gttcaagaag attagctaa                           519
```

<210> SEQ ID NO 877
<211> LENGTH: 172
<212> TYPE: PRT
<213> ORGANISM: Artificial sequence
<220> FEATURE:
<223> OTHER INFORMATION: Synthetic

<400> SEQUENCE: 877

```
Met Lys His His His His His His Val Phe Thr Leu Asp Asp Phe Val
1               5                   10                  15

Gly Asp Trp Glu Gln Thr Ala Ala Tyr Asn Leu Asp Gln Val Leu Glu
            20                  25                  30

Gln Gly Gly Val Ser Ser Leu Leu Gln Asn Leu Ala Val Ser Val Thr
        35                  40                  45

Pro Ile Met Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
                85                  90                  95

Phe Lys Val Ile Leu Pro Tyr Gly Thr Leu Val Ile Asp Gly Val Thr
            100                 105                 110

Pro Asn Lys Leu Asn Tyr Phe Gly Arg Pro Tyr Glu Gly Ile Ala Val
        115                 120                 125

Phe Asp Gly Lys Lys Ile Thr Thr Thr Gly Thr Leu Trp Asn Gly Asn
    130                 135                 140

Lys Ile Ile Asp Glu Arg Leu Ile Thr Pro Asp Gly Ser Ser Gly Val
145                 150                 155                 160

Ser Val Ser Gly Trp Arg Leu Phe Lys Lys Ile Ser
                165                 170
```

<210> SEQ ID NO 878
<211> LENGTH: 525
<212> TYPE: DNA
<213> ORGANISM: Artificial sequence
<220> FEATURE:
<223> OTHER INFORMATION: Synthetic

<400> SEQUENCE: 878

```
atgaaacatc accatcacca tcatgtcttc acactcgacg atttcgttgg ggactgggaa      60
```

-continued

```
cagacagccg cctacaacct ggaccaagtc cttgaacagg gaggtgtgtc cagtttgctg      120
cagaatctcg ccgtgtccgt aactccgatc atgaggattg tccggagcgg tgaaaatgcc      180
ctgaagatcg acatccatgt catcatcccg tatgaaggtc tgagcgccga ccaaatggcc      240
cagatcgaag aggtgtttaa ggtggtgtac cctgtggatg atcatcactt taaggtgatc      300
ctgccctatg gcacactggt aatcgacggg gttacgccga acaagctgaa ctatttcgga      360
cggccgtatg aaggcatcgc cgtgttcgac ggcaaaaaga tcactaccac agggaccctg      420
tggaacggca acaaaattat cgacgagcgc ctgatcaccc ccgacggctc gagcggtggc      480
tcgagcggtg tgagcggctg gcggctgttc aagaagatta gctaa                      525
```

```
<210> SEQ ID NO 879
<211> LENGTH: 174
<212> TYPE: PRT
<213> ORGANISM: Artificial sequence
<220> FEATURE:
<223> OTHER INFORMATION: Synthetic

<400> SEQUENCE: 879

Met Lys His His His His His His Val Phe Thr Leu Asp Asp Phe Val
1               5                   10                  15

Gly Asp Trp Glu Gln Thr Ala Ala Tyr Asn Leu Asp Gln Val Leu Glu
            20                  25                  30

Gln Gly Gly Val Ser Ser Leu Leu Gln Asn Leu Ala Val Ser Val Thr
            35                  40                  45

Pro Ile Met Arg Ile Val Arg Ser Gly Glu Asn Ala Leu Lys Ile Asp
        50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
                85                  90                  95

Phe Lys Val Ile Leu Pro Tyr Gly Thr Leu Val Ile Asp Gly Val Thr
                100                 105                 110

Pro Asn Lys Leu Asn Tyr Phe Gly Arg Pro Tyr Glu Gly Ile Ala Val
            115                 120                 125

Phe Asp Gly Lys Lys Ile Thr Thr Thr Gly Thr Leu Trp Asn Gly Asn
        130                 135                 140

Lys Ile Ile Asp Glu Arg Leu Ile Thr Pro Asp Gly Ser Ser Gly Gly
145                 150                 155                 160

Ser Ser Gly Val Ser Gly Trp Arg Leu Phe Lys Lys Ile Ser
                165                 170
```

```
<210> SEQ ID NO 880
<211> LENGTH: 531
<212> TYPE: DNA
<213> ORGANISM: Artificial sequence
<220> FEATURE:
<223> OTHER INFORMATION: Synthetic

<400> SEQUENCE: 880
atgaaacatc accatcacca tcatgtcttc acactcgacg atttcgttgg ggactgggaa       60
cagacagccg cctacaacct ggaccaagtc cttgaacagg gaggtgtgtc cagtttgctg      120
cagaatctcg ccgtgtccgt aactccgatc atgaggattg tccggagcgg tgaaaatgcc      180
ctgaagatcg acatccatgt catcatcccg tatgaaggtc tgagcgccga ccaaatggcc      240
cagatcgaag aggtgtttaa ggtggtgtac cctgtggatg atcatcactt taaggtgatc      300
```

579 580

-continued

```
ctgccctatg gcacactggt aatcgacggg gttacgccga acaagctgaa ctatttcgga    360
cggccgtatg aaggcatcgc cgtgttcgac ggcaaaaaga tcactaccac agggaccctg    420
tggaacggca acaaaattat cgacgagcgc ctgatcaccc ccgacggctc gagcggtggc    480
tcgagcggtg tttccgtgag cggctggcgg ctgttcaaga agattagcta a             531
```

```
<210> SEQ ID NO 881
<211> LENGTH: 176
<212> TYPE: PRT
<213> ORGANISM: Artificial sequence
<220> FEATURE:
<223> OTHER INFORMATION: Synthetic

<400> SEQUENCE: 881

Met Lys His His His His His His Val Phe Thr Leu Asp Asp Phe Val
1               5                   10                  15

Gly Asp Trp Glu Gln Thr Ala Ala Tyr Asn Leu Asp Gln Val Leu Glu
            20                  25                  30

Gln Gly Gly Val Ser Ser Leu Leu Gln Asn Leu Ala Val Ser Val Thr
        35                  40                  45

Pro Ile Met Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
            85                  90                  95

Phe Lys Val Ile Leu Pro Tyr Gly Thr Leu Val Ile Asp Gly Val Thr
            100                 105                 110

Pro Asn Lys Leu Asn Tyr Phe Gly Arg Pro Tyr Glu Gly Ile Ala Val
        115                 120                 125

Phe Asp Gly Lys Lys Ile Thr Thr Thr Gly Thr Leu Trp Asn Gly Asn
    130                 135                 140

Lys Ile Ile Asp Glu Arg Leu Ile Thr Pro Asp Gly Ser Ser Gly Gly
145                 150                 155                 160

Ser Ser Gly Val Ser Val Ser Gly Trp Arg Leu Phe Lys Lys Ile Ser
                165                 170                 175
```

```
<210> SEQ ID NO 882
<211> LENGTH: 498
<212> TYPE: DNA
<213> ORGANISM: Artificial sequence
<220> FEATURE:
<223> OTHER INFORMATION: Synthetic

<400> SEQUENCE: 882
atggtcttca cactcgaaga tttcgttggg gactgggaac agacagccgc ctacaacctg     60
gaccaagtcc ttgaacaggg aggtgtgtcc agtttgctgc agaatctcgc cgtgtccgta    120
actccgatcc aaaggattgt ccggagcggt gaaaatgccc tgaagatcga catccatgtc    180
atcatcccgt atgaaggtct gagcgccgac caaatggccc agatcgaaga ggtgtttaag    240
gtggtgtacc ctgtggatga tcatcacttt aaggtgatcc tgccctatgg cacactggta    300
atcgacgggg ttacgccgaa catgctgaac tatttcggac ggccgtatga aggcatcgcc    360
gtgttcgacg gcaaaaagat cactgtaaca gggaccctgt ggaacggcaa caaaattatc    420
gacgagcgcc tgatcacccc cgacggctcc atgctgttcc gagtaaccat caacagccat    480
catcaccatc accactaa                                                  498
```

<210> SEQ ID NO 883
<211> LENGTH: 165
<212> TYPE: PRT
<213> ORGANISM: Artificial sequence
<220> FEATURE:
<223> OTHER INFORMATION: Synthetic

<400> SEQUENCE: 883

```
Met Val Phe Thr Leu Glu Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Gln Arg Ile Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Met Leu Asn Tyr Phe
            100                 105                 110

Gly Arg Pro Tyr Glu Gly Ile Ala Val Phe Asp Gly Lys Lys Ile Thr
            115                 120                 125

Val Thr Gly Thr Leu Trp Asn Gly Asn Lys Ile Ile Asp Glu Arg Leu
    130                 135                 140

Ile Thr Pro Asp Gly Ser Met Leu Phe Arg Val Thr Ile Asn Ser His
145                 150                 155                 160

His His His His His
                165
```

<210> SEQ ID NO 884
<211> LENGTH: 501
<212> TYPE: DNA
<213> ORGANISM: Artificial sequence
<220> FEATURE:
<223> OTHER INFORMATION: Synthetic

<400> SEQUENCE: 884

```
atggtgagcg gctggcggct gttcaagaag attagccacc atcaccatca ccatcatcac      60
ttcacactcg acgatttcgt tggggactgg aacagacag ccgcctacaa cctggaccaa     120
gtccttgaac agggaggtgt gtccagtttg ctgcagaatc tcgccgtgtc cgtaactccg     180
atcatgagga ttgtccggag cggtgaaaat gccctgaaga tcgacatcca tgtcatcatc     240
ccgtatgaag gtctgagcgc cgaccaaatg gcccagatcg aagaggtgtt taaggtggtg     300
taccctgtgg atgatcatca ctttaaggtg atcctgccct atggcacact ggtaatcgac     360
ggggttacgc cgaacaagct gaactatttc ggacggccgt atgaaggcat cgccgtgttc     420
gacggcaaaa agatcactac cacagggacc ctgtggaacg gcaacaaaat tatcgacgag     480
cgcctgatca cccccgacta a                                               501
```

<210> SEQ ID NO 885
<211> LENGTH: 166
<212> TYPE: PRT
<213> ORGANISM: Artificial sequence
<220> FEATURE:
<223> OTHER INFORMATION: Synthetic

<400> SEQUENCE: 885

```
Met Val Ser Gly Trp Arg Leu Phe Lys Lys Ile Ser His His His His
1               5                   10                  15

His His His His Phe Thr Leu Asp Asp Phe Val Gly Asp Trp Glu Gln
                20                  25                  30

Thr Ala Ala Tyr Asn Leu Asp Gln Val Leu Glu Gln Gly Gly Val Ser
        35                  40                  45

Ser Leu Leu Gln Asn Leu Ala Val Ser Val Thr Pro Ile Met Arg Ile
    50                  55                  60

Val Arg Ser Gly Glu Asn Ala Leu Lys Ile Asp Ile His Val Ile Ile
65                  70                  75                  80

Pro Tyr Glu Gly Leu Ser Ala Asp Gln Met Ala Gln Ile Glu Glu Val
                85                  90                  95

Phe Lys Val Val Tyr Pro Val Asp Asp His His Phe Lys Val Ile Leu
            100                 105                 110

Pro Tyr Gly Thr Leu Val Ile Asp Gly Val Thr Pro Asn Lys Leu Asn
        115                 120                 125

Tyr Phe Gly Arg Pro Tyr Glu Gly Ile Ala Val Phe Asp Gly Lys Lys
    130                 135                 140

Ile Thr Thr Thr Gly Thr Leu Trp Asn Gly Asn Lys Ile Ile Asp Glu
145                 150                 155                 160

Arg Leu Ile Thr Pro Asp
                165
```

<210> SEQ ID NO 886
<211> LENGTH: 510
<212> TYPE: DNA
<213> ORGANISM: Artificial sequence
<220> FEATURE:
<223> OTHER INFORMATION: Synthetic

<400> SEQUENCE: 886

```
atgaaacatc accatcacca tcatgtgagc ggctggcggc tgttcaagaa gattagcggc        60
agctccggtt tcacactcga cgatttcgtt ggggactggg aacagacagc cgcctacaac       120
ctggaccaag tccttgaaca gggaggtgtg tccagtttgc tgcagaatct cgccgtgtcc       180
gtaactccga tcatgaggat tgtccggagc ggtgaaaatg ccctgaagat cgacatccat       240
gtcatcatcc cgtatgaagg tctgagcgcc gaccaaatgg cccagatcga agaggtgttt       300
aaggtggtgt accctgtgga tgatcatcac tttaaggtga tcctgcccta tggcacactg       360
gtaatcgacg gggttacgcc gaacaagctg aactatttcg gacggccgta tgaaggcatc       420
gccgtgttcg acggcaaaaa gatcactacc acagggaccc tgtggaacgg caacaaaatt       480
atcgacgagc gcctgatcac ccccgactaa                                        510
```

<210> SEQ ID NO 887
<211> LENGTH: 169
<212> TYPE: PRT
<213> ORGANISM: Artificial sequence
<220> FEATURE:
<223> OTHER INFORMATION: Synthetic

<400> SEQUENCE: 887

```
Met Lys His His His His His His Val Ser Gly Trp Arg Leu Phe Lys
1               5                   10                  15

Lys Ile Ser Gly Ser Ser Gly Phe Thr Leu Asp Asp Phe Val Gly Asp
                20                  25                  30
```

```
Trp Glu Gln Thr Ala Ala Tyr Asn Leu Asp Gln Val Leu Glu Gln Gly
        35                  40                  45

Gly Val Ser Ser Leu Leu Gln Asn Leu Ala Val Ser Val Thr Pro Ile
    50                  55                  60

Met Arg Ile Val Arg Ser Gly Glu Asn Ala Leu Lys Ile Asp Ile His
65                  70                  75                  80

Val Ile Ile Pro Tyr Glu Gly Leu Ser Ala Asp Gln Met Ala Gln Ile
                85                  90                  95

Glu Glu Val Phe Lys Val Val Tyr Pro Val Asp Asp His His Phe Lys
                100                 105                 110

Val Ile Leu Pro Tyr Gly Thr Leu Val Ile Asp Gly Val Thr Pro Asn
        115                 120                 125

Lys Leu Asn Tyr Phe Gly Arg Pro Tyr Glu Gly Ile Ala Val Phe Asp
        130                 135                 140

Gly Lys Lys Ile Thr Thr Thr Gly Thr Leu Trp Asn Gly Asn Lys Ile
145                 150                 155                 160

Ile Asp Glu Arg Leu Ile Thr Pro Asp
                165
```

```
<210> SEQ ID NO 888
<211> LENGTH: 507
<212> TYPE: DNA
<213> ORGANISM: Artificial sequence
<220> FEATURE:
<223> OTHER INFORMATION: Synthetic

<400> SEQUENCE: 888
atggtgagcg ctggcggct gttcaagaag attagcggca gctccggttt cacactcgac      60
gatttcgttg gggactggga acagacagcc gcctacaacc tggaccaagt ccttgaacag     120
ggaggtgtgt ccagtttgct gcagaatctc gccgtgtccg taactccgat catgaggatt     180
gtccggagcg gtgaaaatgc cctgaagatc gacatccatg tcatcatccc gtatgaaggt     240
ctgagcgccg accaaatggc ccagatcgaa gaggtgttta aggtggtgta ccctgtggat     300
gatcatcact ttaaggtgat cctgccctat ggcacactgg taatcgacgg ggttacgccg     360
aacaagctga actatttcgg acggccgtat gaaggcatcg ccgtgttcga cggcaaaaag     420
atcactacca cagggaccct gtggaacggc aacaaaatta tcgacgagcg cctgatcacc     480
cccgaccatc accatcacca tcattaa                                        507
```

```
<210> SEQ ID NO 889
<211> LENGTH: 168
<212> TYPE: PRT
<213> ORGANISM: Artificial sequence
<220> FEATURE:
<223> OTHER INFORMATION: Synthetic

<400> SEQUENCE: 889

Met Val Ser Gly Trp Arg Leu Phe Lys Lys Ile Ser Gly Ser Ser Gly
1               5                   10                  15

Phe Thr Leu Asp Asp Phe Val Gly Asp Trp Glu Gln Thr Ala Ala Tyr
                20                  25                  30

Asn Leu Asp Gln Val Leu Glu Gln Gly Gly Val Ser Ser Leu Leu Gln
        35                  40                  45

Asn Leu Ala Val Ser Val Thr Pro Ile Met Arg Ile Val Arg Ser Gly
    50                  55                  60

Glu Asn Ala Leu Lys Ile Asp Ile His Val Ile Ile Pro Tyr Glu Gly
```

```
65                  70                  75                  80

Leu Ser Ala Asp Gln Met Ala Gln Ile Glu Glu Val Phe Lys Val Val
                85                  90                  95

Tyr Pro Val Asp Asp His His Phe Lys Val Ile Leu Pro Tyr Gly Thr
                100                 105                 110

Leu Val Ile Asp Gly Val Thr Pro Asn Lys Leu Asn Tyr Phe Gly Arg
            115                 120                 125

Pro Tyr Glu Gly Ile Ala Val Phe Asp Gly Lys Lys Ile Thr Thr Thr
        130                 135                 140

Gly Thr Leu Trp Asn Gly Asn Lys Ile Ile Asp Glu Arg Leu Ile Thr
145                 150                 155                 160

Pro Asp His His His His His His
                165
```

<210> SEQ ID NO 890
<211> LENGTH: 498
<212> TYPE: DNA
<213> ORGANISM: Artificial sequence
<220> FEATURE:
<223> OTHER INFORMATION: Synthetic

<400> SEQUENCE: 890

```
atggtcttca cactcgaaga tttcgttggg gactgggaac agacagccgc ctacaacctg      60
gaccaagtcc ttgaacaggg aggtgtgtcc agtttgctgc agaatctcgc cgtgtccgta     120
actccgatcc aaaggattgt ccggagcggt gaaaatgccc tgaagatcga catccatgtc     180
atcatcccgt atgaaggtct gagcgccgac caaatggccc agatcgaaga ggtgtttaag     240
gtggtgtacc ctgtggatga tcatcacttt aaggtgatcc tgccctatgg cacactggta     300
atcgacgggg ttacgccgaa catgctgaac tatttcggac ggccgtatga aggcatcgcc     360
gtgttcgacg gcaaaaagat cactgtaaca gggaccctgt ggaacgagaa caaaattatc     420
gacgagcgcc tgatcacccc cgacggctcc atgctgttcc gagtaaccat caacagccat     480
catcaccatc accactaa                                                   498
```

<210> SEQ ID NO 891
<211> LENGTH: 165
<212> TYPE: PRT
<213> ORGANISM: Artificial sequence
<220> FEATURE:
<223> OTHER INFORMATION: Synthetic

<400> SEQUENCE: 891

```
Met Val Phe Thr Leu Glu Asp Phe Val Gly Asp Trp Lys Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Gln Arg Met Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Met Leu Asn Tyr Phe
                100                 105                 110
```

-continued

```
Gly Arg Pro Tyr Glu Gly Ile Ala Val Phe Asp Gly Lys Lys Ile Thr
        115                 120                 125

Val Thr Gly Thr Leu Trp Asn Asp Val Lys Ile Ile Asp Glu Arg Leu
    130                 135                 140

Ile Thr Pro Asp Gly Ser Met Ser Phe Arg Val Thr Ile Asn Ser His
145                 150                 155                 160

His His His His His
                165
```

```
<210> SEQ ID NO 892
<211> LENGTH: 498
<212> TYPE: DNA
<213> ORGANISM: Artificial sequence
<220> FEATURE:
<223> OTHER INFORMATION: Synthetic

<400> SEQUENCE: 892
atggtcttca cactcgaaga tttcgttggg gactggaagc agacagccgc ctacaacctg      60
gaccaagtcc ttgaacaggg aggtgtgtcc agtttgctgc agaatctcgc cgtgtccgta     120
actccgatcc aaaggatggt ccggagcggt gaaaatgccc tgaagatcga catccatgtc     180
atcatcccgt atgaaggtct gagcgccgac caaatggccc agatcgaaga ggtgtttaag     240
gtggtgtacc ctgtggatga tcatcacttt aaggtgatcc tgccctatgg cacactggta     300
atcgacgggg ttacgccgaa catgctgaac tatttcggac ggccgtatga aggcatcgcc     360
gtgttcgacg gcaaaaagat cactgtaaca gggaccctgt ggaacggcaa caaaattatc     420
gacgagcgcc tgatcacccc cgacggctcc atgtccttcc gagtaaccat caacagccat     480
catcaccatc accactaa                                                   498
```

```
<210> SEQ ID NO 893
<211> LENGTH: 165
<212> TYPE: PRT
<213> ORGANISM: Artificial sequence
<220> FEATURE:
<223> OTHER INFORMATION: Synthetic

<400> SEQUENCE: 893

Met Val Phe Thr Leu Glu Asp Phe Val Gly Asp Trp Lys Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Gln Arg Met Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Met Leu Asn Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Thr Pro Asp Gly Ser Met Ser Phe Arg Val Thr Ile Asn Ser His
145                 150                 155                 160
```

His His His His His
          165

<210> SEQ ID NO 894
<211> LENGTH: 498
<212> TYPE: DNA
<213> ORGANISM: Artificial sequence
<220> FEATURE:
<223> OTHER INFORMATION: Synthetic

<400> SEQUENCE: 894
atggtcttca cactcgaaga tttcgttggg gactggaagc agacagccgc ctacaacctg        60
gaccaagtcc ttgaacaggg aggtgtgtcc agtttgctgc agaatctcgc cgtgtccgta       120
actccgatcc aaaggatggt ccggagcggt gaaaatgccc tgaagatcga catccatgtc       180
atcatcccgt atgaaggtct gagcgccgac caaatggccc agatcgaaga ggtgtttaag       240
gtggtgtacc ctgtggatga tcatcacttt aaggtgatcc tgccctatgg cacactggta       300
atcgacgggg ttacgccgaa catgctgaac tatttcggac ggccgtatga aggcatcgcc       360
gtgttcgacg gcaaaaagat cactgtaaca gggaccctgt ggaacggcgt caaaattatc       420
gacgagcgcc tgatcacccc cgacggctcc atgtccttcc gagtaaccat caacagccat       480
catcaccatc accactaa                                                     498

<210> SEQ ID NO 895
<211> LENGTH: 165
<212> TYPE: PRT
<213> ORGANISM: Artificial sequence
<220> FEATURE:
<223> OTHER INFORMATION: Synthetic

<400> SEQUENCE: 895

Met Val Phe Thr Leu Glu Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Gln Arg Met Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Met Leu Asn Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Thr Pro Asp Gly Ser Met Leu Phe Arg Val Thr Ile Asn Ser His
145                 150                 155                 160

His His His His His
            165

<210> SEQ ID NO 896
<211> LENGTH: 498
<212> TYPE: DNA

<213> ORGANISM: Artificial sequence
<220> FEATURE:
<223> OTHER INFORMATION: Synthetic

<400> SEQUENCE: 896

```
atggtcttca cactcgaaga tttcgttggg gactggaagc agacagccgc ctacaacctg      60
gaccaagtcc ttgaacaggg aggtgtgtcc agtttgctgc agaatctcgc cgtgtccgta     120
actccgatcc aaaggatggt ccggagcggt gaaaatgccc tgaagatcga catccatgtc     180
atcatcccgt atgaaggtct gagcgccgac caaatggccc agatcgaaga ggtgtttaag     240
gtggtgtacc ctgtggatga tcatcacttt aaggtgatcc tgccctatgg cacactggta     300
atcgacgggg ttacgccgaa catgctgaac tatttcggac ggccgtatga aggcatcgcc     360
gtgttcgacg gcaaaaagat cactgtaaca gggaccctgt ggaacggcaa caaaattatc     420
gacgagcgcc tgatcacccc cgacggctcc atgctgttcc gagtaaccat caacagccat     480
catcaccatc accactaa                                                     498
```

<210> SEQ ID NO 897
<211> LENGTH: 165
<212> TYPE: PRT
<213> ORGANISM: Artificial sequence
<220> FEATURE:
<223> OTHER INFORMATION: Synthetic

<400> SEQUENCE: 897

```
Met Val Phe Thr Leu Glu Asp Phe Val Gly Asp Trp Lys Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Gln Arg Met Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Met Leu Asn Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Thr Pro Asp Gly Ser Met Leu Phe Arg Val Thr Ile Asn Ser His
145                 150                 155                 160

His His His His His
                165
```

<210> SEQ ID NO 898
<211> LENGTH: 498
<212> TYPE: DNA
<213> ORGANISM: Artificial sequence
<220> FEATURE:
<223> OTHER INFORMATION: Synthetic

<400> SEQUENCE: 898

```
atggtcttca cactcgaaga tttcgttggg gactggaagc agacagccgc ctacaacctg      60
```

-continued

```
gaccaagtcc ttgaacaggg aggtgtgtcc agtttgctgc agaatctcgc cgtgtccgta    120
actccgatcc aaaggatggt ccggagcggt gaaaatgccc tgaagatcga catccatgtc    180
atcatcccgt atgaaggtct gagcgccgac caaatggccc agatcgaaga ggtgtttaag    240
gtggtgtacc ctgtggatga tcatcacttt aaggtgatcc tgccctatgg cacactggta    300
atcgacgggg ttacgccgaa catgctgaac tatttcggac ggccgtatga aggcatcgcc    360
gtgttcgacg gcaaaaagat cactgtaaca gggaccctgt ggaacgacgt caaaattatc    420
gacgagcgcc tgatcacccc cgacggctcc atgctgttcc gagtaaccat caacagccat    480
catcaccatc accactaa                                                  498
```

```
<210> SEQ ID NO 899
<211> LENGTH: 165
<212> TYPE: PRT
<213> ORGANISM: Artificial sequence
<220> FEATURE:
<223> OTHER INFORMATION: Synthetic

<400> SEQUENCE: 899

Met Val Phe Thr Leu Glu Asp Phe Val Gly Asp Trp Lys Gln Thr Ala
1               5                   10                  15

Ala Tyr Asn Leu Asp Gln Val Leu Glu Gln Gly Gly Val Ser Ser Leu
                20                  25                  30

Leu Gln Asn Leu Ala Val Ser Val Thr Pro Ile Gln Arg Met Val Arg
            35                  40                  45

Ser Gly Glu Asn Ala Leu Lys Ile Asp Ile His Val Ile Ile Pro Tyr
        50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Met Leu Asn Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Asp Val Lys Ile Ile Asp Glu Arg Leu
    130                 135                 140

Ile Thr Pro Asp Gly Ser Met Leu Phe Arg Val Thr Ile Asn Ser His
145                 150                 155                 160

His His His His His
                165
```